(12) United States Patent
Dillon et al.

(10) Patent No.: US 12,115,163 B2
(45) Date of Patent: *Oct. 15, 2024

(54) COMBINATION THERAPY COMPRISING A MAT2A INHIBITOR AND A TYPE II PRMT INHIBITOR

(71) Applicant: IDEAYA BIOSCIENCES, INC., South San Francisco, CA (US)

(72) Inventors: Michael Patrick Dillon, South San Francisco, CA (US); Claire L. Neilan, South San Francisco, CA (US); Marcus Michael Fischer, South San Francisco, CA (US); Kimberline Yang Gerrick, South San Francisco, CA (US)

(73) Assignee: IDEAYA BIOSCIENCES, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/405,638

(22) Filed: Jan. 5, 2024

(65) Prior Publication Data
US 2024/0173326 A1 May 30, 2024

Related U.S. Application Data

(63) Continuation of application No. 18/501,729, filed on Nov. 3, 2023, which is a continuation of application No. PCT/US2022/072693, filed on Jun. 1, 2022.

(60) Provisional application No. 63/364,360, filed on May 9, 2022, provisional application No. 63/362,438, filed on Apr. 4, 2022, provisional application No. 63/196,008, filed on Jun. 2, 2021.

(51) Int. Cl.
| | |
|---|---|
| A61K 31/519 | (2006.01) |
| A61K 31/502 | (2006.01) |
| A61P 35/00 | (2006.01) |

(52) U.S. Cl.
CPC .......... *A61K 31/519* (2013.01); *A61K 31/502* (2013.01); *A61P 35/00* (2018.01)

(58) Field of Classification Search
CPC ...................................................... A61P 35/00
See application file for complete search history.

(56) References Cited

U.S. PATENT DOCUMENTS

| | | | |
|---|---|---|---|
| 2018/0371551 A1 | 12/2018 | Marjon et al. | |
| 2024/0108626 A1* | 4/2024 | Dillon | A61K 45/06 |

FOREIGN PATENT DOCUMENTS

| | | | | |
|---|---|---|---|---|
| WO | WO-2020123395 A1 * | 6/2020 | ........... | A61K 31/517 |
| WO | WO-2021050915 A1 * | 3/2021 | ........... | A61K 31/502 |

OTHER PUBLICATIONS

International Search Report and Written Opinion for International Application No. PCT/US2022/072693 mailed Sep. 23, 2022, 14 pages.
Marjon et al., "MTAP Deletions in Cancer Create Vulnerability to Targeting of the MAT2A/PRMT5/RIOK1 Axis", *Cell Reports* 15(3):574-587 (2016).
U.S. Appl. No. 18/501,729, filed Nov. 3, 2023, Michael Patrick Dillon.

* cited by examiner

*Primary Examiner* — Andrew D Kosar
*Assistant Examiner* — Gillian A Hutter
(74) *Attorney, Agent, or Firm* — Lathrop GPM LLP; Brian C. Trinque; Nicole Sassu

(57) ABSTRACT

Provided herein is a combination product comprising a methionine adenosyltransferase II alpha (MAT2A) inhibitor and a Type II protein arginine methyltransferase (Type II PRMT) inhibitor. The combination product is useful for the treatment of a variety of cancers, including solid tumors. The combination product is useful for the treatment of any number of MAT2A-associated and/or PRMT-associated diseases.

17 Claims, 30 Drawing Sheets

A    Compound B (µM)

| Compound A (µM) | 0.009 | 0.039 | 0.156 | 0.625 | 2.5 | 10 |
|---|---|---|---|---|---|---|
| 0.009 | -6 | 13 | 9 | 3 | 0 | 0 |
| 0.039 | -9 | 5 | 13 | 19 | 0 | 0 |
| 0.156 | 1 | 20 | 31 | 22 | 0 | 0 |
| 0.625 | -5 | 7 | 24 | 28 | 0 | 0 |
| 2.5 | 0 | 6 | 16 | 27 | 0 | 0 |
| 10 | -12 | 0 | 14 | 32 | 0 | 0 |

B    Compound B (µM)

| Compound A (µM) | 0.009 | 0.039 | 0.156 | 0.625 | 2.5 | 10 |
|---|---|---|---|---|---|---|
| 0.009 | -6 | 13 | 9 | 3 | 0 | 0 |
| 0.039 | -9 | 5 | 13 | 19 | 0 | 0 |
| 0.156 | 1 | 20 | 30 | 21 | 0 | 0 |
| 0.625 | -5 | 7 | 24 | 17 | 0 | 0 |
| 2.5 | 0 | 6 | 16 | 12 | -1 | 0 |
| 10 | -12 | 0 | 13 | 16 | -1 | 0 |

FIG. 6

C Compound B (μM)

| Compound A (μM) | 0.009 | 0.039 | 0.156 | 0.625 | 2.5 | 10 |
|---|---|---|---|---|---|---|
| 0.009 | -6 | 13 | 9 | 3 | 0 | 0 |
| 0.039 | -9 | 5 | 12 | 19 | 0 | 0 |
| 0.156 | 1 | 19 | 25 | 22 | 0 | 0 |
| 0.625 | -5 | 5 | 19 | 28 | 0 | 0 |
| 2.5 | 0 | 6 | 16 | 27 | 0 | 0 |
| 10 | -12 | 0 | 14 | 32 | 0 | 0 |

D Compound C (μM)

| Compound A (μM) | 0.00122 | 0.00244 | 0.00488 | 0.0098 | 0.0195 | 0.039 | 0.078 | 0.156 | 0.313 | 0.625 | 1.25 |
|---|---|---|---|---|---|---|---|---|---|---|---|
| 0.0008 | -15 | -13 | -9 | 0 | 8 | -14 | -1 | -18 | 3 | -8 | 0 |
| 0.002 | 11 | -20 | 0 | 11 | 24 | -7 | 0 | -13 | -20 | 0 | 1 |
| 0.005 | 4 | -2 | -15 | 1 | 7 | -23 | -1 | 1 | -2 | 14 | 6 |
| 0.0128 | -1 | 9 | 4 | 5 | 7 | -3 | 5 | 7 | 11 | 25 | 11 |
| 0.032 | -1 | 12 | -1 | 13 | 8 | 2 | 15 | 13 | 29 | 29 | 14 |
| 0.08 | 1 | -1 | -4 | 11 | 6 | 11 | 8 | 24 | 33 | 32 | 17 |
| 0.2 | 6 | 2 | 9 | 3 | 9 | 7 | 22 | 34 | 43 | 36 | 18 |
| 0.5 | 11 | -1 | 12 | 4 | 9 | 11 | 25 | 43 | 49 | 42 | 19 |
| 1.25 | -3 | 1 | 11 | 11 | 8 | 18 | 20 | 37 | 51 | 42 | 19 |

Compound C (μM)

| Compound A (μM) | 0.00122 | 0.00244 | 0.00488 | 0.0098 | 0.0195 | 0.039 | 0.078 | 0.156 | 0.313 | 0.625 | 1.25 |
|---|---|---|---|---|---|---|---|---|---|---|---|
| 0.0008 | -15 | -13 | -9 | 0 | 8 | -14 | -1 | -18 | -3 | -8 | 0 |
| 0.002 | 11 | -20 | 0 | 11 | 24 | -7 | 0 | -13 | -20 | -1 | 1 |
| 0.005 | 4 | -2 | -15 | 1 | 7 | -24 | -1 | 1 | -2 | 14 | 6 |
| 0.0128 | -1 | 9 | 4 | 5 | 7 | -3 | 4 | 7 | 10 | 25 | 11 |
| 0.032 | -1 | 12 | -1 | 13 | 8 | 2 | 14 | 12 | 28 | 29 | 14 |
| 0.08 | 1 | -1 | -4 | 11 | 6 | 11 | 7 | 23 | 32 | 31 | 16 |
| 0.2 | 6 | 2 | 9 | 3 | 9 | 6 | 20 | 30 | 39 | 33 | 16 |
| 0.5 | 11 | -1 | 12 | 4 | 9 | 11 | 23 | 38 | 39 | 35 | 16 |
| 1.25 | -3 | 1 | 11 | 11 | 8 | 17 | 19 | 32 | 37 | 30 | 13 |

F

Compound C (μM)

| Compound A (μM) | 0.00122 | 0.00244 | 0.00488 | 0.0098 | 0.0195 | 0.039 | 0.078 | 0.156 | 0.313 | 0.625 | 1.25 |
|---|---|---|---|---|---|---|---|---|---|---|---|
| 0.0008 | -15 | -13 | -9 | 0 | 8 | -14 | -1 | -18 | -3 | -8 | 0 |
| 0.002 | 11 | -20 | 0 | 11 | 24 | -7 | 0 | -13 | -20 | 0 | 1 |
| 0.005 | 4 | -2 | -15 | 1 | 7 | -24 | -1 | 1 | -2 | 14 | 6 |
| 0.0128 | -1 | 9 | 4 | 5 | 7 | -3 | 4 | 6 | 10 | 25 | 11 |
| 0.032 | -1 | 12 | -1 | 13 | 8 | 1 | 14 | 11 | 28 | 29 | 14 |
| 0.08 | 1 | -1 | -4 | 11 | 6 | 10 | 5 | 21 | 31 | 32 | 17 |
| 0.2 | 5 | 2 | 9 | 3 | 8 | 5 | 19 | 28 | 39 | 36 | 18 |
| 0.5 | 11 | -1 | 12 | 3 | 9 | 10 | 22 | 37 | 43 | 42 | 19 |
| 1.25 | -3 | 1 | 11 | 11 | 7 | 17 | 19 | 34 | 46 | 42 | 19 |

FIG. 6 (cont'd)

G     Compound D (µM)

| Compound A (µM) | 0.009 | 0.039 | 0.156 | 0.625 | 2.5 | 10 |
|---|---|---|---|---|---|---|
| 0.009 | -22 | -7 | -3 | -1 | 9 | 0 |
| 0.039 | -5 | -25 | -6 | 7 | 14 | 0 |
| 0.156 | -1 | -10 | 0 | 21 | 19 | 0 |
| 0.625 | -24 | -9 | -2 | 13 | 19 | 0 |
| 2.5 | -14 | -7 | -4 | 12 | 19 | 0 |
| 10 | -5 | -2 | 1 | 13 | 20 | 0 |

H     Compound D (µM)

| Compound A (µM) | 0.009 | 0.039 | 0.156 | 0.625 | 2.5 | 10 |
|---|---|---|---|---|---|---|
| 0.009 | -22 | -7 | -3 | -1 | 9 | 0 |
| 0.039 | -5 | -25 | -6 | 7 | 14 | 0 |
| 0.156 | -1 | -10 | 0 | 21 | 19 | 0 |
| 0.625 | -24 | -9 | -2 | 13 | 14 | -1 |
| 2.5 | -14 | -7 | -4 | 12 | 12 | -1 |
| 10 | -5 | -2 | 1 | 13 | 12 | -1 |

FIG. 6 (cont'd)

K Compound E (μM)

| Compound A (μM) | 0.009 | 0.039 | 0.156 | 0.625 | 2.5 | 10 |
|---|---|---|---|---|---|---|
| 0.009 | -3 | -12 | -9 | 6 | -13 | 11 |
| 0.039 | -5 | -11 | 5 | -5 | -10 | 11 |
| 0.156 | -8 | 0 | -4 | 0 | -9 | 13 |
| 0.625 | -3 | -10 | 0 | 4 | -2 | 11 |
| 2.5 | -3 | -1 | 2 | -6 | -2 | 9 |
| 10 | 2 | -10 | -3 | -2 | -4 | 7 |

L Compound E (μM)

| Compound A (μM) | 0.009 | 0.039 | 0.156 | 0.625 | 2.5 | 10 |
|---|---|---|---|---|---|---|
| 0.009 | -3 | -12 | -9 | 9 | -6 | 13 |
| 0.039 | -5 | -11 | 6 | -3 | -1 | 15 |
| 0.156 | -8 | 0 | -4 | 2 | 2 | 18 |
| 0.625 | -3 | -10 | 1 | 7 | 11 | 19 |
| 2.5 | -3 | -2 | 2 | -3 | 11 | 18 |
| 10 | 2 | -10 | -2 | 1 | 10 | 18 |

FIG. 6 (cont'd)

M Compound F (μM)

| Compound A (μM) | 0.009 | 0.039 | 0.156 | 0.625 | 2.5 | 10 |
|---|---|---|---|---|---|---|
| 0.009 | -8 | -11 | 6 | 18 | 4 | -1 |
| 0.039 | -13 | -9 | 14 | 29 | 9 | 3 |
| 0.156 | -12 | -1 | 17 | 34 | 10 | 4 |
| 0.625 | 1 | 6 | 22 | 38 | 11 | 7 |
| 2.5 | 3 | 4 | 21 | 38 | 14 | 6 |
| 10 | -4 | 3 | 18 | 38 | 12 | 7 |

N Compound F (μM)

| Compound A (μM) | 0.009 | 0.039 | 0.156 | 0.625 | 2.5 | 10 |
|---|---|---|---|---|---|---|
| 0.009 | -8 | -11 | 3 | 11 | 0 | -4 |
| 0.039 | -13 | -9 | 11 | 19 | 3 | -1 |
| 0.156 | -12 | -1 | 14 | 22 | 4 | -2 |
| 0.625 | 1 | 6 | 20 | 23 | 2 | 0 |
| 2.5 | 3 | 4 | 19 | 21 | 4 | -2 |
| 10 | -4 | 3 | 16 | 19 | 2 | -2 |

FIG. 6 (cont'd)

A Compound B (µM)

|  | 0.009 | 0.039 | 0.156 | 0.625 | 2.5 | 10 |
|---|---|---|---|---|---|---|
| 0.009 | 13 | 13 | 4 | -2 | 0 | 0 |
| 0.039 | 23 | 17 | 6 | -1 | 0 | 0 |
| 0.156 | 13 | 19 | 8 | 0 | 0 | 0 |
| 0.625 | 8 | 12 | 8 | 1 | 0 | 0 |
| 2.5 | 5 | 9 | 8 | 1 | 0 | 0 |
| 10 | 6 | 9 | 8 | 1 | 0 | 0 |

Compound A (µM)

B Compound B (µM)

|  | 0.009 | 0.039 | 0.156 | 0.625 | 2.5 | 10 |
|---|---|---|---|---|---|---|
| 0.009 | 0 | 5 | 0 | -4 | -1 | 0 |
| 0.039 | -1 | 2 | -2 | -4 | -1 | -1 |
| 0.156 | -2 | -1 | -2 | -5 | -2 | -1 |
| 0.625 | -2 | -2 | -4 | -4 | -2 | -1 |
| 2.5 | -3 | -3 | -3 | -4 | -2 | -1 |
| 10 | -2 | -2 | -3 | -4 | -2 | -1 |

Compound A (µM)

FIG. 7

C     Compound B (µM)

| Compound A (µM) | 0.009 | 0.039 | 0.156 | 0.625 | 2.5 | 10 |
|---|---|---|---|---|---|---|
| 0.009 | 9 | 12 | 4 | -2 | 0 | 0 |
| 0.039 | 13 | 14 | 6 | -1 | 0 | 0 |
| 0.156 | 11 | 13 | 8 | 0 | 0 | 0 |
| 0.625 | 8 | 11 | 8 | 1 | 0 | 0 |
| 2.5 | 5 | 9 | 8 | 1 | 0 | 0 |
| 10 | 6 | 9 | 8 | 1 | 0 | 0 |

D     Compound C (µM)

| Compound A (µM) | 0.00122 | 0.00244 | 0.00488 | 0.0098 | 0.0195 | 0.039 | 0.078 | 0.156 | 0.313 | 0.625 | 1.25 |
|---|---|---|---|---|---|---|---|---|---|---|---|
| 0.0008 | -9 | -3 | -3 | -17 | -3 | 3 | -1 | -1 | -1 | 0 | -1 |
| 0.002 | 18 | 5 | 6 | -22 | 3 | 6 | 5 | 0 | -4 | 0 | 0 |
| 0.005 | 0 | -8 | 23 | 19 | 22 | 16 | 7 | 4 | 0 | 1 | 1 |
| 0.0128 | 13 | 7 | 24 | 35 | 33 | 19 | 9 | 4 | 2 | 2 | 1 |
| 0.032 | 13 | 17 | 26 | 31 | 35 | 23 | 12 | 6 | 5 | 3 | 4 |
| 0.08 | 6 | 13 | 14 | 18 | 23 | 26 | 16 | 1 | 6 | 5 | 4 |
| 0.2 | 1 | 4 | 10 | 11 | 13 | 16 | 17 | 10 | 7 | 7 | 6 |
| 0.5 | 1 | 2 | 4 | 7 | 9 | 10 | 11 | 12 | 8 | 7 | 7 |
| 1.25 | -4 | -2 | 3 | 4 | 7 | 8 | 9 | 9 | 9 | 8 | 8 |

Compound C (μM)

| Compound A (μM) | 0.00122 | 0.00244 | 0.00488 | 0.0098 | 0.0195 | 0.039 | 0.078 | 0.156 | 0.313 | 0.625 | 1.25 |
|---|---|---|---|---|---|---|---|---|---|---|---|
| 0.0008 | -11 | -5 | -4 | -19 | -4 | 2 | -2 | -2 | -2 | 0 | -2 |
| 0.002 | 17 | 1 | 3 | -25 | 0 | 4 | 4 | -1 | -4 | 0 | -1 |
| 0.005 | -1 | -11 | 14 | 12 | 16 | 12 | 5 | 2 | -2 | -1 | -1 |
| 0.0128 | 11 | 4 | 17 | 19 | 20 | 9 | 3 | -1 | -2 | -2 | -3 |
| 0.032 | 12 | 15 | 20 | 19 | 13 | 6 | 0 | -2 | -3 | -4 | -3 |
| 0.08 | 5 | 11 | 10 | 9 | 7 | 2 | -2 | -3 | -5 | -6 | -6 |
| 0.2 | 0 | 3 | 7 | 4 | 2 | -1 | -4 | -7 | -7 | -6 | -7 |
| 0.5 | 1 | 1 | 2 | 2 | 0 | -4 | -5 | -6 | -7 | -7 | -7 |
| 1.25 | -5 | -3 | 1 | 0 | -1 | -3 | -5 | -7 | -7 | -7 | -7 |

F

Compound C (μM)

| Compound A (μM) | 0.00122 | 0.00244 | 0.00488 | 0.0098 | 0.0195 | 0.039 | 0.078 | 0.156 | 0.313 | 0.625 | 1.25 |
|---|---|---|---|---|---|---|---|---|---|---|---|
| 0.0008 | -11 | -5 | -5 | -19 | -3 | 2 | -1 | -1 | -1 | 0 | -1 |
| 0.002 | 16 | 1 | 2 | -25 | 1 | 5 | 5 | 0 | -4 | 0 | 0 |
| 0.005 | -2 | -12 | 14 | 12 | 18 | 14 | 7 | 4 | 0 | 1 | 1 |
| 0.0128 | 11 | 3 | 17 | 21 | 24 | 15 | 8 | 4 | 2 | 2 | 1 |
| 0.032 | 11 | 15 | 21 | 22 | 20 | 16 | 10 | 6 | 5 | 3 | 4 |
| 0.08 | 5 | 11 | 12 | 14 | 16 | 15 | 12 | 10 | 6 | 5 | 4 |
| 0.2 | 1 | 4 | 10 | 9 | 11 | 12 | 11 | 8 | 7 | 7 | 6 |
| 0.5 | 1 | 2 | 4 | 6 | 8 | 9 | 9 | 10 | 8 | 7 | 7 |
| 1.25 | -4 | -2 | 3 | 4 | 6 | 8 | 9 | 8 | 8 | 8 | 8 |

FIG. 7 (cont'd)

G Compound D (μM)

| Compound A (μM) | 0.009 | 0.039 | 0.156 | 0.625 | 2.5 | 10 |
|---|---|---|---|---|---|---|
| 0.009 | 13 | 29 | 12 | 2 | -1 | 0 |
| 0.039 | 8 | 21 | 16 | 2 | 0 | 0 |
| 0.156 | 3 | 12 | 19 | 4 | 0 | 0 |
| 0.625 | 0 | 8 | 13 | 4 | 0 | 0 |
| 2.5 | 0 | 7 | 11 | 4 | 1 | 1 |
| 10 | 2 | 8 | 10 | 5 | 0 | 1 |

H Compound D (μM)

| Compound A (μM) | 0.009 | 0.039 | 0.156 | 0.625 | 2.5 | 10 |
|---|---|---|---|---|---|---|
| 0.009 | 5 | 13 | 5 | -1 | -2 | -1 |
| 0.039 | 2 | 4 | 1 | -3 | -2 | -1 |
| 0.156 | 0 | 2 | 0 | -3 | -3 | -2 |
| 0.625 | -2 | 0 | -1 | -4 | -3 | -2 |
| 2.5 | -2 | 1 | -1 | -3 | -3 | -2 |
| 10 | 0 | 1 | -2 | -3 | -3 | -2 |

FIG. 7 (cont'd)

I  Compound D (μM)

| Compound A (μM) | 0.009 | 0.039 | 0.156 | 0.625 | 2.5 | 10 |
|---|---|---|---|---|---|---|
| 0.009 | 7 | 19 | 11 | 2 | -1 | 0 |
| 0.039 | 5 | 13 | 13 | 2 | 0 | 0 |
| 0.156 | 2 | 10 | 13 | 4 | 0 | 0 |
| 0.625 | 0 | 7 | 11 | 4 | 0 | 0 |
| 2.5 | 0 | 7 | 10 | 4 | 1 | 1 |
| 10 | 2 | 8 | 10 | 5 | 0 | 1 |

J  Compound E (μM)

| Compound A (μM) | 0.009 | 0.039 | 0.156 | 0.625 | 2.5 | 10 |
|---|---|---|---|---|---|---|
| 0.009 | -7 | 14 | 22 | 7 | 0 | 0 |
| 0.039 | -12 | 8 | 26 | 9 | 1 | 0 |
| 0.156 | 1 | 8 | 15 | 12 | 2 | 1 |
| 0.625 | -4 | 6 | 10 | 13 | 3 | 1 |
| 2.5 | 0 | 4 | 9 | 11 | 3 | 2 |
| 10 | 2 | 5 | 8 | 10 | 3 | 1 |

FIG. 7 (cont'd)

K     Compound E (μM)

| Compound A (μM) | 0.009 | 0.039 | 0.156 | 0.625 | 2.5 | 10 |
|---|---|---|---|---|---|---|
| 0.009 | -12 | -1 | 5 | 1 | -3 | -1 |
| 0.039 | -15 | -2 | 3 | -2 | -3 | -2 |
| 0.156 | -1 | 1 | 0 | -2 | -4 | -2 |
| 0.625 | -6 | 1 | 0 | -2 | -3 | -2 |
| 2.5 | -1 | 0 | 0 | -2 | -3 | -2 |
| 10 | 0 | 1 | 0 | -2 | -3 | -2 |

L     Compound E (μM)

| Compound A (μM) | 0.009 | 0.039 | 0.156 | 0.625 | 2.5 | 10 |
|---|---|---|---|---|---|---|
| 0.009 | -9 | 7 | 17 | 7 | 0 | 0 |
| 0.039 | -12 | 5 | 16 | 9 | 1 | 0 |
| 0.156 | 1 | 7 | 12 | 10 | 2 | 1 |
| 0.625 | -4 | 5 | 9 | 10 | 3 | 1 |
| 2.5 | 0 | 4 | 8 | 10 | 3 | 2 |
| 10 | 1 | 5 | 8 | 10 | 3 | 1 |

FIG. 7 (cont'd)

M Compound F (μM)

| Compound A (μM) | 0.009 | 0.039 | 0.156 | 0.625 | 2.5 | 10 |
|---|---|---|---|---|---|---|
| 0.009 | 11 | 15 | 3 | 3 | 6 | 2 |
| 0.039 | 6 | 12 | 8 | 8 | 7 | 7 |
| 0.156 | 1 | 5 | 8 | 8 | 9 | 9 |
| 0.625 | 2 | 4 | 6 | 6 | 6 | 7 |
| 2.5 | 1 | 4 | 6 | 5 | 7 | 7 |
| 10 | 2 | 4 | 6 | 7 | 6 | 6 |

N Compound F (μM)

| Compound A (μM) | 0.009 | 0.039 | 0.156 | 0.625 | 2.5 | 10 |
|---|---|---|---|---|---|---|
| 0.009 | 2 | -5 | -10 | -10 | -7 | -10 |
| 0.039 | 0 | -8 | -12 | -10 | -11 | -12 |
| 0.156 | -3 | -10 | -12 | -12 | -11 | -10 |
| 0.625 | -2 | -10 | -11 | -11 | -11 | -11 |
| 2.5 | -3 | -9 | -10 | -12 | -10 | -10 |
| 10 | -2 | -9 | -11 | -10 | -10 | -10 |

FIG. 7 (cont'd)

O Compound F (µM)

| Compound A (µM) | 0.009 | 0.039 | 0.156 | 0.625 | 2.5 | 10 |
|---|---|---|---|---|---|---|
| 0.009 | 5 | 8 | 3 | 3 | 6 | 2 |
| 0.039 | 5 | 8 | 7 | 8 | 7 | 7 |
| 0.156 | 1 | 5 | 8 | 8 | 9 | 9 |
| 0.625 | 2 | 4 | 6 | 6 | 6 | 7 |
| 2.5 | 1 | 4 | 6 | 5 | 7 | 7 |
| 10 | 2 | 4 | 6 | 7 | 6 | 6 |

P Compound G (µM)

| Compound A (µM) | 0.00122 | 0.00244 | 0.00488 | 0.0098 | 0.0195 | 0.039 | 0.078 | 0.156 | 0.313 | 0.625 | 1.25 |
|---|---|---|---|---|---|---|---|---|---|---|---|
| 0.0008 | 15 | -19 | -9 | 7 | -7 | -10 | -3 | -6 | -5 | 4 | -1 |
| 0.002 | 9 | -11 | -22 | -6 | -2 | -12 | -4 | -5 | 2 | 3 | 1 |
| 0.005 | -3 | -6 | -9 | -8 | 10 | 10 | 17 | 20 | 17 | 12 | 1 |
| 0.0128 | -8 | -4 | -3 | -4 | 7 | 12 | 26 | 28 | 19 | 13 | 3 |
| 0.032 | -5 | 0 | -5 | -1 | 4 | 11 | 16 | 27 | 25 | 14 | 8 |
| 0.08 | -3 | -4 | -4 | -4 | 2 | 5 | 12 | 19 | 21 | 17 | 8 |
| 0.2 | 1 | -4 | -4 | -2 | 1 | 6 | 8 | 12 | 15 | 16 | 11 |
| 0.5 | -3 | -3 | -3 | -2 | 1 | 2 | 6 | 10 | 10 | 12 | 12 |
| 1.25 | -2 | -3 | -2 | -4 | 1 | 4 | 5 | 7 | 8 | 10 | 10 |

Compound G (μM)

| Compound A (μM) | 0.00122 | 0.00244 | 0.00488 | 0.0098 | 0.0195 | 0.039 | 0.078 | 0.156 | 0.313 | 0.625 | 1.25 |
|---|---|---|---|---|---|---|---|---|---|---|---|
| 0.0008 | 13 | -22 | -12 | 3 | -10 | -13 | -6 | -9 | -7 | 2 | -2 |
| 0.002 | 7 | -14 | -26 | -13 | -9 | -19 | -10 | -11 | -2 | 0 | -1 |
| 0.005 | -5 | -9 | -13 | -15 | -1 | -3 | 5 | 10 | 9 | 6 | -3 |
| 0.0128 | -9 | -6 | -6 | -9 | -2 | -1 | 6 | 10 | 5 | 3 | -4 |
| 0.032 | -6 | -2 | -8 | -5 | -3 | 0 | 0 | 5 | 4 | -2 | -3 |
| 0.08 | -4 | -5 | -6 | -7 | -3 | -3 | 1 | 3 | 0 | -3 | -6 |
| 0.2 | 1 | -5 | -6 | -4 | -3 | 0 | 0 | 0 | -1 | -3 | -5 |
| 0.5 | -3 | -4 | -4 | -4 | -2 | -3 | -1 | 0 | -3 | -3 | -6 |
| 1.25 | -2 | -4 | -3 | -5 | -4 | 0 | -1 | -2 | -3 | 4 | -6 |

R

Compound G (μM)

| Compound A (μM) | 0.00122 | 0.00244 | 0.00488 | 0.0098 | 0.0195 | 0.039 | 0.078 | 0.156 | 0.313 | 0.625 | 1.25 |
|---|---|---|---|---|---|---|---|---|---|---|---|
| 0.0008 | 14 | -21 | -11 | 5 | -9 | -11 | -4 | -7 | -5 | 3 | -1 |
| 0.002 | 8 | -13 | -24 | -11 | -6 | -15 | -6 | -7 | 1 | 3 | 1 |
| 0.005 | -4 | -7 | -11 | -12 | 3 | 2 | 11 | 17 | 15 | 11 | 1 |
| 0.0128 | -8 | -4 | -4 | -6 | 3 | 6 | 15 | 20 | 15 | 12 | 3 |
| 0.032 | -5 | -1 | -5 | -2 | 3 | 8 | 11 | 17 | 17 | 11 | 7 |
| 0.08 | -3 | -4 | -4 | -4 | 1 | 4 | 10 | 15 | 14 | 11 | 7 |
| 0.2 | 1 | -4 | -4 | -2 | 1 | 5 | 8 | 11 | 12 | 11 | 9 |
| 0.5 | -3 | -3 | -3 | -2 | 1 | 1 | 5 | 9 | 9 | 10 | 8 |
| 1.25 | -2 | -3 | -2 | -4 | -1 | 4 | 5 | 6 | 8 | 9 | 8 |

FIG. 7 (cont'd)

A Compound B (µM)

|  | 0.009 | 0.039 | 0.156 | 0.625 | 2.5 | 10 |
|---|---|---|---|---|---|---|
| 0.009 | -4 | 7 | 16 | 5 | -1 | 0 |
| 0.039 | 6 | 14 | 18 | 4 | 0 | 1 |
| 0.156 | 10 | 12 | 17 | 8 | 0 | 1 |
| 0.625 | 6 | 13 | 13 | 7 | 0 | 0 |
| 2.5 | 6 | 8 | 8 | 8 | -1 | 1 |
| 10 | 4 | 7 | 8 | 6 | -1 | 1 |

Compound A (µM)

B Compound B (µM)

|  | 0.009 | 0.039 | 0.156 | 0.625 | 2.5 | 10 |
|---|---|---|---|---|---|---|
| 0.009 | -13 | -9 | -8 | -10 | -10 | -5 |
| 0.039 | -2 | -1 | -4 | -11 | -9 | -4 |
| 0.156 | 2 | -1 | -4 | -9 | -9 | -4 |
| 0.625 | -1 | 0 | -5 | -10 | -10 | -6 |
| 2.5 | 0 | -4 | -9 | -10 | -11 | -5 |
| 10 | -2 | -4 | -7 | -13 | -12 | -5 |

Compound A (µM)

FIG. 8

C Compound B (μM)

|  | 0.009 | 0.039 | 0.156 | 0.625 | 2.5 | 10 |
|---|---|---|---|---|---|---|
| 0.009 | -4 | 7 | 13 | 5 | -1 | 0 |
| 0.039 | 6 | 14 | 15 | 4 | 0 | 1 |
| 0.156 | 10 | 12 | 15 | 8 | 0 | 1 |
| 0.625 | 6 | 13 | 12 | 7 | 0 | 0 |
| 2.5 | 6 | 8 | 8 | 7 | -1 | 1 |
| 10 | 4 | 7 | 8 | 4 | -1 | 1 |

Compound A (μM)

D Compound C (μM)

|  | 0.009 | 0.039 | 0.156 | 0.625 | 2.5 | 10 |
|---|---|---|---|---|---|---|
| 0.009 | 23 | 34 | 7 | 1 | 2 | 1 |
| 0.039 | 15 | 21 | 11 | 3 | 5 | 2 |
| 0.156 | 10 | 12 | 13 | 7 | 6 | 4 |
| 0.625 | 4 | 8 | 11 | 6 | 4 | 3 |
| 2.5 | 4 | 7 | 9 | 4 | 6 | 4 |
| 10 | -1 | 4 | 8 | 5 | 4 | 2 |

Compound A (μM)

FIG. 8 (cont'd)

E Compound C (μM)

| Compound A (μM) | 0.009 | 0.039 | 0.156 | 0.625 | 2.5 | 10 |
|---|---|---|---|---|---|---|
| 0.009 | 19 | 14 | -2 | -6 | -5 | -6 |
| 0.039 | 12 | 5 | -6 | -9 | -7 | -10 |
| 0.156 | 8 | 0 | -7 | -8 | -9 | -10 |
| 0.625 | 2 | -2 | -8 | -10 | -12 | -13 |
| 2.5 | 3 | -2 | -9 | -13 | -11 | -13 |
| 10 | -2 | -5 | -9 | -12 | -12 | -14 |

F Compound C (μM)

| Compound A (μM) | 0.009 | 0.039 | 0.156 | 0.625 | 2.5 | 10 |
|---|---|---|---|---|---|---|
| 0.009 | 19 | 21 | 7 | 1 | 2 | 1 |
| 0.039 | 13 | 15 | 9 | 3 | 5 | 2 |
| 0.156 | 10 | 10 | 10 | 7 | 6 | 4 |
| 0.625 | 4 | 7 | 9 | 6 | 4 | 3 |
| 2.5 | 4 | 7 | 8 | 4 | 6 | 4 |
| 10 | -1 | 4 | 8 | 5 | 4 | 2 |

FIG. 8 (cont'd)

G Compound F (μM)

| Compound A (μM) | 0.009 | 0.039 | 0.156 | 0.625 | 2.5 | 10 |
|---|---|---|---|---|---|---|
| 0.009 | 6 | 31 | 25 | 3 | 1 | 5 |
| 0.039 | 4 | 16 | 19 | 6 | 3 | 7 |
| 0.156 | 7 | 10 | 14 | 11 | 6 | 7 |
| 0.625 | 4 | 6 | 10 | 12 | 7 | 10 |
| 2.5 | 5 | 6 | 11 | 12 | 8 | 8 |
| 10 | 5 | 8 | 12 | 11 | 10 | 11 |

H Compound F (μM)

| Compound A (μM) | 0.009 | 0.039 | 0.156 | 0.625 | 2.5 | 10 |
|---|---|---|---|---|---|---|
| 0.009 | 5 | 23 | 9 | -7 | -7 | -3 |
| 0.039 | 3 | 10 | -1 | -12 | -13 | -8 |
| 0.156 | 6 | 6 | -2 | -12 | -13 | -12 |
| 0.625 | 3 | 2 | -4 | -11 | -13 | -9 |
| 2.5 | 5 | 2 | -4 | -11 | -12 | -12 |
| 10 | 4 | 4 | -3 | -11 | -10 | -9 |

FIG. 8 (cont'd)

COMBINATION THERAPY COMPRISING A MAT2A INHIBITOR AND A TYPE II PRMT INHIBITOR

RELATED APPLICATIONS

This application claims priority to U.S. Provisional Application No. 63/196,008, filed Jun. 2, 2021; U.S. Provisional Application No. 63/362,438, filed Apr. 4, 2022; and U.S. Provisional Application No. 63/364,360, filed May 9, 2022; the entire contents of which are hereby incorporated by reference in their entireties.

BACKGROUND

Cancer is a leading cause of death throughout the world. A limitation of prevailing therapeutic approaches, e.g., chemotherapy and immunotherapy, is that their cytotoxic effects are not restricted to cancer cells and adverse side effects can occur within normal tissues.

Methionine adenosyltransferase 2A (MAT2A) is an enzyme that utilizes methionine (Met) and adenosine triphosphate (ATP) to generate s-adenosyl methionine (SAM). SAM is a primary methyl donor in cells used to methylate several substrates including DNA, RNA and proteins. One methylase that utilizes SAM as a methyl donor is protein arginine N-methyltransferase 5 (PRMT5). While SAM is required for PRMT5 activity, PRMT5 is competitively inhibited by 5'methylthioadenosine (MTA). Since MTA is part of the methionine salvage pathway, cellular MTA levels stay low in a process initiated by methylthioadenosine phosphorylase (MTAP).

PRMT5 is a type II arginine methyltransferase that regulates essential cellular functions, including the regulation of cell cycle progression, apoptosis and the DNA-damage response, by symmetrically dimethylating proteins involved in transcription and signaling. However, data from genome-wide genetic perturbation screens using shRNA has revealed a selective requirement for PRMT5 activity in MTAP-deleted cancer cell lines (Kruykov et al, 2016; Marjon et al, 2016 and Markarov et al, 2016). The accumulation of MTA caused by MTAP-deletion in these cell lines partially inhibits PRMT5, rendering those cells selectively sensitive to additional PRMT5 inhibition.

Certain PRMT5 inhibitors have been developed, yet they do not demonstrate selectivity for MTAP-deleted cancer cell lines. This lack of selectivity can be explained by the mechanisms of action of the inhibitors, as they are either SAM-uncompetitive or SAM-competitive inhibitors and therefore, MTAP-agnostic (Kruykov et al, 2016; Marjon et al., 2016 and Markarov et al., 2016).

An increase in selectivity for MTAP-deleted/MTA accumulating cells can be achieved by using an inhibitor that binds PRMT5 uncompetitively/cooperatively with MTA (WO2021050915, WO2021086879, WO2021/163344, WO2022/026892, and U.S. Ser. No. 11/077,101). A PRMT5 inhibitor that binds in an MTA-uncompetitive or MTA-cooperative manner will have increased binding to PRMT5 in the presence of MTA over the binding of the same inhibitor in the absence of MTA. Thus, such an inhibitor would bind with apparent greater potency in the presence of high concentrations of MTA and would therefore result in preferential inhibition of PRMT5 in MTA-accumulating cells relative to normal cells.

Despite many recent advances in cancer therapies, there remains a need for more effective and/or enhanced treatment for those individuals suffering the effects of cancer.

SUMMARY

Provided herein is a combination product comprising a methionine adenosyltransferase II alpha (MAT2A) inhibitor and a Type II protein arginine methyltransferase (Type II PRMT) inhibitor. The combination product is useful for the treatment of a variety of cancers, including solid tumors. The combination product is also useful for the treatment of any number of MAT2A-associated and/or PRMT-associated diseases. The combination product is useful for the treatment of a variety of diseases or disorders treatable by inhibiting MAT2A. The combination therapy is also useful for treating MTAP-deficient tumors. The combination product is useful for the treatment of a variety of diseases or disorders treatable by inhibiting Type II PRMT, for example, PRMT5 (also referred herein as Type II PRMT5).

Thus, in one aspect, provided herein is a method of treating cancer in a subject in need thereof, comprising administering to the subject a combination therapy comprising a methionine adenosyltransferase II alpha (MAT2A) inhibitor and Type II protein arginine methyltransferase (Type II PRMT) inhibitor. In an embodiment, the Type II PRMT inhibitor is a PRMT5 inhibitor.

In another aspect, provided herein is a first pharmaceutical composition comprising a therapeutically effective amount of a MAT2A inhibitor and a second pharmaceutical composition comprising a therapeutically effective amount of Type II PRMT inhibitor. In an embodiment, the Type II PRMT inhibitor is a Type II PRMT5 inhibitor.

In another aspect, provided herein are methods of treating cancer in a subject in need thereof, the methods comprising administering to the subject a combination comprising a MAT2A inhibitor and a Type II PRMT inhibitor, thereby treating the cancer in the subject. In an embodiment, the Type II PRMT inhibitor is a Type II PRMT5 inhibitor.

In another aspect, provided herein are methods of treating cancer in a subject in need thereof, the methods comprising administering to the subject a combination comprising a MAT2A inhibitor and a Type II PRMT inhibitor, together with at least a pharmaceutically acceptable carrier, thereby treating the cancer in the subject. In an embodiment, the Type II PRMT inhibitor is a Type II PRMT5 inhibitor.

In an embodiment, provided herein are methods of treating cancer in a subject in need thereof, the methods comprising administering to the subject a therapeutically effective amount of a pharmaceutical composition comprising a MAT2A inhibitor and a therapeutically effective amount of a pharmaceutical composition comprising a Type II PRMT inhibitor, thereby treating the cancer in the subject. In an embodiment, the Type II PRMT inhibitor is a Type II PRMT5 inhibitor.

In another aspect, provided herein is a combination of a MAT2A inhibitor and a Type II PRMT inhibitor. In an embodiment, the Type II PRMT inhibitor is a PRMT5 inhibitor.

In an embodiment, provided herein are methods of treating a disease or disorder treatable by inhibiting MAT2A and/or Type II PRMT in a subject in need thereof, the methods comprising administering to the subject a combination comprising a MAT2A inhibitor and a Type II PRMT inhibitor, thereby treating the disease or disorder in the subject. In an embodiment, the Type II PRMT inhibitor is a PRMT5 inhibitor. In an embodiment, the disease or disorder is cancer.

In an embodiment, provided herein are methods of treating a disease or disorder treatable by inhibiting MAT2A and/or Type II PRMT in a subject in need thereof, the methods comprising administering to the subject a combination comprising a MAT2A inhibitor and a Type II PRMT inhibitor, together with at least a pharmaceutically acceptable carrier, thereby treating the disease or disorder in the subject. In an embodiment, the Type II PRMT inhibitor is a PRMT5 inhibitor. In an embodiment, the disease or disorder is cancer.

In an embodiment, the methionine adenosyltransferase II alpha (MAT2A) inhibitor is a compound of Formula I:

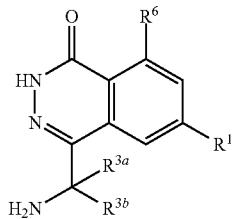

(I)

or a pharmaceutically acceptable salt thereof.

In another embodiment, the Type II PRMT inhibitor is a protein arginine methyltransferase 5 (PRMT5) inhibitor, a protein arginine methyltransferase 7 (PRMT7) inhibitor, or a protein arginine methyltransferase 9 (PRMT9) inhibitor. In yet another embodiment, the Type II PRMT inhibitor is a protein arginine methyltransferase 5 (PRMT5) inhibitor.

In another aspect, provided herein is a combination product comprising Compound A:

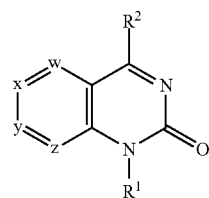

Compound A or a pharmaceutically acceptable salt thereof, and a PRMT5 inhibitor, or a pharmaceutically acceptable salt thereof.

In an embodiment, the Type II PRMT inhibitor is a compound of Formula II:

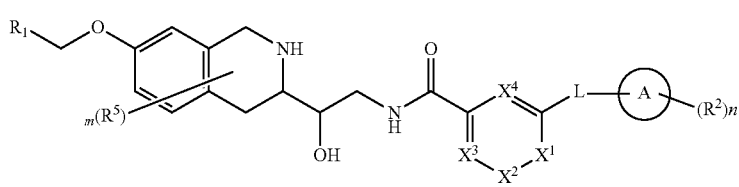

or a pharmaceutically acceptable salt thereof.

In another embodiment, the Type II PRMT inhibitor is a compound of Formula III:

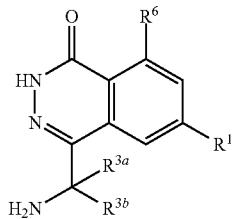

(III)

or a pharmaceutically acceptable salt thereof.

In an embodiment, the Type II PRMT inhibitor is Compound B:

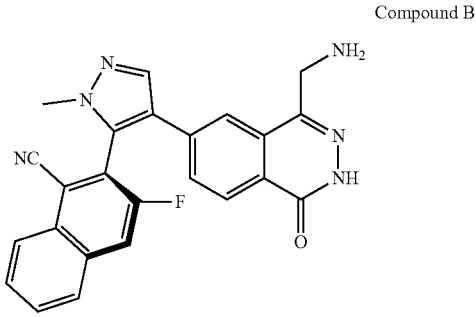

Compound B or a pharmaceutically acceptable salt thereof.

In another embodiment, the Type II PRMT5 inhibitor is a compound of Formula IV:

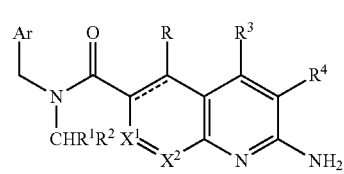

(IV)

or a pharmaceutically acceptable salt thereof; wherein the variables are defined herein.

In another embodiment, the Type II PRMT5 inhibitor is a compound of Formula (V):

(II)

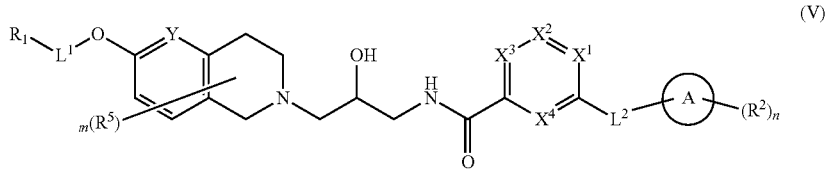

(V)

or a pharmaceutically acceptable salt thereof;

In yet another embodiment, the PRMT type II inhibitor is a compound of Formula VI:

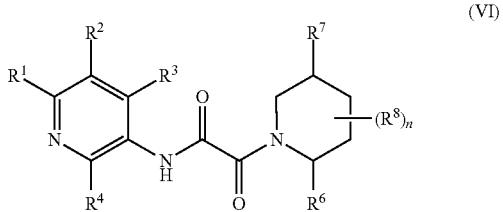

(VI)

or a pharmaceutically acceptable salt thereof;

In still another embodiment, the cancer is characterized by a reduction or absence of MTAP gene expression, absence of the MTAP gene, reduced function of MTAP protein, reduced level of MTAP protein, MTA accumulation, absence of MTAP protein, or combination thereof.

BRIEF DESCRIPTION OF THE DRAWINGS

FIGS. 7A-R show the combination benefit of Compound A and MTA-cooperative PRMT5 inhibitors in the HCT116 MTAP$^{-/-}$ cell line.

DETAILED DESCRIPTION

Figure 1:
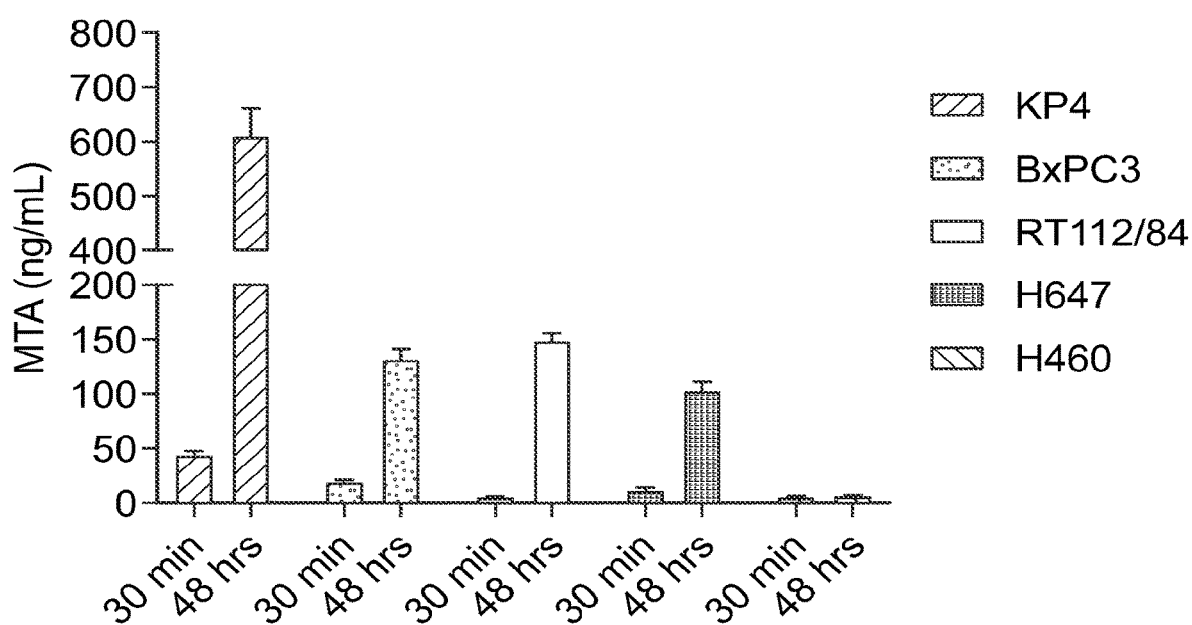
FIG. 1 shows a change in MTA levels in cell lines at baseline and following 48 hours of cell culture.

Provided herein is a combination therapy comprising a methionine adenosyltransferase II alpha (MAT2A) inhibitor, or a pharmaceutically acceptable salt thereof, and a Type II protein arginine methyltransferase (Type II PRMT) inhibitor, or a pharmaceutically acceptable salt thereof. The combination therapy is useful for the treatment of a variety of cancers, including solid tumors. The combination therapy can also be useful for treatment of cancer characterized by a reduction or absence of MTAP gene expression, absence of the MTAP gene, reduced function of MTAP protein, reduced level of MTAP protein, MTA accumulation, absence of MTAP protein, or combination thereof. In another aspect, the combination therapy is useful for the treatment of any number of MAT2A-associated and/or PRMT-associated diseases. In another aspect, the combination therapy is useful for the treatment of a variety of diseases or disorders treatable by inhibiting MAT2A. In another aspect, the combination therapy is also useful for treating MTAP-deficient tumors. In yet another aspect, the combination therapy is useful for the treatment of a variety of diseases or disorders treatable by inhibiting Type II PRMT, for example, PRMT5.

Administering a combination of a methionine adenosyltransferase II alpha (MAT2A) inhibitor and Type II protein arginine methyltransferase (Type II PRMT) inhibitor can provide beneficial effects for treating cancer, e.g., MTAP-null cancer, in a subject. Such an approach—combination or co-administration of the two types of agents—may offer an uninterrupted treatment to an subject in need over a clinically relevant treatment period.

Definitions

Listed below are definitions of various terms used herein. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

As used in the specification and in the claims, the term "comprising" may include the embodiments "consisting of" and "consisting essentially of." The terms "comprise(s)," "include(s)," "having," "has," "may," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated compounds, which allows the presence of only the named compounds, along with any pharmaceutically acceptable carriers, and excludes other compounds.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt. % to about 5 wt. %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include $\pm 1\%$, $\pm 2\%$, $\pm 3\%$, $\pm 4\%$, $\pm 5\%$, $\pm 6\%$, $\pm 7\%$, $\pm 8\%$, $\pm 9\%$, or $\pm 10\%$, of the numerical value(s) being modified. In addition, the phrase "about 'x' to 'y'" includes "about 'x' to about 'y'".

The terms "combination," "therapeutic combination," "pharmaceutical combination," or "combination product" as used herein refer to either a fixed combination in one dosage unit form, or non-fixed combination in separate dosage forms, or a kit of parts for the combined administration where two or more therapeutic agents may be administered independently, at the same time or separately within time intervals.

The term "combination therapy" or "combination product" refers to the administration of two or more therapeutic agents to treat a therapeutic condition or disorder described in the present disclosure. Such administration encompasses co-administration of these therapeutic agents in a substantially simultaneous manner, such as in a single formulation having a fixed ratio of active ingredients or in separate formulations (e.g., capsules and/or intravenous formulations) for each active ingredient. In addition, such administration also encompasses use of each type of therapeutic agent in a sequential or separate manner, either at approximately the same time or at different times. Regardless of whether the active ingredients are administered as a single formulation or in separate formulations, the drugs are administered to the same patient as part of the same course of therapy. In any case, the treatment regimen will provide beneficial effects in treating the conditions or disorders described herein.

As used herein, the term "treating" or "treatment" refers to inhibiting a disease; for example, inhibiting a disease, condition, or disorder in an individual who is experiencing or displaying the pathology or symptomology of the disease, condition, or disorder (i.e., arresting further development of the pathology and/or symptomology) or ameliorating the disease; for example, ameliorating a disease, condition, or disorder in an individual who is experiencing or displaying the pathology or symptomology of the disease, condition, or disorder (i.e., reversing the pathology and/or symptomology) such as decreasing the severity of the disease.

The term "prevent," "preventing," or "prevention" as used herein, comprises the prevention of at least one symptom associated with or caused by the state, disease or disorder being prevented.

As used herein, the term "patient," "individual," or "subject" refers to a human or a non-human mammal. Non-human mammals include, for example, livestock and pets, such as ovine, bovine, porcine, canine, feline and marine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein a parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts described herein include the conventional non-toxic salts of the parent compound formed, for example, from non-toxic inorganic or organic acids. The pharmaceutically acceptable salts discussed herein can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are used. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound with a pharmaceutically acceptable carrier. The pharmaceutical composition facilitates administration of the composition to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful to the patient such that it may perform its intended function. Typically, such constructs are carried or transported from one organ, or portion of the body, to another organ, or portion of the body.

Each carrier must be "acceptable" in the sense of being compatible with the other ingredients of the formulation, including the compound disclosed herein, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of a compound disclosed herein, and are physiologically acceptable to the patient. Supplementary active compounds may also be incorporated into the compositions. The "pharmaceutically acceptable carrier" may further include a pharmaceutically acceptable salt of the compound(s) disclosed herein. Other additional ingredients that may be included in the pharmaceutical compositions are known in the art and described, for example, in Remington's Pharmaceutical Sciences (Genaro, Ed., Mack Publishing Co., 1985, Easton, PA), which is incorporated herein by reference.

The term "single formulation" as used herein refers to a single carrier or vehicle formulated to deliver effective amounts of both therapeutic agents to a patient. The single vehicle is designed to deliver an effective amount of each of the agents, along with any pharmaceutically acceptable carriers or excipients. In some embodiments, the vehicle is a tablet, capsule, pill, or a patch. In other embodiments, the vehicle is a solution or a suspension.

The combination of agents described herein may display a synergistic effect. The term "synergistic effect" or "synergy" as used herein, refers to action of two agents such as, for example, a methionine adenosyltransferase II alpha (MAT2A) inhibitor and Type II protein arginine methyltransferase (Type II PRMT) inhibitor, producing an effect, for example, slowing the symptomatic progression of cancer or symptoms thereof, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

As used herein, the terms "uncompetitive binding," "uncompetitive inhibition," "cooperative binding," and "cooperative inhibition" (e.g., MTA-uncompetitive binding, MTA-uncompetitive inhibition, MTA-cooperative binding, MTA-cooperative inhibition) refer to binding of an inhibitor to a protein (e.g., PRMT5) that is increased in the presence of a co-factor (e.g., MTA) over the binding of the same inhibitor in the absence of the co-factor.

As used herein "methionine adenosyltransferase II alpha inhibitor" or "MAT2A inhibitor" means an agent that modulates the activity of MAT2A or an agent that inhibits the production of S-adenosylmethionine (SAM) by methionine adenosyltransferase 2A (MAT2A).

As used herein, "Type II protein arginine methyltransferase inhibitor" or "Type II PRMT inhibitor" means an agent that modulates the activity of Type II PRMT. "Type II protein arginine methyltransferase inhibitor" or "Type II PRMT inhibitor" also means an agent that inhibits any one or more of the following: protein arginine methyltransferase 5 (PRMT5), protein arginine methyltransferase 7 (PRMT7), and protein arginine methyltransferase 9 (PRMT9). In some embodiments, the Type II PRMT inhibitor is a small molecule compound.

In some embodiments, the Type II PRMT inhibitor selectively inhibits any one or more of the following: protein arginine methyltransferase 5 (PRMT5), protein arginine methyltransferase 7 (PRMT7), and protein arginine methyltransferase 9 (PRMT9). In some embodiments, the Type II PRMT inhibitor is a selective inhibitor of PRMT5, PRMT7, and PRMT9.

In an embodiment, provided herein is a combination therapy comprising an effective amount of a methionine adenosyltransferase II alpha (MAT2A) inhibitor and Type II protein arginine methyltransferase (Type II PRMT) inhibitor. An "effective amount" of a combination of agents (i.e., methionine adenosyltransferase II alpha (MAT2A) inhibitor and PRMT type II inhibitor) is an amount sufficient to provide an observable improvement over the baseline clinically observable signs and symptoms of the disorders treated with the combination.

An "oral dosage form" includes a unit dosage form prescribed or intended for oral administration.

"Alkyl" means a linear saturated monovalent hydrocarbon radical of one to six carbon atoms (i.e. $C_{1-6}$ means one to six carbons) or a branched saturated monovalent hydrocarbon radical of three to six carbon atoms (i.e. $C_{3-6}$ means three to six carbons).

Alkyl can include any number of carbons, such as $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. Example of alkyl groups include methyl, ethyl, propyl, 2-propyl, butyl, pentyl, and the like. It will be recognized by a person skilled in the art that the term "alkyl" may include "alkylene" groups.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkenyl" means a linear monovalent hydrocarbon radical of two to six carbon atoms or a branched monovalent hydrocarbon radical of three to six carbon atoms containing a double bond, e.g., propenyl, butenyl, and the like.

"Alkynyl" means a linear monovalent hydrocarbon radical of two to six carbon atoms or a branched monovalent hydrocarbon radical of three to six carbon atoms containing a triple bond, e.g., ethynyl, propynyl, butynyl, and the like.

"Alkoxy" means a —OR radical where R is alkyl as defined above, e.g., methoxy, ethoxy, propoxy, or 2-propoxy, n-, iso-, or tert-butoxy, and the like.

"Alkoxyalkyl" means a linear monovalent hydrocarbon radical of one to six carbon atoms or a branched monovalent hydrocarbon radical of three to six carbons substituted with one alkoxy group, as defined above, e.g., 2-methoxyethyl, 1-, 2-, or 3-methoxypropyl, 2-ethoxyethyl, and the like.

"Alkoxyalkoxy" means a —OR radical where R is alkoxyalkyl as defined above e.g., methoxyethyloxy, ethyloxypropyloxy, and the like.

"Alkoxyalkylamino" means a —NRR' radical where R is hydrogen or alkyl and R' is alkoxyalkyl, each as defined above e.g., methoxyethylamino, methoxypropylamino, and the like.

"Alkylcarbonyl" means a —C(O)R radical where R is alkyl as defined herein, e.g., methylcarbonyl, ethylcarbonyl, and the like.

"Alkoxycarbonyl" means a —C(O)OR radical where R is alkyl as defined above, e.g., methoxycarbonyl, ethoxycarbonyl, and the like.

"Alkoxycarboxyalkyl" means an alkyl radical as defined above, that is substituted with an alkoxycarboxy group e.g., methylcarboxymethyl, ethylcarboxyethyl, and the like.

"Alkylthio" means a —SR radical where R is alkyl as defined above, e.g., methylthio, ethylthio, and the like.

"Alkylsulfonyl" means a —SO$_2$R radical where R is alkyl as defined above, e.g., methylsulfonyl, ethylsulfonyl, and the like.

"Alkylsulfonylalkyl" means a -(alkylene)-SO$_2$R radical where R is alkyl as defined above, e.g., methylsulfonylethyl, ethylsulfonylmethyl, and the like.

"Amino" means a —NH$_2$.

"Alkylamino" means a —NHR radical where R is alkyl as defined above, e.g., methylamino, ethylamino, propylamino, or 2-propylamino, and the like.

"Aminoalkyl" means a linear monovalent hydrocarbon radical of one to six carbon atoms or a branched monovalent hydrocarbon radical of three to six carbons substituted with —NR'R" where R' and R" are independently hydrogen, alkyl, haloalkyl, hydroxyalkyl, alkoxyalkyl, or alkylcarbonyl, each as defined herein, e.g., aminomethyl, aminoethyl, methylaminomethyl, and the like.

"Aminoalkoxy" means a —OR radical where R is aminoalkyl as defined above e.g., aminoethyloxy, methylaminopropyloxy, dimethylaminoethyloxy, diethylaminopropyloxy, and the like.

"Aminoalkylamino" means a —NRR' radical where R is hydrogen or alkyl and R' is aminoalkyl, each as defined above e.g., aminoethylamino, methylaminopropylamino, dimethylaminoethylamino, diethylaminopropylamino, and the like.

"Aminocarbonyl" means a —CONH$_2$ radical.

"Alkylaminocarbonyl" means a —CONHR radical where R is alkyl as defined above, e.g., methylaminocarbonyl, ethylaminocarbonyl and the like.

"Aminosulfonyl" means a —SO$_2$NH$_2$ radical.

"Aminosulfonylalkyl" means a -(alkylene)SO$_2$NRR' radical where R is hydrogen or alkyl and R' is hydrogen, alkyl, or cycloalkyl, or R and R' together with the nitrogen atom to which they are attached form heterocyclyl, as defined above, e.g., methylaminosulfonylethyl, dimethylsulfonylethyl, and the like.

"Alkylaminosulfonyl" means a —SO$_2$NHR radical where R is alkyl as defined above, e.g., methylaminosulfonyl, ethylaminosulfonyl and the like.

"Aminocarbonylalkyl" means a -(alkylene)-CONRR' radical where R' and R" are independently hydrogen, alkyl, haloalkyl, hydroxyalkyl, or alkoxyalkyl, each as defined herein, e.g., aminocarbonylethyl, methylaminocarbonylethyl, dimethylaminocarbonylethyl, and the like.

"Aminosulfonylalkyl" means a -(alkylene)-SO$_2$NRR' radical where R' and R" are independently hydrogen, alkyl, haloalkyl, hydroxyalkyl, or alkoxyalkyl, each as defined herein, e.g., aminosulfonylethyl, methylaminosulfonylethyl, dimethylaminosulfonylethyl, and the like.

"Aryl" means a monovalent monocyclic or bicyclic aromatic hydrocarbon radical of 6 to 10 ring atoms e.g., phenyl or naphthyl.

"Aralkyl" means a -(alkylene)-R radical where R is aryl as defined above e.g., benzyl, phenethyl, and the like.

"Bridged cycloalkyl" means a saturated monocyclic 5- to 7-membered hydrocarbon radical in which two non-adjacent ring atoms are linked by a (CRR')$_n$ group where n is 1 to 3 and each R is independently H or methyl (also referred to herein as the bridging group). The bridged cycloalkyl is optionally substituted with one or two substituents independently selected from alkyl, halo, alkoxy, hydroxy, or cyano. Examples of bridged cycloalkyl include but are not limited to bicyclo[2.2.1]heptane, bicyclo[2.2.2]octane, etc.

"Bridged cycloalkylalkyl" means -(alkylnene)-R radical where R is bridged cycloalkyl as defined above. Examples include, but are not limited to, bicyclo[2.2.1]heptylmethyl, and the like.

"Bridged heterocyclyl" means a saturated monocyclic ring having 5 to 7 ring carbon ring atoms in which two non-adjacent ring atoms are linked by a (CRR')$_n$ group where n is 1 to 3 and each R is independently H or methyl (also may be referred to herein as "bridging" group) and further wherein one or two ring carbon atoms, including an atom in the bridging group, is replaced by a heteroatom selected from N, O, or S(O)$_n$, where n is an integer from 0 to 2. Bridged heterocyclyl is optionally substituted with one or two substituents independently selected from alkyl, halo, alkoxy, hydroxy, or cyano. Examples include, but are not limited to, 2-azabicyclo[2.2.2]octane, quinuclidine, 7-oxabicyclo[2.2.1]heptane, and the like.

"Bridged heterocyclylalkyl" means -(alkylene)-R radical where R is bridged heterocyclyl (including specific bridged heterocyclyl rings) as defined above.

"Cycloalkyl" means a monocyclic monovalent hydrocarbon radical of three to six carbon atoms (e.g., C$_{3-6}$ cycloalkyl) which may be saturated or contains one double bond. Cycloalkyl can include any number of carbons, such as C$_{3-6}$, C$_{4-6}$, and C$_{5-6}$. Partially unsaturated cycloalkyl groups have one or more double in the ring, but cycloalkyl groups are not aromatic. Saturated monocyclic cycloalkyl rings include, for example, cyclopropyl, cyclobutyl, cyclopentyl, and cyclohexyl. Cycloalkyl may be unsubstituted or substituted with one or two substituents independently selected from alkyl, halo, alkoxy, hydroxy, or cyano. Examples include, but are not limited to, cyclopropyl, cyclobutyl, cyclopentyl, cyclohexyl, 1-cyanocycloprop-1-yl, 1-cyanomethylcycloprop-1-yl, 3-fluorocyclohexyl, and the like. When cycloalkyl contains a double bond, it may be referred to herein as cycloalkenyl.

"Cycloalkylalkyl" means -(alkylene)-R radical where R is cycloalkyl as defined above. Examples include, but are not limited to, cyclopropylmethyl, cyclobutylmethyl, and the like.

"Cycloalkylalkyloxy" means —O—R radical where R is cycloalkylalkyl as defined above. Examples include, but are not limited to, cyclopropylmethyloxy, cyclobutylmethyloxy, and the like.

"Cycloalkyloxyalkyl" means -(alkylene)-OR radical where R is cycloalkyl as defined above. Examples include, but are not limited to, cyclopropyloxymethyl, cyclopropyloxyethyl, cyclobutyloxyethyl, and the like.

"Cycloalkylsulfonylamino" means —NRSO$_2$—R' radical where R is hydrogen or alkyl and R' is cycloalkyl, each as defined above. Examples include, but are not limited to, cyclopropylsulfonylamino, N-cyclopropylsulfonylN(CH$_3$), and the like.

"Cyanoalkyl" means an alkyl radical as defined above, that is substituted with a cyano group, e.g., cyanomethyl, cyanoethyl, and the like.

"Carboxy" means —COOH radical.

"Carboxyalkyl" means an alkyl radical as defined above, that is substituted with a carboxy group e.g., carboxymethyl, carboxyethyl, and the like.

"Deuteroalkyl" means alkyl radical, as defined above, wherein one to six hydrogen atoms in alkyl chain are replaced by deuterium atoms. Examples include, but are not limited to, —CD$_3$, —CH$_2$CHD$_2$, and the like.

"Dialkylamino" means a —NRR' radical where R and R' are alkyl as defined above, e.g., dimethylamino, methylethylamino, and the like.

"Dialkylaminocarbonyl" means a —CONRR' radical where R and R' are alkyl as defined above, e.g., dimethylaminocarbonyl, diethylaminocarbonyl and the like.

"Dialkylaminosulfonyl" means a —SO$_2$NRR' radical where R and R' are alkyl as defined above, e.g., dimethylaminosulfonyl, diethylaminosulfonyl and the like.

"Fused cycloalkyl" means a saturated monovalent hydrocarbon radical of three to six carbon atoms that is fused to phenyl or a five- or six-membered heteroaryl ring, as defined herein, and is optionally substituted with one, two, or three substituents independently selected from alkyl, halo, alkoxy, haloalkyl, haloalkoxy, hydroxy, and cyano. Examples include, but are not limited to, tetrahydronaphthyl, 4,5,6,7-tetrahydro-1H-indolyl, 4,5,6,7-tetrahydrobenzoxazolyl, and the like.

"Fused heterocyclyl" means heterocyclyl as defined herein that is fused to cycloalkyl, phenyl or a five- or six-membered heteroaryl ring, as defined herein. Fused heterocyclyl is optionally substituted with one or two substituents independently selected from alkyl, halo, alkoxy, hydroxy, or cyano. Examples include, but are not limited to, 4,5,6,7-tetrahydro-1H-pyrrolo[2,3-b]pyridinyl, 1,2,3,4-tetrahydroquinolinyl, 3,4-dihydroquinolin-2(1H)-one, and the like.

"Fused heterocyclylalkyl" means -(alkylene)-R radical where R is fused heterocyclyloxy (including specific fused heterocyclyl rings) as defined above.

"Halo" means fluoro, chloro, bromo, or iodo, preferably fluoro or chloro.

"Haloalkyl" means alkyl radical as defined above, which is substituted with one to five halogen atoms, such as fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like. When the alkyl is substituted with only fluoro, it can be referred to as fluoroalkyl. As for alkyl group, haloalkyl groups can have any suitable number of carbon atoms, such as C$_{1-6}$.

"Haloalkoxy" means a —OR radical where R is haloalkyl as defined above e.g., —OCF$_3$, —OCHF$_2$, and the like. When R is haloalkyl where the alkyl is substituted with only fluoro, it is referred to as fluoroalkoxy.

"Haloalkoxyalkyl" means an alkyl radical that is substituted with haloalkoxy, each as defined above, e.g., trifluoromethoxyethyl, and the like.

"Heteroalkylene" means a linear saturated divalent hydrocarbon radical of two to six carbon atoms or a branched saturated divalent hydrocarbon radical of three to six carbon atoms wherein one carbon atom are replaced with —O—, —NR—, —NR'CO—, —CONR'—, SO$_2$NR'—, or —NR'SO$_2$—, where R and R' are independently H or alkyl as defined herein, unless stated otherwise, e.g., —CH$_2$O—, —OCH$_2$—, —(CH$_2$)$_2$O—, —O(CH$_2$)$_2$—, —(CH$_2$)$_2$NH—, —NH(CH$_2$)$_2$—, and the like.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxy-ethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Hydroxyalkoxy" means a —OR radical where R is hydroxyalkyl as defined above e.g., hydroxyethyloxy, hydroxypropyloxy, and the like.

"Hydroxyalkylamino" means a —NRR' radical where R is hydrogen or alkyl and R' is hydroxyalkyl, each as defined above e.g., hydroxyethylamino, hydroxypropylamino, and the like.

"Heteroaryl" means a monovalent monocyclic or bicyclic aromatic radical of 5 to 10 ring atoms, unless otherwise stated, where one or more, (in one embodiment, one, two, or three), ring atoms are heteroatom selected from N, O, or S, the remaining ring atoms being carbon. Non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl, and the like. As defined herein, the terms "heteroaryl" and "aryl" are mutually exclusive. When the heteroaryl ring contains 5- or 6 ring atoms it is also referred to herein as 5- or 6-membered heteroaryl.

"Heteroaralkyl" means a -(alkylene)-R radical where R is heteroaryl (including specific rings) as defined above.

"Heteroaryloxy" means —OR where R is heteroaryl (including specific rings) as defined above.

"Heteroaralkyloxy" means a —O-(alkylene)-R radical where R is heteroaryl (including specific rings) as defined above.

"Heteroarylcarbonyl" means —COR where R is heteroaryl (including specific rings) as defined above.

"Heteroarylamino" means —NRR' where R is hydrogen or alkyl and R' is heteroaryl (including specific rings) as defined above.

"Heterocyclyl" means a saturated or unsaturated monovalent monocyclic group of 4 to 8 ring atoms in which one or two ring atoms are heteroatom selected from N, O, or S(O)$_n$, where n is an integer from 0 to 2, the remaining ring atoms being C. Additionally, one or two ring carbon atoms in the heterocyclyl ring can optionally be replaced by a —CO— group. More specifically the term heterocyclyl includes, but is not limited to, azetidinyl, oxetanyl, pyrrolidino, piperidino, homopiperidino, 2-oxopyrrolidinyl, 2-oxopiperidinyl, morpholino, piperazino, tetrahydro-pyranyl, thiomorpholino, and the like. When the heterocyclyl ring is unsaturated it can contain one or two ring double bonds provided that the ring is not aromatic. When heterocyclyl contains at least one nitrogen atom, it may be referred to herein as heterocycloamino.

"Heterocyclylalkyl" means -(alkylene)-R radical where R is heterocyclyl (including specific heterocyclyl rings) as defined above. For example, oxetanylethyl, piperidinylethyl, and the like.

"Heterocyclyloxy" means —OR radical where R is heterocyclyl (including specific heterocyclyl rings) as defined above.

"Heterocyclylalkyloxy" means —O-(alkylene)-R radical where R is heterocyclyl (including specific heterocyclyl rings) as defined above. For example, oxetanylethyloxy, piperidinylethyloxy, and the like.

"Heterocyclylcarbonyl" means —COR where R is heterocyclyl (including specific rings) as defined above.

"Heterocyclylamino" means —NRR' radical where R is hydrogen or alkyl and R' is heterocyclyl (including specific heterocyclyl rings) as defined above.

"Heterocyclyloxyalkyl" means -(alkylene)-OR radical where R is heterocyclyl (including specific heterocyclyl rings) as defined above. For example, oxetanyloxyethyl, piperidinyloxyethyl, and the like.

"Heterocyclyloxyalkoxy" means —O-(alkylene)-R radical where R is heterocyclyloxy (including specific heterocyclyl rings) as defined above. For example, oxetanyloxyethyloxy, piperidinyloxyethyloxy, and the like.

"Heterocyclyloxyalkylamino" means —NR-(alkylene)-R' radical where R is hydrogen or alkyl and R' is heterocyclyloxy (including specific heterocyclyl rings) as defined above. For example, oxetanyloxyethylamino, piperidinyloxyethylamino, and the like.

"Oxo," as used herein, alone or in combination, refers to =(O).

"Optionally substituted aryl" means aryl that is optionally substituted with one, two, or three substituents independently selected from alkyl, cycloalkyl, carboxy, alkoxycarbonyl, hydroxy, hydroxyalkyl, alkoxy, alkylsulfonyl, amino, alkylamino, dialkylamino, halo, haloalkyl, haloalkoxy, and cyano.

"Optionally substituted heteroaryl" means heteroaryl as defined above that is optionally substituted with one, two, or three substituents independently selected from alkyl, alkylsulfonyl, cycloalkyl, carboxy, alkoxycarbonyl, hydroxy, alkoxy, halo, haloalkyl, haloalkoxy, amino, alkylamino, dialkylamino, and cyano.

"Optionally substituted heterocyclyl" means heterocyclyl as defined above that is optionally substituted with one, two, or three substituents independently selected from alkyl, alkylsulfonyl, cycloalkyl, carboxy, alkoxycarbonyl, hydroxy, hydroxyalkyl, alkoxy, alkoxyalkyl, aminoalkyl, halo, haloalkyl, haloalkoxy, and cyano, unless stated otherwise.

"Spirocycloalkyl" means a saturated bicyclic ring having 6 to 10 ring carbon atoms wherein the rings are connected through only one atom, the connecting atom is also called the spiroatom, most often a quaternary carbon ("spiro carbon"). The spirocycloalkyl ring is optionally substituted with one or two substituents independently selected from alkyl, halo, alkoxy, hydroxy, and cyano. Representative examples include, but are not limited to, spiro[3.3]heptane, spiro[3.4]octane, spiro[3.5]nonane, spiro[4.4]nonane (1:2:1:1), and the like.

"Spirocycloalkylalkyl" means -(alkylene)-R radical where R is spirocycloalkyl (including specific spirocycloalkyl) as defined above.

"Spiroheterocyclyl" means a saturated bicyclic ring having 6 to 10 ring atoms in which one, two, or three ring atoms are heteroatom selected from N, O, or $S(O)_n$, where n is an integer from 0 to 2, the remaining ring atoms being C and the rings are connected through only one atom, the connecting atom is also called the spiroatom, most often a quaternary carbon ("spiro carbon"). Spiroheterocyclyl is optionally substituted with one or two substituents independently selected from alkyl, halo, alkoxy, hydroxy, or cyano. Examples include, but are not limited to, Representative examples include, but are not limited to, 2,6-diazaspiro[3.3]heptane, 2,6-diazaspiro[3.4]octane, 2-azaspiro[3.4]octane, 2-azaspiro[3.5]-nonane, 2,7-diazaspiro[4.4]nonane, and the like.

"Spiroheterocyclylalkyl" means -(alkylene)-R radical where R is spiroheterocyclyl (including specific spiroheterocyclyl) as defined above.

"Sulfonylamino" means a —NRSO$_2$R' radical where R is hydrogen or alkyl, and R' is alkyl, optionally substituted aryl, optionally substituted heteroaryl, or optionally substituted heterocyclyl, each group as defined herein.

"Substituted cycloalkyl" means a saturated monocyclic monovalent hydrocarbon radical of three to six carbon atoms that is substituted with one, two or three substituents where two of the three substitutents are independently selected from alkyl, halo, alkoxy, hydroxy, haloalkyl, or haloalkoxy and the third substituent is alkyl, halo, hydroxyalkyl, haloalkyl, haloalkoxy, or cyano. Examples include, but are not limited to, 3-hydroxy-3-trifluorocyclobutyl, 2,2-dimethyl-3-hydroxycyclobutyl, and the like.

"Substituted cycloalkylalkyl" means -(alkylene)-substituted cycloalkyl, each term is defined herein. Examples include, but are not limited to, 1-hydroxymethylcycloprop-1-ylmethyl, and the like.

"Ureido" means a —NHCONRR' radical where R and R' are independently hydrogen or alkyl, as defined above, e.g., —NHCONHmethyl, —NHCON(CH$_3$)$_2$, and the like.

"Thioureidoalkyl" means a -(alkylene)-NHSO$_2$NRR' radical where R and R' are independently hydrogen or alkyl, as defined above, e.g., -ethylene-NHSO$_2$NHmethyl, -propylene-NHSO$_2$NH$_2$, and the like.

Combination Product

Provided herein is a combination product comprising a methionine adenosyltransferase II alpha (MAT2A) inhibitor, or a pharmaceutically acceptable salt thereof, and Type II protein arginine methyltransferase (Type II PRMT) inhibitor, or a pharmaceutically acceptable salt thereof. The combination product is useful for the treatment of a variety of cancers, including MTAP-null cancers. In another aspect, the combination product is useful for the treatment of any number of MAT2A-associated and/or PRMT-associated diseases. In another aspect, the combination product is useful for the treatment of a disease or disorder treatable by inhibiting MAT2A. In another aspect, the combination product is useful for the treating MTAP-deficient tumors. In another aspect, the combination product is useful for the treatment of a variety of diseases or disorders treatable by inhibiting Type II PRMT, for example, PRMT5. In another aspect, the combination product is useful for the treating MTA-accumulating disease, for example, cancer.

In an embodiment, provided herein is a combination of a MAT2A inhibitor and a PRMT5 inhibitor.

In an embodiment, the methionine adenosyltransferase II alpha (MAT2A) inhibitor is a compound of Formula I:

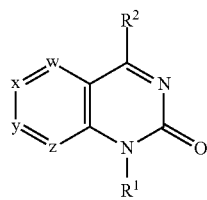

(I)

or a pharmaceutically acceptable salt thereof;
wherein
w is $CR^3$ or N; x is $CR^4$ or N; y is $CR^5$ or N; and z is $CR^6$ or N, wherein:
$R^3$ is hydrogen, alkyl, alkenyl, alkynyl, alkoxy, alkylsulfonyl, halo, haloalkyl, haloalkoxy, cycloalkyl, cycloalkylalkyloxy, cyano, amino, alkylamino, dialkylamino, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroaralkyloxy, heteroarylamino, heterocyclyl, heterocyclyloxy, heterocyclylamino, heterocyclylalkyloxy, heterocyclyloxyalkoxy, or heterocyclyloxyalkylamino, wherein heterocyclyl or heteroaryl, by itself or as part of another group, is unsubstituted or substituted with $R^a$, $R^b$, or $R^c$ independently selected from alkyl, cycloalkyl, haloalkyl, haloalkoxy, alkoxy, hydroxy, halo, cyano, alkoxycarbonyl, hydroxyalkyl, alkoxyalkyl, or aminoalkyl;
$R^5$ is hydrogen, alkyl, alkenyl, alkynyl, alkoxy, alkylsulfonyl, halo, haloalkyl, haloalkoxy, cycloalkyl, cyano, amino, alkylamino, dialkylamino, alkoxycarbonyl, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroarylamino, heterocyclyl, heterocyclyloxy, heterocyclylamino, heterocyclyloxyalkoxy, or heterocyclyloxyalkylamino, wherein heterocyclyl or heteroaryl, by itself or as part of another group, is unsubstituted or substituted with $R^a$, $R^b$, or $R^c$ independently selected from alkyl, cycloalkyl, haloalkyl, haloalkoxy, alkoxy, hydroxy, halo, cyano, hydroxyalkyl, alkoxyalkyl, or aminoalkyl;
$R^4$ and $R^6$ are independently hydrogen, alkyl, alkenyl, alkynyl, alkoxy, alkylthio, alkylsulfonyl, halo, haloalkyl, haloalkoxy, cycloalkyl, cyano, amino, alkylamino, dialkylamino, aminocarbonyl, alkylaminocarbonyl, or dialkylaminocarbonyl; provided that: (i) no more than two of w, x, y, and z can be N and (ii) at least one of $R^3$, $R^4$, $R^5$, and $R^6$ is other than hydrogen;
$R^1$ is $R^7$ wherein $R^7$ is cycloalkyl, bridged cycloalkyl, fused cycloalkyl, spirocycloalkyl, aryl, heteroaryl, heterocyclyl, bridged heterocyclyl, fused heterocyclyl, or spiroheterocyclyl, wherein aryl, heteroaryl, or heterocyclyl is unsubstituted or substituted with $R^d$, $R^e$, or $R^f$;
$R^2$ is alkyl, haloalkyl, hydroxyalkyl, alkoxyalkyl, aminoalkyl, aminocarbonylalkyl, aminosulfonylalkyl, —O—$R^8$, —$NR^9R^{10}$, or —$X^b$—$R^{11}$ wherein:
$R^8$ is alkyl, haloalkyl, hydroxyalkyl, alkoxyalkyl, aminoalkyl, cycloalkyl, cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heterocyclyl, heterocyclylalkyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^g$, $R^h$, or $R^i$;
$R^9$ is hydrogen, alkyl, deuteroalkyl, or cycloalkyl; and
$R^{10}$ is hydrogen, alkyl, deuteroalkyl, haloalkyl, hydroxyalkyl, alkoxyalkyl, haloalkoxyalkyl, aminoalkyl, aminosulfonylalkyl, thioureidoalkyl, alkylsulfonyl, alkylsulfonylalkyl, cyanoalkyl, alkylcarbonyl, alkoxycarbonyl, alkylaminocarbonyl, dialkylaminocarbonyl, aminocarbonylalkyl, cycloalkyl, cycloalkylalkyl, substituted cycloalkyl, substituted cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heteroarylcarbonyl, heterocyclyl, heterocyclylalkyl, heterocyclylcarbonyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^j$, $R^k$, or $R^l$;
$X^b$ is a bond or alkylene; and
$R^{11}$ is cycloalkyl, bridged cycloalkyl, fused cycloalkyl, spirocycloalkyl, heteroaryl, heterocyclyl, bridged heterocyclyl, fused heterocyclyl, or spiroheterocyclyl, wherein heteroaryl or heterocyclyl is unsubstituted or substituted with $R^m$, $R^n$, or $R^o$; and
$R^d$, $R^e$, $R^g$, $R^h$, $R^j$, $R^k$, $R^m$, and $R^n$ are independently selected from alkyl, haloalkyl, haloalkoxy, alkoxy, hydroxy, alkylsulfonyl, halo, cyano, carboxy, alkoxycarbonyl, hydroxyalkyl, alkoxyalkyl, aminoalkyl, aminosulfonyl, alkylaminosulfonyl, dialkylaminosulfonyl, sulfonylamino, aminocarbonyl, alkylaminocarbonyl, dialkylaminocarbonyl, heterocyclylcarbonyl, and ureido; and
$R^f$, $R^i$, $R^l$, and $R^o$ are independently selected from alkyl, cycloalkyl, haloalkyl, haloalkoxy, alkoxy, hydroxy, halo, amino, alkylamino, cycloalkylsulfonylamino, cyano, cyanoalkyl, alkoxycarbonylalkyl, carboxyalkyl, aminocarbonylalkyl, or —$X^c$—$R^{12}$ where $X^c$ is bond, alkylene, or heteroalkylene and $R^{12}$ is optionally substituted aryl, optionally substituted heteroaryl, and optionally substituted heterocyclyl; provided that when $R^1$ is heterocyclyl then $R^f$ is not hydroxy;
provided that:
(1) when

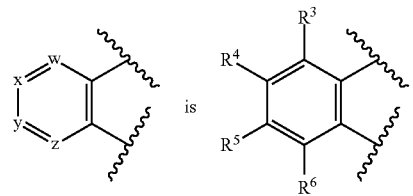

where: (a) when $R^2$ is piperazin-1-yl, 2-methylpiperazin-1-yl, or 1H-benzo[d][1,2,3]triazol-1-yl, $R^3$ and $R^6$ are hydrogen, $R^4$ is chloro and $R^5$ is bromo or 5-methylindazol-4-yl, then $R^1$ is not 2-isopropylphenyl; (b) when $R^2$ and $R^6$ are methyl and $R^4$, and $R^5$ are hydrogen; or $R^2$ and $R^3$ are methyl and $R^4$, $R^5$, and $R^6$ are hydrogen, then $R^1$ is not 2,5-, 2,6- or 2,8-dimethylquinolin-4-yl or 2-methyl-5-methoxy-, 2-methyl-6-methoxy- or 2-methyl-8-methoxyquinolin-4-yl;

(c) when R² is amino or acetylamino, R⁴ is dimethylamino, and R³, R⁵, and R⁶ are hydrogen, then R¹ is not 4-hydroxy-5-hydroxymethyl-tetrahydrofuran-2-yl; (d) when R⁵ is fluoro, R³, R⁴ and R⁶ are hydrogen, and R² is 4-aminocarbonylmethyl-2-methylphenylamino, then R¹ is not 4-fluoro-2-(2-thiazol-2-ylmethoxy)phenyl, 4-fluoro-2-(2-pyridin-2-ylmethoxy)phenyl, or 4-chloro-2-methoxyphenyl; (e) when R⁶ is fluoro, R³, R⁴ and R⁵ are hydrogen, and R² is 4-aminocarbonylmethyl-2-methylphenylamino, then R¹ is not 4-fluoro-2-methoxyphenyl; (f) when R¹ is 4-chloro-2-ethoxyphenyl, R⁵ is fluoro, and R³, R⁴ and R⁶ are hydrogen, then R² is not 3-(2-oxoimidazolidin-1-yl)-2-methylphenylamino;

(2) when

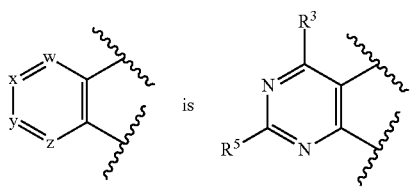

then when R¹ is 4-hydroxy-5-hydroxymethylfuran-1-yl, R⁵ is amino, and R³ is methoxy; then R² is not amino; and (3) when

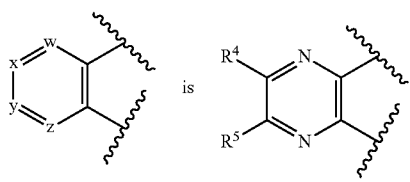

then when R¹ is 4-hydroxy-5-hydroxymethylfuran-1-yl, one of R⁴ and R⁵ is hydrogen, and the other of R⁴ and R⁵ is methyl or both of R⁴ and R⁵ are methyl, then R² is not amino.

In some embodiments, the compound of Formula (I) is: where
w is CR³ or N; x is CR⁴ or N; y is CR⁵ or N; and z is CR⁶ or N, provided that no more than two of w, x, y, and z can be N, wherein:
R³ is hydrogen, alkyl, alkenyl, alkynyl, alkoxy, alkylsulfonyl, halo, haloalkyl, haloalkoxy, cycloalkyl, cycloalkylalkyloxy, cyano, amino, alkylamino, dialkylamino, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroaralkyloxy, heteroarylamino, heterocyclyl, heterocyclyloxy, heterocyclylamino, heterocyclylalkyloxy, heterocyclyloxyalkoxy, or heterocyclyloxyalkylamino, wherein heterocyclyl or heteroaryl, by itself or as part of another group, is unsubstituted or substituted with Rᵃ, Rᵇ, and/or Rᶜ independently selected from alkyl, cycloalkyl, haloalkyl, haloalkoxy, alkoxy, hydroxy, halo, cyano, alkoxycarbonyl, hydroxyalkyl, alkoxyalkyl, or aminoalkyl;
R⁵ is alkyl, alkenyl, alkynyl, alkoxy, alkylsulfonyl, halo, haloalkyl, haloalkoxy, cycloalkyl, cyano, amino, alkylamino, dialkylamino, alkoxyalkyl, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroarylamino, heterocyclyl, heterocyclyloxy, heterocyclylamino, heterocyclyloxyalkyl, or heterocyclyloxyalkylamino, wherein heterocyclyl or heteroaryl, by itself or as part of another group, is unsubstituted or substituted with Rᵃ, Rᵇ, and/or Rᶜ independently selected from alkyl, cycloalkyl, haloalkyl, haloalkoxy, alkoxy, hydroxy, halo, cyano, hydroxyalkyl, alkoxyalkyl, or aminoalkyl;
R⁴ and R⁶ are independently hydrogen, alkyl, alkenyl, alkynyl, alkoxy, alkylthio, alkylsulfonyl, halo, haloalkyl, haloalkoxy, cycloalkyl, cyano, amino, alkylamino, dialkylamino, aminocarbonyl, alkylaminocarbonyl, or dialkylaminocarbonyl;
R¹ is R⁷ wherein R⁷ is cycloalkyl, bridged cycloalkyl, fused cycloalkyl, spirocycloalkyl, aryl, heteroaryl, pyrrolidinyl, piperidinyl, piperazinyl, oxetanyl, morpholinyl, bridged heterocyclyl, fused heterocyclyl, or spiroheterocyclyl, wherein aryl, heteroaryl, or heterocyclyl is unsubstituted or substituted with Rᵈ, Rᵉ, and/or Rᶠ;
R² is alkyl, haloalkyl, hydroxyalkyl, alkoxyalkyl, aminoalkyl, aminocarbonylalkyl, aminosulfonylalkyl, —O—R⁸, —NR⁹R¹⁰, or —Xᵇ—R¹¹ wherein:
R⁸ is alkyl, haloalkyl, hydroxyalkyl, alkoxyalkyl, aminoalkyl, cycloalkyl, cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heterocyclyl, heterocyclylalkyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with Rᵍ, Rʰ, and/or Rⁱ;
R⁹ is hydrogen, alkyl, deuteroalkyl, or cycloalkyl; and
R¹⁰ is hydrogen, alkyl, deuteroalkyl, haloalkyl, hydroxyalkyl, alkoxyalkyl, haloalkoxyalkyl, aminoalkyl, aminosulfonylalkyl, thioureidoalkyl, alkylsulfonyl, alkylsulfonylalkyl, cyanoalkyl, alkylcarbonyl, alkoxycarbonyl, alkylaminocarbonyl, dialkylaminocarbonyl, aminocarbonylalkyl, cycloalkyl, cycloalkylalkyl, substituted cycloalkyl, substituted cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heteroarylcarbonyl, heterocyclyl, heterocyclylalkyl, heterocyclylcarbonyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with Rʲ, Rᵏ, and/or Rˡ;
Xᵇ is a bond or alkylene; and
R¹¹ is cycloalkyl, bridged cycloalkyl, fused cycloalkyl, spirocycloalkyl, monocyclic heteroaryl, oxetanyl, azetidinyl, 2-oxoazetidinyl, pyrrolidinyl, 2-oxopyrrolidinyl, piperidinyl, or morpholinyl, bridged heterocyclyl, fused heterocyclyl, or spiroheterocyclyl, wherein heteroaryl or heterocyclyl is unsubstituted or substituted with Rᵐ, Rⁿ, and/or Rᵒ; and
Rᵈ, Rᵉ, Rᵍ, Rʰ, Rʲ, Rᵏ, Rᵐ, and Rⁿ are independently selected from alkyl, haloalkyl, haloalkoxy, alkoxy, hydroxy, alkylsulfonyl, halo, cyano, carboxy, alkoxycarbonyl, hydroxyalkyl, alkoxyalkyl, aminoalkyl, aminosulfonyl, alkylaminosulfonyl, dialkylaminosulfonyl, sulfonylamino, aminocarbonyl, alkylaminocarbonyl, dialkylaminocarbonyl, heterocyclylcarbonyl, and ureido; and $R^f$, $R^i$, $R^l$, and $R^o$ are independently selected from alkyl, cycloalkyl, haloalkyl, haloalkoxy, alkoxy, hydroxy, halo, amino, alkylamino, cycloalkylsulfonylamino, cyano, cyanoalkyl, alkoxycarbonylalkyl, carboxyalkyl, or $-X^c-R^{12}$ where $X^c$ is bond, alkylene, or heteroalkylene and $R^{12}$ is optionally substituted aryl, or optionally substituted heteroaryl; provided that when $R^1$ is pyrrolidinyl, piperidinyl, piperazinyl, oxetanyl, or morpholinyl then $R^f$ is not hydroxy; or a pharmaceutically acceptable salt thereof.

In another embodiment, $R^4$ and $R^6$ are independently hydrogen, alkyl, alkenyl, alkynyl, alkoxy, alkylsulfonyl, halo, haloalkyl, haloalkoxy, cycloalkyl, cyano, amino, alkylamino, dialkylamino, aminocarbonyl, alkylaminocarbonyl, or dialkylaminocarbonyl; provided that: (i) no more than two of w, x, y, and z can be N and (ii) at least one of $R^3$, $R^4$, $R^5$, and $R^6$ is other than hydrogen;

$R^{10}$ is hydrogen, alkyl, deuteroalkyl, haloalkyl, hydroxyalkyl, alkoxyalkyl, aminoalkyl, alkylsulfonyl, alkylsulfonylalkyl, cyanoalkyl, alkylcarbonyl, alkoxycarbonyl, alkylaminocarbonyl, dialkylaminocarbonyl, aminocarbonylalkyl, cycloalkyl, cycloalkylalkyl, substituted cycloalkyl, substituted cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heteroarylcarbonyl, heterocyclyl, heterocyclylalkyl, heterocyclylcarbonyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^j$, $R^k$, or $R^l$; and $R^f$, $R^i$, $R^l$, and $R^o$ are independently selected from alkyl, cycloalkyl, haloalkyl, haloalkoxy, alkoxy, hydroxy, halo, amino, cycloalkylsulfonylamino, cyano, cyanoalkyl, alkoxycarbonylalkyl, carboxyalkyl, aminocarbonylalkyl, or $-X^c-R^{12}$ where $X^c$ is bond, alkylene, or heteroalkylene and $R^{12}$ is optionally substituted aryl, optionally substituted heteroaryl, and optionally substituted heterocyclyl; provided that when $R^1$ is heterocyclyl then $R^f$ is not hydroxy.

In yet another embodiment, $R^3$ and $R^5$ are independently hydrogen, alkyl, alkenyl, alkynyl, alkoxy, alkylsulfonyl, halo, haloalkyl, haloalkoxy, cycloalkyl, cyano, amino, alkylamino, dialkylamino, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroarylamino, heterocyclyl, heterocyclyloxy, heterocyclylamino, heterocyclyloxyalkoxy, or heterocyclyloxyalkylamino, wherein heterocyclyl or heteroaryl, by itself or as part of another group, is unsubstituted or substituted with $R^a$, $R^b$, or $R^c$ independently selected from alkyl, cycloalkyl, haloalkyl, haloalkoxy, alkoxy, hydroxy, halo, cyano, hydroxyalkyl, alkoxyalkyl, or aminoalkyl;

$R^1$ is $R^7$ wherein $R^7$ is cycloalkyl, bridged cycloalkyl, fused cycloalkyl, spirocycloalkyl, phenyl, heteroaryl, heterocyclyl, bridged heterocyclyl, fused heterocyclyl, or spiroheterocyclyl, wherein phenyl, heteroaryl, or heterocyclyl is unsubstituted or substituted with $R^d$, $R^e$, or $R^f$;

$R^9$ is hydrogen, alkyl or cycloalkyl;

$R^{10}$ is hydrogen, alkyl, haloalkyl, hydroxyalkyl, alkoxyalkyl, aminoalkyl, alkylcarbonyl, alkoxycarbonyl, alkylaminocarbonyl, dialkylaminocarbonyl, aminocarbonylalkyl, cycloalkyl, cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heteroarylcarbonyl, heterocyclyl, heterocyclylalkyl, heterocyclylcarbonyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^j$, $R^k$, or $R^l$;

$R^d$, $R^e$, $R^g$, $R^h$, $R^j$, $R^k$, $R^m$, and $R^n$ are independently selected from alkyl, haloalkyl, haloalkoxy, alkoxy, alkylsulfonyl, halo, cyano, carboxy, alkoxycarbonyl, hydroxyalkyl, alkoxyalkyl, aminoalkyl, aminosulfonyl, alkylaminosulfonyl, dialkylaminosulfonyl, sulfonylamino, aminocarbonyl, alkylaminocarbonyl, dialkylaminocarbonyl, heterocyclylcarbonyl, and ureido; and $R^f$, $R^i$, $R^l$, and $R^o$ are independently selected from alkyl, haloalkyl, haloalkoxy, alkoxy, hydroxy, halo, cyano, or $-X^c-R^{12}$ where $X^c$ is bond, alkylene or heteroalkylene and $R^{12}$ is optionally substituted aryl, optionally substituted heteroaryl, or optionally substituted heterocyclyl.

In still another embodiment, the methionine adenosyltransferase II alpha (MAT2A) inhibitor is a compound of Formula (IIIa), (IIIb), (IIIc), (IIId), (IIIe), or (IIIg):

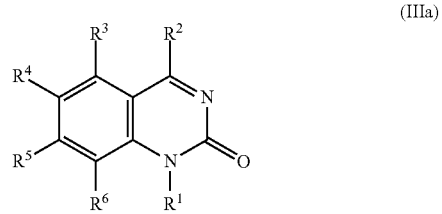

(IIIa)

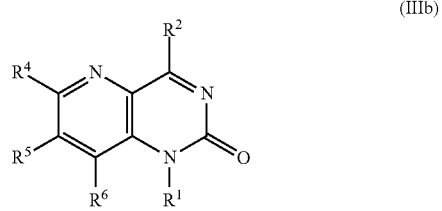

(IIIb)

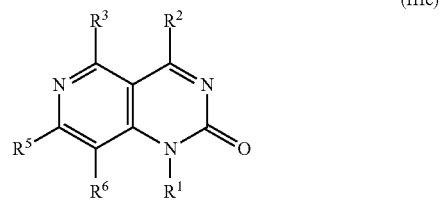

(IIIc)

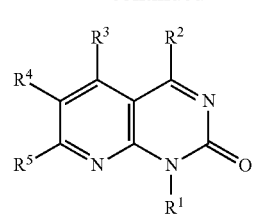

(IIId)

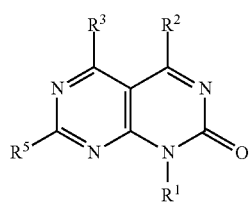

(IIIe)

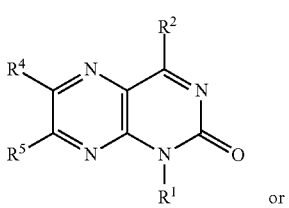

(IIIf)

or

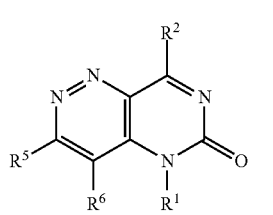

(IIIg)

or a pharmaceutically acceptable salt thereof.

In an embodiment, the methionine adenosyltransferase II alpha (MAT2A) inhibitor is a compound of Formula IIIa, or a pharmaceutically acceptable salt thereof. In another embodiment, the methionine adenosyltransferase II alpha (MAT2A) inhibitor is a compound of Formula IIIb, or a pharmaceutically acceptable salt thereof. In yet another embodiment, the methionine adenosyltransferase II alpha (MAT2A) inhibitor is a compound of Formula IIIc, or a pharmaceutically acceptable salt thereof. In still another embodiment, the methionine adenosyltransferase II alpha (MAT2A) inhibitor is a compound of Formula Id, or a pharmaceutically acceptable salt thereof. In an embodiment, the methionine adenosyltransferase II alpha (MAT2A) inhibitor is a compound of Formula IIIe, or a pharmaceutically acceptable salt thereof. In another embodiment, the methionine adenosyltransferase II alpha (MAT2A) inhibitor is a compound of Formula IIIf, or a pharmaceutically acceptable salt thereof. In yet another embodiment, the methionine adenosyltransferase II alpha (MAT2A) inhibitor is a compound of Formula IIIg, or a pharmaceutically acceptable salt thereof.

In an embodiment, the methionine adenosyltransferase II alpha (MAT2A) inhibitor is a compound of Formula Id, or a pharmaceutically acceptable salt thereof, wherein
$R^3$ is hydrogen, alkyl, alkenyl, alkynyl, alkoxy, alkylsulfonyl, halo, haloalkyl, haloalkoxy, cycloalkyl, cycloalkylalkyloxy, cyano, amino, alkylamino, dialkylamino, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroaralkyloxy, heteroarylamino, heterocyclyl, heterocyclyloxy, heterocyclylamino, heterocyclylalkyloxy, heterocycyloxyalkoxy, or heterocyclyloxyalkylamino, wherein heterocyclyl or heteroaryl, by itself or as part of another group, is unsubstituted or substituted with $R^a$, $R^b$, or $R^c$ independently selected from alkyl, cycloalkyl, haloalkyl, haloalkoxy, alkoxy, hydroxy, halo, cyano, alkoxycarbonyl, hydroxyalkyl, alkoxyalkyl, or aminoalkyl;

$R^5$ is hydrogen, alkyl, alkenyl, alkynyl, alkoxy, alkylsulfonyl, halo, haloalkyl, haloalkoxy, cycloalkyl, cyano, amino, alkylamino, dialkylamino, alkoxycarbonyl, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroarylamino, heterocyclyl, heterocyclyloxy, heterocyclylamino, heterocyclyloxyalkoxy, or heterocyclyloxyalkylamino, wherein heterocyclyl or heteroaryl, by itself or as part of another group, is unsubstituted or substituted with $R^a$, $R^b$, or $R^c$ independently selected from alkyl, cycloalkyl, haloalkyl, haloalkoxy, alkoxy, hydroxy, halo, cyano, hydroxyalkyl, alkoxyalkyl, or aminoalkyl;

$R^4$ is hydrogen, alkyl, alkenyl, alkynyl, alkoxy, alkylthio, alkylsulfonyl, halo, haloalkyl, haloalkoxy, cycloalkyl, cyano, amino, alkylamino, dialkylamino, aminocarbonyl, alkylaminocarbonyl, or dialkylaminocarbonyl; provided that at least one of $R^3$, $R^4$, and $R^5$ is other than hydrogen;

$R^1$ is $R^7$ wherein $R^7$ is cycloalkyl, bridged cycloalkyl, fused cycloalkyl, spirocycloalkyl, aryl, heteroaryl, heterocyclyl, bridged heterocyclyl, fused heterocyclyl, or spiroheterocyclyl, wherein aryl, heteroaryl, or heterocyclyl is unsubstituted or substituted with $R^d$, R, or f $R^2$ is alkyl, haloalkyl, hydroxyalkyl, alkoxyalkyl, aminoalkyl, aminocarbonylalkyl, aminosulfonylalkyl, —O—$R^8$, or —N$R^9R^{10}$ wherein:

$R^8$ is alkyl, haloalkyl, hydroxyalkyl, alkoxyalkyl, aminoalkyl, cycloalkyl, cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heterocyclyl, heterocyclylalkyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^g$, $R^h$, or $R^i$;

$R^9$ is hydrogen, alkyl, deuteroalkyl, or cycloalkyl; and $R^{10}$ is hydrogen, alkyl, deuteroalkyl, haloalkyl, hydroxyalkyl, alkoxyalkyl, haloalkoxyalkyl, aminoalkyl, aminosulfonylalkyl, thioureidoalkyl, alkylsulfonyl, alkylsulfonylalkyl, cyanoalkyl, alkylcarbonyl, alkoxycarbonyl, alkylaminocarbonyl, dialkylaminocarbonyl, aminocarbonylalkyl, cycloalkyl, cycloalkylalkyl, substituted cycloalkyl, substituted cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heteroarylcarbonyl, heterocyclyl, heterocyclylalkyl, heterocyclylcarbonyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^j$, $R^k$, or $R^l$; and $R^d$, $R^e$, $R^g$, $R^h$, $R^j$, $R^k$, $R^m$ and $R^n$ are independently selected from alkyl, haloalkyl, haloalkoxy, alkoxy, hydroxy, alkylsulfonyl, halo, cyano, carboxy, alkoxycarbonyl, hydroxyalkyl, alkoxyalkyl, aminoalkyl, aminosulfonyl, alkylaminosulfonyl, dialkylaminosulfonyl, sulfonylamino, aminocarbonyl, alkylaminocarbonyl, dialkylaminocarbonyl, heterocyclylcarbonyl, and ureido; and $R^f$, $R^i$, $R^l$, and $R^o$ are independently selected from alkyl, cycloalkyl, haloalkyl, haloalkoxy, alkoxy, hydroxy, halo, amino, alkylamino, cycloalkylsulfonylamino, cyano, cyanoalkyl, alkoxycarbonylalkyl, carboxyalkyl, aminocarbonylalkyl, or —$X^c$—$R^{12}$ where $X^c$ is bond, alkylene, or heteroalkylene and $R^{12}$ is optionally substituted aryl, optionally substituted heteroaryl, and optionally substituted heterocyclyl; provided that when $R^1$ is heterocyclyl then $R^f$ is not hydroxy.

In another embodiment, $R^3$ is hydrogen, alkyl, alkenyl, alkynyl, alkoxy, alkylsulfonyl, halo, haloalkyl, haloalkoxy, cycloalkyl, cycloalkylalkyloxy, cyano, amino, alkylamino, dialkylamino, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroaralkyloxy, heteroarylamino, heterocyclyl, heterocyclyloxy, heterocyclylamino, heterocyclylalkyloxy, heterocyclyloxyalkoxy, or heterocyclyloxyalkylamino, wherein heterocyclyl or heteroaryl, by itself or as part of another group, is unsubstituted or substituted with $R^a$, $R^b$, or $R^c$ independently selected from alkyl, cycloalkyl, haloalkyl, haloalkoxy, alkoxy, hydroxy, halo, cyano, alkoxycarbonyl, hydroxyalkyl, alkoxyalkyl, or aminoalkyl;

$R^5$ is alkyl, alkenyl, alkynyl, alkoxy, alkylsulfonyl, halo, haloalkyl, haloalkoxy, cycloalkyl, cyano, amino, alkylamino, dialkylamino, alkoxycarbonyl, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroarylamino, heterocyclyl, heterocyclyloxy, heterocyclylamino, heterocyclyloxyalkoxy, or heterocyclyloxyalkylamino, wherein heterocyclyl or heteroaryl, by itself or as part of another group, is unsubstituted or substituted with $R^a$, $R^b$, and/or $R^c$ independently selected from alkyl, cycloalkyl, haloalkyl, haloalkoxy, alkoxy, hydroxy, halo, cyano, hydroxyalkyl, alkoxyalkyl, or aminoalkyl;

$R^4$ is hydrogen, alkyl, alkenyl, alkynyl, alkoxy, alkylthio, alkylsulfonyl, halo, haloalkyl, haloalkoxy, cycloalkyl, cyano, amino, alkylamino, dialkylamino, aminocarbonyl, alkylaminocarbonyl, or dialkylaminocarbonyl;

$R^1$ is $R^7$ wherein $R^7$ is cycloalkyl, bridged cycloalkyl, fused cycloalkyl, spirocycloalkyl, aryl, heteroaryl, pyrrolidinyl, piperidinyl, piperazinyl, oxetanyl, morpholinyl, bridged heterocyclyl, fused heterocyclyl, or spiroheterocyclyl, wherein aryl, heteroaryl, or heterocyclyl is unsubstituted or substituted with $R^d$, $R^e$, and/or $R^f$;

$R^2$ is alkyl, haloalkyl, hydroxyalkyl, alkoxyalkyl, aminoalkyl, aminocarbonylalkyl, aminosulfonylalkyl, —O—$R^8$, —$NR^9R^{10}$, wherein:

$R^8$ is alkyl, haloalkyl, hydroxyalkyl, alkoxyalkyl, aminoalkyl, cycloalkyl, cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heterocyclyl, heterocyclylalkyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^g$, $R^h$, or $R^i$;

$R^9$ is hydrogen, alkyl, deuteroalkyl, or cycloalkyl;

$R^{10}$ is hydrogen, alkyl, deuteroalkyl, haloalkyl, hydroxyalkyl, alkoxyalkyl, haloalkoxyalkyl, aminoalkyl, aminosulfonylalkyl, thioureidoalkyl, alkylsulfonyl, alkylsulfonylalkyl, cyanoalkyl, alkylcarbonyl, alkoxycarbonyl, alkylaminocarbonyl, dialkylaminocarbonyl, aminocarbonylalkyl, cycloalkyl, cycloalkylalkyl, substituted cycloalkyl, substituted cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heteroarylcarbonyl, heterocyclyl, heterocyclylalkyl, heterocyclylcarbonyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^i$, $R^k$, or $R^l$;

$R^d$, $R^e$, $R^g$, $R^h$, $R^j$, $R^k$, $R^m$, and $R^n$ are independently selected from alkyl, haloalkyl, haloalkoxy, alkoxy, hydroxy, alkylsulfonyl, halo, cyano, carboxy, alkoxycarbonyl, hydroxyalkyl, alkoxyalkyl, aminoalkyl, aminosulfonyl, alkylaminosulfonyl, dialkylaminosulfonyl, sulfonylamino, aminocarbonyl, alkylaminocarbonyl, dialkylaminocarbonyl, heterocyclylcarbonyl, and ureido; and $R^f$, $R^i$, $R^l$, and $R^o$ are independently selected from alkyl, cycloalkyl, haloalkyl, haloalkoxy, alkoxy, hydroxy, halo, amino, alkylamino, cycloalkylsulfonylamino, cyano, cyanoalkyl, alkoxycarbonylalkyl, carboxyalkyl, or —$X^c$—$R^{12}$ where $X^c$ is bond, alkylene, or heteroalkylene and $R^{12}$ is optionally substituted aryl, or optionally substituted heteroaryl; provided that when $R^1$ is pyrrolidinyl, piperidinyl, piperazinyl, oxetanyl, or morpholinyl then $R^f$ is not hydroxy; or a pharmaceutically acceptable salt thereof.

In an embodiment of Formula IIId, or a pharmaceutically acceptable salt thereof, $R^1$ is $R^7$ wherein $R^7$ is aryl optionally substituted with $R^d$, $R^e$, or $R^f$;

$R^2$ is —$NR^9R^{10}$, wherein $R^9$ is hydrogen or alkyl; and $R^{10}$ is hydrogen or alkyl;

$R^3$ is hydrogen;

$R^4$ is hydrogen;

$R^5$ is haloalkyl; and $R^d$, $R^e$, and $R^f$ are each, independently, halo.

In still another embodiment, $R^2$ is —$NR^9R^{10}$. In an embodiment, $R^2$ is —$OR^8$. In another embodiment, $R^2$ is $R^{11}$.

In yet another embodiment, $R^9$ is deuteroalkyl. In still another embodiment, $R^9$ is hydrogen. In an embodiment, $R^9$ is alkyl. In another embodiment, $R^9$ is methyl or ethyl.

In an embodiment, $R^{10}$ is hydrogen, alkyl, haloalkyl, hydroxyalkyl, alkoxyalkyl, aminoalkyl, alkylcarbonyl, alkoxycarbonyl, alkylaminocarbonyl, dialkylaminocarbonyl, alkylaminocarbonylalkyl, or dialkylaminocarbonylalkyl. In another embodiment, $R^{10}$ is hydrogen.

In yet another embodiment, $R^8$ and $R^{10}$ are alkyl. In still another embodiment, $R^8$ and $R^{10}$ are methyl.

In an embodiment, $R^8$ and $R^{10}$ are independently cycloalkyl or cycloalkylalkyl, each ring may independently be unsubstituted or substituted with one or two substituents independently selected from alkyl, halo, or cyano.

In another embodiment, $R^8$ and $R^{10}$ are independently cyclopropyl, cyclobutyl, 1-methylcyclopropyl, (cis)-3-hydroxy-3-methylcyclobutyl, (cis)-3-hydroxy-2,2-dimethylcyclobutyl, 1-cyanocyclobutyl, cyclopropylmethyl, 1-hydroxycyclopropmethyl, 1-fluorocyclopropmethyl, (trans)-3-hydroxy-1-methylcyclobutyl, (cis)-3-cyanocyclobutyl, 1-methylcyclobutyl, (cis)-3-hydroxycyclobutyl, (trans)-3-hydroxycyclobutyl, (trans)-3-cyanocyclobutyl, (2S,1R)-2-hydroxycyclobutyl, (1S,2S)-2-hydroxycyclobutyl, (1S,2R)-2-hydroxycyclobutyl, (1R,2R)-2-hydroxycyclobutyl, (1R,2R)-2-fluorocyclopropyl, 1-fluorocyclopropylmethyl, (1S,2R)-2-fluorocyclopropyl, (1R,2S)-2-fluorocyclopropyl, (1S,2S)-2-fluorocyclopropyl, 2,2-difluorocyclopropyl, (R)-1-cyclopropylethyl, or 2,2-difluorocyclopropylmethyl.

In yet another embodiment, $R^8$ and $R^{10}$ are independently cyclopropyl, cyclobutyl, 1-methylcyclopropyl, (cis)-3-hydroxy-3-methylcyclobutyl, (cis)-3-hydroxy-2,2-dimethylcyclobutyl, 1-cyanocyclobutyl, (trans)-3-hydroxy-1-methylcyclobutyl (cis)-3-cyanocyclobutyl, 1-methylcyclobutyl, (cis)-3-hydroxycyclobutyl, (trans)-3-hydroxycyclobutyl, (trans)-3-cyanocyclobutyl, (2S,1R)-2-hydroxycyclobutyl, (1S,2S)-2-hydroxycyclobutyl, (1S,2R)-2-hydroxycyclobutyl, (1R,2R)-2-hydroxycyclobutyl, (1R,2R)-2-fluorocyclopropyl, (1S,2R)-2-fluorocyclopropyl, (1R,2S)-2-fluorocyclopropyl, (1 S,2S)-2-fluorocyclopropyl, or 2,2-difluorocyclopropyl.

In still another embodiment, $R^8$ and $R^{10}$ are independently cyclopropylmethyl, 1-hydroxycyclopropmethyl, 1-fluorocyclopropmethyl, 1-fluorocyclopropylmethyl, (R)-1-cyclopropylethyl, or 2,2-difluorocyclopropylmethyl.

In an embodiment, $R^8$ and $R^{10}$ are independently heteroaryl or heteroaralkyl wherein heteroaryl, by itself or as part heteroaralkyl, is unsubstituted or substituted with $R^j$, $R^k$, or $R^l$.

In another embodiment, $R^8$ and $R^{10}$ are heteroaryl independently selected from pyrazolyl, oxazolyl, isoxazolyl, imidazolyl, thienyl, pyrrolyl, pyridinyl, pyrimidinyl, pyrazinyl, pyridazinyl, quinolinyl, isoquinolinyl, indolyl, and indazolyl, each ring is either unsubstituted or substituted with $R^j$, $R^k$, or $R^l$.

In yet another embodiment, $R^8$ and $R^{10}$ are heteroaryl independently selected from pyrazolyl, imidazolyl, thienyl, pyrrolyl, pyridinyl, pyrimidinyl, pyrazinyl, pyridazinyl, quinolinyl, isoquinolinyl, indolyl, and indazolyl, each ring is either unsubstituted or substituted with $R^j$, $R^k$, or $R^l$.

In still another embodiment, $R^8$ and $R^{10}$ are heteroaralkyl independently selected from pyrazolylmethyl, pyrazolylethyl, oxazolylmethyl, isoxazolylmethyl, imidazolylmethyl, imidazolylethyl, thienylmethyl, thienylethyl, pyrrolylmethyl, pyrrolylethyl, pyridinylmethyl, pyridinylethyl, pyrimidinylmethyl, pyrimidinylethyl, pyrazinylmethyl, pyrazinylethyl, pyridazinylmethyl, pyridazinylethyl, quinolinylmethyl, quinolinylethyl, isoquinolinylmethyl, isoquinolinylethyl, indolylmethyl, indolylethyl, indazolylmethyl and indazolylethyl, each ring is either unsubstituted or substituted with $R^j$, $R^k$, or $R^l$.

In an embodiment, $R^8$ and $R^{10}$ are heteroaralkyl independently selected from pyrazolylmethyl, pyrazolylethyl, imidazolylmethyl, imidazolylethyl, thienylmethyl, thienylethyl, pyrrolylmethyl, pyrrolylethyl, pyridinylmethyl, pyridinylethyl, pyrimidinylmethyl, pyrimidinylethyl, pyrazinylmethyl, pyrazinylethyl, pyridazinylmethyl, pyridazinylethyl, quinolinylmethyl, quinolinylethyl, isoquinolinylmethyl, isoquinolinylethyl, indolylmethyl, indolylethyl, indazolylmethyl and indazolylethyl, each ring is either unsubstituted or substituted with $R^j$, $R^k$, or $R^l$.

In another embodiment, $R^8$ and $R^{10}$ are 1-methyl-1H-pyrazol-5-yl, isoxazol-4-yl, 3-methyl-1,2,4-oxadiazol-5-yl, 5-methylisoxazol-3-yl, 5-methylisoxazol-4-yl, 3-methoxyisoxazol-5-yl, 3,5-dimethylisoxazol-4-yl, 3-methylisoxazol-4-yl, thiazol-4-yl, thiazol-5-yl, isothiazol-4-yl, pyridin-2-yl, pyridin-3-yl, pyridin-4-yl, 2-(difluoromethyl)pyridin-4-yl, 2-(difluoromethoxy)pyridin-4-yl, 5-methoxypyridin-3-yl, 6-methylpyridin-3-yl, 6-methoxypyridin-3-yl, 3-cyanopyridin-4-yl, 3-methoxypyridin-4-yl, 3-fluoropyridin-4-yl, 3-chloropyridin-4-yl, 2-(trifluoromethyl)pyridin-4-yl, 2-methylpyridin-4-yl, pyrimidin-5-yl, 1-methyl-1H-imidazol-4-yl, 1-methylpyrazol-3-ylmethyl, 3-methoxyisoxazol-5-ylmethyl, oxazol-2-ylmethyl, oxazol-4-ylmethyl, oxazol-5-ylmethyl, isoxazol-3-ylmethyl, isoxazol-4-ylmethyl, isoxazol-5-ylmethyl, 1-methyl-1H-pyrazol-3-ylmethyl, 1-methyl-1H-pyrazol-4-ylmethyl, 1-methyl-1H-pyrazol-5-ylmethyl, pyridin-4-ylmethyl, pyridin-3-ylmethyl, or pyridin-2-ylmethyl.

In yet another embodiment,
$R^2$ is $R^{11}$; and
$R^{11}$ is heterocyclyl which is unsubstituted or substituted with $R^m$, $R^n$, or $R^o$.

In still another embodiment, $R^{11}$ is oxetanyl, azetidinyl, 2-oxoazetidinyl, pyrrolidinyl, 2-oxopyrrolidinyl, piperidinyl, piperazinyl, or morpholinyl, each ring is unsubstituted or substituted with $R^m$, $R^n$, or $R^o$.

In an embodiment, $R^{11}$ is azetidin-1-yl, 4-hydroxyazetidin-1-yl, 4-methylaminocarbonylazetidin-1-yl, 4-dimethylaminocarbonylazetidin-1-yl, 2-hydromethyl-azetidin-1-yl, 2-methylazetidin-1-yl, 2-oxoazetidin-1-yl, pyrrolidin-1-yl, 2-oxopyrrolidin-1-yl, 3-hydroxypyrrolidin-1-yl, 3,3-dimethylpyrrolidin-1-yl, 3-methoxypyrrolidin-1-yl, 3-hydroxy-3-methylpyrrolidin-1-yl, piperidin-1-yl, 2-carboxypiperidin-1-yl, 2-aminocarbonylpiperidin-1-yl, piperazin-1-yl, 4-methylpiperazin-1-yl, or morpholin-4-yl.

In another embodiment,
$R^5$ is alkyl, alkoxy, halo, haloalkyl, haloalkoxy, cycloalkyl, cyano, aminocarbonyl, heteroaryl, heterocyclyl, wherein heterocyclyl or heteroaryl is unsubstituted or substituted with $R^a$, $R^b$, or $R^c$; and
$R^a$, $R^b$, or $R^c$ are each independently selected from alkyl, cycloalkyl, haloalkyl, haloalkoxy, alkoxy, hydroxy, halo, cyano, hydroxyalkyl, alkoxyalkyl, or aminoalkyl.

In yet another embodiment,
$R^5$ is methyl, ethyl, isopropyl, tert-butyl, methoxy, ethoxy, fluoro, chloro, bromo, trifluoromethyl, difluoromethyl, trifluoromethoxy, difluoromethoxy, cyclopropyl, cyclopentyl, cyano, pyrazolyl, imidazolyl, thienyl, thiazolyl, oxazolyl, isoxazolyl, pyridinyl, pyrimidinyl, oxetan-3-yl, pyrrolidin-1-yl, tetrahydrofuranyl, 2-oxoazetidin-1-yl, or 2-oxopyrrolidin-1-yl, wherein heterocyclyl or heteroaryl rings are unsubstituted or substituted with $R^a$, $R^b$, or $R^4$; and
$R^a$, $R^b$, and $R^c$ are each independently selected from alkyl, cycloalkyl, haloalkyl, haloalkoxy, alkoxy, hydroxy, halo, cyano, hydroxyalkyl, alkoxyalkyl, or aminoalkyl.

In still another embodiment, $R^5$ is chloro, methyl, ethyl, trifluoromethyl, 1,1-difluoroethyl, or cyclopropyl. In an embodiment, $R^5$ is chloro, ethyl, or trifluoromethyl.

In another embodiment, $R^4$ and $R^6$ are independently selected from hydrogen, methyl, chloro, fluoro, bromo, methoxy, methylthio, methylsulfonyl, trifluoromethyl, trifluoromethoxy, cyano, amino, methylamino, dimethylamino, methylaminocarbonyl, or dimethylaminocarbonyl.

In yet another embodiment,
$R^4$ is hydrogen, fluoro, bromo, methyl, methoxy, or cyano; and
$R^6$ is hydrogen.

In still another embodiment, $R^4$ and $R^6$ are hydrogen.

In an embodiment, $R^3$ is hydrogen, alkyl, alkoxy, alkylsulfonyl, halo, haloalkyl, haloalkoxy, cycloalkyl, cyano, amino, alkylamino, dialkylamino, aminocarbonyl, alkylaminocarbonyl, or dialkylaminocarbonyl. In another embodiment, $R^3$ is hydrogen or methoxy. In yet another embodiment, $R^3$ is hydrogen.

In still another embodiment, $R^3$ is methyl, ethyl, methoxy, ethoxy, fluoro, chloro, bromo, trifluoromethyl, difluoromethyl, trifluoromethoxy, difluoromethoxy, cyclopropyl, cyano, methylsulfonyl, aminocarbonyl, methylamino, or dimethylamino.

In an embodiment,
$R^1$ is $R^7$;
$R^7$ is phenyl which is unsubstituted or substituted with $R^d$, $R^e$, or $R^f$;
$R^d$ and $R^e$ are independently selected from alkyl, haloalkyl, haloalkoxy, alkoxy, alkylsulfonyl, halo, cyano, carboxy, alkoxycarbonyl, hydroxyalkyl, alkoxyalkyl, aminoalkyl, aminosulfonyl, alkylaminosulfonyl, dialkylaminosulfonyl, sulfonylamino, aminocarbonyl, alkylaminocarbonyl, dialkylaminocarbonyl, heterocyclylcarbonyl, and ureido; and
$R^f$ is selected from alkyl, haloalkyl, haloalkoxy, alkoxy, hydroxy, halo, and cyano.

In another embodiment,
$R^1$ is $R^7$;
$R^7$ is phenyl which is unsubstituted or substituted with $R^d$, $R^e$ or $R^f$
$R^d$ and $R^e$ are independently selected from methyl, ethyl, fluoro, chloro, bromo, methoxy, ethoxy, cyclopropyl, cyano, methylsulfonyl, methoxymethyl, aminomethyl, 2-hydroxyethyl, or 3-hydroxypropyl; and $R^f$ is selected from hydroxy, fluoro, chloro, cyano. and methyl.

In yet another embodiment,
$R^1$ is $R^7$;
$R^7$ is phenyl which is unsubstituted or substituted with $R^f$; and
$R^f$ is fluoro, chloro, bromo, or methyl, wherein $R^f$ is attached to carbon atoms on the phenyl ring that is ortho to the carbon atom of the phenyl ring attached to quinazolone nitrogen.

In still another embodiment,
$R^1$ is $R^7$;
$R^7$ is heteroaryl which is unsubstituted or substituted with $R^d$, $R^e$, $R^f$
$R^d$ and $R^e$ are independently selected from alkyl, haloalkyl, haloalkoxy, alkoxy, alkylsulfonyl, halo, cyano, carboxy, alkoxycarbonyl, hydroxyalkyl, alkoxyalkyl, aminoalkyl, aminosulfonyl, alkylaminosulfonyl, dialkylaminosulfonyl, sulfonylamino, aminocarbonyl, alkylaminocarbonyl, dialkylaminocarbonyl, heterocyclylcarbonyl, and ureido; and
$R^f$ is selected from alkyl, haloalkyl, haloalkoxy, alkoxy, hydroxy, halo, and cyano.

In an embodiment,
$R^1$ is $R^7$;
$R^7$ is 5 or 6-membered heteroaryl ring which is unsubstituted or substituted with $R^d$ or $R^e$;
$R^d$ and $R^e$ are each independently selected from methyl, ethyl, fluoro, chloro, bromo, methoxy, ethoxy, cyclopropyl, cyano, methylsulfonyl, methoxymethyl, aminomethyl, 2-hydroxyethyl, and 3-hydroxypropyl.

In another embodiment,
$R^1$ pyridinyl which is unsubstituted or substituted with $R^f$;
$R^f$ is fluoro, chloro, bromo, or methyl and wherein $R^f$ is attached to carbon atoms on the pyridinyl ring that is ortho to the carbon atom of the pyridinyl ring attached to quinazolone nitrogen.

In yet another embodiment, the methionine adenosyltransferase II alpha (MAT2A) inhibitor is selected from the group consisting of a compound from Table 1, or a pharmaceutically acceptable salt thereof.

TABLE 1

| Cpd. No. | Structure | Name | Mass Spec. |
| --- | --- | --- | --- |
| 1 | 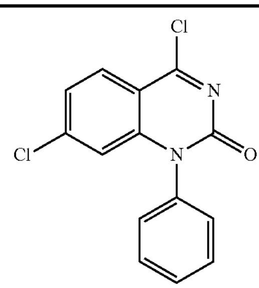 | 4,7-dichloro-1-phenylquinazolin-2(1H)-one | |
| 2 | 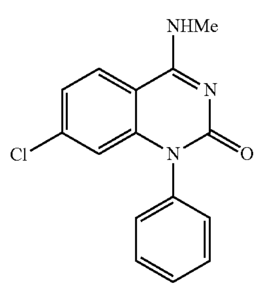 [SMILES: CNc1nc(=O)n(-c2ccccc2)c2cc(Cl)ccc12] | 7-chloro-4-(methylamino)-1-phenyl-quinazolin-2(1H)-one | |

TABLE 1-continued

| Cpd. No. | Structure | Name | Mass Spec. |
|---|---|---|---|
| 3 | 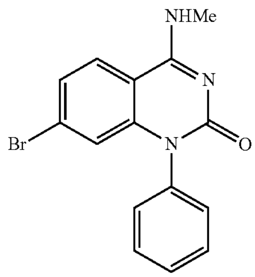 [SMILES: CNc1nc(=O)n(-c2ccccc2)c2cc(Br)ccc12] | 7-bromo-4-(methylamino)-1-phenyl-quinazolin-2(1H)-one | |
| 4 | 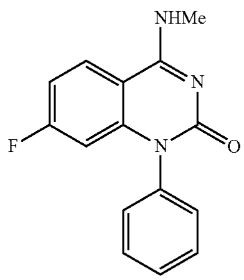 [SMILES: CNc1nc(=O)n(-c2ccccc2)c2cc(F)ccc12] | 7-fluoro-1-phenylquinazolin-2(1H)-one | |
| 5 | 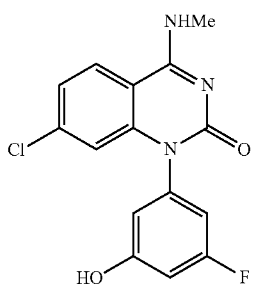 [SMILES: CNc1nc(=O)n(-c2cc(O)cc(F)c2)c2cc(Cl)ccc12] | 7-Chloro-1-(5-fluoro-3-hydroxy-phenyl)-4-(methylamino)-hydroquinazolin-2-one | |
| 6 | 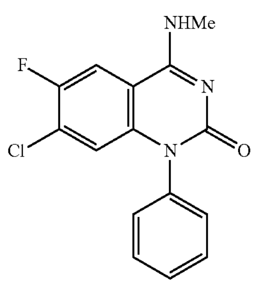 [SMILES: CNc1nc(=O)n(-c2ccccc2)c2cc(Cl)c(F)cc12] | 7-chloro-6-fluoro-4-(methylamino)-1-phenyl-quinazolin-2(1H)-one | |
| 7 | 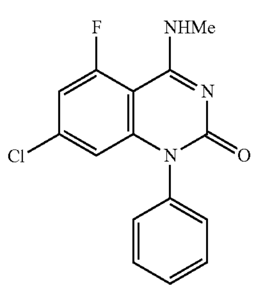 [SMILES: CNc1nc(=O)n(-c2ccccc2)c2cc(Cl)cc(F)c12] | 7-chloro-5-fluoro-4-(methylamino)-1-phenyl-quinazolin-2(1H)-one | |

TABLE 1-continued
| Cpd. No. | Structure | Name | Mass Spec. |
|---|---|---|---|
| 8 | 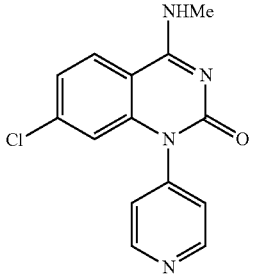 [SMILES: CNc1nc(=O)n(-c2ccncc2)c2cc(Cl)ccc12] | 7-chloro-4-(methylamino)-1-(pyridin-4-yl)-quinazolin-2(1H)-one | |
| 9 | 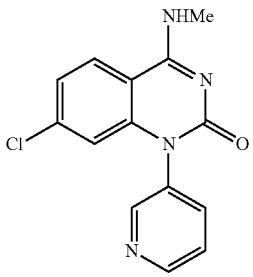 | 7-chloro-4-(methylamino)-1-(pyridin-3-yl)-quinazolin-2(1H)-one | |
| 10 | 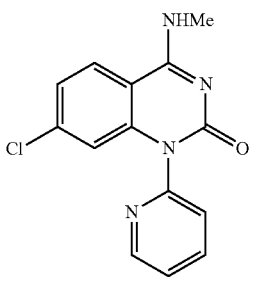 [SMILES: CNc1nc(=O)n(-c2ccccn2)c2cc(Cl)ccc12] | 7-chloro-4-(methylamino)-1-(pyridin-2-yl)-quinazolin-2(1H)-one | |
| 11 | 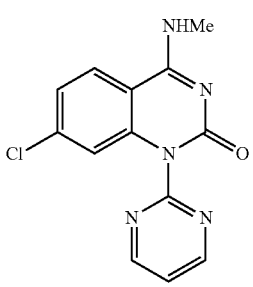 [SMILES: CNc1nc(=O)n(-c2ncccn2)c2cc(Cl)ccc12] | 7-chloro-4-(methylamino)-1-pyrimidin-2-yl-quinazolin-2(1H)-one | |
| 12 | 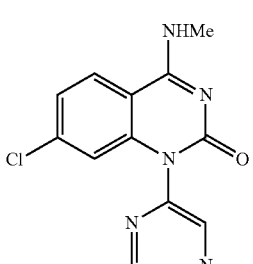 | 7-chloro-4-(methylamino)-1-(pyrazin-2-yl)-quinazolin-2(1H)-one | |

TABLE 1-continued

| Cpd. No. | Structure | Name | Mass Spec. |
|---|---|---|---|
| 13 | 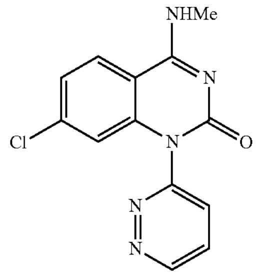 [SMILES: CNc1nc(=O)n(-c2cccnn2)c2cc(Cl)ccc12] | 7-chloro-4-(methylamino)-1-(pyridazin-3-yl)-quinazolin-2(1H)-one | |
| 14 | 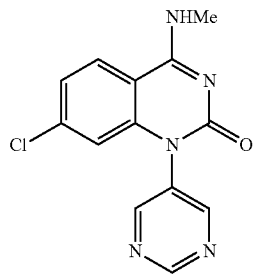 [SMILES: CNc1nc(=O)n(-c2cncnc2)c2cc(Cl)ccc12] | 7-chloro-4-(methylamino)-1-(pyrimidin-5-yl)-quinazolin-2(1H)-one | |
| 15 | 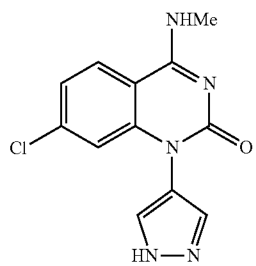 [SMILES: CNc1nc(=O)n(-c2cn[nH]c2)c2cc(Cl)ccc12] | 7-chloro-4-(methylamino)-1-(1H-pyrazol-4-yl)-quinazolin-2(1H)-one | |
| 16 | 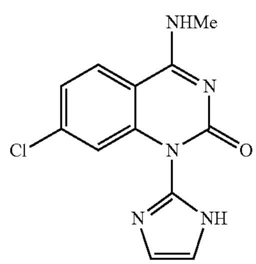 [SMILES: CNc1nc(=O)n(-c2ncc[nH]2)c2cc(Cl)ccc12] | 7-chloro-1-(1H-imidazol-2-yl)-4-(methylamino)-quinazolin-2(1H)-one | |
| 17 | 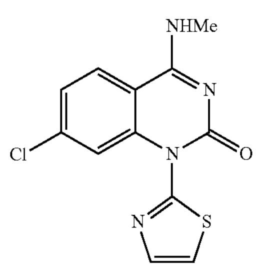 [SMILES: CNc1nc(=O)n(-c2nccs2)c2cc(Cl)ccc12] | 7-chloro-4-(methylamino)-1-(thiazol-2-yl)-quinazolin-2(1H)-one | |

TABLE 1-continued

| Cpd. No. | Structure | Name | Mass Spec. |
|---|---|---|---|
| 18 | 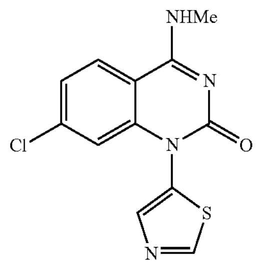 [SMILES: CNc1nc(=O)n(-c2cncs2)c2cc(Cl)ccc12] | 7-chloro-4-(methylamino)-1-(thiazol-5-yl)-quinazolin-2(1H)-one | |
| 19 | 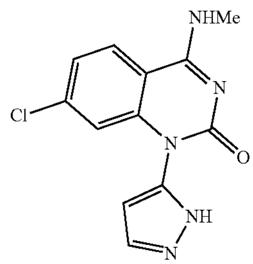 [SMILES: CNc1nc(=O)n(-c2ccn[nH]2)c2cc(Cl)ccc12] | 7-chloro-4-(methylamino)-1-(1H-pyrazol-5-yl)-quinazolin-2(1H)-one | |
| 20 | 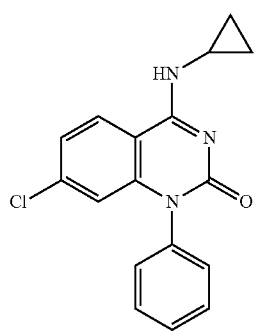 [SMILES: O=c1nc(NC2CC2)c2ccc(Cl)cc2n1-c1ccccc1] | 7-chloro-4-(cyclopropylamino)-1-phenylquinazolin-2(1H)-one | |
| 21 | 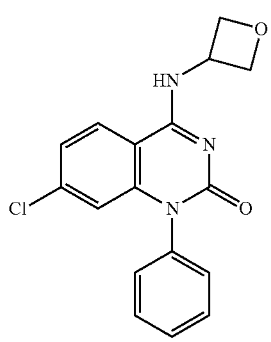 [SMILES: O=c1nc(NC2COC2)c2ccc(Cl)cc2n1-c1ccccc1] | 7-Chloro-4-(oxetan-3-ylamino)-1-phenylquinazolin-2(1H)-one | |
| 22 | 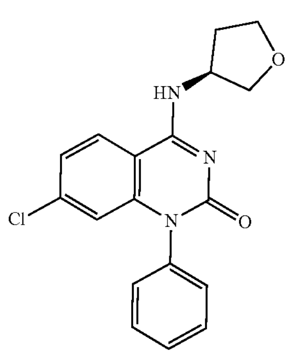 [SMILES: O=c1nc(N[C@H]2CCOC2)c2ccc(Cl)cc2n1-c1ccccc1] | (S)-7-chloro-1-phenyl-4-((tetrahydro-furan-3-yl)amino)-quinazolin-2(1H)-one | |

TABLE 1-continued

| Cpd. No. | Structure | Name | Mass Spec. |
|---|---|---|---|
| 23 | 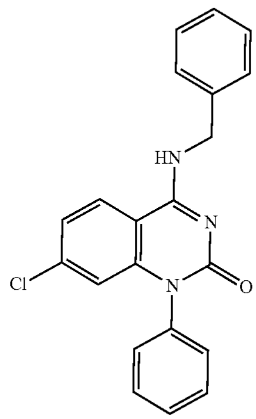 [SMILES: O=c1nc(NCc2ccccc2)c2ccc(Cl)cc2n1-c1ccccc1] | 4-(benzylamino)-7-chloro-1-phenyl-quinazolin-2(1H)-one | |
| 24 | 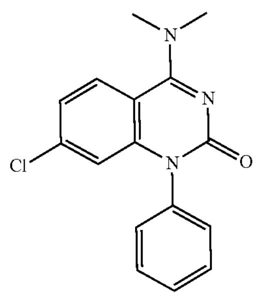 [SMILES: CN(C)c1nc(=O)n(-c2ccccc2)c2cc(Cl)ccc12] | 7-chloro-4-(dimethylamino)-1-phenyl-quinazolin-2(1H)-one | |
| 25 | 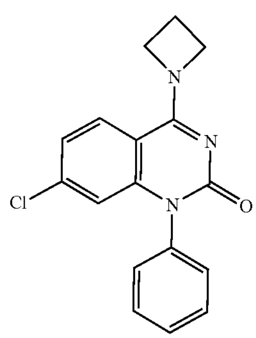 [SMILES: O=c1nc(N2CCC2)c2ccc(Cl)cc2n1-c1ccccc1] | 4-(azetidin-1-yl)-7-chloro-1-phenyl-quinazolin-2(1H)-one | |
| 26 | 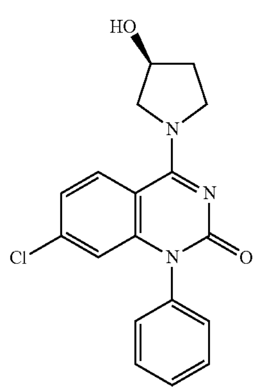 [SMILES: O=c1nc(N2CC[C@H](O)C2)c2ccc(Cl)cc2n1-c1ccccc1] | (S)-7-chloro-4-(3-hydroxypyrrolidin-1-yl)-1-phenylquinazolin-2(1H)-one | |

TABLE 1-continued

| Cpd. No. | Structure | Name | Mass Spec. |
|---|---|---|---|
| 27 | 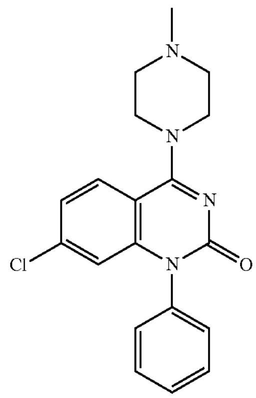 [SMILES: CN1CCN(c2nc(=O)n(-c3ccccc3)c3cc(Cl)ccc23)CC1] | 7-chloro-4-(4-methylpiperazin-1-yl)-1-phenyl-quinazolin-2(1H)-one | |
| 28 | 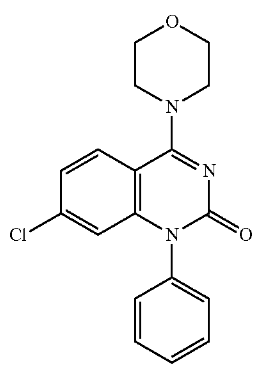 [SMILES: O=c1nc(N2CCOCC2)c2ccc(Cl)cc2n1-c1ccccc1] | 7-chloro-4-morpholino-1-phenyl-quinazolin-2(1H)-one | |
| 29 | 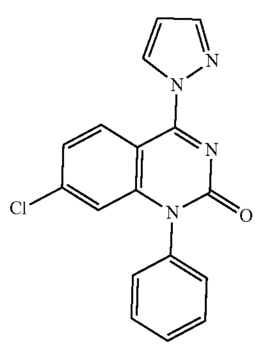 [SMILES: O=c1nc(-n2cccn2)c2ccc(Cl)cc2n1-c1ccccc1] | 7-chloro-1-phenyl-4-(1H-pyrazol-1-yl)quinazolin-2(1H)-one | |
| 30 | 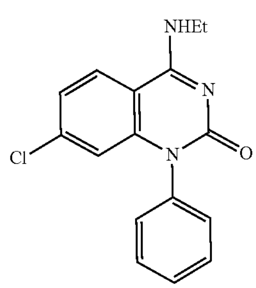 | 7-chloro-4-(ethylamino)-1-phenyl-quinazolin-2(1H)-one | |

TABLE 1-continued
| Cpd. No. | Structure | Name | Mass Spec. |
|---|---|---|---|
| 31 | 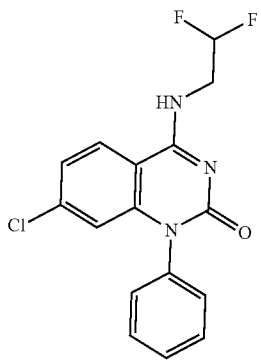 [SMILES: O=c1nc(NCC(F)F)c2ccc(Cl)cc2n1-c1ccccc1] | 7-chloro-4-((2,2-difluoroethyl)amino)-1-phenyl-quinazolin-2(1H)-one | |
| 32 | 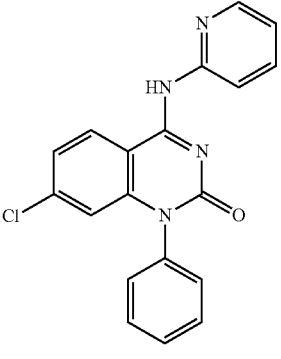 [SMILES: O=c1nc(Nc2ccccn2)c2ccc(Cl)cc2n1-c1ccccc1] | 7-chloro-1-phenyl-4-(pyridin-2-yl-amino)quinazolin-2(1H)-one | |
| 33 | 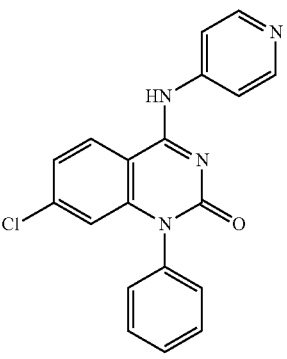 [SMILES: O=c1nc(Nc2ccncc2)c2ccc(Cl)cc2n1-c1ccccc1] | 7-chloro-1-phenyl-4-(pyridin-4-yl-amino)quinazolin-2(1H)-one | |
| 34 | 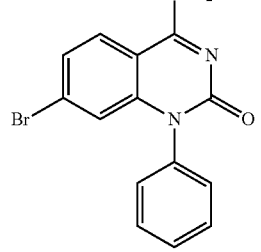 | 7-bromo-4-(dimethylamino)-1-phenyl-quinazolin-2(1H)-one | |

TABLE 1-continued

| Cpd. No. | Structure | Name | Mass Spec. |
|---|---|---|---|
| 35 | 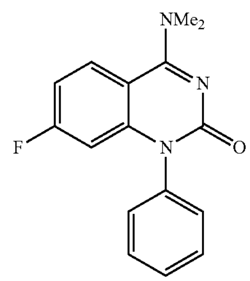 | 4-(dimethylamino)-7-fluoro-1-phenyl-quinazolin-2(1H)-one | |
| 36 | 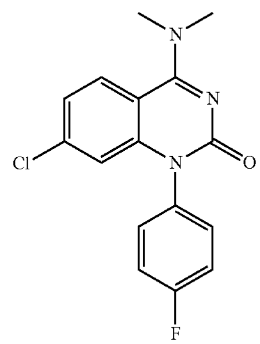 [SMILES: CN(C)c1nc(=O)n(-c2ccc(F)cc2)c2cc(Cl)ccc12] | 4-(dimethylamino)-7-chloro-1-(4-fluorophenyl)-hydroquinazolin-2-one | |
| 37 | 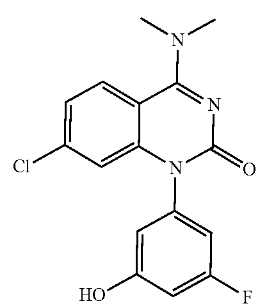 [SMILES: CN(C)c1nc(=O)n(-c2cc(O)cc(F)c2)c2cc(Cl)ccc12] | 4-(dimethylamino)-7-chloro-1-(5-fluoro-3-hydroxyphenyl)hydroquinazolin-2-one | |
| 38 | 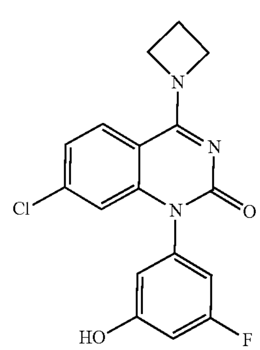 [SMILES: O=c1nc(N2CCC2)c2ccc(Cl)cc2n1-c1cc(O)cc(F)c1] | 4-azetidinyl-7-chloro-1-(5-fluoro-3-hydroxy-phenyl)hydroquinazolin-2-one | |

TABLE 1-continued
| Cpd. No. | Structure | Name | Mass Spec. |
|---|---|---|---|
| 39 | 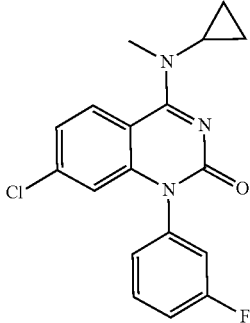 [SMILES: CN(c1nc(=O)n(-c2cccc(F)c2)c2cc(Cl)ccc12)C1CC1] | 7-chloro-4-(cyclopropylmethylamino)-1-(3-fluorophenyl)hydroquinazolin-2-one | |
| 40 | 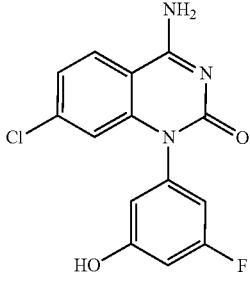 [SMILES: Nc1nc(=O)n(-c2cc(O)cc(F)c2)c2cc(Cl)ccc12] | 4-amino-7-chloro-1-(5-fluoro-3-hydroxyphenyl)-hydroquinazolin-2-one | |
| 41 | 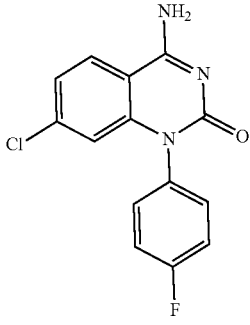 [SMILES: Nc1nc(=O)n(-c2ccc(F)cc2)c2cc(Cl)ccc12] | 4-amino-7-chloro-1-(4-fluorophenyl)-hydro-quinazolin-2-one | |
| 42 | 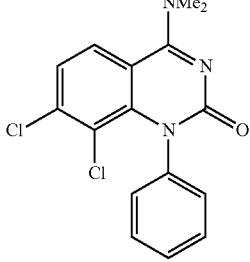 | 7,8-dichloro-4-(dimethylamino)-1-phenylquinazolin-2(1H)-one | |
| 43 | 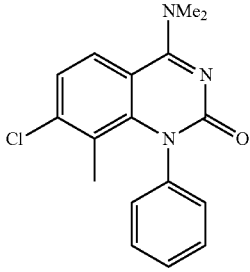 [SMILES: Cc1c(Cl)ccc2c(N(C)C)nc(=O)n(-c3ccccc3)c12] | 7-chloro-4-(dimethylamino)-8-methyl-1-phenyl-quinazolin-2(1H)-one | |

TABLE 1-continued

| Cpd. No. | Structure | Name | Mass Spec. |
|---|---|---|---|
| 44 | 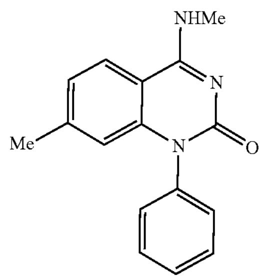 [SMILES: CNc1nc(=O)n(-c2ccccc2)c2cc(C)ccc12] | 7-methyl-4-(methylamino)-1-phenyl-quinazolin-2(1H)-one | |
| 45 | 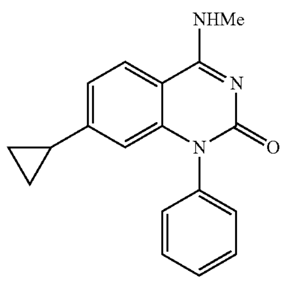 [SMILES: CNc1nc(=O)n(-c2ccccc2)c2cc(C3CC3)ccc12] | 7-cyclopropyl-4-(methylamino)-1-phenylquinazolin-2(1H)-one | |
| 46 | 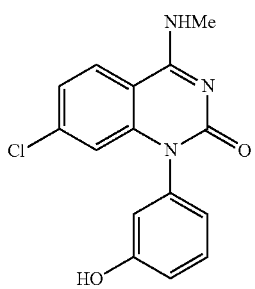 [SMILES: CNc1nc(=O)n(-c2cccc(O)c2)c2cc(Cl)ccc12] | 7-chloro-1-(3-hydroxyphenyl)-4-(methylamino)-hydroquinazolin-2-one | |
| 47 | 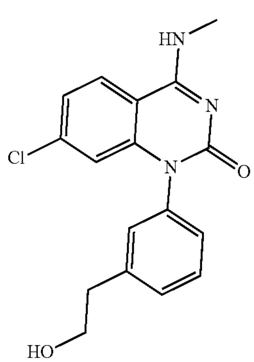 [SMILES: CNc1nc(=O)n(-c2cccc(CCO)c2)c2cc(Cl)ccc12] | 7-chloro-1-[3-(2-hydroxyethyl)phenyl]-4-(methylamino)-hydroquinazolin-2-one | |
| 48 | 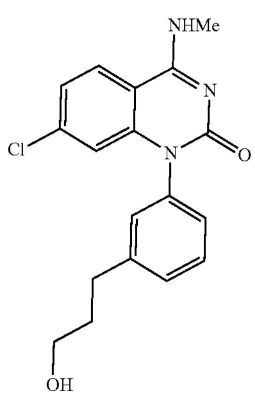 [SMILES: CNc1nc(=O)n(-c2cccc(CCCO)c2)c2cc(Cl)ccc12] | 7-chloro-1-[3-(3-hydroxypropyl)-phenyl]-4-(methylamino)hydro-quinazolin-2-one | |

TABLE 1-continued

| Cpd. No. | Structure | Name | Mass Spec. |
|---|---|---|---|
| 49 | 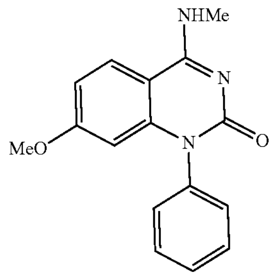 [SMILES: CNc1nc(=O)n(-c2ccccc2)c2cc(OC)ccc12] | 7-methoxy-4-(methylamino)-1-phenyl-quinazolin-2(1H)-one | |
| 50 | 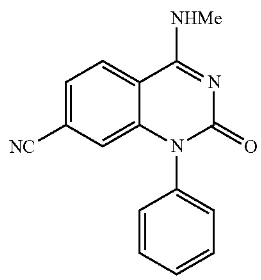 [SMILES: CNc1nc(=O)n(-c2ccccc2)c2cc(C#N)ccc12] | 4-(methylamino)-2-oxo-1-phenyl-1,2-dihydro-quinazoline-7-carbonitrile | |
| 51 | 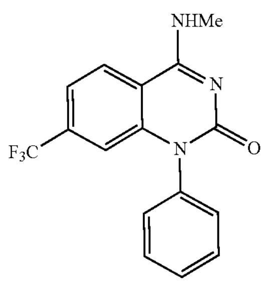 [SMILES: CNc1nc(=O)n(-c2ccccc2)c2cc(C(F)(F)F)ccc12] | 4-(methylamino)-1-phenyl-7-(trifluoro-methyl)-quinazolin-2(1H)-one | |
| 52 | 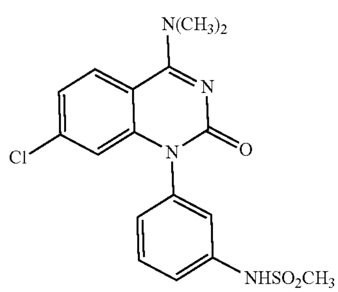 | N-(3-(7-chloro-4-(dimethylamino)-2-oxoquinazolin-1(2H)-yl)phenyl)-methanesulfonamide | |
| 54 | 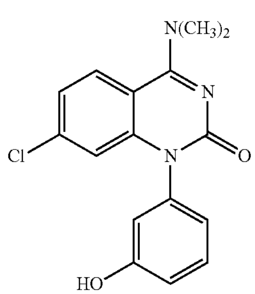 [SMILES: CN(C)c1nc(=O)n(-c2cccc(O)c2)c2cc(Cl)ccc12] | 4-(dimethylamino)-7-chloro-1-(3-hydroxyphenyl)hydroquinazolin-2-one | |

TABLE 1-continued

| Cpd. No. | Structure | Name | Mass Spec. |
|---|---|---|---|
| 55 | 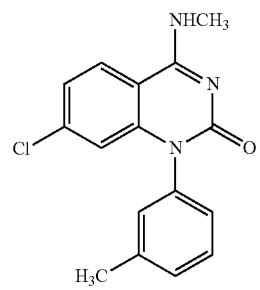 [SMILES: CNc1nc(=O)n(-c2cccc(C)c2)c2cc(Cl)ccc12] | 7-Chloro-4-(methylamino)-1-(3-methylphenyl)hydroquinazolin-2-one | |
| 56 | 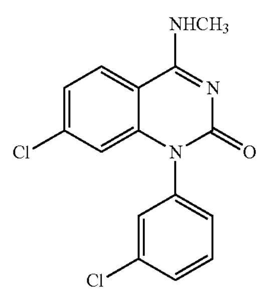 [SMILES: CNc1nc(=O)n(-c2cccc(Cl)c2)c2cc(Cl)ccc12] | 7-Chloro-1-(3-chlorophenyl)-4-(methylamino)hydroquinazolin-2-one | |
| 57 | 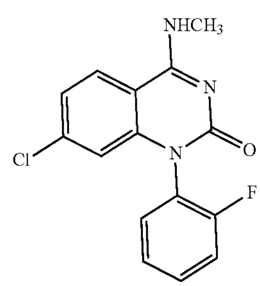 [SMILES: CNc1nc(=O)n(-c2ccccc2F)c2cc(Cl)ccc12] | 7-chloro-1-(2-fluorophenyl)-4-(methylamino)quinazolin-2(1H)-one | |
| 58 | 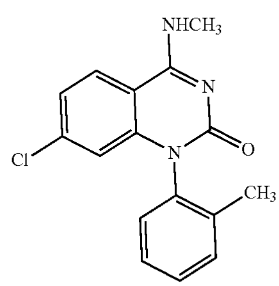 [SMILES: CNc1nc(=O)n(-c2ccccc2C)c2cc(Cl)ccc12] | 7-Chloro-4-(methylamino)-1-(2-methylphenyl)hydroquinazolin-2-one | |
| 59 | 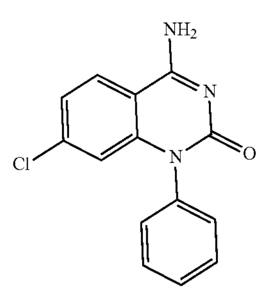 [SMILES: Nc1nc(=O)n(-c2ccccc2)c2cc(Cl)ccc12] | 4-amino-7-chloro-1-phenylquinazolin-2(1H)-one | |

TABLE 1-continued

| Cpd. No. | Structure | Name | Mass Spec. |
|---|---|---|---|
| 60 | 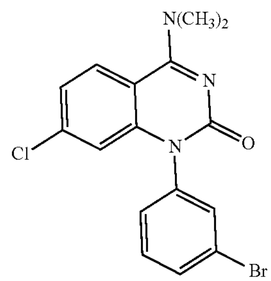 [SMILES: CN(C)c1nc(=O)n(-c2cccc(Br)c2)c2cc(Cl)ccc12] | 1-(3-bromophenyl)-7-chloro-4-(dimethylamino)quinazolin-2(1H)-one | |
| 61 | 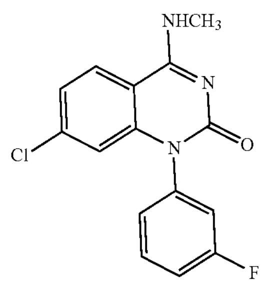 [SMILES: CNc1nc(=O)n(-c2cccc(F)c2)c2cc(Cl)ccc12] | 7-chloro-1-(3-fluorophenyl)-4-(methylamino)quinazolin-2(1H)-one | |
| 62 | 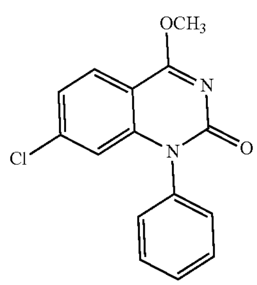 [SMILES: COc1nc(=O)n(-c2ccccc2)c2cc(Cl)ccc12] | 7-chloro-4-methoxy-1-phenyl-quinazolin-2(1H)-one | |
| 63 | 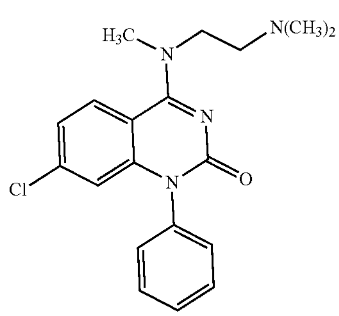 [SMILES: CN(C)CCN(C)c1nc(=O)n(-c2ccccc2)c2cc(Cl)ccc12] | 7-chloro-4-((2-(dimethylamino)ethyl)-(methyl)-amino)-1-phenylquinazolin-2(1H)-one | |
| 64 | 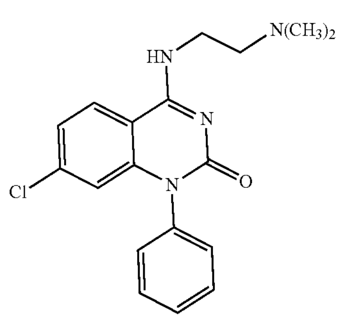 [SMILES: CN(C)CCNc1nc(=O)n(-c2ccccc2)c2cc(Cl)ccc12] | 7-chloro-4-((2-(dimethylamino)ethyl)-amino)-1-phenylquinazolin-2(1H)-one | |

TABLE 1-continued

| Cpd. No. | Structure | Name | Mass Spec. |
|---|---|---|---|
| 65 | 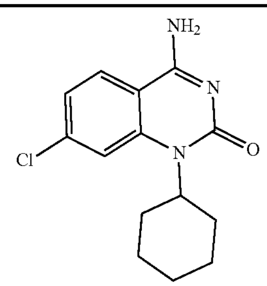 | 4-amino-7-chloro-1-cyclohexyl-quinazolin-2(1H)-one | |
| 66 | 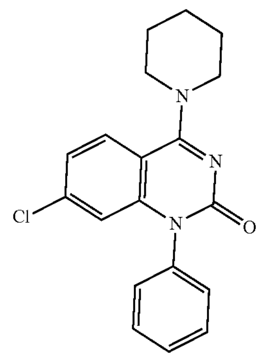 [SMILES: O=c1nc(N2CCCCC2)c2ccc(Cl)cc2n1-c1ccccc1] | 7-chloro-1-phenyl-4-(piperidin-1-yl)-quinazolin-2(1H)-one | |
| 67 | 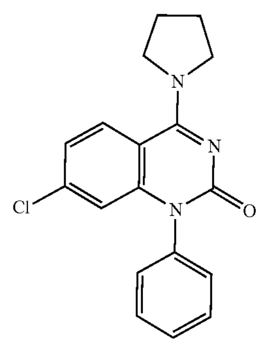 [SMILES: O=c1nc(N2CCCC2)c2ccc(Cl)cc2n1-c1ccccc1] | 7-chloro-1-phenyl-4-(pyrrolidin-1-yl)-quinazolin-2(1H)-one | |
| 68 | 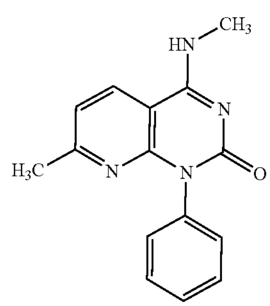 [SMILES: CNc1nc(=O)n(-c2ccccc2)c2nc(C)ccc12] | 7-methyl-4-(methylamino)-1-phenyl-pyrido[2,3-d]pyrimidin-2(1H)-one | |
| 69 | 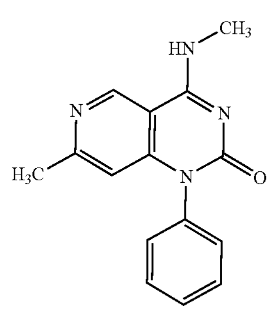 [SMILES: CNc1nc(=O)n(-c2ccccc2)c2cc(C)ncc12] | 7-methyl-4-(methylamino)-1-phenyl-pyrido[4,3-d]pyrimidin-2(1H)-one | |

TABLE 1-continued
| Cpd. No. | Structure | Name | Mass Spec. |
|---|---|---|---|
| 70 | 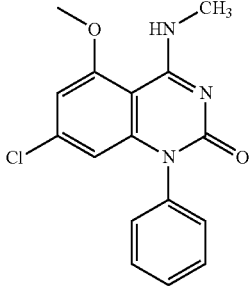 [SMILES: CNc1nc(=O)n(-c2ccccc2)c2cc(Cl)cc(OC)c12] | 7-chloro-5-methoxy-4-(methylamino)-1-phenylquinazolin-2(1H)-one | |
| 71 | 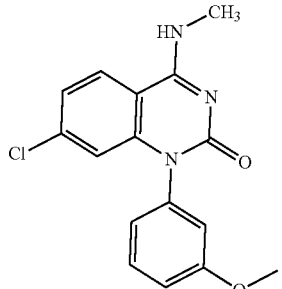 | 7-chloro-1-(3-methoxyphenyl)-4-(methylamino)quinazolin-2(1H)-one | |
| 73 | 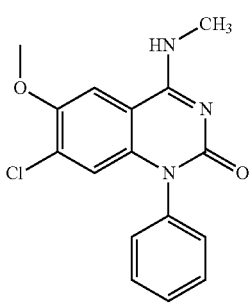 [SMILES: CNc1nc(=O)n(-c2ccccc2)c2cc(Cl)c(OC)cc12] | 7-chloro-6-methoxy-4-(methylamino)-1-phenylquinazolin-2(1H)-one | |
| 74 | 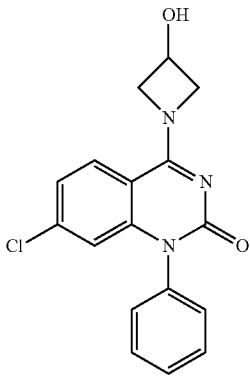 [SMILES: O=c1nc(N2CC(O)C2)c2ccc(Cl)cc2n1-c1ccccc1] | 7-chloro-4-(3-hydroxyazetidin-1-yl)-1-phenylquinazolin-2(1H)-one | |
| 75 | 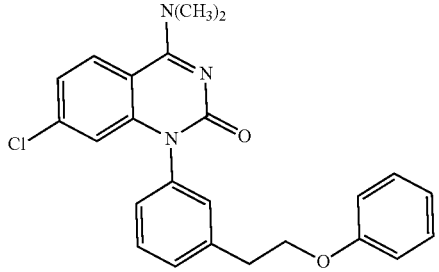 [SMILES: CN(C)c1nc(=O)n(-c2cccc(CCOc3ccccc3)c2)c2cc(Cl)ccc12] | 7-chloro-4-(dimethylamino)-1-(3-(2-phenoxyethyl)phenyl)quinazolin-2(1H)-one | |

TABLE 1-continued

| Cpd. No. | Structure | Name | Mass Spec. |
|---|---|---|---|
| 76 | 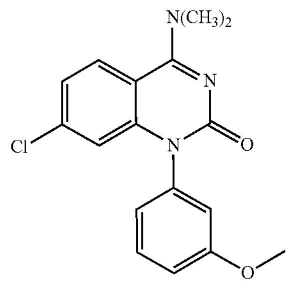 [SMILES: COc1cccc(-n2c(=O)nc(N(C)C)c3ccc(Cl)cc32)c1] | 4-(dimethylamino)-7-chloro-1-(3-methoxyphenyl)hydroquinazolin-2-one | |
| 77 | 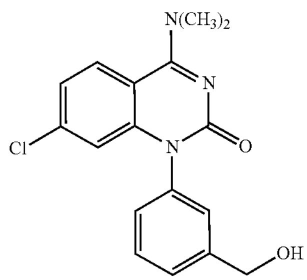 [SMILES: CN(C)c1nc(=O)n(-c2cccc(CO)c2)c2cc(Cl)ccc12] | 4-(dimethylamino)-7-chloro-1-[3-(hydroxymethyl)phenyl]hydroquinazolin-2-one | |
| 78 | 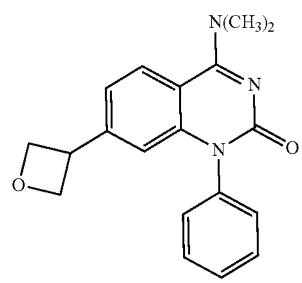 [SMILES: CN(C)c1nc(=O)n(-c2ccccc2)c2cc(C3COC3)ccc12] | 4-(dimethylamino)-7-(oxetan-3-yl)-1-phenylquinazolin-2(1H)-one | |
| 79 | 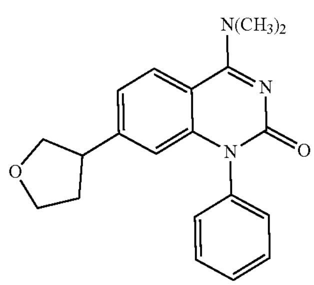 [SMILES: CN(C)c1nc(=O)n(-c2ccccc2)c2cc(C3CCOC3)ccc12] | 4-(dimethylamino)-1-phenyl-7-(tetrahydrofuran-3-yl)quinazolin-2(1H)-one | |
| 80 | 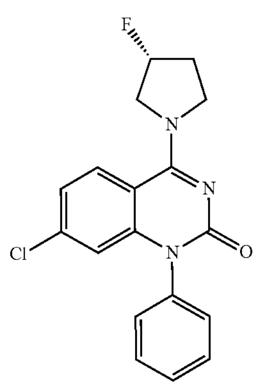 [SMILES: O=c1nc(N2CC[C@@H](F)C2)c2ccc(Cl)cc2n1-c1ccccc1] | (R)-7-chloro-4-(3-fluoropyrrolidin-1-yl)-1-phenylquinazolin-2(1H)-one | |

TABLE 1-continued

| Cpd. No. | Structure | Name | Mass Spec. |
|---|---|---|---|
| 81 | 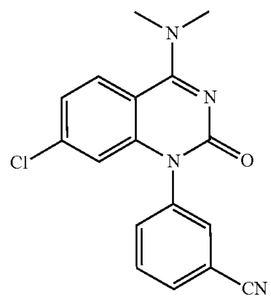 [SMILES: CN(C)c1nc(=O)n(-c2cccc(C#N)c2)c2cc(Cl)ccc12] | 3-[4-(dimethylamino)-7-chloro-2-oxohydroquinazolinyl] benzenecarbonitrile | |
| 82 | 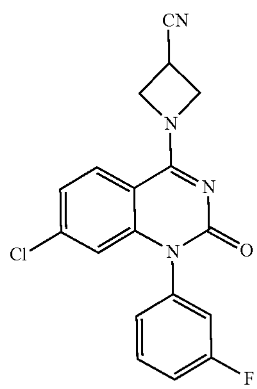 [SMILES: N#CC1CN(c2nc(=O)n(-c3cccc(F)c3)c3cc(Cl)ccc23)C1] | 1-(7-chloro-1-(3-fluorophenyl)-2-oxo-1,2-dihydroquinazolin-4-yl)azetidine-3-carbonitrile | |
| 83 | 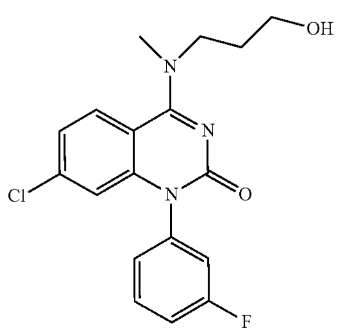 [SMILES: CN(CCCO)c1nc(=O)n(-c2cccc(F)c2)c2cc(Cl)ccc12] | 7-chloro-1-(3-fluorophenyl)-4-((3-hydroxypropyl)(methyl)amino) quinazolin-2(1H)-one | |
| 85 | 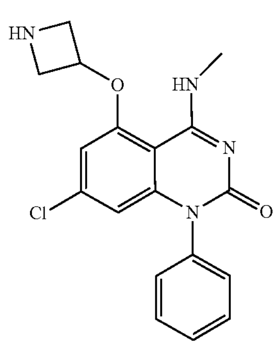 [SMILES: CNc1nc(=O)n(-c2ccccc2)c2cc(Cl)cc(OC3CNC3)c12] | 5-azetidin-3-yloxy-7-chloro-4-(methyl-amino)-1-phenylhydroquinazolin-2-one | m/z [M + H]+ 357.1 |

TABLE 1-continued

| Cpd. No. | Structure | Name | Mass Spec. |
|---|---|---|---|
| 86 | 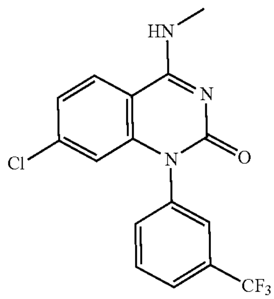 [SMILES: CNc1nc(=O)n(-c2cccc(C(F)(F)F)c2)c2cc(Cl)ccc12] | 7-chloro-4-(methylamino)-1-[3-(trifluoromethyl)phenyl]hydroquinazolin-2-one | m/z [M + H]+ 354.04 |
| 87 | 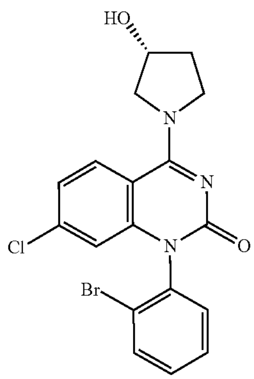 [SMILES: O=c1nc(N2CC[C@@H](O)C2)c2ccc(Cl)cc2n1-c1ccccc1Br] | 4-((3R)-3-hydroxypyrrolidin-1-yl)-1-(2-bromophenyl)-7-chlorohydroquinazolin-2-one | m/z [M + H]+ 420.04 |
| 88 | 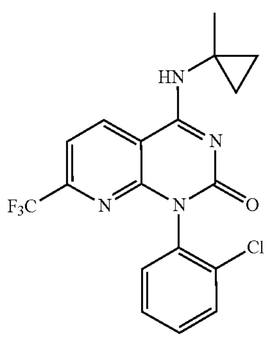 [SMILES: CC1(Nc2nc(=O)n(-c3ccccc3Cl)c3nc(C(F)(F)F)ccc23)CC1] | 1-(2-chlorophenyl)-4-((1-methylcyclopropyl)amino)-7-(trifluoromethyl)-pyrido[2,3-d]pyrimidin-2(1H)-one | m/z [M + H]+ 395.05 |
| 89 | 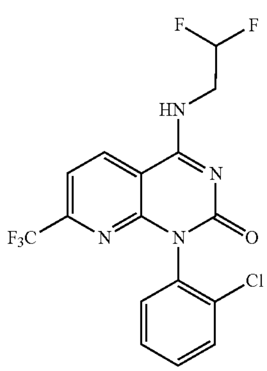 [SMILES: O=c1nc(NCC(F)F)c2ccc(C(F)(F)F)nc2n1-c1ccccc1Cl] | 1-(2-chlorophenyl)-4-[(2,2-difluoroethyl)amino]-7-(trifluoromethyl)-pyrido[2,3-d]-pyrimidin-2(1H)-one | m/z [M + H]+ 405.1 |

TABLE 1-continued

| Cpd. No. | Structure | Name | Mass Spec. |
|---|---|---|---|
| 90 | 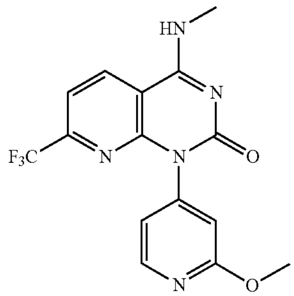 [SMILES: CNc1nc(=O)n(-c2ccnc(OC)c2)c2nc(C(F)(F)F)ccc12] | 1-(2-methoxypyridin-4-yl)-4-(methylamino)-7-(trifluoromethyl)pyrido[2,3-d]-pyrimidin-2(1H)-one | m/z [M + H]+ 352.0 |
| 91 | 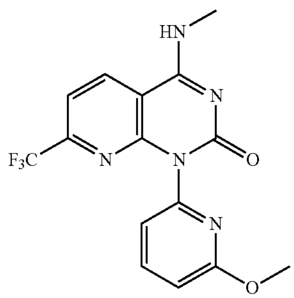 [SMILES: CNc1nc(=O)n(-c2cccc(OC)n2)c2nc(C(F)(F)F)ccc12] | 1-(6-methoxypyridin-2-yl)-4-(methylamino)-7-(trifluoromethyl)-pyrido[2,3-d]pyrimidin-2(1H)-one | m/z [M + H]+ 352.0 |
| 92 | 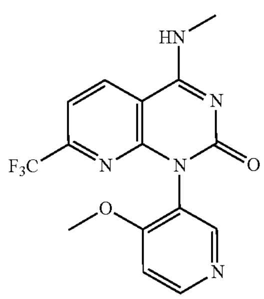 [SMILES: CNc1nc(=O)n(-c2cnccc2OC)c2nc(C(F)(F)F)ccc12] | 1-(4-methoxypyridin-3-yl)-4-(methylamino)-7-(trifluoromethyl)pyrido[2,3-d]pyrimidin-2(1H)-one | m/z [M + H]+ 352.0 |
| 93 | 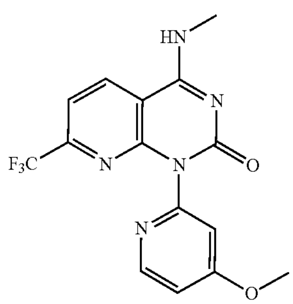 [SMILES: CNc1nc(=O)n(-c2cc(OC)ccn2)c2nc(C(F)(F)F)ccc12] | 1-(4-methoxypyridin-2-yl)-4-(methylamino)-7-(trifluoromethyl)pyrido[2,3-d]pyrimidin-2(1H)-one | m/z [M + H]+ 352.0 |
| 94 | 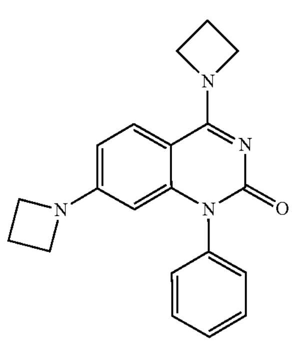 [SMILES: O=c1nc(N2CCC2)c2ccc(N3CCC3)cc2n1-c1ccccc1] | 4,7-di(azetidin-1-yl)-1-phenylhydroquinazolin-2-one | m/z [M + H]+ 333.2 |

TABLE 1-continued

| Cpd. No. | Structure | Name | Mass Spec. |
|---|---|---|---|
| 94 | 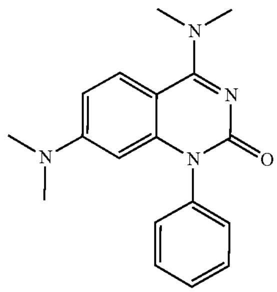 [SMILES: CN(C)c1ccc2c(N(C)C)nc(=O)n(-c3ccccc3)c2c1] | 4,7-bis(dimethylamino)-1-phenylhydro-quinazolin-2-one | m/z [M + H]+ 309.2 |
| 96 | 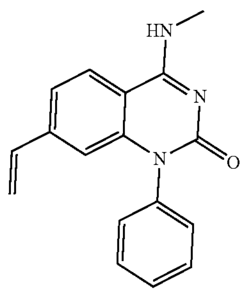 [SMILES: C=Cc1ccc2c(NC)nc(=O)n(-c3ccccc3)c2c1] | 4-(methylamino)-1-phenyl-7-vinylhydro-quinazolin-2-one | m/z [M + H]+ 278.15 |
| 97 | 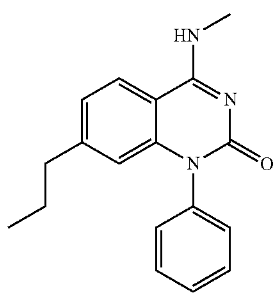 [SMILES: CCCc1ccc2c(NC)nc(=O)n(-c3ccccc3)c2c1] | 4-(methylamino)-1-phenyl-7-propylhydroquinazolin-2-one | m/z [M + H]+ 294.2 |
| 99 | 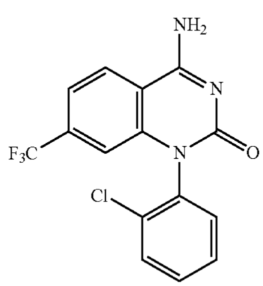 [SMILES: Nc1nc(=O)n(-c2ccccc2Cl)c2cc(C(F)(F)F)ccc12] | 4-amino-1-(2-chlorophenyl)-7-(trifluoromethyl)hydroquinazolin-2-one | m/z [M + H]+ 340.0 |
| 100 | 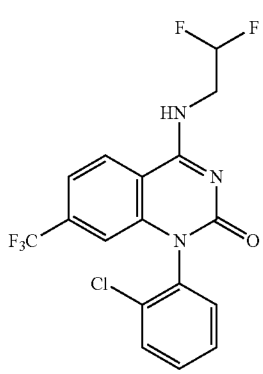 [SMILES: O=c1nc(NCC(F)F)c2ccc(C(F)(F)F)cc2n1-c1ccccc1Cl] | 1-(2-chlorophenyl)-4-[(2,2-difluoroethyl)amino]-7-(trifluoromethyl)hydroquinazolin-2-one | m/z [M + H]+ 404.0 |

TABLE 1-continued

| Cpd. No. | Structure | Name | Mass Spec. |
|---|---|---|---|
| 101 | 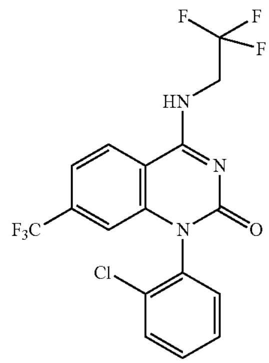 [SMILES: O=c1nc(NCC(F)(F)F)c2ccc(C(F)(F)F)cc2n1-c1ccccc1Cl] | 1-(2-chlorophenyl)-4-[(2,2,2-trifluoro-ethyl)amino]-7-(trifluoromethyl)hydro-quinazolin-2-one | m/z [M + H]+ 422.0 |
| 102 | 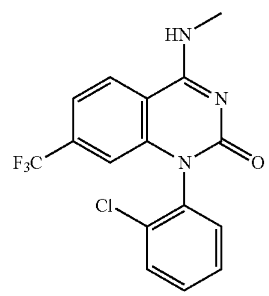 [SMILES: CNc1nc(=O)n(-c2ccccc2Cl)c2cc(C(F)(F)F)ccc12] | 1-(2-chlorophenyl)-4-(methylamino)-7-(trifluoromethyl)hydroquinazolin-2-one | m/z [M + H]+ 354.1 |
| 103 | 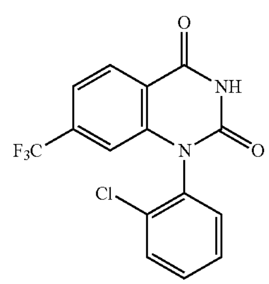 [SMILES: O=c1[nH]c(=O)n(-c2ccccc2Cl)c2cc(C(F)(F)F)ccc12] | 1-(2-chlorophenyl)-7-(trifluoromethyl)-1,3-dihydroquinazoline-2,4-dione | m/z [M + H]+ 341.0 |
| 104 | 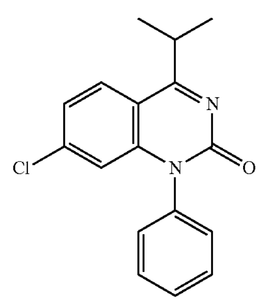 [SMILES: CC(C)c1nc(=O)n(-c2ccccc2)c2cc(Cl)ccc12] | 7-chloro-4-(methylethyl)-1-phenylhydro-quinazolin-2-one | m/z [M + H]+ 299.19 |
| 105 | 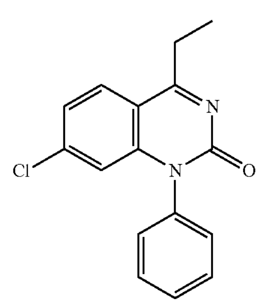 [SMILES: CCc1nc(=O)n(-c2ccccc2)c2cc(Cl)ccc12] | 7-chloro-4-ethyl-1-phenylhydro-quinazolin-2-one | m/z [M + H]+ 285.21 |

TABLE 1-continued

| Cpd. No. | Structure | Name | Mass Spec. |
|---|---|---|---|
| 106 | 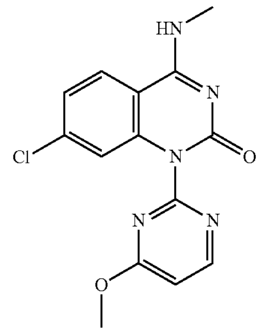 [SMILES: CNc1nc(=O)n(-c2nccc(OC)n2)c2cc(Cl)ccc12] | 7-chloro-1-(4-methoxypyrimidin-2-yl)-4-(methylamino)hydroquinazolin-2-one | m/z [M + H]+ 318.12 |
| 107 | 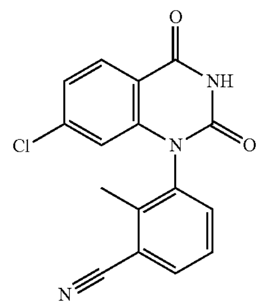 [SMILES: Cc1c(C#N)cccc1-n1c(=O)[nH]c(=O)c2ccc(Cl)cc21] | 3-(7-chloro-2,4-dioxo-3,4-dihydro-quinazolin-1(2H)-yl)-2-methyl-benzonitrile | m/z [M + H]+ 310.13 |
| 108 | 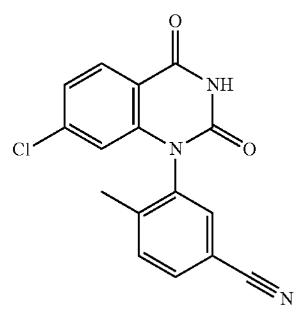 [SMILES: Cc1ccc(C#N)cc1-n1c(=O)[nH]c(=O)c2ccc(Cl)cc21] | 3-(7-chloro-2,4-dioxo-3,4-dihydro-quinazolin-1(2H)-yl)-4-methyl-benzonitrile | m/z [M + H]+ 310.06 |
| 109 | 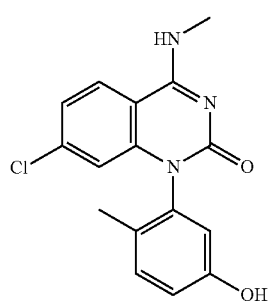 [SMILES: CNc1nc(=O)n(-c2cc(O)ccc2C)c2cc(Cl)ccc12] | 7-chloro-1-(3-hydroxy-6-methylphenyl)-4-(methylamino)hydroquinazolin-2-one | m/z [M + H]+ 316.18 |
| 110 | 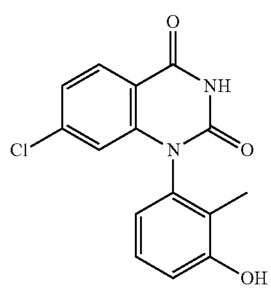 [SMILES: Cc1c(O)cccc1-n1c(=O)[nH]c(=O)c2ccc(Cl)cc21] | 7-chloro-1-(3-hydroxy-2-methylphenyl)-1,3-dihydroquinazoline-2,4-dione | m/z [M + H]+ 303.13 |

TABLE 1-continued

| Cpd. No. | Structure | Name | Mass Spec. |
|---|---|---|---|
| 112 | 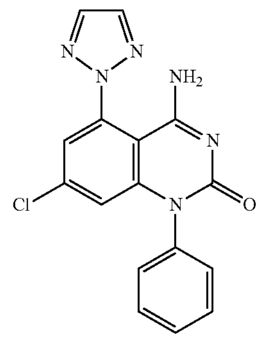 [SMILES: Nc1nc(=O)n(-c2ccccc2)c2cc(Cl)cc(-n3nccn3)c12] | 4-amino-7-chloro-1-phenyl-5-(1,2,3-triazol-2-yl)hydroquinazolin-2-one | m/z [M + H]+ 339.11 |
| 113 | 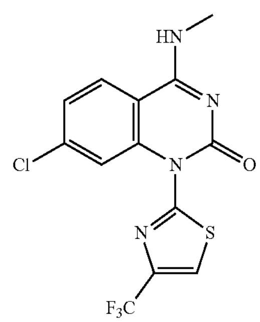 [SMILES: CNc1nc(=O)n(-c2nc(C(F)(F)F)cs2)c2cc(Cl)ccc12] | 7-chloro-4-(methylamino)-1-[4-(trifluoromethyl)(1,3-thiazol-2-yl)]hydroquinazolin-2-one | m/z [M + H]+ 361.0 |
| 114 | 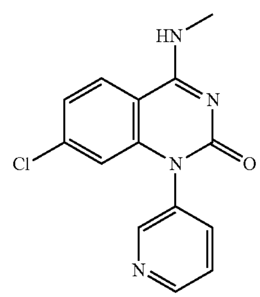 [SMILES: CNc1nc(=O)n(-c2cccnc2)c2cc(Cl)ccc12] | 7-chloro-4-(methylamino)-1-(3-pyridyl)-hydroquinazolin-2-one | m/z [M + H]+ 287.1 |
| 115 | 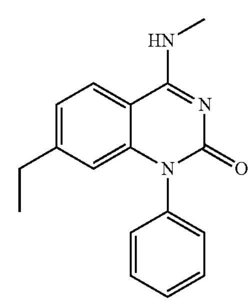 [SMILES: CCc1ccc2c(NC)nc(=O)n(-c3ccccc3)c2c1] | 7-ethyl-4-(methylamino)-1-phenylhydro-quinazolin-2-one | m/z [M + H]+ 280.1 |
| 116 | 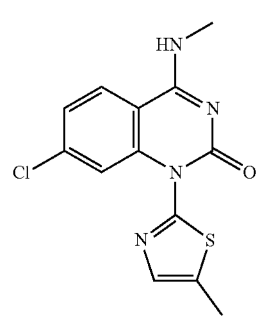 [SMILES: CNc1nc(=O)n(-c2ncc(C)s2)c2cc(Cl)ccc12] | 7-chloro-1-(5-methyl(1,3-thiazol-2-yl))-4-(methylamino)hydroquinazolin-2-one | m/z [M + H]+ 307.0 |

TABLE 1-continued

| Cpd. No. | Structure | Name | Mass Spec. |
|---|---|---|---|
| 117 | 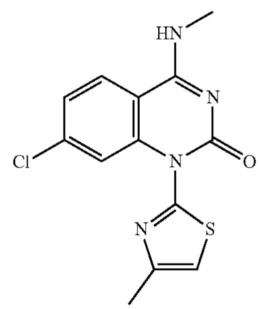 [SMILES: CNc1nc(=O)n(-c2nc(C)cs2)c2cc(Cl)ccc12] | 7-chloro-1-(4-methyl(1,3-thiazol-2-yl))-4-(methylamino)hydroquinazolin-2-one | m/z [M + H]+ 307.0 |
| 118 | 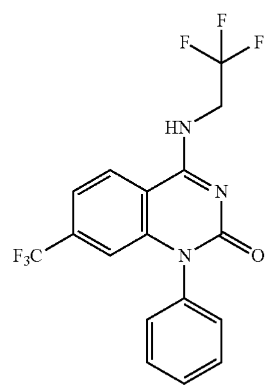 [SMILES: O=c1nc(NCC(F)(F)F)c2ccc(C(F)(F)F)cc2n1-c1ccccc1] | 1-phenyl-4-[(2,2,2-trifluoroethyl)amino]-7-(trifluoromethyl)hydroquinazolin-2-one | m/z [M + H]+ 388.0 |
| 119 | 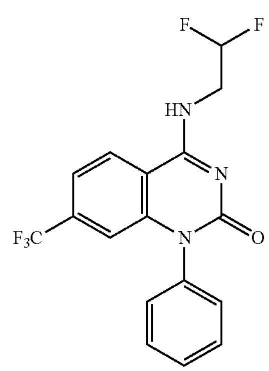 [SMILES: O=c1nc(NCC(F)F)c2ccc(C(F)(F)F)cc2n1-c1ccccc1] | 4-[(2,2-difluoroethyl)amino]-1-phenyl-7-(trifluoromethyl)hydroquinazolin-2-one | m/z [M + H]+ 370.0 |
| 120 | 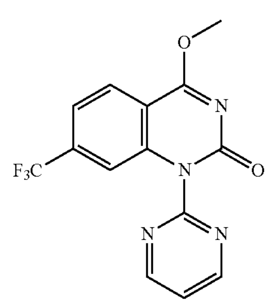 [SMILES: COc1nc(=O)n(-c2ncccn2)c2cc(C(F)(F)F)ccc12] | 4-methoxy-1-pyrimidin-2-yl-7-(trifluoro-methyl)hydroquinazolin-2-one | m/z [M + H]+ 323.0 |

TABLE 1-continued

| Cpd. No. | Structure | Name | Mass Spec. |
|---|---|---|---|
| 121 | 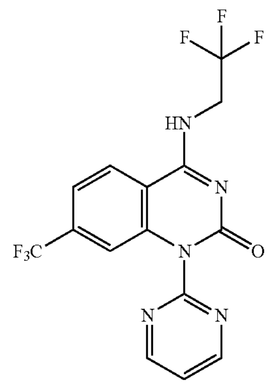 [SMILES: O=c1nc(NCC(F)(F)F)c2ccc(C(F)(F)F)cc2n1-c1ncccn1] | 1-pyrimidin-2-yl-4-[(2,2,2-trifluoro-ethyl)amino]-7-(trifluoromethyl)hydro-quinazolin-2-one | m/z [M + H]+ 390.0 |
| 122 | 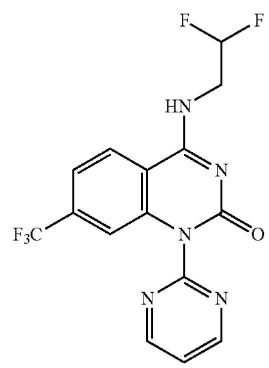 [SMILES: O=c1nc(NCC(F)F)c2ccc(C(F)(F)F)cc2n1-c1ncccn1] | 4-[(2,2-difluoroethyl)amino]-1-pyrimidin-2-yl-7-(trifluoromethyl)hydro-quinazolin-2-one | m/z [M + H]+ 372.0 |
| 123 | 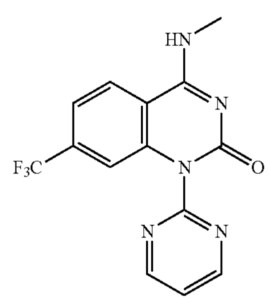 [SMILES: CNc1nc(=O)n(-c2ncccn2)c2cc(C(F)(F)F)ccc12] | 4-(methylamino)-1-pyrimidin-2-yl-7-(trifluoromethyl)hydroquinazolin-2-one | m/z [M + H]+ 322.0 |
| 124 | 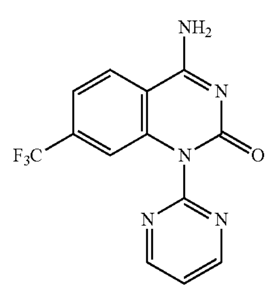 [SMILES: Nc1nc(=O)n(-c2ncccn2)c2cc(C(F)(F)F)ccc12] | 4-amino-1-pyrimidin-2-yl-7-(trifluoromethyl)hydroquinazolin-2-one | m/z [M + H]+ 308.0 |

TABLE 1-continued

| Cpd. No. | Structure | Name | Mass Spec. |
|---|---|---|---|
| 125 | 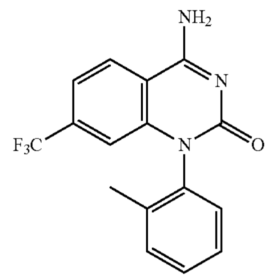 [SMILES: Cc1ccccc1-n1c(=O)nc(N)c2ccc(C(F)(F)F)cc21] | 4-amino-1-(2-methylphenyl)-7-(trifluoromethyl)hydroquinazolin-2-one | m/z [M + H]+ 320.0 |
| 126 | 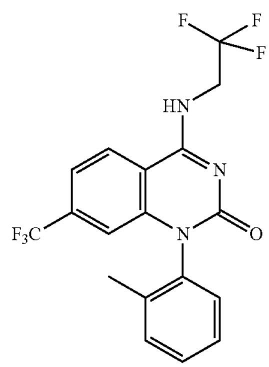 [SMILES: Cc1ccccc1-n1c(=O)nc(NCC(F)(F)F)c2ccc(C(F)(F)F)cc21] | 1-(2-methylphenyl)-4-[(2,2,2-trifluoroethyl)amino]-7-(trifluoromethyl)hydroquinazolin-2-one | m/z [M + H]+ 402.0 |
| 127 | 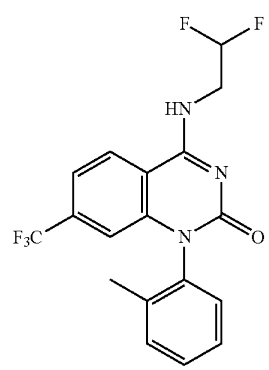 [SMILES: Cc1ccccc1-n1c(=O)nc(NCC(F)F)c2ccc(C(F)(F)F)cc21] | 4-[(2,2-difluoroethyl)amino]-1-(2-methylphenyl)-7-(trifluoromethyl)hydro-quinazolin-2-one | m/z [M + H]+ 384.0 |
| 128 | 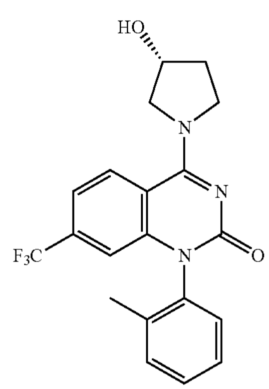 [SMILES: Cc1ccccc1-n1c(=O)nc(N2CC[C@@H](O)C2)c2ccc(C(F)(F)F)cc21] | 4-((3R)-3-hydroxypyrrolidin-1-yl)-1-(2-methylphenyl)-7-(trifluoromethyl)hydro-quinazolin-2-one | m/z [M + H]+ 390.0 |

TABLE 1-continued

| Cpd. No. | Structure | Name | Mass Spec. |
|---|---|---|---|
| 129 | 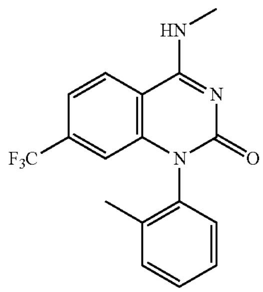 [SMILES: CNc1nc(=O)n(-c2ccccc2C)c2cc(C(F)(F)F)ccc12] | 4-(methylamino)-1-(2-methylphenyl)-7-(trifluoromethyl)hydroquinazolin-2-one | m/z [M + H]+ 334.0 |
| 130 | 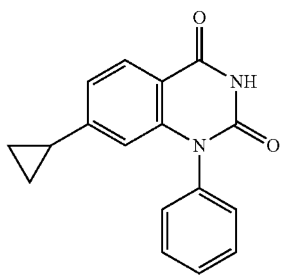 [SMILES: O=c1[nH]c(=O)n(-c2ccccc2)c2cc(C3CC3)ccc12] | 7-cyclopropyl-1-phenyl-1,3-dihydro-quinazoline-2,4-dione | m/z [M + H]+ 279.21 |
| 132 | 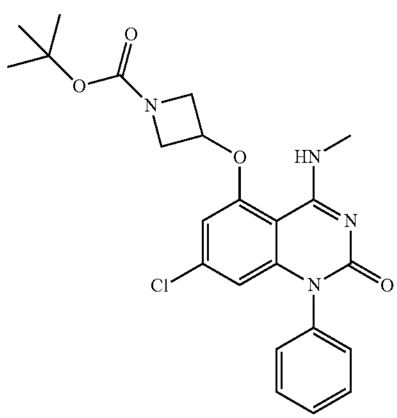 [SMILES: CNc1nc(=O)n(-c2ccccc2)c2cc(Cl)cc(OC3CN(C(=O)OC(C)(C)C)C3)c12] | tert-butyl 3-[7-chloro-4-(methylamino)-2-oxo-1-phenylhydroquinazolin-5-yl-oxy]azetidinecarboxylate | m/z [M + H]+ 457.13 |
| 133 | 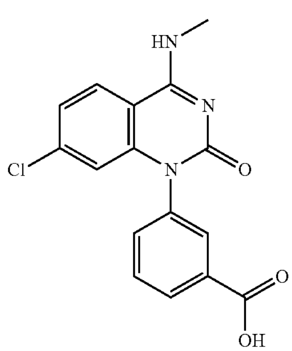 [SMILES: CNc1nc(=O)n(-c2cccc(C(=O)O)c2)c2cc(Cl)ccc12] | 3-[7-chloro-4-(methylamino)-2-oxo-hydroquinazolin-1-yl]benzoic acid | m/z [M + H]+ 330.11 |

TABLE 1-continued
| Cpd. No. | Structure | Name | Mass Spec. |
|---|---|---|---|
| 134 | 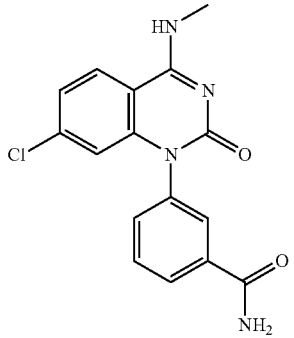 [SMILES: CNc1nc(=O)n(-c2cccc(C(N)=O)c2)c2cc(Cl)ccc12] | 3-[7-chloro-4-(methylamino)-2-oxo-hydroquinazolin-1-yl]benzamide | m/z [M + H]+ 329.11 |
| 135 | 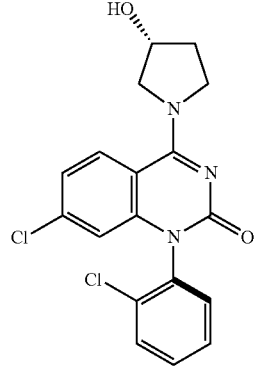 | 4-((3R)-3-hydroxypyrrolidin-1-yl)-7-chloro-1-(2-chlorophenyl)hydro-quinazolin-2-one | m/z [M + H]+ 376.10 |
| 136 | 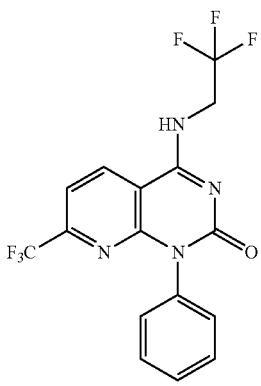 | 1-phenyl-4-((2,2,2-trifluoroethyl)amino)-7-(trifluoromethyl)pyrido[2,3-d]-pyrimidin-2(1H)-one | m/z [M + H]+ 389.0 |
| 137 | 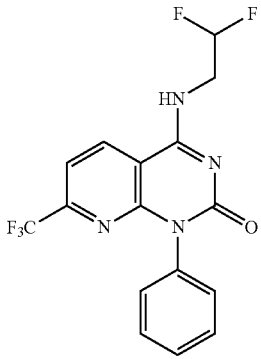 [SMILES: O=c1nc(NCC(F)F)c2ccc(C(F)(F)F)nc2n1-c1ccccc1] | 4-((2,2-difluoroethyl)amino)-1-phenyl-7-(trifluoromethyl)pyrido[2,3-d]pyrimidin-2(1H)-one | m/z [M + H]+ 371.0 |

TABLE 1-continued

| Cpd. No. | Structure | Name | Mass Spec. |
|---|---|---|---|
| 138 | 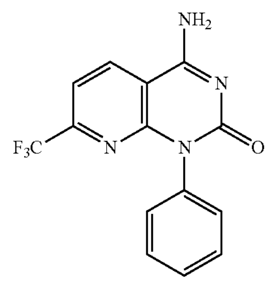 [SMILES: Nc1nc(=O)n(-c2ccccc2)c2nc(C(F)(F)F)ccc12] | 4-amino-1-phenyl-7-(trifluoromethyl)-hydropyridino[2,3-d]pyrimidin-2-one | m/z [M + H]+ 307.0 |
| 139 | 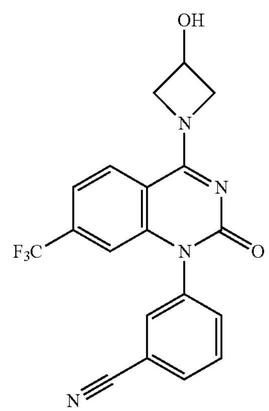 [SMILES: N#Cc1cccc(-n2c(=O)nc(N3CC(O)C3)c3ccc(C(F)(F)F)cc32)c1] | 3-[4-(3-hydroxyazetidinyl)-2-oxo-7-(trifluoromethyl)hydroquinazolinyl]-benzenecarbonitrile | m/z [M + H]+ 387.0 |
| 140 | 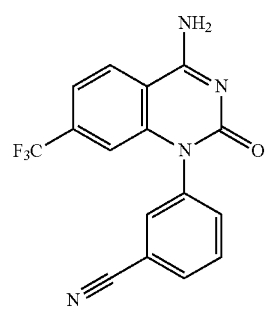 [SMILES: N#Cc1cccc(-n2c(=O)nc(N)c3ccc(C(F)(F)F)cc32)c1] | 3-[4-amino-2-oxo-7-(trifluoromethyl)-hydroquinazolinyl]benzenecarbonitrile | m/z [M + H]+ 331.0 |
| 141 | 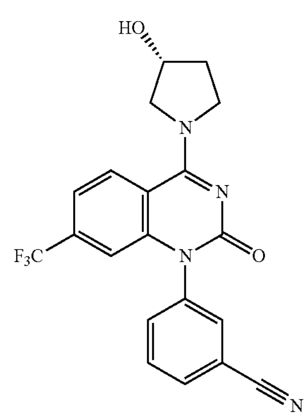 [SMILES: N#Cc1cccc(-n2c(=O)nc(N3CC[C@@H](O)C3)c3ccc(C(F)(F)F)cc32)c1] | 3-[4-((3R)-3-hydroxypyrrolidinyl)-2-oxo-7-(trifluoromethyl)hydro-quinazolinyl]-benzenecarbonitrile | m/z [M + H]+ 401.1 |

TABLE 1-continued

| Cpd. No. | Structure | Name | Mass Spec. |
|---|---|---|---|
| 142 | 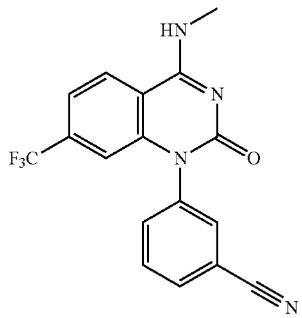 | 3-[4-(methylamino)-2-oxo-7-(trifluoromethyl)hydroquinazolinyl]benzenecarbonitrile | m/z [M + H]+ 345.1 |
| 143 | 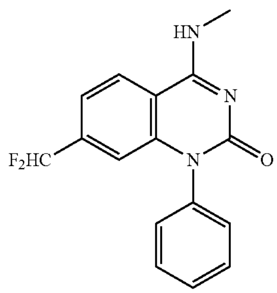 [SMILES: CNc1nc(=O)n(-c2ccccc2)c2cc(C(F)F)ccc12] | 7-(difluoromethyl)-4-(methylamino)-1-phenylhydroquinazolin-2-one | m/z [M + H]+ 302.0 |
| 144 | 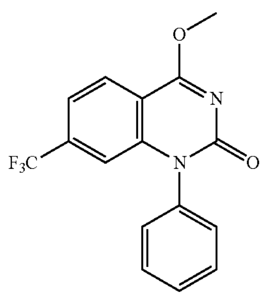 [SMILES: COc1nc(=O)n(-c2ccccc2)c2cc(C(F)(F)F)ccc12] | 4-methoxy-1-phenyl-7-(trifluoromethyl)-hydroquinazolin-2-one | m/z [M + H]+ 321.0 |
| 145 | 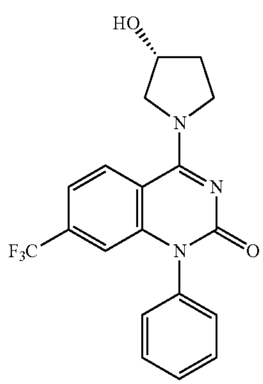 [SMILES: O=c1nc(N2CC[C@@H](O)C2)c2ccc(C(F)(F)F)cc2n1-c1ccccc1] | 4-((3R)-3-hydroxypyrrolidinyl)-1-phenyl-7-(trifluoromethyl)hydroquinazolin-2-one | m/z [M + H]+ 376.0 |
| 146 | 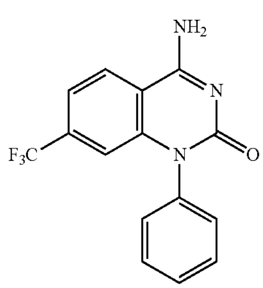 [SMILES: Nc1nc(=O)n(-c2ccccc2)c2cc(C(F)(F)F)ccc12] | 4-amino-1-phenyl-7-(trifluoromethyl)-hydroquinazolin-2-one | m/z [M + H]+ 306.0 |

TABLE 1-continued

| Cpd. No. | Structure | Name | Mass Spec. |
|---|---|---|---|
| 147 | 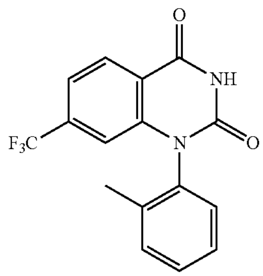 [SMILES: Cc1ccccc1-n1c(=O)[nH]c(=O)c2ccc(C(F)(F)F)cc21] | 1-(2-methylphenyl)-7-(trifluoromethyl)-1,3-dihydroquinazoline-2,4-dione | m/z [M + H]+ 321.0 |
| 148 | 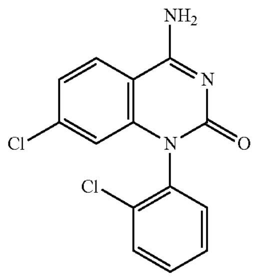 [SMILES: Nc1nc(=O)n(-c2ccccc2Cl)c2cc(Cl)ccc12] | 4-amino-7-chloro-1-(2-chlorophenyl)-hydroquinazolin-2-one | m/z [M + H]+ 307.06 |
| 149 | 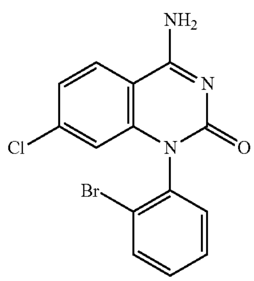 [SMILES: Nc1nc(=O)n(-c2ccccc2Br)c2cc(Cl)ccc12] | 4-amino-1-(2-bromophenyl)-7-chloro-hydroquinazolin-2-one | m/z [M + H]+ 349.98 |
| 150 | 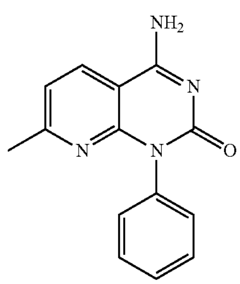 | 4-amino-7-methyl-1-phenylhydro-pyridino[2,3-d]pyrimidin-2-one | m/z [M + H]+ 353.24 |
| 151 | 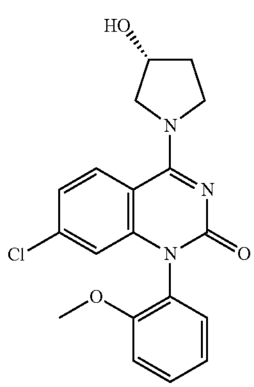 [SMILES: COc1ccccc1-n1c(=O)nc(N2CC[C@@H](O)C2)c2ccc(Cl)cc21] | 4-((3R)-3-hydroxypyrrolidin-1-yl)-7-chloro-1-(2-methoxyphenyl)hydro-quinazolin-2-one | m/z [M + H]+ 372.10 |

TABLE 1-continued

| Cpd. No. | Structure | Name | Mass Spec. |
| --- | --- | --- | --- |
| 153 | 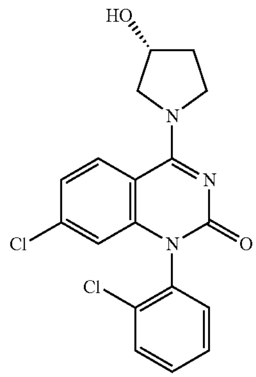 [SMILES: O=c1nc(N2CC[C@@H](O)C2)c2ccc(Cl)cc2n1-c1ccccc1Cl] | 4-((3R)-3-hydroxypyrrolidin-1-yl)-7-chloro-1-(2-chlorophenyl)hydroquinazolin-2-one | m/z [M + H]+ 376.04 |
| 154 | 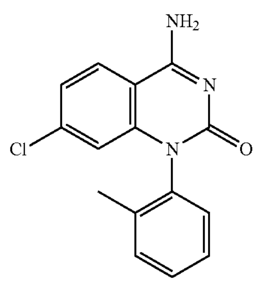 | 4-amino-7-chloro-1-(2-methylphenyl)-hydroquinazolin-2-one | m/z [M + H]+ 386.0 |
| 155 | 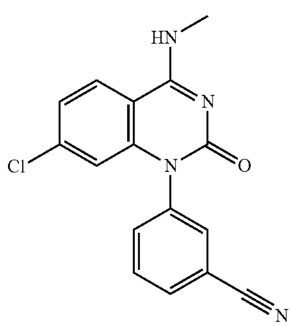 [SMILES: CNc1nc(=O)n(-c2cccc(C#N)c2)c2cc(Cl)ccc12] | 3-[7-chloro-4-(methylamino)-2-oxo-hydroquinazolinyl]benzenecarbonitrile | m/z [M + H]+ 311.12 |
| 156 | 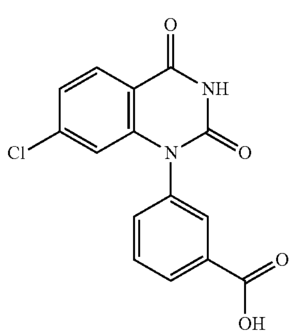 [SMILES: O=C(O)c1cccc(-n2c(=O)[nH]c(=O)c3ccc(Cl)cc32)c1] | 3-(7-chloro-4-hydroxy-2-oxohydroquinazolinyl)benzoic acid | m/z [M + H]+ 317.06 |

TABLE 1-continued

| Cpd. No. | Structure | Name | Mass Spec. |
|---|---|---|---|
| 157 | 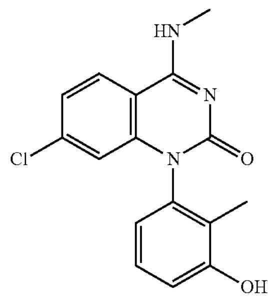 [SMILES: CNc1nc(=O)n(-c2cccc(O)c2C)c2cc(Cl)ccc12] | 7-chloro-1-(3-hydroxy-2-methylphenyl)-4-(methylamino)hydroquinazolin-2-one | m/z [M + H]+ 316.12 |
| 159 | 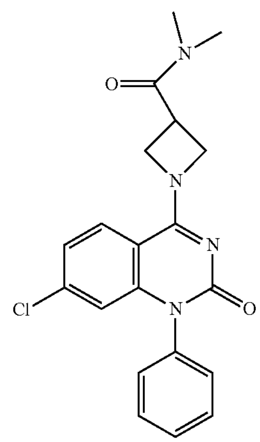 [SMILES: CN(C)C(=O)C1CN(c2nc(=O)n(-c3ccccc3)c3cc(Cl)ccc23)C1] | [1-(7-chloro-2-oxo-1-phenylhydroquinazolin-4-yl)azetidin-3-yl]-N,N-dimethylcarboxamide | m/z [M + H]+ 383.1 |
| 160 | 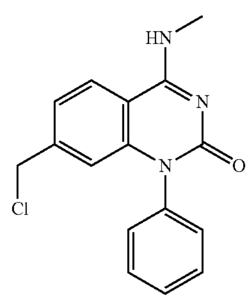 [SMILES: CNc1nc(=O)n(-c2ccccc2)c2cc(CCl)ccc12] | 7-(chloromethyl)-4-(methylamino)-1-phenylhydroquinazolin-2-one | m/z [M + H]+ 300.0 |
| 161 | 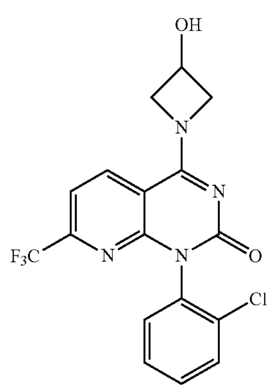 [SMILES: O=c1nc(N2CC(O)C2)c2ccc(C(F)(F)F)nc2n1-c1ccccc1Cl] | 1-(2-chlorophenyl)-4-(3-hydroxyazetidinyl)-7-(trifluoromethyl)pyrido[2,3-d]pyrimidin-2(1H)-one | m/z [M + H]+ 397.1 |

TABLE 1-continued

| Cpd. No. | Structure | Name | Mass Spec. |
|---|---|---|---|
| 162 | 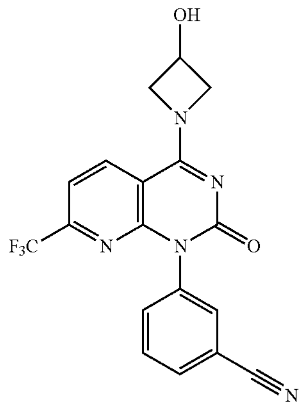 [SMILES: N#Cc1cccc(-n2c(=O)nc(N3CC(O)C3)c3ccc(C(F)(F)F)nc32)c1] | 3-(4-(3-hydroxyazetidin-1-yl)-2-oxo-7-(trifluoromethyl)pyrido[2,3-d]pyrimidin-1(2H)-yl)benzonitrile | m/z [M + H]+ 388.1 |
| 163 | 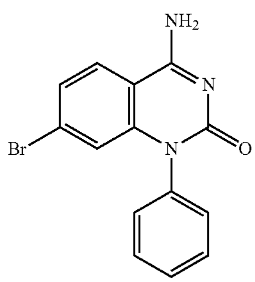 [SMILES: Nc1nc(=O)n(-c2ccccc2)c2cc(Br)ccc12] | 4-amino-7-bromo-1-phenylhydroquinazolin-2-one | m/z [M + H]+ 316.0 |
| 164 | 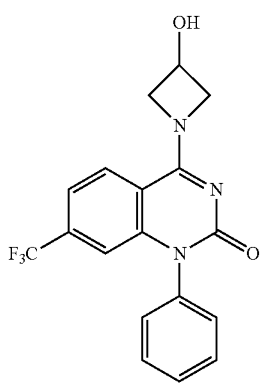 [SMILES: O=c1nc(N2CC(O)C2)c2ccc(C(F)(F)F)cc2n1-c1ccccc1] | 4-(3-hydroxyazetidin-1-yl)-1-phenyl-7-(trifluoromethyl)pyrido[2,3-d]pyrimidin-2(1H)-one | m/z [M + H]+ 362.0 |
| 165 | 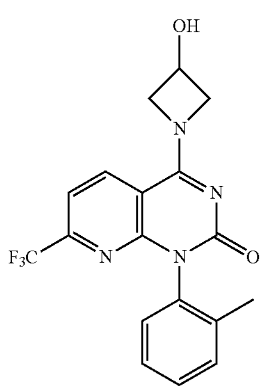 [SMILES: Cc1ccccc1-n1c(=O)nc(N2CC(O)C2)c2ccc(C(F)(F)F)nc21] | 4-(3-hydroxyazetidinyl)-1-(2-methylphenyl)-7-(trifluoromethyl)pyrido[2,3-d]pyrimidin-2(1H)-one | m/z [M + H]+ 377.24 |

TABLE 1-continued

| Cpd. No. | Structure | Name | Mass Spec. |
|---|---|---|---|
| 166 | 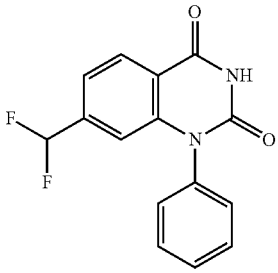 [SMILES: O=c1[nH]c(=O)n(-c2ccccc2)c2cc(C(F)F)ccc12] | 7-(difluoromethyl)-1-phenyl-1,3-dihydroquinazoline-2,4-dione | m/z [M + H]+ 289.0 |
| 167 | 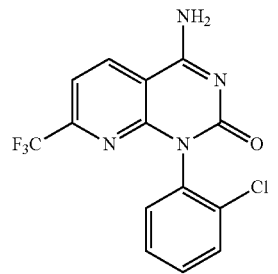 [SMILES: Nc1nc(=O)n(-c2ccccc2Cl)c2nc(C(F)(F)F)ccc12] | 4-amino-1-(2-chlorophenyl)-7-(trifluoro-methyl)pyrido[2,3-d]pyrimidin-2(1H)-one | m/z [M + H]+ 341.10 |
| 168 | 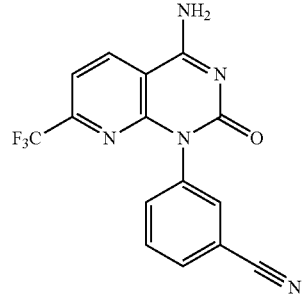 [SMILES: N#Cc1cccc(-n2c(=O)nc(N)c3ccc(C(F)(F)F)nc32)c1] | 3-(4-amino-2-oxo-7-(trifluoromethyl)-pyrido[2,3-d]pyrimidin-1(2H)-yl)-benzonitrile | m/z [M + H]+ 332.10 |
| 169 | 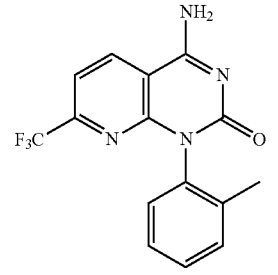 [SMILES: Cc1ccccc1-n1c(=O)nc(N)c2ccc(C(F)(F)F)nc21] | 4-amino-1-(2-methylphenyl)-7-(trifluoromethyl)pyrido[2,3-d]pyrimidin-2(1H)-one | m/z [M + H]+ 321.1 |
| 170 | 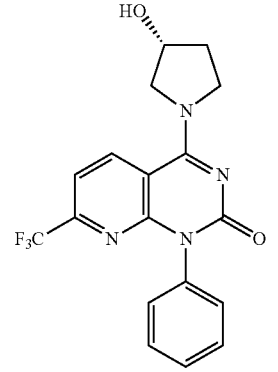 [SMILES: O=c1nc(N2CC[C@@H](O)C2)c2ccc(C(F)(F)F)nc2n1-c1ccccc1] | (R)-4-(3-hydroxypyrrolidin-1-yl)-1-phenyl-7-(trifluoromethyl)pyrido[2,3-d]-pyrimidin-2(1H)-one | m/z [M + H]+ 377.15 |

TABLE 1-continued

| Cpd. No. | Structure | Name | Mass Spec. |
|---|---|---|---|
| 171 | 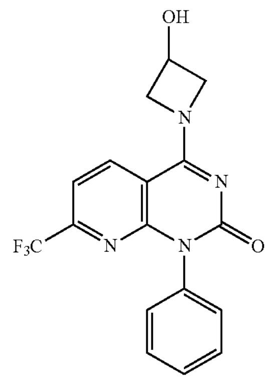 [SMILES: O=c1nc(N2CC(O)C2)c2ccc(C(F)(F)F)nc2n1-c1ccccc1] | 4-(3-hydroxyazetidin-1-yl)-1-phenyl-7-(trifluoromethyl)pyrido[2,3-d]pyrimidin-2(1H)-one | m/z [M + H]+ 363.0 |
| 172 | 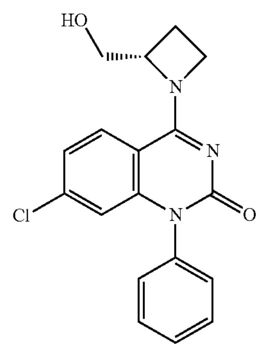 [SMILES: O=c1nc(N2CC[C@H]2CO)c2ccc(Cl)cc2n1-c1ccccc1] | (S)-7-chloro-4-(2-(hydroxymethyl)-azetidin-1-yl)-1-phenylquinazolin-2(1H)-one | m/z [M + H]+ 342.1 |
| 173 | 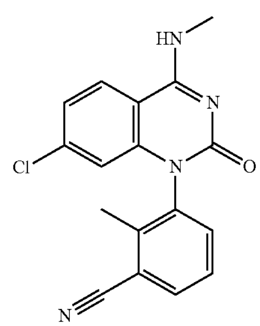 [SMILES: CNc1nc(=O)n(-c2cccc(C#N)c2C)c2cc(Cl)ccc12] | 3-[7-chloro-4-(methylamino)-2-oxo-hydroquinazolinyl]-2-methylbenzene-carbonitrile | m/z [M + H]+ 325.11 |
| 174 | 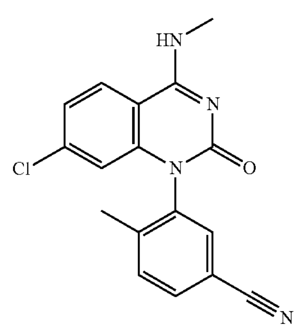 [SMILES: CNc1nc(=O)n(-c2cc(C#N)ccc2C)c2cc(Cl)ccc12] | 3-(7-chloro-4-(methylamino)-2-oxo-quinazolin-1(2H)-yl)-2-methyl-benzonitrile | m/z [M + H]+ 325.11 |

TABLE 1-continued

| Cpd. No. | Structure | Name | Mass Spec. |
|---|---|---|---|
| 175 | 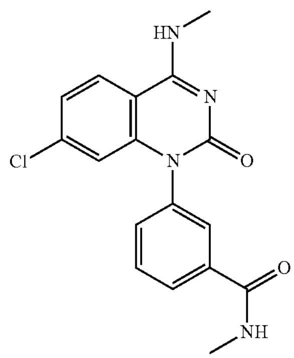 [SMILES: CNC(=O)c1cccc(-n2c(=O)nc(NC)c3ccc(Cl)cc32)c1] | 3-(7-chloro-4-(methylamino)-2-oxo-quinazolin-1(2H)-yl)benzamide | m/z [M + H]+ 343.1 |
| 176 | 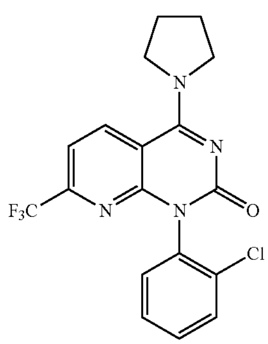 [SMILES: O=c1nc(N2CCCC2)c2ccc(C(F)(F)F)nc2n1-c1ccccc1Cl] | 1-(2-chlorophenyl)-4-(pyrrolidin-1-yl)-7-(trifluoromethyl)pyrido[2,3-d]pyrimidin-2(1H)-one | m/z [M + H]+ 395.10 |
| 177 | 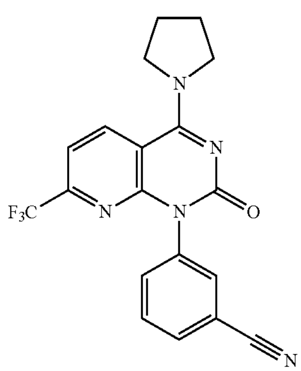 [SMILES: N#Cc1cccc(-n2c(=O)nc(N3CCCC3)c3ccc(C(F)(F)F)nc32)c1] | 3-(2-oxo-4-(pyrrolidin-1-yl)-7-(trifluoro-methyl)pyrido[2,3-d]pyrimidin-1(2H)-yl)benzonitrile | m/z [M + H]+ 385.15 |
| 178 | 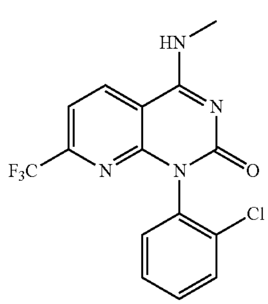 [SMILES: CNc1nc(=O)n(-c2ccccc2Cl)c2nc(C(F)(F)F)ccc12] | 1-(2-chlorophenyl)-4-(methylamino)-7-(trifluoromethyl)pyrido[2,3-d]pyrimidin-2(1H)-one | m/z [M + H]+ 355.10 |

TABLE 1-continued

| Cpd. No. | Structure | Name | Mass Spec. |
|---|---|---|---|
| 179 | 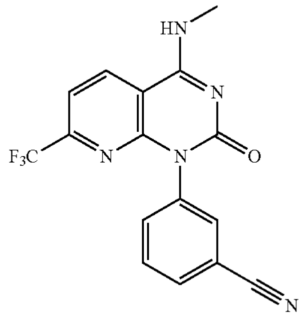 [SMILES: CNc1nc(=O)n(-c2cccc(C#N)c2)c2nc(C(F)(F)F)ccc12] | 3-[4-(methylamino)-2-oxo-7-(trifluoromethyl)pyrido[2,3-d]pyrimidin-1(2H)-yl)benzonitrile | m/z [M + H]+ 346.1 |
| 180 | 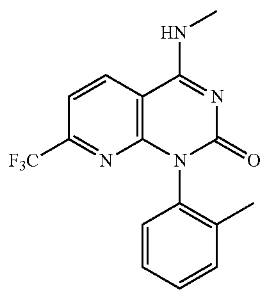 | 4-(methylamino)-1-(2-methylphenyl)-7-(trifluoromethyl)pyrido[2,3-d]pyrimidin-2(1H)-one | m/z [M + H]+ 335.10 |
| 181 | 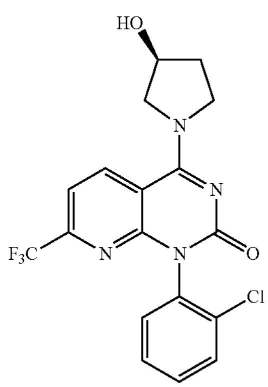 [SMILES: O=c1nc(N2CC[C@H](O)C2)c2ccc(C(F)(F)F)nc2n1-c1ccccc1Cl] | (S)-1-(2-chlorophenyl)-4-(3-hydroxypyrrolidin-1-yl)-7-(trifluoromethyl)pyrido[2,3-d]pyrimidin-2(1H)-one | m/z [M + H]+ 411.10 |
| 182 | 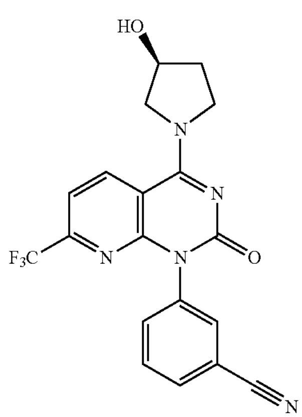 [SMILES: N#Cc1cccc(-n2c(=O)nc(N3CC[C@H](O)C3)c3ccc(C(F)(F)F)nc32)c1] | (S)-3-(4-(3-hydroxypyrrolidin-1-yl)-2-oxo-7-(trifluoromethyl)pyrido[2,3-d]pyrimidin-1(2H)-yl)benzonitrile | m/z [M + H]+ 402.1 |

TABLE 1-continued

| Cpd. No. | Name | Mass Spec. |
|---|---|---|
| 183 | (R)-4-(3-hydroxypyrrolidin-1-yl)-1-(o-tolyl)-7-(trifluoromethyl)pyrido[2,3-d]-pyrimidin-2(1H)-one | m/z [M + H]+ 391.2 |
| 184 | 4-(methylamino)-1-phenyl-7-(trifluoromethyl)pyrido[2,3-d]-pyrimidin-2(1H)-one | m/z [M + H]+ 321.1 |
| 185 | 7-chloro-5-(2-hydroxyethoxy)-4-(methylamino)-1-phenylhydroquinazolin-2-one | m/z [M + H]+ 346.17 |
| 186 | 7-chloro-4-[2-(hydroxymethyl)azetidin-1-yl]-1-phenylhydroquinazolin-2-one | m/z [M + H]+ 342.17 |

TABLE 1-continued

| Cpd. No. | Structure | Name | Mass Spec. |
|---|---|---|---|
| 187 | 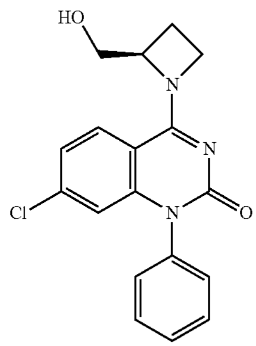 [SMILES: O=c1nc(N2CC[C@@H]2CO)c2ccc(Cl)cc2n1-c1ccccc1] | (R)-7-chloro-4-(2-(hydroxymethyl)-azetidin-1-yl)-1-phenylquinazolin-2(1H)-one | m/z [M + H]+ 342.17 |
| 188 | 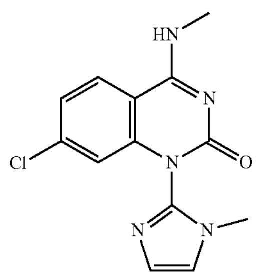 [SMILES: CNc1nc(=O)n(-c2nccn2C)c2cc(Cl)ccc12] | 7-chloro-4-(methylamino)-1-(1-methyl-imidazol-2-yl)hydroquinazolin-2-one | m/z [M + H]+ 290.0 |
| 189 | 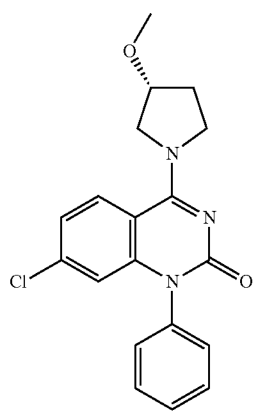 [SMILES: CO[C@@H]1CCN(c2nc(=O)n(-c3ccccc3)c3cc(Cl)ccc23)C1] | (R)-7-chloro-4-(3-methoxypyrrolidin-1-yl)-1-phenylquinazolin-2(1H)-one | m/z [M + H]+ 356.24 |
| 190 | 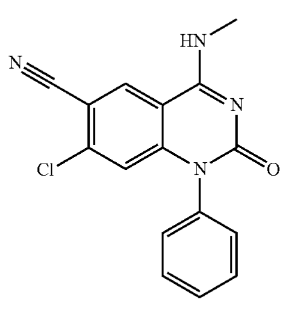 [SMILES: CNc1nc(=O)n(-c2ccccc2)c2cc(Cl)c(C#N)cc12] | 7-chloro-4-(methylamino)-2-oxo-1-phenylhydroquinazoline-6-carbonitrile | m/z [M + H]+ 311.18 |
| 191 | 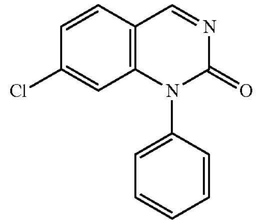 [SMILES: O=c1ncc2ccc(Cl)cc2n1-c1ccccc1] | 7-chloro-1-phenylhydroquinazolin-2-one | m/z [M + H]+ 257.26 |

TABLE 1-continued

| Cpd. No. | Structure | Name | Mass Spec. |
|---|---|---|---|
| 192 | 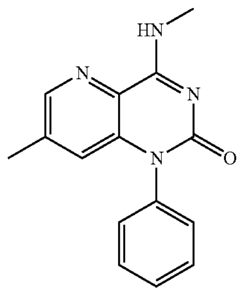 [SMILES: CNc1nc(=O)n(-c2ccccc2)c2cc(C)cnc12] | 7-methyl-4-(methylamino)-1-phenyl-pyrido[3,2-d]pyrimidin-2(1H)-one | m/z [M + H]+ 267.29 |
| 193 | 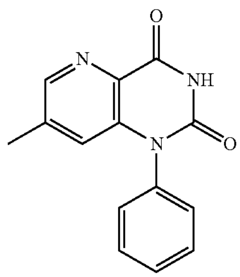 [SMILES: Cc1cnc2c(=O)[nH]c(=O)n(-c3ccccc3)c2c1] | 7-methyl-1-phenylpyrido[3,2-d]-pyrimidine-2,4(1H,3H)-dione | m/z [M + H]+ 254.24 |
| 194 | 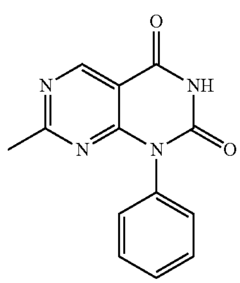 [SMILES: Cc1ncc2c(=O)[nH]c(=O)n(-c3ccccc3)c2n1] | 7-methyl-1-phenylpyrimido[4,5-d]-pyrimidine-2,4(1H,3H)-dione | m/z [M + H]+ 254.26 |
| 195 | 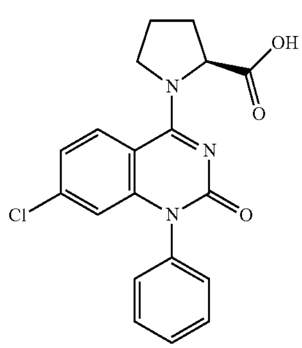 [SMILES: O=C(O)[C@@H]1CCCN1c1nc(=O)n(-c2ccccc2)c2cc(Cl)ccc12] | (2S)-1-(7-chloro-2-oxo-1-phenylhydro-quinazolin-4-yl)pyrrolidine-2-carboxylic acid | m/z [M + H]+ 370.12 |

TABLE 1-continued

| Cpd. No. | Structure | Name | Mass Spec. |
|---|---|---|---|
| 196 | 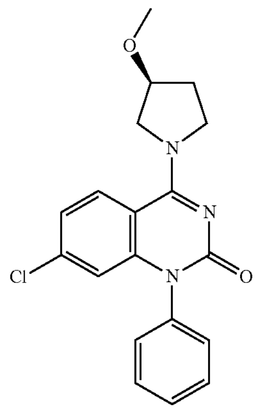 [SMILES: CO[C@H]1CCN(c2nc(=O)n(-c3ccccc3)c3cc(Cl)ccc23)C1] | (S)-7-chloro-4-(3-methoxypyrrolidin-1-yl)-1-phenylquinazolin-2(1H)-one | m/z [M + H]+ 356.24 |
| 197 | 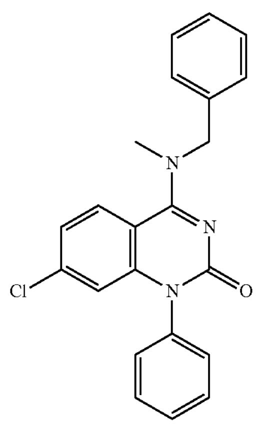 [SMILES: CN(Cc1ccccc1)c1nc(=O)n(-c2ccccc2)c2cc(Cl)ccc12] | 7-chloro-4-[methylbenzylamino]-1-phenylhydroquinazolin-2-one | m/z [M + H]+ 376.24 |
| 188 | 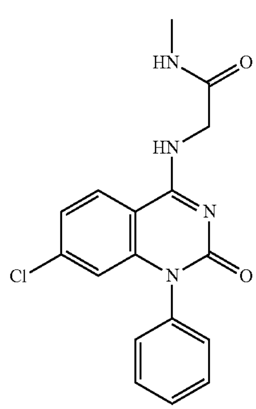 [SMILES: CNC(=O)CNc1nc(=O)n(-c2ccccc2)c2cc(Cl)ccc12] | 2-((7-chloro-2-oxo-1-phenyl-1,2-dihydroquinazolin-4-yl)(methyl)amino)-N-methylacetamide | m/z [M + H]+ 343.10 |

TABLE 1-continued

| Cpd. No. | Structure | Name | Mass Spec. |
|---|---|---|---|
| 199 | 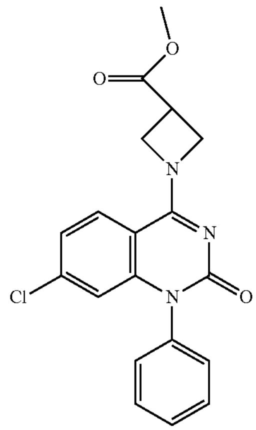 [SMILES: COC(=O)C1CN(c2nc(=O)n(-c3ccccc3)c3cc(Cl)ccc23)C1] | methyl 1-(7-chloro-2-oxo-1-phenyl-1,2-dihydroquinazolin-4-yl)azetidine-3-carboxylate | m/z [M + H]+ 370.10 |
| 200 | 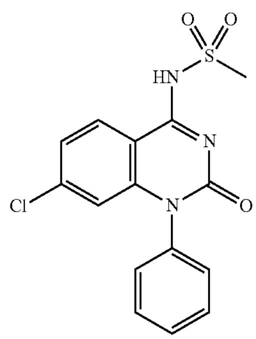 [SMILES: CS(=O)(=O)Nc1nc(=O)n(-c2ccccc2)c2cc(Cl)ccc12] | N-(7-chloro-2-oxo-1-phenyl-1,2-dihydroquinazolin-4-yl)methanesulfonamide | m/z [M + H]+ 350.04 |
| 201 | 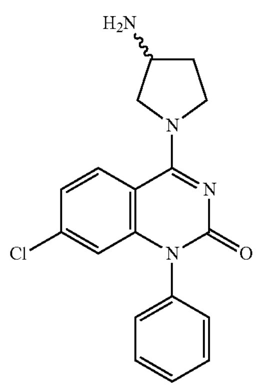 [SMILES: NC1CCN(c2nc(=O)n(-c3ccccc3)c3cc(Cl)ccc23)C1] | 4-(3-aminopyrrolidin-1-yl)-7-chloro-1-phenylquinazolin-2(1H)-one | m/z [M + H]+ 341.11 |
| 202 | 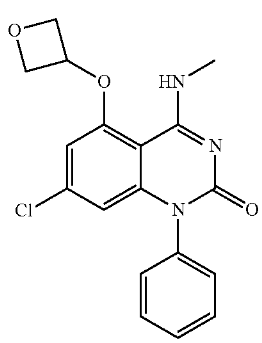 [SMILES: CNc1nc(=O)n(-c2ccccc2)c2cc(Cl)cc(OC3COC3)c12] | 7-chloro-4-(methylamino)-5-oxetan-3-yloxy-1-phenylhydroquinazolin-2-one | m/z [M + H]+ 358.10 |

TABLE 1-continued

| Cpd. No. | Structure | Name | Mass Spec. |
|---|---|---|---|
| 203 | 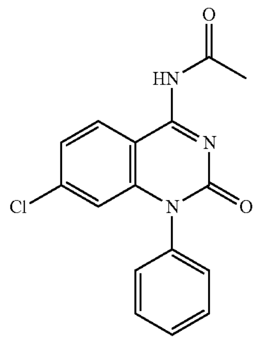 [SMILES: CC(=O)Nc1nc(=O)n(-c2ccccc2)c2cc(Cl)ccc12] | N-(7-chloro-2-oxo-1-phenyl-1,2-dihydroquinazolin-4-yl)acetamide | m/z [M + H]+ 314.12 |
| 204 | 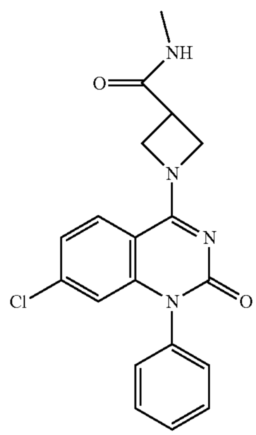 [SMILES: CNC(=O)C1CN(c2nc(=O)n(-c3ccccc3)c3cc(Cl)ccc23)C1] | 1-(7-chloro-2-oxo-1-phenyl-1,2-dihydroquinazolin-4-yl)-N-methyl-azetidine-3-carboxamide | m/z [M + H]+ 369.22 |
| 205 | 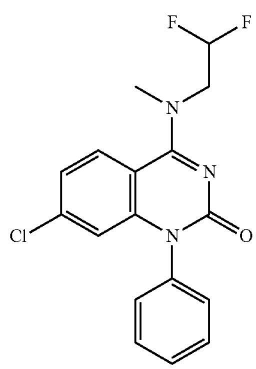 [SMILES: CN(CC(F)F)c1nc(=O)n(-c2ccccc2)c2cc(Cl)ccc12] | 4-[(2,2-difluoroethyl)methylamino]-7-chloro-1-phenylhydroquinazolin-2-one | m/z [M + H]+ 350.10 |
| 206 | 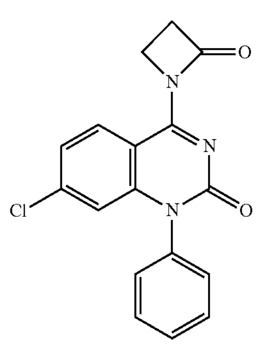 [SMILES: O=C1CCN1c1nc(=O)n(-c2ccccc2)c2cc(Cl)ccc12] | 7-chloro-4-(2-oxoazetidin-1-yl)-1-phenylhydroquinazolin-2-one | m/z [M + H]+ 326.17 |

TABLE 1-continued

| Cpd. No. | Structure | Name | Mass Spec. |
|---|---|---|---|
| 207 | 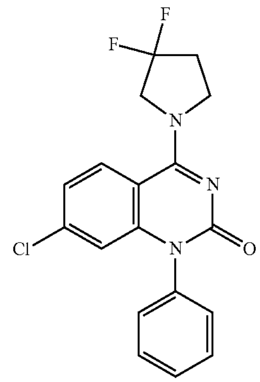 [SMILES: O=c1nc(N2CCC(F)(F)C2)c2ccc(Cl)cc2n1-c1ccccc1] | 4-(3,3-difluoropyrrolidin-1-yl)-7-chloro-1-phenylhydroquinazolin-2-one | m/z [M + H]+ 328.17 |
| 208 | 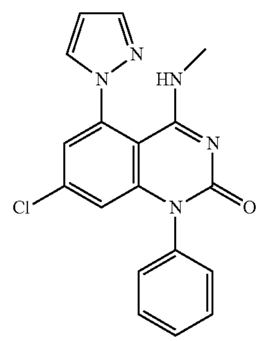 [SMILES: CNc1nc(=O)n(-c2ccccc2)c2cc(Cl)cc(-n3cccn3)c12] | 7-chloro-4-(methylamino)-1-phenyl-5-(1H-pyrazol-1-yl)quinazolin-2(1H)-one | m/z [M + H]+ 352.18 |
| 209 | 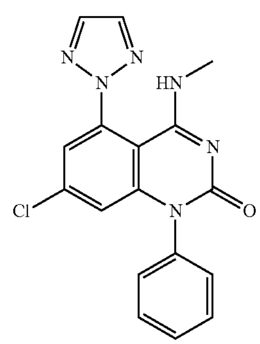 [SMILES: CNc1nc(=O)n(-c2ccccc2)c2cc(Cl)cc(-n3nccn3)c12] | 7-chloro-4-(methylamino)-1-phenyl-5-(1,2,3-triazol-2-yl)quinazolin-2(1H)-one | m/z [M + H]+ 353.1 |
| 210 | 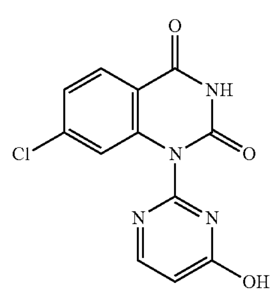 [SMILES: O=c1[nH]c(=O)n(-c2nccc(O)n2)c2cc(Cl)ccc12] | 7-chloro-1-(4-hydroxypyrimidin-2-yl)-1,3-dihydroquinazoline-2,4-dione | m/z [M + H]+ 291.0 |

TABLE 1-continued

| Cpd. No. | Structure | Name | Mass Spec. |
|---|---|---|---|
| 211 | 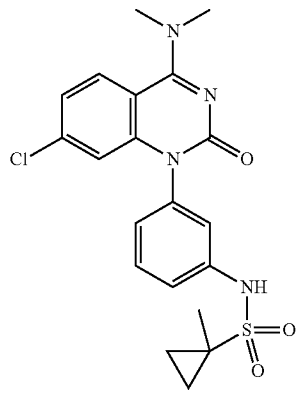 [SMILES: CN(C)c1nc(=O)n(-c2cccc(NS(=O)(=O)C3(C)CC3)c2)c2cc(Cl)ccc12] | 4-(dimethylamino)-7-chloro-1-(3-{[(methylcyclopropyl)sulfonyl]amino}phenyl)-hydroquinazolin-2-one | m/z [M + H]+ 433.1 |
| 212 | 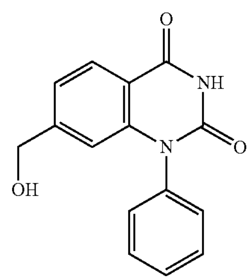 [SMILES: O=c1[nH]c(=O)n(-c2ccccc2)c2cc(CO)ccc12] | 7-(hydroxymethyl)-1-phenyl-1,3-dihydroquinazoline-2,4-dione | m/z [M + H]+ 269.0 |
| 213 | 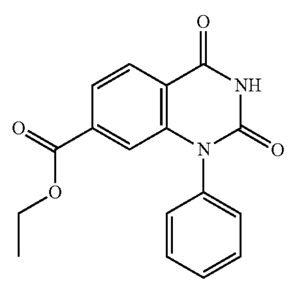 [SMILES: CCOC(=O)c1ccc2c(=O)[nH]c(=O)n(-c3ccccc3)c2c1] | ethyl 2,4-dioxo-1-phenyl-1,3-dihydro-quinazoline-7-carboxylate | m/z [M + H]+ 311.0 |
| 214 | 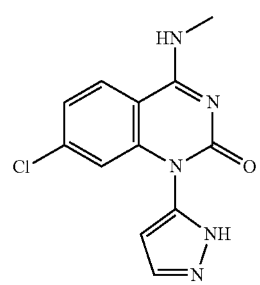 [SMILES: CNc1nc(=O)n(-c2ccn[nH]2)c2cc(Cl)ccc12] | 7-chloro-4-(methylamino)-1-pyrazol-5-ylhydroquinazolin-2-one | m/z [M + H]+ 276.1 |
| 215 | 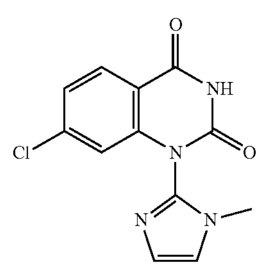 [SMILES: Cn1ccnc1-n1c(=O)[nH]c(=O)c2ccc(Cl)cc21] | 7-chloro-1-(1-methylimidazol-2-yl)-1,3-dihydroquinazoline-2,4-dione | m/z [M + H]+ 277.1 |

TABLE 1-continued

| Cpd. No. | Structure | Name | Mass Spec. |
|---|---|---|---|
| 216 | 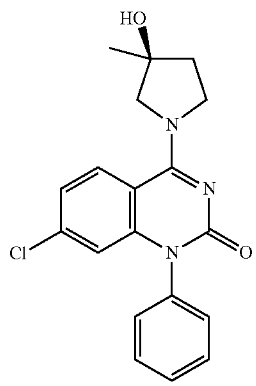 [SMILES: C[C@]1(O)CCN(c2nc(=O)n(-c3ccccc3)c3cc(Cl)ccc23)C1] | 4-((3S)-3-hydroxy-3-methylpyrrolidin-1-yl)-7-chloro-1-phenylhydroquinazolin-2-one | m/z [M + H]+ 256.12 |
| 217 | 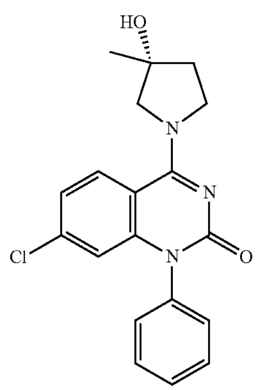 [SMILES: C[C@@]1(O)CCN(c2nc(=O)n(-c3ccccc3)c3cc(Cl)ccc23)C1] | 4-((3R)-3-hydroxy-3-methylpyrrolidin-1-yl)-7-chloro-1-phenylhydroquinazolin-2-one | m/z [M + H]+ 256.12 |
| 218 | 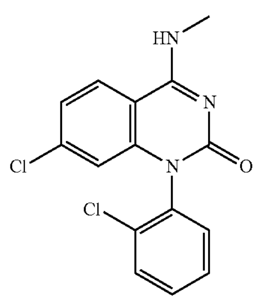 [SMILES: CNc1nc(=O)n(-c2ccccc2Cl)c2cc(Cl)ccc12] | 7-chloro-1-(2-chlorophenyl)-4-(methylamino)quinazolin-2(1H)-one | m/z [M + H]+ 320.0 |
| 219 | 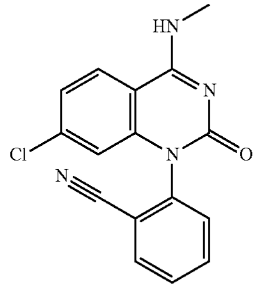 [SMILES: CNc1nc(=O)n(-c2ccccc2C#N)c2cc(Cl)ccc12] | 2-(7-chloro-4-(methylamino)-2-oxoquinazolin-1(2H)-yl)benzonitrile | m/z [M + H]+ 311.0 |

TABLE 1-continued

| Cpd. No. | Structure | Name | Mass Spec. |
|---|---|---|---|
| 220 | 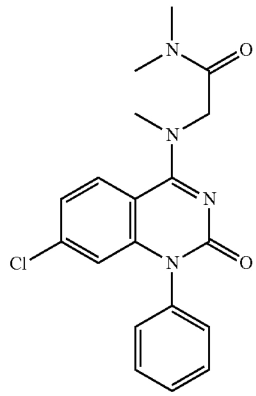 [SMILES: CN(C)C(=O)CN(C)c1nc(=O)n(-c2ccccc2)c2cc(Cl)ccc12] | 2-((7-chloro-2-oxo-1-phenyl-1,2-dihydroquinazolin-4-yl)(methyl)amino)-N,N-dimethylacetamide | m/z [M + H]+ 371.18 |
| 221 | 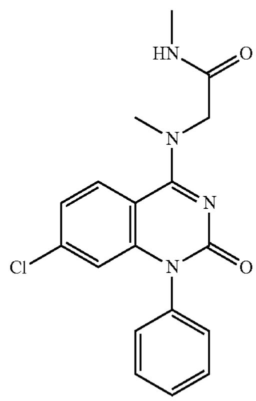 [SMILES: CNC(=O)CN(C)c1nc(=O)n(-c2ccccc2)c2cc(Cl)ccc12] | 2-((7-chloro-2-oxo-1-phenyl-1,2-dihydroquinazolin-4-yl)(methyl)amino)-,N-methylacetamide | m/z [M + H]+ 357.12 |
| 222 | 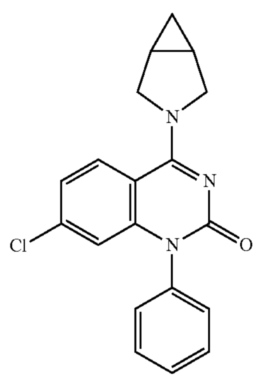 [SMILES: O=c1nc(N2CC3CC3C2)c2ccc(Cl)cc2n1-c1ccccc1] | 4-(3-azabicyclo[3.1.0]hex-3-yl)-7-chloro-1-phenylhydroquinazolin-2-one | m/z [M + H]+ 338.13 |
| 223 | 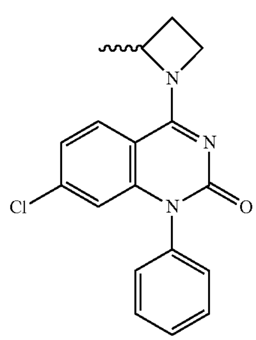 [SMILES: CC1CCN1c1nc(=O)n(-c2ccccc2)c2cc(Cl)ccc12] | 7-chloro-4-(2-methylazetidin-1-yl)-1-phenylhydroquinazolin-2-one | m/z [M + H]+ 326.13 |

TABLE 1-continued

| Cpd. No. | Structure | Name | Mass Spec. |
|---|---|---|---|
| 224 | 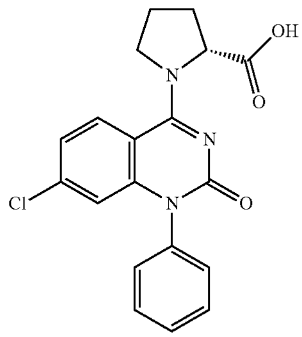 [SMILES: O=C(O)[C@H]1CCCN1c1nc(=O)n(-c2ccccc2)c2cc(Cl)ccc12] | (2R)-1-(7-chloro-2-oxo-1-phenylhydro-quinazolin-4-yl)pyrrolidine-2-carboxylic acid | m/z [M + H]+ 370.12 |
| 225 | 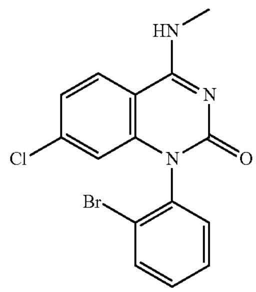 [SMILES: CNc1nc(=O)n(-c2ccccc2Br)c2cc(Cl)ccc12] | 1-(2-bromophenyl)-7-chloro-4-(methylamino)quinazolin-2(1H)-one | m/z [M + H]+ 364.0 |
| 226 | 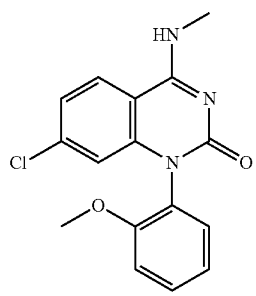 [SMILES: CNc1nc(=O)n(-c2ccccc2OC)c2cc(Cl)ccc12] | 7-chloro-1-(2-methoxyphenyl)-4-(methylamino)hydroquinazolin-2-one | m/z [M + H]+ 316.0 |
| 227 | 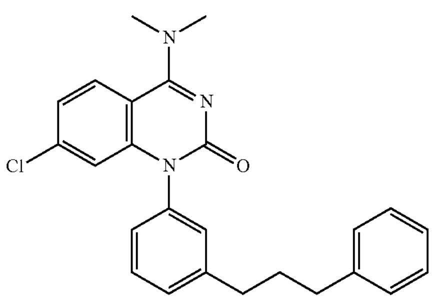 [SMILES: CN(C)c1nc(=O)n(-c2cccc(CCCc3ccccc3)c2)c2cc(Cl)ccc12] | 4-(dimethylamino)-7-chloro-1-[3-(3-phenylpropyl)phenyl]hydroquinazolin-2-one | m/z [M + H]+ 418.2 |
| 228 | 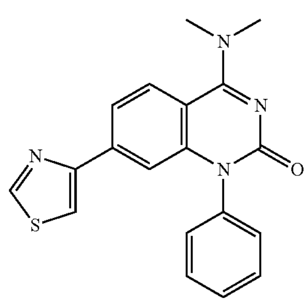 [SMILES: CN(C)c1nc(=O)n(-c2ccccc2)c2cc(-c3cscn3)ccc12] | 4-(dimethylamino)-1-phenyl-7-(1,3-thiazol-4-yl)hydroquinazolin-2-one | m/z [M + H]+ 349.0 |

TABLE 1-continued

| Cpd. No. | Structure | Name | Mass Spec. |
|---|---|---|---|
| 229 | 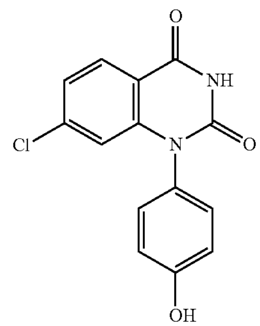 [SMILES: O=c1[nH]c(=O)n(-c2ccc(O)cc2)c2cc(Cl)ccc12] | 7-chloro-1-(4-hydroxyphenyl)-1,3-dihydroquinazoline-2,4-dione | m/z [M + H]+ 289.1 |
| 230 | 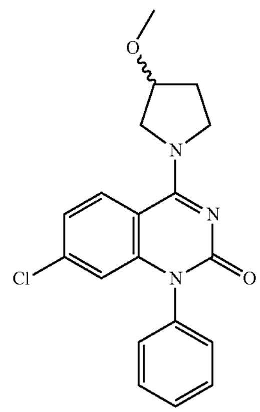 [SMILES: COC1CCN(c2nc(=O)n(-c3ccccc3)c3cc(Cl)ccc23)C1] | 7-chloro-4-(3-methoxypyrrolidin-1-yl)-1-phenylquinazolin-2(1H)-one | m/z [M + H]+ 356.12 |
| 231 | 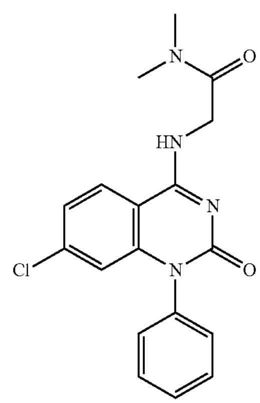 [SMILES: CN(C)C(=O)CNc1nc(=O)n(-c2ccccc2)c2cc(Cl)ccc12] | 2-[(7-chloro-2-oxo-1-phenyl-1,2-dihydroquinazolin-4-yl)amino]-N,N-dimethylacetamide | m/z [M + H]+ 357.12 |
| 232 | 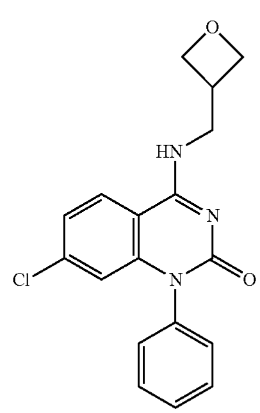 [SMILES: O=c1nc(NCC2COC2)c2ccc(Cl)cc2n1-c1ccccc1] | 7-chloro-4-[(oxetan-3-ylmethyl)amino]-1-phenylhydroquinazolin-2-one | m/z [M + H]+ 342.23 |

TABLE 1-continued

| Cpd. No. | Structure | Name | Mass Spec. |
|---|---|---|---|
| 233 | 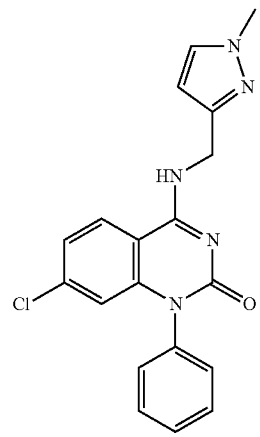 [SMILES: Cn1ccc(CNc2nc(=O)n(-c3ccccc3)c3cc(Cl)ccc23)n1] | 7-chloro-4-{[(1-methylpyrazol-3-yl)-methyl]amino}-1-phenylhydro-quinazolin-2-one | m/z [M + H]+ 366.24 |
| 234 | 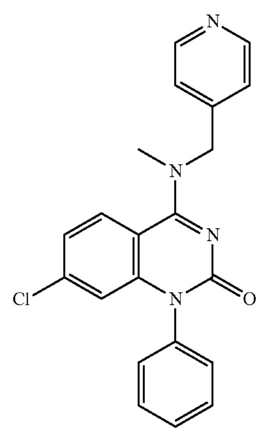 [SMILES: CN(Cc1ccncc1)c1nc(=O)n(-c2ccccc2)c2cc(Cl)ccc12] | 7-chloro-4-[methyl(pyridin-4-ylmethyl)-amino]-1-phenylhydroquinazolin-2-one | m/z [M + H]+ 377.1 |
| 235 | 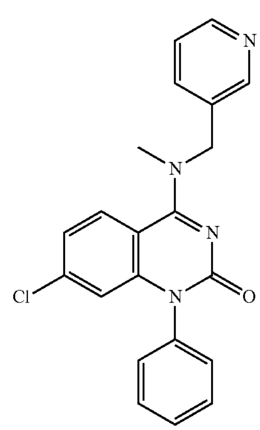 [SMILES: CN(Cc1cccnc1)c1nc(=O)n(-c2ccccc2)c2cc(Cl)ccc12] | 7-chloro-4-[methyl(pyridin-3-ylmethyl)-amino]-1-phenylhydroquinazolin-2-one | m/z [M + H]+ 377.24 |

TABLE 1-continued

| Cpd. No. | Structure | Name | Mass Spec. |
|---|---|---|---|
| 236 | 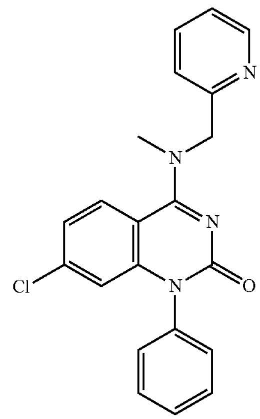 [SMILES: CN(Cc1ccccn1)c1nc(=O)n(-c2ccccc2)c2cc(Cl)ccc12] | 7-chloro-4-[methyl(pyridin-2-ylmethyl)-amino]-1-phenylhydroquinazolin-2-one | m/z [M + H]+ 377.12 |
| 237 | 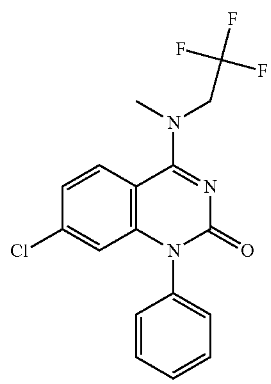 [SMILES: CN(CC(F)(F)F)c1nc(=O)n(-c2ccccc2)c2cc(Cl)ccc12] | 7-chloro-4-[methyl(2,2,2-trifluoroethyl)-amino]-1-phenylhydroquinazolin-2-one | m/z [M + H]+ 368.18 |
| 238 | 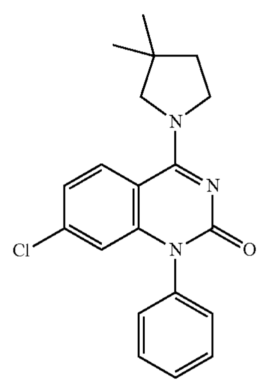 [SMILES: CC1(C)CCN(c2nc(=O)n(-c3ccccc3)c3cc(Cl)ccc23)C1] | 4-(3,3-dimethylpyrrolidin-1-yl)-7-chloro-1-phenylhydroquinazolin-2-one | m/z [M + H]+ 354.12 |
| 239 | 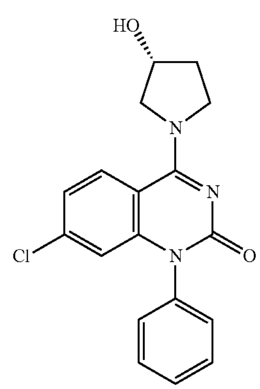 [SMILES: O=c1nc(N2CC[C@@H](O)C2)c2ccc(Cl)cc2n1-c1ccccc1] | 4-((3R)-3-hydroxypyrrolidinyl)-7-chloro-1-phenylhydroquinazolin-2-one | m/z [M + H]+ 342.19 |

TABLE 1-continued

| Cpd. No. | Structure | Name | Mass Spec. |
|---|---|---|---|
| 240 | 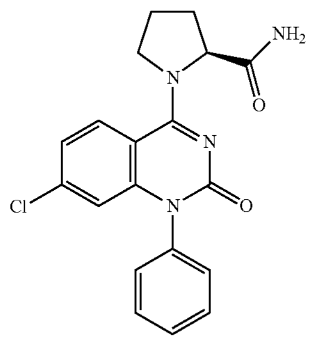 [SMILES: NC(=O)[C@@H]1CCCN1c1nc(=O)n(-c2ccccc2)c2cc(Cl)ccc12] | (2S)-1-(7-chloro-2-oxo-1-phenylhydro-quinazolin-4-yl)pyrrolidine-2-carboxamide | m/z [M + H]+ 369.18 |
| 241 | 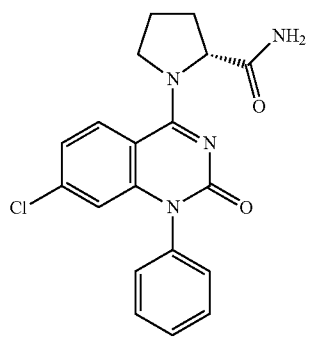 [SMILES: NC(=O)[C@H]1CCCN1c1nc(=O)n(-c2ccccc2)c2cc(Cl)ccc12] | (2R)-1-(7-chloro-2-oxo-1-phenylhydro-quinazolin-4-yl)pyrrolidine-2-carboxamide | m/z [M + H]+ 369.19 |
| 242 | 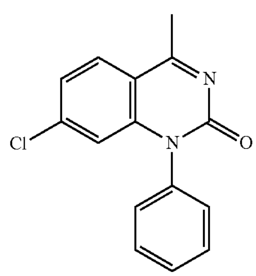 [SMILES: Cc1nc(=O)n(-c2ccccc2)c2cc(Cl)ccc12] | 7-chloro-4-methyl-1-phenylhydro-quinazolin-2-one | m/z [M + H]+ 271.1 |
| 243 | 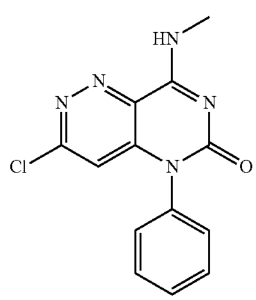 [SMILES: CNc1nc(=O)n(-c2ccccc2)c2cc(Cl)nnc12] | 3-chloro-8-(methylamino)-5-phenyl-5-hydropyrimidino[5,4-c]pyridazin-6-one | m/z [M + H]+ 288.16 |
| 244 | 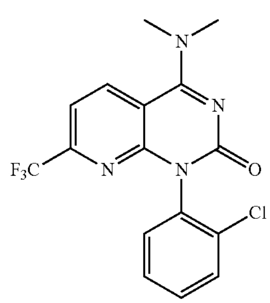 [SMILES: CN(C)c1nc(=O)n(-c2ccccc2Cl)c2nc(C(F)(F)F)ccc12] | 1-(2-chlorophenyl)-4-(dimethylamino)-7-(trifluoromethyl)pyrido[2,3-d]-pyrimidin-2(1H)-one | m/z [M + H]+ 369.05 |

TABLE 1-continued

| Cpd. No. | Structure | Name | Mass Spec. |
|---|---|---|---|
| 245 | 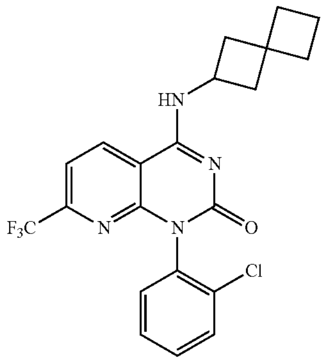 [SMILES: O=c1nc(NC2CC3(CCC3)C2)c2ccc(C(F)(F)F)nc2n1-c1ccccc1Cl] | 1-(2-chlorophenyl)-4-(spiro[3.3]heptan-2-ylamino)-7-(trifluoromethyl)pyrido-[2,3-d]pyrimidin-2(1H)-one | m/z [M + H]+ 435.10 |
| 246 | 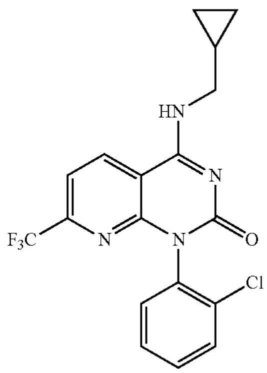 [SMILES: O=c1nc(NCC2CC2)c2ccc(C(F)(F)F)nc2n1-c1ccccc1Cl] | 1-(2-chlorophenyl)-4-((cyclopropyl-methyl)amino)-7-(trifluoromethyl)-pyrido[2,3-d]pyrimidin-2(1H)-one | m/z [M + H]+ 395.05 |
| 247 | 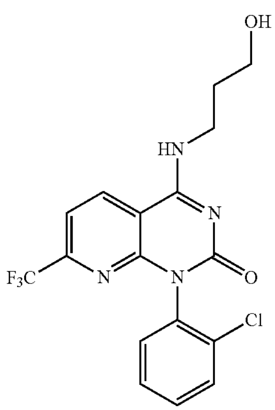 [SMILES: O=c1nc(NCCCO)c2ccc(C(F)(F)F)nc2n1-c1ccccc1Cl] | 1-(2-chlorophenyl)-4-[(3-hydroxy-propyl)amino]-7-(trifluoromethyl)-pyrido[2,3-d]pyrimidin-2(1H)-one | m/z [M + H]+ 399.05 |
| 248 | 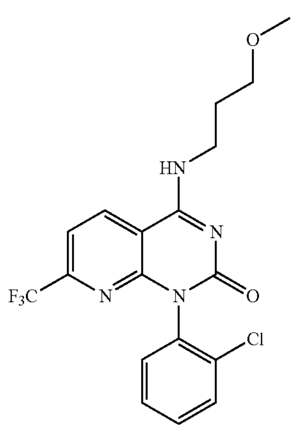 [SMILES: COCCCNc1nc(=O)n(-c2ccccc2Cl)c2nc(C(F)(F)F)ccc12] | 1-(2-chlorophenyl)-4-[(3-methoxy-propyl)amino]-7-(trifluoromethyl)-pyrido[2,3-d]pyrimidin-2(1H)-onE | m/z [M + H]+ 413.10 |

TABLE 1-continued

| Cpd. No. | Structure | Name | Mass Spec. |
|---|---|---|---|
| 249 | 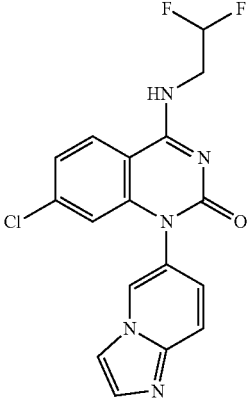 [SMILES: O=c1nc(NCC(F)F)c2ccc(Cl)cc2n1-c1ccc2nccn2c1] | 4-[(2,2-difluoroethyl)amino]-7-chloro-1-(4-hydroimidazo[1,2-a]pyridin-6-yl)-hydroquinazolin-2-one | m/z [M + H]+ 376.0 |
| 250 | 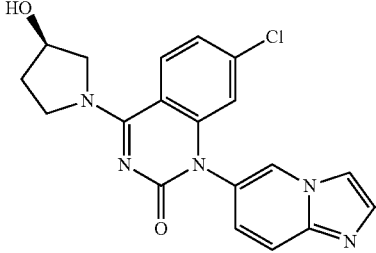 [SMILES: O=c1nc(N2CC[C@@H](O)C2)c2ccc(Cl)cc2n1-c1ccc2nccn2c1] | 4-((3R)-3-hydroxypyrrolidin-1-yl)-7-chloro-1-(4-hydroimidazo[1,2-a]pyridin-6-yl)-hydroquinazolin-2-one | m/z [M + H]+ 382.00 |
| 251 | 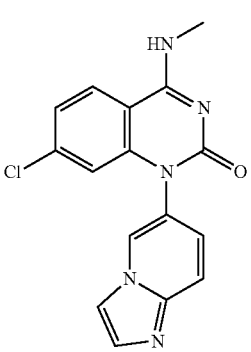 [SMILES: CNc1nc(=O)n(-c2ccc3nccn3c2)c2cc(Cl)ccc12] | 7-chloro-1-(4-hydroimidazo[1,2-a]-pyridin-6-yl)-4-(methylamino)hydro-quinazolin-2-one | m/z [M + H]+ 326.00 |
| 252 | 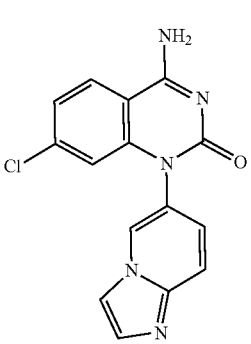 [SMILES: Nc1nc(=O)n(-c2ccc3nccn3c2)c2cc(Cl)ccc12] | 4-amino-7-chloro-1-(4-hydroimidazo-[1,2-a]pyridin-6-yl)hydroquinazolin-2-one | m/z [M + H]+ 312.00 |

TABLE 1-continued

| Cpd. No. | Structure | Name | Mass Spec. |
|---|---|---|---|
| 253 | 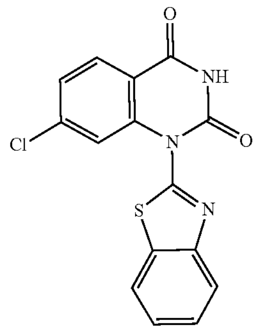 [SMILES: O=c1[nH]c(=O)n(-c2nc3ccccc3s2)c2cc(Cl)ccc12] | 1-benzothiazol-2-yl-7-chloro-1,3-dihydroquinazoline-2,4-dione | m/z [M + H]+ 330.0 |
| 254 | 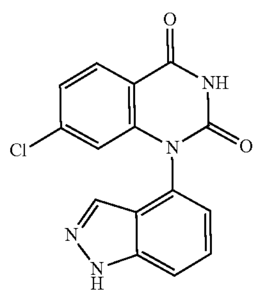 [SMILES: O=c1[nH]c(=O)n(-c2cccc3[nH]ncc23)c2cc(Cl)ccc12] | 1-(1H-indazol-4-yl)-7-chloro-1,3-dihydroquinazoline-2,4-dione | m/z [M + H]+ 313.0 |
| 255 | 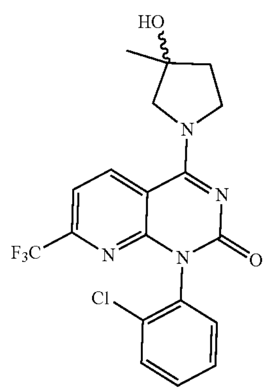 [SMILES: CC1(O)CCN(c2nc(=O)n(-c3ccccc3Cl)c3nc(C(F)(F)F)ccc23)C1] | 1-(2-chlorophenyl)-4-(3-hydroxy-3-methylpyrrolidin-1-yl)-7-(trifluoromethyl)hydropyridino-[2,3-d]pyrimidin-2-one | m/z [M + H]+ 425.37 |
| 256 | 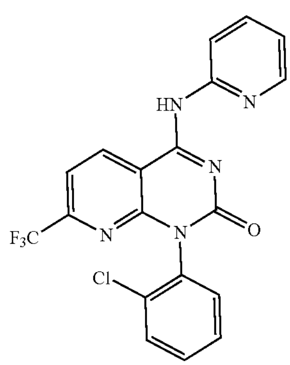 [SMILES: O=c1nc(Nc2ccccn2)c2ccc(C(F)(F)F)nc2n1-c1ccccc1Cl] | 1-(2-chlorophenyl)-4-(2-pyridylamino)-7-(trifluoromethyl)pyrido[2,3-d]-pyrimidin-2(1H)-one | m/z [M + H]+ 418.35 |

TABLE 1-continued

| Cpd. No. | Structure | Name | Mass Spec. |
|---|---|---|---|
| 257 | 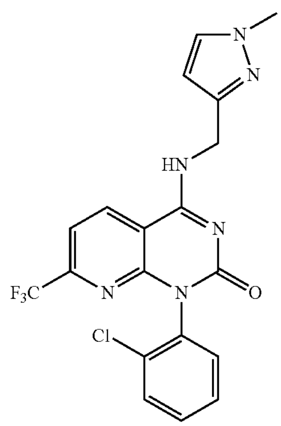 [SMILES: Cn1ccc(CNc2nc(=O)n(-c3ccccc3Cl)c3nc(C(F)(F)F)ccc23)n1] | 1-(2-chlorophenyl)-4-{[(1-methyl-pyrazol-3-yl)methyl]amino}-7-(trifluoro-methyl)-pyrido[2,3-d]pyrimidin-2(1H)-one | m/z [M + H]+ 435.35 |
| 258 | 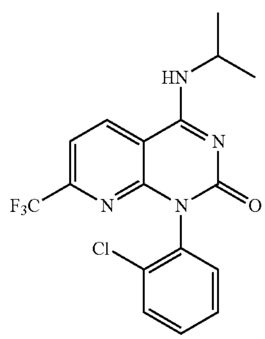 [SMILES: CC(C)Nc1nc(=O)n(-c2ccccc2Cl)c2nc(C(F)(F)F)ccc12] | 1-(2-chlorophenyl)-4-[(methylethyl)-amino]-7-(trifluoromethyl)pyrido[2,3-d]-pyrimidin-2(1H)-one | m/z [M + H]+ 383.34 |
| 259 | 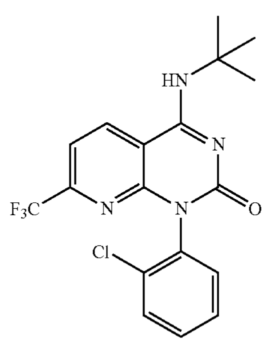 [SMILES: CC(C)(C)Nc1nc(=O)n(-c2ccccc2Cl)c2nc(C(F)(F)F)ccc12] | 4-[(tert-butyl)amino]-1-(2-chloro-phenyl)-7-(trifluoromethyl)pyrido-[2,3-d]pyrimidin-2(1H)-one | m/z [M + H]+ 397.39 |
| 260 | 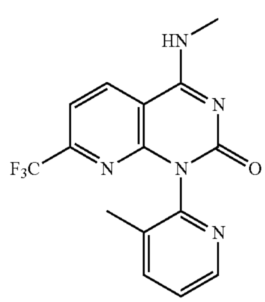 [SMILES: CNc1nc(=O)n(-c2ncccc2C)c2nc(C(F)(F)F)ccc12] | 1-(3-methyl(2-pyridyl))-4-(methyl-amino)-7-(trifluoromethyl)pyrido[2,3-d]-pyrimidin-2(1H)-one | m/z [M + H]+ 336.37 |

TABLE 1-continued

| Cpd. No. | Structure | Name | Mass Spec. |
|---|---|---|---|
| 261 | 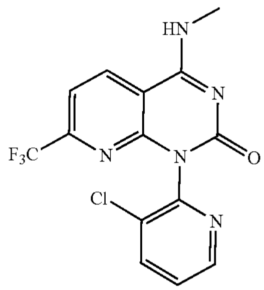 [SMILES: CNc1nc(=O)n(-c2ncccc2Cl)c2nc(C(F)(F)F)ccc12] | 1-(3-chloro(2-pyridyl))-4-(methyl-amino)-7-(trifluoromethyl)pyrido[2,3-d]-pyrimidin-2(1H)-one | m/z [M + H]+ 356.36 |
| 262 | 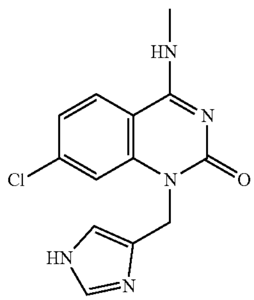 [SMILES: CNc1nc(=O)n(Cc2c[nH]cn2)c2cc(Cl)ccc12] | 7-chloro-1-(imidazol-4-ylmethyl)-4-(methylamino)hydroquinazolin-2-one | m/z [M + H]+ 290.36 |
| 263 | 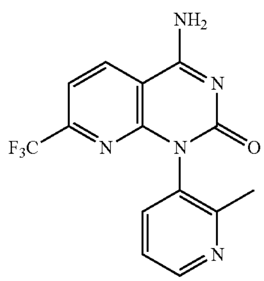 [SMILES: Cc1ncccc1-n1c(=O)nc(N)c2ccc(C(F)(F)F)nc21] | 4-amino-1-(2-methyl(3-pyridyl))-7-(trifluoromethyl pyrido[2,3-d]pyrimidin-2(1H)-one | m/z [M + H]+ 322.10 |
| 264 | 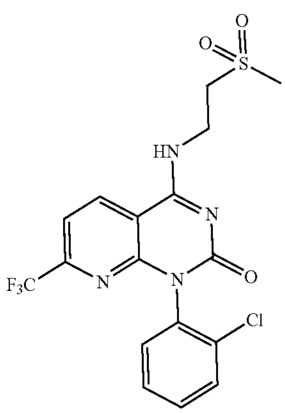 [SMILES: CS(=O)(=O)CCNc1nc(=O)n(-c2ccccc2Cl)c2nc(C(F)(F)F)ccc12] | 1-(2-chlorophenyl)-4-{[2-(methyl-sulfonyl)ethyl]amino}-7-(trifluoro-methyl)pyrido[2,3-d]pyrimidin-2(1H)-one | m/z [M + H]+ 447.00 |
| 265 | 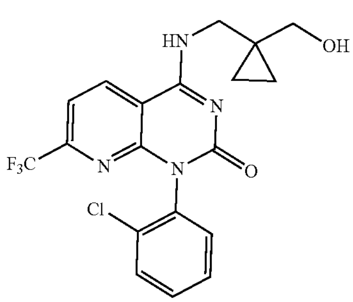 [SMILES: O=c1nc(NCC2(CO)CC2)c2ccc(C(F)(F)F)nc2n1-c1ccccc1Cl] | 1-(2-chlorophenyl)-4-(((1-(hydroxy-methyl)cyclopropyl)methyl)amino)-7-(trifluoromethyl)-pyrido[2,3-d]-pyrimidin-2(1H)-one | m/z [M + H]+ 425.00 |

TABLE 1-continued

| Cpd. No. | Structure | Name | Mass Spec. |
|---|---|---|---|
| 266 | 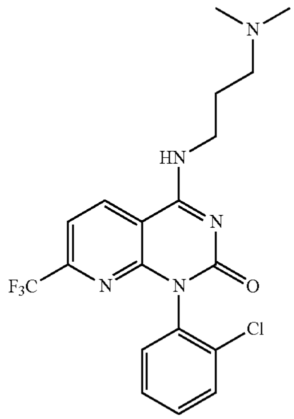 [SMILES: CN(C)CCCNc1nc(=O)n(-c2ccccc2Cl)c2nc(C(F)(F)F)ccc12] | 4-{[3-(dimethylamino)propyl]amino}-1-(2-chlorophenyl)-7-(trifluoromethyl)-pyrido[2,3-d]pyrimidin-2(1H)-one | m/z [M + H]+ 426.00 |
| 267 | 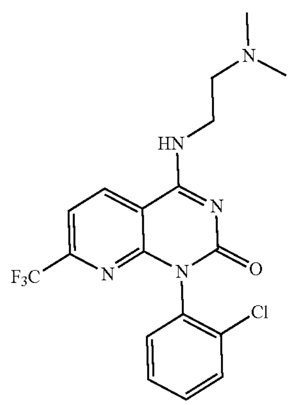 [SMILES: CN(C)CCNc1nc(=O)n(-c2ccccc2Cl)c2nc(C(F)(F)F)ccc12] | 4-{[2-(dimethylamino)ethyl]amino}-1-(2-chlorophenyl)-7-(trifluoromethyl)-pyrido[2,3-d]pyrimidin-2(1H)-one | m/z [M + H]+ 412.00 |
| 268 | 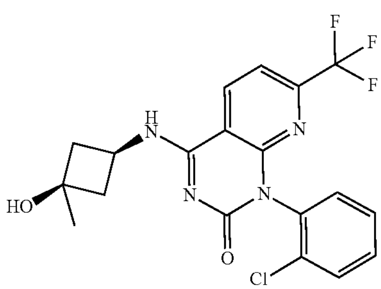 [SMILES: C[C@]1(O)C[C@@H](Nc2nc(=O)n(-c3ccccc3Cl)c3nc(C(F)(F)F)ccc23)C1] | 1-(2-chlorophenyl)-4-(((1s,3s)-3-hydroxy-3-methylcyclobutyl)amino)-7-(trifluoromethyl)pyrido[2,3-d]pyrimidin-2(1H)-one | m/z [M + H]+ 425.00 |
| 269 | 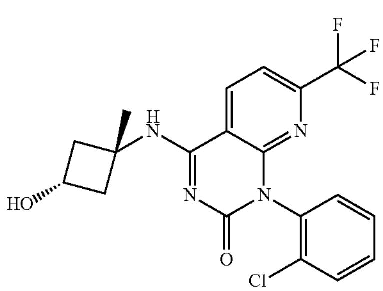 [SMILES: C[C@]1(Nc2nc(=O)n(-c3ccccc3Cl)c3nc(C(F)(F)F)ccc23)C[C@@H](O)C1] | 1-(2-chlorophenyl)-4-(((1s,3s)-3-hydroxy-1-methylcyclobutyl)amino)-7-(trifluoromethyl)pyrido[2,3-d]pyrimidin-2(1H)-one | m/z [M + H]+ 425.00 |

TABLE 1-continued

| Cpd. No. | Structure | Name | Mass Spec. |
|---|---|---|---|
| 270 | 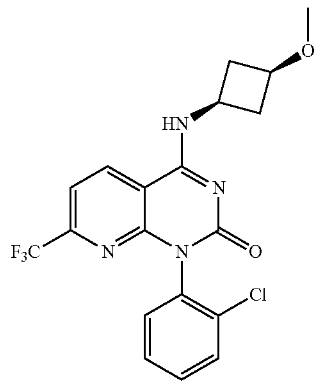 [SMILES: CO[C@H]1C[C@@H](Nc2nc(=O)n(-c3ccccc3Cl)c3nc(C(F)(F)F)ccc23)C1] | 1-(2-chlorophenyl)-4-(((1s,3s)-3-methoxycyclobutyl)amino)-7-(trifluoro-methyl)pyrido[2,3-d]pyrimidin-2(1H)-one | m/z [M + H]+ 425.00 |
| 271 | 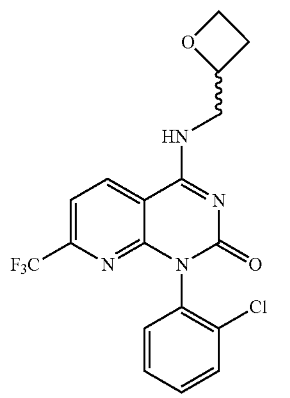 [SMILES: O=c1nc(NCC2CCO2)c2ccc(C(F)(F)F)nc2n1-c1ccccc1Cl] | 1-(2-chlorophenyl)-4-[(oxetan-2-ylmethyl)amino]-7-(trifluoromethyl)-pyrido[2,3-d]pyrimidin-2(1H)-one | m/z [M + H]+ 411.00 |
| 272 | 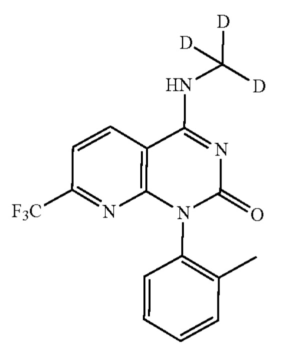 [SMILES: [2H]C([2H])([2H])Nc1nc(=O)n(-c2ccccc2C)c2nc(C(F)(F)F)ccc12] | 4-((methyl-d3)amino)-1-(2-methyl-phenyl)-7-(trifluoromethyl)pyrido[2,3-d]pyrimidin-2(1H)-one | m/z [M + H]+ 338.20 |
| 273 | 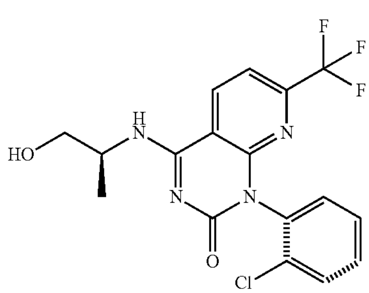 | 4-[((1S)-2-hydroxy-isopropyl)amino]-(1Ra)-(2-chlorophenyl)-7-(trifluoro-methyl)-pyrido[2,3-d]pyrimidin-2(1H)-one | m/z [M + H]+ 399.00 |

TABLE 1-continued

| Cpd. No. | Structure | Name | Mass Spec. |
|---|---|---|---|
| 274 | 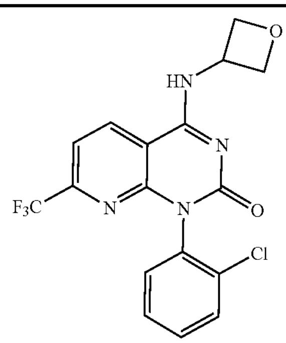 | 1-(2-chlorophenyl)-4-(oxetan-3-yl-amino)-7-(trifluoromethyl)pyrido[2,3-d]pyrimidin-2(1H)-one | m/z [M + H]+ 397.0 |
| 275 | 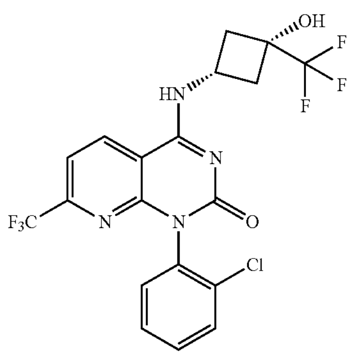 [SMILES: O=c1nc(N[C@H]2C[C@](O)(C(F)(F)F)C2)c2ccc(C(F)(F)F)nc2n1-c1ccccc1Cl] | 4-{[(cis)-3-hydroxy-3-(trifluoromethyl)-cyclobutyl]amino}-1-(2-chlorophenyl)-7-(trifluoromethyl)pyrido[2,3-d]-pyrimidin-2(1H)-one | m/z [M + H]+ 479.00 |
| 276 | 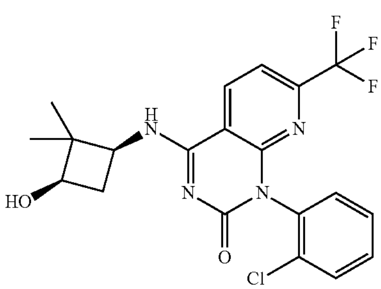 [SMILES: CC1(C)[C@H](O)C[C@@H]1Nc1nc(=O)n(-c2ccccc2Cl)c2nc(C(F)(F)F)ccc12] | 4-[((cis)-3-hydroxy-2,2-dimethylcyclo-butyl)amino]-1-(2-chlorophenyl)-7-(trifluoromethyl)-pyrido[2,3-d]-pyrimidin-2(1H)-one | m/z [M + H]+ 439.00 |
| 277 | 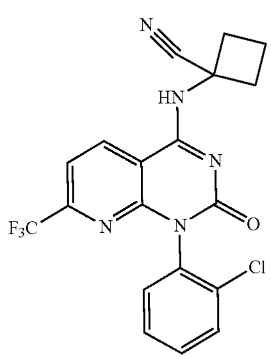 [SMILES: N#CC1(Nc2nc(=O)n(-c3ccccc3Cl)c3nc(C(F)(F)F)ccc23)CCC1] | 1-((1-(2-chlorophenyl)-2-oxo-7-(trifluoromethyl)-1,2-dihydropyrido[2,3-d]pyrimidin-4-yl)amino)cyclobutane-1-carbonitrile | m/z [M + H]+ 420.00 |

TABLE 1-continued

| Cpd. No. | Structure | Name | Mass Spec. |
|---|---|---|---|
| 278 | 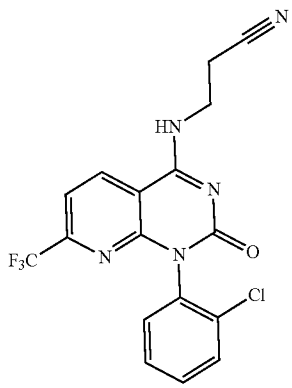 [SMILES: N#CCCNc1nc(=O)n(-c2ccccc2Cl)c2nc(C(F)(F)F)ccc12] | 3-((1-(2-chlorophenyl)-2-oxo-7-(trifluoro-methyl)-1,2-dihydropyrido-[2,3-d]pyrimidin-4-yl)amino)-propanenitrile | m/z [M + H]+ 394.00 |
| 279 | 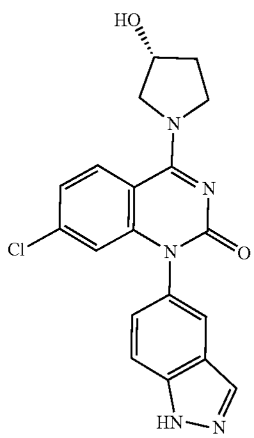 [SMILES: O=c1nc(N2CC[C@@H](O)C2)c2ccc(Cl)cc2n1-c1ccc2[nH]ncc2c1] | (R)-7-chloro-4-(3-hydroxypyrrolidin-1-yl)-1-(1H-indazol-5-yl)quinazolin-2(1H)-one | m/z [M + H]+ 382.0 |
| 280 | 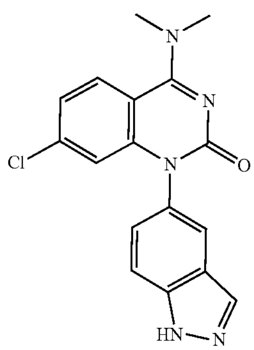 [SMILES: CN(C)c1nc(=O)n(-c2ccc3[nH]ncc3c2)c2cc(Cl)ccc12] | 7-chloro-4-(dimethylamino)-1-(1H-indazol-5-yl)quinazolin-2(1H)-one | m/z [M + H]+ 340.0 |
| 281 | 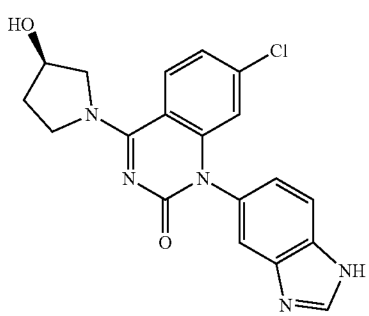 [SMILES: O=c1nc(N2CC[C@@H](O)C2)c2ccc(Cl)cc2n1-c1ccc2[nH]cnc2c1] | (R)-7-chloro-4-(3-hydroxypyrrolidin-1-yl)-1-(1H-benzimidazol-5-yl)quinazolin-2(1H)-one | m/z [M + H]+ 382.0 |

TABLE 1-continued

| Cpd. No. | Structure | Name | Mass Spec. |
|---|---|---|---|
| 282 | 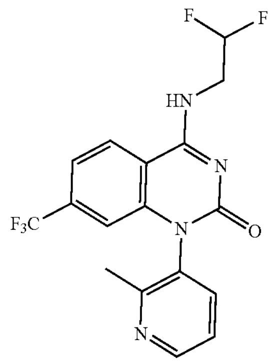 [SMILES: Cc1ncccc1-n1c(=O)nc(NCC(F)F)c2ccc(C(F)(F)F)cc21] | 4-((2,2-difluoroethyl)amino)-1-(2-methylpyridin-3-yl)-7-(trifluoromethyl)-quinazolin-2(1H)-one | m/z [M + H]+ 385.0 |
| 283 | 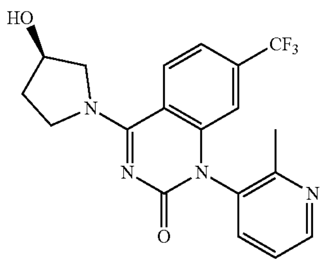 [SMILES: Cc1ncccc1-n1c(=O)nc(N2CC[C@@H](O)C2)c2ccc(C(F)(F)F)cc21] | 4-((3R)-3-hydroxypyrrolidinyl)-1-(2-methylpyridin-3-yl))-7-(trifluoromethyl)-hydroquinazolin-2-one | m/z [M + H]+ 391.0 |
| 284 | 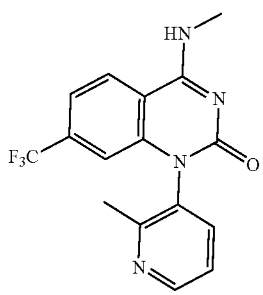 [SMILES: CNc1nc(=O)n(-c2cccnc2C)c2cc(C(F)(F)F)ccc12] | 1-(2-methylpyridin-3-yl))-4-(methyl-amino)-7-(trifluoromethyl)hydro-quinazolin-2-one | m/z [M + H]+ 335.0 |
| 285 | 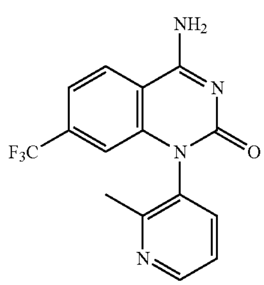 [SMILES: Cc1ncccc1-n1c(=O)nc(N)c2ccc(C(F)(F)F)cc21] | 4-amino-1-(2-methylpyridin-3-yl))-7-(trifluoromethyl)hydroquinazolin-2-one | m/z [M + H]+ 321.0 |
| 286 | 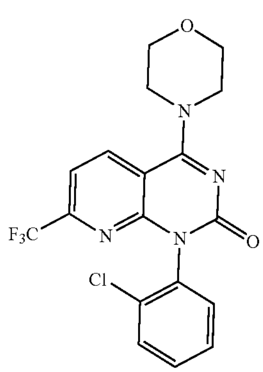 [SMILES: O=c1nc(N2CCOCC2)c2ccc(C(F)(F)F)nc2n1-c1ccccc1Cl] | 1-(2-chlorophenyl)-4-morpholin-4-yl-7-(trifluoromethyl)pyrido[2,3-d]pyrimidin-2(1H)-one | m/z [M + H]+ 411.40 |

TABLE 1-continued

| Cpd. No. | Structure | Name | Mass Spec. |
|---|---|---|---|
| 287 | 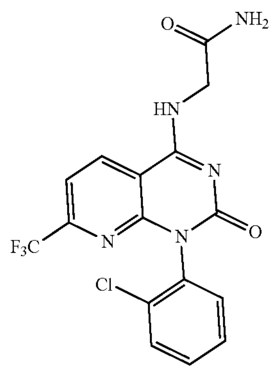 [SMILES: NC(=O)CNc1nc(=O)n(-c2ccccc2Cl)c2nc(C(F)(F)F)ccc12] | 2-((1-(2-chlorophenyl)-2-oxo-7-(trifluoromethyl)-1,2-dihydropyrido[2,3-d]pyrimidin-4-yl)amino)acetamide | m/z [M + H]+ 398.36 |
| 288 | 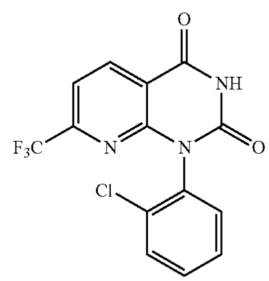 [SMILES: O=c1[nH]c(=O)n(-c2ccccc2Cl)c2nc(C(F)(F)F)ccc12] | 1-(2-chlorophenyl)-4-hydroxy-7-(trifluoromethyl)hydropyridino[2,3-d]-pyrimidin-2-one | m/z [M + H]+ 342.31 |
| 289 | 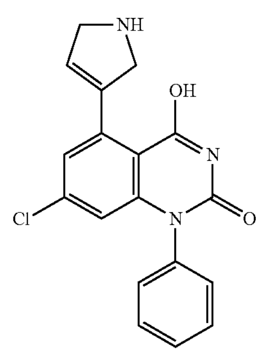 [SMILES: O=c1nc(O)c2c(C3=CCNC3)cc(Cl)cc2n1-c1ccccc1] | 7-chloro-5-(2,5-dihydro-1H-pyrrol-3-yl)-4-hydroxy-1-phenylquinazolin-2(1H)-one | m/z [M + H]+ 340.37 |
| 290 | 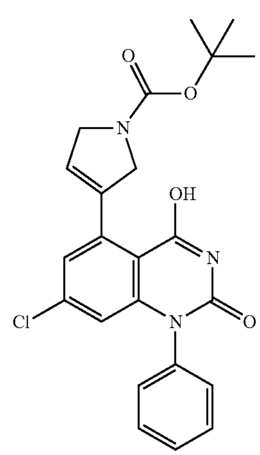 [SMILES: CC(C)(C)OC(=O)N1CC=C(c2cc(Cl)cc3c2c(O)nc(=O)n3-c2ccccc2)C1] | tert-butyl 3-(7-chloro-4-hydroxy-2-oxo-1-phenyl-1,2-dihydroquinazolin-5-yl)-2,5-dihydro-1H-pyrrole-1-carboxylate | m/z [M + H]+ 440.12 |

TABLE 1-continued

| Cpd. No. | Structure | Name | Mass Spec. |
|---|---|---|---|
| 291 | 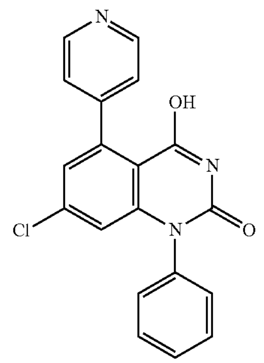 [SMILES: O=c1nc(O)c2c(-c3ccncc3)cc(Cl)cc2n1-c1ccccc1] | 7-chloro-4-hydroxy-1-phenyl-5-(pyridin-4-yl)quinazolin-2(1H)-one | m/z [M + H]+ 350.09 |
| 292 | 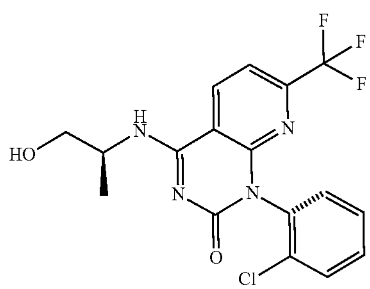 | 4-[((1S)-2-hydroxy-isopropyl)amino]-(1Sa)-(2-chlorophenyl)-7-(trifluoro-methyl)-pyrido[2,3-d]pyrimidin-2(1H)-one | m/z [M + H]+ 399.10 |
| 293 | 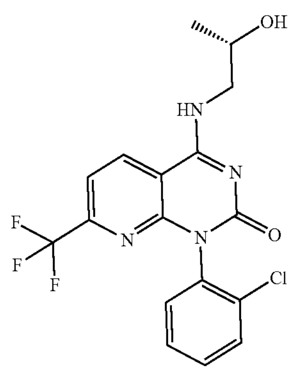 [SMILES: C[C@H](O)CNc1nc(=O)n(-c2ccccc2Cl)c2nc(C(F)(F)F)ccc12] | 4-[((2S)-2-hydroxypropyl)amino]-1-(2-chlorophenyl)-7-(trifluoromethyl)-pyrido[2,3-d]pyrimidin-2(1H)-one | m/z [M + H]+ 399.10 |
| 294 | 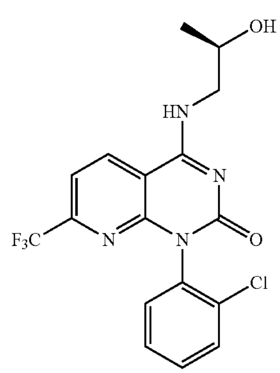 [SMILES: C[C@@H](O)CNc1nc(=O)n(-c2ccccc2Cl)c2nc(C(F)(F)F)ccc12] | 4-[((2R)-2-hydroxypropyl)amino]-1-(2-chlorophenyl)-7-(trifluoromethyl)-pyrido[2,3-d]pyrimidin-2(1H)-one | m/z [M + H]+ 399.10 |

TABLE 1-continued

| Cpd. No. | Structure | Name | Mass Spec. |
|---|---|---|---|
| 295 | 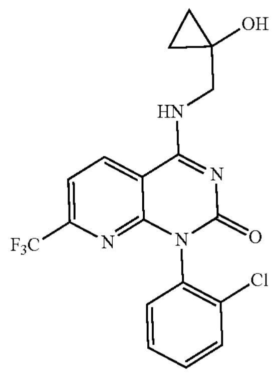 [SMILES: O=c1nc(NCC2(O)CC2)c2ccc(C(F)(F)F)nc2n1-c1ccccc1Cl] | 1-(2-chlorophenyl)-4-{[(hydroxycyclo-propyl)methyl]amino}-7-(trifluoro-methyl)-pyrido[2,3-d]pyrimidin-2(1H)-one | m/z [M + H]+ 411.10 |
| 296 | 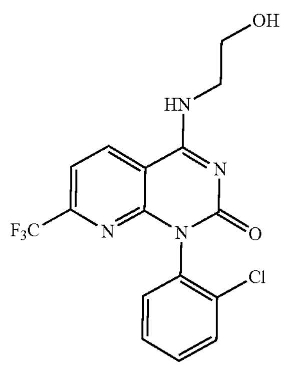 [SMILES: O=c1nc(NCCO)c2ccc(C(F)(F)F)nc2n1-c1ccccc1Cl] | 1-(2-chlorophenyl)-4-[(2-hydroxy-ethyl)amino]-7-(trifluoromethyl) pyrido[2,3-d]pyrimidin-2(1H)-one | m/z [M + H]+ 385.10 |
| 297 | 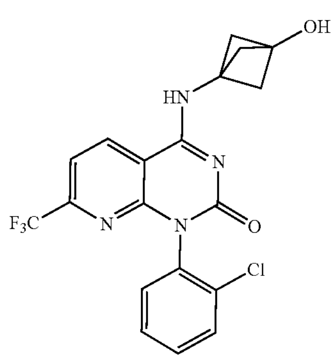 [SMILES: O=c1nc(NC23CC(O)(C2)C3)c2ccc(C(F)(F)F)nc2n1-c1ccccc1Cl] | 1-(2-chlorophenyl)-4-[(3-hydroxy-bicyclo[1.1.1]pentyl)amino]-7-(trifluoro-methyl)-pyrido[2,3-d]pyrimidin-2(1H)-one | m/z [M + H]+ 423.10 |
| 298 | 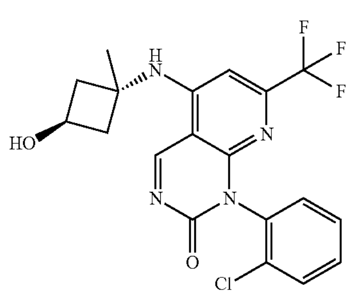 [SMILES: C[C@]1(Nc2cc(C(F)(F)F)nc3c2cnc(=O)n3-c2ccccc2Cl)C[C@H](O)C1] | 4-[((trans)-3-hydroxy-1-methylcyclo-butyl)amino]-1-(2-chlorophenyl)-7-(trifluoromethyl)-pyrido[2,3-d]pyrimidin-2(1H)-one | m/z [M + H]+ 425.10 |

TABLE 1-continued

| Cpd. No. | Structure | Name | Mass Spec. |
|---|---|---|---|
| 299 | 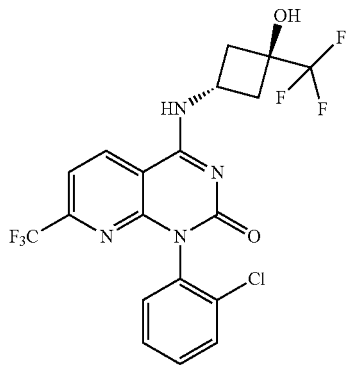 [SMILES: O=c1nc(N[C@H]2C[C@@](O)(C(F)(F)F)C2)c2ccc(C(F)(F)F)nc2n1-c1ccccc1Cl] | 4-{[(trans)-3-hydroxy-3-(trifluoromethyl)cyclobutyl]amino}-1-(2-chlorophenyl)-7-(trifluoromethyl)pyrido-[2,3-d]pyrimidin-2(1H)-one | m/z [M + H]+ 479.10 |
| 300 | 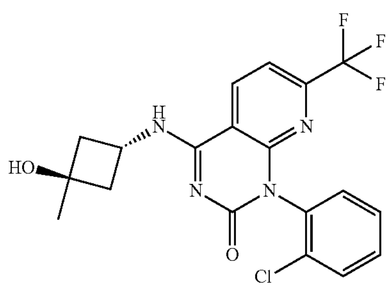 [SMILES: C[C@]1(O)C[C@H](Nc2nc(=O)n(-c3ccccc3Cl)c3nc(C(F)(F)F)ccc23)C1] | 4-[((trans)-3-hydroxy-3-methylcyclobutyl)amino]-1-(2-chlorophenyl)-7-(trifluoromethyl)pyrido[2,3-d]pyrimidin-2(1H)-one | m/z [M + H]+ 425.10 |
| 301 | 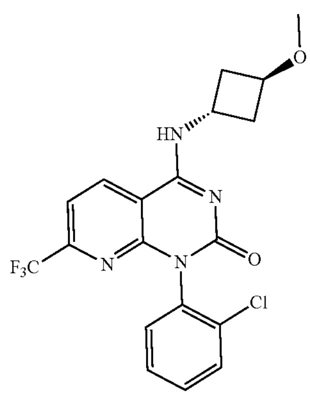 [SMILES: CO[C@H]1C[C@H](Nc2nc(=O)n(-c3ccccc3Cl)c3nc(C(F)(F)F)ccc23)C1] | 4-[(trans)-3-methoxycyclobutyl)amino]-1-(2-chlorophenyl)-7-(trifluoromethyl)-pyrido[2,3-d]pyrimidin-2(1H)-one | m/z [M + H]+ 425.10 |
| 302 | 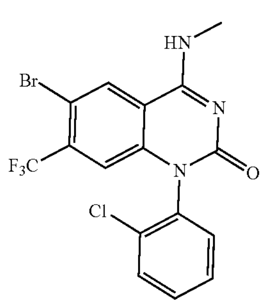 [SMILES: CNc1nc(=O)n(-c2ccccc2Cl)c2cc(C(F)(F)F)c(Br)cc12] | 6-bromo-1-(2-chlorophenyl)-4-(methylamino)-7-(trifluoromethyl)-quinazolin-2(1H)-one | m/z [M + H]+ 432.0 |

TABLE 1-continued

| Cpd. No. | Structure | Name | Mass Spec. |
|---|---|---|---|
| 303 | 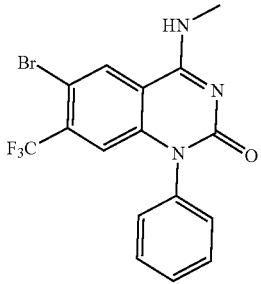 [SMILES: CNc1nc(=O)n(-c2ccccc2)c2cc(C(F)(F)F)c(Br)cc12] | 6-bromo-4-(methylamino)-1-phenyl-7-(trifluoromethyl)quinazolin-2(1H)-one | m/z [M + H]+ 398.0 |
| 304 | 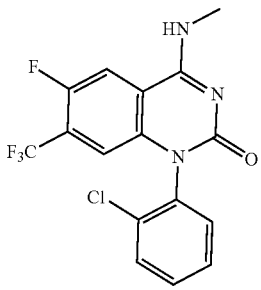 [SMILES: CNc1nc(=O)n(-c2ccccc2Cl)c2cc(C(F)(F)F)c(F)cc12] | 1-(2-chlorophenyl)-6-fluoro-4-(methyl-amino)-7-(trifluoromethyl)hydro-quinazolin-2-one | m/z [M + H]+ 372.0 |
| 305 | 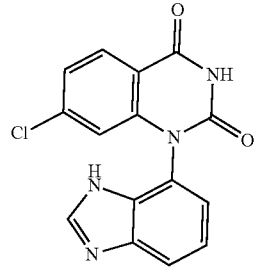 [SMILES: O=c1[nH]c(=O)n(-c2cccc3nc[nH]c23)c2cc(Cl)ccc12] | 1-benzimidazol-7-yl-7-chloro-1,3-dihydroquinazoline-2,4-dione | m/z [M + H]+ 313.0 |
| 306 | 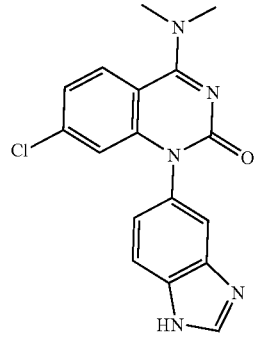 [SMILES: CN(C)c1nc(=O)n(-c2ccc3[nH]cnc3c2)c2cc(Cl)ccc12] | 1-benzimidazol-5-yl-4-(dimethylamino)-7-chlorohydroquinazolin-2-one | m/z [M + H]+ 340.0 |
| 307 | 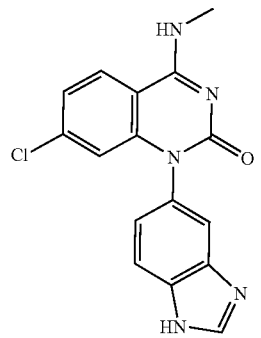 [SMILES: CNc1nc(=O)n(-c2ccc3[nH]cnc3c2)c2cc(Cl)ccc12] | 1-benzimidazol-5-yl-7-chloro-4-(methyl-amino)hydroquinazolin-2-one | m/z [M + H]+ 326.0 |

TABLE 1-continued

| Cpd. No. | Structure | Name | Mass Spec. |
|---|---|---|---|
| 308 | 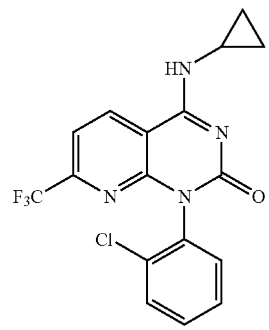 | 1-(2-chlorophenyl)-4-(cyclopropyl-amino)-7-(trifluoromethyl)pyrido[2,3-d]pyrimidin-2(1H)-one | m/z [M + H]+ 381.28 |
| 309 | 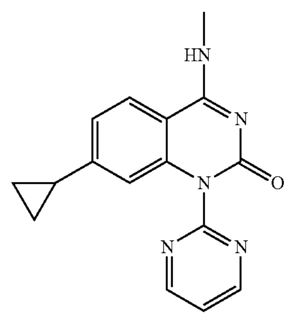 [SMILES: CNc1nc(=O)n(-c2ncccn2)c2cc(C3CC3)ccc12] | 7-cyclopropyl-4-(methylamino)-1-pyrimidin-2-ylhydroquinazolin-2-one | m/z [M + H]+ 294.30 |
| 310 | 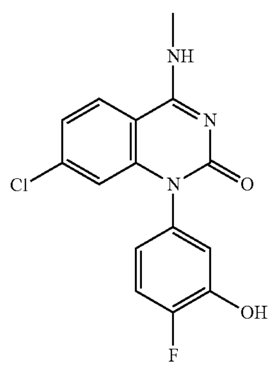 [SMILES: CNc1nc(=O)n(-c2ccc(F)c(O)c2)c2cc(Cl)ccc12] | 7-chloro-1-(4-fluoro-3-hydroxyphenyl)-4-(methylamino)hydroquinazolin-2-one | m/z [M + H]+ 320.34 |
| 311 | 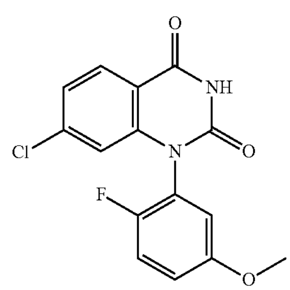 [SMILES: COc1ccc(F)c(-n2c(=O)[nH]c(=O)c3ccc(Cl)cc32)c1] | 7-chloro-1-(2-fluoro-5-methoxyphenyl)-quinazoline-2,4(1H,3H)-dione | m/z [M + H]+ 321.31 |
| 312 | 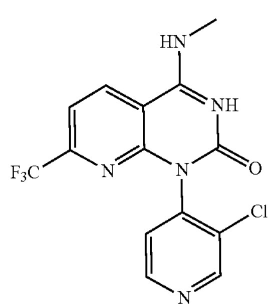 [SMILES: CNc1nc(=O)n(-c2ccncc2Cl)c2nc(C(F)(F)F)ccc12] | 1-(3-chloro-pyridin-4-yl))-4-(methyl-amino)-7-(trifluoromethyl)pyrido[2,3-d]-pyrimidin-2(1H)-one | m/z [M + H]+ 356.00 |

TABLE 1-continued

| Cpd. No. | Structure | Name | Mass Spec. |
|---|---|---|---|
| 313 | 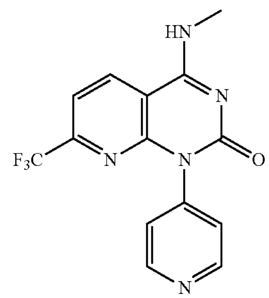 [SMILES: CNc1nc(=O)n(-c2ccncc2)c2nc(C(F)(F)F)ccc12] | 4-(methylamino)-1-(pyridin-4-yl))-7-(trifluoromethyl)pyrido[2,3-d]pyrimidin-2(1H)-one | m/z [M + H]+ 322.00 |
| 314 | 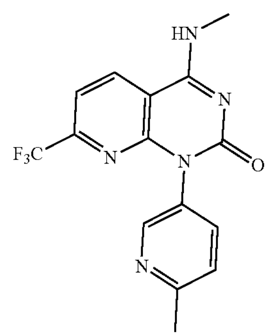 [SMILES: CNc1nc(=O)n(-c2ccc(C)nc2)c2nc(C(F)(F)F)ccc12] | 1-(6-methyl-pyridin-3-yl))-4-(methyl-amino)-7-(trifluoromethyl)pyrido[2,3-d]-pyrimidin-2(1H)-one | m/z [M + H]+ 336.0 |
| 315 | 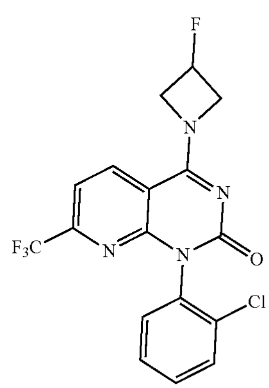 [SMILES: O=c1nc(N2CC(F)C2)c2ccc(C(F)(F)F)nc2n1-c1ccccc1Cl] | 1-(2-chlorophenyl)-4-(3-fluoroazetidin-1-yl)-7-(trifluoromethyl)pyrido[2,3-d]pyrimidin-2(1H)-one | m/z [M + H]+ 399.10 |
| 316 | 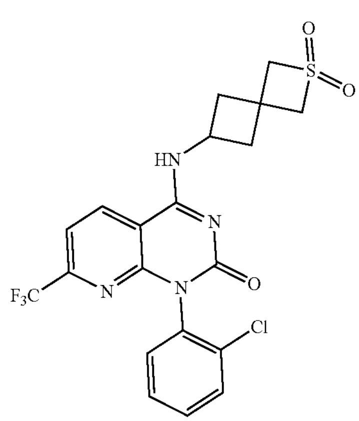 [SMILES: O=c1nc(NC2CC3(C2)CS(=O)(=O)C3)c2ccc(C(F)(F)F)nc2n1-c1ccccc1Cl] | 1-(2-chlorophenyl)-4-((2,2-dioxido-2-thiaspiro[3.3]heptan-6-yl)amino)-7-(trifluoromethyl)pyrido[2,3-d]pyrimidin-2(1H)-one | m/z [M + H]+ 485.10 |

TABLE 1-continued

| Cpd. No. | Structure | Name | Mass Spec. |
|---|---|---|---|
| 317 | 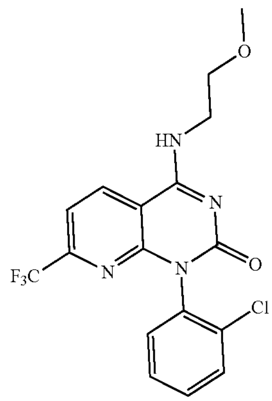 [SMILES: COCCNc1nc(=O)n(-c2ccccc2Cl)c2nc(C(F)(F)F)ccc12] | 1-(2-chlorophenyl)-4-[(2-methoxyethyl)-amino]-7-(trifluoromethyl)pyrido[2,3-d]-pyrimidin-2(1H)-one | m/z [M + H]+ 399.10 |
| 318 | 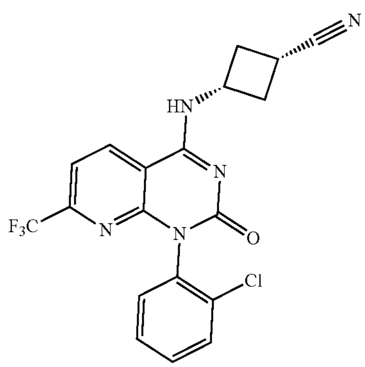 [SMILES: N#C[C@H]1C[C@@H](Nc2nc(=O)n(-c3ccccc3Cl)c3nc(C(F)(F)F)ccc23)C1] | (1s,3s)-3-((1-(2-chlorophenyl)-2-oxo-7-(trifluoromethyl)-1,2-dihydropyrido[2,3-d]pyrimidin-4-yl)amino)cyclobutane-1-carbonitrile | m/z [M + H]+ 420.10 |
| 319 | 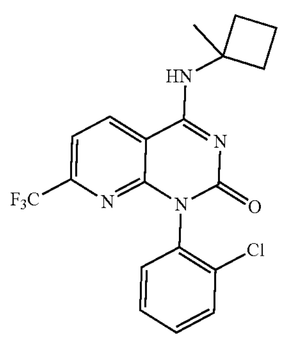 [SMILES: CC1(Nc2nc(=O)n(-c3ccccc3Cl)c3nc(C(F)(F)F)ccc23)CCC1] | 1-(2-chlorophenyl)-4-[(methylcyclo-butyl)amino]-7-(trifluoromethyl)pyrido-[2,3-d]pyrimidin-2(1H)-one | m/z [M + H]+ 409.20 |
| 320 | 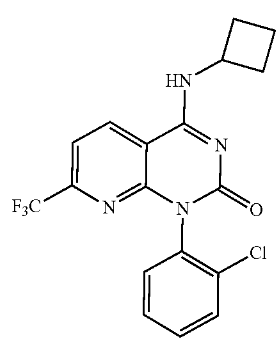 [SMILES: O=c1nc(NC2CCC2)c2ccc(C(F)(F)F)nc2n1-c1ccccc1Cl] | 1-(2-chlorophenyl)-4-(cyclobutylamino)-7-(trifluoromethyl)pyrido[2,3-d]-pyrimidin-2(1H)-one | m/z [M + H]+ 395.10 |

TABLE 1-continued

| Cpd. No. | Structure | Name | Mass Spec. |
|---|---|---|---|
| 321 | 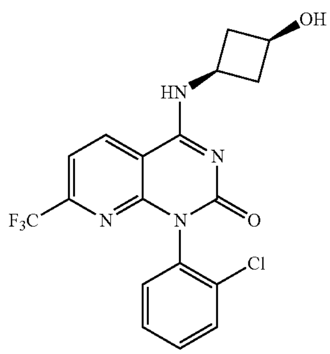 [SMILES: O=c1nc(N[C@H]2C[C@@H](O)C2)c2ccc(C(F)(F)F)nc2n1-c1ccccc1Cl] | (1s,3s)-3-((1-(2-chlorophenyl)-2-oxo-7-(trifluoromethyl)-1,2-dihydropyrido[2,3-d]pyrimidin-4-yl)amino)cyclobutane-1-carbonitrile | m/z [M + H]+ 411.10 |
| 322 | 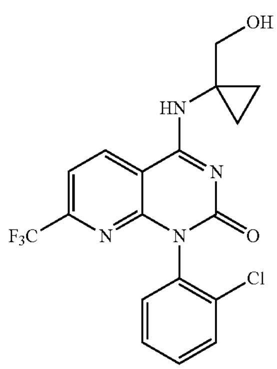 [SMILES: O=c1nc(NC2(CO)CC2)c2ccc(C(F)(F)F)nc2n1-c1ccccc1Cl] | 1-(2-chlorophenyl)-4-{[(hydroxy-methyl)cyclopropyl]amino}-7-(trifluoro-methyl)-pyrido[2,3-d]pyrimidin-2(1H)-one | m/z [M + H]+ 411.10 |
| 323 | 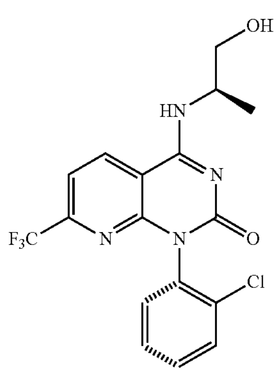 | (R)-(1S$_a$)-(2-chlorophenyl)-4-((1-hydroxypropan-2-yl)amino)-7-(trifluoro-methyl)pyrido-[2,3-d]pyrimidin-2(1H)-one | m/z [M + H]+ 399.10 |
| 324 | 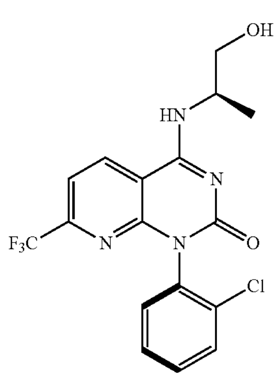 | (R)-(1R$_a$)-(2-chlorophenyl)-4-((1-hydroxypropan-2-yl)amino)-7-(trifluoro-methyl)pyrido-[2,3-d]pyrimidin-2(1H)-one | m/z [M + H]+ 399.10 |

TABLE 1-continued

| Cpd. No. | Structure | Name | Mass Spec. |
|---|---|---|---|
| 325 | 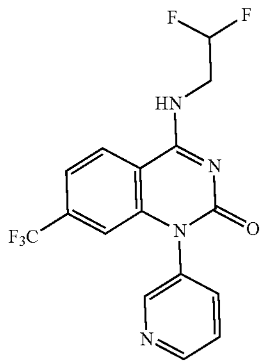 [SMILES: O=c1nc(NCC(F)F)c2ccc(C(F)(F)F)cc2n1-c1cccnc1] | 4-[(2,2-difluoroethyl)amino]-1-(pyridin-3-yl)-7-(trifluoromethyl)hydro-quinazolin-2-one | m/z [M + H]+ 371.0 |
| 326 | 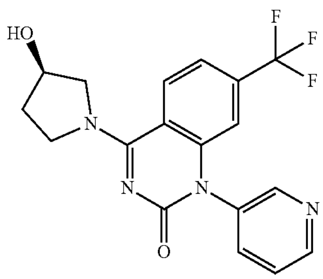 [SMILES: O=c1nc(N2CC[C@@H](O)C2)c2ccc(C(F)(F)F)cc2n1-c1cccnc1] | 4-((3R)-3-hydroxypyrrolidinyl)-1-(pyridin-3-yl)-7-(trifluoromethyl)-hydroquinazolin-2-one | m/z [M + H]+ 372.0 |
| 327 | 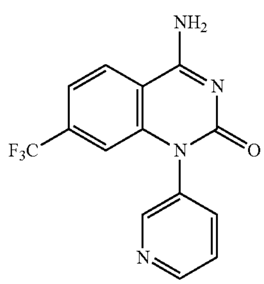 [SMILES: Nc1nc(=O)n(-c2cccnc2)c2cc(C(F)(F)F)ccc12] | 4-amino-1-(pyridin-3-yl)-7-(trifluoromethyl)hydroquinazolin-2-one | m/z [M + H]+ 307.0 |
| 328 | 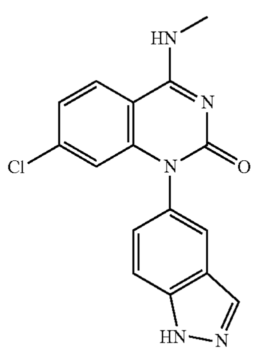 [SMILES: CNc1nc(=O)n(-c2ccc3[nH]ncc3c2)c2cc(Cl)ccc12] | 1-(1H-indazol-5-yl)-7-chloro-4-(methyl-amino)hydroquinazolin-2-one | m/z [M + H]+ 326.0 |
| 329 | 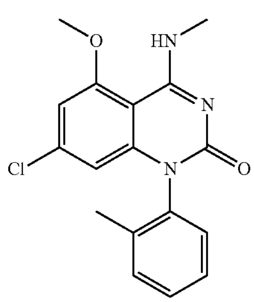 [SMILES: CNc1nc(=O)n(-c2ccccc2C)c2cc(Cl)cc(OC)c12] | 7-chloro-5-methoxy-4-(methylamino)-1-(2-methylphenyl)hydroquinazolin-2-one | m/z [M + H]+ 330.1 |

TABLE 1-continued

| Cpd. No. | Structure | Name | Mass Spec. |
|---|---|---|---|
| 330 | 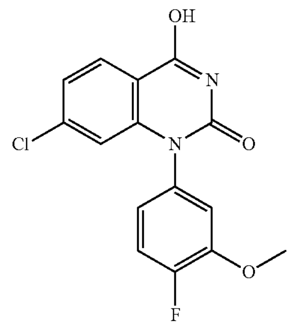 [SMILES: COc1cc(-n2c(=O)nc(O)c3ccc(Cl)cc32)ccc1F] | 7-chloro-1-(4-fluoro-3-methoxyphenyl)-4-hydroxyhydroquinazolin-2-one | m/z [M + H]+ 319.05 |
| 331 | 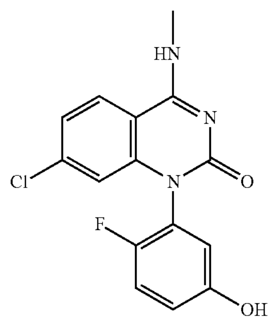 [SMILES: CNc1nc(=O)n(-c2cc(O)ccc2F)c2cc(Cl)ccc12] | 7-chloro-1-(6-fluoro-3-hydroxyphenyl)-4-(methylamino)hydroquinazolin-2-one | m/z [M + H]+ 319.06 |
| 332 | 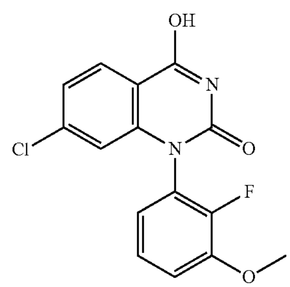 [SMILES: COc1cccc(-n2c(=O)nc(O)c3ccc(Cl)cc32)c1F] | 7-chloro-1-(2-fluoro-3-methoxyphenyl)-4-hydroxyhydroquinazolin-2-one | m/z [M + H]+ 320.06 |
| 333 | 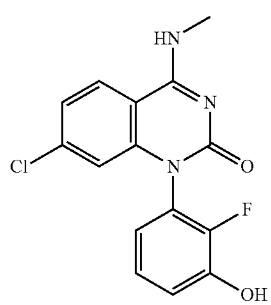 | 7-chloro-1-(2-fluoro-3-hydroxyphenyl)-4-(methylamino)quinazolin-2(1H)-one | m/z [M + H]+ 320.27 |
| 334 | 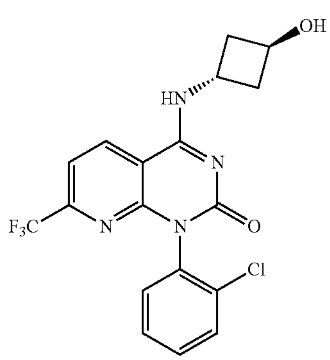 [SMILES: O=c1nc(N[C@H]2C[C@H](O)C2)c2ccc(C(F)(F)F)nc2n1-c1ccccc1Cl] | 1-(2-chlorophenyl)-4-(((1r,3r)-3-hydroxycyclobutyl)amino)-7-(trifluoro-methyl)pyrido[2,3-d]pyrimidin-2(1H)-one | m/z [M + H]+ 411.00 |

TABLE 1-continued

| Cpd. No. | Structure | Name | Mass Spec. |
|---|---|---|---|
| 335 | 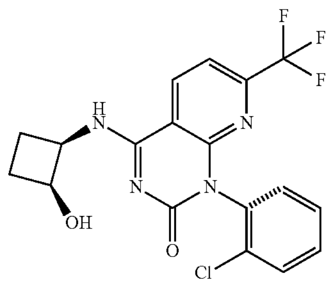 | 4-[((2S,1R)-2-hydroxycyclobutyl)-amino]-(1S$_a$)-(2-chlorophenyl)-7-(trifluoromethyl)hydro-pyrido[2,3-d]-pyrimidin-2(1H)-one | m/z [M + H]+ 411.00 |
| 336 | 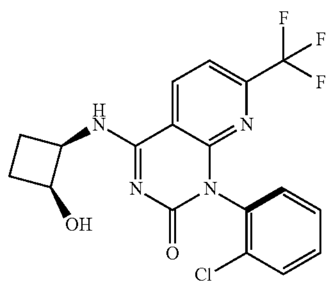 | 4-[((2S,1R)-2-hydroxycyclo-butyl)amino]-(1R$_a$)-(2-chlorophenyl)-7-(trifluoromethyl)hydro-pyridino[2,3-d]-pyrimidin-2-one | m/z [M + H]+ 411.00 |
| 337 | 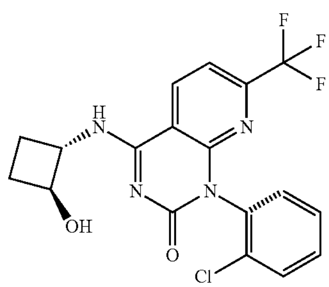 | 4-[((1S,2S)-2-hydroxycyclobutyl)-amino]-(1Sa)-(2-chlorophenyl)-7-(trifluoromethyl)hydro-pyridino[2,3-d]-pyrimidin-2-one | m/z [M + H]+ 411.00 |
| 338 | 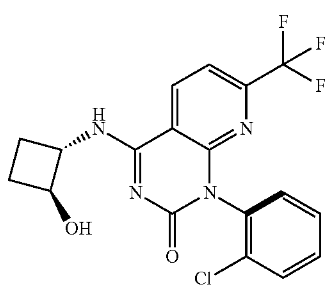 | 4-[((1S,2S)-2-hydroxycyclobutyl)-amino]-(1Ra)-(2-chlorophenyl)-7-(trifluoromethyl)hydro-pyridino[2,3-d]-pyrimidin-2-one | m/z [M + H]+ 411.00 |
| 339 | 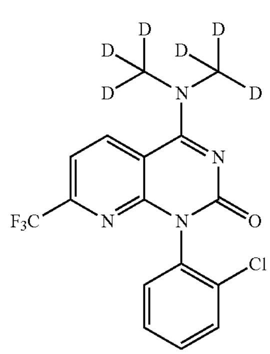 [SMILES: [2H]C([2H])([2H])N(c1nc(=O)n(-c2ccccc2Cl)c2nc(C(F)(F)F)ccc12)C([2H])([2H])[2H]] | 4-(bis(methyl-d3)amino)-1-(2-chloro-phenyl)-7-(trifluoromethyl)-pyrido[2,3-d]pyrimidin-2(1H)-one | m/z [M + H]+ 375.00 |

TABLE 1-continued

| Cpd. No. | Structure | Name | Mass Spec. |
|---|---|---|---|
| 340 | 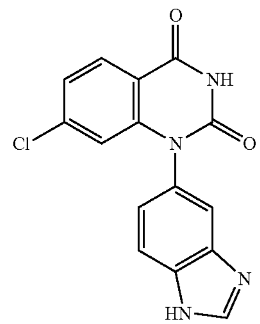 [SMILES: O=c1[nH]c(=O)n(-c2ccc3[nH]cnc3c2)c2cc(Cl)ccc12] | 1-(1H-benzo[d]imidazol-5-yl)-7-chloro-quinazoline-2,4(1H,3H)-dione | m/z [M + H]+ 313.0 |
| 341 | 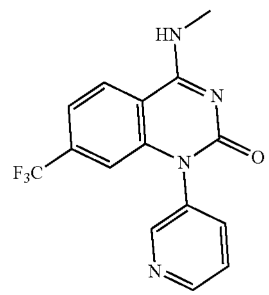 [SMILES: CNc1nc(=O)n(-c2cccnc2)c2cc(C(F)(F)F)ccc12] | 4-(methylamino)-1-(pyridin-3-yl)-7-(trifluoromethyl)hydroquinazolin-2-one | m/z [M + H]+ 321.0 |
| 342 | 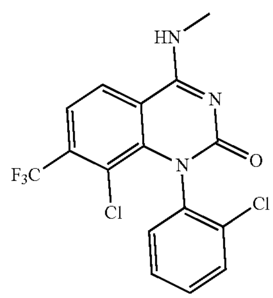 [SMILES: CNc1nc(=O)n(-c2ccccc2Cl)c2c(Cl)c(C(F)(F)F)ccc12] | 8-chloro-1-(2-chlorophenyl)-4-(methylamino)-7-(trifluoromethyl)-hydroquinazolin-2-one | m/z [M + H]+ 388.0 |
| 343 | 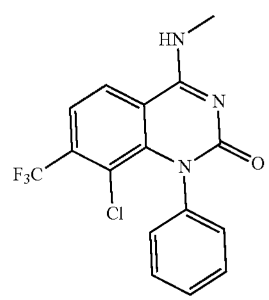 [SMILES: CNc1nc(=O)n(-c2ccccc2)c2c(Cl)c(C(F)(F)F)ccc12] | 8-chloro-4-(methylamino)-1-phenyl-7-(trifluoromethyl)hydroquinazolin-2-one | m/z [M + H]+ 354.04 |
| 344 | 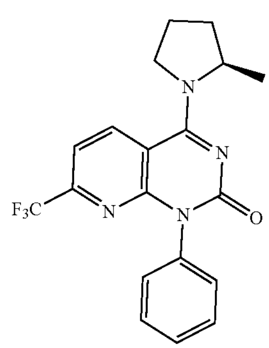 [SMILES: C[C@@H]1CCCN1c1nc(=O)n(-c2ccccc2)c2nc(C(F)(F)F)ccc12] | 4-((2R)-2-methylpyrrolidin-1-yl)-1-phenyl-7-(trifluoromethyl)pyrido[2,3-d]-pyrimidin-2(1H)-one | m/z [M + H]+ 375.1 |

TABLE 1-continued

| Cpd. No. | Structure | Name | Mass Spec. |
|---|---|---|---|
| 345 | 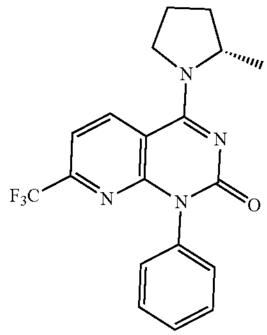 [SMILES: C[C@H]1CCCN1c1nc(=O)n(-c2ccccc2)c2nc(C(F)(F)F)ccc12] | 4-((2S)-2-methylpyrrolidin-1-yl)-1-phenyl-7-(trifluoromethyl)pyrido[2,3-d]-pyrimidin-2(1H)-one | m/z [M + H]+ 375.1 |
| 346 | 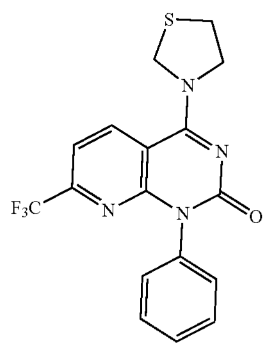 [SMILES: O=c1nc(N2CCSC2)c2ccc(C(F)(F)F)nc2n1-c1ccccc1] | 1-phenyl-4-(1,3-thiazolidin-3-yl)-7-(trifluoromethyl)pyrido[2,3-d]-pyrimidin-2(1H)-one | m/z [M + H]+ 379.1 |
| 347 | 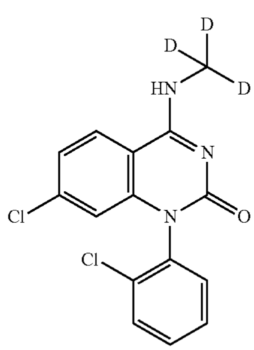 [SMILES: [2H]C([2H])([2H])Nc1nc(=O)n(-c2ccccc2Cl)c2cc(Cl)ccc12] | 7-chloro-1-(2-chlorophenyl)-4-((methyl-d3)amino)quinazolin-2(1H)-one | m/z [M + H]+ 324.1 |
| 348 | 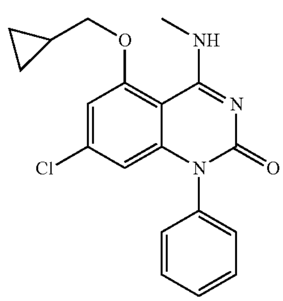 [SMILES: CNc1nc(=O)n(-c2ccccc2)c2cc(Cl)cc(OCC3CC3)c12] | 7-chloro-5-(cyclopropylmethoxy)-4-(methylamino)-1-phenylhydro-quinazolin-2-one | m/z [M + H]+ 356.32 |

TABLE 1-continued

| Cpd. No. | Structure | Name | Mass Spec. |
|---|---|---|---|
| 349 | 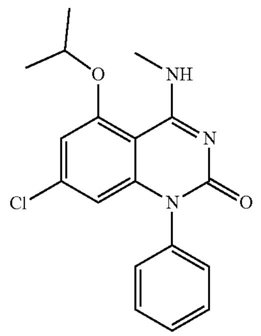 [SMILES: CNc1nc(=O)n(-c2ccccc2)c2cc(Cl)cc(OC(C)C)c12] | 7-chloro-4-(methylamino)-5-(methyl-ethoxy)-1-phenylhydroquinazolin-2-one | m/z [M + H]+ 344.33 |
| 350 | 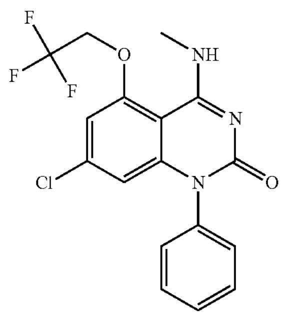 [SMILES: CNc1nc(=O)n(-c2ccccc2)c2cc(Cl)cc(OCC(F)(F)F)c12] | 7-chloro-4-(methylamino)-1-phenyl-5-(2,2,2-trifluoroethoxy)hydroquinazolin-2-one | m/z [M + H]+ 384.31 |
| 351 | 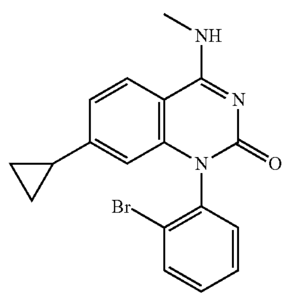 [SMILES: CNc1nc(=O)n(-c2ccccc2Br)c2cc(C3CC3)ccc12] | 1-(2-bromophenyl)-7-cyclopropyl-4-(methylamino)hydroquinazolin-2-one | m/z [M + H]+ 370.26 |
| 352 | 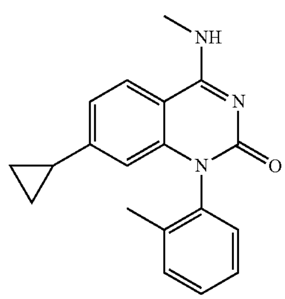 [SMILES: CNc1nc(=O)n(-c2ccccc2C)c2cc(C3CC3)ccc12] | 7-cyclopropyl-4-(methylamino)-1-(2-methylphenyl)hydroquinazolin-2-one | m/z [M + H]+ 306.33 |
| 353 | 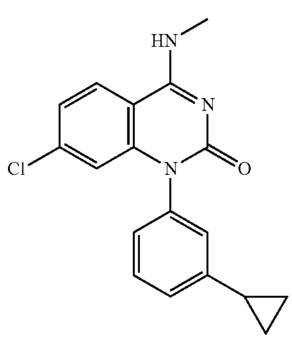 [SMILES: CNc1nc(=O)n(-c2cccc(C3CC3)c2)c2cc(Cl)ccc12] | 7-chloro-1-(3-cyclopropylphenyl)-4-(methylamino)hydroquinazolin-2-one | m/z [M + H]+ 326.32 |

TABLE 1-continued

| Cpd. No. | Structure | Name | Mass Spec. |
|---|---|---|---|
| 354 | 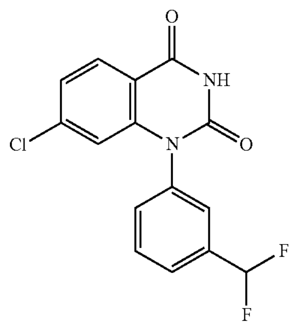 [SMILES: O=c1[nH]c(=O)n(-c2cccc(C(F)F)c2)c2cc(Cl)ccc12] | 7-chloro-1-(3-difluoromethylphenyl)-quinazoline-2,4(1H,3H)-dione | m/z [M + H]+ 323.26 |
| 355 | 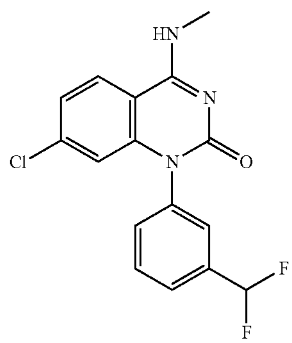 [SMILES: CNc1nc(=O)n(-c2cccc(C(F)F)c2)c2cc(Cl)ccc12] | 7-chloro-1-(3-(difluoromethyl)phenyl)-4-(methylamino)-3,4-dihydroquinazolin-2(1H)-one | m/z [M + H]+ 336.30 |
| 356 | 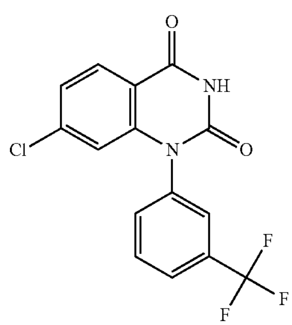 [SMILES: O=c1[nH]c(=O)n(-c2cccc(C(F)(F)F)c2)c2cc(Cl)ccc12] | 7-chloro-1-(3-trifluoromethylphenyl)-quinazoline-2,4(1H,3H)-dione | m/z [M + H]+ 339.29 |
| 357 | 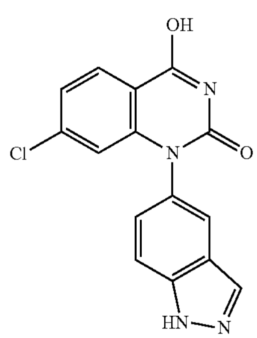 [SMILES: O=c1nc(O)c2ccc(Cl)cc2n1-c1ccc2[nH]ncc2c1] | 1-(1H-indazol-5-yl)-7-chloro-4-hydroxy-hydroquinazolin-2-one | m/z [M + H]+ 313.0 |

TABLE 1-continued

| Cpd. No. | Structure | Name | Mass Spec. |
|---|---|---|---|
| 358 | 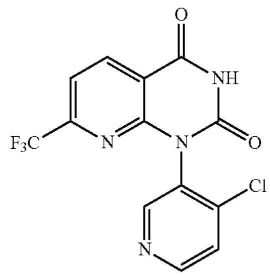 [SMILES: O=c1[nH]c(=O)n(-c2cnccc2Cl)c2nc(C(F)(F)F)ccc12] | 1-(4-chloropyridin-3-yl)-7-(trifluoro-methyl)pyrido[2,3-d]pyrimidine-2,4(1H,3H)-dione | m/z [M + H]+ 343.0 |
| 359 | 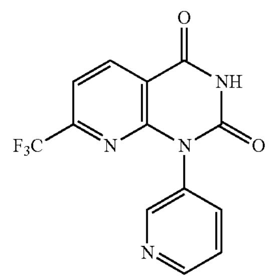 [SMILES: O=c1[nH]c(=O)n(-c2cccnc2)c2nc(C(F)(F)F)ccc12] | 1-(pyridin-3-yl)-7-(trifluoromethyl)-pyrido[2,3-d]pyrimidine-2,4(1H,3H)-dione | m/z [M + H]+ 309.00 |
| 360 | 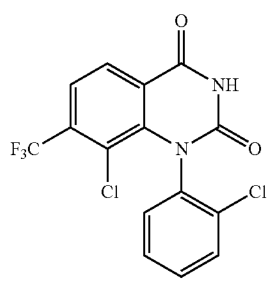 [SMILES: O=c1[nH]c(=O)n(-c2ccccc2Cl)c2c(Cl)c(C(F)(F)F)ccc12] | 8-chloro-1-(2-chlorophenyl)-7-(trifluoro-methyl)pyrido[2,3-d]pyrimidine-2,4(1H,3H)-dione-1 | m/z [M − H]− 373.0 |
| 361 | 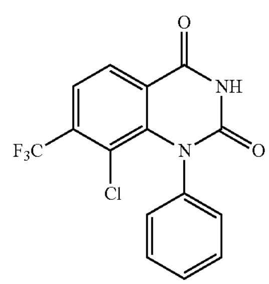 [SMILES: O=c1[nH]c(=O)n(-c2ccccc2)c2c(Cl)c(C(F)(F)F)ccc12] | 8-chloro-1-phenyl-7-(trifluoromethyl)-pyrido[2,3-d]pyrimidine-2,4(1H,3H)-dione | m/z [M − H]− 339.0 |
| 362 | 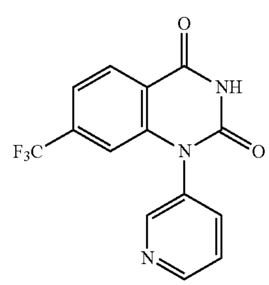 [SMILES: O=c1[nH]c(=O)n(-c2cccnc2)c2cc(C(F)(F)F)ccc12] | 1-(pyridin-3-yl)-7-(trifluoromethyl)-1,3-dihydroquinazoline-2,4-dione | m/z [M + H]+ 308.0 |

TABLE 1-continued

| Cpd. No. | Structure | Name | Mass Spec. |
|---|---|---|---|
| 363 | 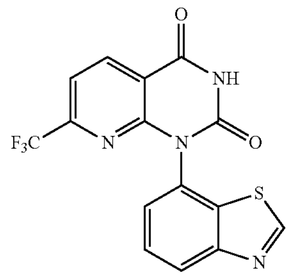 [SMILES: O=c1[nH]c(=O)n(-c2cccc3ncsc23)c2nc(C(F)(F)F)ccc12] | 1-benzothiazol-7-yl-7-(trifluoromethyl)-pyrido[2,3-d]pyrimidine-2,4(1H,3H)-dione | m/z [M + H]+ 365.0 |
| 364 | 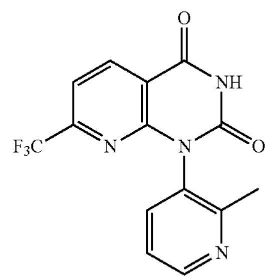 [SMILES: Cc1ncccc1-n1c(=O)[nH]c(=O)c2ccc(C(F)(F)F)nc21] | 1-(2-methylpyridin-3-yl)-7-(trifluoromethyl)pyrido[2,3-d]pyrimidine-2,4(1H,3H)-dione | m/z [M + H]+ 323.1 |
| 365 | 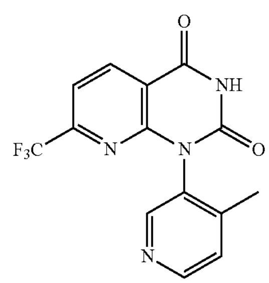 [SMILES: Cc1ccncc1-n1c(=O)[nH]c(=O)c2ccc(C(F)(F)F)nc21] | 1-(4-methylpyridin-3-yl)-7-(trifluoromethyl)pyrido[2,3-d]pyrimidine-2,4(1H,3H)-dione | m/z [M + H]+ 323.1 |
| 366 | 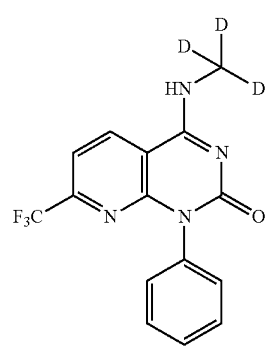 [SMILES: [2H]C([2H])([2H])Nc1nc(=O)n(-c2ccccc2)c2nc(C(F)(F)F)ccc12] | 4-((methyl-d3)amino)-1-phenyl-7-(trifluoromethyl)pyrido[2,3-d]pyrimidin-2(1H)-one | m/z [M + H]+ 324.1 |
| 367 | 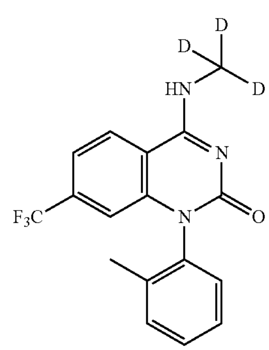 [SMILES: [2H]C([2H])([2H])Nc1nc(=O)n(-c2ccccc2C)c2cc(C(F)(F)F)ccc12] | 4-((methyl-d3)amino)-1-(o-tolyl)-7-(trifluoromethyl)quinazolin-2(1H)-one | m/z [M + H]+ 337.2 |

TABLE 1-continued

| Cpd. No. | Structure | Name | Mass Spec. |
|---|---|---|---|
| 368 | 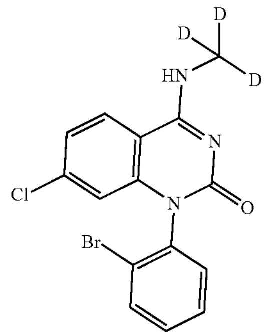 [SMILES: [2H]C([2H])([2H])Nc1nc(=O)n(-c2ccccc2Br)c2cc(Cl)ccc12] | 1-(2-bromophenyl)-7-chloro-4-((methyl-d3)amino)quinazolin-2(1H)-one | m/z [M + H]+ 367.0 |
| 369 | 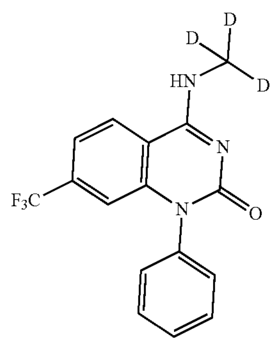 [SMILES: [2H]C([2H])([2H])Nc1nc(=O)n(-c2ccccc2)c2cc(C(F)(F)F)ccc12] | 4-((methyl-d3)amino)-1-phenyl-7-(trifluoromethyl)quinazolin-2(1H)-one | m/z [M + H]+ 323.2 |
| 370 | 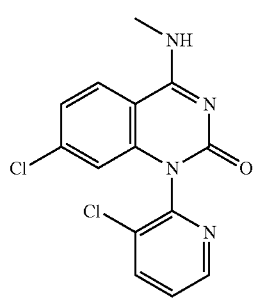 [SMILES: CNc1nc(=O)n(-c2ncccc2Cl)c2cc(Cl)ccc12] | 7-chloro-1-(3-chloro(2-pyridyl))-4-(methylamino)hydroquinazolin-2-one | m/z [M + H]+ 321.26 |
| 371 | 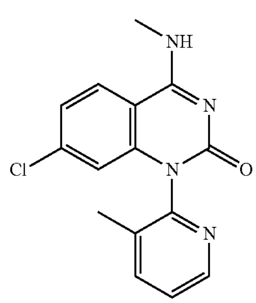 [SMILES: CNc1nc(=O)n(-c2ncccc2C)c2cc(Cl)ccc12] | 7-chloro-1-(3-methylpyridin-2-yl))-4-(methylamino)hydroquinazolin-2-one | m/z [M + H]+ 301.3 |

TABLE 1-continued

| Cpd. No. | Structure | Name | Mass Spec. |
|---|---|---|---|
| 372 | 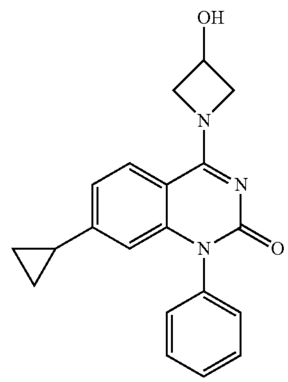 [SMILES: O=c1nc(N2CC(O)C2)c2ccc(C3CC3)cc2n1-c1ccccc1] | 7-cyclopropyl-4-(3-hydroxyazetidin-1-yl)-1-phenylhydroquinazolin-2-one | m/z [M + H]+ 334.36 |
| 373 | 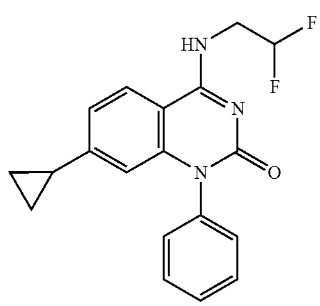 [SMILES: O=c1nc(NCC(F)F)c2ccc(C3CC3)cc2n1-c1ccccc1] | 7-cyclopropyl-4-((2-fluoropropyl)-amino)-1-phenylquinazolin-2(1H)-one | m/z [M + H]+ 342.35 |
| 374 | 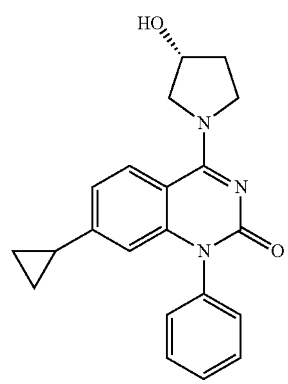 [SMILES: O=c1nc(N2CC[C@@H](O)C2)c2ccc(C3CC3)cc2n1-c1ccccc1] | 4-((3R)-3-hydroxypyrrolidinyl)-7-cyclopropyl-1-phenylhydroquinazolin-2-one | m/z [M + H]+ 348.37 |
| 375 | 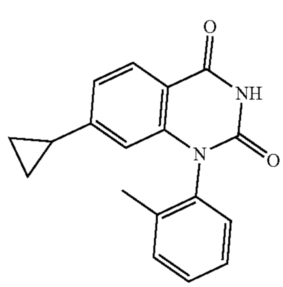 [SMILES: Cc1ccccc1-n1c(=O)[nH]c(=O)c2ccc(C3CC3)cc21] | 7-cyclopropyl-1-(o-tolyl)quinazoline-2,4(1H,3H)-dione | m/z [M + H]+ 293.25 |

TABLE 1-continued

| Cpd. No. | Structure | Name | Mass Spec. |
|---|---|---|---|
| 376 | 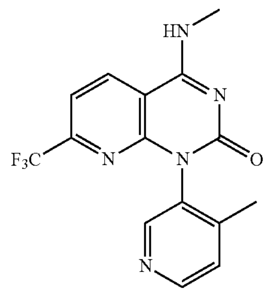 [SMILES: CNc1nc(=O)n(-c2cnccc2C)c2nc(C(F)(F)F)ccc12] | 4-(methylamino)-1-(4-methylpyridin-3-yl)-7-(trifluoromethyl)pyrido[2,3-d]-pyrimidin-2(1H)-one | m/z [M + H]+ 336.1 |
| 377 | 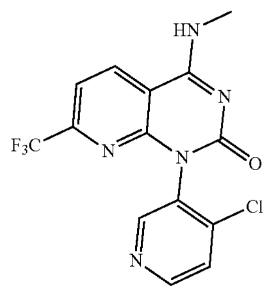 [SMILES: CNc1nc(=O)n(-c2cnccc2Cl)c2nc(C(F)(F)F)ccc12] | 1-(4-chloropyridin-3-yl)-4-(methyl-amino)-7-(trifluoromethyl)pyrido[2,3-d]pyrimidin-2(1H)-one | m/z [M + H]+ 356.00 |
| 378 | 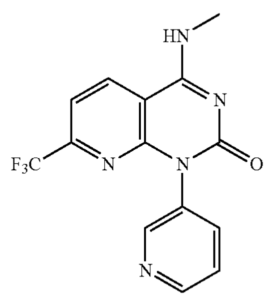 [SMILES: CNc1nc(=O)n(-c2cccnc2)c2nc(C(F)(F)F)ccc12] | 4-(methylamino)-1-(pyridin-3-yl)-7-(trifluoromethyl)pyrido[2,3-d]pyrimidin-2(1H)-one | m/z [M + H]+ 322.10 |
| 379 | 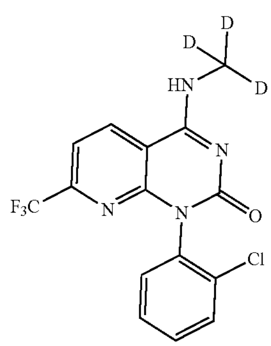 [SMILES: [2H]C([2H])([2H])Nc1nc(=O)n(-c2ccccc2Cl)c2nc(C(F)(F)F)ccc12] | 1-(2-chlorophenyl)-4-((methyl-d3)-amino)-7-(trifluoromethyl)pyrido[2,3-d]pyrimidin-2(1H)-one | m/z [M + H]+ 358.00 |
| 380 | 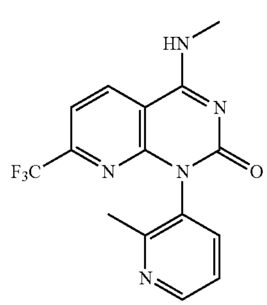 [SMILES: CNc1nc(=O)n(-c2cccnc2C)c2nc(C(F)(F)F)ccc12] | 4-(methylamino)-1-(2-methylpyridin-3-yl)-7-(trifluoromethyl)pyrido[2,3-d]-pyrimidin-2(1H)-one | m/z [M + H]+ 336.1 |

TABLE 1-continued

| Cpd. No. | Structure | Name | Mass Spec. |
|---|---|---|---|
| 381 | 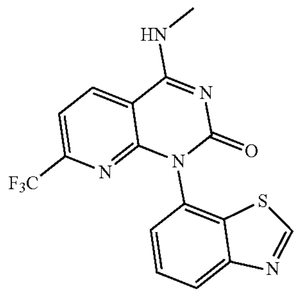 [SMILES: CNc1nc(=O)n(-c2cccc3ncsc23)c2nc(C(F)(F)F)ccc12] | 1-benzothiazol-7-yl-4-(methylamino)-7-(trifluoromethyl)pyrido[2,3-d]pyrimidin-2(1H)-one | m/z [M + H]+ 378.0 |
| 382 | 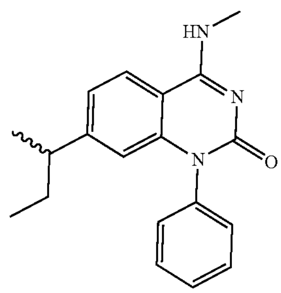 [SMILES: CCC(C)c1ccc2c(NC)nc(=O)n(-c3ccccc3)c2c1] | 4-(methylamino)-7-(methylpropyl)-1-phenylhydroquinazolin-2-one | m/z [M + H]+ 308.2 |
| 383 | 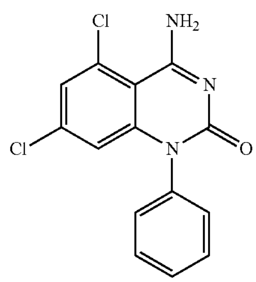 [SMILES: Nc1nc(=O)n(-c2ccccc2)c2cc(Cl)cc(Cl)c12] | 4-amino-5,7-dichloro-1-phenyl-hydroquinazolin-2-one | m/z [M + H]+ 306.23 |
| 384 | 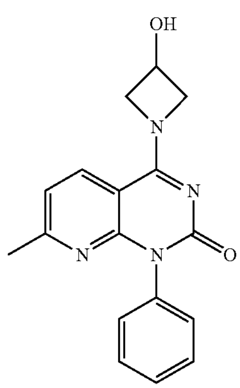 [SMILES: Cc1ccc2c(N3CC(O)C3)nc(=O)n(-c3ccccc3)c2n1] | 4-(3-hydroxyazetidin-1-yl)-7-methyl-1-phenylpyrido[2,3-d]pyrimidin-2(1H)-one | m/z [M + H]+ 309.32 |
| 385 | 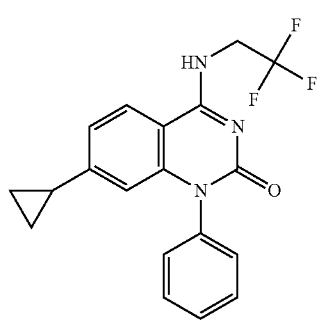 [SMILES: O=c1nc(NCC(F)(F)F)c2ccc(C3CC3)cc2n1-c1ccccc1] | 7-cyclopropyl-1-phenyl-4-[(2,2,2-trifluoroethyl)amino]hydroquinazolin-2-one | m/z [M + H]+ 360.36 |

TABLE 1-continued

| Cpd. No. | Structure | Name | Mass Spec. |
|---|---|---|---|
| 386 | 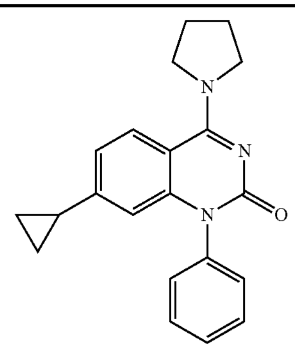 | 7-cyclopropyl-1-phenyl-4-pyrrolidin-1-ylhydroquinazolin-2-one | m/z [M + H]+ 332.38 |
| 387 | 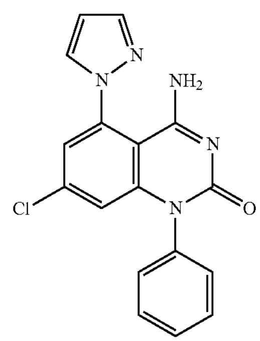 | 4-amino-7-chloro-1-phenyl-5-pyrazol-1-ylhydroquinazolin-2-one | m/z [M + H]+ 338.31 |
| 388 | 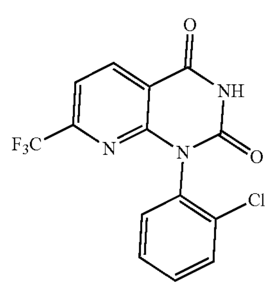 [SMILES: O=c1[nH]c(=O)n(-c2ccccc2Cl)c2nc(C(F)(F)F)ccc12] | 1-(2-chlorophenyl)-7-(trifluoromethyl)-1,3-dihydropyridino[2,3-d]pyrimidine-2,4-dione | m/z [M + H]+ 342.0 |
| 389 | 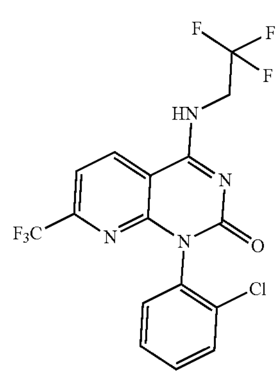 [SMILES: O=c1nc(NCC(F)(F)F)c2ccc(C(F)(F)F)nc2n1-c1ccccc1Cl] | 1-(2-chlorophenyl)-4-[(2,2,2-trifluoro-ethyl)amino]-7-(trifluoro-methyl)-pyrido[2,3-d]pyrimidin-2(1H)-one | m/z [M + H]+ 423.10 |

TABLE 1-continued

| Cpd. No. | Structure | Name | Mass Spec. |
|---|---|---|---|
| 390 | 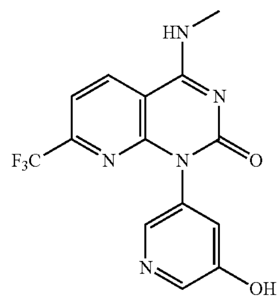 [SMILES: CNc1nc(=O)n(-c2cncc(O)c2)c2nc(C(F)(F)F)ccc12] | 1-(5-hydroxypyridin-3-yl)-4-(methylamino)-7-(trifluoromethyl)pyrido[2,3-d]-pyrimidin-2(1H)-one | m/z [M + H]+ 338.10 |
| 391 | 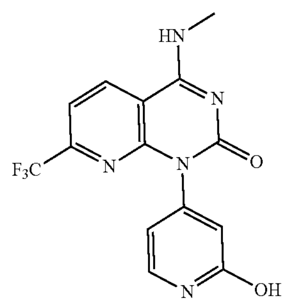 [SMILES: CNc1nc(=O)n(-c2ccnc(O)c2)c2nc(C(F)(F)F)ccc12] | 1-(2-hydroxypyridin-4-yl)-4-(methylamino)-7-(trifluoromethyl)-pyrido[2,3-d]pyrimidin-2(1H)-one | m/z [M + H]+ 338.10 |
| 392 | 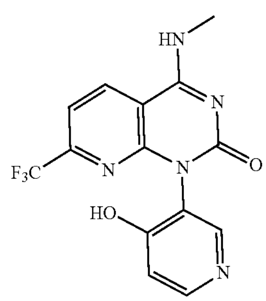 [SMILES: CNc1nc(=O)n(-c2cnccc2O)c2nc(C(F)(F)F)ccc12] | 1-(4-hydroxypyridin-3-yl)-4-(methylamino)-7-(trifluoromethyl)pyrido[2,3-d]-pyrimidin-2(1H)-one | m/z [M + H]+ 338.10 |
| 393 | 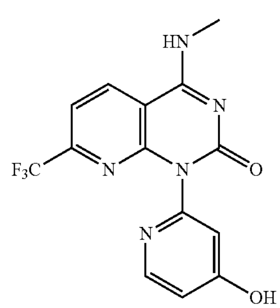 [SMILES: CNc1nc(=O)n(-c2cc(O)ccn2)c2nc(C(F)(F)F)ccc12] | 1-(5-hydroxypyridin-2-yl)-4-(methylamino)-7-(trifluoromethyl)pyrido[2,3-d]-pyrimidin-2(1H)-one | m/z [M + H]+ 338.10 |
| 394 | 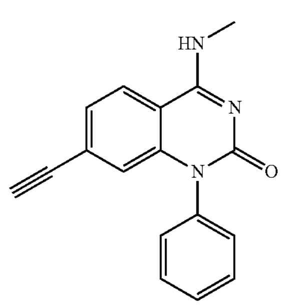 [SMILES: C#Cc1ccc2c(NC)nc(=O)n(-c3ccccc3)c2c1] | 7-ethynyl-4-(methylamino)-1-phenyl-hydroquinazolin-2-one | m/z [M + H]+ 276.0 |

TABLE 1-continued

| Cpd. No. | Structure | Name | Mass Spec. |
|---|---|---|---|
| 395 | 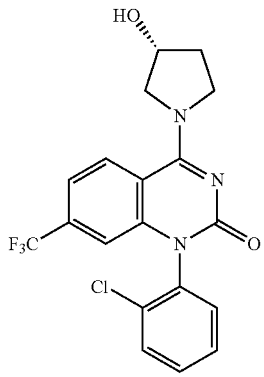 [SMILES: O=c1nc(N2CC[C@@H](O)C2)c2ccc(C(F)(F)F)cc2n1-c1ccccc1Cl] | 4-((3R)-3-hydroxypyrrolidin-1-yl)-1-(2-chlorophenyl)-7-(trifluoromethyl)hydro-quinazolin-2-one | m/z [M + H]+ 410.0 |
| 396 | 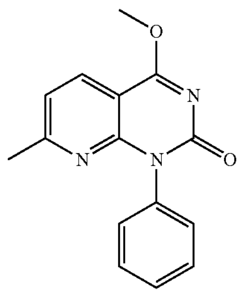 [SMILES: COc1nc(=O)n(-c2ccccc2)c2nc(C)ccc12] | 4-methoxy-7-methyl-1-phenylpyrido[2,3-d]pyrimidin-2(1H)-one | m/z [M + H]+ 268.12 |
| 397 | 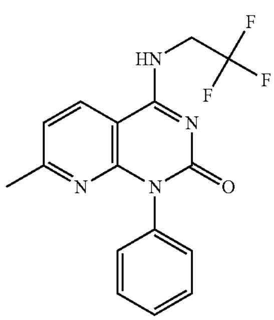 [SMILES: Cc1ccc2c(NCC(F)(F)F)nc(=O)n(-c3ccccc3)c2n1] | 7-methyl-1-phenyl-4-[(2,2,2-trifluoroethyl)amino]pyrido[2,3-d]pyrimidin-2(1H)-one | m/z [M + H]+ 335.16 |
| 398 | 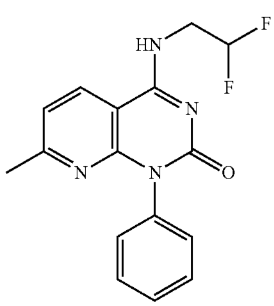 [SMILES: Cc1ccc2c(NCC(F)F)nc(=O)n(-c3ccccc3)c2n1] | 4-[(2,2-difluoroethyl)amino]-7-methyl-1-phenylpyrido[2,3-d]pyrimidin-2(1H)-one | m/z [M + H]+ 317.17 |
| 399 | 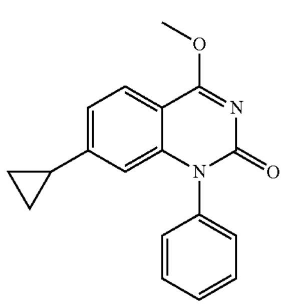 [SMILES: COc1nc(=O)n(-c2ccccc2)c2cc(C3CC3)ccc12] | 7-cyclopropyl-4-methoxy-1-phenyl-hydroquinazolin-2-one | m/z [M + H]+ 293.1 |

TABLE 1-continued

| Cpd. No. | Structure | Name | Mass Spec. |
|---|---|---|---|
| 400 | 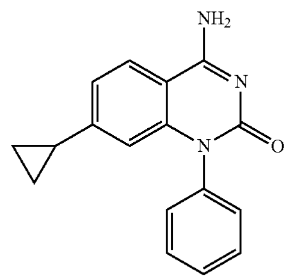 [SMILES: Nc1nc(=O)n(-c2ccccc2)c2cc(C3CC3)ccc12] | 4-amino-7-cyclopropyl-1-phenylhydro-quinazolin-2-one | m/z [M + H]+ 278.21 |
| 401 | 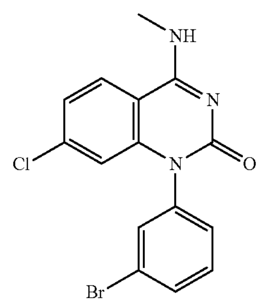 [SMILES: CNc1nc(=O)n(-c2cccc(Br)c2)c2cc(Cl)ccc12] | 1-(3-bromophenyl)-7-chloro-4-(methylamino)hydroquinazolin-2-one | m/z [M + H]+ 363.97 |
| 402 | 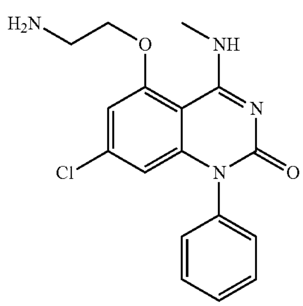 [SMILES: CNc1nc(=O)n(-c2ccccc2)c2cc(Cl)cc(OCCN)c12] | 5-(2-aminoethoxy)-7-chloro-4-(methyl-amino)-1-phenylhydroquinazolin-2-one | m/z [M + H]+ 345.1 |
| 403 | 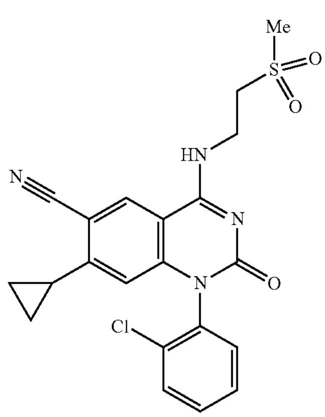 [SMILES: CS(=O)(=O)CCNc1nc(=O)n(-c2ccccc2Cl)c2cc(C3CC3)c(C#N)cc12] | 1-(2-chlorophenyl)-7-cyclopropyl-4-((2-(methylsulfonyl)ethyl)amino)-2-oxo-1,2-dihydroquinazoline-6-carbonitrile | m/z [M + H]+ 443.1 |

TABLE 1-continued

| Cpd. No. | Structure | Name | Mass Spec. |
|---|---|---|---|
| 404 | 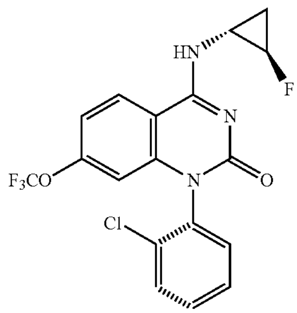 | 4-[((1R,2R)-2-fluorocyclopropyl)-amino]-1-(2-chlorophenyl)-7-(trifluoromethoxy)hydroquinazolin-2-one | m/z [M + H]+ 414.0. |
| 405 | 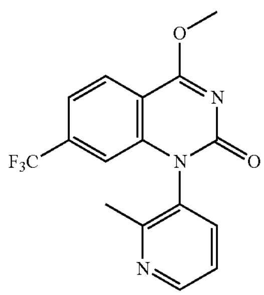 [SMILES: COc1nc(=O)n(-c2cccnc2C)c2cc(C(F)(F)F)ccc12] | 4-methoxy-7-methyl-1-(2-methyl-pyridin-3-yl)quinazolin-2(1H)-one | m/z [M + H]+ 336.40 |
| 406 | 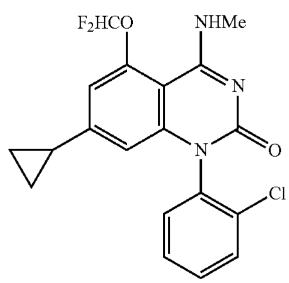 [SMILES: CNc1nc(=O)n(-c2ccccc2Cl)c2cc(C3CC3)cc(OC(F)F)c12] | 5-(difluoromethoxy)-1-(2-chlorophenyl)-7-cyclopropyl-4-(methylamino)hydro-quinazolin-2-one | m/z [M + H]+ 392.3. |
| 407 | 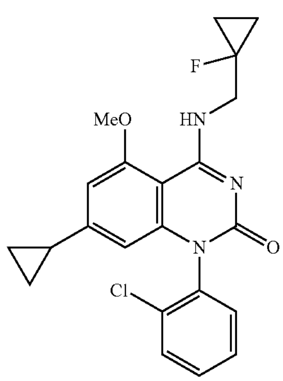 [SMILES: COc1cc(C2CC2)cc2c1c(NCC1(F)CC1)nc(=O)n2-c1ccccc1Cl] | 1-(2-chlorophenyl)-7-cyclopropyl-4-{[(fluorocyclopropyl)methyl]amino}-5-methoxyhydroquinazolin-2-one | m/z [M + H]+ 414.39 |

TABLE 1-continued

| Cpd. No. | Structure | Name | Mass Spec. |
|---|---|---|---|
| 408 | 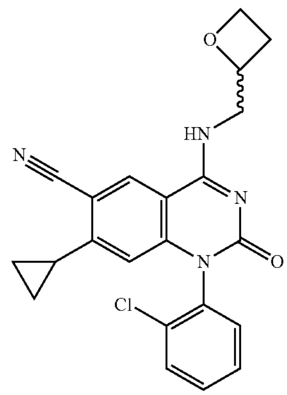 [SMILES: N#Cc1cc2c(NCC3CCO3)nc(=O)n(-c3ccccc3Cl)c2cc1C1CC1] | 1-(2-chlorophenyl)-7-cyclopropyl-4-((oxetan-2-ylmethyl)amino)-2-oxo-1,2-dihydroquinazoline-6-carbonitrile | m/z [M + H]+ 407.0 |
| 409 | 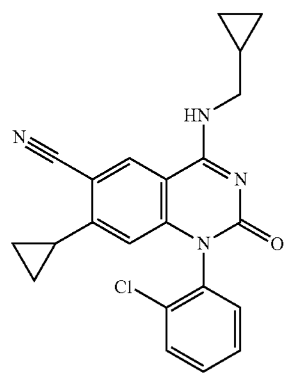 [SMILES: N#Cc1cc2c(NCC3CC3)nc(=O)n(-c3ccccc3Cl)c2cc1C1CC1] | 1-(2-chlorophenyl)-7-cyclopropyl-4-((cyclopropylmethyl)amino)-2-oxo-1,2-dihydroquinazoline-6-carbonitrile | m/z [M + H]+ 391.0 |
| 410 | 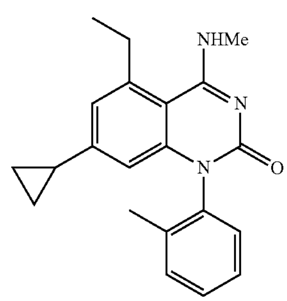 [SMILES: CCc1cc(C2CC2)cc2c1c(NC)nc(=O)n2-c1ccccc1C] | 7-cyclopropyl-5-ethyl-4-(methylamino)-1-(2-methylphenyl)hydroquinazolin-2-one | m/z [M + H]+ 334.37. |
| 411 | 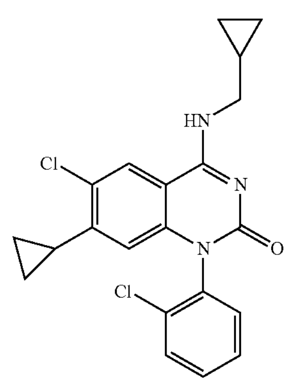 [SMILES: O=c1nc(NCC2CC2)c2cc(Cl)c(C3CC3)cc2n1-c1ccccc1Cl] | 6-chloro-1-(2-chlorophenyl)-7-cyclopropyl-4-[(cyclopropylmethyl)amino]-hydroquinazolin-2-one | m/z [M + H]+ 400.1. |

TABLE 1-continued

| Cpd. No. | Structure | Name | Mass Spec. |
|---|---|---|---|
| 412 | 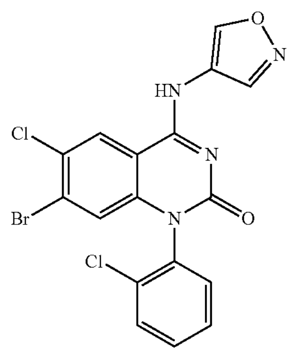 [SMILES: O=c1nc(Nc2cnoc2)c2cc(Cl)c(Br)cc2n1-c1ccccc1Cl] | 7-bromo-6-chloro-1-(2-chlorophenyl)-4-(isoxazol-4-ylamino)hydroquinazolin-2-one | m/z [M + H]+ 452.9 (major) |
| 413 | 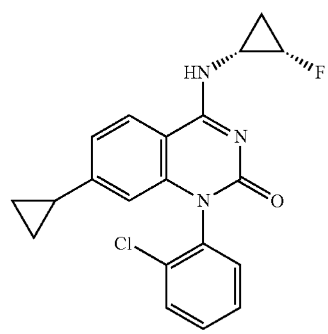 [SMILES: O=c1nc(N[C@@H]2C[C@@H]2F)c2ccc(C3CC3)cc2n1-c1ccccc1Cl] | 4-[((2S,1R)-2-fluorocyclopropyl)amino]-1-(2-chlorophenyl)-7-cyclopropyl-hydroquinazolin-2-one | m/z [M + H]+ 370.0 |
| 414 | 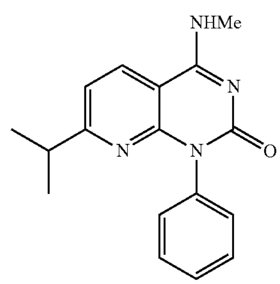 [SMILES: CNc1nc(=O)n(-c2ccccc2)c2nc(C(C)C)ccc12] | 4-(methylamino)-7-(methylethyl)-1-phenylpyrido[2,3-d]pyrimidin-2(1H)-one | m/z [M + H]+ 295.1 |
| 415 | 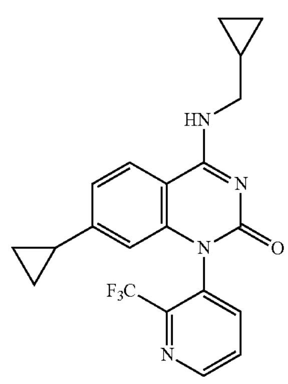 [SMILES: O=c1nc(NCC2CC2)c2ccc(C3CC3)cc2n1-c1cccnc1C(F)(F)F] | 7-cyclopropyl-4-[(cyclopropylmethyl)amino]-1-[2-(trifluoromethyl)(3-pyridyl)]hydroquinazolin-2-one | m/z [M + H]+ 399.1 |

TABLE 1-continued

| Cpd. No. | Structure | Name | Mass Spec. |
|---|---|---|---|
| 416 | 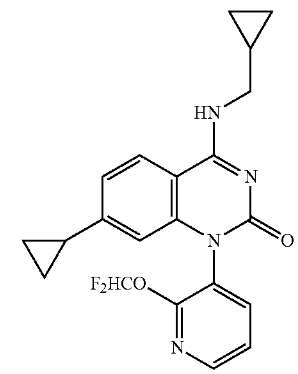 [SMILES: O=c1nc(NCC2CC2)c2ccc(C3CC3)cc2n1-c1cccnc1OC(F)F] | 1-[2-(difluoromethoxy)(3-pyridyl)]-7-cyclopropyl-4-[(cyclopropylmethyl)-amino]hydroquinazolin-2-one | m/z [M + H]+ 401.1. |
| 417 | 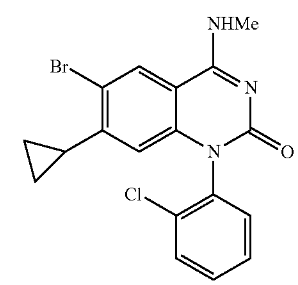 [SMILES: CNc1nc(=O)n(-c2ccccc2Cl)c2cc(C3CC3)c(Br)cc12] | 6-bromo-1-(2-chlorophenyl)-7-cyclopropyl-4-(methylamino)hydroquinazolin-2-one | m/z [M + H]+ 404.0 |
| 418 | 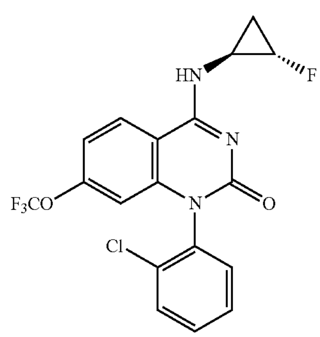 [SMILES: O=c1nc(N[C@H]2C[C@@H]2F)c2ccc(OC(F)(F)F)cc2n1-c1ccccc1Cl] | 1-(2-chlorophenyl)-4-(((1S,2S)-2-fluorocyclopropyl)amino)-7-(trifluoromethoxy)quinazolin-2(1H)-one | m/z [M + H]+ 414.0. |
| 419 | 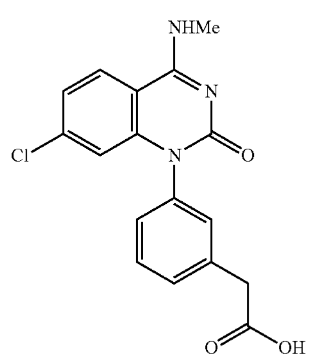 [SMILES: CNc1nc(=O)n(-c2cccc(CC(=O)O)c2)c2cc(Cl)ccc12] | 2-(3-(7-chloro-4-(methylamino)-2-oxoquinazolin-1(2H)-yl)phenyl)acetic acid | m/z [M + H]+ 344.30. |

TABLE 1-continued

| Cpd. No. | Structure | Name | Mass Spec. |
|---|---|---|---|
| 420 | 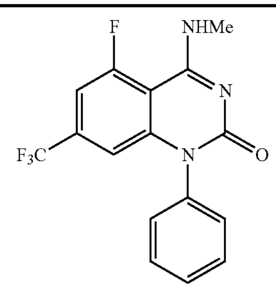 | 5-fluoro-4-(methylamino)-1-phenyl-7-(trifluoromethyl)hydroquinazolin-2-one | m/z [M + H]+ 338.1. |
| 421 | 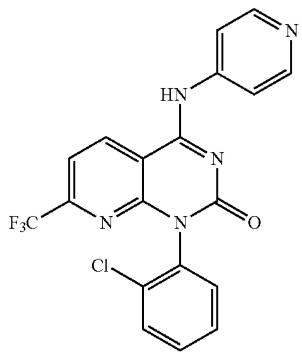 [SMILES: O=c1nc(Nc2ccncc2)c2ccc(C(F)(F)F)nc2n1-c1ccccc1Cl] | 1-(2-chlorophenyl)-4-(pyridin-4-yl-amino)-7-(trifluoromethyl)pyrido[2,3-d]-pyrimidin-2(1H)-one | m/z [M + H]+ 418.00. |
| 422 | 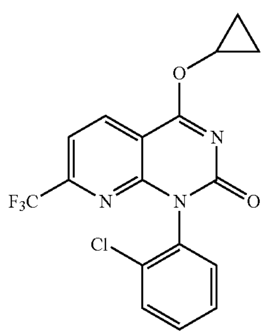 [SMILES: O=c1nc(OC2CC2)c2ccc(C(F)(F)F)nc2n1-c1ccccc1Cl] | 1-(2-chlorophenyl)-4-cyclopropoxy-7-(trifluoromethyl)pyrido[2,3-d]pyrimidin-2(1H)-one | m/z [M + H]+ 382.33 |
| 423 | 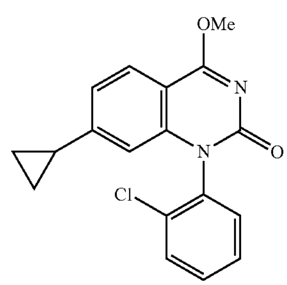 [SMILES: COc1nc(=O)n(-c2ccccc2Cl)c2cc(C3CC3)ccc12] | 1-(2-chlorophenyl)-7-cyclopropyl-4-methoxyhydroquinazolin-2-one | m/z [M + H]+ 327.16. |
| 424 | 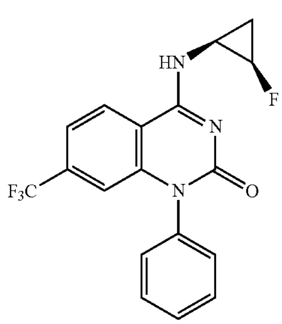 [SMILES: O=c1nc(N[C@H]2C[C@H]2F)c2ccc(C(F)(F)F)cc2n1-c1ccccc1] | 4-(((1S,2R)-2-fluorocyclopropyl)amino)-1-phenyl-7-(trifluoromethyl)quinazolin-2(1H)-one | m/z [M + H]+ 364.1 |

TABLE 1-continued

| Cpd. No. | Structure | Name | Mass Spec. |
|---|---|---|---|
| 425 | 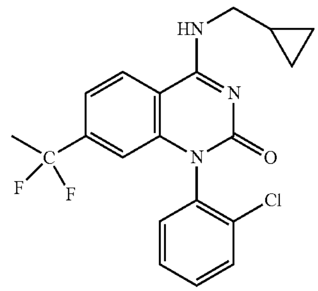 [SMILES: CC(F)(F)c1ccc2c(NCC3CC3)nc(=O)n(-c3ccccc3Cl)c2c1] | 1-(2-chlorophenyl)-4-((cyclopropyl-methyl)amino)-7-(1,1-difluoroethyl)-quinazolin-2(1H)-one | m/z [M + H]+ 390.1 |
| 426 | 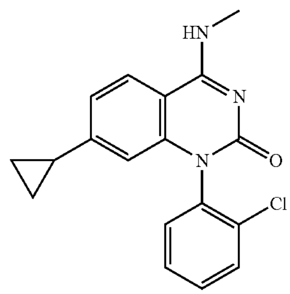 [SMILES: CNc1nc(=O)n(-c2ccccc2Cl)c2cc(C3CC3)ccc12] | 1-(2-chlorophenyl)-7-cyclopropyl-4-(methylamino)quinazolin-2(1H)-one | m/z [M + H]+ 326.0 |
| 427 | 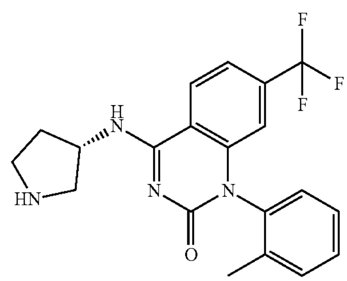 [SMILES: Cc1ccccc1-n1c(=O)nc(N[C@H]2CCNC2)c2ccc(C(F)(F)F)cc21] | (S)-4-(pyrrolidin-3-ylamino)-1-(o-tolyl)-7-(trifluoromethyl)quinazolin-2(1H)-one | m/z [M + H]+ 389.15 |
| 428 | 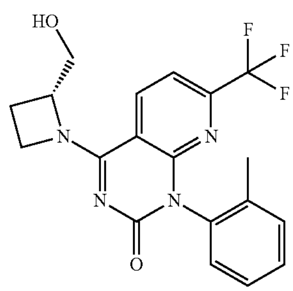 [SMILES: Cc1ccccc1-n1c(=O)nc(N2CC[C@@H]2CO)c2ccc(C(F)(F)F)nc21] | (R)-4-(2-(hydroxymethyl)azetidin-1-yl)-1-(o-tolyl)-7-(trifluoromethyl)pyrido-[2,3-d]pyrimidin-2(1H)-one | m/z [M + H]+ 391.1 |
| 429 | 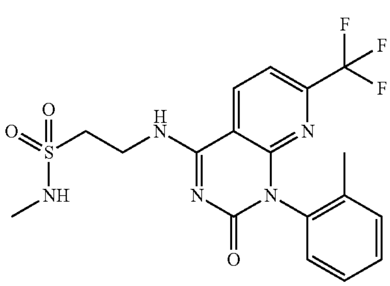 [SMILES: CNS(=O)(=O)CCNc1nc(=O)n(-c2ccccc2C)c2nc(C(F)(F)F)ccc12] | N-methyl-2-((2-oxo-1-(o-tolyl)-7-(trifluoromethyl)-1,2-dihydropyrido[2,3-d]pyrimidin-4-yl)amino)ethane-1-sulfonamide | m/z [M + H]+ 442.1 |

TABLE 1-continued

| Cpd. No. | Structure | Name | Mass Spec. |
|---|---|---|---|
| 430 | 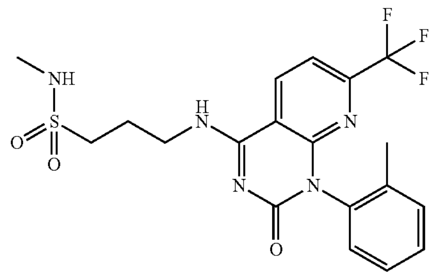 [SMILES: CNS(=O)(=O)CCCNc1nc(=O)n(-c2ccccc2C)c2nc(C(F)(F)F)ccc12] | N-methyl-3-((2-oxo-1-(o-tolyl)-7-(trifluoromethyl)-1,2-dihydropyrido[2,3-d]pyrimidin-4-yl)amino)propane-1-sulfonamide | m/z [M + H]+ 456.1 |
| 431 | 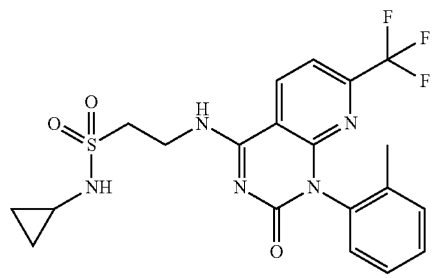 [SMILES: Cc1ccccc1-n1c(=O)nc(NCCS(=O)(=O)NC2CC2)c2ccc(C(F)(F)F)nc21] | N-cyclopropyl-2-((2-oxo-1-(o-tolyl)-7-(trifluoromethyl)-1,2-dihydropyrido[2,3-d]pyrimidin-4-yl)amino)ethane-1-sulfonamide | m/z [M + H]+ 468.1 |
| 432 | 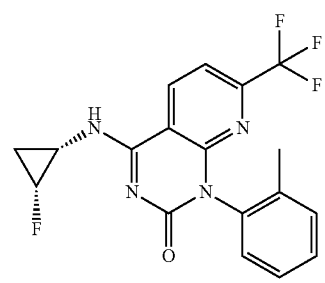 [SMILES: Cc1ccccc1-n1c(=O)nc(N[C@H]2C[C@H]2F)c2ccc(C(F)(F)F)nc21] | 4-(((1S,2R)-2-fluorocyclopropyl)amino)-1-(o-tolyl)-7-(trifluoromethyl)pyrido-[2,3-d]pyrimidin-2(1H)-one | m/z [M + H]+ 379.1 |
| 433 | 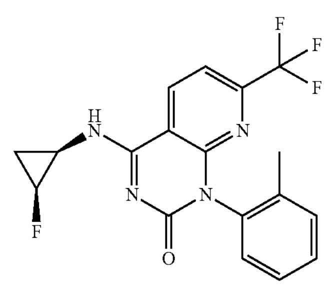 [SMILES: Cc1ccccc1-n1c(=O)nc(N[C@@H]2C[C@@H]2F)c2ccc(C(F)(F)F)nc21] | 4-(((1R,2S)-2-fluorocyclopropyl)amino)-1-(o-tolyl)-7-(trifluoromethyl)pyrido-[2,3-d]pyrimidin-2(1H)-one | m/z [M + H]+ 379.1 |
| 434 | 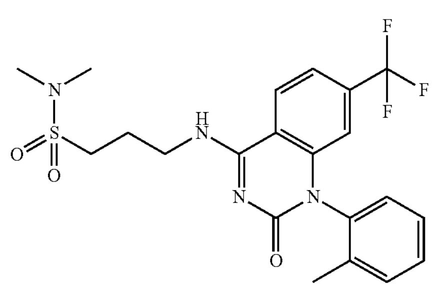 [SMILES: Cc1ccccc1-n1c(=O)nc(NCCCS(=O)(=O)N(C)C)c2ccc(C(F)(F)F)cc21] | N,N-dimethyl-3-((2-oxo-1-(o-tolyl)-7-(trifluoromethyl)-1,2-dihydroquinazolin-4-yl)amino)propane-1-sulfonamide | m/z [M + H]+ 469.1 |

TABLE 1-continued

| Cpd. No. | Structure | Name | Mass Spec. |
|---|---|---|---|
| 435 | 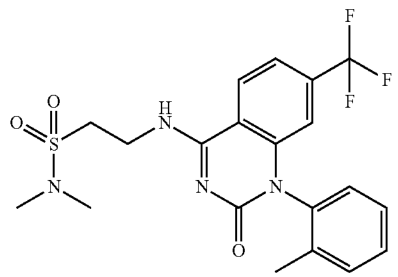 [SMILES: Cc1ccccc1-n1c(=O)nc(NCCS(=O)(=O)N(C)C)c2ccc(C(F)(F)F)cc21] | N,N-dimethyl-2-((2-oxo-1-(o-tolyl)-7-(trifluoromethyl)-1,2-dihydroquinazolin-4-yl)amino)ethane-1-sulfonamide | m/z [M + H]+ 455.1 |
| 436 | 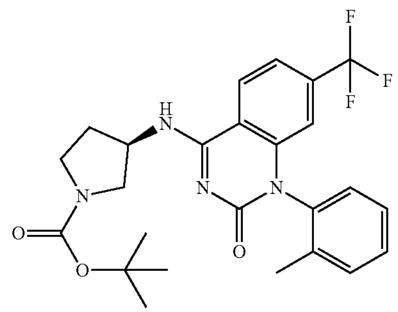 [SMILES: Cc1ccccc1-n1c(=O)nc(N[C@@H]2CCN(C(=O)OC(C)(C)C)C2)c2ccc(C(F)(F)F)cc21] | tert-butyl (R)-3-((2-oxo-1-(o-tolyl)-7-(trifluoromethyl)-1,2-dihydroquinazolin-4-yl)amino)pyrrolidine-1-carboxylate | m/z [M + H]+ 489.2 |
| 437 | 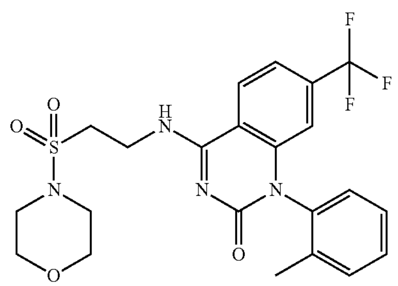 [SMILES: Cc1ccccc1-n1c(=O)nc(NCCS(=O)(=O)N2CCOCC2)c2ccc(C(F)(F)F)cc21] | 4-((2-(morpholinosulfonyl)ethyl)amino)-1-(o-tolyl)-7-(trifluoromethyl)-quinazolin-2(1H)-one | m/z [M + H]+ 497.1 |
| 438 | 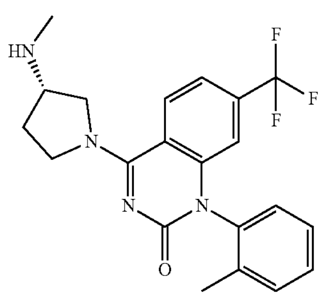 [SMILES: CN[C@H]1CCN(c2nc(=O)n(-c3ccccc3C)c3cc(C(F)(F)F)ccc23)C1] | (S)-4-(3-(methylamino)pyrrolidin-1-yl)-1-(o-tolyl)-7-(trifluoromethyl)-quinazolin-2(1H)-one | m/z [M + H]+ 403.1 |
| 439 | 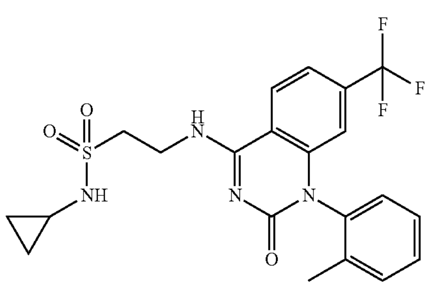 [SMILES: Cc1ccccc1-n1c(=O)nc(NCCS(=O)(=O)NC2CC2)c2ccc(C(F)(F)F)cc21] | N-cyclopropyl-2-((2-oxo-1-(o-tolyl)-7-(trifluoromethyl)-1,2-dihydroquinazolin-4-yl)amino)ethane-1-sulfonamide | m/z [M + H]+ 467.1 |

TABLE 1-continued

| Cpd. No. | Structure | Name | Mass Spec. |
|---|---|---|---|
| 440 | 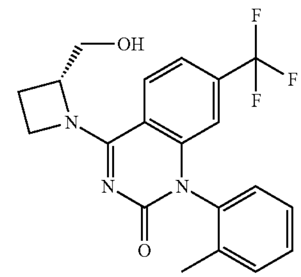 [SMILES: Cc1ccccc1-n1c(=O)nc(N2CC[C@@H]2CO)c2ccc(C(F)(F)F)cc21] | (R)-4-(2-(hydroxymethyl)azetidin-1-yl)-1-(o-tolyl)-7-(trifluoromethyl)-quinazolin-2(1H)-one | m/z [M + H]+ 390.1 |
| 441 | 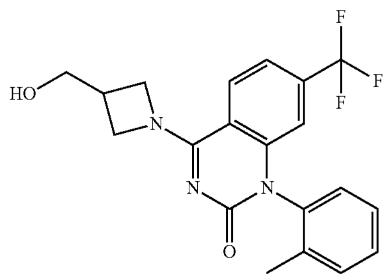 [SMILES: Cc1ccccc1-n1c(=O)nc(N2CC(CO)C2)c2ccc(C(F)(F)F)cc21] | 4-(3-(hydroxymethyl)azetidin-1-yl)-1-(o-tolyl)-7-(trifluoromethyl)quinazolin-2(1H)-one | m/z [M + H]+ 390.1 |
| 442 | 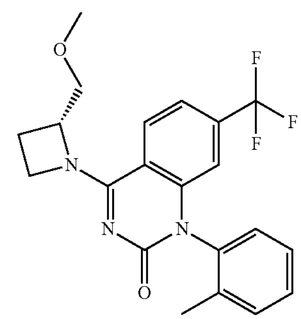 [SMILES: COC[C@H]1CCN1c1nc(=O)n(-c2ccccc2C)c2cc(C(F)(F)F)ccc12] | (R)-4-(2-(methoxymethyl)azetidin-1-yl)-1-(o-tolyl)-7-(trifluoromethyl)-quinazolin-2(1H)-one | m/z [M + H]+ 404 |
| 443 | 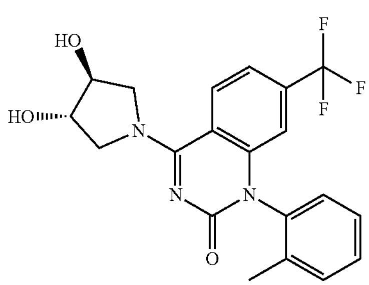 [SMILES: Cc1ccccc1-n1c(=O)nc(N2C[C@H](O)[C@@H](O)C2)c2ccc(C(F)(F)F)cc21] | 4-((3S,4S)-3,4-dihydroxypyrrolidin-1-yl)-1-(o-tolyl)-7-(trifluoromethyl)-quinazolin-2(1H)-one | m/z [M + H]+ 406.1 |
| 444 | 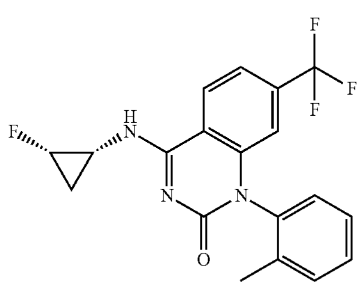 [SMILES: Cc1ccccc1-n1c(=O)nc(N[C@@H]2C[C@@H]2F)c2ccc(C(F)(F)F)cc21] | 4-(((1R,2S)-2-fluorocyclopropyl)amino)-1-(o-tolyl)-7-(trifluoromethyl)-quinazolin-2(1H)-one | m/z [M + H]+ 378.1 |

TABLE 1-continued

| Cpd. No. | Structure | Name | Mass Spec. |
|---|---|---|---|
| 445 | 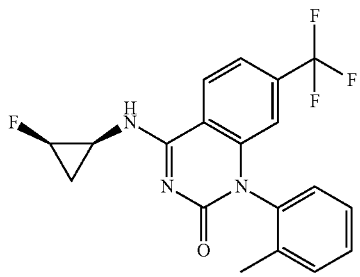 [SMILES: Cc1ccccc1-n1c(=O)nc(N[C@H]2C[C@H]2F)c2ccc(C(F)(F)F)cc21] | 4-(((1S,2R)-2-fluorocyclopropyl)amino)-1-(o-tolyl)-7-(trifluoromethyl)-quinazolin-2(1H)-one | m/z [M + H]+ 378.1 |
| 446 | 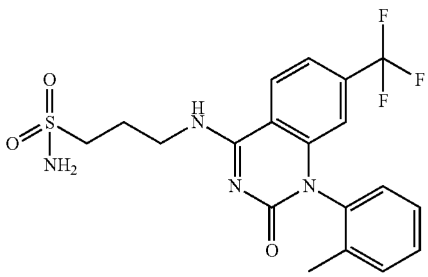 [SMILES: Cc1ccccc1-n1c(=O)nc(NCCCS(N)(=O)=O)c2ccc(C(F)(F)F)cc21] | 3-((2-oxo-1-(o-tolyl)-7-(trifluoromethyl)-1,2-dihydroquinazolin-4-yl)-amino)propane-1-sulfonamide | m/z [M + H]+ 441.1 |
| 447 | 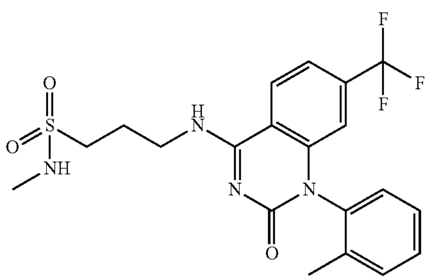 [SMILES: CNS(=O)(=O)CCCNc1nc(=O)n(-c2ccccc2C)c2cc(C(F)(F)F)ccc12] | N-methyl-3-((2-oxo-1-(o-tolyl)-7-(trifluoromethyl)-1,2-dihydroquinazolin-4-yl)amino)propane-1-sulfonamide | m/z [M + H]+ 455.1 |
| 448 | 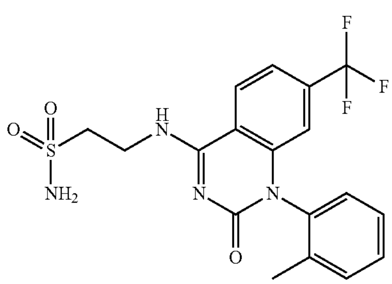 [SMILES: Cc1ccccc1-n1c(=O)nc(NCCS(N)(=O)=O)c2ccc(C(F)(F)F)cc21] | 2-((2-oxo-1-(o-tolyl)-7-(trifluoromethyl)-1,2-dihydroquinazolin-4-yl)-amino)ethane-1-sulfonamide | m/z [M + H]+ 427.05 |
| 449 | 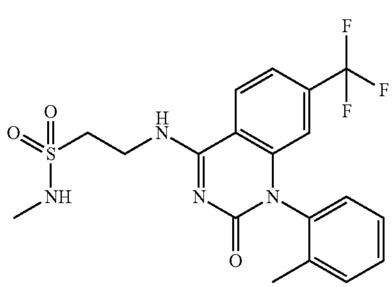 [SMILES: CNS(=O)(=O)CCNc1nc(=O)n(-c2ccccc2C)c2cc(C(F)(F)F)ccc12] | N-methyl-2-((2-oxo-1-(o-tolyl)-7-(trifluoromethyl)-1,2-dihydroquinazolin-4-yl)amino)ethane-1-sulfonamide | m/z [M + H]+ 441.1 |

TABLE 1-continued

| Cpd. No. | Structure | Name | Mass Spec. |
|---|---|---|---|
| 450 | 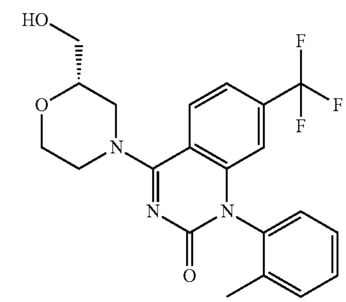 [SMILES: Cc1ccccc1-n1c(=O)nc(N2CCO[C@H](CO)C2)c2ccc(C(F)(F)F)cc21] | (S)-4-(2-(hydroxymethyl)morpholino)-1-(o-tolyl)-7-(trifluoromethyl)quinazolin-2(1H)-one | m/z [M + H]⁺ 420.1 |
| 451 | 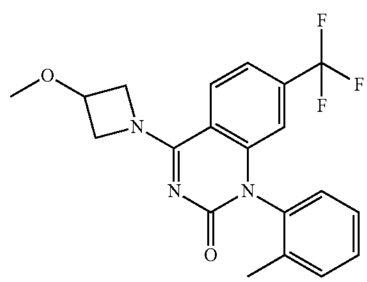 [SMILES: COC1CN(c2nc(=O)n(-c3ccccc3C)c3cc(C(F)(F)F)ccc23)C1] | 4-(3-methoxyazetidin-1-yl)-1-(o-tolyl)-7-(trifluoromethyl)quinazolin-2(1H)-one | m/z [M + H]⁺ 390.1 |
| 452 | 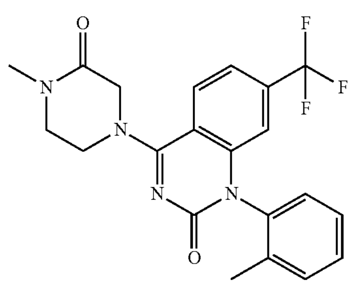 [SMILES: Cc1ccccc1-n1c(=O)nc(N2CCN(C)C(=O)C2)c2ccc(C(F)(F)F)cc21] | (4-(4-methyl-3-oxopiperazin-1-yl)-1-(o-tolyl)-7-(trifluoromethyl)quinazolin-2(1H)-one | m/z [M + H]⁺ 417.1 |
| 453 | 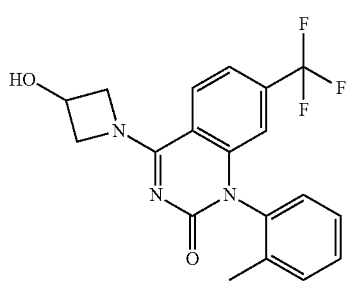 [SMILES: Cc1ccccc1-n1c(=O)nc(N2CC(O)C2)c2ccc(C(F)(F)F)cc21] | 4-(3-hydroxyazetidin-1-yl)-1-(o-tolyl)-7-(trifluoromethyl)quinazolin-2(1H)-one | m/z [M + H]⁺ 376.1 |
| 454 | 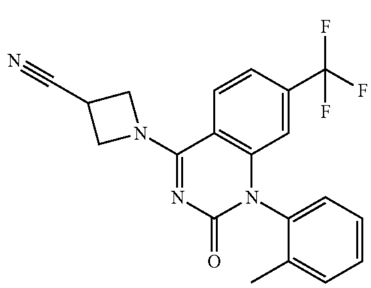 [SMILES: Cc1ccccc1-n1c(=O)nc(N2CC(C#N)C2)c2ccc(C(F)(F)F)cc21] | 1-(2-oxo-1-(o-tolyl)-7-(trifluoromethyl)-1,2-dihydroquinazolin-4-yl)azetidine-3-carbonitrile | m/z [M + H]⁺ 385.1 |

TABLE 1-continued

| Cpd. No. | Structure | Name | Mass Spec. |
|---|---|---|---|
| 455 | 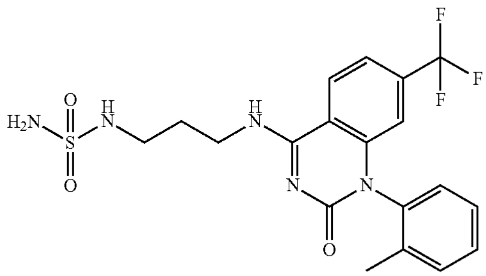 [SMILES: Cc1ccccc1-n1c(=O)nc(NCCCNS(N)(=O)=O)c2ccc(C(F)(F)F)cc21] | amino(3-{[1-(2-methylphenyl)-2-oxo-7-(trifluoromethyl)hydroquinazolin-4-yl]-amino}propyl)sulfonamide | m/z [M + H]+ 456.1 |
| 456 | 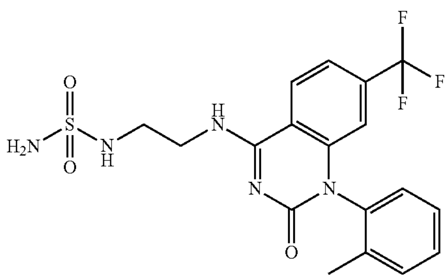 [SMILES: Cc1ccccc1-n1c(=O)nc(NCCNS(N)(=O)=O)c2ccc(C(F)(F)F)cc21] | amino(2-{[1-(2-methylphenyl)-2-oxo-7-(trifluoromethyl)hydroquinazolin-4-yl]-amino}ethyl)sulfonamide | m/z [M + H]+ 442.1 |
| 457 | 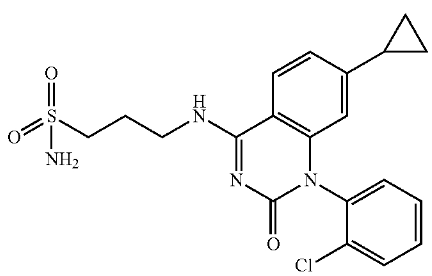 [SMILES: NS(=O)(=O)CCCNc1nc(=O)n(-c2ccccc2Cl)c2cc(C3CC3)ccc12] | (3-((1-(2-chlorophenyl)-7-cyclopropyl-2-oxo-1,2-dihydroquinazolin-4-yl)-amino)propane-1-sulfonamide | m/z [M + H]+ 433.1 |
| 458 | 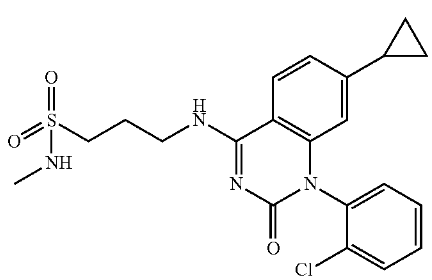 [SMILES: CNS(=O)(=O)CCCNc1nc(=O)n(-c2ccccc2Cl)c2cc(C3CC3)ccc12] | 3-((1-(2-chlorophenyl)-7-cyclopropyl-2-oxo-1,2-dihydroquinazolin-4-yl)amino)-N-methylpropane-1-sulfonamide | m/z [M + H]+ 447.0 |
| 459 | 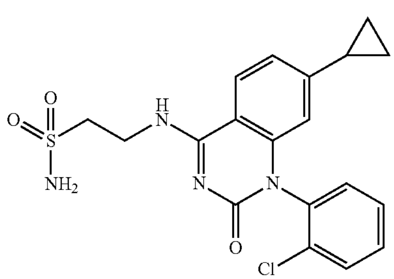 [SMILES: NS(=O)(=O)CCNc1nc(=O)n(-c2ccccc2Cl)c2cc(C3CC3)ccc12] | 2-((1-(2-chlorophenyl)-7-cyclopropyl-2-oxo-1,2-dihydroquinazolin-4-yl)-amino)ethane-1-sulfonamide | m/z [M + H]+ 419.0 |

TABLE 1-continued

| Cpd. No. | Structure | Name | Mass Spec. |
|---|---|---|---|
| 460 | 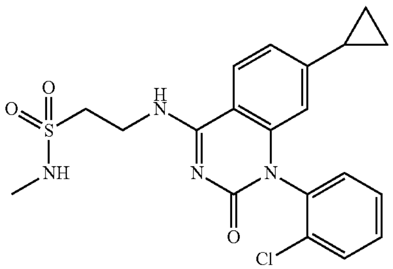 [SMILES: CNS(=O)(=O)CCNc1nc(=O)n(-c2ccccc2Cl)c2cc(C3CC3)ccc12] | 2-((1-(2-chlorophenyl)-7-cyclopropyl-2-oxo-1,2-dihydroquinazolin-4-yl)amino)-N-methylethane-1-sulfonamide | m/z [M + H]+ 433.1 |
| 461 | 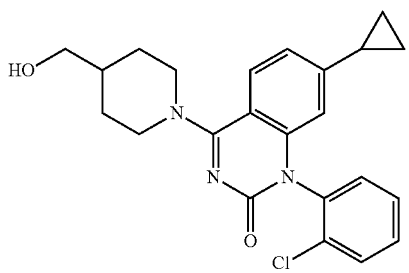 [SMILES: O=c1nc(N2CCC(CO)CC2)c2ccc(C3CC3)cc2n1-c1ccccc1Cl] | 1-(2-chlorophenyl)-7-cyclopropyl-4-(4-(hydroxymethyl)piperidin-1-yl)-quinazolin-2(1H)-one | m/z [M + H]+ 410.1 |
| 462 | 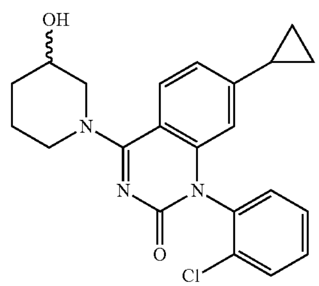 [SMILES: O=c1nc(N2CCCC(O)C2)c2ccc(C3CC3)cc2n1-c1ccccc1Cl] | 1-(2-chlorophenyl)-7-cyclopropyl-4-(3-hydroxypiperidin-1-yl)quinazolin-2(1H)-one | m/z [M + H]+ 396.1 |
| 463 | 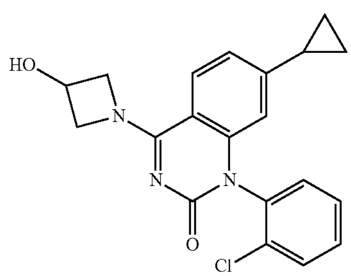 [SMILES: O=c1nc(N2CC(O)C2)c2ccc(C3CC3)cc2n1-c1ccccc1Cl] | 1-(2-chlorophenyl)-7-cyclopropyl-4-(3-hydroxyazetidin-1-yl)quinazolin-2(1H)-one | m/z [M + H]+ 368.1 |
| 464 | 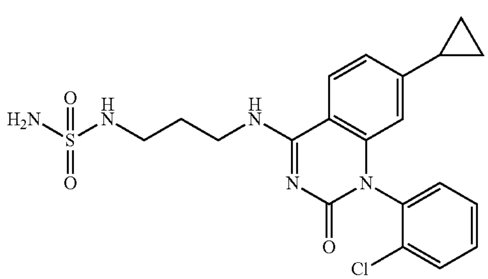 [SMILES: NS(=O)(=O)NCCCNc1nc(=O)n(-c2ccccc2Cl)c2cc(C3CC3)ccc12] | (3-{[1-(2-chlorophenyl)-7-cyclopropyl-2-oxohydroquinazolin-4-yl]amino}-propyl) sulfonamide | m/z [M + H]+ 448.1 |

TABLE 1-continued

| Cpd. No. | Structure | Name | Mass Spec. |
|---|---|---|---|
| 465 | 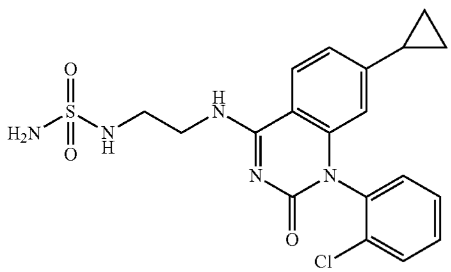 [SMILES: NS(=O)(=O)NCCNc1nc(=O)n(-c2ccccc2Cl)c2cc(C3CC3)ccc12] | (2-{[1-(2-chlorophenyl)-7-cyclopropyl-2-oxohydroquinazolin-4-yl]amino}-ethyl)sulfonamide | m/z [M + H]+ 434.0 |
| 466 | 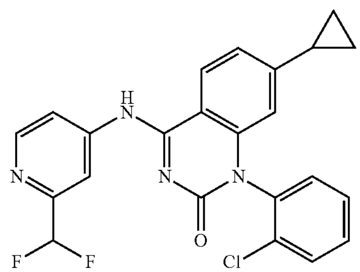 [SMILES: O=c1nc(Nc2ccnc(C(F)F)c2)c2ccc(C3CC3)cc2n1-c1ccccc1Cl] | 1-(2-chlorophenyl)-7-cyclopropyl-4-((2-(difluoromethyl)pyridin-4-yl)amino)-quinazolin-2(1H)-one | m/z [M + H]+ 439.1 |
| 467 | 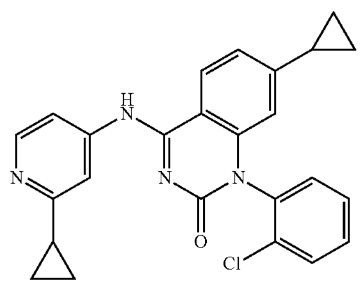 [SMILES: O=c1nc(Nc2ccnc(C3CC3)c2)c2ccc(C3CC3)cc2n1-c1ccccc1Cl] | 1-(2-chlorophenyl)-7-cyclopropyl-4-((2-cyclopropylpyridin-4-yl)amino)-quinazolin-2(1H)-one | m/z [M + H]+ 429.1 |
| 468 | 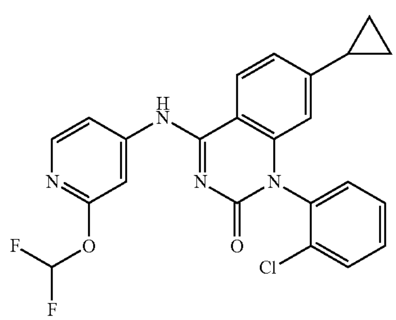 [SMILES: O=c1nc(Nc2ccnc(OC(F)F)c2)c2ccc(C3CC3)cc2n1-c1ccccc1Cl] | 1-(2-chlorophenyl)-7-cyclopropyl-4-((2-(difluoromethoxy)pyridin-4-yl)amino)-quinazolin-2(1H)-one | m/z [M + H]+ 455.1 |
| 469 | 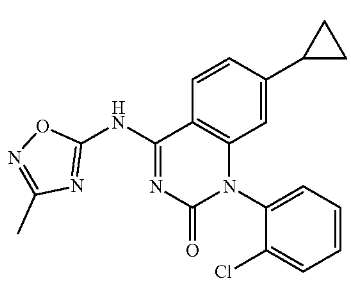 [SMILES: Cc1noc(Nc2nc(=O)n(-c3ccccc3Cl)c3cc(C4CC4)ccc23)n1] | 1-(2-chlorophenyl)-7-cyclopropyl-4-((3-methyl-1,2,4-oxadiazol-5-yl)amino)-quinazolin-2(1H)-one | m/z [M + H]+ 394.1 |

TABLE 1-continued

| Cpd. No. | Structure | Name | Mass Spec. |
|---|---|---|---|
| 470 | 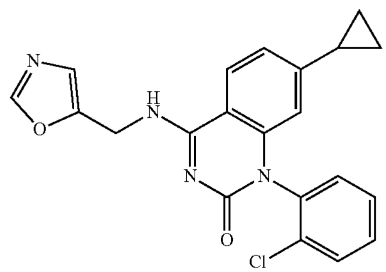 [SMILES: O=c1nc(NCc2cnco2)c2ccc(C3CC3)cc2n1-c1ccccc1Cl] | 1-(2-chlorophenyl)-7-cyclopropyl-4-((oxazol-5-ylmethyl)amino)quinazolin-2(1H)-one | m/z [M + H]+ 393.1 |
| 471 | 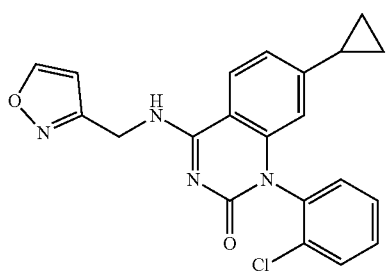 [SMILES: O=c1nc(NCc2ccon2)c2ccc(C3CC3)cc2n1-c1ccccc1Cl] | 1-(2-chlorophenyl)-7-cyclopropyl-4-((isoxazol-3-ylmethyl)amino)quinazolin-2(1H)-one | m/z [M + H]+ 393.1 |
| 472 | 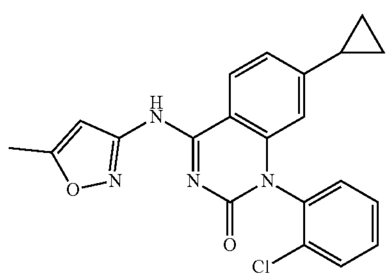 [SMILES: Cc1cc(Nc2nc(=O)n(-c3ccccc3Cl)c3cc(C4CC4)ccc23)no1] | 1-(2-chlorophenyl)-7-cyclopropyl-4-((5-methylisoxazol-3-yl)amino)quinazolin-2(1H)-one | m/z [M + H]+ 393.1 |
| 473 | 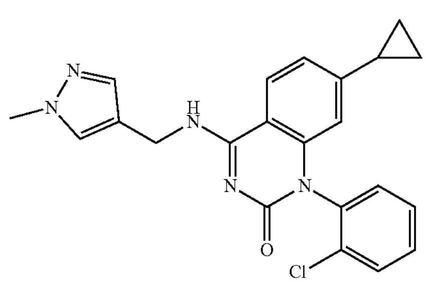 [SMILES: Cn1cc(CNc2nc(=O)n(-c3ccccc3Cl)c3cc(C4CC4)ccc23)cn1] | 1-(2-chlorophenyl)-7-cyclopropyl-4-(((1-methyl-1H-pyrazol-4-yl)methyl)amino)-quinazolin-2(1H)-one | m/z [M + H]+ 406.1 |
| 474 | 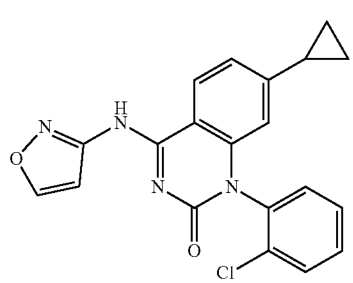 [SMILES: O=c1nc(Nc2ccon2)c2ccc(C3CC3)cc2n1-c1ccccc1Cl] | 1-(2-chlorophenyl)-7-cyclopropyl-4-(isoxazol-3-ylamino)quinazolin-2(1H)-one | m/z [M + H]+ 379.05 |

TABLE 1-continued

| Cpd. No. | Structure | Name | Mass Spec. |
| --- | --- | --- | --- |
| 475 | 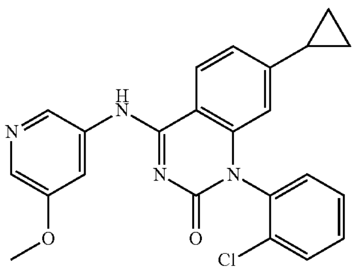 [SMILES: COc1cncc(Nc2nc(=O)n(-c3ccccc3Cl)c3cc(C4CC4)ccc23)c1] | 1-(2-chlorophenyl)-7-cyclopropyl-4-((5-methoxypyridin-3-yl)amino)quinazolin-2(1H)-one | m/z [M + H]+ 419.1 |
| 476 | 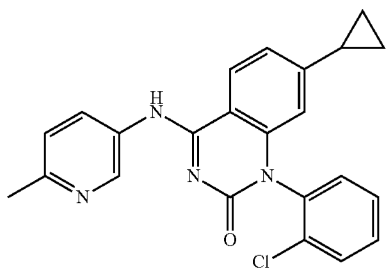 [SMILES: Cc1ccc(Nc2nc(=O)n(-c3ccccc3Cl)c3cc(C4CC4)ccc23)cn1] | 1-(2-chlorophenyl)-7-cyclopropyl-4-((6-methylpyridin-3-yl)amino)quinazolin-2(1H)-one | m/z [M + H]+ 403.1 |
| 477 | 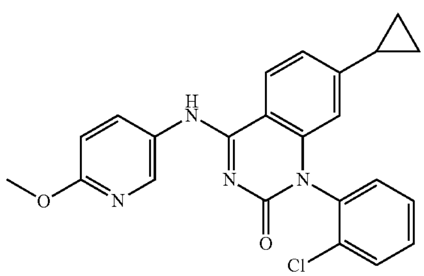 [SMILES: COc1ccc(Nc2nc(=O)n(-c3ccccc3Cl)c3cc(C4CC4)ccc23)cn1] | 1-(2-chlorophenyl)-7-cyclopropyl-4-((6-methoxypyridin-3-yl)amino)quinazolin-2(1H)-one | m/z [M + H]+ 419.1 |
| 478 | 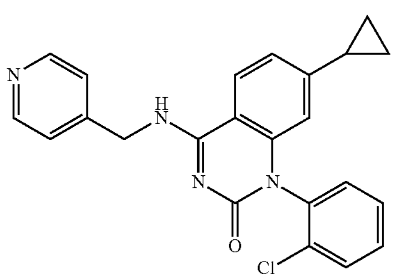 [SMILES: O=c1nc(NCc2ccncc2)c2ccc(C3CC3)cc2n1-c1ccccc1Cl] | 1-(2-chlorophenyl)-7-cyclopropyl-4-((pyridin-4-ylmethyl)amino)quinazolin-2(1H)-one | m/z [M + H]+ 403.1 |
| 479 | 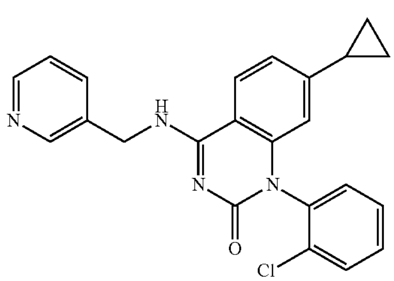 [SMILES: O=c1nc(NCc2cccnc2)c2ccc(C3CC3)cc2n1-c1ccccc1Cl] | 1-(2-chlorophenyl)-7-cyclopropyl-4-((pyridin-3-ylmethyl)amino)quinazolin-2(1H)-one | m/z [M + H]+ 403.1 |

TABLE 1-continued

| Cpd. No. | Structure | Name | Mass Spec. |
|---|---|---|---|
| 480 | 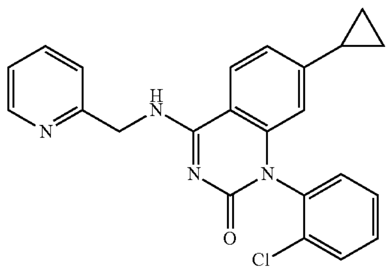 [SMILES: O=c1nc(NCc2ccccn2)c2ccc(C3CC3)cc2n1-c1ccccc1Cl] | 1-(2-chlorophenyl)-7-cyclopropyl-4-((pyridin-2-ylmethyl)amino)quinazolin-2(1H)-one | m/z [M + H]+ 403.1 |
| 481 | 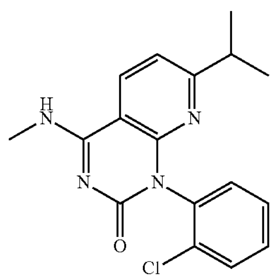 [SMILES: CNc1nc(=O)n(-c2ccccc2Cl)c2nc(C(C)C)ccc12] | 1-(2-chlorophenyl)-7-isopropyl-4-(methylamino)pyrido[2,3-d]pyrimidin-2(1H)-one | m/z [M + H]+ 329.1 |
| 482 | 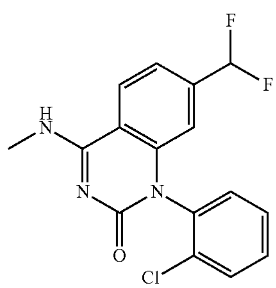 [SMILES: CNc1nc(=O)n(-c2ccccc2Cl)c2cc(C(F)F)ccc12] | 1-(2-chlorophenyl)-7-(difluoromethyl)-4-(methylamino)quinazolin-2(1H)-one | m/z [M + H]+ 336.0 |
| 483 | 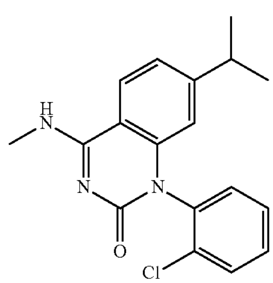 [SMILES: CNc1nc(=O)n(-c2ccccc2Cl)c2cc(C(C)C)ccc12] | 1-(2-chlorophenyl)-7-isopropyl-4-(methylamino)quinazolin-2(1H)-one | m/z [M + H]+ 328.1 |
| 484 | 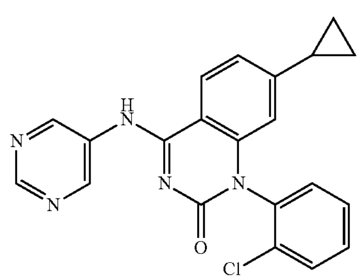 [SMILES: O=c1nc(Nc2cncnc2)c2ccc(C3CC3)cc2n1-c1ccccc1Cl] | 1-(2-chlorophenyl)-7-cyclopropyl-4-(pyrimidin-5-ylamino)quinazolin-2(1H)-one | m/z [M + H]+ 390.05 |

TABLE 1-continued

| Cpd. No. | Structure | Name | Mass Spec. |
|---|---|---|---|
| 485 | 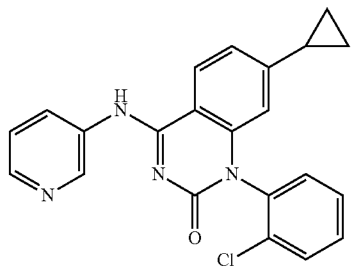 [SMILES: O=c1nc(Nc2cccnc2)c2ccc(C3CC3)cc2n1-c1ccccc1Cl] | 1-(2-chlorophenyl)-7-cyclopropyl-4-(pyridin-3-ylamino)quinazolin-2(1H)-one | m/z [M + H]⁺ 389.05 |
| 486 | 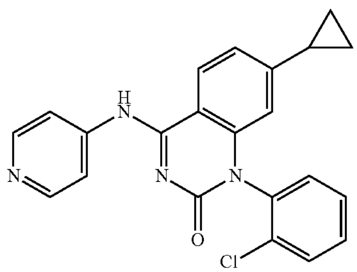 [SMILES: O=c1nc(Nc2ccncc2)c2ccc(C3CC3)cc2n1-c1ccccc1Cl] | 1-(2-chlorophenyl)-7-cyclopropyl-4-(pyridin-4-ylamino)quinazolin-2(1H)-one | m/z [M + H]⁺ 389.05 |
| 487 | 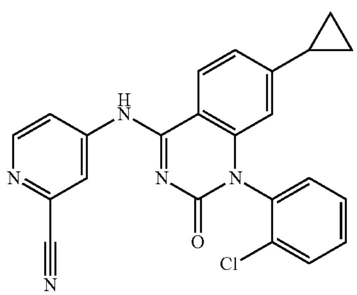 [SMILES: N#Cc1cc(Nc2nc(=O)n(-c3ccccc3Cl)c3cc(C4CC4)ccc23)ccn1] | 4-((1-(2-chlorophenyl)-7-cyclopropyl-2-oxo-1,2-dihydroquinazolin-4-yl)amino)picolinonitrile | m/z [M + H]⁺ 414.1 |
| 488 | 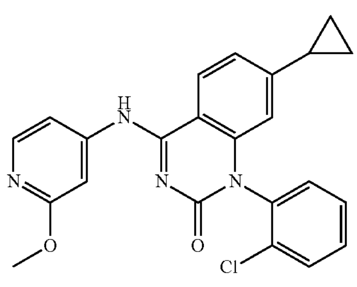 | 1-(2-chlorophenyl)-7-cyclopropyl-4-((2-methoxypyridin-4-yl)amino)quinazolin-2(1H)-one | m/z [M + H]⁺ 419.1 |
| 489 | 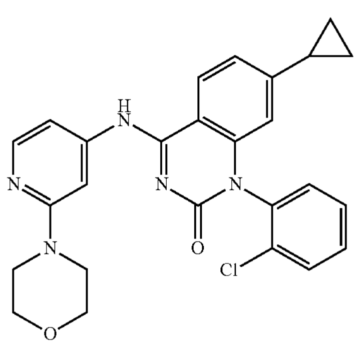 [SMILES: O=c1nc(Nc2ccnc(N3CCOCC3)c2)c2ccc(C3CC3)cc2n1-c1ccccc1Cl] | 1-(2-chlorophenyl)-7-cyclopropyl-4-((2-morpholinopyridin-4-yl)amino)quinazolin-2(1H)-one | m/z [M + H]⁺ 474.1 |

TABLE 1-continued

| Cpd. No. | Structure | Name | Mass Spec. |
|---|---|---|---|
| 490 | 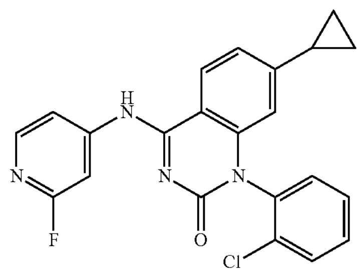 [SMILES: O=c1nc(Nc2ccnc(F)c2)c2ccc(C3CC3)cc2n1-c1ccccc1Cl] | 1-(2-chlorophenyl)-7-cyclopropyl-4-((2-fluoropyridin-4-yl)amino)quinazolin-2(1H)-one | m/z [M + H]+ 407.0 |
| 491 | 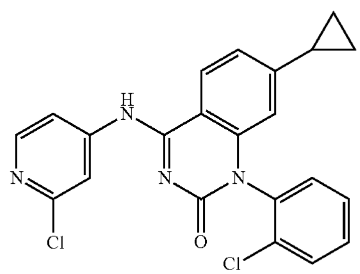 [SMILES: O=c1nc(Nc2ccnc(Cl)c2)c2ccc(C3CC3)cc2n1-c1ccccc1Cl] | 1-(2-chlorophenyl)-4-((2-chloropyridin-4-yl)amino)-7-cyclopropylquinazolin-2(1H)-one | m/z [M + H]+ 423.0 |
| 492 | 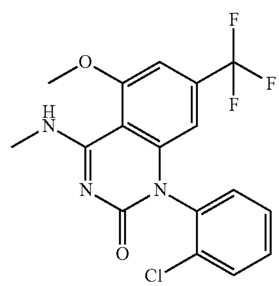 [SMILES: CNc1nc(=O)n(-c2ccccc2Cl)c2cc(C(F)(F)F)cc(OC)c12] | 1-(2-chlorophenyl)-5-methoxy-4-(methylamino)-7-(trifluoromethyl)-quinazolin-2(1H)-one | m/z [M + H]+ 384.1 |
| 493 | 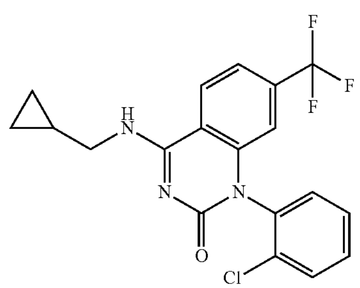 [SMILES: O=c1nc(NCC2CC2)c2ccc(C(F)(F)F)cc2n1-c1ccccc1Cl] | 1-(2-chlorophenyl)-4-((cyclopropylmethyl)amino)-7-(trifluoromethyl)-quinazolin-2(1H)-one | m/z [M + H]+ 394.1 |
| 494 | 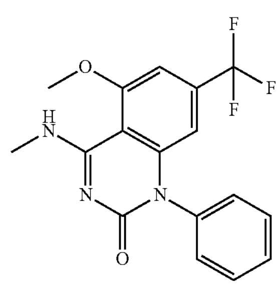 [SMILES: CNc1nc(=O)n(-c2ccccc2)c2cc(C(F)(F)F)cc(OC)c12] | 5-methoxy-4-(methylamino)-1-phenyl-7-(trifluoromethyl)quinazolin-2(1H)-one | m/z [M + H]+ 350.1 |

TABLE 1-continued

| Cpd. No. | Structure | Name | Mass Spec. |
|---|---|---|---|
| 495 | 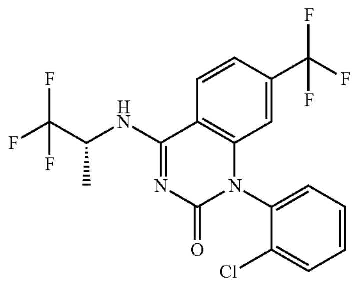 [SMILES: C[C@@H](Nc1nc(=O)n(-c2ccccc2Cl)c2cc(C(F)(F)F)ccc12)C(F)(F)F] | (R)-1-(2-chlorophenyl)-7-(trifluoromethyl)-4-((1,1,1-trifluoropropan-2-yl)-amino)quinazolin-2(1H)-one | m/z [M + H]+ 436.0 |
| 496 | 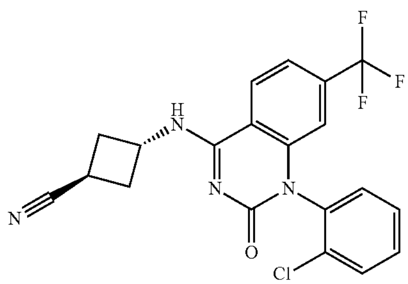 [SMILES: N#C[C@H]1C[C@H](Nc2nc(=O)n(-c3ccccc3Cl)c3cc(C(F)(F)F)ccc23)C1] | (1,3-trans)-3-((1-(2-chlorophenyl)-2-oxo-7-(trifluoromethyl)-1,2-dihydroquinazolin-4-yl)amino)-cyclobutane-1-carbonitrile | m/z [M + H]+ 419.05 |
| 497 | 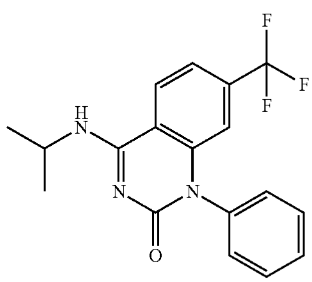 [SMILES: CC(C)Nc1nc(=O)n(-c2ccccc2)c2cc(C(F)(F)F)ccc12] | 4-(isopropylamino)-1-phenyl-7-(trifluoromethyl)quinazolin-2(1H)-one | m/z [M + H]+ 348.1 |
| 498 | 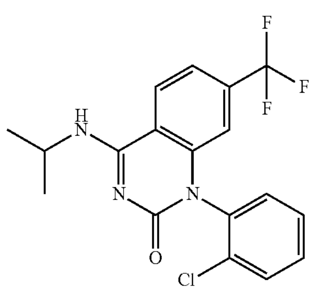 [SMILES: CC(C)Nc1nc(=O)n(-c2ccccc2Cl)c2cc(C(F)(F)F)ccc12] | 1-(2-chlorophenyl)-4-(isopropylamino)-7-(trifluoromethyl)quinazolin-2(1H)-one | m/z [M + H]+ 382.0 |
| 499 | 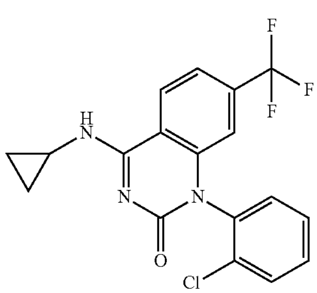 [SMILES: O=c1nc(NC2CC2)c2ccc(C(F)(F)F)cc2n1-c1ccccc1Cl] | 1-(2-chlorophenyl)-4-(cyclopropylamino)-7-(trifluoromethyl)quinazolin-2(1H)-one | m/z [M + H]+ 380.0 |

TABLE 1-continued

| Cpd. No. | Structure | Name | Mass Spec. |
|---|---|---|---|
| 500 | 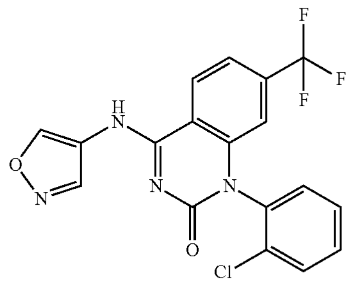 [SMILES: O=c1nc(Nc2cnoc2)c2ccc(C(F)(F)F)cc2n1-c1ccccc1Cl] | 1-(2-chlorophenyl)-4-(isoxazol-4-yl-amino)-7-(trifluoromethyl)quinazolin-2(1H)-one | m/z [M + H]+ 406.75 |
| 501 | 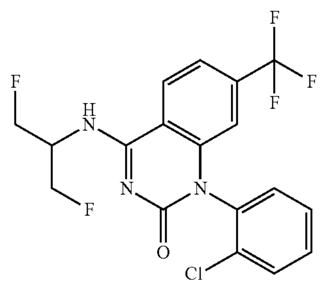 [SMILES: O=c1nc(NC(CF)CF)c2ccc(C(F)(F)F)cc2n1-c1ccccc1Cl] | 1-(2-chlorophenyl)-4-((1,3-difluoropropan-2-yl)amino)-7-(trifluoromethyl)-quinazolin-2(1H)-one | m/z [M + H]+ 418.1 |
| 502 | 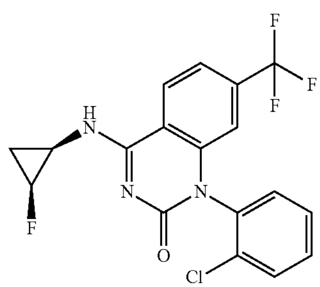 [SMILES: O=c1nc(N[C@@H]2C[C@@H]2F)c2ccc(C(F)(F)F)cc2n1-c1ccccc1Cl] | 1-(2-chlorophenyl)-4-(((1R,2S)-2-fluorocyclopropyl)amino)-7-(trifluoromethyl)quinazolin-2(1H)-one | m/z [M + H]+ 398.05 |
| 503 | 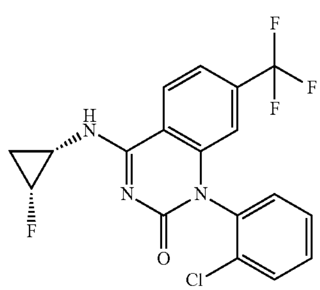 [SMILES: O=c1nc(N[C@H]2C[C@H]2F)c2ccc(C(F)(F)F)cc2n1-c1ccccc1Cl] | 1-(2-chlorophenyl)-4-(((1S,2R)-2-fluorocyclopropyl)amino)-7-(trifluoromethyl)quinazolin-2(1H)-one | m/z [M + H]+ 398.1 |
| 504 | 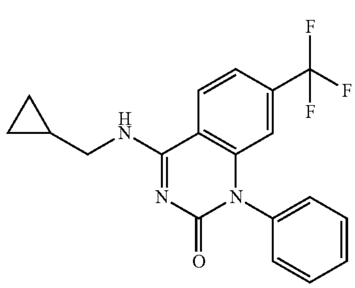 [SMILES: O=c1nc(NCC2CC2)c2ccc(C(F)(F)F)cc2n1-c1ccccc1] | 4-((cyclopropylmethyl)amino)-1-phenyl-7-(trifluoromethyl)quinazolin-2(1H)-one | m/z [M + H]+ 360.1 |

TABLE 1-continued

| Cpd. No. | Structure | Name | Mass Spec. |
|---|---|---|---|
| 505 | 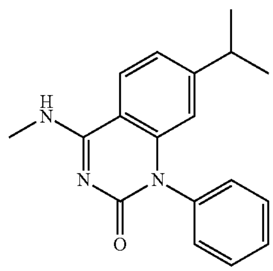 [SMILES: CNc1nc(=O)n(-c2ccccc2)c2cc(C(C)C)ccc12] | 7-isopropyl-4-(methylamino)-1-phenyl-quinazolin-2(1H)-one | m/z [M + H]+ 294.2 |
| 506 | 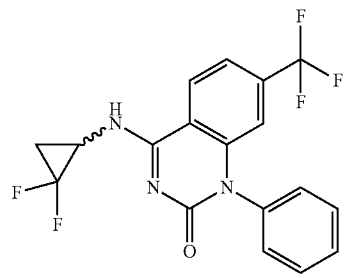 [SMILES: O=c1nc(NC2CC2(F)F)c2ccc(C(F)(F)F)cc2n1-c1ccccc1] | 4-((2,2-difluorocyclopropyl)amino)-1-phenyl-7-(trifluoromethyl)quinazolin-2(1H)-one | m/z [M + H]+ 382.05 |
| 507 | 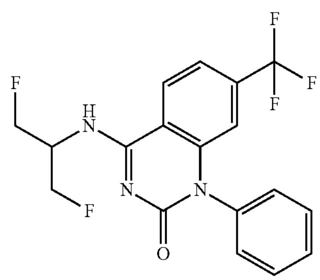 [SMILES: O=c1nc(NC(CF)CF)c2ccc(C(F)(F)F)cc2n1-c1ccccc1] | 4-((1,3-difluoropropan-2-yl)amino)-1-phenyl-7-(trifluoromethyl)quinazolin-2(1H)-one | m/z [M + H]+ 384.1 |
| 508 | 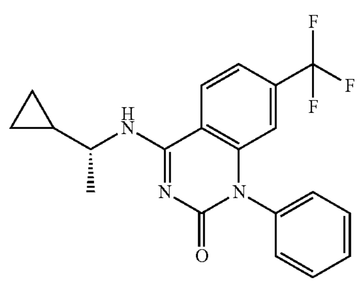 [SMILES: C[C@@H](Nc1nc(=O)n(-c2ccccc2)c2cc(C(F)(F)F)ccc12)C1CC1] | (R)-4-((1-cyclopropylethyl)amino)-1-phenyl-7-(trifluoromethyl)quinazolin-2(1H)-one | m/z [M + H]+ 374.1 |
| 509 | 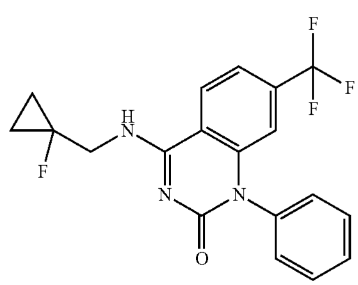 [SMILES: O=c1nc(NCC2(F)CC2)c2ccc(C(F)(F)F)cc2n1-c1ccccc1] | 4-(((1-fluorocyclopropyl)methyl)amino)-1-phenyl-7-(trifluoromethyl)quinazolin-2(1H)-one | m/z [M + H]+ 378.1 |

TABLE 1-continued

| Cpd. No. | Structure | Name | Mass Spec. |
|---|---|---|---|
| 510 | 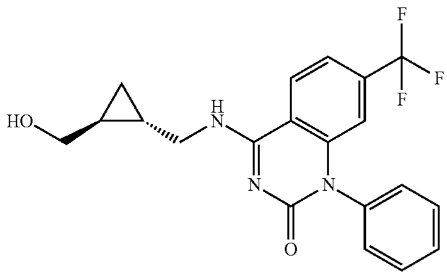 [SMILES: O=c1nc(NC[C@H]2C[C@@H]2CO)c2ccc(C(F)(F)F)cc2n1-c1ccccc1] | 4-((((trans)-2-(hydroxymethyl)cyclopropyl)methyl)amino)-1-phenyl-7-(trifluoromethyl)quinazolin-2(1H)-one | m/z [M + H]+ 390.1 |
| 511 | 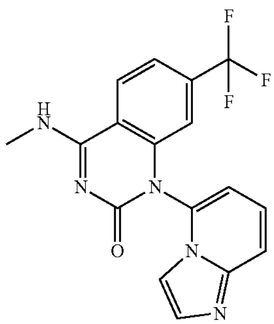 [SMILES: CNc1nc(=O)n(-c2cccc3nccn23)c2cc(C(F)(F)F)ccc12] | 1-(imidazo[1,2-a]pyridin-5-yl)-4-(methylamino)-7-(trifluoromethyl)-quinazolin-2(1H)-one | m/z [M + H]+ 360.1 |
| 512 | 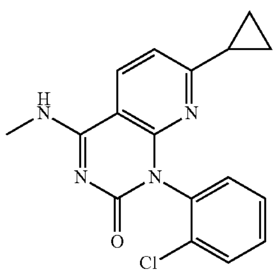 [SMILES: CNc1nc(=O)n(-c2ccccc2Cl)c2nc(C3CC3)ccc12] | 1-(2-chlorophenyl)-7-cyclopropyl-4-(methylamino)pyrido[2,3-d]pyrimidin-2(1H)-one | m/z [M + H]+ 327.1 |
| 513 | 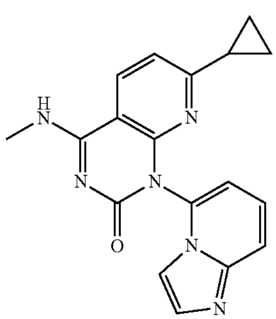 [SMILES: CNc1nc(=O)n(-c2cccc3nccn23)c2nc(C3CC3)ccc12] | 7-cyclopropyl-1-(imidazo[1,2-a]pyridin-5-yl)-4-(methylamino)pyrido[2,3-d]-pyrimidin-2(1H)-one | m/z [M + H]+ 333.1 |
| 514 | 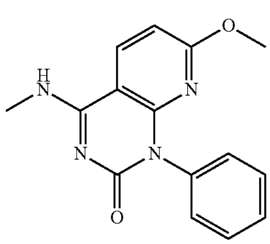 | 7-methoxy-4-(methylamino)-1-phenyl-pyrido[2,3-d]pyrimidin-2(1H)-one | m/z [M + H]+ 283.1 |

TABLE 1-continued

| Cpd. No. | Structure | Name | Mass Spec. |
|---|---|---|---|
| 515 | 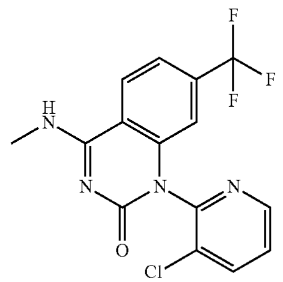 [SMILES: CNc1nc(=O)n(-c2ncccc2Cl)c2cc(C(F)(F)F)ccc12] | 1-(3-chloropyridin-2-yl)-4-(methylamino)-7-(trifluoromethyl)quinazolin-2(1H)-one | m/z [M + H]+ 355.0 |
| 516 | 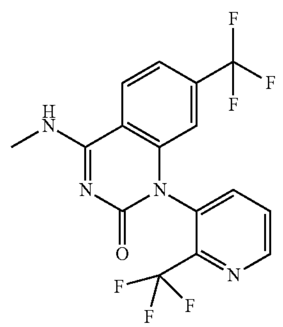 [SMILES: CNc1nc(=O)n(-c2cccnc2C(F)(F)F)c2cc(C(F)(F)F)ccc12] | 4-(methylamino)-7-(trifluoromethyl)-1-(2-(trifluoromethyl)pyridin-3-yl)-quinazolin-2(1H)-one | m/z [M + H]+ 389.1 |
| 517 | 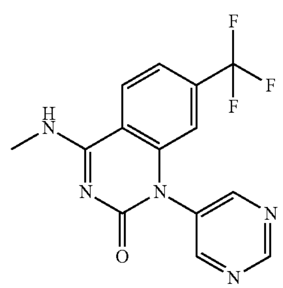 [SMILES: CNc1nc(=O)n(-c2cncnc2)c2cc(C(F)(F)F)ccc12] | 4-(methylamino)-1-(pyrimidin-5-yl)-7-(trifluoromethyl)quinazolin-2(1H)-one | m/z [M + H]+ 322.1 |
| 518 | 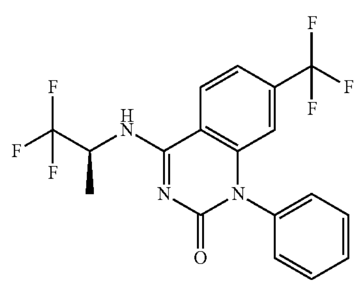 [SMILES: C[C@H](Nc1nc(=O)n(-c2ccccc2)c2cc(C(F)(F)F)ccc12)C(F)(F)F] | (S)-1-phenyl-7-(trifluoromethyl)-4-((1,1,1-trifluoropropan-2-yl)amino)-quinazolin-2(1H)-one | m/z [M + H]+ 402.1 |
| 519 | 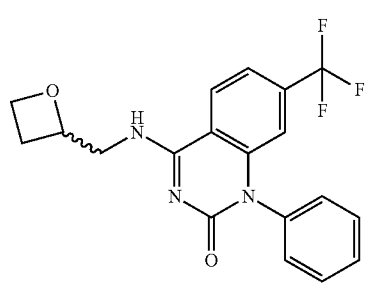 [SMILES: O=c1nc(NCC2CCO2)c2ccc(C(F)(F)F)cc2n1-c1ccccc1] | 4-((oxetan-2-ylmethyl)amino)-1-phenyl-7-(trifluoromethyl)quinazolin-2(1H)-one | m/z [M + H]+ 376.1 |

TABLE 1-continued

| Cpd. No. | Structure | Name | Mass Spec. |
|---|---|---|---|
| 520 | 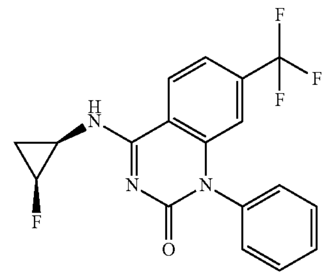 [SMILES: O=c1nc(N[C@@H]2C[C@@H]2F)c2ccc(C(F)(F)F)cc2n1-c1ccccc1] | 4-(((1R,2S)-2-fluorocyclopropyl)amino)-1-phenyl-7-(trifluoromethyl)quinazolin-2(1H)-one | m/z [M + H]+ 364.1 |
| 521 | 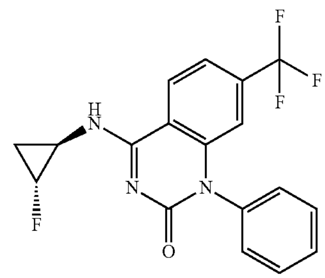 [SMILES: O=c1nc(N[C@@H]2C[C@H]2F)c2ccc(C(F)(F)F)cc2n1-c1ccccc1] | 4-(((1,2-trans)-2-fluorocyclopropyl)-amino)-1-phenyl-7-(trifluoromethyl)quinazolin-2(1H)-one | m/z [M + H]+ 364.1 |
| 522 | 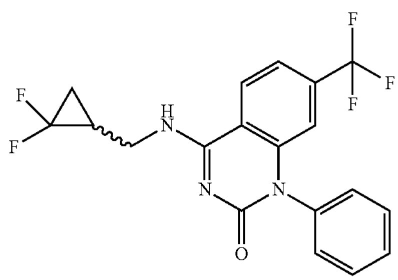 [SMILES: O=c1nc(NCC2CC2(F)F)c2ccc(C(F)(F)F)cc2n1-c1ccccc1] | 4-(((2,2-difluorocyclopropyl)methyl)-amino)-1-phenyl-7-(trifluoromethyl)-quinazolin-2(1H)-one | m/z [M + H]+ 396.1 |
| 523 | 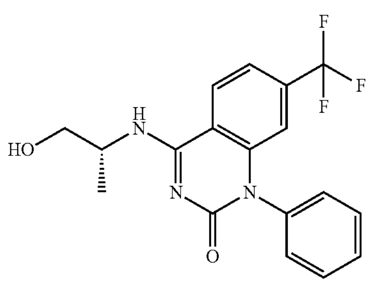 [SMILES: C[C@H](CO)Nc1nc(=O)n(-c2ccccc2)c2cc(C(F)(F)F)ccc12] | (R)-4-((1-hydroxypropan-2-yl)amino)-1-phenyl-7-(trifluoromethyl)quinazolin-2(1H)-one | m/z [M + H]+ 364.1 |
| 524 | 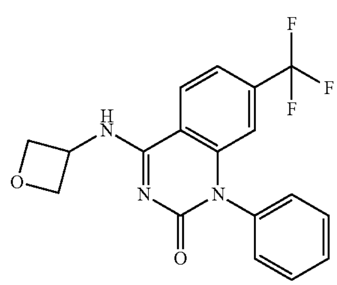 [SMILES: O=c1nc(NC2COC2)c2ccc(C(F)(F)F)cc2n1-c1ccccc1] | 4-(oxetan-3-ylamino)-1-phenyl-7-(trifluoromethyl)quinazolin-2(1H)-one | m/z [M + H]+ 362.1 |

TABLE 1-continued

| Cpd. No. | Structure | Name | Mass Spec. |
|---|---|---|---|
| 525 | 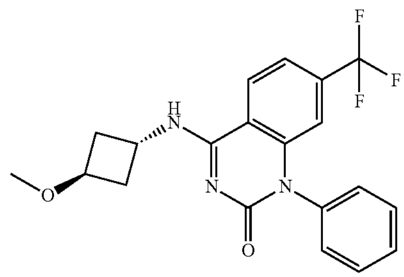 [SMILES: CO[C@H]1C[C@H](Nc2nc(=O)n(-c3ccccc3)c3cc(C(F)(F)F)ccc23)C1] | 4-(((1,3-trans)-3-methoxycyclobutyl)-amino)-1-phenyl-7-(trifluoromethyl)-quinazolin-2(1H)-one | m/z [M + H]⁺ 390.1 |
| 526 | 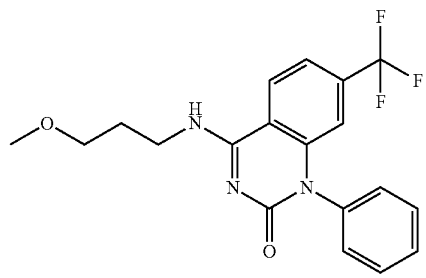 [SMILES: COCCCNc1nc(=O)n(-c2ccccc2)c2cc(C(F)(F)F)ccc12] | 4-((3-methoxypropyl)amino)-1-phenyl-7-(trifluoromethyl)quinazolin-2(1H)-one | m/z [M + H]⁺ 378.1 |
| 527 | 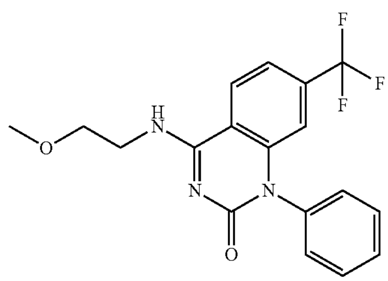 [SMILES: COCCNc1nc(=O)n(-c2ccccc2)c2cc(C(F)(F)F)ccc12] | 4-((2-methoxyethyl)amino)-1-phenyl-7-(trifluoromethyl)quinazolin-2(1H)-one | m/z [M + H]⁺ 364.1 |
| 528 | 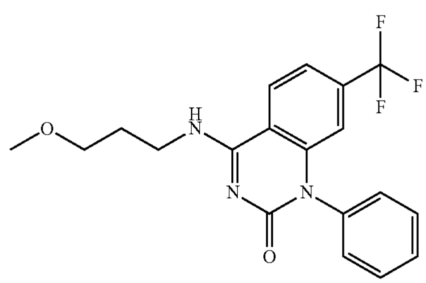 [SMILES: COCCCNc1nc(=O)n(-c2ccccc2)c2cc(C(F)(F)F)ccc12] | 4-((3-methoxypropyl)amino)-1-phenyl-7-(trifluoromethyl)quinazolin-2(1H)-one | m/z [M + H]⁺ 378.1 |
| 530 | 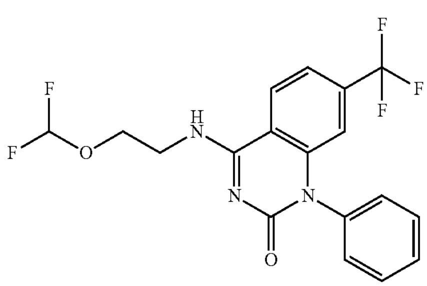 [SMILES: O=c1nc(NCCOC(F)F)c2ccc(C(F)(F)F)cc2n1-c1ccccc1] | 4-((2-(difluoromethoxy)ethyl)amino)-1-phenyl-7-(trifluoromethyl)quinazolin-2(1H)-one | m/z [M + H]⁺ 400.1 |

TABLE 1-continued

| Cpd. No. | Structure | Name | Mass Spec. |
|---|---|---|---|
| 531 | 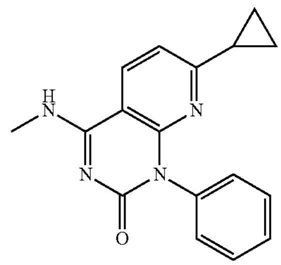 [SMILES: CNc1nc(=O)n(-c2ccccc2)c2nc(C3CC3)ccc12] | 7-cyclopropyl-4-(methylamino)-1-phenylpyrido[2,3-d]pyrimidin-2(1H)-one | m/z [M + H]+ 293.1 |
| 532 | 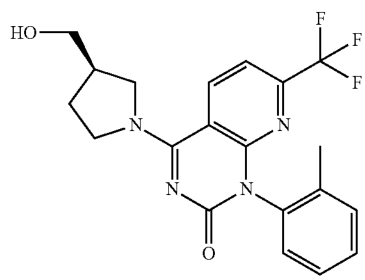 [SMILES: Cc1ccccc1-n1c(=O)nc(N2CC[C@@H](CO)C2)c2ccc(C(F)(F)F)nc21] | (R)-4-(3-(hydroxymethyl)pyrrolidin-1-yl)-1-(o-tolyl)-7-(trifluoromethyl)-pyrido[2,3-d]pyrimidin-2(1H)-one | m/z [M + H]+ 405.00 |
| 533 | 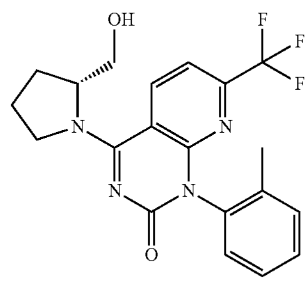 [SMILES: Cc1ccccc1-n1c(=O)nc(N2CCC[C@@H]2CO)c2ccc(C(F)(F)F)nc21] | (R)-4-(2-(hydroxymethyl)pyrrolidin-1-yl)-1-(o-tolyl)-7-(trifluoromethyl)pyrido-[2,3-d]pyrimidin-2(1H)-one | m/z [M + H]+ 405.00 |
| 534 | 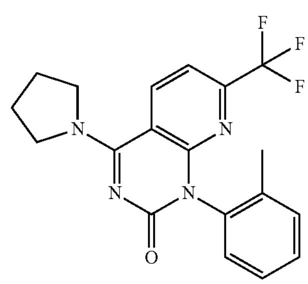 [SMILES: Cc1ccccc1-n1c(=O)nc(N2CCCC2)c2ccc(C(F)(F)F)nc21] | 4-(pyrrolidin-1-yl)-1-(o-tolyl)-7-(trifluoromethyl)pyrido[2,3-d]pyrimidin-2(1H)-one | m/z [M + H]+ 375.2 |
| 535 | 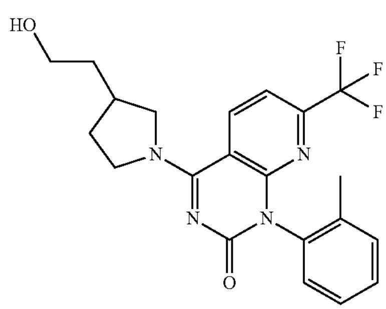 [SMILES: Cc1ccccc1-n1c(=O)nc(N2CCC(CCO)C2)c2ccc(C(F)(F)F)nc21] | 4-(3-(2-hydroxyethyl)pyrrolidin-1-yl)-1-(o-tolyl)-7-(trifluoromethyl)quinazolin-2(1H)-one | m/z [M + H]+ 418.1 |

TABLE 1-continued

| Cpd. No. | Structure | Name | Mass Spec. |
|---|---|---|---|
| 536 | 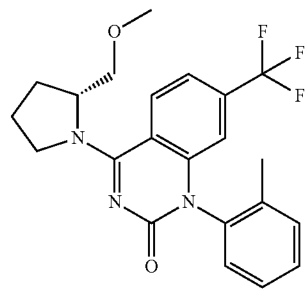 [SMILES: COC[C@H]1CCCN1c1nc(=O)n(-c2ccccc2C)c2cc(C(F)(F)F)ccc12] | (R)-4-(2-(methoxymethyl)pyrrolidin-1-yl)-1-(o-tolyl)-7-(trifluoromethyl)-quinazolin-2(1H)-one | m/z [M + H]+ 418.1 |
| 537 | 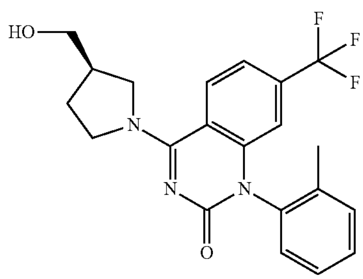 [SMILES: Cc1ccccc1-n1c(=O)nc(N2CC[C@@H](CO)C2)c2ccc(C(F)(F)F)cc21] | (R)-4-(3-(hydroxymethyl)pyrrolidin-1-yl)-1-(o-tolyl)-7-(trifluoromethyl)-quinazolin-2(1H)-one | m/z [M + H]+ 404.1 |
| 538 | 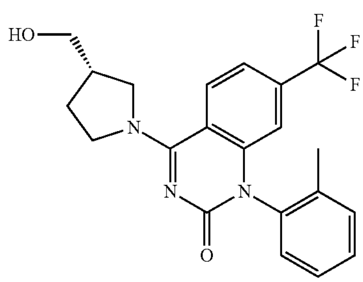 [SMILES: Cc1ccccc1-n1c(=O)nc(N2CC[C@H](CO)C2)c2ccc(C(F)(F)F)cc21] | (S)-4-(3-(hydroxymethyl)pyrrolidin-1-yl)-1-(o-tolyl)-7-(trifluoromethyl)-quinazolin-2(1H)-one | m/z [M + H]+ 404.1 |
| 539 | 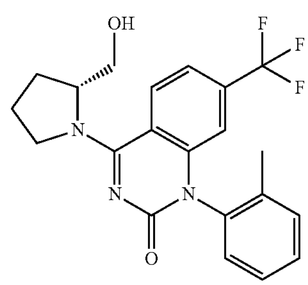 [SMILES: Cc1ccccc1-n1c(=O)nc(N2CCC[C@@H]2CO)c2ccc(C(F)(F)F)cc21] | (R)-4-(2-(hydroxymethyl)pyrrolidin-1-yl)-1-(o-tolyl)-7-(trifluoromethyl)-quinazolin-2(1H)-one | m/z [M + H]+ 404.1 |
| 540 | 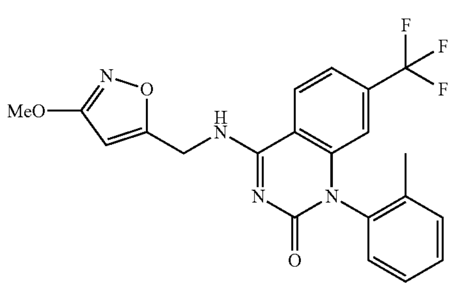 [SMILES: COc1cc(CNc2nc(=O)n(-c3ccccc3C)c3cc(C(F)(F)F)ccc23)on1] | 4-(((3-methoxyisoxazol-5-yl)methyl)-amino)-1-(o-tolyl)-7-(trifluoromethyl)-quinazolin-2(1H)-one | m/z [M + H]+ 431.1 |

TABLE 1-continued

| Cpd. No. | Structure | Name | Mass Spec. |
|---|---|---|---|
| 541 | 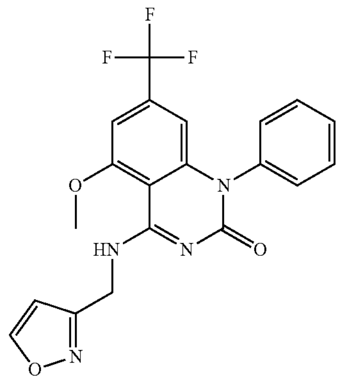 [SMILES: COc1cc(C(F)(F)F)cc2c1c(NCc1ccon1)nc(=O)n2-c1ccccc1] | 4-((isoxazol-3-ylmethyl)amino)-5-methoxy-1-phenyl-7-(trifluoromethyl)-quinazolin-2(1H)-one | m/z [M + H]$^+$ 417.1 |
| 542 | 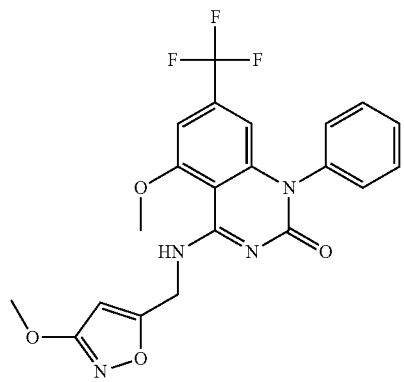 [SMILES: COc1cc(CNc2nc(=O)n(-c3ccccc3)c3cc(C(F)(F)F)cc(OC)c23)on1] | 5-methoxy-4-(((3-methoxyisoxazol-5-yl)methyl)amino)-1-phenyl-7-(trifluoromethyl)quinazolin-2(1H)-one | m/z [M + H]$^+$ 447.1 |
| 543 | 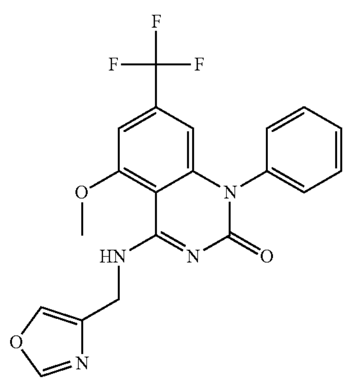 [SMILES: COc1cc(C(F)(F)F)cc2c1c(NCc1cocn1)nc(=O)n2-c1ccccc1] | 5-methoxy-4-((oxazol-4-ylmethyl)-amino)-1-phenyl-7-(trifluoromethyl)-quinazolin-2(1H)-one | m/z [M + H]$^+$ 417.1 |
| 544 | 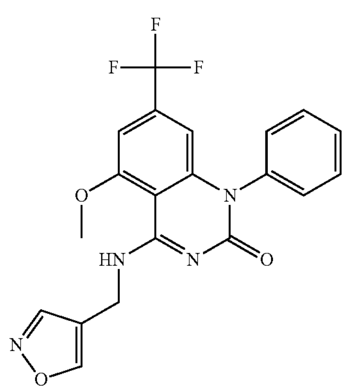 [SMILES: COc1cc(C(F)(F)F)cc2c1c(NCc1cnoc1)nc(=O)n2-c1ccccc1] | 4-((isoxazol-4-ylmethyl)amino)-5-methoxy-1-phenyl-7-(trifluoromethyl)-quinazolin-2(1H)-one | m/z [M + H]$^+$ 417.1 |

TABLE 1-continued

| Cpd. No. | Structure | Name | Mass Spec. |
|---|---|---|---|
| 545 | 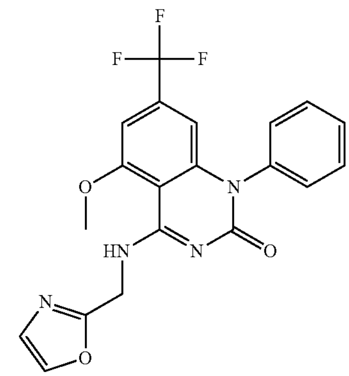 [SMILES: COc1cc(C(F)(F)F)cc2c1c(NCc1ncco1)nc(=O)n2-c1ccccc1] | 5-methoxy-4-((oxazol-2-ylmethyl)-amino)-1-phenyl-7-(trifluoromethyl)quinazolin-2(1H)-one | m/z [M + H]+ 417.1 |
| 546 | 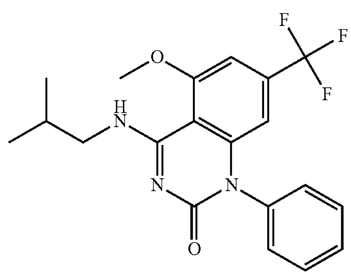 [SMILES: COc1cc(C(F)(F)F)cc2c1c(NCC(C)C)nc(=O)n2-c1ccccc1] | 4-(isobutylamino)-5-methoxy-1-phenyl-7-(trifluoromethyl)quinazolin-2(1H)-one | m/z [M + H]+ 392.15 |
| 547 | 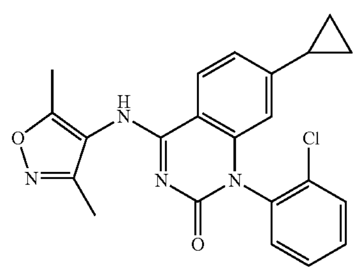 [SMILES: Cc1noc(C)c1Nc1nc(=O)n(-c2ccccc2Cl)c2cc(C3CC3)ccc12] | 1-(2-chlorophenyl)-7-cyclopropyl-4-((3,5-dimethylisoxazol-4-yl)amino)-quinazolin-2(1H)-one | m/z [M + H]+ 407.1 |
| 548 | 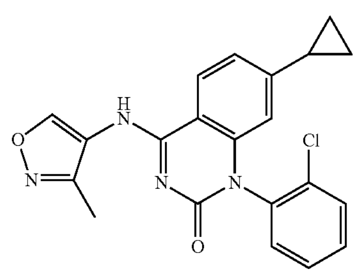 [SMILES: Cc1nocc1Nc1nc(=O)n(-c2ccccc2Cl)c2cc(C3CC3)ccc12] | 1-(2-chlorophenyl)-7-cyclopropyl-4-((3-methylisoxazol-4-yl)amino)quinazolin-2(1H)-one | m/z [M + H]+ 393.1 |
| 549 | 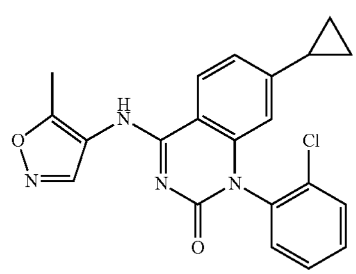 [SMILES: Cc1oncc1Nc1nc(=O)n(-c2ccccc2Cl)c2cc(C3CC3)ccc12] | 1-(2-chlorophenyl)-7-cyclopropyl-4-((5-methylisoxazol-4-yl)amino)quinazolin-2(1H)-one | m/z [M + H]+ 393.1 |

TABLE 1-continued

| Cpd. No. | Structure | Name | Mass Spec. |
|---|---|---|---|
| 550 | 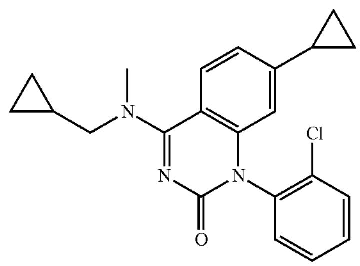 [SMILES: CN(CC1CC1)c1nc(=O)n(-c2ccccc2Cl)c2cc(C3CC3)ccc12] | 1-(2-chlorophenyl)-7-cyclopropyl-4-((cyclopropylmethyl)(methyl)amino)quinazolin-2(1H)-one | m/z [M + H]+ 380.15 |
| 551 | 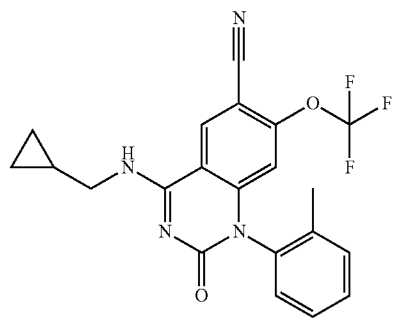 [SMILES: Cc1ccccc1-n1c(=O)nc(NCC2CC2)c2cc(C#N)c(OC(F)(F)F)cc21] | 4-((cyclopropylmethyl)amino)-2-oxo-1-(o-tolyl)-7-(trifluoromethoxy)-1,2-dihydroquinazoline-6-carbonitrile | m/z [M + H]+ 415.1 |
| 552 | 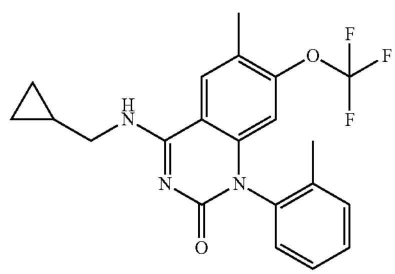 [SMILES: Cc1cc2c(NCC3CC3)nc(=O)n(-c3ccccc3C)c2cc1OC(F)(F)F] | 4-((cyclopropylmethyl)amino)-6-methyl-1-(o-tolyl)-7-(trifluoromethoxy)-quinazolin-2(1H)-one | m/z [M + H]+ 404.1 |
| 553 | 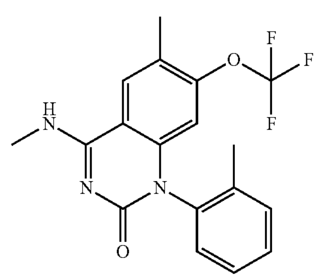 [SMILES: CNc1nc(=O)n(-c2ccccc2C)c2cc(OC(F)(F)F)c(C)cc12] | 6-methyl-4-(methylamino)-1-(o-tolyl)-7-(trifluoromethoxy)quinazolin-2(1H)-one | m/z [M + H]+ 364.1 |
| 554 | 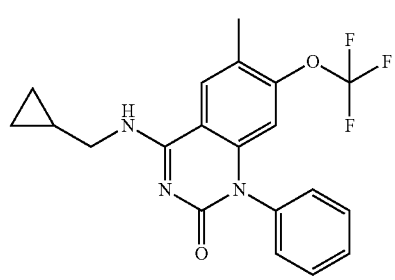 [SMILES: Cc1cc2c(NCC3CC3)nc(=O)n(-c3ccccc3)c2cc1OC(F)(F)F] | 4-((cyclopropylmethyl)amino)-6-methyl-1-phenyl-7-(trifluoromethoxy)-quinazolin-2(1H)-one | m/z [M + H]+ 390.1 |

TABLE 1-continued

| Cpd. No. | Structure | Name | Mass Spec. |
|---|---|---|---|
| 555 | 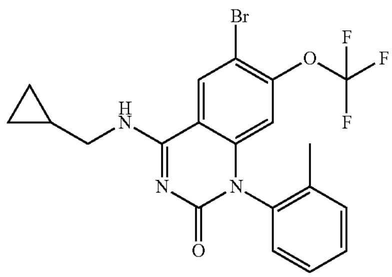 [SMILES: Cc1ccccc1-n1c(=O)nc(NCC2CC2)c2cc(Br)c(OC(F)(F)F)cc21] | 6-bromo-4-((cyclopropylmethyl)amino)-1-(o-tolyl)-7-(trifluoromethoxy)-quinazolin-2(1H)-one | m/z [M + H]+ 468.0, 470.0 |
| 556 | 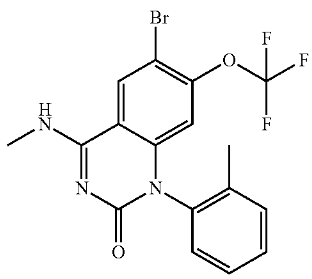 [SMILES: CNc1nc(=O)n(-c2ccccc2C)c2cc(OC(F)(F)F)c(Br)cc12] | 6-bromo-4-(methylamino)-1-(o-tolyl)-7-(trifluoromethoxy)quinazolin-2(1H)-one | m/z [M + H]+ 430.0, 428.0 |
| 557 | 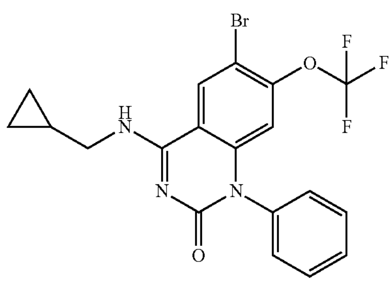 [SMILES: O=c1nc(NCC2CC2)c2cc(Br)c(OC(F)(F)F)cc2n1-c1ccccc1] | 6-bromo-4-((cyclopropylmethyl)amino)-1-phenyl-7-(trifluoromethoxy)-quinazolin-2(1H)-one | m/z [M + H]+ 456.1, 454.1 |
| 558 | 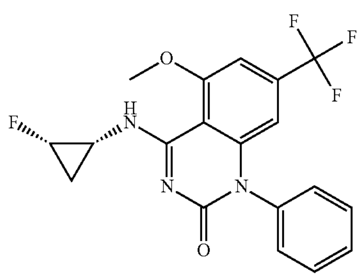 [SMILES: COc1cc(C(F)(F)F)cc2c1c(N[C@@H]1C[C@@H]1F)nc(=O)n2-c1ccccc1] | 4-(((1R,2S)-2-fluorocyclopropyl)amino)-5-methoxy-1-phenyl-7-(trifluoromethyl)-quinazolin-2(1H)-one | m/z [M + H]+ 394.05 |
| 559 | 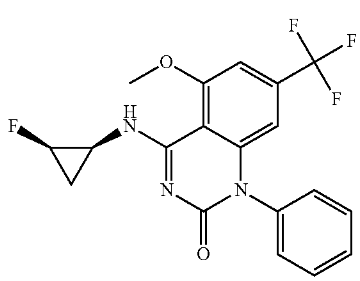 [SMILES: COc1cc(C(F)(F)F)cc2c1c(N[C@H]1C[C@H]1F)nc(=O)n2-c1ccccc1] | 4-(((1S,2R)-2-fluorocyclopropyl)amino)-5-methoxy-1-phenyl-7-(trifluoromethyl)-quinazolin-2(1H)-one | m/z [M + H]+ 394.05 |

TABLE 1-continued

| Cpd. No. | Structure | Name | Mass Spec. |
|---|---|---|---|
| 560 | 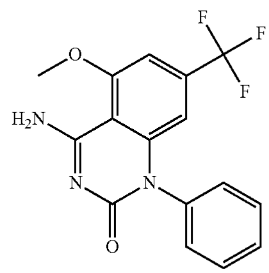 [SMILES: COc1cc(C(F)(F)F)cc2c1c(N)nc(=O)n2-c1ccccc1] | 4-amino-5-methoxy-1-phenyl-7-(trifluoromethyl)quinazolin-2(1H)-one | m/z [M + H]+ 336.0 |
| 561 | 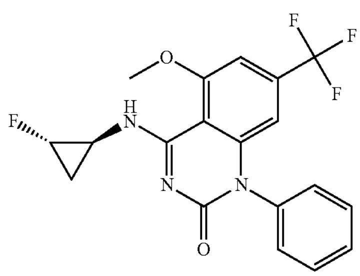 [SMILES: COc1cc(C(F)(F)F)cc2c1c(N[C@H]1C[C@@H]1F)nc(=O)n2-c1ccccc1] | 4-(((trans)-2-fluorocyclopropyl)amino)-5-methoxy-1-phenyl-7-(trifluoromethyl)-quinazolin-2(1H)-one | m/z [M + H]+ 394.05 |
| 562 | 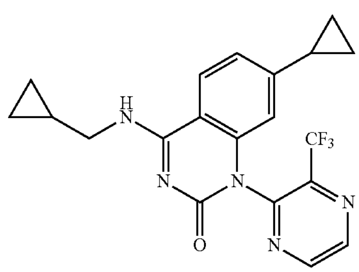 [SMILES: O=c1nc(NCC2CC2)c2ccc(C3CC3)cc2n1-c1nccnc1C(F)(F)F] | 7-cyclopropyl-4-(cyclopropylmethylamino)-1-(3-(trifluoromethyl)pyrazin-2-yl)-quinazolin-2(1H)-one | m/z [M + H]+ 402.1 |
| 563 | 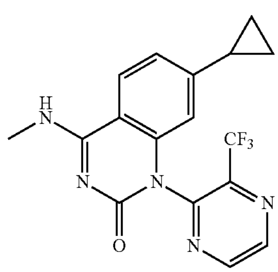 | 7-cyclopropyl-4-(methylamino)-1-(3-(trifluoromethyl)pyrazin-2-yl)quinazolin-2(1H)-one | m/z [M + H]+ 362.1 |
| 564 | 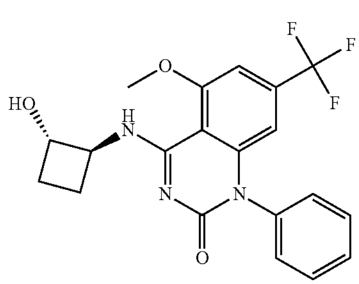 [SMILES: COc1cc(C(F)(F)F)cc2c1c(N[C@H]1CC[C@@H]1O)nc(=O)n2-c1ccccc1] | 4-(((trans)-2-hydroxycyclobutyl)amino)-5-methoxy-1-phenyl-7-(trifluoromethyl)-quinazolin-2(1H)-one | m/z [M + H]+ 406.1 |

TABLE 1-continued

| Cpd. No. | Structure | Name | Mass Spec. |
|---|---|---|---|
| 565 | 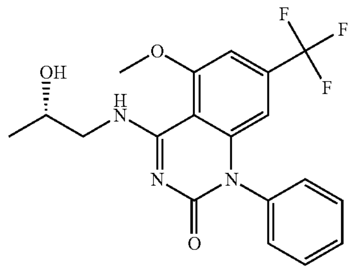 [SMILES: COc1cc(C(F)(F)F)cc2c1c(NC[C@H](C)O)nc(=O)n2-c1ccccc1] | (S)-4-((2-hydroxypropyl)amino)-5-methoxy-1-phenyl-7-(trifluoromethyl)-quinazolin-2(1H)-one | m/z [M + H]+ 394.1 |
| 566 | 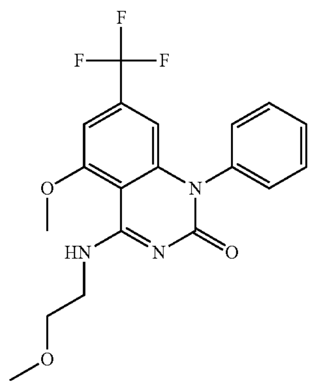 [SMILES: COCCNc1nc(=O)n(-c2ccccc2)c2cc(C(F)(F)F)cc(OC)c12] | 5-methoxy-4-((2-methoxyethyl)amino)-1-phenyl-7-(trifluoromethyl)quinazolin-2(1H)-one | m/z [M + H]+ 394.1 |
| 567 | 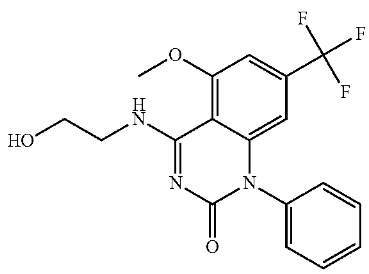 [SMILES: COc1cc(C(F)(F)F)cc2c1c(NCCO)nc(=O)n2-c1ccccc1] | 4-((2-hydroxyethyl)amino)-5-methoxy-1-phenyl-7-(trifluoromethyl)quinazolin-2(1H)-one | m/z [M + H]+ 380.1 |
| 568 | 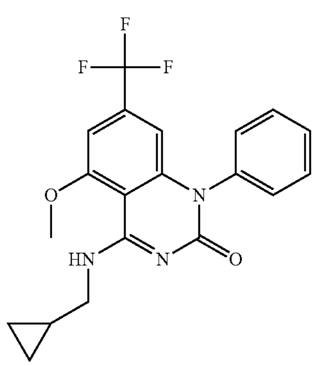 [SMILES: COc1cc(C(F)(F)F)cc2c1c(NCC1CC1)nc(=O)n2-c1ccccc1] | 4-((cyclopropylmethyl)amino)-5-methoxy-1-phenyl-7-(trifluoromethyl)-quinazolin-2(1H)-one | m/z [M + H]+ 390.1 |
| 569 | 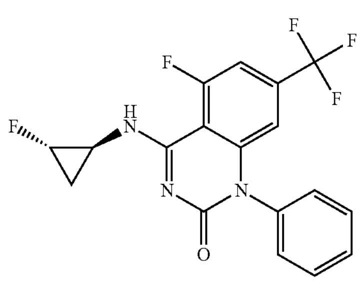 [SMILES: O=c1nc(N[C@H]2C[C@@H]2F)c2c(F)cc(C(F)(F)F)cc2n1-c1ccccc1] | 5-fluoro-4-((trans-2-fluorocyclopropyl)-amino)-1-phenyl-7-(trifluoromethyl)-quinazolin-2(1H)-one | m/z [M + H]+ 382.1 |

TABLE 1-continued

| Cpd. No. | Structure | Name | Mass Spec. |
|---|---|---|---|
| 570 | 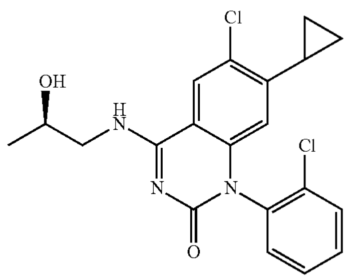 [SMILES: C[C@@H](O)CNc1nc(=O)n(-c2ccccc2Cl)c2cc(C3CC3)c(Cl)cc12] | (R)-6-chloro-1-(2-chlorophenyl)-7-cyclopropyl-4-((2-hydroxypropyl)-amino)-quinazolin-2(1H)-one | m/z [M + H]+ 405.05 |
| 571 | 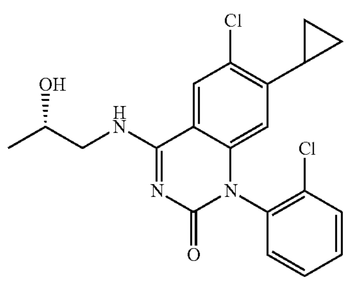 [SMILES: C[C@H](O)CNc1nc(=O)n(-c2ccccc2Cl)c2cc(C3CC3)c(Cl)cc12] | (S)-6-chloro-1-(2-chlorophenyl)-7-cyclopropyl-4-((2-hydroxypropyl)-amino)-quinazolin-2(1H)-one | m/z [M + H]+ 405.1 |
| 572 | 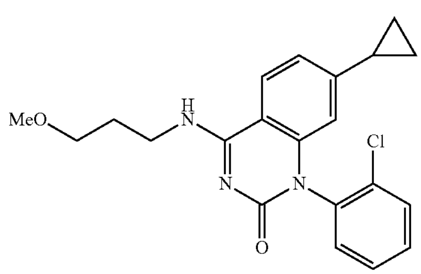 [SMILES: COCCCNc1nc(=O)n(-c2ccccc2Cl)c2cc(C3CC3)ccc12] | 1-(2-chlorophenyl)-7-cyclopropyl-4-((3-methoxypropyl)amino)quinazolin-2(1H)-one | m/z [M + H]+ 384.1 |
| 573 | 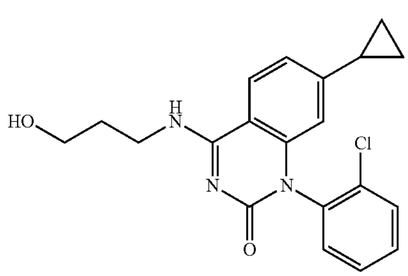 [SMILES: O=c1nc(NCCCO)c2ccc(C3CC3)cc2n1-c1ccccc1Cl] | 1-(2-chlorophenyl)-7-cyclopropyl-4-((3-hydroxypropyl)amino)quinazolin-2(1H)-one | m/z [M + H]+ 370.1 |
| 574 | 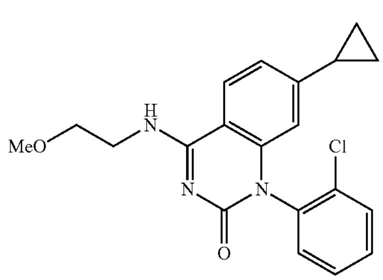 [SMILES: COCCNc1nc(=O)n(-c2ccccc2Cl)c2cc(C3CC3)ccc12] | 1-(2-chlorophenyl)-7-cyclopropyl-4-((2-methoxyethyl)amino)quinazolin-2(1H)-one | m/z [M + H]+ 370.1 |

TABLE 1-continued

| Cpd. No. | Structure | Name | Mass Spec. |
|---|---|---|---|
| 575 | 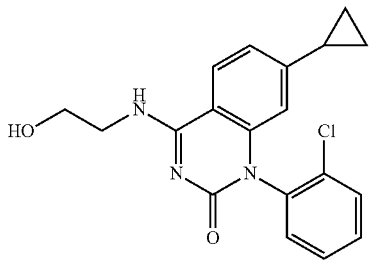 [SMILES: O=c1nc(NCCO)c2ccc(C3CC3)cc2n1-c1ccccc1Cl] | 1-(2-chlorophenyl)-7-cyclopropyl-4-((2-hydroxyethyl)amino)quinazolin-2(1H)-one | m/z [M + H]+ 356.1 |
| 576 | 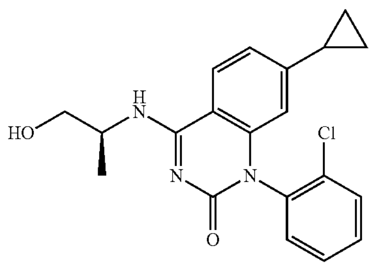 [SMILES: C[C@@H](CO)Nc1nc(=O)n(-c2ccccc2Cl)c2cc(C3CC3)ccc12] | 1-(2-chlorophenyl)-7-cyclopropyl-4-(((S)-1-hydroxypropan-2-yl)amino)-quinazolin-2(1H)-one | m/z [M + H]+ 370.1 |
| 577 | 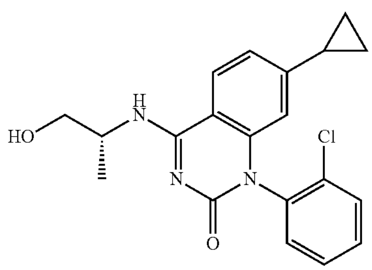 [SMILES: C[C@H](CO)Nc1nc(=O)n(-c2ccccc2Cl)c2cc(C3CC3)ccc12] | 1-(2-chlorophenyl)-7-cyclopropyl-4-(((R)-1-hydroxypropan-2-yl)amino)-quinazolin-2(1H)-one | m/z [M + H]+ 370.1 |
| 578 | 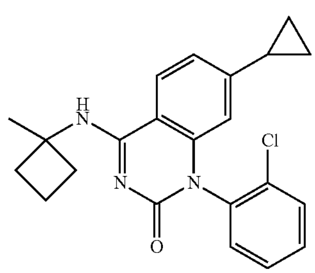 [SMILES: CC1(Nc2nc(=O)n(-c3ccccc3Cl)c3cc(C4CC4)ccc23)CCC1] | 1-(2-chlorophenyl)-7-cyclopropyl-4-((1-methylcyclobutyl)amino)quinazolin-2(1H)-one | m/z [M + H]+ 380.15 |
| 579 | 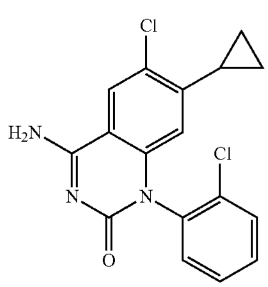 [SMILES: Nc1nc(=O)n(-c2ccccc2Cl)c2cc(C3CC3)c(Cl)cc12] | 4-amino-6-chloro-1-(2-chlorophenyl)-7-cyclopropylquinazolin-2(1H)-one | m/z [M + H]+ 347.0 |

TABLE 1-continued

| Cpd. No. | Structure | Name | Mass Spec. |
|---|---|---|---|
| 580 | 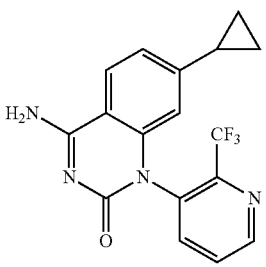 [SMILES: Nc1nc(=O)n(-c2cccnc2C(F)(F)F)c2cc(C3CC3)ccc12] | 4-amino-7-cyclopropyl-1-(2-(trifluoro-methyl)pyridin-3-yl)quinazolin-2(1H)-one | m/z [M + H]+ 347.0 |
| 581 | 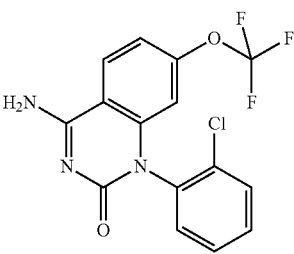 [SMILES: Nc1nc(=O)n(-c2ccccc2Cl)c2cc(OC(F)(F)F)ccc12] | 4-amino-1-(2-chlorophenyl)-7-(trifluoromethoxy)quinazolin-2(1H)-one | m/z [M + H]+ 356.0 |
| 582 | 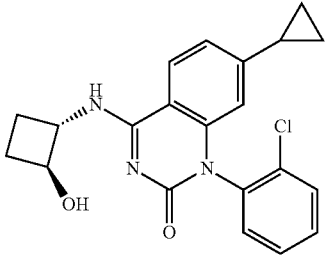 [SMILES: O=c1nc(N[C@H]2CC[C@@H]2O)c2ccc(C3CC3)cc2n1-c1ccccc1Cl] | 1-(2-chlorophenyl)-7-cyclopropyl-4-(((trans)-2-hydroxycyclobutyl)amino)-quinazolin-2(1H)-one | m/z [M + H]+ 382.1 |
| 583 | 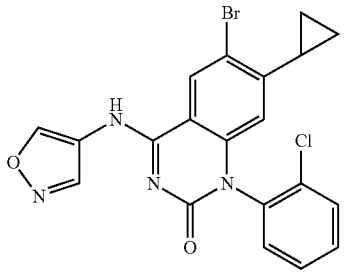 [SMILES: O=c1nc(Nc2cnoc2)c2cc(Br)c(C3CC3)cc2n1-c1ccccc1Cl] | 6-bromo-1-(2-chlorophenyl)-7-cyclopropyl-4-(isoxazol-4-ylamino)-quinazolin-2(1H)-one | m/z [M + H]+ 458.0 |
| 584 | 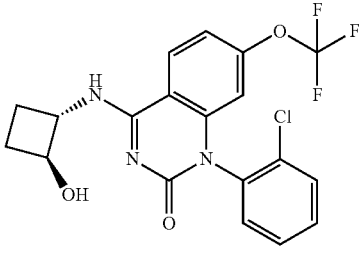 [SMILES: O=c1nc(N[C@H]2CC[C@@H]2O)c2ccc(OC(F)(F)F)cc2n1-c1ccccc1Cl] | 1-(2-chlorophenyl)-4-(((trans)-2-hydroxycyclobutyl)amino)-7-(trifluoromethoxy)-quinazolin-2(1H)-one | m/z [M + H]+ 426.1 |

TABLE 1-continued

| Cpd. No. | Structure | Name | Mass Spec. |
|---|---|---|---|
| 585 | 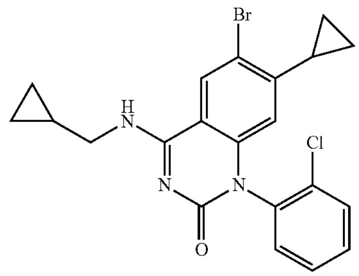 [SMILES: O=c1nc(NCC2CC2)c2cc(Br)c(C3CC3)cc2n1-c1ccccc1Cl] | 6-bromo-1-(2-chlorophenyl)-7-cyclopropyl-4-((cyclopropylmethyl)-amino)-quinazolin-2(1H)-one | m/z [M + H]+ 445.0 |
| 586 | 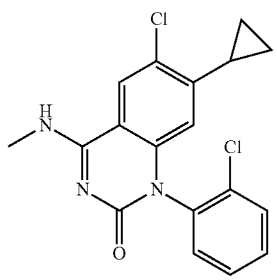 [SMILES: CNc1nc(=O)n(-c2ccccc2Cl)c2cc(C3CC3)c(Cl)cc12] | 6-chloro-1-(2-chlorophenyl)-7-cyclopropyl-4-(methylamino)quinazolin-2(1H)-one | m/z [M + H]+ 360.0 |
| 587 | 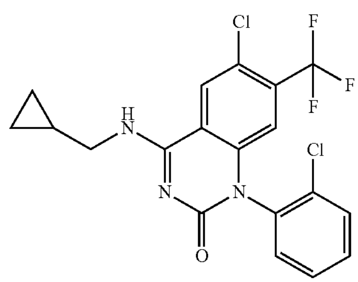 [SMILES: O=c1nc(NCC2CC2)c2cc(Cl)c(C(F)(F)F)cc2n1-c1ccccc1Cl] | 6-chloro-1-(2-chlorophenyl)-4-((cyclopropylmethyl)amino)-7-(trifluoromethyl)-quinazolin-2(1H)-one | m/z [M + H]+ 428.0 |
| 588 | 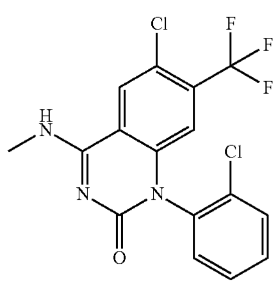 [SMILES: CNc1nc(=O)n(-c2ccccc2Cl)c2cc(C(F)(F)F)c(Cl)cc12] | 6-chloro-1-(2-chlorophenyl)-4-(methylamino)-7-(trifluoromethyl)-quinazolin-2(1H)-one | m/z [M + H]+ 388.0 |
| 589 | 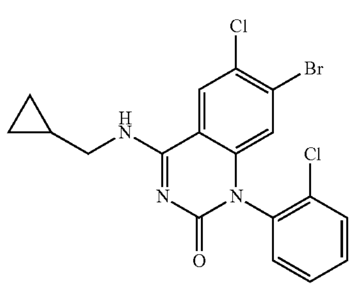 [SMILES: O=c1nc(NCC2CC2)c2cc(Cl)c(Br)cc2n1-c1ccccc1Cl] | 7-bromo-6-chloro-1-(2-chlorophenyl)-4-((cyclopropylmethyl)amino)quinazolin-2(1H)-one | m/z [M + H]+ 439.9 |

TABLE 1-continued

| Cpd. No. | Structure | Name | Mass Spec. |
|---|---|---|---|
| 590 | 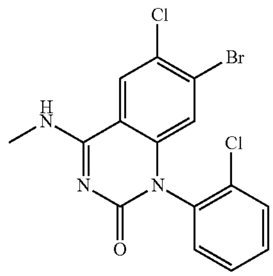 [SMILES: CNc1nc(=O)n(-c2ccccc2Cl)c2cc(Br)c(Cl)cc12] | 7-bromo-6-chloro-1-(2-chlorophenyl)-4-(methylamino)quinazolin-2(1H)-one | m/z [M + H]+ 399.9 |
| 591 | 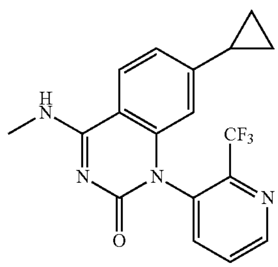 [SMILES: CNc1nc(=O)n(-c2cccnc2C(F)(F)F)c2cc(C3CC3)ccc12] | 7-cyclopropyl-4-(methylamino)-1-(2-(trifluoromethyl)pyridin-3-yl)quinazolin-2(1H)-one | m/z [M + H]+ 361.1 |
| 592 | 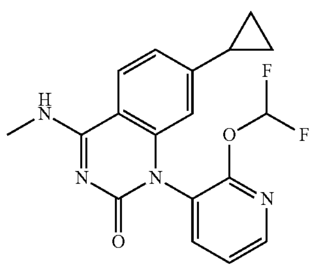 [SMILES: CNc1nc(=O)n(-c2cccnc2OC(F)F)c2cc(C3CC3)ccc12] | 7-cyclopropyl-1-(2-(difluoromethoxy)pyridin-3-yl)-4-(methylamino)-quinazolin-2(1H)-one | m/z [M + H]+ 359.1 |
| 593 | 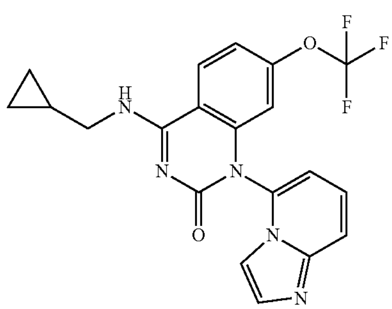 [SMILES: O=c1nc(NCC2CC2)c2ccc(OC(F)(F)F)cc2n1-c1cccc2nccn12] | 4-((cyclopropylmethyl)amino)-1-(imidazo[1,2-a]pyridin-5-yl)-7-(trifluoromethoxy)-quinazolin-2(1H)-one | m/z [M + H]+ 416.1 |
| 594 | 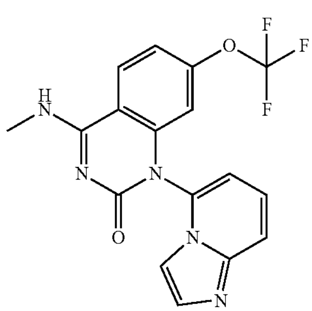 [SMILES: CNc1nc(=O)n(-c2cccc3nccn23)c2cc(OC(F)(F)F)ccc12] | 1-(imidazo[1,2-a]pyridin-5-yl)-4-(methylamino)-7-(trifluoromethoxy)-quinazolin-2(1H)-one | m/z [M + H]+ 376.1 |

TABLE 1-continued

| Cpd. No. | Structure | Name | Mass Spec. |
|---|---|---|---|
| 595 | 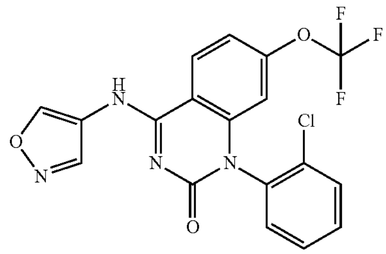 [SMILES: O=c1nc(Nc2cnoc2)c2ccc(OC(F)(F)F)cc2n1-c1ccccc1Cl] | 1-(2-chlorophenyl)-4-(isoxazol-4-ylamino)-7-(trifluoromethoxy)-quinazolin-2(1H)-one | m/z [M + H]+ 423.0 |
| 596 | 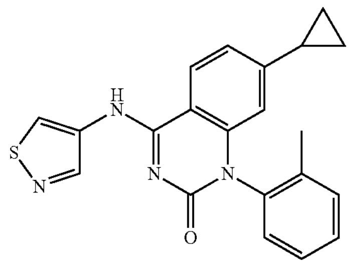 [SMILES: Cc1ccccc1-n1c(=O)nc(Nc2cnsc2)c2ccc(C3CC3)cc21] | 7-cyclopropyl-4-(isothiazol-4-ylamino)-1-(o-tolyl)quinazolin-2(1H)-one | m/z [M + H]+ 375.1 |
| 597 | 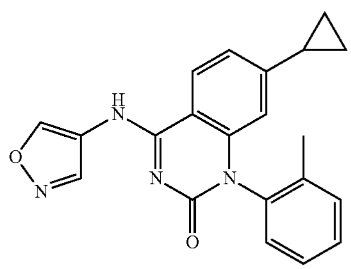 [SMILES: Cc1ccccc1-n1c(=O)nc(Nc2cnoc2)c2ccc(C3CC3)cc21] | 7-cyclopropyl-4-(isoxazol-4-ylamino)-1-(o-tolyl)quinazolin-2(1H)-one | m/z [M + H]+ 359.1 |
| 598 | 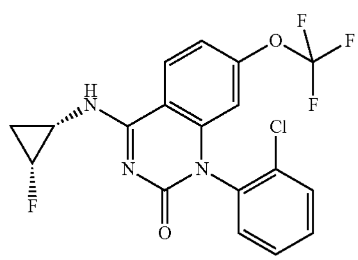 [SMILES: O=c1nc(N[C@H]2C[C@H]2F)c2ccc(OC(F)(F)F)cc2n1-c1ccccc1Cl] | 1-(2-chlorophenyl)-4-(((1S,2R)-2-fluorocyclopropyl)amino)-7-(trifluoromethoxy)-quinazolin-2(1H)-one | m/z [M + H]+ 414.05 |
| 599 | 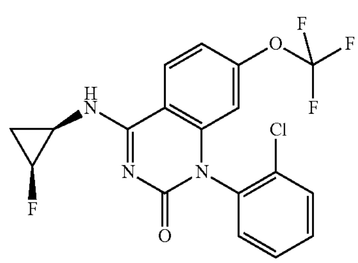 [SMILES: O=c1nc(N[C@@H]2C[C@@H]2F)c2ccc(OC(F)(F)F)cc2n1-c1ccccc1Cl] | 1-(2-chlorophenyl)-4-(((1R,2S)-2-fluorocyclopropyl)amino)-7-(trifluoromethoxy)-quinazolin-2(1H)-one | m/z [M + H]+ 414.05 |
| 600 | 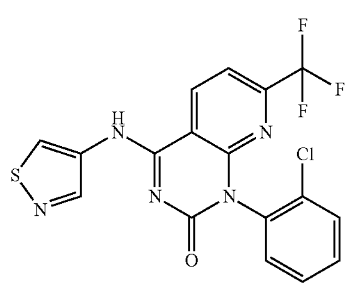 [SMILES: O=c1nc(Nc2cnsc2)c2ccc(C(F)(F)F)nc2n1-c1ccccc1Cl] | 1-(2-chlorophenyl)-4-(isothiazol-4-ylamino)-7-(trifluoromethyl)pyrido[2,3-d]pyrimidin-2(1H)-one | m/z [M + H]+ 424.0 |

TABLE 1-continued

| Cpd. No. | Structure | Name | Mass Spec. |
|---|---|---|---|
| 601 | 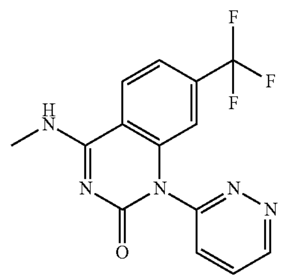 [SMILES: CNc1nc(=O)n(-c2cccnn2)c2cc(C(F)(F)F)ccc12] | 4-(methylamino)-1-(pyridazin-3-yl)-7-(trifluoromethyl)quinazolin-2(1H)-one | m/z [M + H]+ 322.1 |
| 602 | 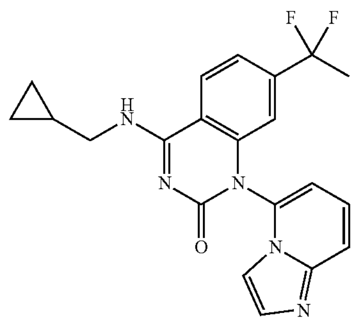 [SMILES: CC(F)(F)c1ccc2c(NCC3CC3)nc(=O)n(-c3cccc4nccn34)c2c1] | 4-((cyclopropylmethyl)amino)-7-(1,1-difluoroethyl)-1-(imidazo[1,2-a]pyridin-5-yl)quinazolin-2(1H)-one | m/z [M + H]+ 396.2 |
| 603 | 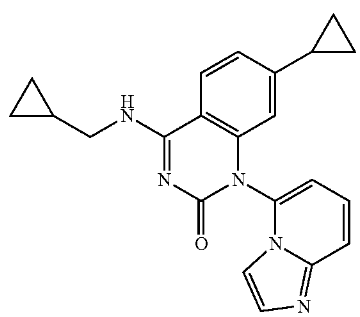 [SMILES: O=c1nc(NCC2CC2)c2ccc(C3CC3)cc2n1-c1cccc2nccn12] | 7-cyclopropyl-4-((cyclopropylmethyl)-amino)-1-(imidazo[1,2-a]pyridin-5-yl)-quinazolin-2(1H)-one | m/z [M + H]+ 372.15 |
| 604 | 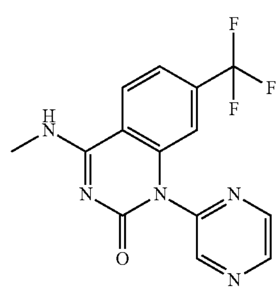 [SMILES: CNc1nc(=O)n(-c2cnccn2)c2cc(C(F)(F)F)ccc12] | 4-(methylamino)-1-(pyrazin-2-yl)-7-(trifluoromethyl)quinazolin-2(1H)-one | m/z [M + H]+ 322.1 |
| 605 | 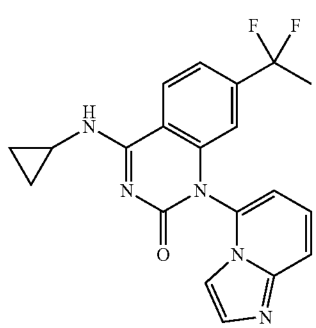 [SMILES: CC(F)(F)c1ccc2c(NC3CC3)nc(=O)n(-c3cccc4nccn34)c2c1] | 4-(cyclopropylamino)-7-(1,1-difluoroethyl)-1-(imidazo[1,2-a]pyridin-5-yl)-quinazolin-2(1H)-one | m/z [M + H]+ 382.2 |

TABLE 1-continued

| Cpd. No. | Structure | Name | Mass Spec. |
|---|---|---|---|
| 606 | 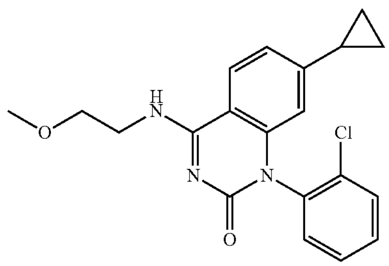 [SMILES: COCCNc1nc(=O)n(-c2ccccc2Cl)c2cc(C3CC3)ccc12] | 1-(2-chlorophenyl)-7-cyclopropyl-4-((2-methoxyethyl)amino)quinazolin-2(1H)-one | m/z [M + H]+ 370.1 |
| 607 | 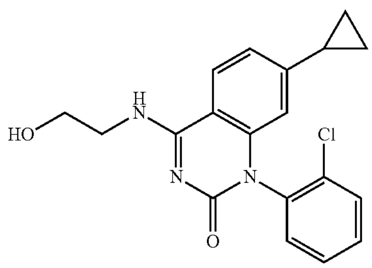 [SMILES: O=c1nc(NCCO)c2ccc(C3CC3)cc2n1-c1ccccc1Cl] | 1-(2-chlorophenyl)-7-cyclopropyl-4-((2-hydroxyethyl)amino)quinazolin-2(1H)-one | m/z [M + H]+ 356.1 |
| 608 | 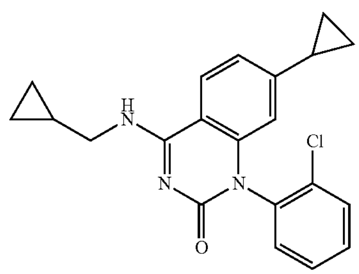 [SMILES: O=c1nc(NCC2CC2)c2ccc(C3CC3)cc2n1-c1ccccc1Cl] | 1-(2-chlorophenyl)-7-cyclopropyl-4-((cyclopropylmethyl)amino)quinazolin-2(1H)-one | m/z [M + H]+ 366.1 |
| 609 | 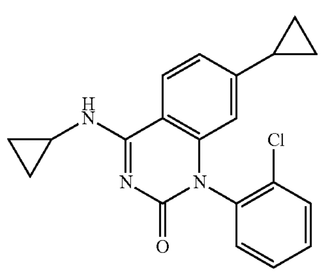 [SMILES: O=c1nc(NC2CC2)c2ccc(C3CC3)cc2n1-c1ccccc1Cl] | 1-(2-chlorophenyl)-7-cyclopropyl-4-(cyclopropylamino)quinazolin-2(1H)-one | m/z [M + H]+ 352.1 |
| 610 | 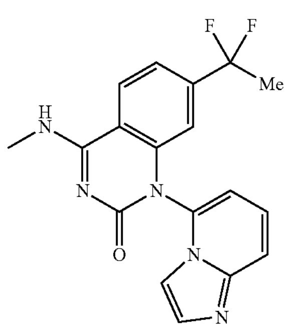 [SMILES: CNc1nc(=O)n(-c2cccc3nccn23)c2cc(C(C)(F)F)ccc12] | 7-(1,1-difluoroethyl)-1-(imidazo[1,2-a]pyridin-5-yl)-4-(methylamino)-quinazolin-2(1H)-one | m/z [M + H]+ 356.1 |

TABLE 1-continued

| Cpd. No. | Structure | Name | Mass Spec. |
|---|---|---|---|
| 611 | 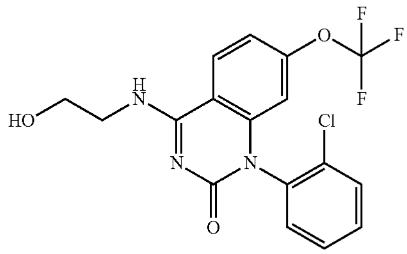 [SMILES: O=c1nc(NCCO)c2ccc(OC(F)(F)F)cc2n1-c1ccccc1Cl] | 1-(2-chlorophenyl)-4-((2-hydroxyethyl)-amino)-7-(trifluoromethoxy)quinazolin-2(1H)-one | m/z [M + H]+ 400.1 |
| 612 | 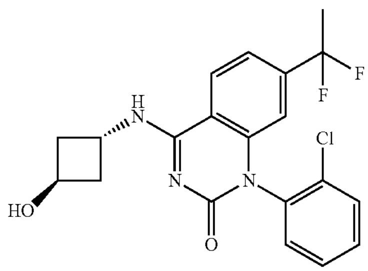 [SMILES: CC(F)(F)c1ccc2c(N[C@H]3C[C@H](O)C3)nc(=O)n(-c3ccccc3Cl)c2c1] | 1-(2-chlorophenyl)-7-(1,1-difluoroethyl)-4-(((trans)-3-hydroxycyclobutyl)amino)-quinazolin-2(1H)-one | m/z [M + H]+ 406.1 |
| 613 | 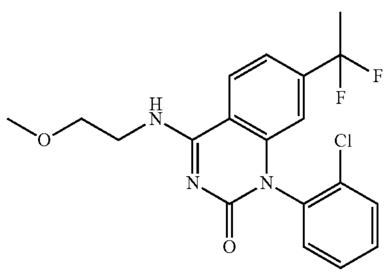 [SMILES: COCCNc1nc(=O)n(-c2ccccc2Cl)c2cc(C(C)(F)F)ccc12] | 1-(2-chlorophenyl)-7-(1,1-difluoroethyl)-4-((2-methoxyethyl)amino)quinazolin-2(1H)-one | m/z [M + H]+ 394.05 |
| 614 | 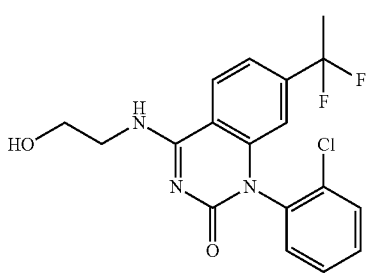 [SMILES: CC(F)(F)c1ccc2c(NCCO)nc(=O)n(-c3ccccc3Cl)c2c1] | 1-(2-chlorophenyl)-7-(1,1-difluoroethyl)-4-((2-hydroxyethyl)amino)quinazolin-2(1H)-one | m/z [M + H]+ 380.05 |
| 615 | 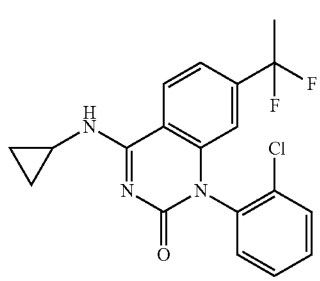 [SMILES: CC(F)(F)c1ccc2c(NC3CC3)nc(=O)n(-c3ccccc3Cl)c2c1] | 1-(2-chlorophenyl)-4-(cyclopropyl-amino)-7-(1,1-difluoroethyl)quinazolin-2(1H)-one | m/z [M + H]+ 376.1 |

TABLE 1-continued

| Cpd. No. | Structure | Name | Mass Spec. |
|---|---|---|---|
| 616 | 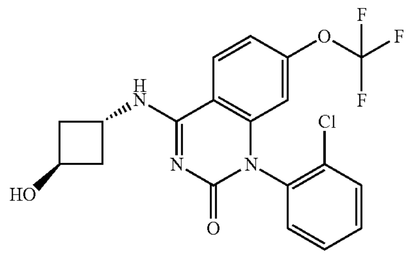 [SMILES: O=c1nc(N[C@H]2C[C@H](O)C2)c2ccc(OC(F)(F)F)cc2n1-c1ccccc1Cl] | 1-(2-chlorophenyl)-4-(((trans)-3-hydroxycyclobutyl)amino)-7-(trifluoromethoxy)-quinazolin-2(1H)-one | m/z [M + H]+ 426.1 |
| 617 | 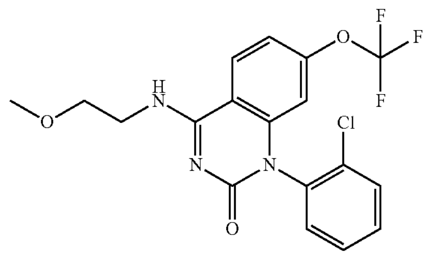 [SMILES: COCCNc1nc(=O)n(-c2ccccc2Cl)c2cc(OC(F)(F)F)ccc12] | 1-(2-chlorophenyl)-4-((2-methoxyethyl)-amino)-7-(trifluoromethoxy)quinazolin-2(1H)-one | m/z [M + H]+ 414.0 |
| 618 | 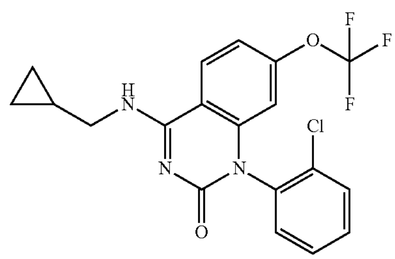 [SMILES: O=c1nc(NCC2CC2)c2ccc(OC(F)(F)F)cc2n1-c1ccccc1Cl] | 1-(2-chlorophenyl)-4-((cyclopropyl-methyl)amino)-7-(trifluoromethoxy)-quinazolin-2(1H)-one | m/z [M + H]+ 410.0 |
| 619 | 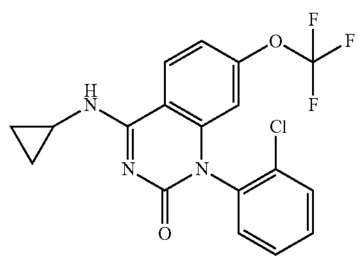 [SMILES: O=c1nc(NC2CC2)c2ccc(OC(F)(F)F)cc2n1-c1ccccc1Cl] | 1-(2-chlorophenyl)-4-(cyclopropyl-amino)-7-(trifluoromethoxy)quinazolin-2(1H)-one | m/z [M + H]+ 396.0 |
| 620 | 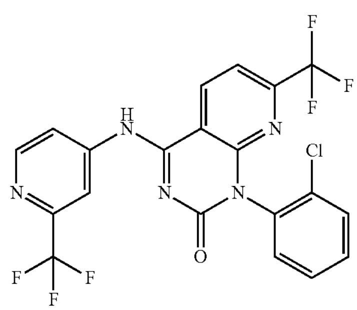 [SMILES: O=c1nc(Nc2ccnc(C(F)(F)F)c2)c2ccc(C(F)(F)F)nc2n1-c1ccccc1Cl] | 1-(2-chlorophenyl)-7-(trifluoromethyl)-4-((2-(trifluoromethyl)pyridin-4-yl)-amino)-pyrido[2,3-d]pyrimidin-2(1H)-one | m/z [M + H]+ 486.05 |
| 621 | 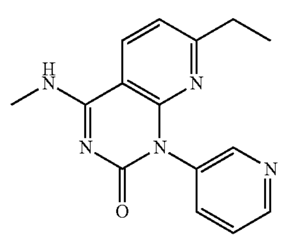 [SMILES: CCc1ccc2c(NC)nc(=O)n(-c3cccnc3)c2n1] | 7-ethyl-4-(methylamino)-1-(pyridin-3-yl)pyrido[2,3-d]pyrimidin-2(1H)-one | m/z [M + H]+ 282.15 |

TABLE 1-continued

| Cpd. No. | Structure | Name | Mass Spec. |
|---|---|---|---|
| 622 | 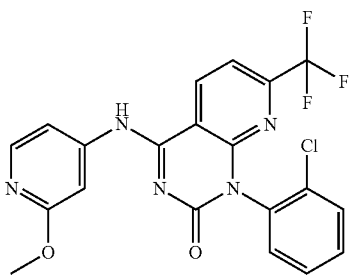 [SMILES: COc1cc(Nc2nc(=O)n(-c3ccccc3Cl)c3nc(C(F)(F)F)ccc23)ccn1] | 1-(2-chlorophenyl)-4-((2-methoxy-pyridin-4-yl)amino)-7-(trifluoromethyl)-pyrido-[2,3-d]pyrimidin-2(1H)-one | m/z [M + H]⁺ 448.1 |
| 623 | 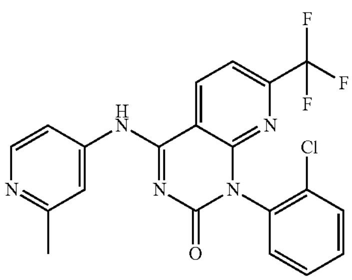 [SMILES: Cc1cc(Nc2nc(=O)n(-c3ccccc3Cl)c3nc(C(F)(F)F)ccc23)ccn1] | 1-(2-chlorophenyl)-4-((2-methylpyridin-4-yl)amino)-7-(trifluoromethyl)-pyrido[2,3-d]pyrimidin-2(1H)-one | |
| 624 | 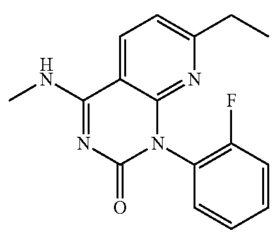 [SMILES: CCc1ccc2c(NC)nc(=O)n(-c3ccccc3F)c2n1] | 7-ethyl-1-(2-fluorophenyl)-4-(methyl-amino)pyrido[2,3-d]pyrimidin-2(1H)-one | m/z [M + H]⁺ 299.1 |
| 625 | 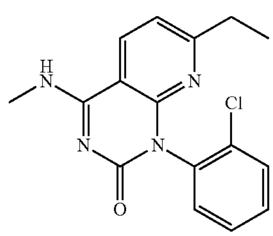 [SMILES: CCc1ccc2c(NC)nc(=O)n(-c3ccccc3Cl)c2n1] | 1-(2-chlorophenyl)-7-ethyl-4-(methyl-amino)pyrido[2,3-d]pyrimidin-2(1H)-one | m/z [M + H]⁺ 315.1 |
| 626 | 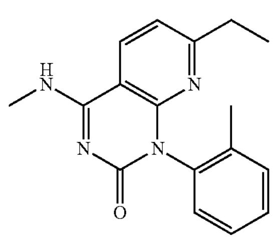 [SMILES: CCc1ccc2c(NC)nc(=O)n(-c3ccccc3C)c2n1] | 7-ethyl-4-(methylamino)-1-(o-tolyl)-pyrido[2,3-d]pyrimidin-2(1H)-one | m/z [M + H]⁺ 295.15 |
| 627 | 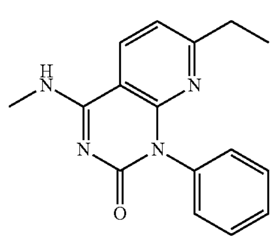 [SMILES: CCc1ccc2c(NC)nc(=O)n(-c3ccccc3)c2n1] | 7-ethyl-4-(methylamino)-1-phenyl-pyrido[2,3-d]pyrimidin-2(1H)-one | m/z [M + H]⁺ 281.2 |

TABLE 1-continued

| Cpd. No. | Structure | Name | Mass Spec. |
|---|---|---|---|
| 628 | 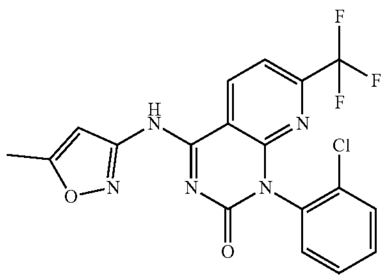 [SMILES: Cc1cc(Nc2nc(=O)n(-c3ccccc3Cl)c3nc(C(F)(F)F)ccc23)no1] | 1-(2-chlorophenyl)-4-((5-methyl-isoxazol-3-yl)amino)-7-(trifluoromethyl)pyrido[2,3-d]pyrimidin-2(1H)-one | m/z [M + H]+ 422.05 |
| 629 | 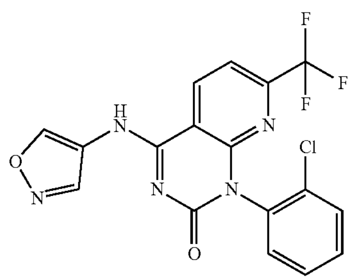 [SMILES: O=c1nc(Nc2cnoc2)c2ccc(C(F)(F)F)nc2n1-c1ccccc1Cl] | 1-(2-chlorophenyl)-4-(isoxazol-4-yl-amino)-7-(trifluoromethyl)pyrido[2,3-d]-pyrimidin-2(1H)-one | m/z [M + H]+ 408.0 |
| 630 | 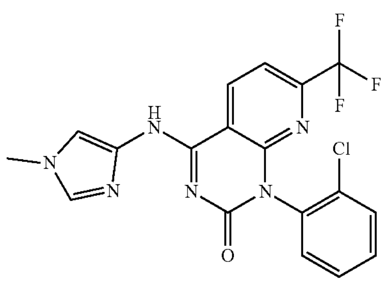 [SMILES: Cn1cnc(Nc2nc(=O)n(-c3ccccc3Cl)c3nc(C(F)(F)F)ccc23)c1] | 1-(2-chlorophenyl)-4-((1-methyl-1H-pyrazol-4-yl)amino)-7-(trifluoromethyl)-pyrido[2,3-d]pyrimidin-2(1H)-one | m/z [M + H]+ 421.0 |
| 631 | 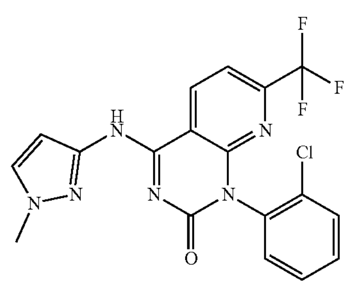 [SMILES: Cn1ccc(Nc2nc(=O)n(-c3ccccc3Cl)c3nc(C(F)(F)F)ccc23)n1] | 1-(2-chlorophenyl)-4-((1-methyl-1H-pyrazol-3-yl)amino)-7-(trifluoromethyl)pyrido-[2,3-d]pyrimidin-2(1H)-one | m/z [M + H]+ 421.0 |
| 632 | 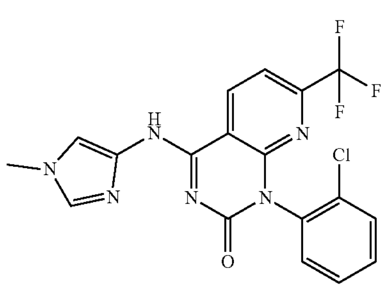 [SMILES: Cn1cnc(Nc2nc(=O)n(-c3ccccc3Cl)c3nc(C(F)(F)F)ccc23)c1] | 1-(2-chlorophenyl)-4-((1-methyl-1H-imidazol-4-yl)amino)-7-(trifluoromethyl)-pyrido[2,3-d]pyrimidin-2(1H)-one | m/z [M + H]+ 421.0 |

TABLE 1-continued

| Cpd. No. | Structure | Name | Mass Spec. |
|---|---|---|---|
| 633 | 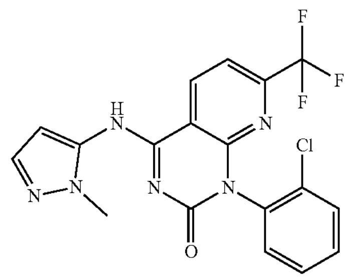 [SMILES: Cn1nccc1Nc1nc(=O)n(-c2ccccc2Cl)c2nc(C(F)(F)F)ccc12] | 1-(2-chlorophenyl)-4-((1-methyl-1H-pyrazol-5-yl)amino)-7-(trifluoromethyl)-pyrido[2,3-d]pyrimidin-2(1H)-one | m/z [M + H]+ 421.0 |
| 634 | 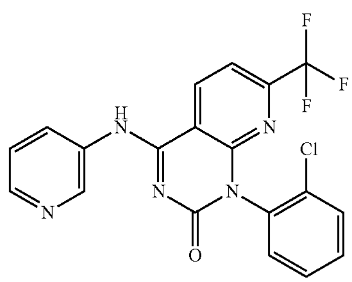 [SMILES: O=c1nc(Nc2cccnc2)c2ccc(C(F)(F)F)nc2n1-c1ccccc1Cl] | 1-(2-chlorophenyl)-4-(pyridin-3-yl-amino)-7-(trifluoromethyl)pyrido[2,3-d]-pyrimidin-2(1H)-one | m/z [M + H]+ 418.0 |
| 635 | 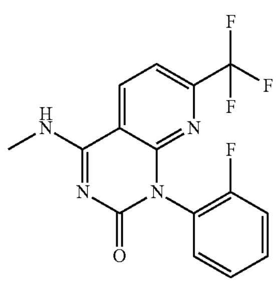 | 1-(2-fluorophenyl)-4-(methylamino)-7-(trifluoromethyl)pyrido[2,3-d]pyrimidin-2(1H)-one | m/z [M + H]+ 339.1 |
| 636 | 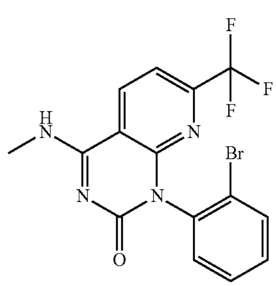 [SMILES: CNc1nc(=O)n(-c2ccccc2Br)c2nc(C(F)(F)F)ccc12] | 1-(2-bromophenyl)-4-(methylamino)-7-(trifluoromethyl)pyrido[2,3-d]pyrimidin-2(1H)-one | m/z [M + H]+ 401.0, 399.0 |
| 637 | 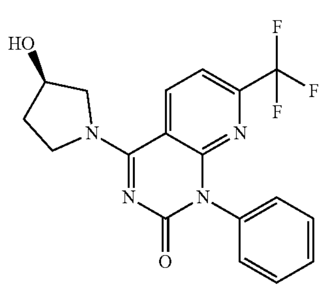 [SMILES: O=c1nc(N2CC[C@@H](O)C2)c2ccc(C(F)(F)F)nc2n1-c1ccccc1] | (R)-4-(3-hydroxypyrrolidin-1-yl)-1-phenyl-7-(trifluoromethyl)pyrido[2,3-d]-pyrimidin-2(1H)-one | m/z [M + H]+ 377.1 |

TABLE 1-continued

| Cpd. No. | Structure | Name | Mass Spec. |
|---|---|---|---|
| 638 | 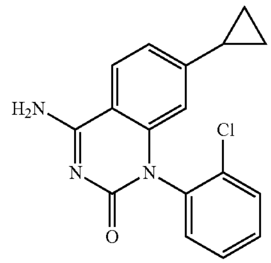 [SMILES: Nc1nc(=O)n(-c2ccccc2Cl)c2cc(C3CC3)ccc12] | 4-amino-1-(2-chlorophenyl)-7-cyclopropylquinazolin-2(1H)-one | m/z [M + H]+ 312.00 |
| 639 | 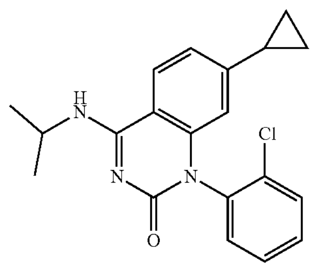 [SMILES: CC(C)Nc1nc(=O)n(-c2ccccc2Cl)c2cc(C3CC3)ccc12] | 1-(2-chlorophenyl)-7-cyclopropyl-4-(isopropylamino)quinazolin-2(1H)-one | m/z [M + H]+ 354.20 |
| 640 | 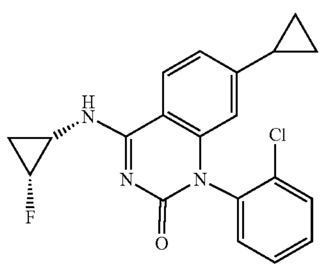 | 1-(2-chlorophenyl)-7-cyclopropyl-4-(((1S,2R)-2-fluorocyclopropyl)amino)-quinazolin-2(1H)-one | m/z [M + H]+ 370.00 |
| 641 | 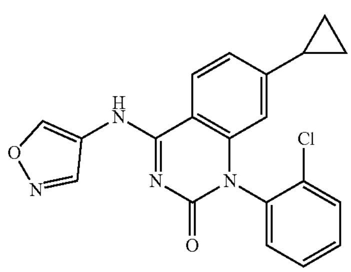 [SMILES: O=c1nc(Nc2cnoc2)c2ccc(C3CC3)cc2n1-c1ccccc1Cl] | 1-(2-chlorophenyl)-7-cyclopropyl-4-(isoxazol-4-ylamino)quinazolin-2(1H)-one | m/z [M + H]+ 379.00 |
| 642 | 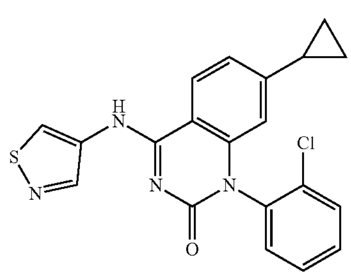 [SMILES: O=c1nc(Nc2cnsc2)c2ccc(C3CC3)cc2n1-c1ccccc1Cl] | 1-(2-chlorophenyl)-7-cyclopropyl-4-(isothiazol-4-ylamino)quinazolin-2(1H)-one | m/z [M + H]+ 395.00 |

TABLE 1-continued

| Cpd. No. | Structure | Name | Mass Spec. |
|---|---|---|---|
| 643 | 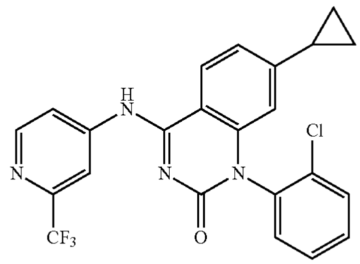 [SMILES: O=c1nc(Nc2ccnc(C(F)(F)F)c2)c2ccc(C3CC3)cc2n1-c1ccccc1Cl] | 1-(2-chlorophenyl)-7-cyclopropyl-4-((2-(trifluoromethyl)pyridin-4-yl)amino)-quinazolin-2(1H)-one | m/z [M + H]+ 457.00 |
| 644 | 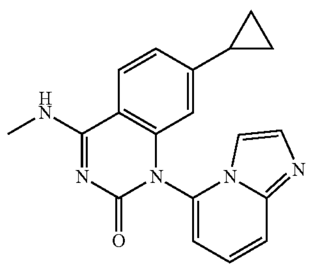 [SMILES: CNc1nc(=O)n(-c2cccc3nccn23)c2cc(C3CC3)ccc12] | 7-cyclopropyl-1-(imidazo[1,2-a]pyridin-5-yl)-4-(methylamino)quinazolin-2(1H)-one | m/z [M + H]+ 332.00 |
| 645 | 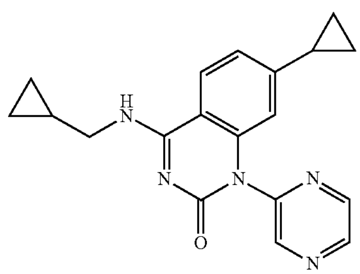 [SMILES: O=c1nc(NCC2CC2)c2ccc(C3CC3)cc2n1-c1cnccn1] | 7-cyclopropyl-4-((cyclopropylmethyl)-amino)-1-(pyrazin-2-yl)quinazolin-2(1H)-one | m/z [M + H]+ 334.20 |
| 646 | 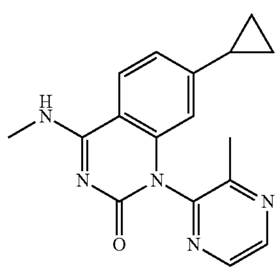 [SMILES: CNc1nc(=O)n(-c2nccnc2C)c2cc(C3CC3)ccc12] | 7-cyclopropyl-4-(methylamino)-1-(3-methylpyrazin-2-yl)quinazolin-2(1H)-one | m/z [M + H]+ 308.20 |
| 647 | 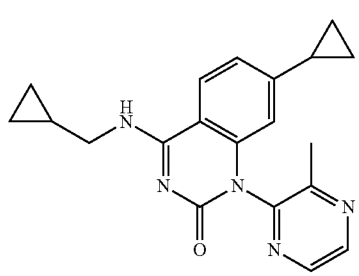 [SMILES: Cc1nccnc1-n1c(=O)nc(NCC2CC2)c2ccc(C3CC3)cc21] | 7-cyclopropyl-4-((cyclopropylmethyl)-amino)-1-(3-methylpyrazin-2-yl)-quinazolin-2(1H)-one | m/z [M + H]+ 348.20 |

TABLE 1-continued

| Cpd. No. | Structure | Name | Mass Spec. |
|---|---|---|---|
| 648 | 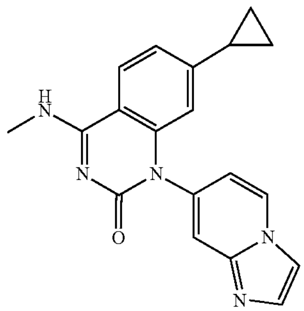 [SMILES: CNc1nc(=O)n(-c2ccn3ccnc3c2)c2cc(C3CC3)ccc12] | 7-cyclopropyl-1-(imidazo[1,2-a]pyridin-7-yl)-4-(methylamino)quinazolin-2(1H)-one | m/z [M + H]+ 332.00 |
| 649 | 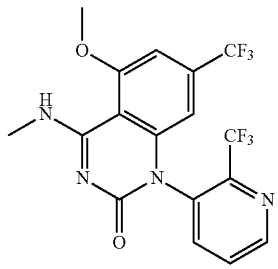 [SMILES: CNc1nc(=O)n(-c2cccnc2C(F)(F)F)c2cc(C(F)(F)F)cc(OC)c12] | 5-methoxy-4-(methylamino)-7-(trifluoromethyl)-1-(2-(trifluoromethyl)-pyridin-3-yl)quinazolin-2(1H)-one | m/z [M + H]+ 419.00 |
| 650 | 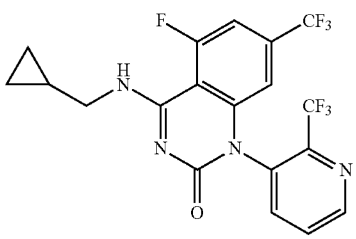 [SMILES: O=c1nc(NCC2CC2)c2c(F)cc(C(F)(F)F)cc2n1-c1cccnc1C(F)(F)F] | 4-((cyclopropylmethyl)amino)-5-fluoro-7-(trifluoromethyl)-1-(2-(trifluoro-methyl)-pyridin-3-yl)quinazolin-2(1H)-one | m/z [M + H]+ 447.00 |
| 651 | 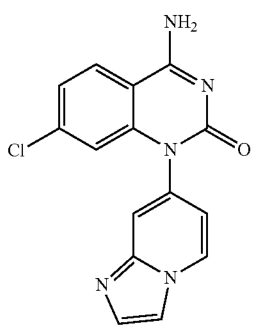 [SMILES: Nc1nc(=O)n(-c2ccn3ccnc3c2)c2cc(Cl)ccc12] | 4-amino-7-chloro-1-(imidazo[1,2-a]-pyridin-7-yl)quinazolin-2(1H)-one | m/z [M + H]+ 312.0 |
| 652 | 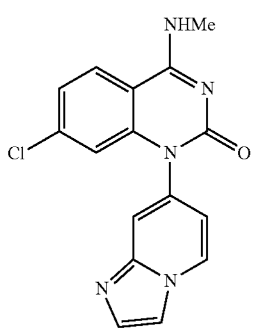 [SMILES: CNc1nc(=O)n(-c2ccn3ccnc3c2)c2cc(Cl)ccc12] | 7-chloro-1-(imidazo[1,2-a]pyridin-7-yl)-4-(methylamino)quinazolin-2(1H)-one | m/z [M + H]+ 326.0 |

TABLE 1-continued

| Cpd. No. | Name | Mass Spec. |
|---|---|---|
| 653 | 7-chloro-4-((2,2-difluoroethyl)amino)-1-(imidazo[1,2-a]pyridin-7-yl)quinazolin-2(1H)-one | m/z [M + H]+ 376.0 |
| 654 | 7-chloro-1-(imidazo[1,2-a]pyridin-5-yl)-4-(methylamino)quinazolin-2(1H)-one | m/z [M + H]+ 326.0 |
| 655 | 1-(2-chlorophenyl)-4-(methylamino)-7-(trifluoromethoxy)quinazolin-2(1H)-one | m/z [M + H]+ 370.1 |
| 656 | 4-amino-1-(2-chlorophenyl)-7-(1,1-difluoroethyl)quinazolin-2(1H)-one | m/z [M + H]+ 336.1 |
| 657 | 1-(2-chlorophenyl)-7-(1,1-difluoroethyl)-4-(isoxazol-4-ylamino)quinazolin-2(1H)-one | m/z [M + H]+ 403.0 |

TABLE 1-continued

| Cpd. No. | Structure | Name | Mass Spec. |
|---|---|---|---|
| 658 | 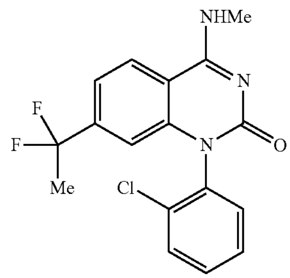 [SMILES: CNc1nc(=O)n(-c2ccccc2Cl)c2cc(C(C)(F)F)ccc12] | 1-(2-chlorophenyl)-7-(1,1-difluoroethyl)-4-(methylamino)quinazolin-2(1H)-one | m/z [M + H]+ 350.1 |
| 659 | 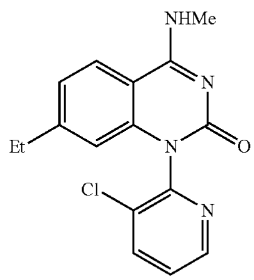 [SMILES: CCc1ccc2c(NC)nc(=O)n(-c3ncccc3Cl)c2c1] | 1-(3-chloropyridin-2-yl)-7-ethyl-4-(methylamino)quinazolin-2(1H)-one | m/z [M + H]+ 315.0 |
| 660 | 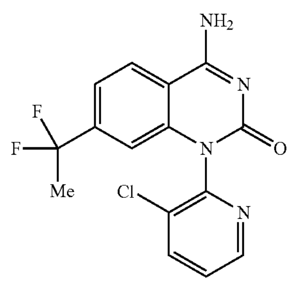 | 4-amino-1-(3-chloropyridin-2-yl)-7-(1,1-difluoroethyl)quinazolin-2(1H)-one | m/z [M + H]+ 337.0. |
| 661 | 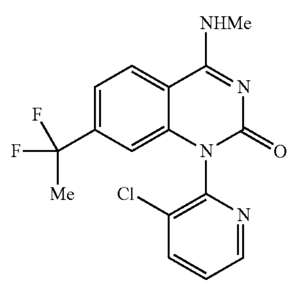 [SMILES: CNc1nc(=O)n(-c2ncccc2Cl)c2cc(C(C)(F)F)ccc12] | 1-(3-chloropyridin-2-yl)-7-(1,1-difluoroethyl)-4-(methylamino)-quinazolin-2(1H)-one | m/z [M + H]+ 351.0 |
| 662 | 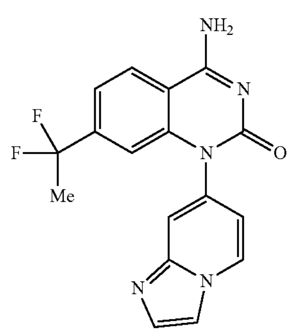 [SMILES: CC(F)(F)c1ccc2c(N)nc(=O)n(-c3ccn4ccnc4c3)c2c1] | 4-amino-7-(1,1-difluoroethyl)-1-(imidazo[1,2-a]pyridin-7-yl)quinazolin-2(1H)-one | m/z [M + H]+ 342.1 |

TABLE 1-continued

| Cpd. No. | Structure | Name | Mass Spec. |
|---|---|---|---|
| 663 | 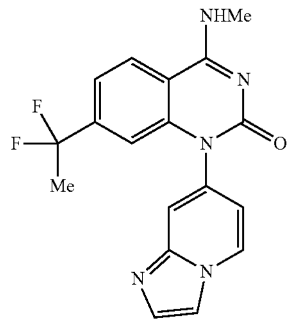 [SMILES: CNc1nc(=O)n(-c2ccn3ccnc3c2)c2cc(C(C)(F)F)ccc12] | 7-(1,1-difluoroethyl)-1-(imidazo[1,2-a]pyridin-7-yl)-4-(methylamino)-quinazolin-2(1H)-one | m/z [M + H]+ 356.0 |
| 664 | 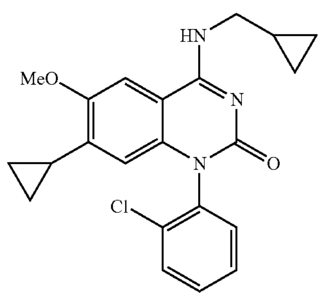 | 1-(2-chlorophenyl)-7-cyclopropyl-4-((cyclopropylmethyl)amino)-6-methoxyquinazolin-2(1H)-one | m/z [M + H]+ 396.2 |
| 665 | 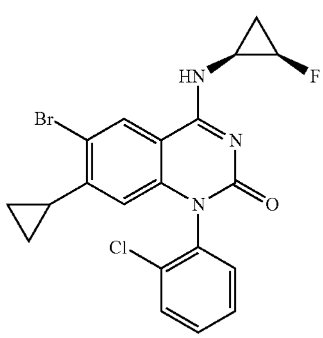 | 6-bromo-1-(2-chlorophenyl)-7-cyclopropyl-4-(((1S,2R)-2-fluorocyclo-propyl)amino)quinazolin-2(1H)-one | m/z [M + H]+ 448.0/450.0 |
| 666 | 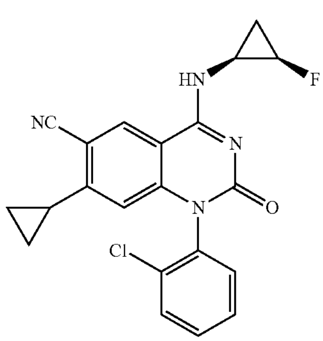 [SMILES: O=c1nc(N[C@H]2C[C@H]2F)c2cc(Br)c(C3CC3)cc2n1-c1ccccc1Cl] | 1-(2-chlorophenyl)-7-cyclopropyl-4-(((1S,2R)-2-fluorocyclopropyl)amino)-2-oxo-1,2-dihydroquinazoline-6-carbonitrile | m/z [M + H]+ 395.0 |

TABLE 1-continued

| Cpd. No. | Structure | Name | Mass Spec. |
|---|---|---|---|
| 667 | 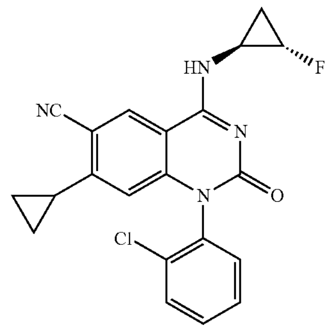 [SMILES: N#Cc1cc2c(N[C@H]3C[C@@H]3F)nc(=O)n(-c3ccccc3Cl)c2cc1C1CC1] | 1-(2-chlorophenyl)-7-cyclopropyl-4-(((trans)-2-fluorocyclopropyl)amino)-2-oxo-1,2-dihydroquinazoline-6-carbonitrile | m/z [M + H]$^+$ 395.0 |
| 668 | 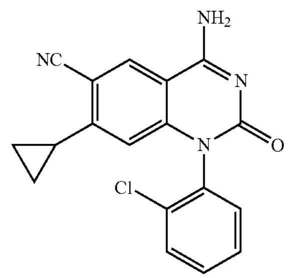 [SMILES: N#Cc1cc2c(N)nc(=O)n(-c3ccccc3Cl)c2cc1C1CC1] | 4-amino-1-(2-chlorophenyl)-7-cyclopropyl-2-oxo-1,2-dihydroquinazoline-6-carbonitrile | m/z [M + H]$^+$ 337.0 |
| 669 | 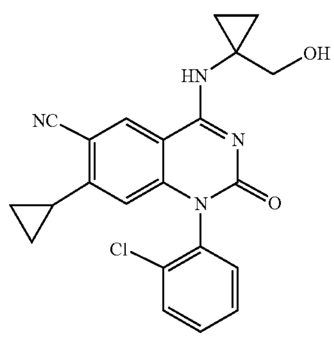 [SMILES: N#Cc1cc2c(NC3(CO)CC3)nc(=O)n(-c3ccccc3Cl)c2cc1C1CC1] | 1-(2-chlorophenyl)-7-cyclopropyl-4-((1-(hydroxymethyl)cyclopropyl)amino)-2-oxo-1,2-dihydroquinazoline-6-carbonitrile | m/z [M + H]$^+$ 421.0 |
| 670 | 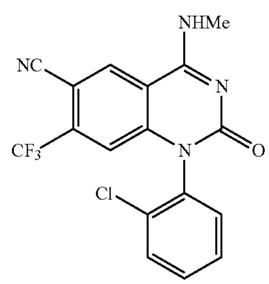 [SMILES: CNc1nc(=O)n(-c2ccccc2Cl)c2cc(C(F)(F)F)c(C#N)cc12] | 1-(2-chlorophenyl)-4-(methylamino)-2-oxo-7-(trifluoromethyl)-1,2-dihydroquinazoline-6-carbonitrile | m/z [M + H]$^+$ 379.0 |
| 671 | 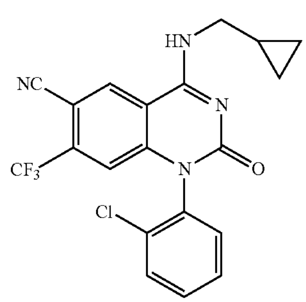 [SMILES: N#Cc1cc2c(NCC3CC3)nc(=O)n(-c3ccccc3Cl)c2cc1C(F)(F)F] | 1-(2-chlorophenyl)-4-((cyclopropylmethyl)amino)-2-oxo-7-(trifluoromethyl)-1,2-dihydroquinazoline-6-carbonitrile | m/z [M + H]$^+$ 419.0 |

TABLE 1-continued

| Cpd. No. | Structure | Name | Mass Spec. |
|---|---|---|---|
| 672 | 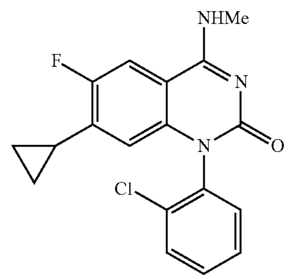 [SMILES: CNc1nc(=O)n(-c2ccccc2Cl)c2cc(C3CC3)c(F)cc12] | 1-(2-chlorophenyl)-7-cyclopropyl-6-fluoro-4-(methylamino)quinazolin-2(1H)-one | m/z [M + H]+ 344.0 |
| 673 | 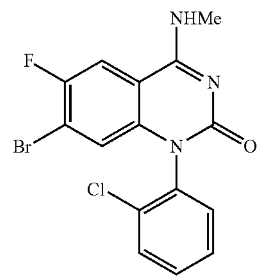 | 7-bromo-1-(2-chlorophenyl)-6-fluoro-4-(methylamino)quinazolin-2(1H)-one | m/z [M + H]+ 381.9/384.0. |
| 674 | 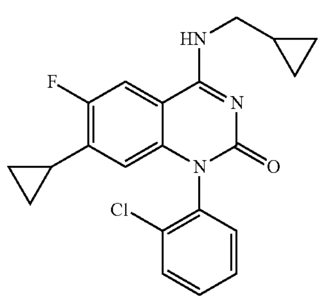 [SMILES: O=c1nc(NCC2CC2)c2cc(F)c(C3CC3)cc2n1-c1ccccc1Cl] | 1-(2-chlorophenyl)-7-cyclopropyl-4-((cyclopropylmethyl)amino)-6-fluoro-quinazolin-2(1H)-one | m/z [M + H]+ 384.0 |
| 675 | 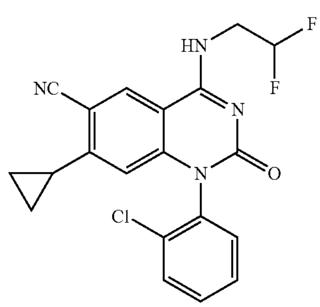 [SMILES: N#Cc1cc2c(NCC(F)F)nc(=O)n(-c3ccccc3Cl)c2cc1C1CC1] | 1-(2-chlorophenyl)-7-cyclopropyl-4-((2,2-difluoroethyl)amino)-2-oxo-1,2-dihydro-quinazoline-6-carbonitrile | m/z [M + H]+ 410.1 |
| 676 | 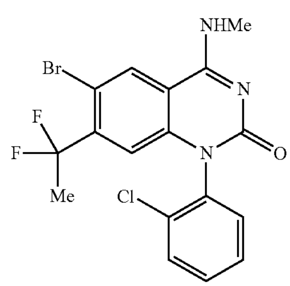 [SMILES: CNc1nc(=O)n(-c2ccccc2Cl)c2cc(C(C)(F)F)c(Br)cc12] | 6-bromo-1-(2-chlorophenyl)-7-(1,1-difluoroethyl)-4-(methylamino)-quinazolin-2(1H)-one | m/z [M + H]+ 428.0/430.0 |

TABLE 1-continued

| Cpd. No. | Structure | Name | Mass Spec. |
|---|---|---|---|
| 677 | 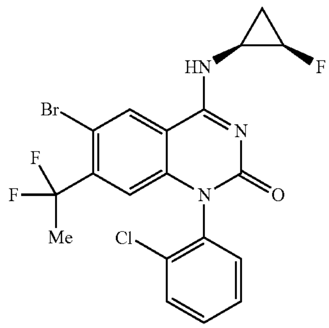 [SMILES: CC(F)(F)c1cc2c(cc1Br)c(N[C@H]1C[C@H]1F)nc(=O)n2-c1ccccc1Cl] | 6-bromo-1-(2-chlorophenyl)-7-(1,1-difluoroethyl)-4-(((1S,2R)-2-fluorocyclopropyl)amino)quinazolin-2(1H)-one | m/z [M + H]+ 472.0/474.0 |
| 678 | 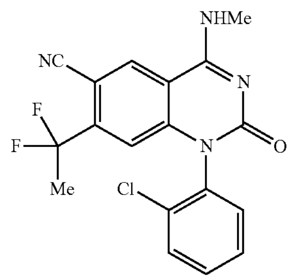 [SMILES: CNc1nc(=O)n(-c2ccccc2Cl)c2cc(C(C)(F)F)c(C#N)cc12] | 1-(2-chlorophenyl)-7-(1,1-difluoroethyl)-4-(methylamino)-2-oxo-1,2-dihydro-quinazoline-6-carbonitrile | m/z [M + H]+ 375.0 |
| 679 | 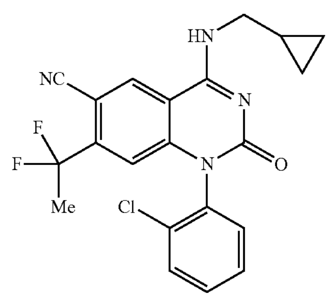 [SMILES: CC(F)(F)c1cc2c(cc1C#N)c(NCC1CC1)nc(=O)n2-c1ccccc1Cl] | 1-(2-chlorophenyl)-4-((cyclopropyl-methyl)amino)-7-(1,1-difluoroethyl)-2-oxo-1,2-dihydroquinazoline-6-carbonitrile | m/z [M + H]+ 415.0 |
| 680 | 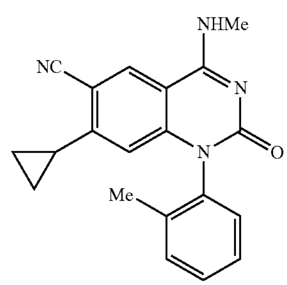 [SMILES: CNc1nc(=O)n(-c2ccccc2C)c2cc(C3CC3)c(C#N)cc12] | 7-cyclopropyl-4-(methylamino)-2-oxo-1-(o-tolyl)-1,2-dihydroquinazoline-6-carbonitrile | m/z [M + H]+ 331.2 |
| 681 | 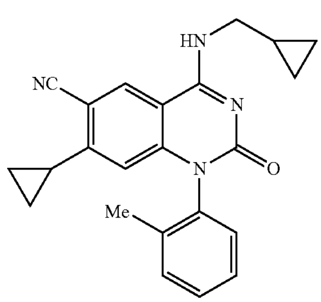 | 7-cyclopropyl-4-((cyclopropylmethyl)-amino)-2-oxo-1-(o-tolyl)-1,2-dihydro-quinazoline-6-carbonitrile | m/z [M + H]+ 371.2 |

TABLE 1-continued

| Cpd. No. | Structure | Name | Mass Spec. |
|---|---|---|---|
| 682 | 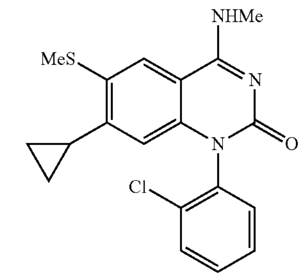 [SMILES: CNc1nc(=O)n(-c2ccccc2Cl)c2cc(C3CC3)c(SC)cc12] | 1-(2-chlorophenyl)-7-cyclopropyl-4-(methylamino)-6-(methylthio)-quinazolin-2(1H)-one | m/z [M + H]+ 372.0 |
| 683 | 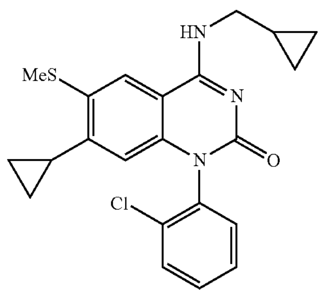 [SMILES: CSc1cc2c(NCC3CC3)nc(=O)n(-c3ccccc3Cl)c2cc1C1CC1] | 1-(2-chlorophenyl)-7-cyclopropyl-4-((cyclopropylmethyl)amino)-6-(methylthio)quinazolin-2(1H)-one | m/z [M + H]+ 412.0 |
| 684 | 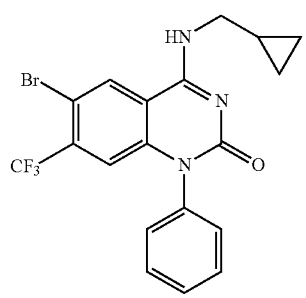 [SMILES: O=c1nc(NCC2CC2)c2cc(Br)c(C(F)(F)F)cc2n1-c1ccccc1] | 6-bromo-4-((cyclopropylmethyl)amino)-1-phenyl-7-(trifluoromethyl)quinazolin-2(1H)-one | m/z [M + H]+ 438.0/440.0 |
| 685 | 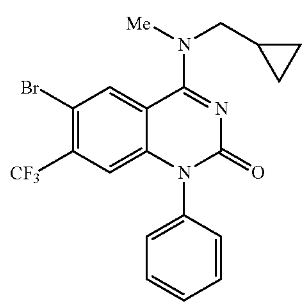 [SMILES: CN(CC1CC1)c1nc(=O)n(-c2ccccc2)c2cc(C(F)(F)F)c(Br)cc12] | 6-bromo-4-((cyclopropylmethyl)(methyl)amino)-1-phenyl-7-(trifluoromethyl)-quinazolin-2(1H)-one | m/z [M + H]+ 452.0/454.0 |
| 686 | 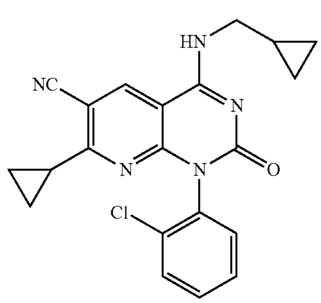 [SMILES: N#Cc1cc2c(NCC3CC3)nc(=O)n(-c3ccccc3Cl)c2nc1C1CC1] | 1-(2-chlorophenyl)-7-cyclopropyl-4-((cyclopropylmethyl)amino)-2-oxo-1,2-dihydropyrido[2,3-d]pyrimidine-6-carbonitrile | m/z [M + H]+ 392.1 |

TABLE 1-continued

| Cpd. No. | Name | Mass Spec. |
|---|---|---|
| 687 | 1-(2-chlorophenyl)-7-cyclopropyl-4-(((1S,2R)-2-fluorocyclopropyl)amino)-2-oxo-1,2-dihydropyrido[2,3-d]-pyrimidine-6-carbonitrile | m/z [M + H]+ 396.0 |
| 688 | 7-chloro-4-((2,2-difluoroethyl)amino)-5-methoxy-1-(o-tolyl)quinazolin-2(1H)-one | m/z [M + H]+ 380.35 |
| 689 | 7-chloro-5-fluoro-4-(((1r,3r)-3-methoxy-cyclobutyl)amino)-1-(o-tolyl)quinazolin-2(1H)-one | m/z [M + H]+ 400.33 |
| 690 | 7-chloro-1-(2-chlorophenyl)-5-methoxy-4-(methylamino)quinazolin-2(1H)-one | m/z [M + H]+ 350.2 |
| 691 | 5-methoxy-4-(methylamino)-1-(o-tolyl)-7-(trifluoromethyl)quinazolin-2(1H)-one | m/z [M + H]+ 364.19 |
| 692 | 5-methoxy-4-(methylamino)-1-phenyl-7-(trifluoromethyl)pyrido[2,3-d]pyrimidin-2(1H)-one | m/z [M + H]+ 351.3 |

TABLE 1-continued

| Cpd. No. | Name | Mass Spec. |
|---|---|---|
| 693 | 1-(2-chloro-6-fluorophenyl)-4-(methylamino)-7-(trifluoromethyl)pyrido [2,3-d]-pyrimidin-2(1H)-one | m/z [M + H]+ 373.2 |
| 694 | 7-cyclopropyl-4-(methylamino)-1-(2-methylpyridin-3-yl)quinazolin-2(1H) one | m/z [M + H]+ 307.22 |
| 695 | 1-(2-chlorophenyl)-4-(3-hydroxy-3-methylpyrrolidin-1-yl)-7-(trifluoro-methyl) pyrido[2,3-d]pyrimidin-2(1H)-one, single unknown enantiomer | m/z [M + H]+ 425.1 |
| 696 | 1-benzyl-4-(methylamino)-7-(trifluoro-methyl)pyrido[2,3-d]pyrimidin-2(1H)-one | m/z [M + H]+ 335.3 |
| 697 | 1-(2-chlorophenyl)-4-(((trans)-2-hydroxycyclobutyl)amino)-7-(trifluoro-methyl)-pyrido[2,3-d]pyrimidin-2(1H)-one, single unknown enantiomer/atropisomer | m/z [M + H]+ 411.3 |

TABLE 1-continued

| Cpd. No. | Structure | Name | Mass Spec. |
|---|---|---|---|
| 698 | 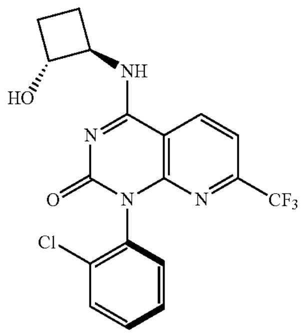 | 1-(2-chlorophenyl)-4-(((trans)-2-hydroxycyclobutyl)amino)-7-(trifluoro-methyl)-pyrido[2,3-d]pyrimidin-2(1H)-one, single unknown enantiomer/atropisomer | m/z [M + H]+ 411.3 |
| 699 | 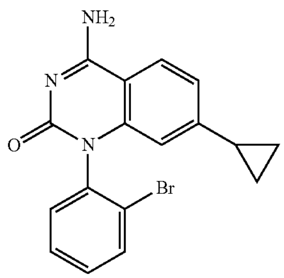 [SMILES: Nc1nc(=O)n(-c2ccccc2Br)c2cc(C3CC3)ccc12] | 4-amino-1-(2-bromophenyl)-7-cyclopropylquinazolin-2(1H)-one | m/z [M + H]+ 356.1 |
| 700 | 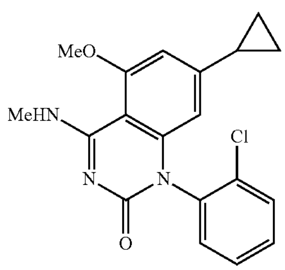 [SMILES: CNc1nc(=O)n(-c2ccccc2Cl)c2cc(C3CC3)cc(OC)c12] | 1-(2-chlorophenyl)-7-cyclopropyl-5-methoxy-(methylamino)quinazolin-2(1H)-one | m/z [M + H]+ 356.35 |
| 701 | 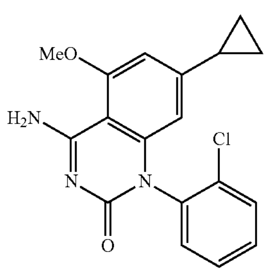 [SMILES: COc1cc(C2CC2)cc2c1c(N)nc(=O)n2-c1ccccc1Cl] | 4-amino-1-(2-chlorophenyl)-7-cyclopropyl-5-methoxyquinazolin-2(1H)-one | m/z [M + H]+ 342.31 |
| 702 | 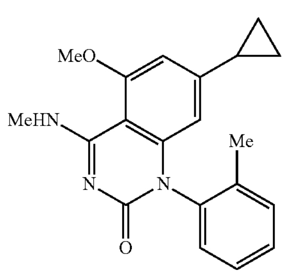 | 7-cyclopropyl-5-methoxy-4-(methylamino)-1-(o-tolyl)quinazolin-2(1H)-one | m/z [M + H]+ 366.44 |

TABLE 1-continued

| Cpd. No. | Structure | Name | Mass Spec. |
|---|---|---|---|
| 703 | 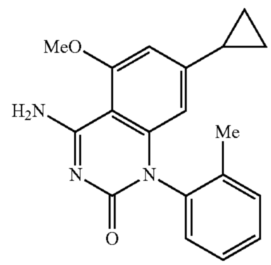 [SMILES: COc1cc(C2CC2)cc2c1c(N)nc(=O)n2-c1ccccc1C] | 4-amino-7-cyclopropyl-5-methoxy-1-(o-tolyl)quinazolin-2(1H)-one | m/z [M + H]+ 322.36 |
| 704 | 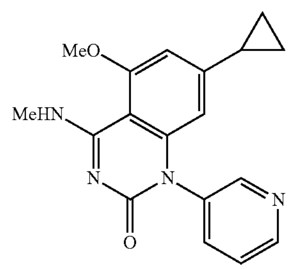 [SMILES: CNc1nc(=O)n(-c2cccnc2)c2cc(C3CC3)cc(OC)c12] | 7-cyclopropyl-5-methoxy-4-(methyl-amino)-1-(pyridin-3-yl)quinazolin-2(1H)-one | m/z [M + H]+ 323.36 |
| 705 | 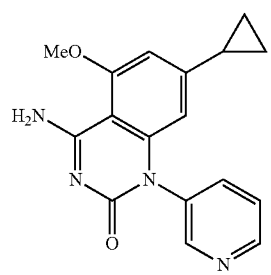 [SMILES: COc1cc(C2CC2)cc2c1c(N)nc(=O)n2-c1cccnc1] | 4-amino-7-cyclopropyl-5-methoxy-1-(pyridin-3-yl) quinazolin-2(1H)-one | m/z [M + H]+ 309.36 |
| 706 | 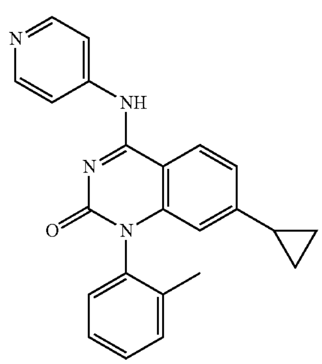 [SMILES: Cc1ccccc1-n1c(=O)nc(Nc2ccncc2)c2ccc(C3CC3)cc21] | 7-cyclopropyl-4-(pyridin-4-ylamino)-1-(o-tolyl)quinazolin-2(1H)-one | m/z [M + H]+ 369.39 |
| 707 | 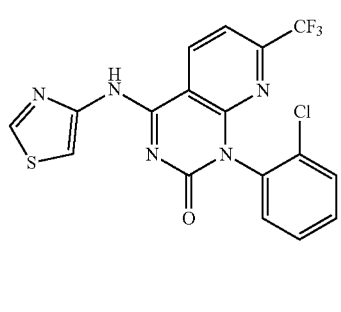 [SMILES: O=c1nc(Nc2cscn2)c2ccc(C(F)(F)F)nc2n1-c1ccccc1Cl] | 1-(2-chlorophenyl)-4-(thiazol-4-ylamino)-7-(trifluoromethyl) pyrido[2,3-d]-pyrimidin-2(1H)-one | m/z [M + H]+ 424.2 |

TABLE 1-continued

| Cpd. No. | Structure | Name | Mass Spec. |
|---|---|---|---|
| 708 | 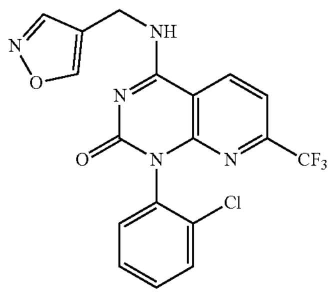 [SMILES: O=c1nc(NCc2cnoc2)c2ccc(C(F)(F)F)nc2n1-c1ccccc1Cl] | 1-(2-chlorophenyl)-4-((isoxazol-4-yl-methyl)amino)-7-(trifluoromethyl) pyrido[2,3-d]pyrimidin-2(1H)-one | m/z [M + H]+ 422.3 |
| 709 | 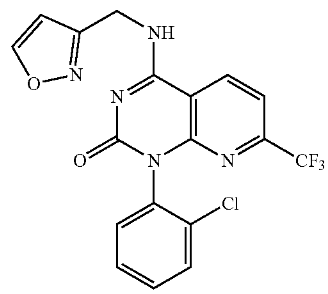 [SMILES: O=c1nc(NCc2ccon2)c2ccc(C(F)(F)F)nc2n1-c1ccccc1Cl] | 1-(2-chlorophenyl)-4-((isoxazol-3-yl-methyl)amino)-7-(trifluoromethyl) pyrido[2,3-d]pyrimidin-2(1H)-one | m/z [M + H]+ 422.3 |
| 710 | 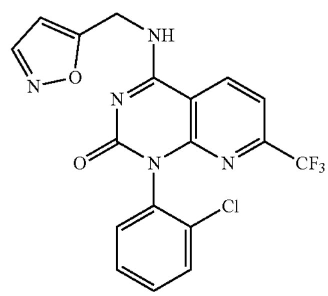 [SMILES: O=c1nc(NCc2ccno2)c2ccc(C(F)(F)F)nc2n1-c1ccccc1Cl] | 1-(2-chlorophenyl)-4-((isoxazol-5-yl-methyl)amino)-7-(trifluoromethyl) pyrido[2,3-d]pyrimidin-2(1H)-one | m/z [M + H]+ 422.2 |
| 711 | 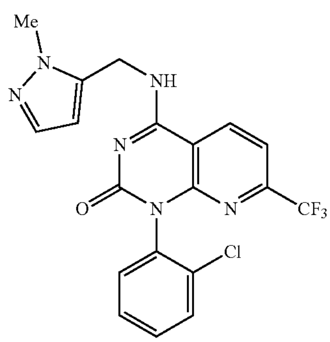 [SMILES: Cn1nccc1CNc1nc(=O)n(-c2ccccc2Cl)c2nc(C(F)(F)F)ccc12] | 1-(2-chlorophenyl)-4-(((1-methyl-1H-pyrazol-5-yl)methyl)amino)-7-(trifluoro-methyl)pyrido[2,3-d]pyrimidin-2(1H)-one | m/z [M + H]+: 435.27 |
| 712 | 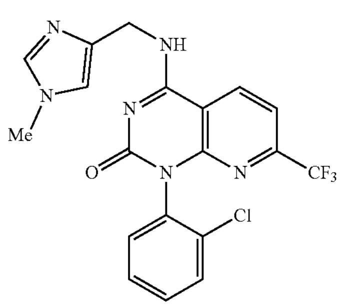 [SMILES: Cn1cnc(CNc2nc(=O)n(-c3ccccc3Cl)c3nc(C(F)(F)F)ccc23)c1] | 2-chlorophenyl)-4-(((1-methyl-1H-imidazol-4-yl)methyl)amino)-7-(trifluoro-methyl)-pyrido[2,3-d]-pyrimidin-2(1H)-one | m/z [M + H]+ 435.27 |

TABLE 1-continued

| Cpd. No. | Structure | Name | Mass Spec. |
|---|---|---|---|
| 713 | 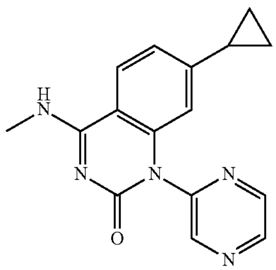 [SMILES: CNc1nc(=O)n(-c2cnccn2)c2cc(C3CC3)ccc12] | cyclopropyl-4-(methylamino)-1-(pyrazin-2-yl)quinazolin-2(1H)-one | m/z [M + H]+ 294.4 |
| 714 | 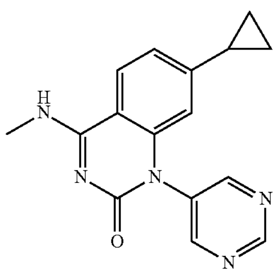 [SMILES: CNc1nc(=O)n(-c2cncnc2)c2cc(C3CC3)ccc12] | 7-cyclopropyl-4-(methylamino)-1-(pyrimidin-5-yl)quinazolin-2(1H)-one | m/z [M + H]+ 294.33 |
| 715 | 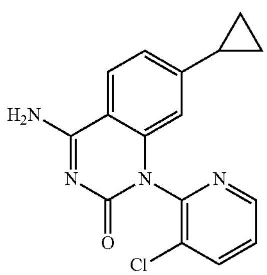 [SMILES: Nc1nc(=O)n(-c2ncccc2Cl)c2cc(C3CC3)ccc12] | 4-amino-1-(3-chloropyridin-2-yl)-7-cyclopropylquinazolin-2(1H)-one | m/z [M + H]+ 313.3 |
| 716 | 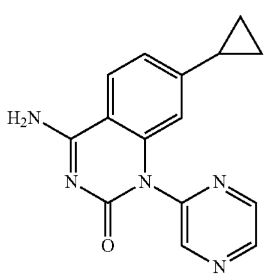 [SMILES: Nc1nc(=O)n(-c2cnccn2)c2cc(C3CC3)ccc12] | 4-amino-7-cyclopropyl-1-(pyrazin-2-yl)-quinazolin-2(1H)-one | m/z [M + H]+ 280.4 |
| 717 | 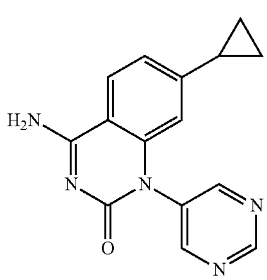 [SMILES: Nc1nc(=O)n(-c2cncnc2)c2cc(C3CC3)ccc12] | 4-amino-7-cyclopropyl-1-(pyrimidin-5-yl)quinazolin-2(1H)-one | m/z [M + H]+ 280.26 |

TABLE 1-continued

| Cpd. No. | Structure | Name | Mass Spec. |
|---|---|---|---|
| 718 | 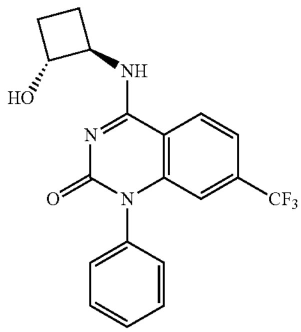 [SMILES: O=c1nc(N[C@@H]2CC[C@H]2O)c2ccc(C(F)(F)F)cc2n1-c1ccccc1] | 4-((trans-2-hydroxycyclobutyl)amino)-1-phenyl-7-(trifluoromethyl)quinazolin-2(1H)-one | m/z [M + H]+ 376.36 |
| 719 | 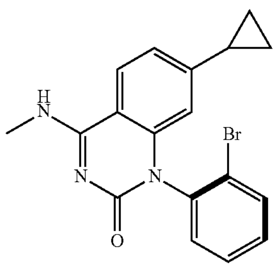 | 1-(2-bromophenyl)-7-cyclopropyl-4-(methylamino)quinazolin-2(1H)-one, a single atropisomer | m/z [M + H] 370.3 |
| 720 | 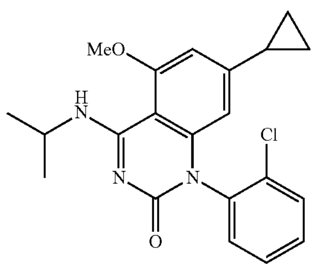 [SMILES: COc1cc(C2CC2)cc2c1c(NC(C)C)nc(=O)n2-c1ccccc1Cl] | 1-(2-chlorophenyl)-7-cyclopropyl-4-(isopropylamino)-5-methoxyquinazolin-2(1H)-one | m/z [M + H]+ 384.4 |
| 721 | 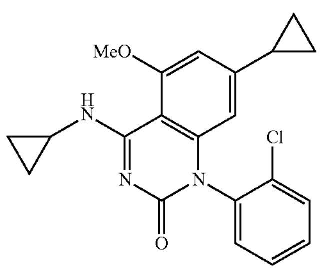 [SMILES: COc1cc(C2CC2)cc2c1c(NC1CC1)nc(=O)n2-c1ccccc1Cl] | 1-(2-chlorophenyl)-7-cyclopropyl-4-(cyclopropylamino)-5-methoxy-quinazolin-2(1H)-one | m/z [M + H]+ 382.35 |
| 722 | 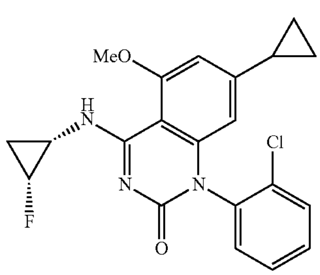 [SMILES: COc1cc(C2CC2)cc2c1c(N[C@H]1C[C@H]1F)nc(=O)n2-c1ccccc1Cl] | 1-(2-chlorophenyl)-7-cyclopropyl-4-(((1S,2R)-2-fluorocyclopropyl)amino)-5-methoxyquinazolin-2(1H)-one | m/z [M + H]+ 400.33 |

TABLE 1-continued

| Cpd. No. | Structure | Name | Mass Spec. |
|---|---|---|---|
| 723 | 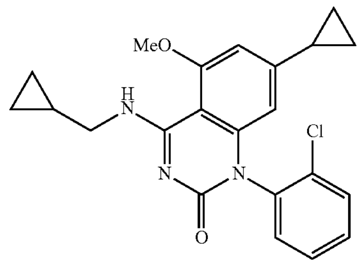 [SMILES: COc1cc(C2CC2)cc2c1c(NCC1CC1)nc(=O)n2-c1ccccc1Cl] | 1-(2-chlorophenyl)-7-cyclopropyl-4-((cyclopropylmethyl)amino)-5-methoxy-quinazolin-2(1H)-one | m/z [M + H]+ 396.4 |
| 724 | 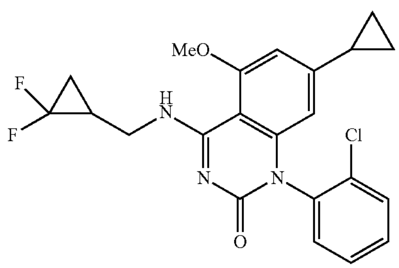 [SMILES: COc1cc(C2CC2)cc2c1c(NCC1CC1(F)F)nc(=O)n2-c1ccccc1Cl] | 1-(2-chlorophenyl)-7-cyclopropyl-4-(((2,2-difluorocyclopropyl)methyl)amino)-5-methoxyquinazolin-2(1H)-one | m/z [M + H]+ 432.4 |
| 725 | 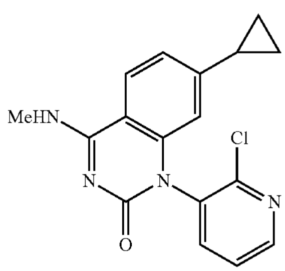 [SMILES: CNc1nc(=O)n(-c2cccnc2Cl)c2cc(C3CC3)ccc12] | 1-(2-chloropyridin-3-yl)-7-cyclopropyl-4-(methylamino)quinazolin-2(1H)-one | m/z [M + H]+ 327.3 |
| 726 | 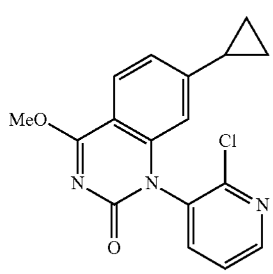 [SMILES: COc1nc(=O)n(-c2cccnc2Cl)c2cc(C3CC3)ccc12] | 1-(2-chloropyridin-3-yl)-7-cyclopropyl-4-methoxyquinazolin-2(1H)-one | m/z [M + H]+ 328.3 |
| 727 | 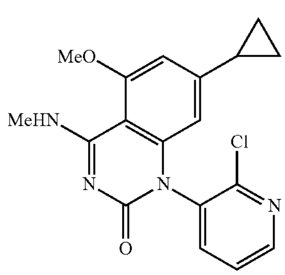 | 1-(2-chloropyridin-3-yl)-7-cyclopropyl-5-methoxy-4-(methylamino)quinazolin-2(1H)-one | m/z [M + H]+ 357.37 |

TABLE 1-continued

| Cpd. No. | Structure | Name | Mass Spec. |
|---|---|---|---|
| 728 | 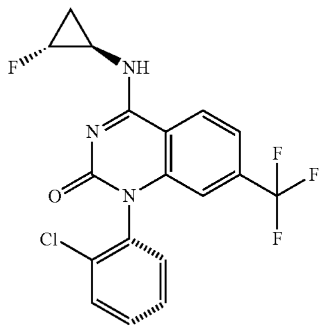 | 1-(2-chlorophenyl)-4-(((1S,2S)-2-fluorocyclopropyl)amino)-7-(trifluoromethyl)-quinazolin-2(1H)-one, single unknown enantiomer/atropisomer | m/z [M + H]+ 398.3 |
| 729 | 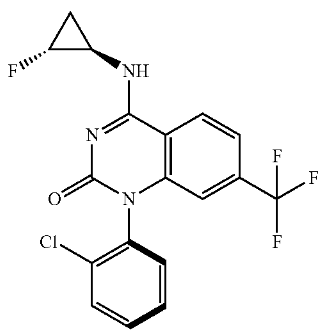 | 1-(2-chlorophenyl)-4-(((1S,2S)-2-fluorocyclopropyl)amino)-7-(trifluoromethyl)-quinazolin-2(1H)-one, single unknown enantiomer/atropisomer | m/z [M + H]+ 398.3 |
| 730 | 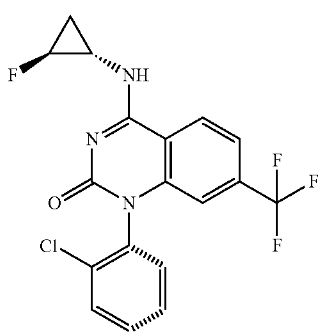 | 1-(2-chlorophenyl)-4-(((1R,2R)-2-fluorocyclopropyl)amino)-7-(trifluoromethyl)-quinazolin-2(1H)-one, single unknown enantiomer/atropisomer | m/z [M + H]+ 398.3 |
| 731 | 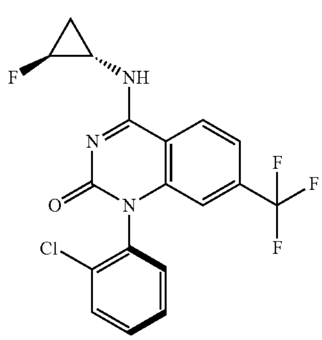 | 1-(2-chlorophenyl)-4-(((1R,2R)-2-fluorocyclopropyl)amino)-7-(trifluoromethyl)-quinazolin-2(1H)-one, single unknown enantiomer/atropisomer | m/z [M + H]+ 398.3 |

TABLE 1-continued

| Cpd. No. | Structure | Name | Mass Spec. |
|---|---|---|---|
| 732 | 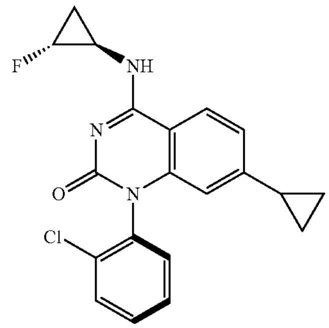 | 1-(2-chlorophenyl)-7-cyclopropyl-4-(((1S,2S)-2-fluorocyclopropyl)amino)-quinazolin-2(1H)-one, single unknown enantiomer/atropisomer | m/z [M + H]+ 370.34 |
| 733 | 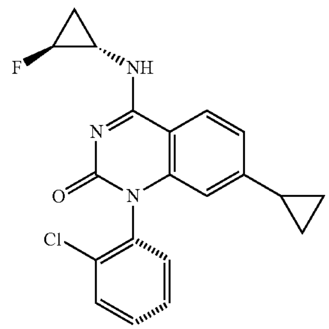 | 1-(2-chlorophenyl)-7-cyclopropyl-4-(((1S,2S)-2-fluorocyclopropyl)amino)-quinazolin-2(1H)-one, single unknown enantiomer/atropisomer | m/z [M + H]+ 370.34 |
| 734 | 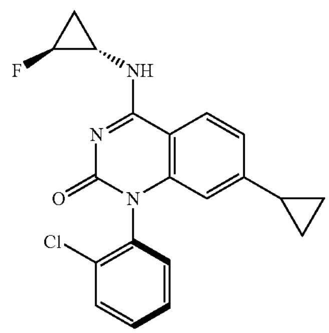 | 1-(2-chlorophenyl)-7-cyclopropyl-4-(((1S,2S)-2-fluorocyclopropyl)amino)-quinazolin-2(1H)-one, single unknown enantiomer/atropisomer | m/z [M + H]+ 370.34 |
| 735 | 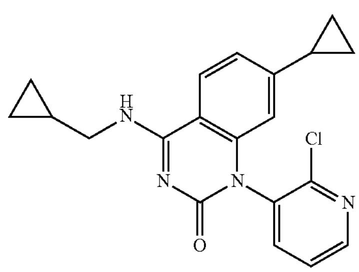 [SMILES: O=c1nc(NCC2CC2)c2ccc(C3CC3)cc2n1-c1cccnc1Cl] | 1-(2-chloropyridin-3-yl)-7-cyclopropyl-4-((cyclopropylmethyl)amino)-quinazolin-2(1H)-one | m/z [M + H]+ 367.4 |
| 736 | 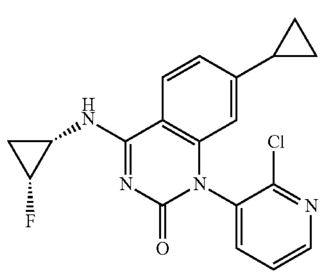 [SMILES: O=c1nc(N[C@H]2C[C@H]2F)c2ccc(C3CC3)cc2n1-c1cccnc1Cl] | 1-(2-chloropyridin-3-yl)-7-cyclopropyl-4-(((1S,2R)-2-fluorocyclopropyl)amino)-quinazolin-2(1H)-one | m/z [M + H]+ 371.3 |

TABLE 1-continued

| Cpd. No. | Structure | Name | Mass Spec. |
|---|---|---|---|
| 737 | 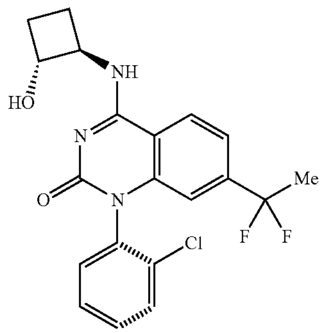 | 1-(2-chlorophenyl)-7-(1,1-difluoroethyl)-4-(((1R,2R)-2-hydroxycyclobutyl)-amino)quinazolin-2(1H)-one, single unknown enantiomer/atropisomer | m/z [M + H]+ 406.37 |
| 738 | 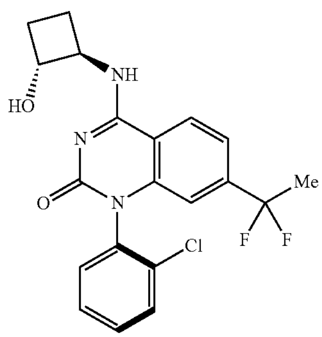 | 1-(2-chlorophenyl)-7-(1,1-difluoroethyl)-4-(((1R,2R)-2-hydroxycyclobutyl)-amino)quinazolin-2(1H)-one, single unknown enantiomer/atropisomer | m/z [M + H]+ 406.37 |
| 739 | 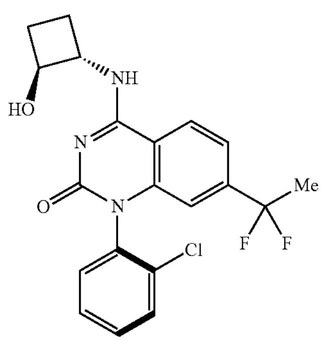 | 1-(2-chlorophenyl)-7-(1,1-difluoroethyl)-4-(((1S,2S)-2-hydroxycyclobutyl)-amino)quinazolin-2(1H)-one, single unknown enantiomer/atropisomer | m/z [M + H]+ 406.37 |
| 740 | 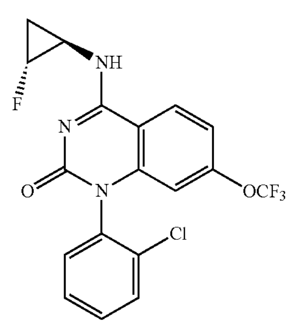 [SMILES: O=c1nc(N[C@@H]2C[C@H]2F)c2ccc(OC(F)(F)F)cc2n1-c1ccccc1Cl] | 1-(2-chlorophenyl)-4-(((1R,2R)-2-fluorocyclopropyl)amino)-7-(trifluoromethoxy)quinazolin-2(1H)-one, single unknown enantiomer | m/z [M + H]+ 414.3 |

TABLE 1-continued

| Cpd. No. | Structure | Name | Mass Spec. |
|---|---|---|---|
| 741 | 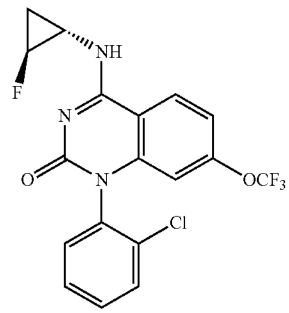 [SMILES: O=c1nc(N[C@H]2C[C@@H]2F)c2ccc(OC(F)(F)F)cc2n1-c1ccccc1Cl] | 1-(2-chlorophenyl)-4-(((1S,2S)-2-fluorocyclopropyl)amino)-7-(trifluoromethoxy)quinazolin-2(1H)-one, single unknown enantiomer | m/z [M + H]⁺ 414.3 |
| 742 | 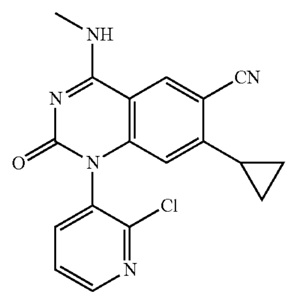 [SMILES: CNc1nc(=O)n(-c2cccnc2Cl)c2cc(C3CC3)c(C#N)cc12] | 1-(2-chloropyridin-3-yl)-7-cyclopropyl-4-(methylamino)-2-oxo-1,2-dihydro-quinazoline-6-carbonitrile | m/z [M + H]⁺ 352.4 |
| 743 | 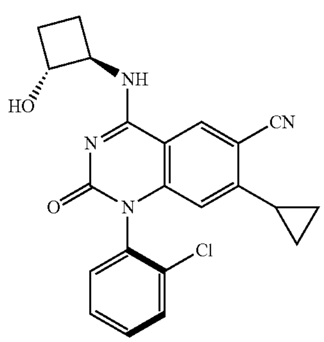 | 1-(2-chlorophenyl)-7-cyclopropyl-4-(((1S,2S)-2-hydroxycyclobutyl)amino)-2-oxo-1,2-dihydroquinazoline-6-carbonitrile, single unknown enantiomer/atropisomer | m/z [M + H]⁺ 407.47 |
| 744 | 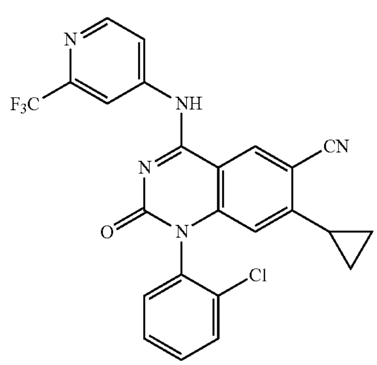 [SMILES: N#Cc1cc2c(Nc3ccnc(C(F)(F)F)c3)nc(=O)n(-c3ccccc3Cl)c2cc1C1CC1] | 1-(2-chlorophenyl)-7-cyclopropyl-2-oxo-4-((2-(trifluoromethyl)pyridin-4-yl)-amino)-1,2-dihydroquinazoline-6-carbonitrile | m/z [M + H]⁺ 482.5 |

TABLE 1-continued

| Cpd. No. | Structure | Name | Mass Spec. |
|---|---|---|---|
| 745 | 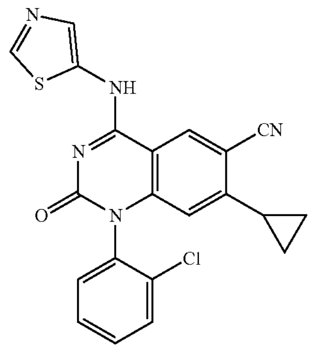 [SMILES: N#Cc1cc2c(Nc3cncs3)nc(=O)n(-c3ccccc3Cl)c2cc1C1CC1] | 1-(2-chlorophenyl)-7-cyclopropyl-2-oxo-4-(thiazol-5-ylamino)-1,2-dihydro-quinazoline-6-carbonitrile | m/z [M + H]+ 420.1 |
| 746 | 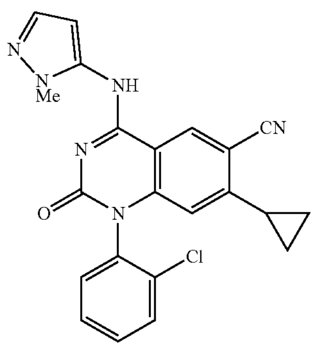 [SMILES: Cn1nccc1Nc1nc(=O)n(-c2ccccc2Cl)c2cc(C3CC3)c(C#N)cc12] | 1-(2-chlorophenyl)-7-cyclopropyl-4-((1-methyl-1H-pyrazol-5-yl)amino)-2-oxo-1,2-dihydroquinazoline-6-carbonitrile | m/z [M + H]+ 417.36 |
| 747 | 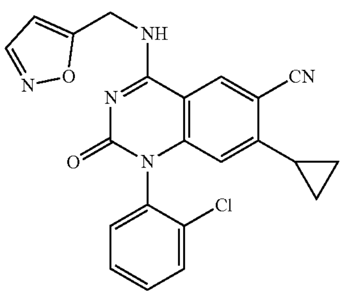 [SMILES: N#Cc1cc2c(NCc3ccno3)nc(=O)n(-c3ccccc3Cl)c2cc1C1CC1] | 1-(2-chlorophenyl)-7-cyclopropyl-4-((isoxazol-5-ylmethyl)amino)-2-oxo-1,2-dihydroquinazoline-6-carbonitrile | m/z [M + H]+ 418.35 |
| 748 | 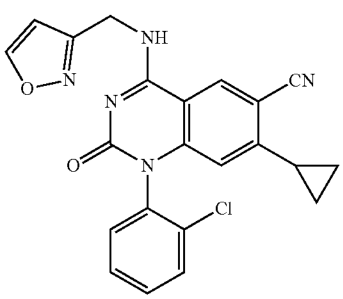 [SMILES: N#Cc1cc2c(NCc3ccon3)nc(=O)n(-c3ccccc3Cl)c2cc1C1CC1] | 1-(2-chlorophenyl)-7-cyclopropyl-4-((isoxazol-3-ylmethyl)amino)-2-oxo-1,2-dihydroquinazoline-6-carbonitrile | m/z [M + H]+ 418.3 |
| 749 | 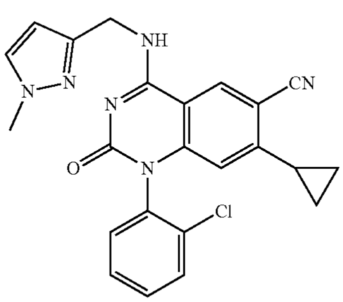 [SMILES: Cn1ccc(CNc2nc(=O)n(-c3ccccc3Cl)c3cc(C4CC4)c(C#N)cc23)n1] | 1-(2-chlorophenyl)-7-cyclopropyl-4-(((1-methyl-1H-pyrazol-3-yl)methyl)amino)-2-oxo-1,2-dihydroquinazoline-6-carbonitrile | m/z [M + H]+ 431.38 |

TABLE 1-continued

| Cpd. No. | Structure | Name | Mass Spec. |
|---|---|---|---|
| 750 | 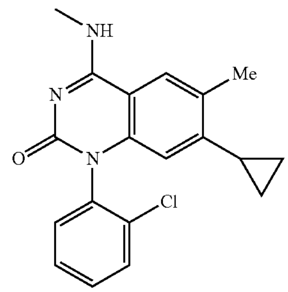 [SMILES: CNc1nc(=O)n(-c2ccccc2Cl)c2cc(C3CC3)c(C)cc12] | 1-(2-chlorophenyl)-7-cyclopropyl-6-methyl-4-(methylamino) quinazolin-2(1H)-one | m/z [M + H]+ 340.34 |
| 751 | 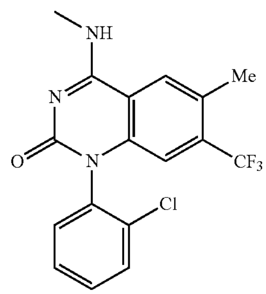 [SMILES: CNc1nc(=O)n(-c2ccccc2Cl)c2cc(C(F)(F)F)c(C)cc12] | 1-(2-chlorophenyl)-6-methyl-4-(methylamino)-7-(trifluoromethyl)-quinazolin-2(1H)-one | m/z [M + H]+ 368.4 |
| 752 | 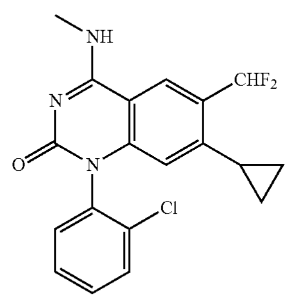 [SMILES: CNc1nc(=O)n(-c2ccccc2Cl)c2cc(C3CC3)c(C(F)F)cc12] | 1-(2-chlorophenyl)-7-cyclopropyl-6-(difluoromethyl)-4-(methylamino)-quinazolin-2(1H)-one | m/z [M + H]+ 376.4 |
| 753 | 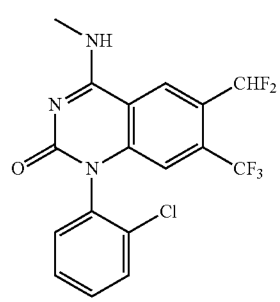 [SMILES: CNc1nc(=O)n(-c2ccccc2Cl)c2cc(C(F)(F)F)c(C(F)F)cc12] | 1-(2-chlorophenyl)-6-(difluoromethyl)-4-(methylamino)-7-(trifluoromethyl)-quinazolin-2(1H)-one | m/z [M + H]+ 404.4 |
| 754 | 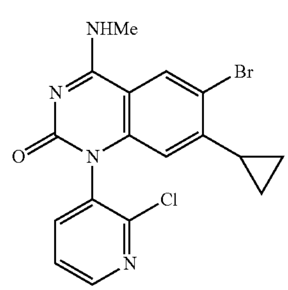 [SMILES: CNc1nc(=O)n(-c2cccnc2Cl)c2cc(C3CC3)c(Br)cc12] | 6-bromo-1-(2-chloropyridin-3-yl)-7-cyclopropyl-4-(methylamino)quinazolin-2(1H)-one | m/z [M + H]+ 405.2 |

TABLE 1-continued

| Cpd. No. | Structure | Name | Mass Spec. |
|---|---|---|---|
| 755 | 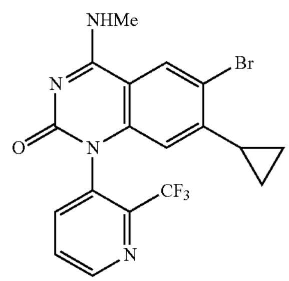 [SMILES: CNc1nc(=O)n(-c2cccnc2C(F)(F)F)c2cc(C3CC3)c(Br)cc12] | 6-bromo-7-cyclopropyl-4-(methyl-amino)-1-(2-(trifluoromethyl)pyridin-3-yl)-quinazolin-2(1H)-one | m/z [M + H]+ 439.4 |
| 756 | 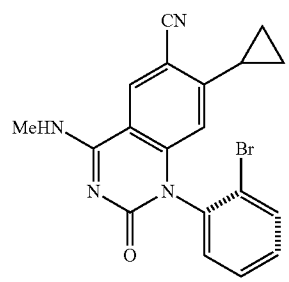 | 1-(2-bromophenyl)-7-cyclopropyl-4-(methylamino)-2-oxo-1,2-dihydro-quinazoline-6-carbonitrile, single unknown atropisomer | m/z [M + H]+ 395.41 |
| 757 | 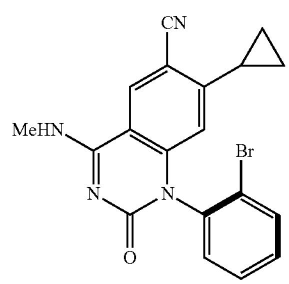 | 1-(2-bromophenyl)-7-cyclopropyl-4-(methylamino)-2-oxo-1,2-dihydro-quinazoline-6-carbonitrile, single unknown atropisomer | m/z [M + H]+ 395.41 |
| 758 | 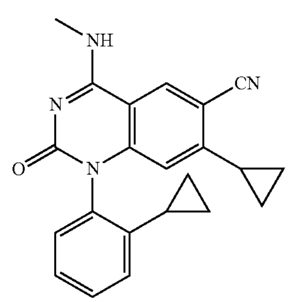 [SMILES: CNc1nc(=O)n(-c2ccccc2C2CC2)c2cc(C3CC3)c(C#N)cc12] | 7-cyclopropyl-1-(2-cyclopropylphenyl)-4-(methylamino)-2-oxo-1,2-dihydro-quinazoline-6-carbonitrile | m/z [M + H]+ 357.40 |
| 759 | 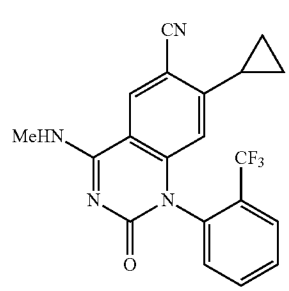 [SMILES: CNc1nc(=O)n(-c2ccccc2C(F)(F)F)c2cc(C3CC3)c(C#N)cc12] | 7-cyclopropyl-4-(methylamino)-2-oxo-1-(2-(trifluoromethyl)phenyl)-1,2-dihydro-quinazoline-6-carbonitrile | m/z [M + H]+ 385.44 |

TABLE 1-continued

| Cpd. No. | Structure | Name | Mass Spec. |
|---|---|---|---|
| 760 | 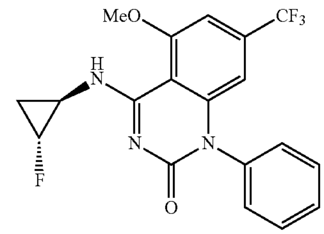 [SMILES: COc1cc(C(F)(F)F)cc2c1c(N[C@@H]1C[C@H]1F)nc(=O)n2-c1ccccc1] | 4-(((1R,2R)-2-fluorocyclopropyl)-amino)-5-methoxy-1-phenyl-7-(trifluoromethyl)quinazolin-2(1H)-one, single unknown enantiomer | m/z [M + H]$^+$ 394.4 |
| 761 | 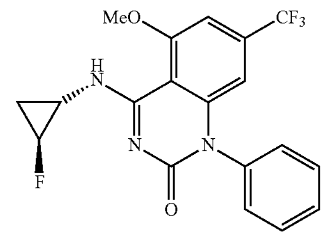 | 4-(((1S,2S)-2-fluorocyclopropyl)amino)-5-methoxy-1-phenyl-7-(trifluoromethyl)quinazolin-2(1H)-one, single unknown enantiomer | m/z [M + H]$^+$ 394.4 |
| 762 | 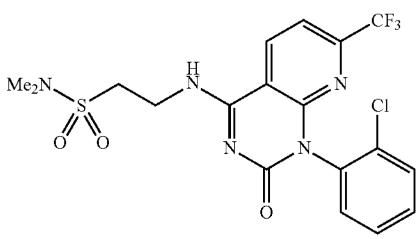 [SMILES: CN(C)S(=O)(=O)CCNc1nc(=O)n(-c2ccccc2Cl)c2nc(C(F)(F)F)ccc12] | 2-((1-(2-chlorophenyl)-2-oxo-7-(trifluoromethyl)-1,2-dihydropyrido[2,3-d]-pyrimidin-4-yl)amino)-N,N-dimethylethanesulfonamide | m/z [M + H]$^+$ 454.19 |
| 763 | 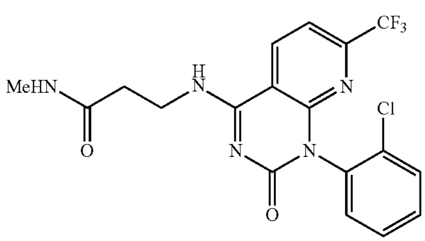 [SMILES: CNC(=O)CCNc1nc(=O)n(-c2ccccc2Cl)c2nc(C(F)(F)F)ccc12] | 3-((1-(2-chlorophenyl)-2-oxo-7-(trifluoromethyl)-1,2-dihydropyrido[2,3-d]-pyrimidin-4-yl)amino)-N-methylpropanamide | m/z [M + H]$^+$ 426.4. |
| 764 | 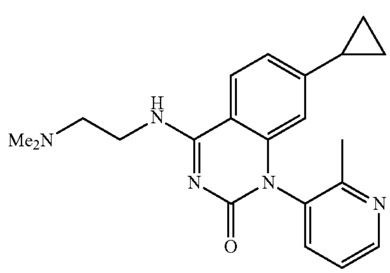 [SMILES: Cc1ncccc1-n1c(=O)nc(NCCN(C)C)c2ccc(C3CC3)cc21] | 7-cyclopropyl-4-((2-(dimethylamino)-ethyl)amino)-1-(2-methylpyridin-3-yl)-quinazolin-2(1H)-one | m/z [M − H]$^+$ 362.52 |
| 765 | 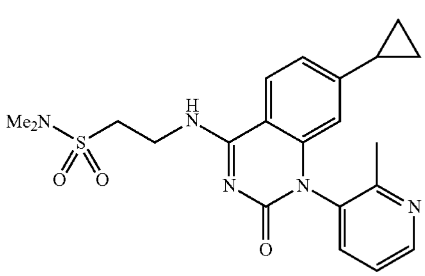 [SMILES: Cc1ncccc1-n1c(=O)nc(NCCS(=O)(=O)N(C)C)c2ccc(C3CC3)cc21] | 2-((7-cyclopropyl-1-(2-methylpyridin-3-yl)-2-oxo-1,2-dihydroquinazolin-4-yl)-amino)-N,N-dimethylethane-1-sulfonamide | m/z [M + H]$^+$ 428.49 |

TABLE 1-continued

| Cpd. No. | Structure | Name | Mass Spec. |
|---|---|---|---|
| 766 | 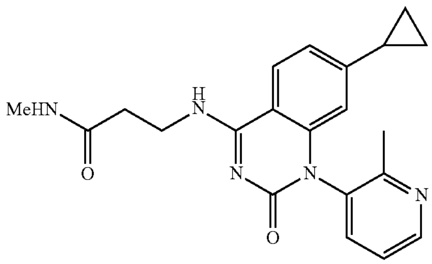 [SMILES: CNC(=O)CCNc1nc(=O)n(-c2cccnc2C)c2cc(C3CC3)ccc12] | 3-((7-cyclopropyl-1-(2-methylpyridin-3-yl)-2-oxo-1,2-dihydroquinazolin-4-yl)-amino)-N-methylpropanamide | m/z [M + H]$^+$ 378.47 |
| 767 | 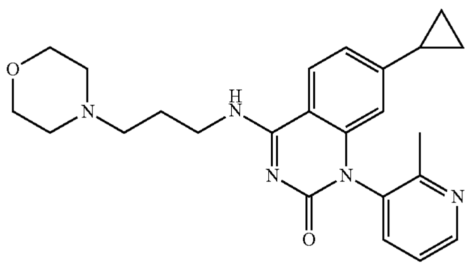 [SMILES: Cc1ncccc1-n1c(=O)nc(NCCCN2CCOCC2)c2ccc(C3CC3)cc21] | 7-cyclopropyl-1-(2-methylpyridin-3-yl)-4-((3-morpholinopropyl)amino)-quinazolin-2(1H)-one | m/z [M + H]$^+$ 420.31 |
| 768 | 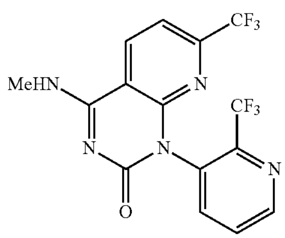 [SMILES: CNc1nc(=O)n(-c2cccnc2C(F)(F)F)c2nc(C(F)(F)F)ccc12] | 4-(methylamino)-7-(trifluoromethyl)-1-(2-(trifluoromethyl)pyridin-3-yl)pyrido[2,3-d]-pyrimidin-2(1H)-one | m/z [M + H]$^+$ 390.4 |
| 769 | 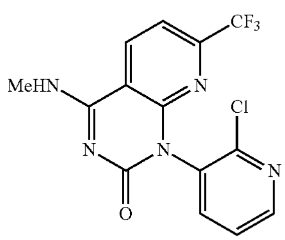 [SMILES: CNc1nc(=O)n(-c2cccnc2Cl)c2nc(C(F)(F)F)ccc12] | 1-(2-chloropyridin-3-yl)-4-(methylamino)-7-(trifluoromethyl)-pyrido[2,3-d]-pyrimidin-2(1H)-one | m/z [M + H]$^+$ 356.3 |
| 770 | 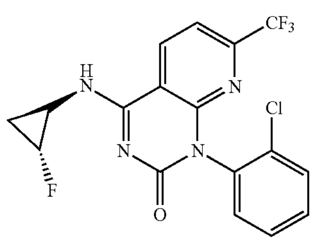 | 1-(2-chlorophenyl)-4-((((1S,2R)-2-fluorocyclopropyl)amino)-7-(trifluoromethyl)pyrido[2,3-d]pyrimidin-2(1H)-one, single unknown enantiomer | m/z [M + H]$^+$ 399.4. |
| 771 | 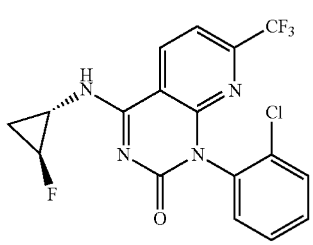 [SMILES: O=c1nc(N[C@H]2C[C@@H]2F)c2ccc(C(F)(F)F)nc2n1-c1ccccc1Cl] | 1-(2-chlorophenyl)-4-((((1R,2S)-2-fluorocyclopropyl)amino)-7-(trifluoromethyl)pyrido[2,3-d]pyrimidin-2(1H)-one, single unknown enantiomer | m/z [M + H]$^+$ 399.4 |

TABLE 1-continued

| Cpd. No. | Structure | Name | Mass Spec. |
|---|---|---|---|
| 772 | 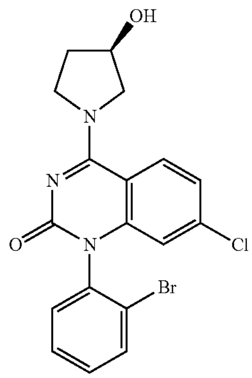 [SMILES: O=c1nc(N2CC[C@@H](O)C2)c2ccc(Cl)cc2n1-c1ccccc1Br] | (R)-1-(2-bromophenyl)-7-chloro-4-(3-hydroxypyrrolidin-1-yl)quinazolin-2(1H)-one | m/z [M + H]+ 420.0, 422.0 |
| 773 | 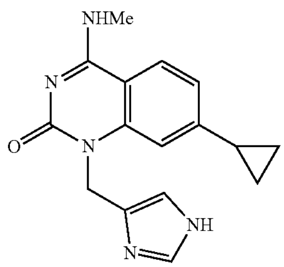 [SMILES: CNc1nc(=O)n(Cc2c[nH]cn2)c2cc(C3CC3)ccc12] | 1-((1H-imidazol-4-yl)methyl)-7-cyclopropyl-4-(methylamino)quinazolin-2(1H)-one | m/z [M + H]+ 294.4 |
| 774 | 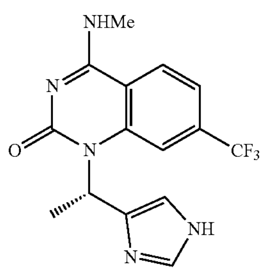 [SMILES: CNc1nc(=O)n([C@@H](C)c2c[nH]cn2)c2cc(C(F)(F)F)ccc12] | (S)-1-(1-(1H-imidazol-4-yl)ethyl)-4-(methylamino)-7-(trifluoromethyl)-quinazolin-2(1H)-one, Single unknown enantiomer | m/z [M + H] 338.3. |
| 775 | 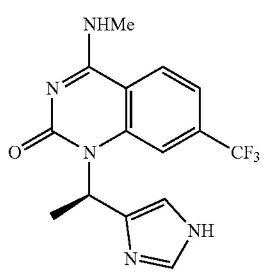 [SMILES: CNc1nc(=O)n([C@H](C)c2c[nH]cn2)c2cc(C(F)(F)F)ccc12] | (R)-1-(1-(1H-imidazol-4-yl)ethyl)-4-(methylamino)-7-(trifluoromethyl)quinazolin-2(1H)-one, single unknown enantiomer | m/z [M + H] 338.3 |
| 776 | 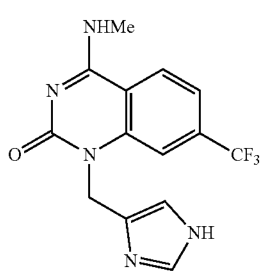 [SMILES: CNc1nc(=O)n(Cc2c[nH]cn2)c2cc(C(F)(F)F)ccc12] | 1-(2-chlorophenyl)-7-cyclopropyl-4-(methylamino)-6-(methylthio)-quinazolin-2(1H)-one | m/z [M + H]+ 324.35 |

In another embodiment, the methionine adenosyltransferase II alpha (MAT2A) inhibitor is Compound A:

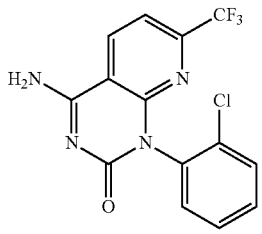 [SMILES: Nc1nc(=O)n(-c2ccccc2Cl)c2nc(C(F)(F)F)ccc12]

or a pharmaceutically acceptable salt thereof. Compound A is also referred to as compound 167 in Table 1.

The methionine adenosyltransferase II alpha (MAT2A) inhibitors described herein, their syntheses, and biological activity against MAT2A can be found in PCT/US2019/065260 (WO2020123395), which is incorporated by reference in its entirety.

In an embodiment, the Type II PRMT inhibitor is a protein arginine methyltransferase 5 (PRMT5) inhibitor, a protein arginine methyltransferase 7 (PRMT7) inhibitor, or a protein arginine methyltransferase 9 (PRMT9) inhibitor. In another embodiment, the Type II PRMT inhibitor is a protein arginine methyltransferase 5 (PRMT5) inhibitor (Type II PRMT5 inhibitor). In yet another embodiment, the Type II PRMT inhibitor is a protein arginine methyltransferase 7 (PRMT7) inhibitor (Type II PRMT7 inhibitor). In still another embodiment, the Type II PRMT inhibitor is a protein arginine methyltransferase 9 (PRMT9) inhibitor (Type II PRMT9 inhibitor).

In another embodiment, the Type II PRMT inhibitor is a protein arginine methyltransferase 5 (PRMT5) inhibitor (Type II PRMT5 inhibitor).

In another embodiment, the PRMT5 inhibitor binds in an MTA-uncompetitive or MTA-cooperative manner. In yet another embodiment, the PRMT5 inhibitor has increased binding to PRMT5 in the presence of MTA over the binding of the same inhibitor in the absence of MTA.

In an embodiment, the Type II PRMT5 inhibitor is a compound of Formula II:

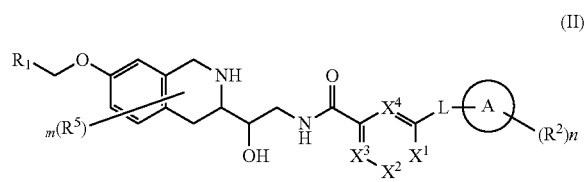

or a pharmaceutically acceptable salt thereof;
wherein
$X^1$, $X^2$, $X^3$, and $X^4$ are each independently N or $CR^X$;
L is a bond, —C(=O)—, —NH— or —O—;
Ring A is a carbocycle, heterocycle or a 5-6 membered monocyclic heteroaryl;

$R^1$ is a 5-6 membered heteroaryl substituted with 0-3 instances of $R^4$;

each $R^2$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, heteroarylalkyl, arylalkyl, cycloalkylalkyl, —$OR^3$, —$N(R^3)_2$, —C(=O)$R^3$, —C(=O)$OR^3$, —$NR^3$C(=O)$R^3$, —$NR^3$C(=O)$OR^3$, —C(=O)$N(R^3)_2$, —OC(=O)$N(R^3)_2$, —S(=O)$R^3$, —S(=O)$_2R^3$, —$SR^3$, —S(=O)(=$NR^3$)$R^3$, —$NR^3$S(=O)$_2R^3$ and —S(=O)$_2N(R^3)_2$;

each $R^3$ is independently selected from H, $C_1$-$C_6$ alkyl, —$C_1$-$C_6$ heteroalkyl, $C_3$-$C_9$ carbocyclyl, 3-7 membered heterocyclyl, cycloalkylalkyl, heterocyclylalkyl, aryl, 5-6 membered heteroaryl, arylalkyl and heteroarylalkyl wherein each alkyl, carbocyclyl, heterocyclyl, cycloalkylalkyl, heterocyclylalkyl, aryl, heteroaryl, arylalkyl and heteroarylalkyl is optionally substituted;

each $R^4$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, cycloalkylalkyl, —$OR^3$, —$N(R^3)_2$, —C(=O)$R^3$, —C(=O)$OR^3$, —$NR^3$C(=O)$R^3$, —$NR^3$C(=O)$OR^3$, —C(=O)$N(R^3)_2$, —OC(=O)$N(R^3)_2$, —S(=O)$R^3$, —S(=O)$_2R^3$, —$SR^3$, —S(=O)(=$NR^3$)$R^3$, —$NR^3$S(=O)$_2R^3$ and —S(=O)$_2N(R^3)_2$;

each $R^x$ is independently selected from hydrogen, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, cycloalkylalkyl, —$OR^3$, —$N(R^3)_2$, —C(=O)$R^3$, —C(=O)$OR^3$, —$NR^3$C(=O)$R^3$, —$NR^3$C(=O)$OR^3$, —C(=O)$N(R^3)_2$, —OC(=O)$N(R^3)_2$, —S(=O)$R^3$, —S(=O)$_2R^3$, —$SR^3$, —S(=O)(=$NR^3$)$R^3$, —$NR^3$S(=O)$_2R^3$ and —S(=O)$_2N(R^3)_2$ wherein each alkyl, carbocyclyl, heterocyclyl, heterocyclylalkyl, cycloalkylalkyl is optionally substituted;

each $R^5$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, $C_6$-$C_{10}$ aryl, 5-10 membered heteroaryl, cycloalkylalkyl, heterocyclylalkyl, arylalkyl, heteroarylalkyl, —$OR^3$, —$N(R^3)_2$, —C(=O)$R^3$, —C(=O)$OR^3$, —$NR^3$C(=O)$R^3$, —$NR^3$C(=O)$OR^3$, —C(=O)$N(R^3)_2$, —OC(=O)$N(R^3)_2$, —S(=O)$R^3$, —S(=O)$_2R^3$, —$SR^3$, —S(=O)(=$NR^3$)$R^3$, —$NR^3$S(=O)$_2R^3$, —S(=O)$_2N(R^3)_2$, or two $R^5$ can be taken together with the atoms to which they are attached to form a —$C_3$-$C_9$ carbocyclyl or a 3-10 membered heterocyclyl;

m is 0, 1, 2 or 3; and n is 0, 1, 2 or 3.

In another embodiment, the Type II PRMT5 inhibitor is selected from the group consisting of a compound from Table 2 (see Table 1 of WO 2021/086879, which is incorporated by reference in its entirety).

TABLE 2
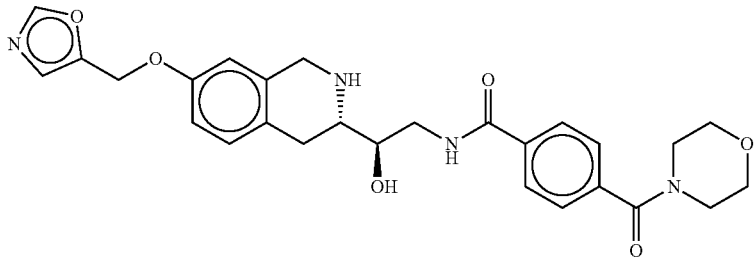
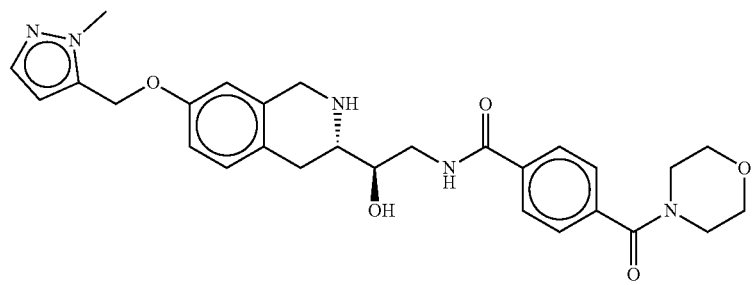
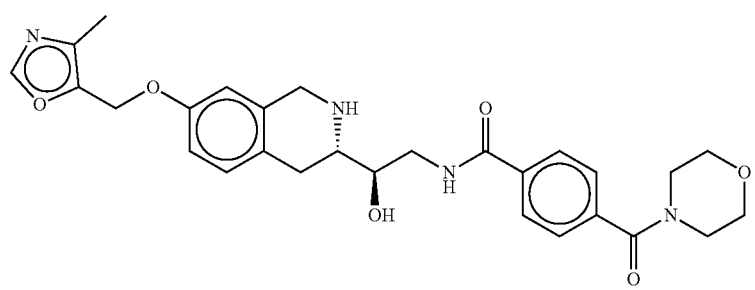
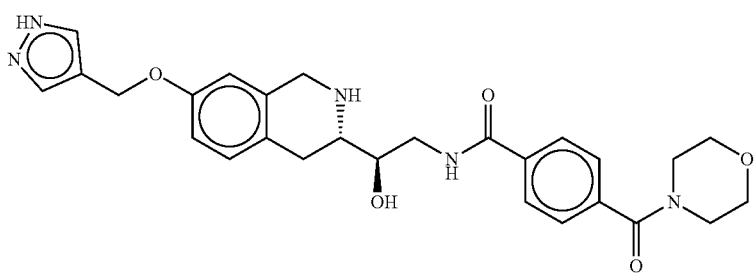
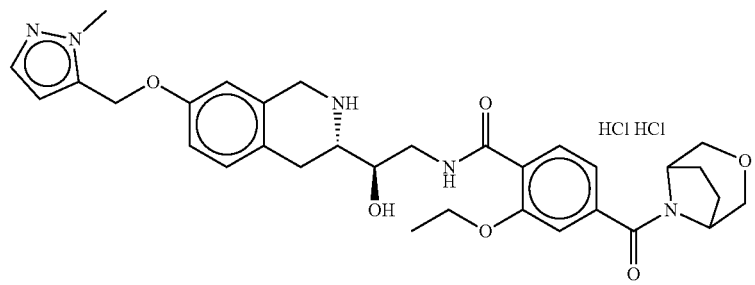

TABLE 2-continued
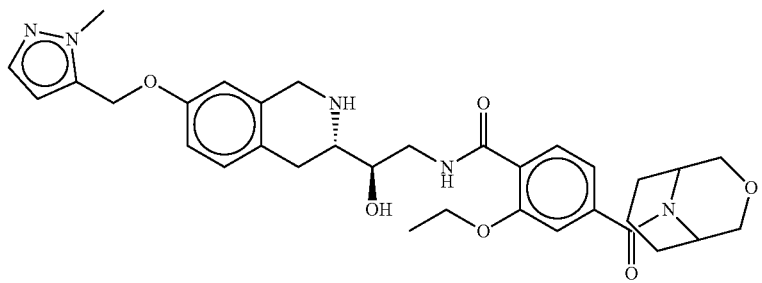
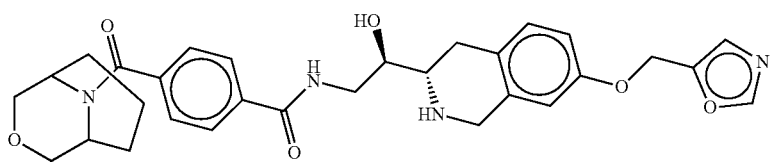
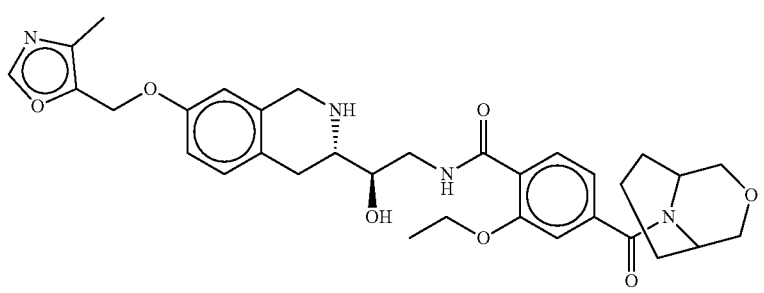
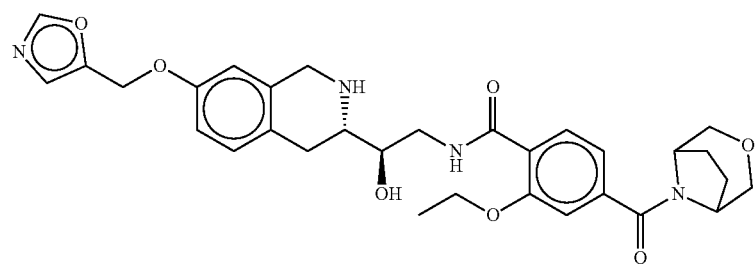

TABLE 2-continued
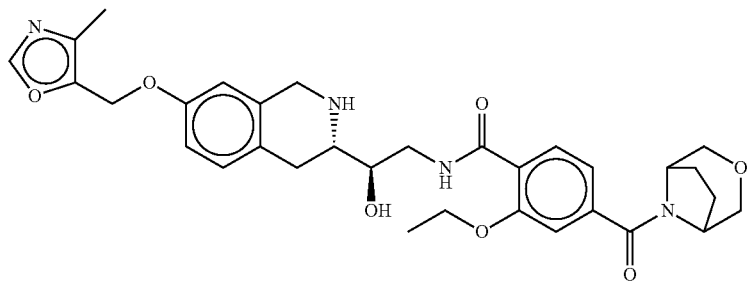
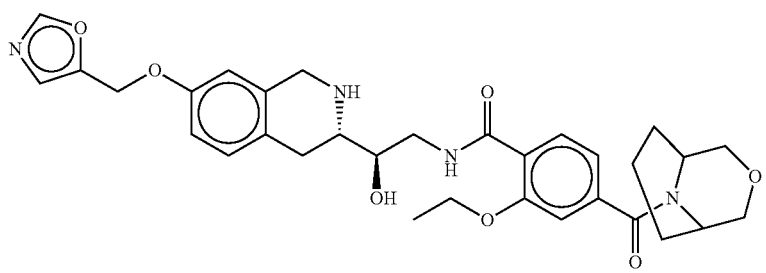
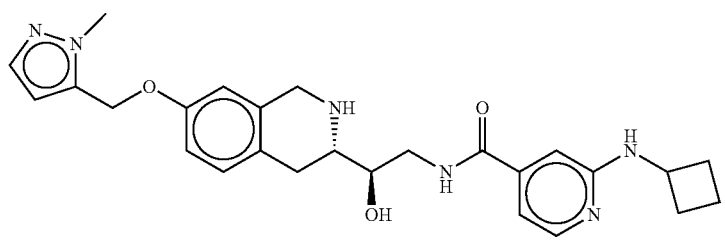
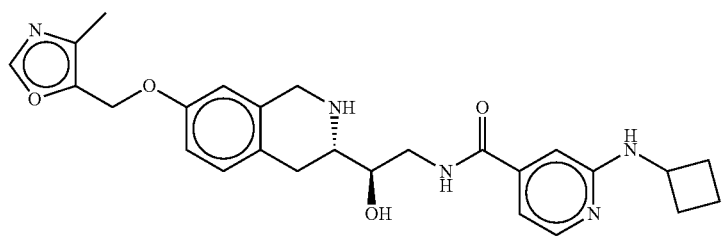
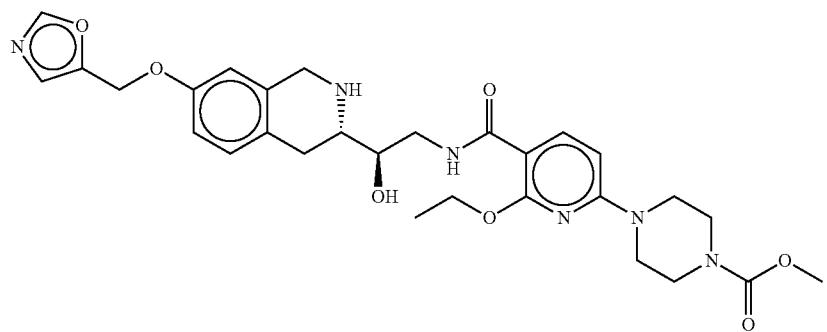

TABLE 2-continued
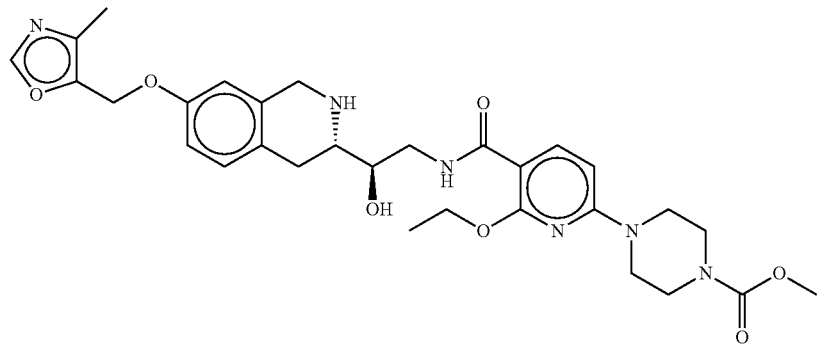
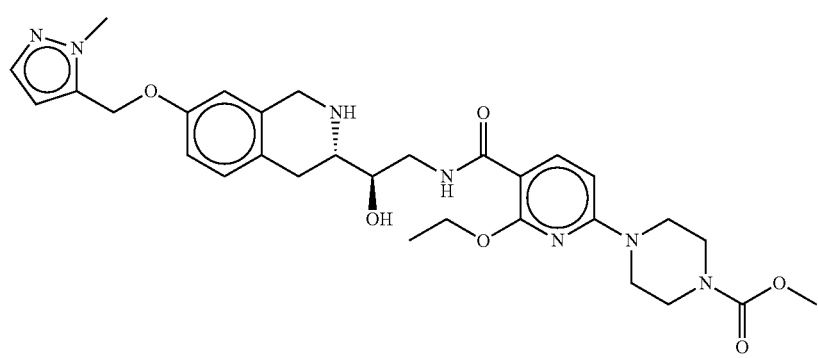
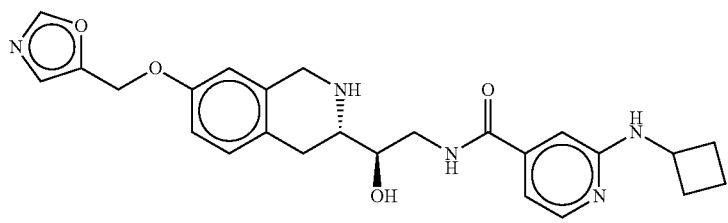
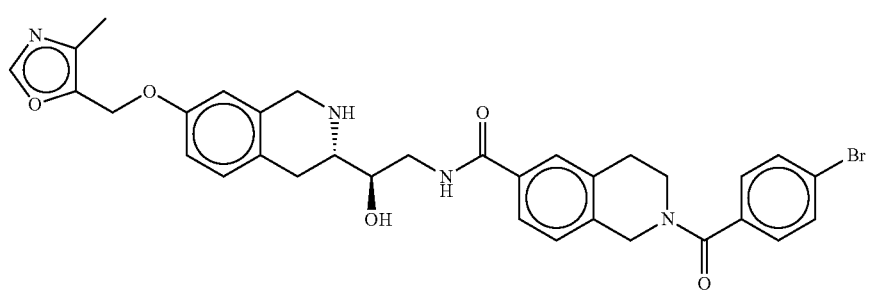
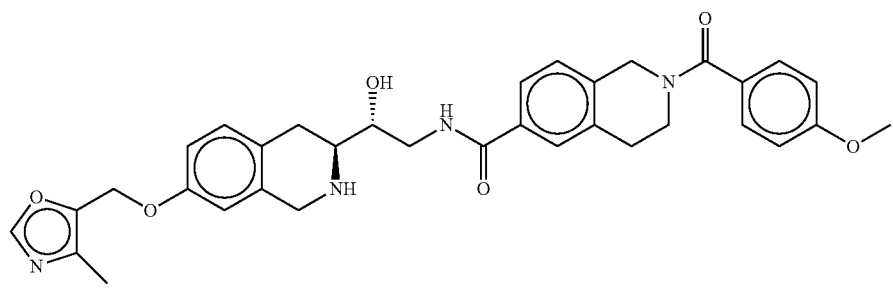

TABLE 2-continued
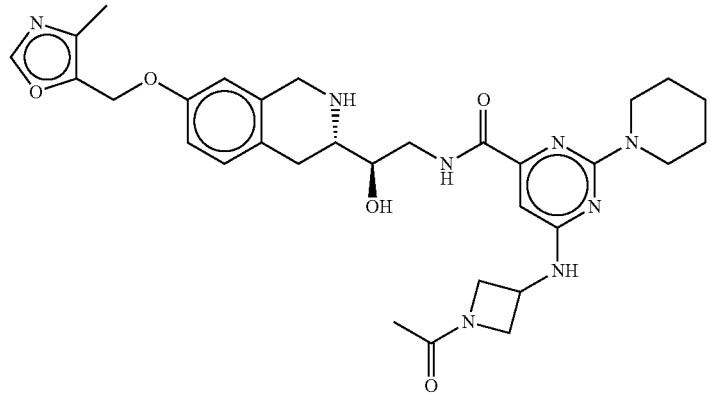
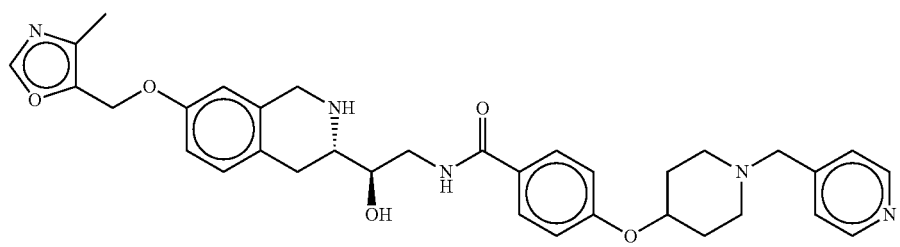
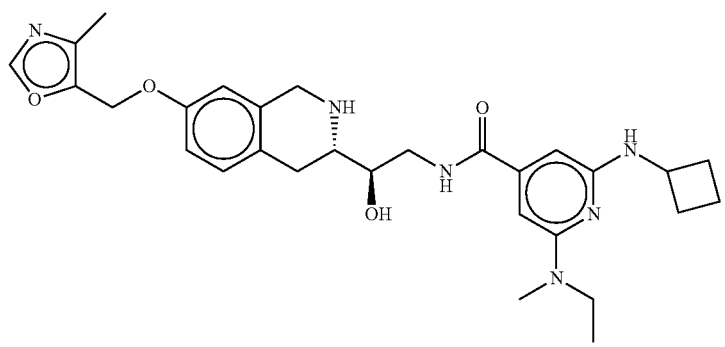
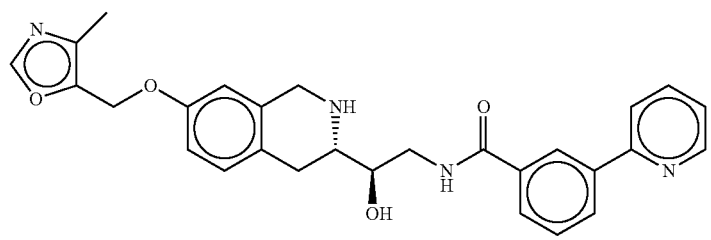
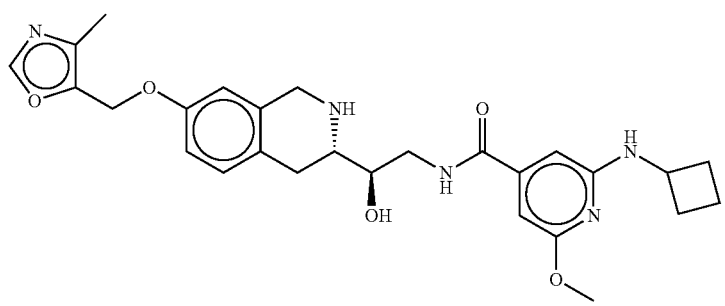

TABLE 2-continued
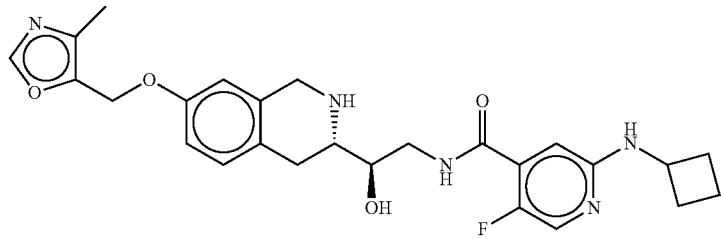
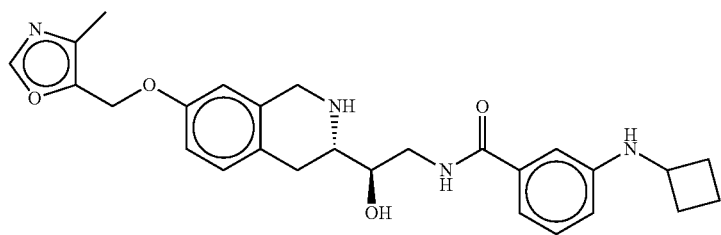
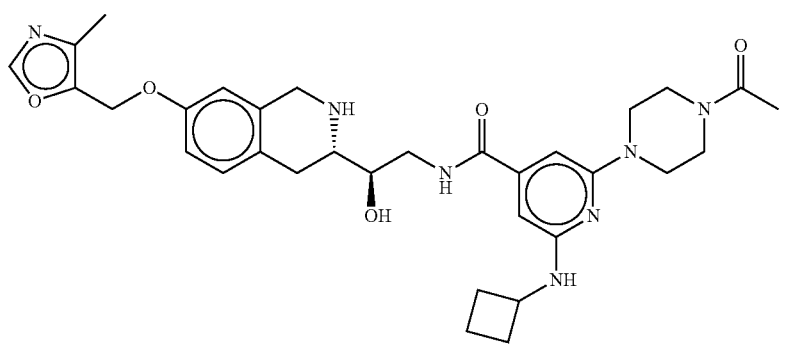
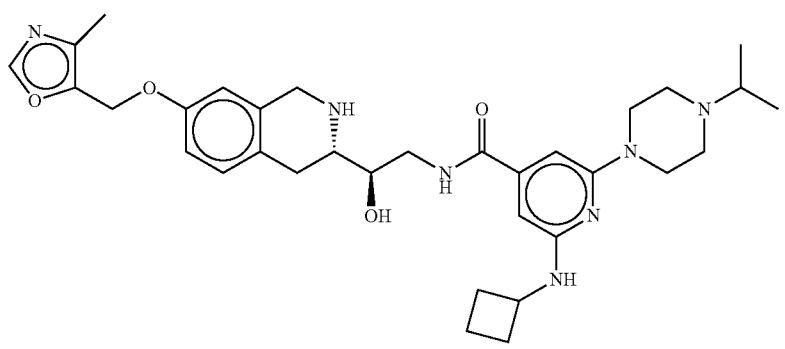
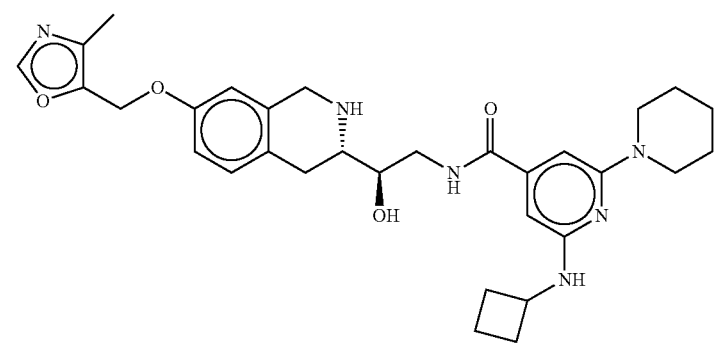

TABLE 2-continued
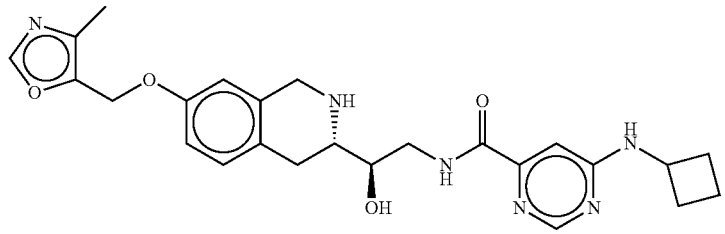
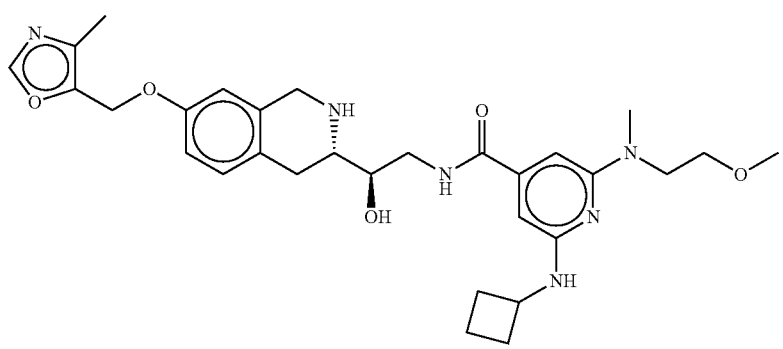
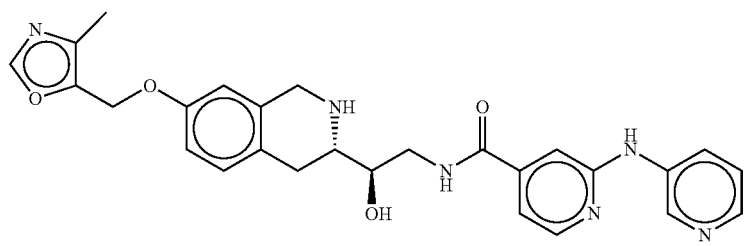
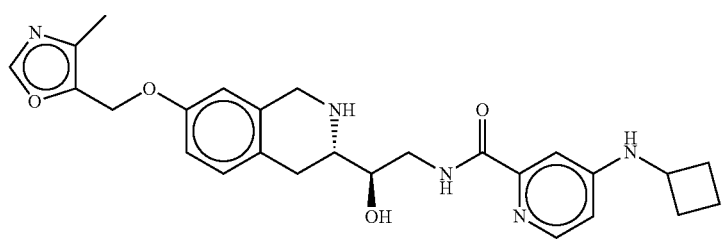
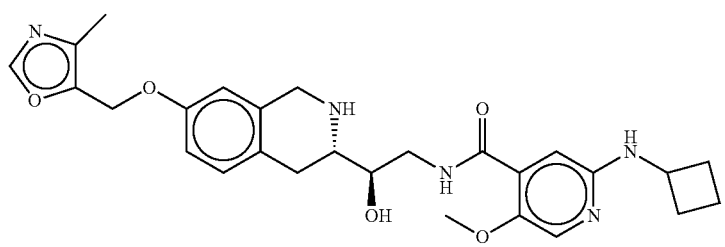

TABLE 2-continued
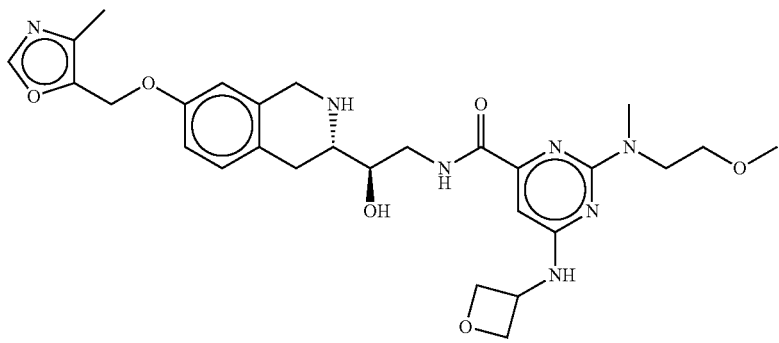
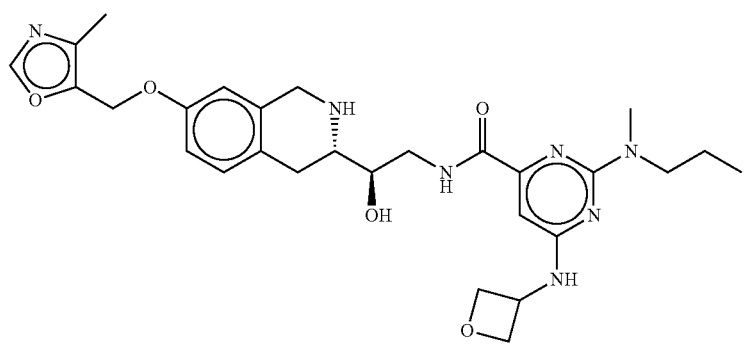
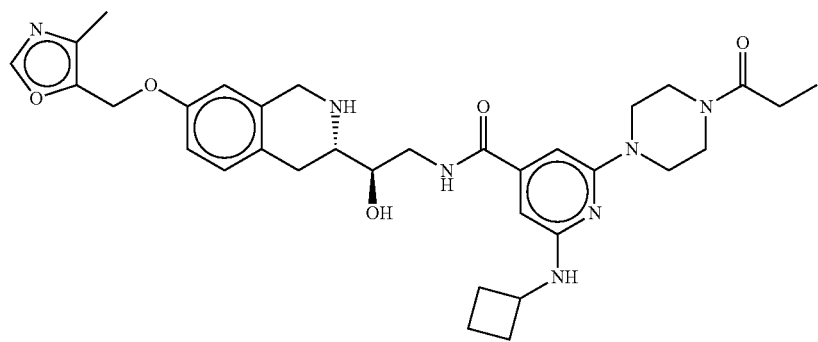
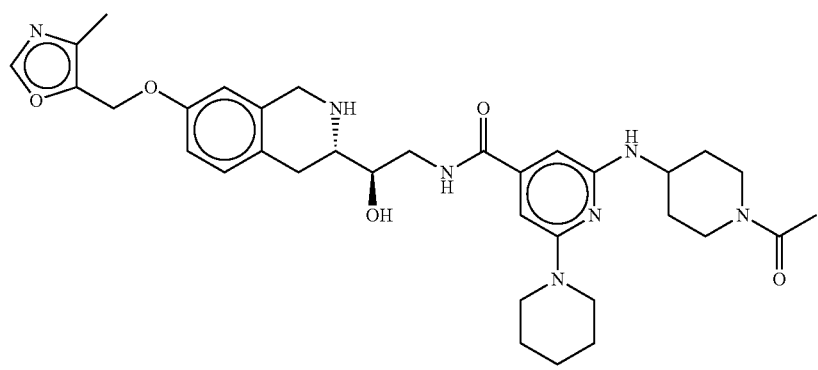

TABLE 2-continued
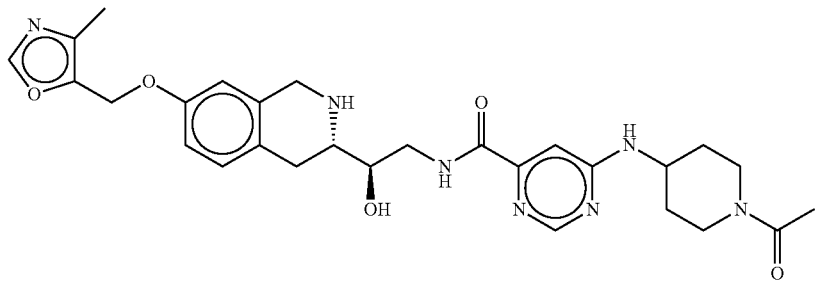
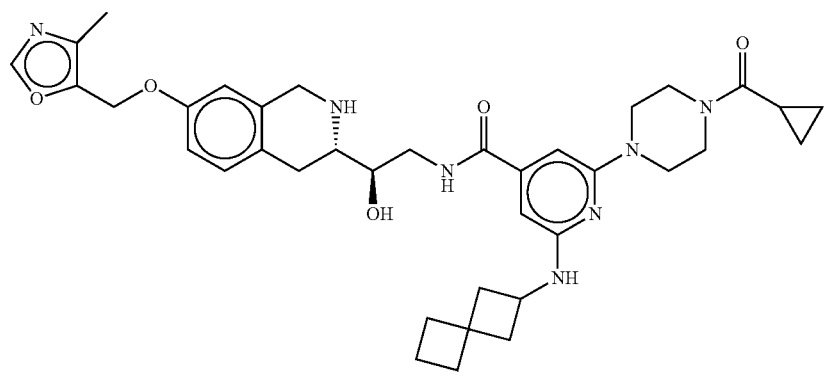
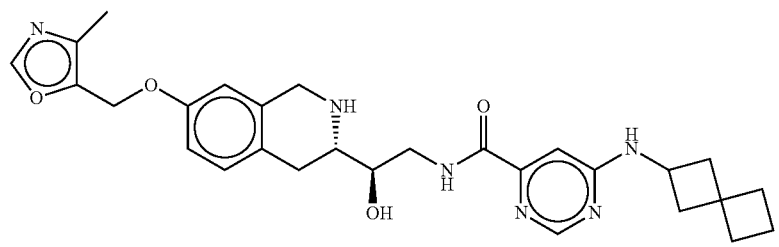
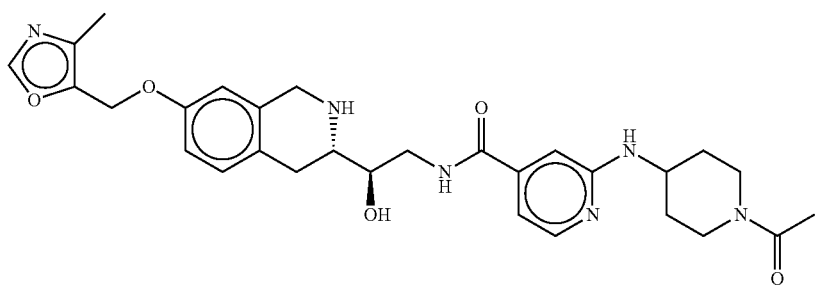
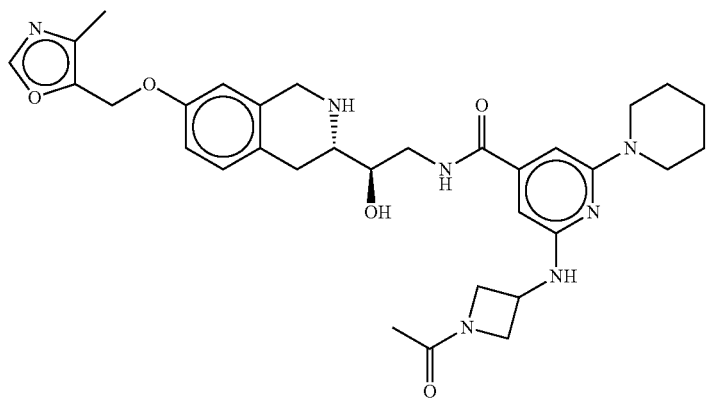

TABLE 2-continued
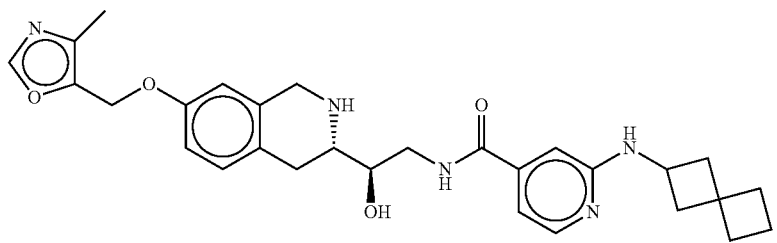
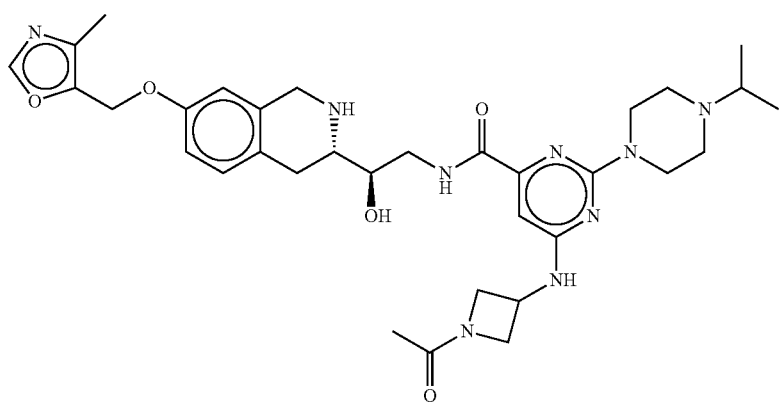
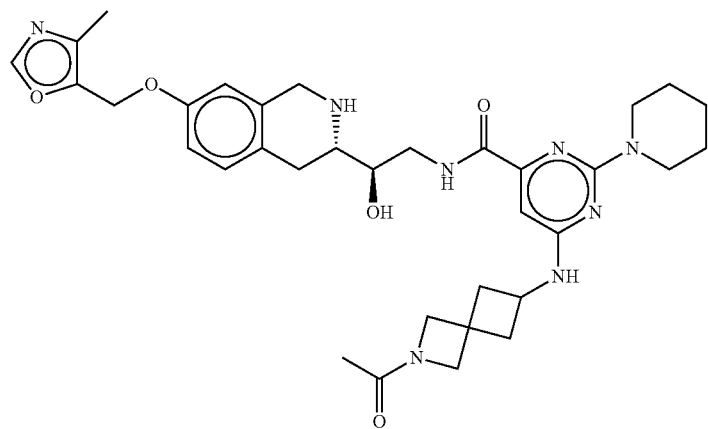
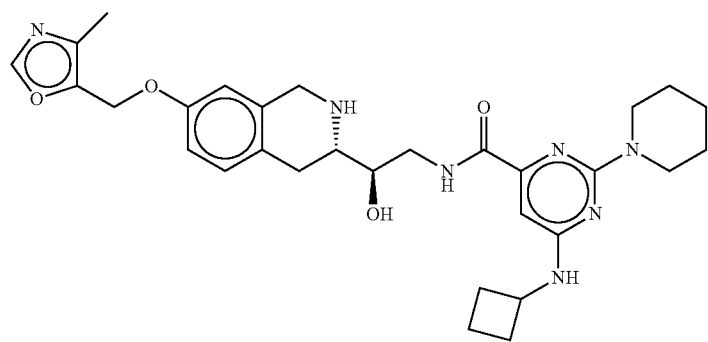

TABLE 2-continued
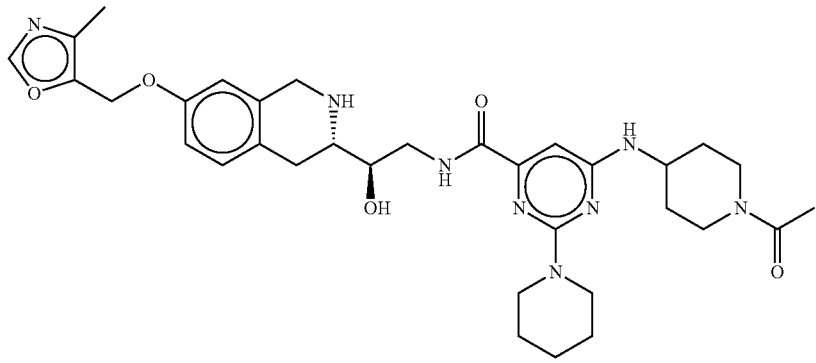
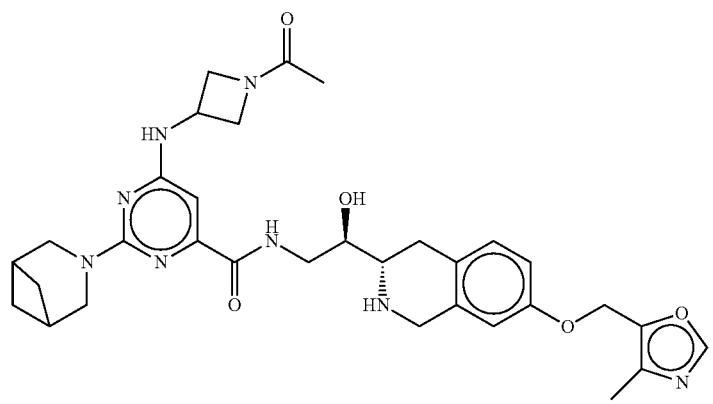
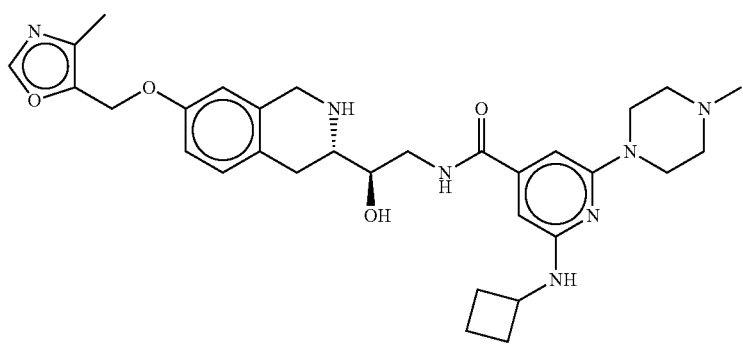
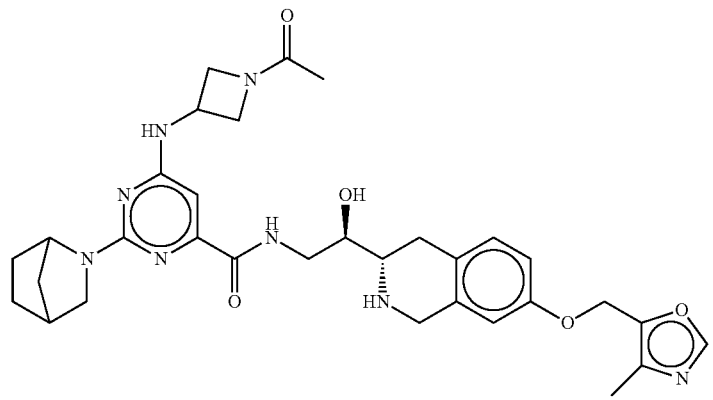

TABLE 2-continued
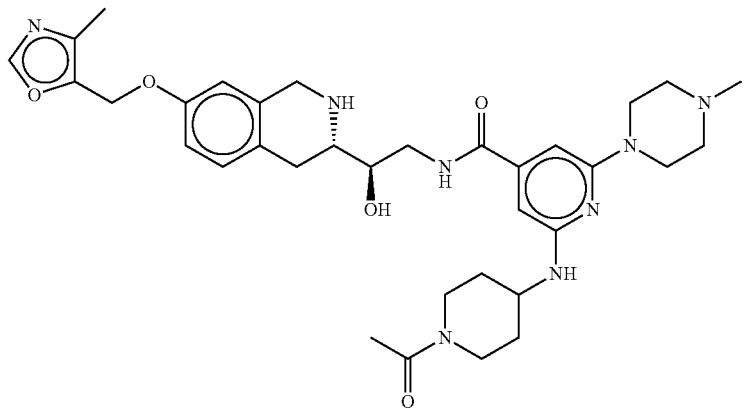
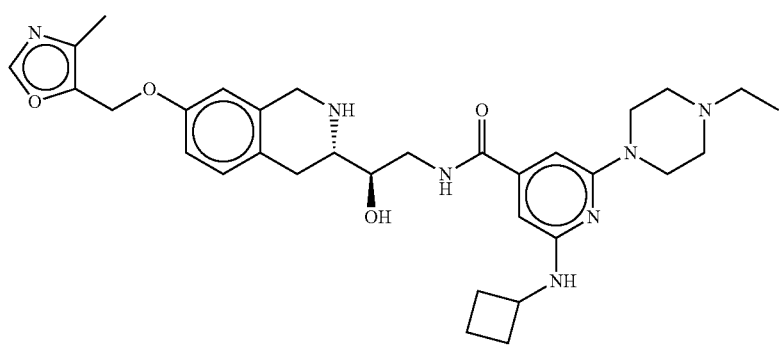
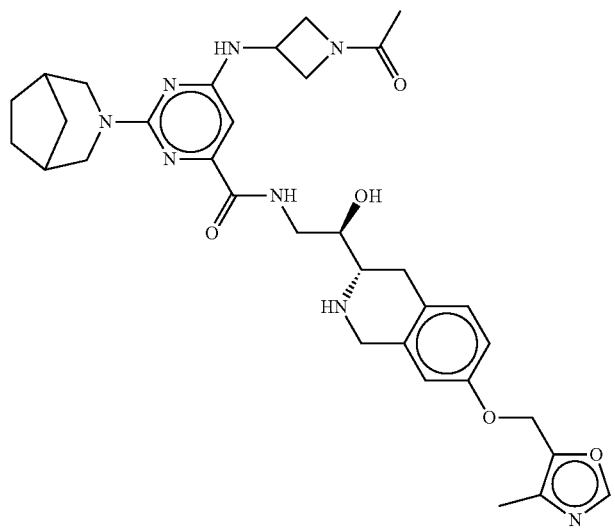
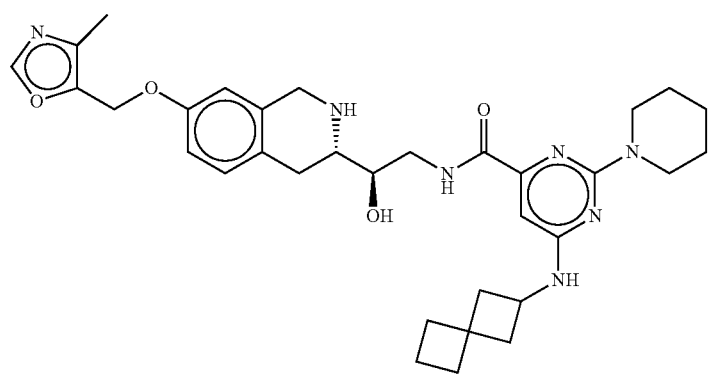

TABLE 2-continued
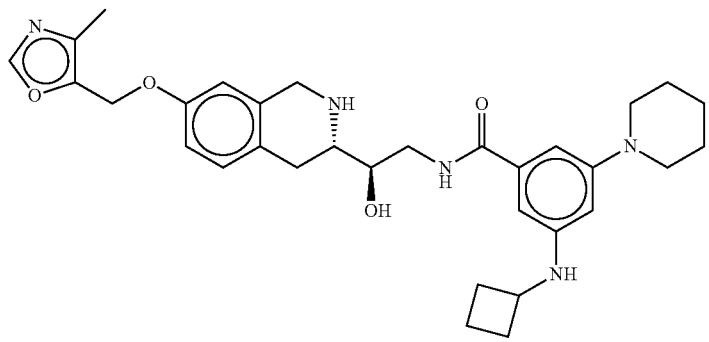
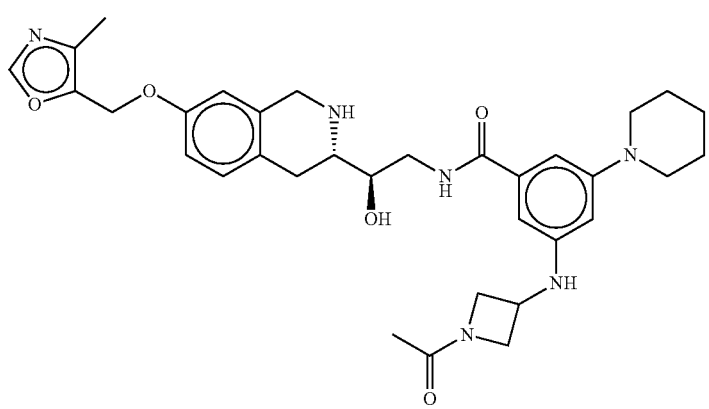
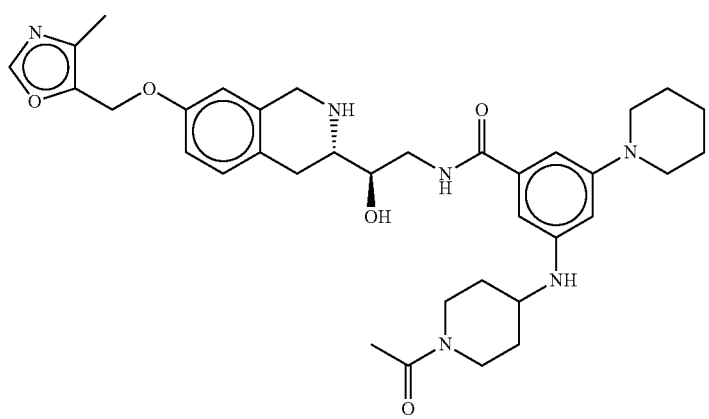
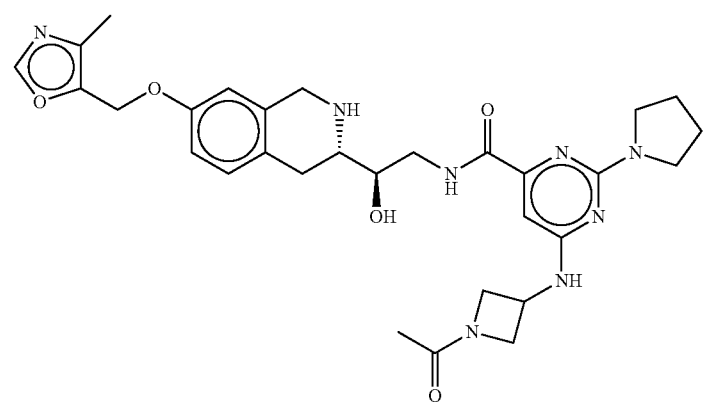

TABLE 2-continued
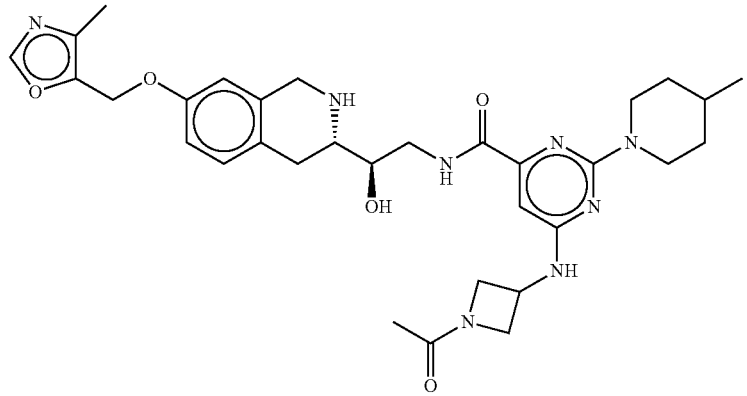
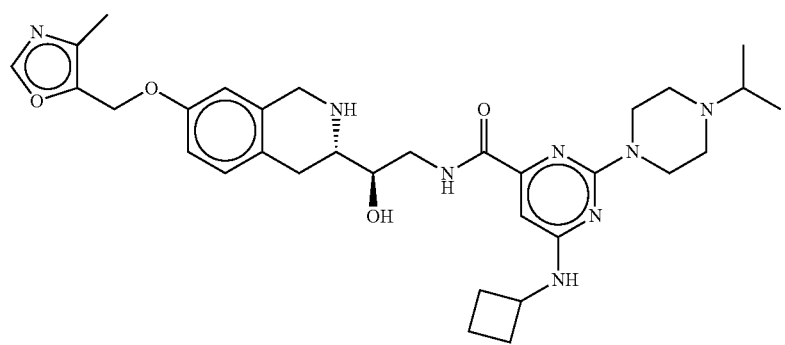
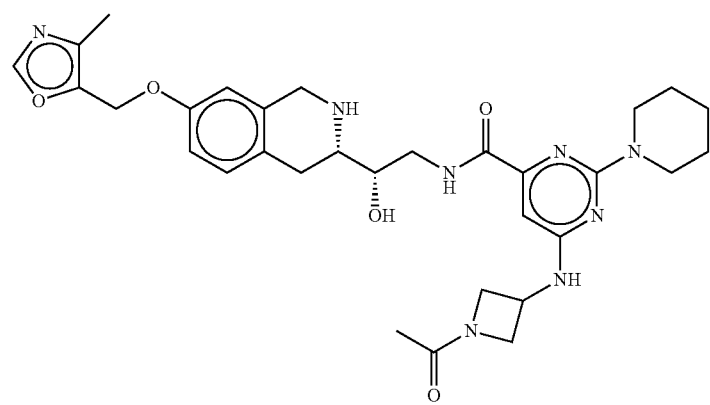
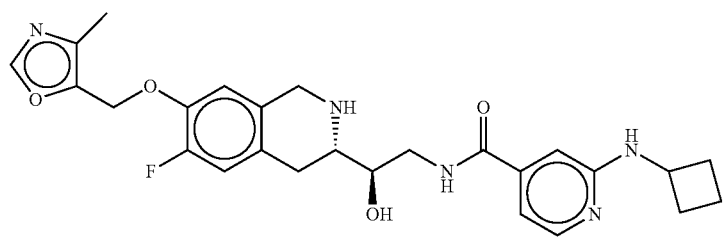

TABLE 2-continued
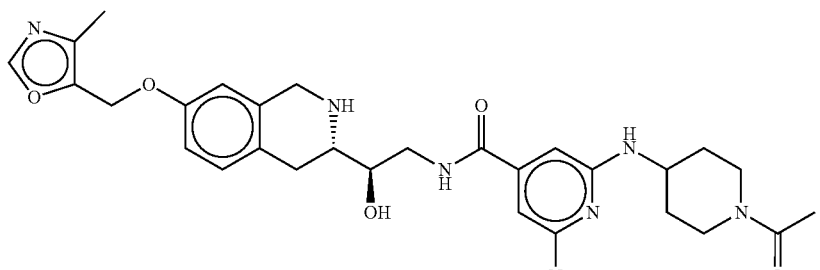
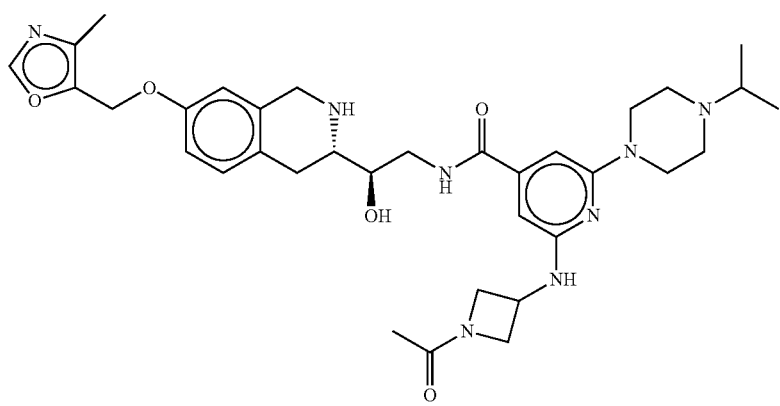
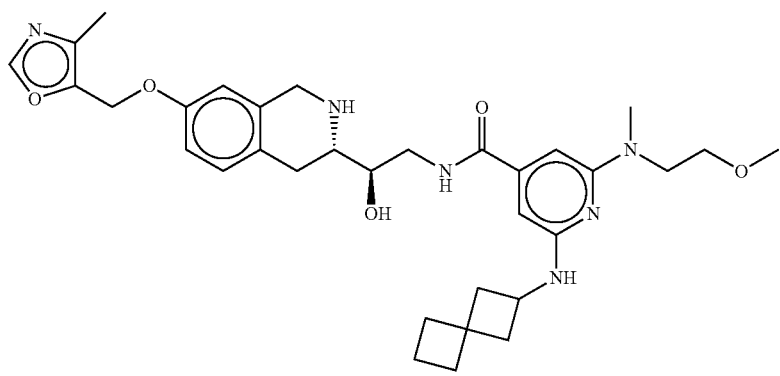
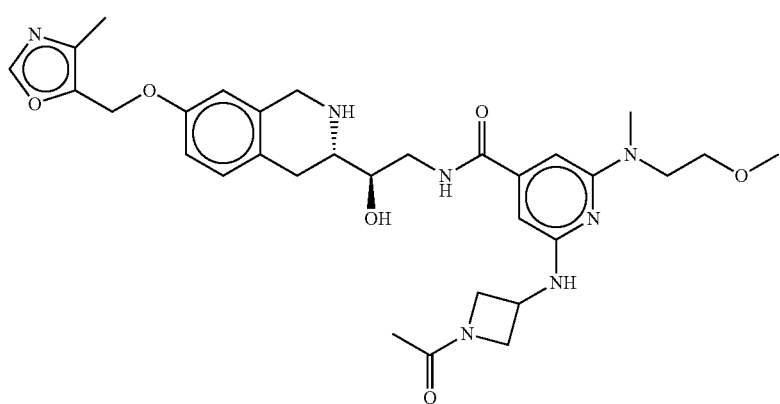

TABLE 2-continued
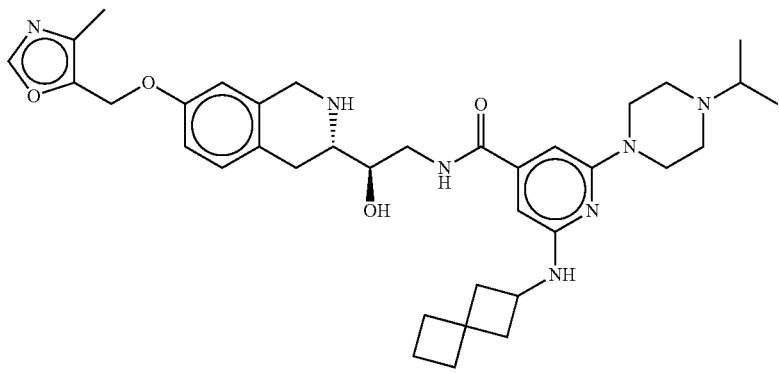
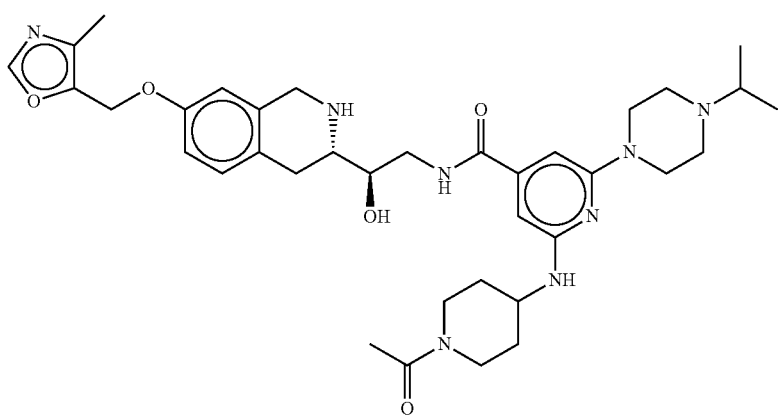
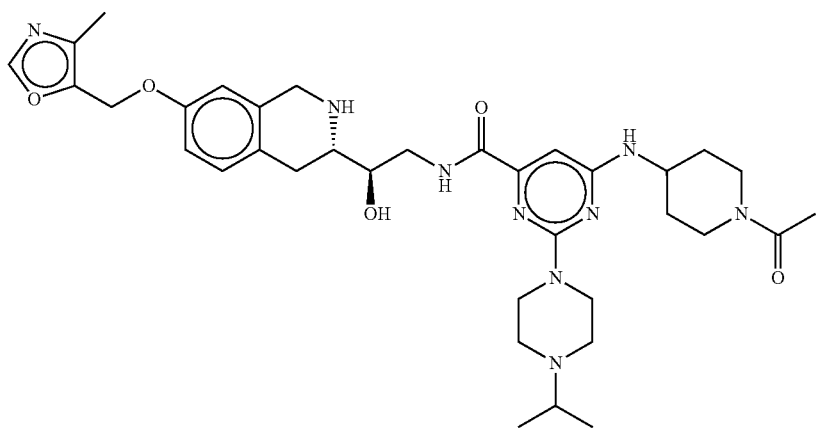
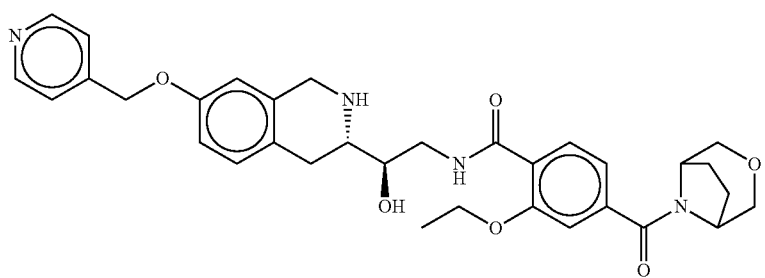

TABLE 2-continued
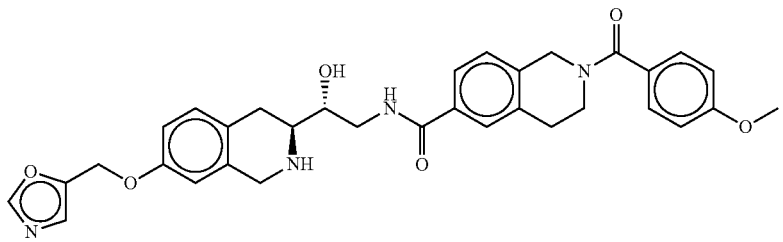
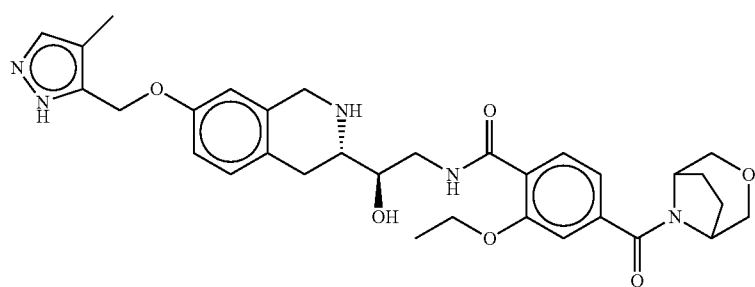
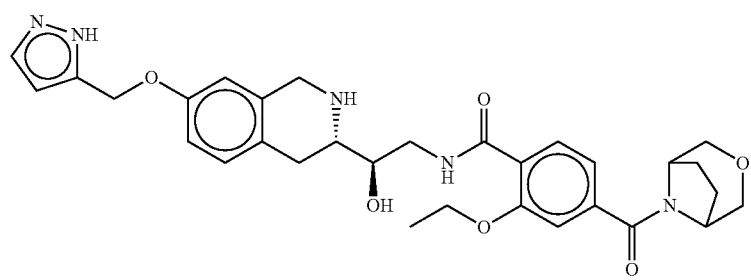
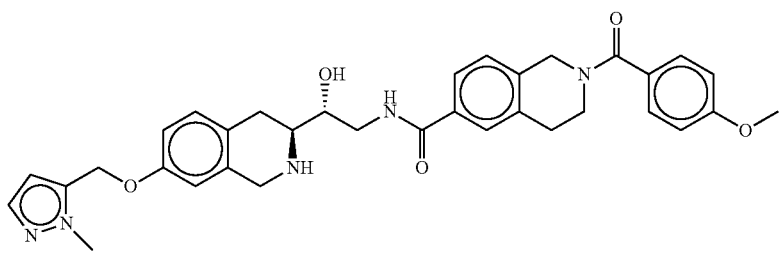
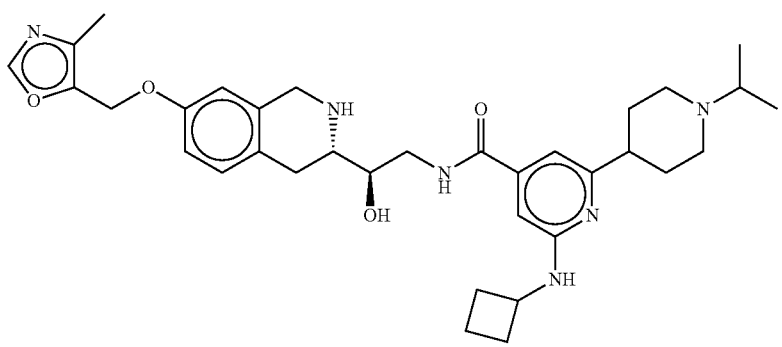

TABLE 2-continued
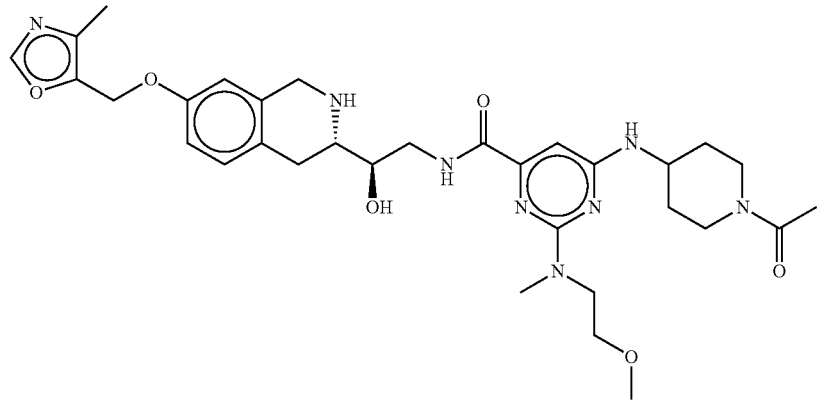
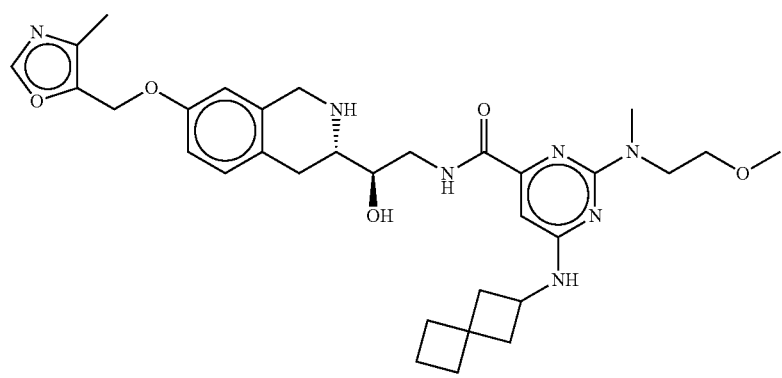
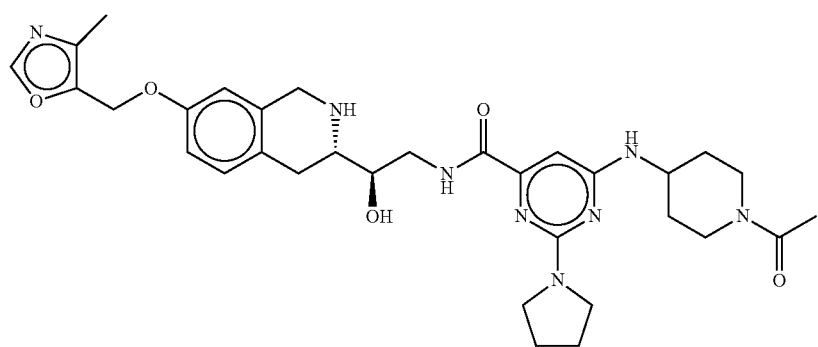
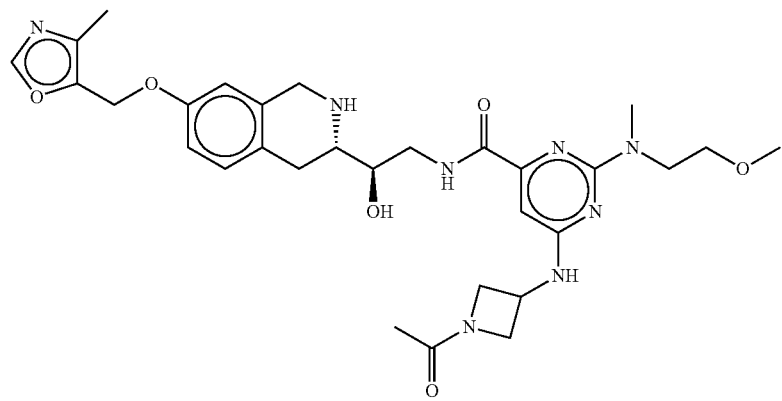

TABLE 2-continued
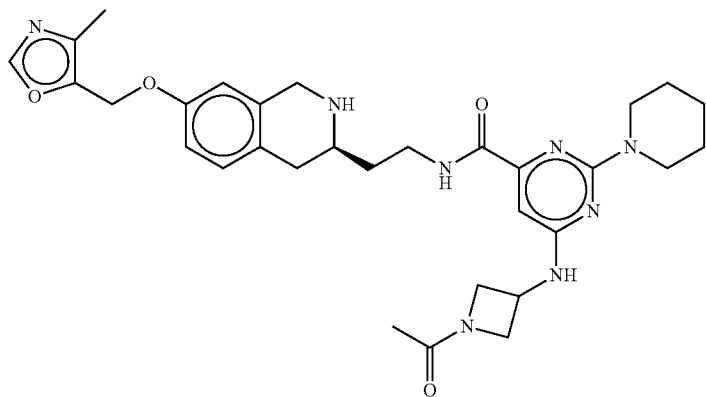
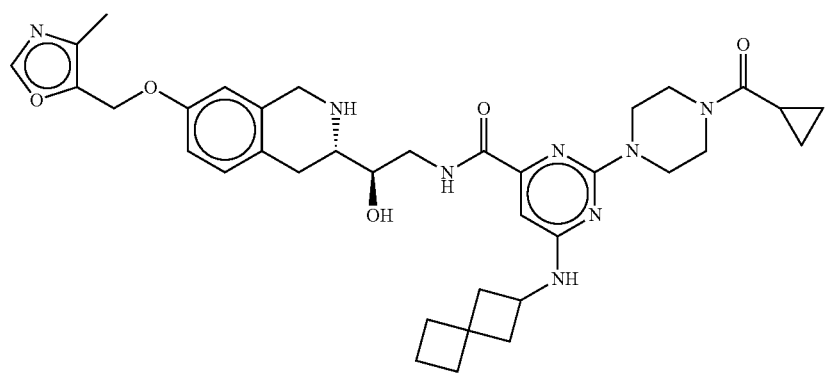
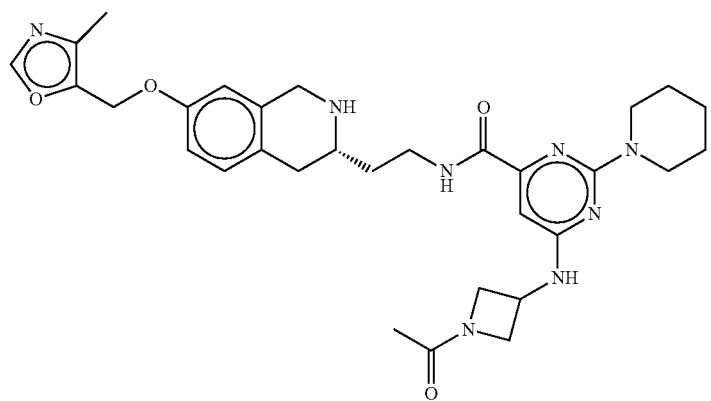
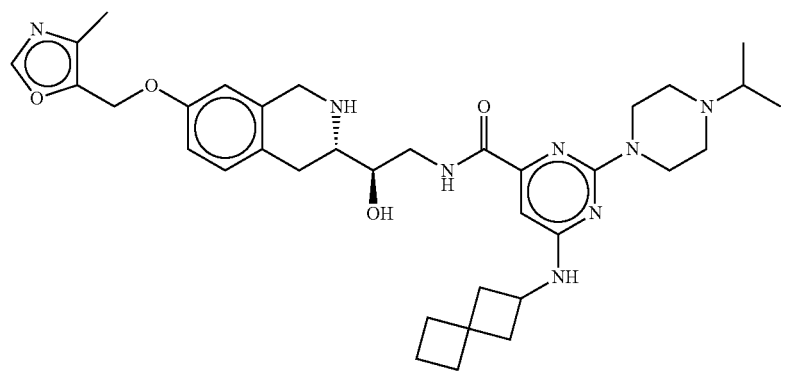
or a pharmaceutically acceptable salt thereof.

In another embodiment, the Type II PRMT5 inhibitor is a compound of Formula III:

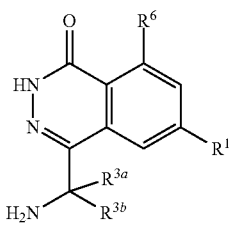

(III)

or a pharmaceutically acceptable salt thereof;
wherein
- $R^1$ is hydrogen, halogen, hydroxyalkyl, -L-CN, —Y—$C_1$-$C_5$alkyl, —Y-cycloalkyl, —Y-heterocyclyl, —Y-aryl, —Y-ar$C_1$-$C_3$alkyl or —Y-heteroaryl, wherein the cycloalkyl, the heterocyclyl, the aryl, and the heteroaryl portions are each optionally substituted with one or more $R^2$;
- each Y is independently a bond or —$NR^4$—;
- each $R^2$ is independently hydroxy, halogen, cyano, cyanomethyl, —$(NR^4)_2$, hydroxyalkyl, alkoxy, —$SO_2C_1$-$C_3$alkyl, —X-ar$C_1$-$C_3$alkyl, heteroalkyl, $C_2$-$C_4$ alkynyl, —X-haloalkyl, —X—$C_1$-$C_5$ alkyl, —Z—$C_1$-$C_5$ alkyl, heterocyclyl, —X-L-cycloalkyl, —Z-cycloalkyl, —X-aryl, —Z-aryl, or —X-heteroaryl, wherein the heterocyclyl, the cycloalkyl, the aryl and the heteroaryl are optionally substituted with one or more $R^5$;
- each X is independently a bond, O, S, —$NR^4$— or —$NR^4C(O)$—
- each Z is independently a bond, —SO—, —$SO_2$—, —CH(OH)— or —C(O)—;
- each L is independently a bond or $C_1$-$C_3$ alkylene;
- $R^{3a}$ and $R^{3b}$ are each independently hydrogen or deuterium, or $R^{3a}$ and $R^{3b}$ together are oxo;
- each $R^4$ is independently hydrogen or $C_1$-$C_3$alkyl;
- each $R^5$ is independently cyano, oxo, halogen, $C_1$-$C_3$ alkyl, hydroxyalkyl, alkoxy, —X-haloalkyl, —Z-cycloalkyl, —X-ar$C_1$-$C_3$alkyl, X-ar $C_1$-$C_3$alkyl substituted with cyano —X-L-cycloalkyl, —X-L-heteroaryl optionally substituted with one or more C1-C3alkyl or oxo, or —X-aryl; and
- $R^6$ is hydrogen, halogen, $C_1$-$C_3$alkyl, haloalkyl or alkoxy.

In another embodiment, the Type II PRMT5 inhibitor is selected from the group consisting of a compound from Table 3 (see WO 2021/050915, which is incorporated by reference in its entirety).

TABLE 3

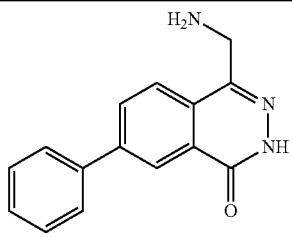

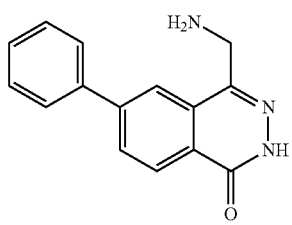 [SMILES: NCc1n[nH]c(=O)c2ccc(-c3ccccc3)cc12]

TABLE 3-continued

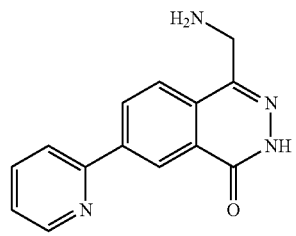 [SMILES: NCc1n[nH]c(=O)c2cc(-c3ccccn3)ccc12]

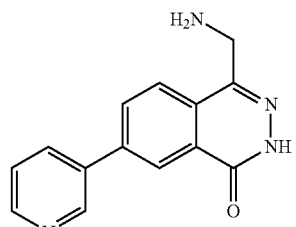

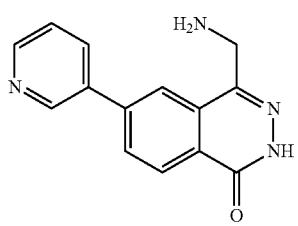 [SMILES: NCc1n[nH]c(=O)c2ccc(-c3cccnc3)cc12]

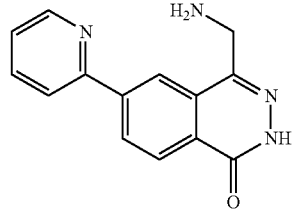 [SMILES: NCc1n[nH]c(=O)c2ccc(-c3ccccn3)cc12]

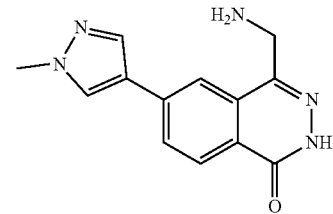 [SMILES: Cn1cc(-c2ccc3c(=O)[nH]nc(CN)c3c2)cn1]

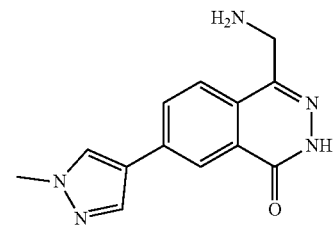 [SMILES: Cn1cc(-c2ccc3c(CN)n[nH]c(=O)c3c2)cn1]

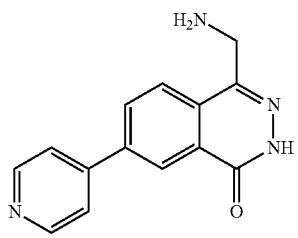 [SMILES: NCc1n[nH]c(=O)c2cc(-c3ccncc3)ccc12]

TABLE 3-continued

TABLE 3-continued
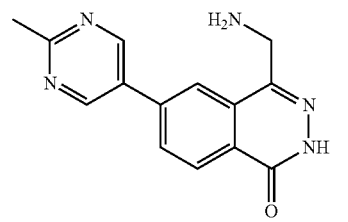 [SMILES: Cc1ncc(-c2ccc3c(=O)[nH]nc(CN)c3c2)cn1]
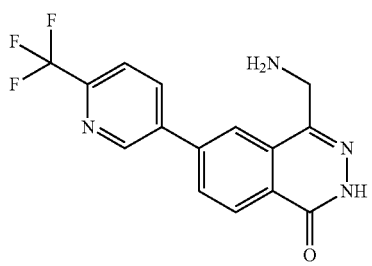 [SMILES: NCc1n[nH]c(=O)c2ccc(-c3ccc(C(F)(F)F)nc3)cc12]
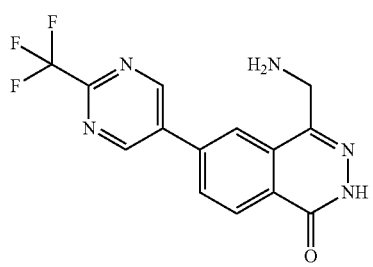 [SMILES: NCc1n[nH]c(=O)c2ccc(-c3cnc(C(F)(F)F)nc3)cc12]
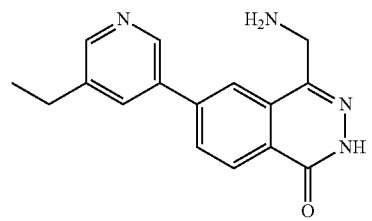 [SMILES: CCc1cncc(-c2ccc3c(=O)[nH]nc(CN)c3c2)c1]
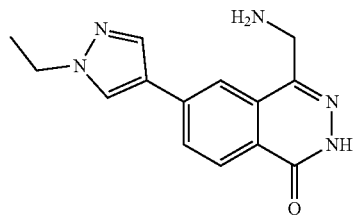 [SMILES: CCn1cc(-c2ccc3c(=O)[nH]nc(CN)c3c2)cn1]
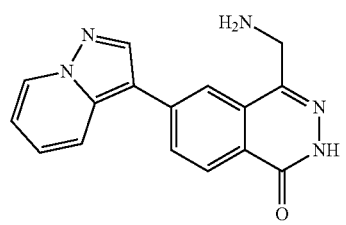 [SMILES: NCc1n[nH]c(=O)c2ccc(-c3cnn4ccccc34)cc12]
TABLE 3-continued
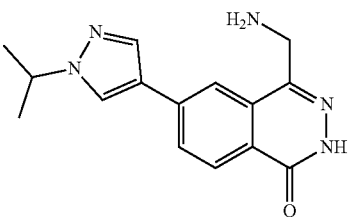 [SMILES: CC(C)n1cc(-c2ccc3c(=O)[nH]nc(CN)c3c2)cn1]
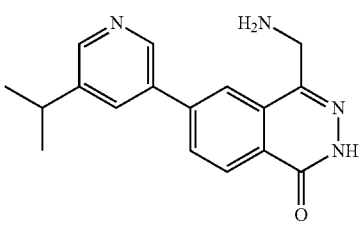 [SMILES: CC(C)c1cncc(-c2ccc3c(=O)[nH]nc(CN)c3c2)c1]
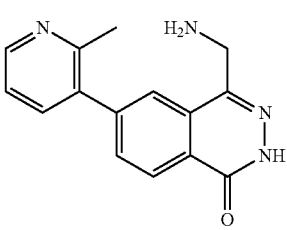
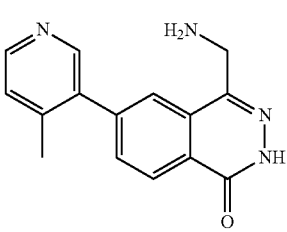 [SMILES: Cc1ccncc1-c1ccc2c(=O)[nH]nc(CN)c2c1]
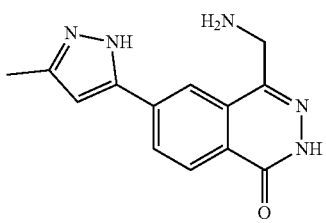 [SMILES: Cc1cc(-c2ccc3c(=O)[nH]nc(CN)c3c2)[nH]n1]
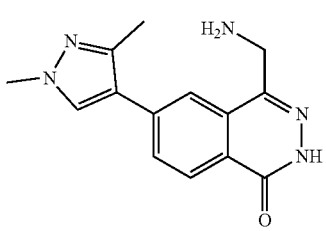 [SMILES: Cc1nn(C)cc1-c1ccc2c(=O)[nH]nc(CN)c2c1]
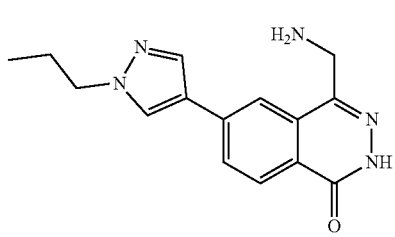 [SMILES: CCCn1cc(-c2ccc3c(=O)[nH]nc(CN)c3c2)cn1]

TABLE 3-continued
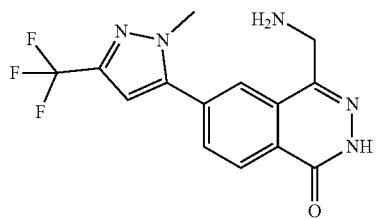 [SMILES: Cn1nc(C(F)(F)F)cc1-c1ccc2c(=O)[nH]nc(CN)c2c1]
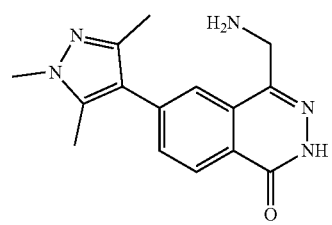 [SMILES: Cc1nn(C)c(C)c1-c1ccc2c(=O)[nH]nc(CN)c2c1]
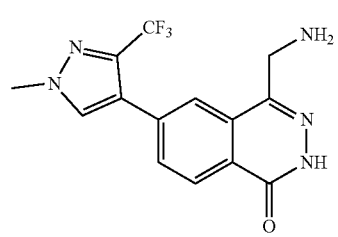 [SMILES: Cn1cc(-c2ccc3c(=O)[nH]nc(CN)c3c2)c(C(F)(F)F)n1]
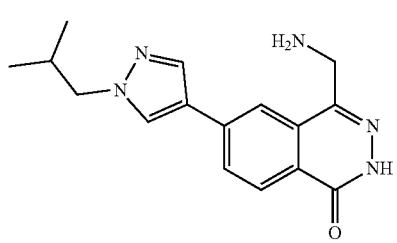 [SMILES: CC(C)Cn1cc(-c2ccc3c(=O)[nH]nc(CN)c3c2)cn1]
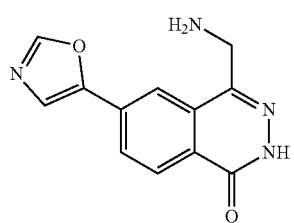
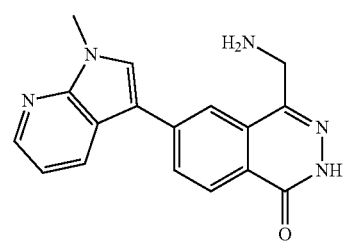 [SMILES: Cn1cc(-c2ccc3c(=O)[nH]nc(CN)c3c2)c2cccnc21]
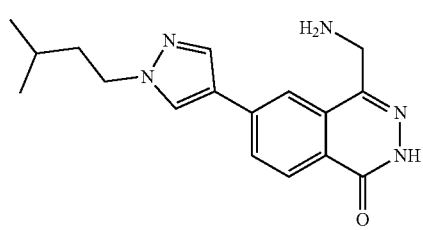 [SMILES: CC(C)CCn1cc(-c2ccc3c(=O)[nH]nc(CN)c3c2)cn1]
TABLE 3-continued
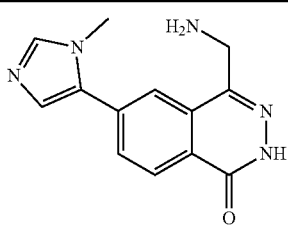
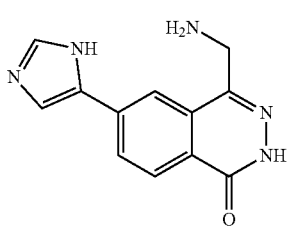 [SMILES: NCc1n[nH]c(=O)c2ccc(-c3cnc[nH]3)cc12]
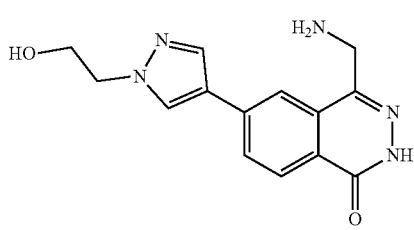 [SMILES: NCc1n[nH]c(=O)c2ccc(-c3cnn(CCO)c3)cc12]
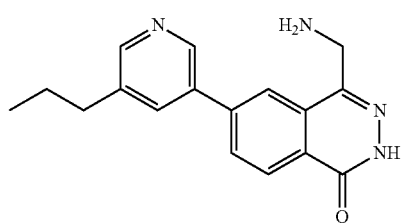 [SMILES: CCCc1cncc(-c2ccc3c(=O)[nH]nc(CN)c3c2)c1]
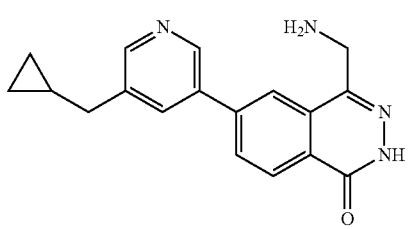 [SMILES: NCc1n[nH]c(=O)c2ccc(-c3cncc(CC4CC4)c3)cc12]
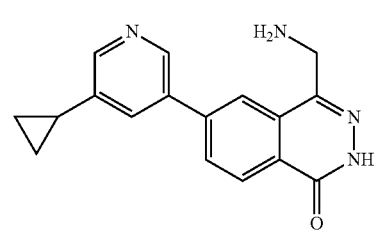 [SMILES: NCc1n[nH]c(=O)c2ccc(-c3cncc(C4CC4)c3)cc12]
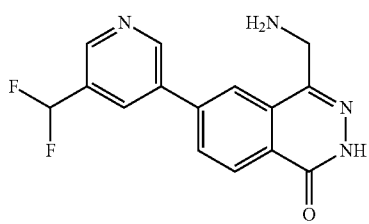 [SMILES: NCc1n[nH]c(=O)c2ccc(-c3cncc(C(F)F)c3)cc12]

TABLE 3-continued
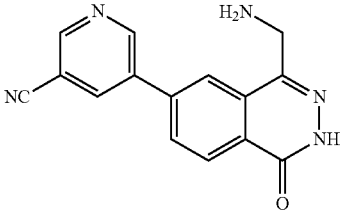
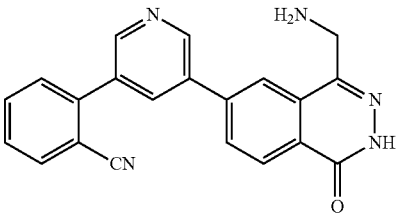 [SMILES: N#Cc1ccccc1-c1cncc(-c2ccc3c(=O)[nH]nc(CN)c3c2)c1]
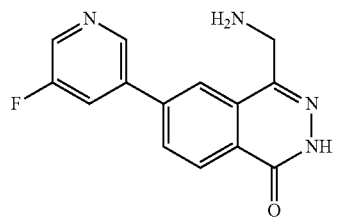 [SMILES: NCc1n[nH]c(=O)c2ccc(-c3cncc(F)c3)cc12]
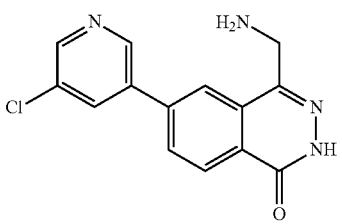 [SMILES: NCc1n[nH]c(=O)c2ccc(-c3cncc(Cl)c3)cc12]
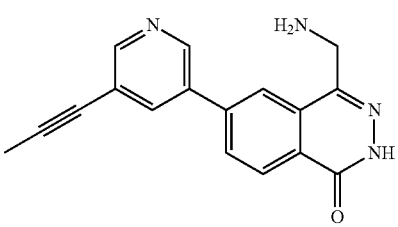 [SMILES: CC#Cc1cncc(-c2ccc3c(=O)[nH]nc(CN)c3c2)c1]
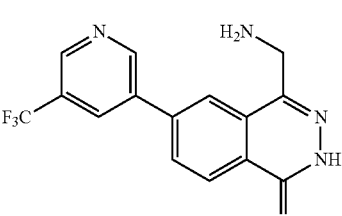
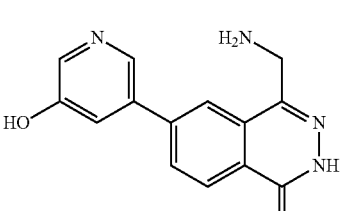
TABLE 3-continued
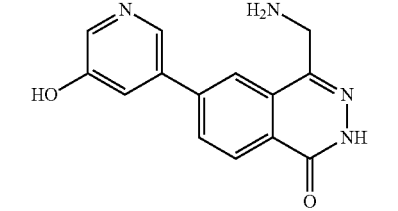
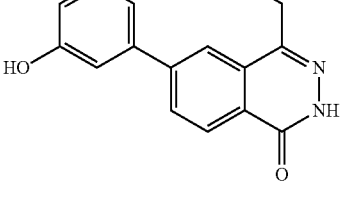
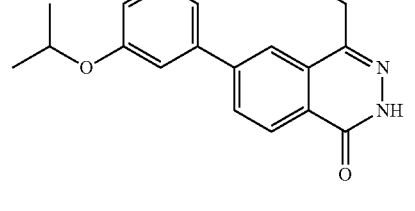
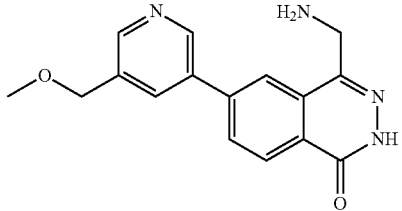 [SMILES: COCc1cncc(-c2ccc3c(=O)[nH]nc(CN)c3c2)c1]
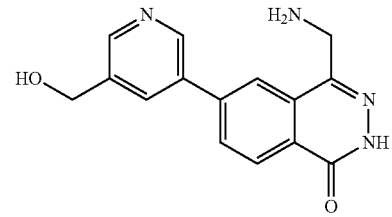 [SMILES: NCc1n[nH]c(=O)c2ccc(-c3cncc(CO)c3)cc12]
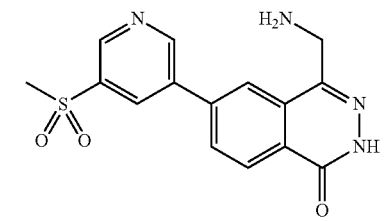 [SMILES: CS(=O)(=O)c1cncc(-c2ccc3c(=O)[nH]nc(CN)c3c2)c1]
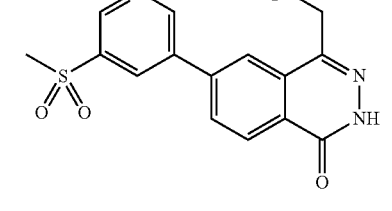

TABLE 3-continued
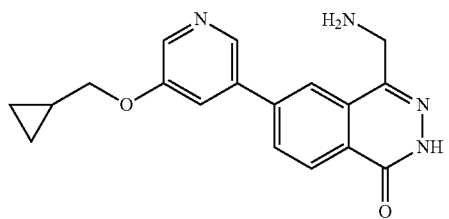 [SMILES: NCc1n[nH]c(=O)c2ccc(-c3cncc(OCC4CC4)c3)cc12]
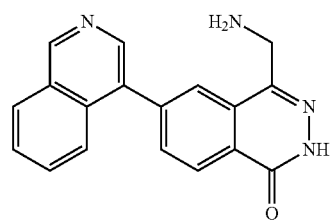 [SMILES: NCc1n[nH]c(=O)c2ccc(-c3cncc4ccccc34)cc12]
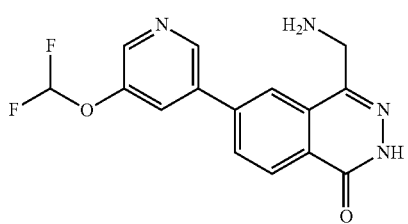 [SMILES: NCc1n[nH]c(=O)c2ccc(-c3cncc(OC(F)F)c3)cc12]
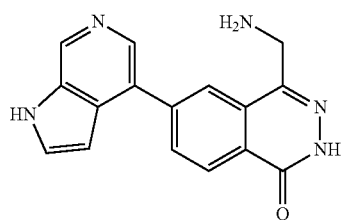 [SMILES: NCc1n[nH]c(=O)c2ccc(-c3cncc4[nH]ccc34)cc12]
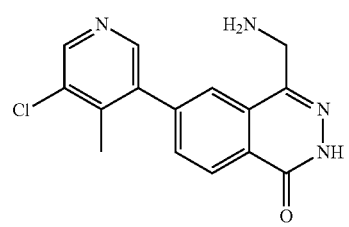 [SMILES: Cc1c(Cl)cncc1-c1ccc2c(=O)[nH]nc(CN)c2c1]
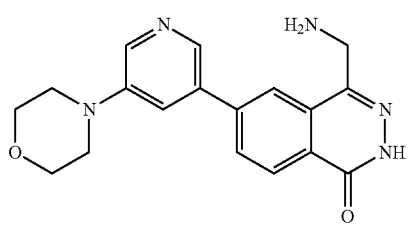
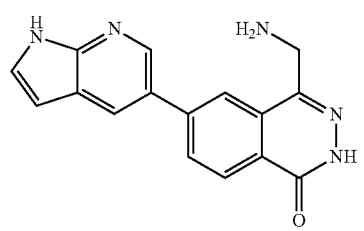
TABLE 3-continued
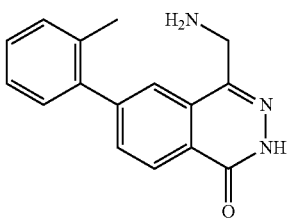 [SMILES: Cc1ccccc1-c1ccc2c(=O)[nH]nc(CN)c2c1]
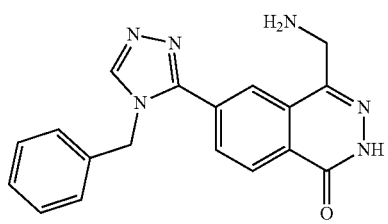 [SMILES: NCc1n[nH]c(=O)c2ccc(-c3nncn3Cc3ccccc3)cc12]
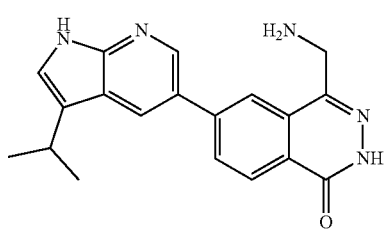 [SMILES: CC(C)c1c[nH]c2ncc(-c3ccc4c(=O)[nH]nc(CN)c4c3)cc12]
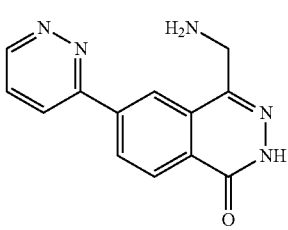 [SMILES: NCc1n[nH]c(=O)c2ccc(-c3cccnn3)cc12]
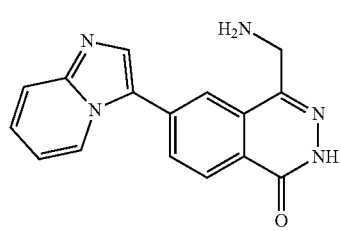 [SMILES: NCc1n[nH]c(=O)c2ccc(-c3cnc4ccccn34)cc12]
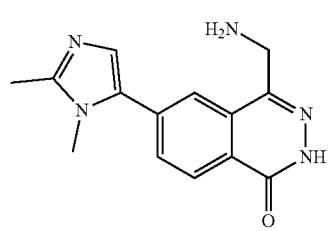 [SMILES: Cc1ncc(-c2ccc3c(=O)[nH]nc(CN)c3c2)n1C]
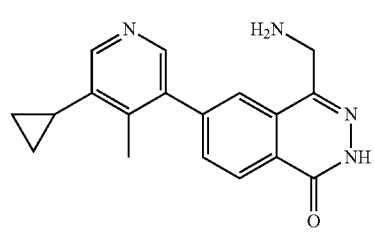

TABLE 3-continued
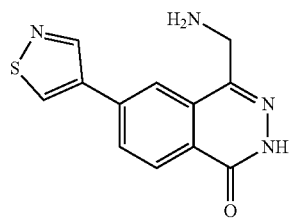 [SMILES: NCc1n[nH]c(=O)c2ccc(-c3cnsc3)cc12]
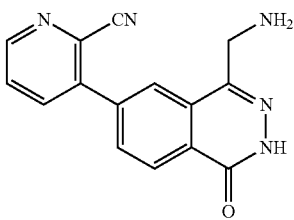 [SMILES: N#Cc1ncccc1-c1ccc2c(=O)[nH]nc(CN)c2c1]
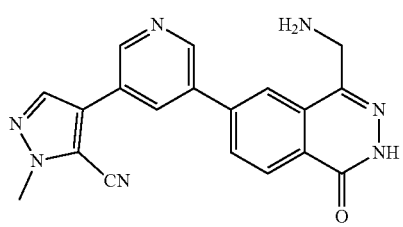 [SMILES: Cn1ncc(-c2cncc(-c3ccc4c(=O)[nH]nc(CN)c4c3)c2)c1C#N]
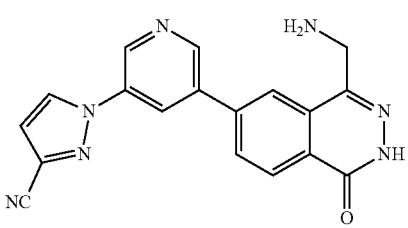 [SMILES: N#Cc1ccn(-c2cncc(-c3ccc4c(=O)[nH]nc(CN)c4c3)c2)n1]
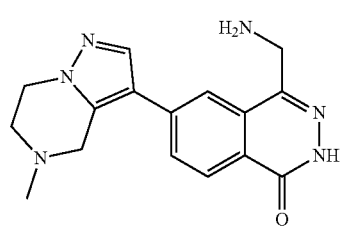 [SMILES: CN1CCn2ncc(-c3ccc4c(=O)[nH]nc(CN)c4c3)c2C1]
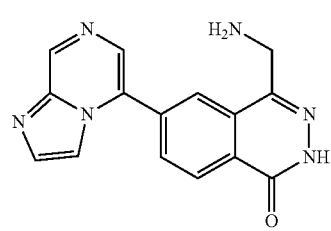 [SMILES: NCc1n[nH]c(=O)c2ccc(-c3cncc4nccn34)cc12]
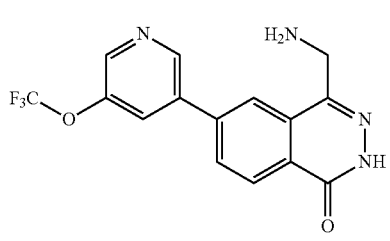
TABLE 3-continued
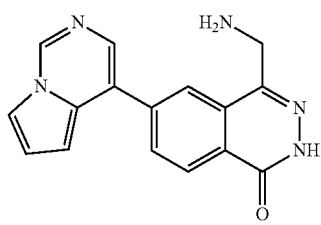 [SMILES: NCc1n[nH]c(=O)c2ccc(-c3cncn4cccc34)cc12]
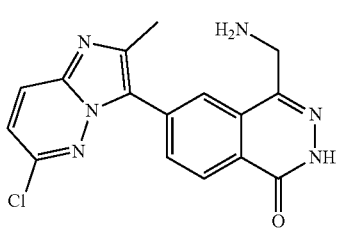
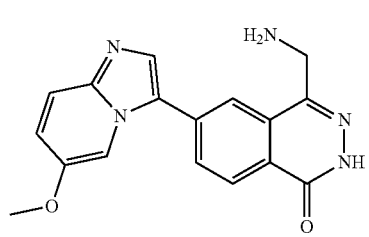 [SMILES: COc1ccc2ncc(-c3ccc4c(=O)[nH]nc(CN)c4c3)n2c1]
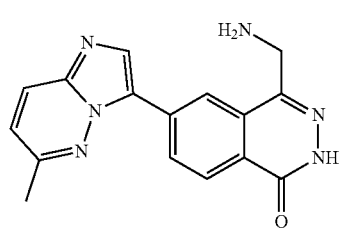 [SMILES: Cc1ccc2ncc(-c3ccc4c(=O)[nH]nc(CN)c4c3)n2n1]
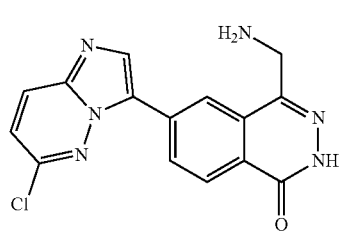 [SMILES: NCc1n[nH]c(=O)c2ccc(-c3cnc4ccc(Cl)nn34)cc12]
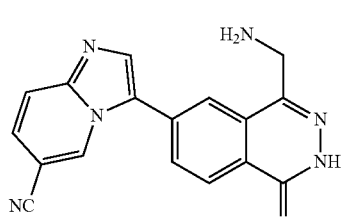
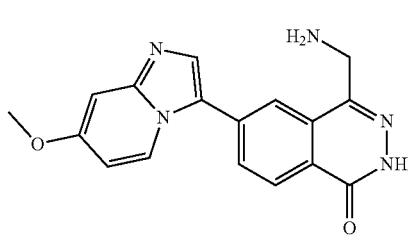 [SMILES: COc1ccn2c(-c3ccc4c(=O)[nH]nc(CN)c4c3)cnc2c1]

TABLE 3-continued
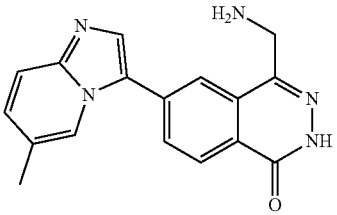 [SMILES: Cc1ccc2ncc(-c3ccc4c(=O)[nH]nc(CN)c4c3)n2c1]
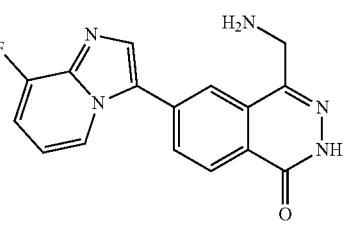
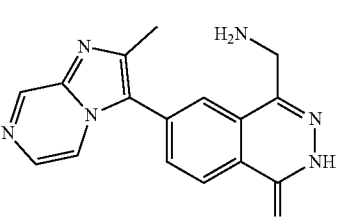
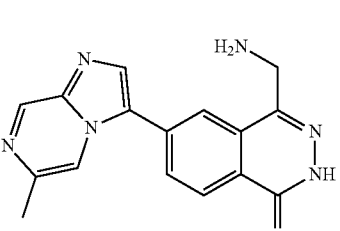
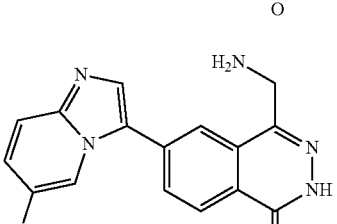
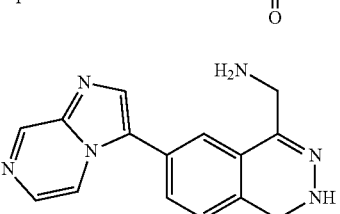
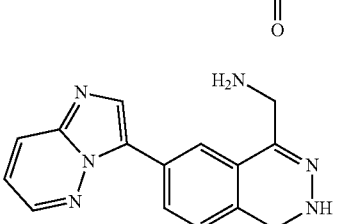
TABLE 3-continued
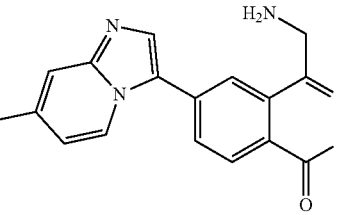
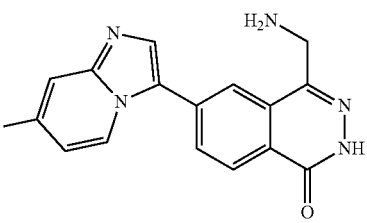
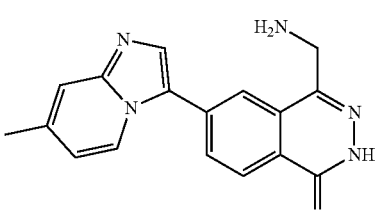
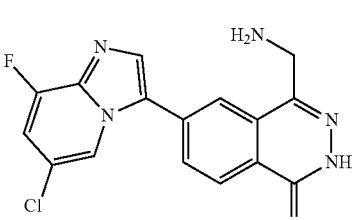
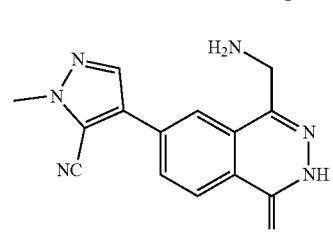
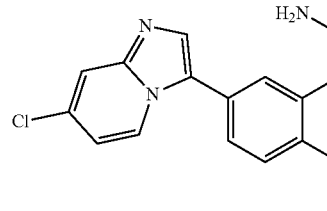

TABLE 3-continued

TABLE 3-continued
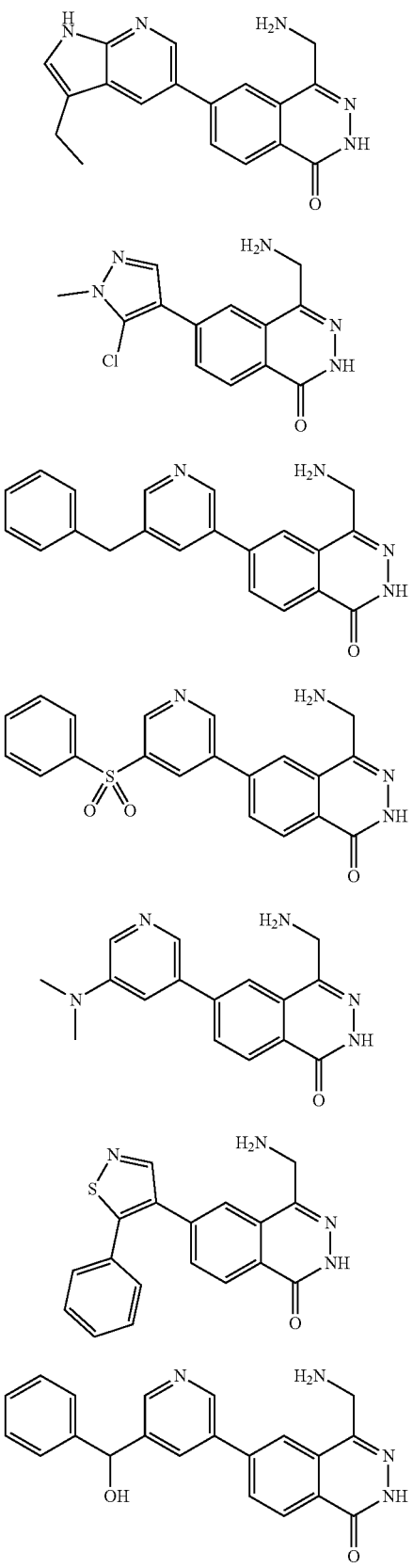
TABLE 3-continued
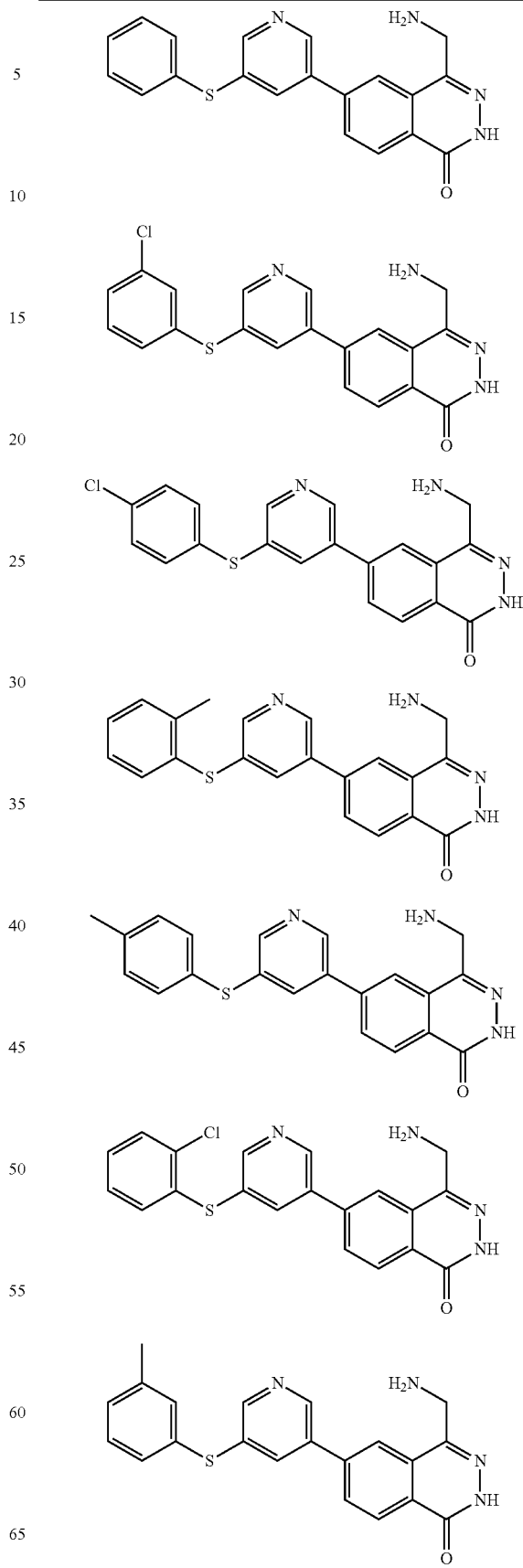

TABLE 3-continued
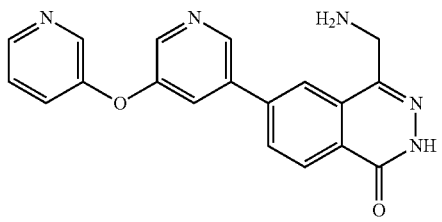 [SMILES: NCc1n[nH]c(=O)c2ccc(-c3cncc(Oc4cccnc4)c3)cc12]
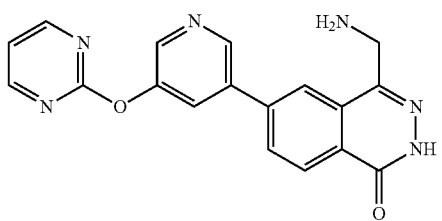 [SMILES: NCc1n[nH]c(=O)c2ccc(-c3cncc(Oc4ncccn4)c3)cc12]
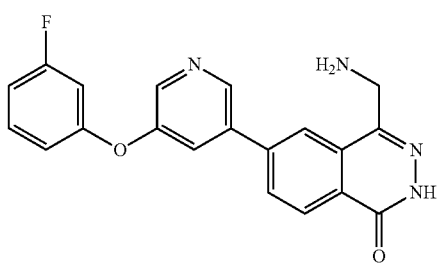 [SMILES: NCc1n[nH]c(=O)c2ccc(-c3cncc(Oc4cccc(F)c4)c3)cc12]
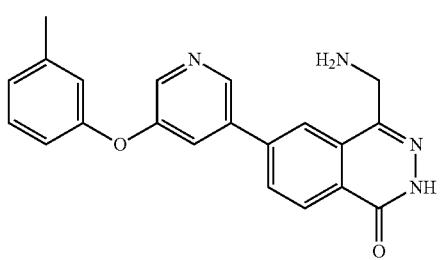 [SMILES: Cc1cccc(Oc2cncc(-c3ccc4c(=O)[nH]nc(CN)c4c3)c2)c1]
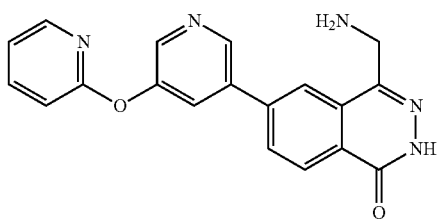 [SMILES: NCc1n[nH]c(=O)c2ccc(-c3cncc(Oc4ccccn4)c3)cc12]
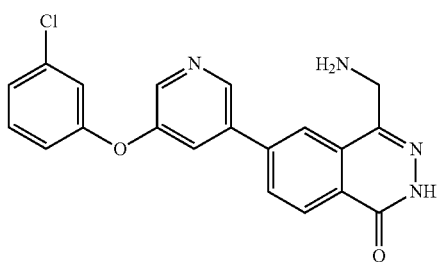
TABLE 3-continued
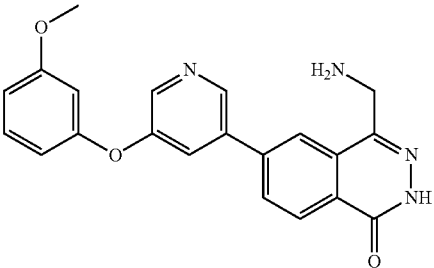 [SMILES: COc1cccc(Oc2cncc(-c3ccc4c(=O)[nH]nc(CN)c4c3)c2)c1]
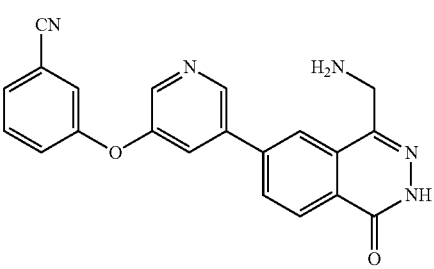 [SMILES: N#Cc1cccc(Oc2cncc(-c3ccc4c(=O)[nH]nc(CN)c4c3)c2)c1]
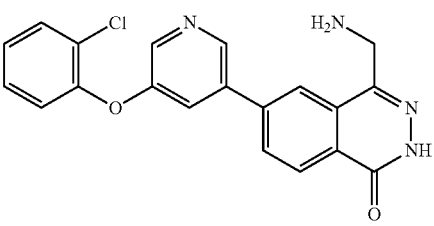
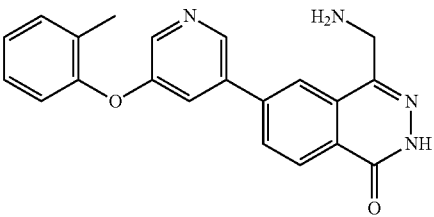
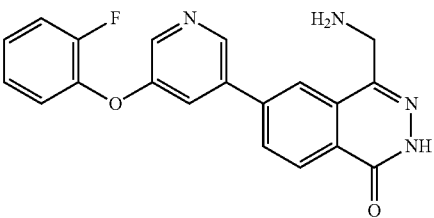 [SMILES: NCc1n[nH]c(=O)c2ccc(-c3cncc(Oc4ccccc4Cl)c3)cc12]
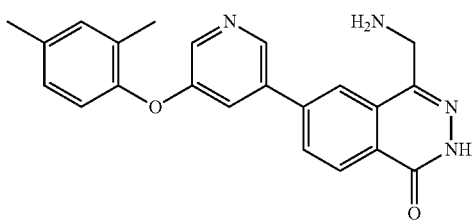 [SMILES: Cc1ccc(Oc2cncc(-c3ccc4c(=O)[nH]nc(CN)c4c3)c2)c(C)c1]

TABLE 3-continued
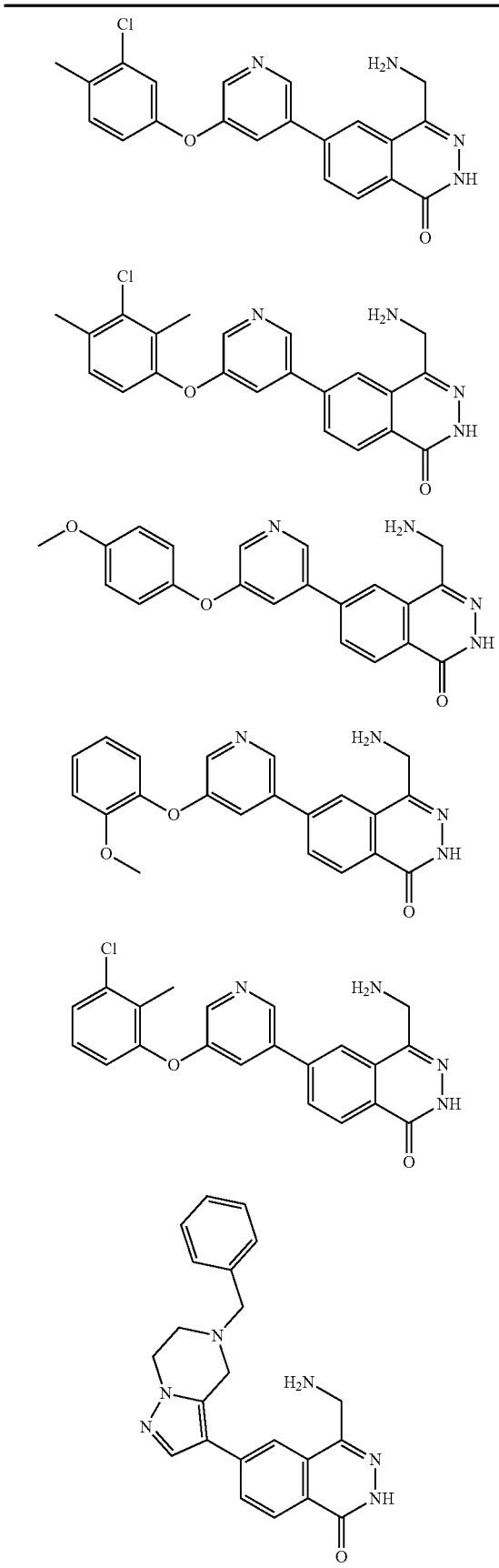
TABLE 3-continued
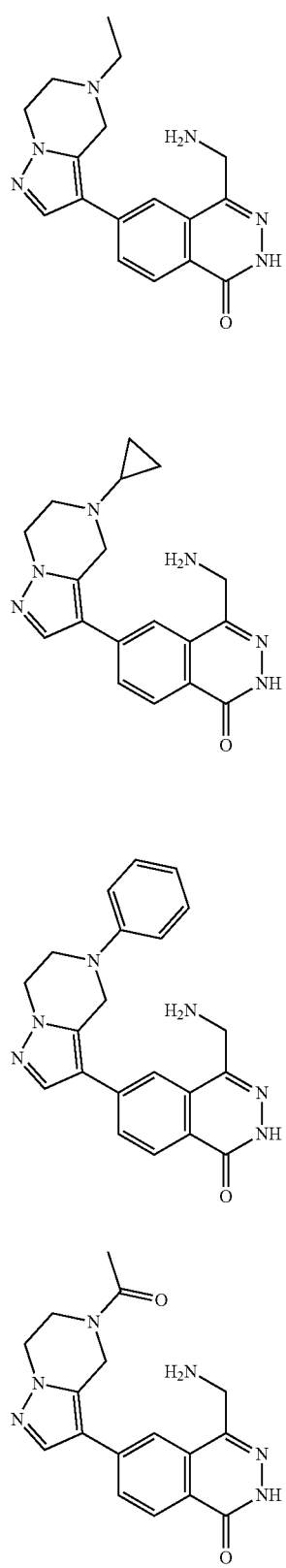

TABLE 3-continued
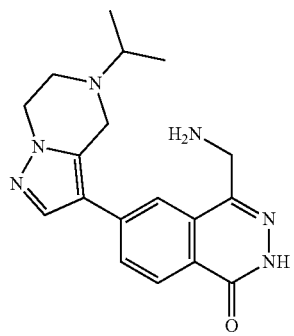 [SMILES: CC(C)N1CCn2ncc(-c3ccc4c(=O)[nH]nc(CN)c4c3)c2C1]
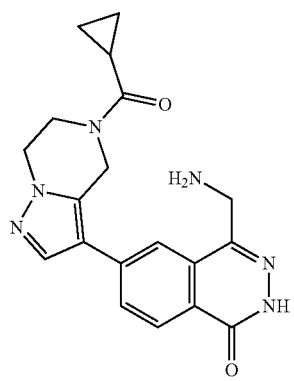 [SMILES: NCc1n[nH]c(=O)c2ccc(-c3cnn4c3CN(C(=O)C3CC3)CC4)cc12]
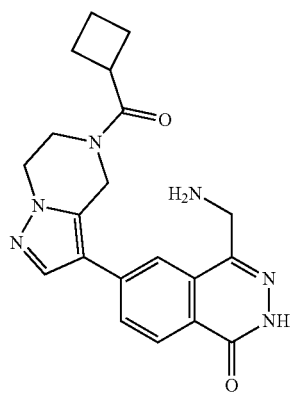 [SMILES: NCc1n[nH]c(=O)c2ccc(-c3cnn4c3CN(C(=O)C3CCC3)CC4)cc12]
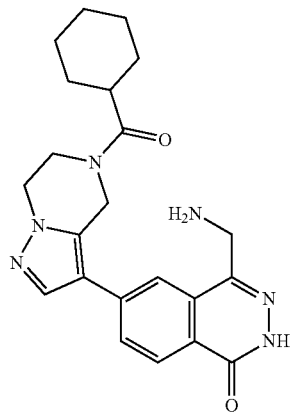 [SMILES: NCc1n[nH]c(=O)c2ccc(-c3cnn4c3CN(C(=O)C3CCCCC3)CC4)cc12]
TABLE 3-continued
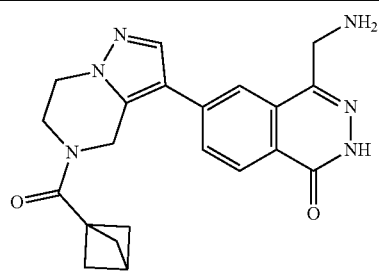
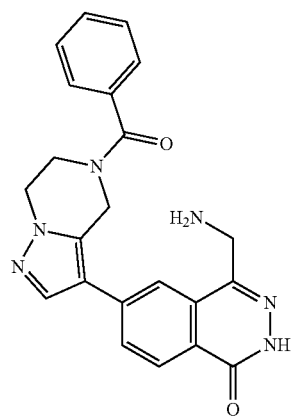 [SMILES: NCc1n[nH]c(=O)c2ccc(-c3cnn4c3CN(C(=O)c3ccccc3)CC4)cc12]
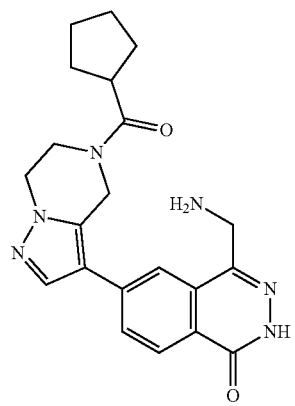 [SMILES: NCc1n[nH]c(=O)c2ccc(-c3cnn4c3CN(C(=O)C3CCCC3)CC4)cc12]
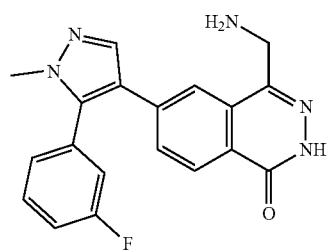 [SMILES: Cn1ncc(-c2ccc3c(=O)[nH]nc(CN)c3c2)c1-c1cccc(F)c1]
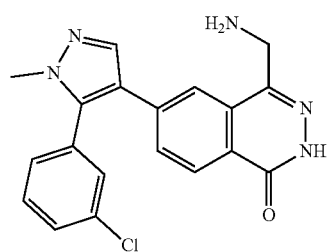

TABLE 3-continued
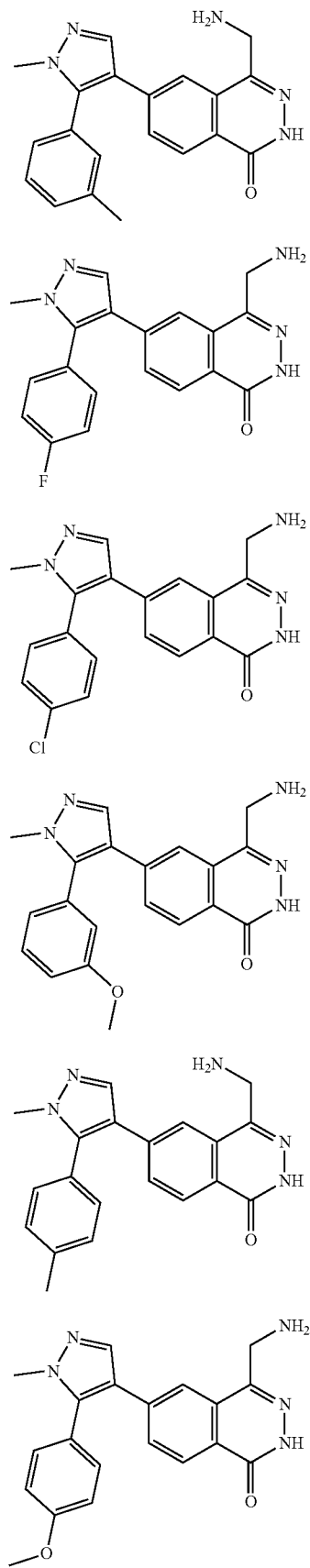
TABLE 3-continued
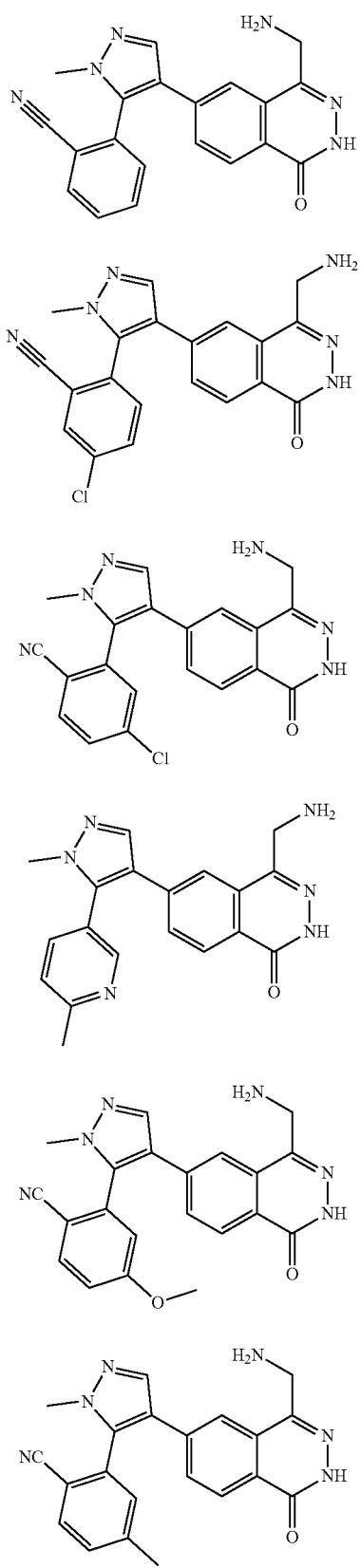

TABLE 3-continued
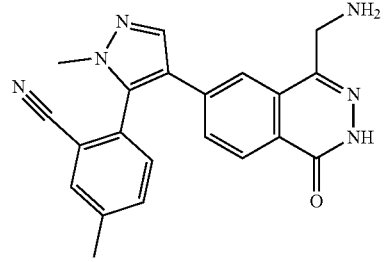 [SMILES: Cc1ccc(-c2c(-c3ccc4c(=O)[nH]nc(CN)c4c3)cnn2C)c(C#N)c1]
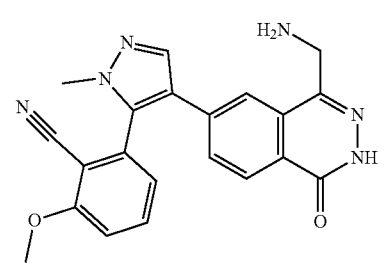 [SMILES: COc1cccc(-c2c(-c3ccc4c(=O)[nH]nc(CN)c4c3)cnn2C)c1C#N]
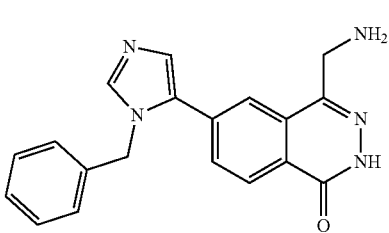 [SMILES: NCc1n[nH]c(=O)c2ccc(-c3cncn3Cc3ccccc3)cc12]
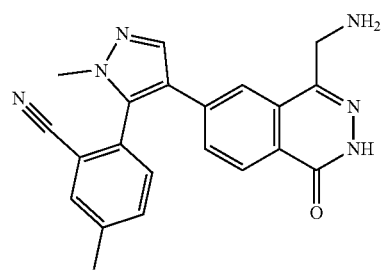 [SMILES: Cc1ccc(-c2c(-c3ccc4c(=O)[nH]nc(CN)c4c3)cnn2C)c(C#N)c1]
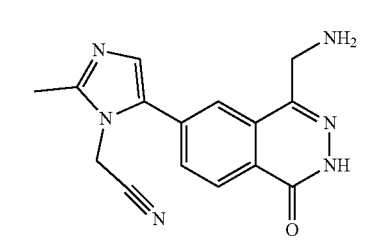 [SMILES: Cc1ncc(-c2ccc3c(=O)[nH]nc(CN)c3c2)n1CC#N]
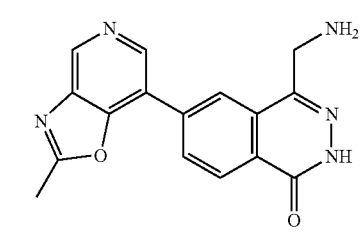 [SMILES: Cc1nc2cncc(-c3ccc4c(=O)[nH]nc(CN)c4c3)c2o1]
TABLE 3-continued
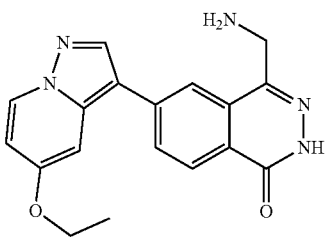 [SMILES: CCOc1ccn2ncc(-c3ccc4c(=O)[nH]nc(CN)c4c3)c2c1]
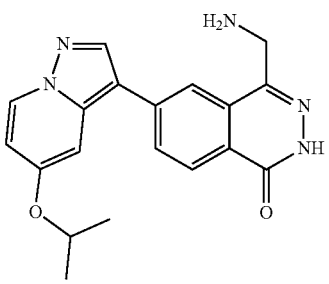 [SMILES: CC(C)Oc1ccn2ncc(-c3ccc4c(=O)[nH]nc(CN)c4c3)c2c1]
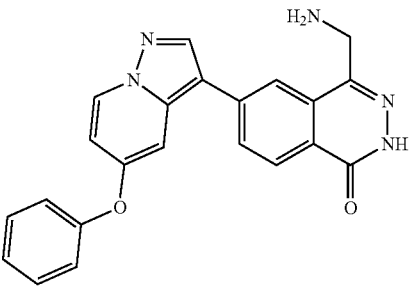 [SMILES: NCc1n[nH]c(=O)c2ccc(-c3cnn4ccc(Oc5ccccc5)cc34)cc12]
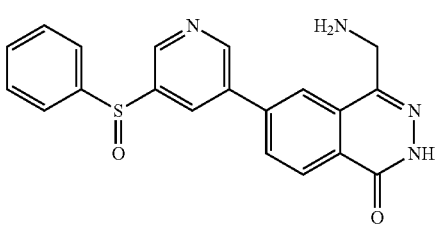 [SMILES: NCc1n[nH]c(=O)c2ccc(-c3cncc(S(=O)c4ccccc4)c3)cc12]
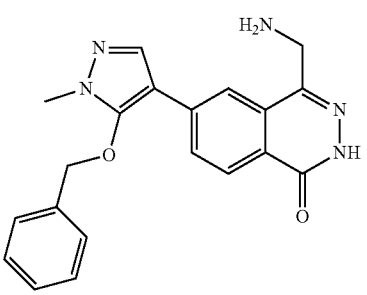 [SMILES: Cn1ncc(-c2ccc3c(=O)[nH]nc(CN)c3c2)c1OCc1ccccc1]
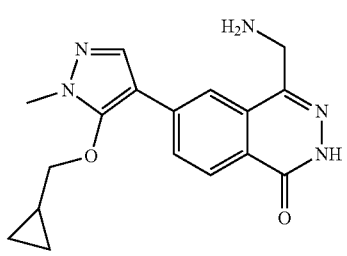 [SMILES: Cn1ncc(-c2ccc3c(=O)[nH]nc(CN)c3c2)c1OCC1CC1]

TABLE 3-continued
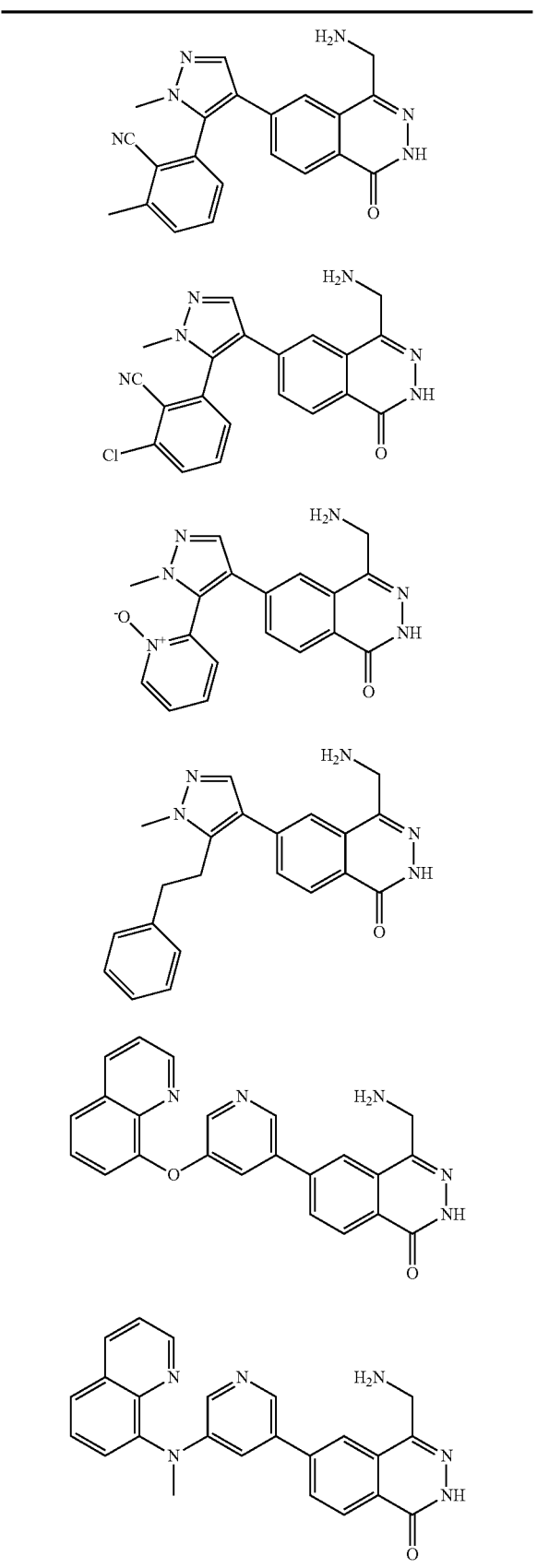
TABLE 3-continued
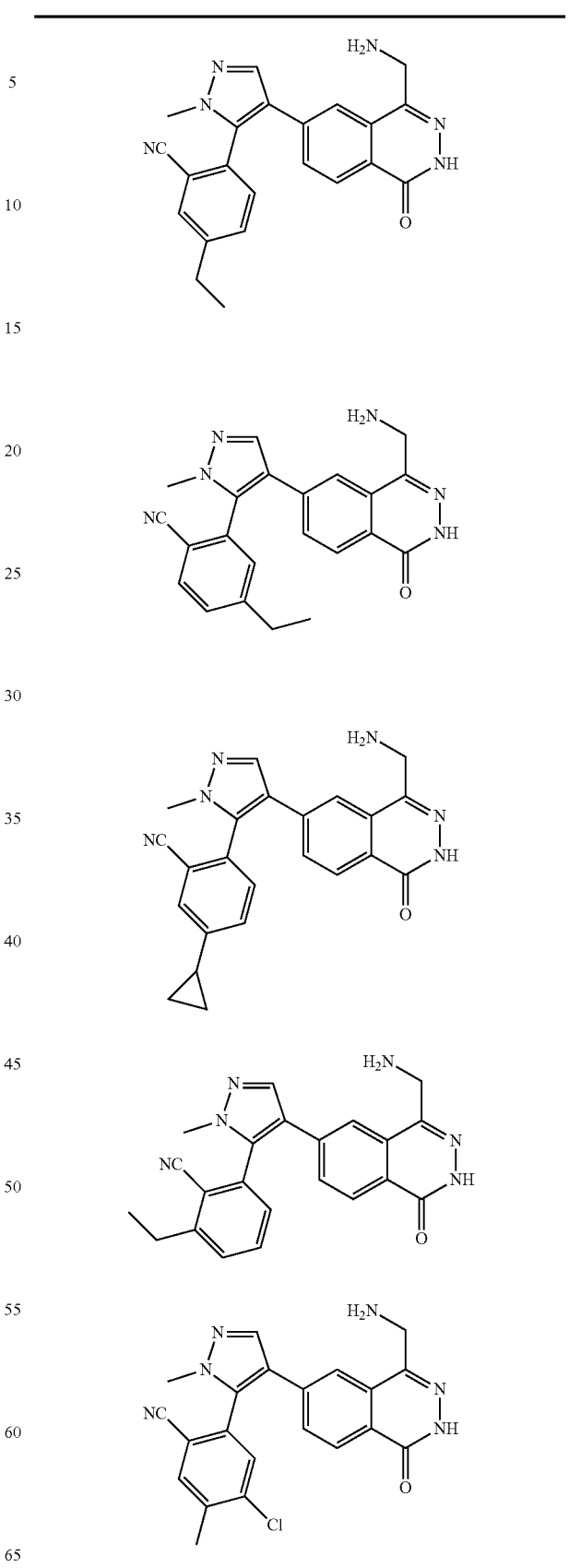

TABLE 3-continued
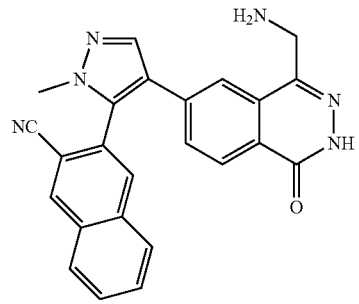 [SMILES: Cn1ncc(-c2ccc3c(=O)[nH]nc(CN)c3c2)c1-c1cc2ccccc2cc1C#N]
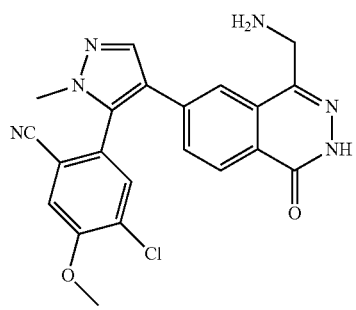 [SMILES: COc1cc(C#N)c(-c2c(-c3ccc4c(=O)[nH]nc(CN)c4c3)cnn2C)cc1Cl]
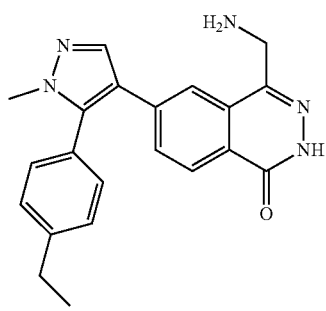 [SMILES: CCc1ccc(-c2c(-c3ccc4c(=O)[nH]nc(CN)c4c3)cnn2C)cc1]
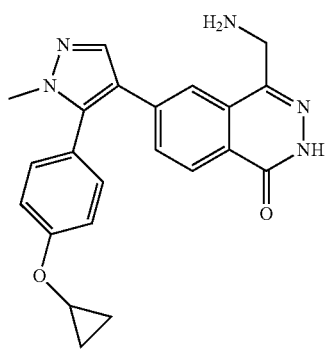 [SMILES: Cn1ncc(-c2ccc3c(=O)[nH]nc(CN)c3c2)c1-c1ccc(OC2CC2)cc1]
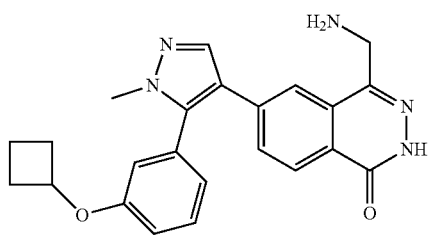 [SMILES: Cn1ncc(-c2ccc3c(=O)[nH]nc(CN)c3c2)c1-c1cccc(OC2CCC2)c1]
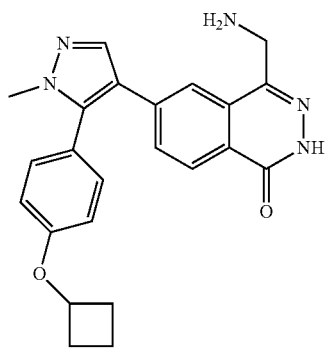 [SMILES: Cn1ncc(-c2ccc3c(=O)[nH]nc(CN)c3c2)c1-c1ccc(OC2CCC2)cc1]

TABLE 3-continued
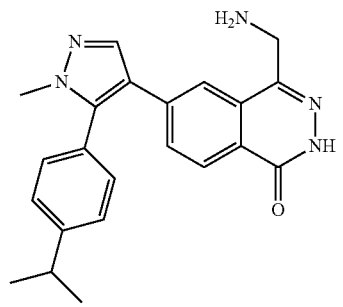 [SMILES: CC(C)c1ccc(-c2c(-c3ccc4c(=O)[nH]nc(CN)c4c3)cnn2C)cc1]
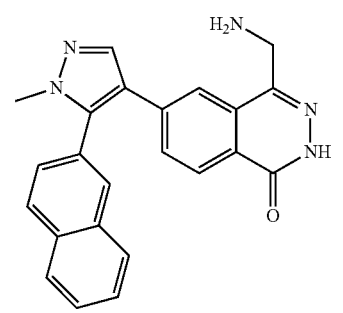 [SMILES: Cn1ncc(-c2ccc3c(=O)[nH]nc(CN)c3c2)c1-c1ccc2ccccc2c1]
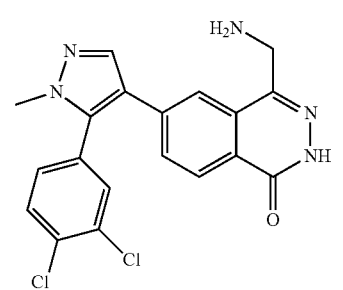 [SMILES: Cn1ncc(-c2ccc3c(=O)[nH]nc(CN)c3c2)c1-c1ccc(Cl)c(Cl)c1]
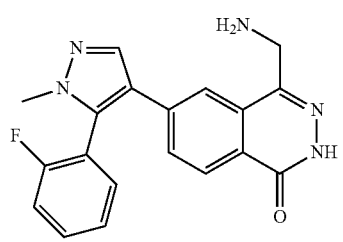 [SMILES: Cn1ncc(-c2ccc3c(=O)[nH]nc(CN)c3c2)c1-c1ccccc1F]
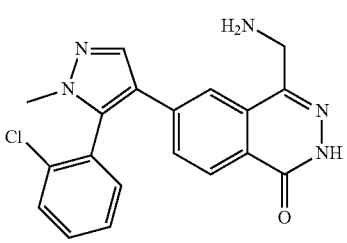 [SMILES: Cn1ncc(-c2ccc3c(=O)[nH]nc(CN)c3c2)c1-c1ccccc1Cl]
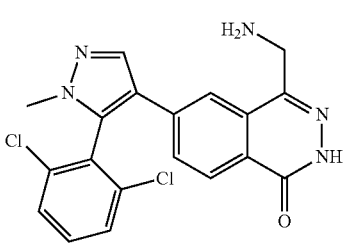 [SMILES: Cn1ncc(-c2ccc3c(=O)[nH]nc(CN)c3c2)c1-c1c(Cl)cccc1Cl]
TABLE 3-continued
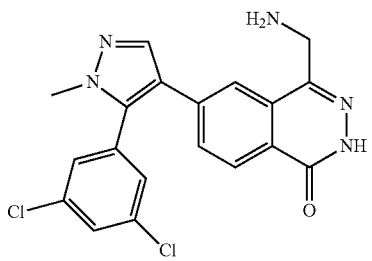 [SMILES: Cn1ncc(-c2ccc3c(=O)[nH]nc(CN)c3c2)c1-c1cc(Cl)cc(Cl)c1]
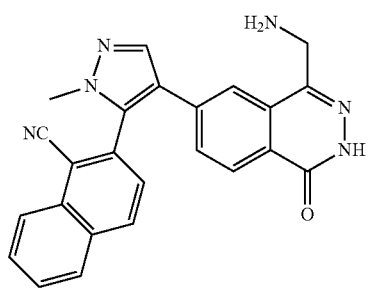 [SMILES: Cn1ncc(-c2ccc3c(=O)[nH]nc(CN)c3c2)c1-c1ccc2ccccc2c1C#N]
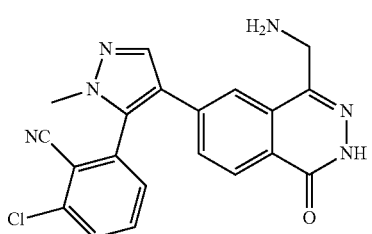
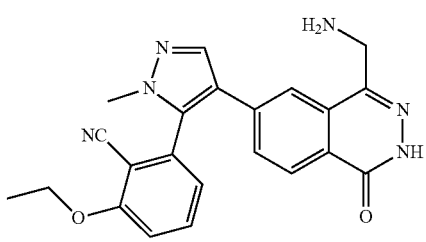 [SMILES: CCOc1cccc(-c2c(-c3ccc4c(=O)[nH]nc(CN)c4c3)cnn2C)c1C#N]
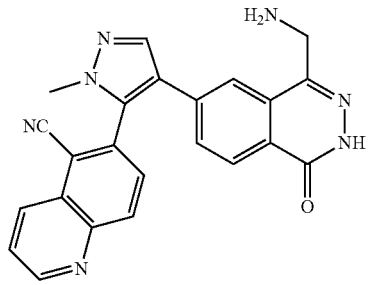 [SMILES: Cn1ncc(-c2ccc3c(=O)[nH]nc(CN)c3c2)c1-c1ccc2ncccc2c1C#N]
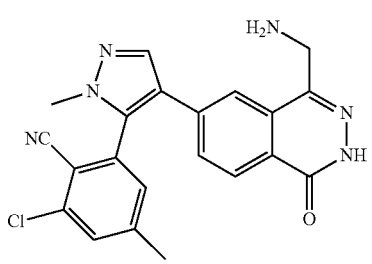 [SMILES: Cc1cc(Cl)c(C#N)c(-c2c(-c3ccc4c(=O)[nH]nc(CN)c4c3)cnn2C)c1]

TABLE 3-continued
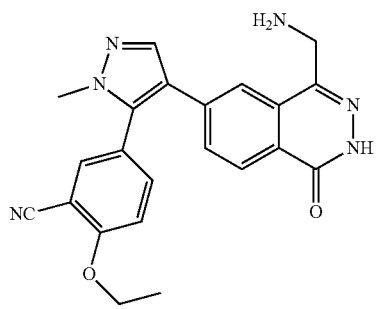 [SMILES: CCOc1ccc(-c2c(-c3ccc4c(=O)[nH]nc(CN)c4c3)cnn2C)cc1C#N]
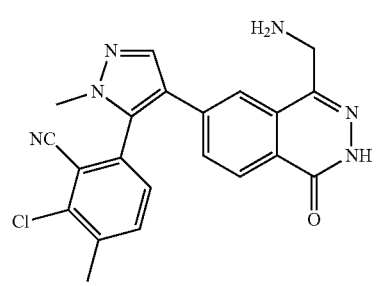 [SMILES: Cc1ccc(-c2c(-c3ccc4c(=O)[nH]nc(CN)c4c3)cnn2C)c(C#N)c1Cl]
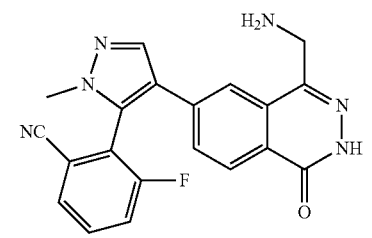 [SMILES: Cn1ncc(-c2ccc3c(=O)[nH]nc(CN)c3c2)c1-c1c(F)cccc1C#N]
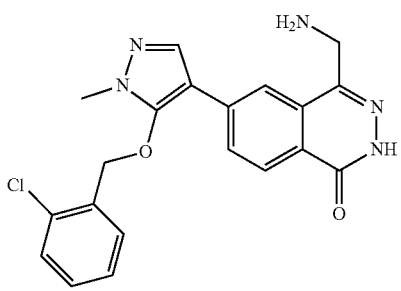 [SMILES: Cn1ncc(-c2ccc3c(=O)[nH]nc(CN)c3c2)c1OCc1ccccc1Cl]
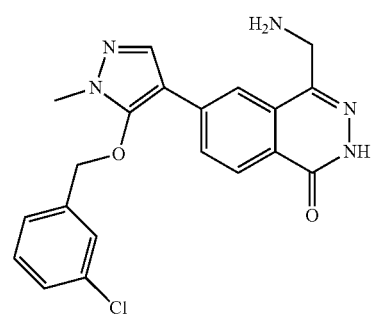 [SMILES: Cn1ncc(-c2ccc3c(=O)[nH]nc(CN)c3c2)c1OCc1cccc(Cl)c1]
TABLE 3-continued
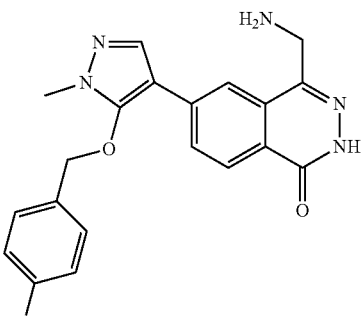
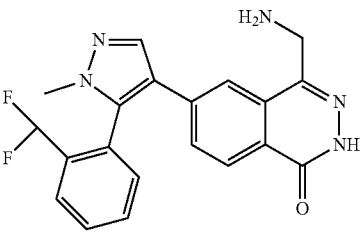 [SMILES: Cn1ncc(-c2ccc3c(=O)[nH]nc(CN)c3c2)c1-c1ccccc1C(F)F]
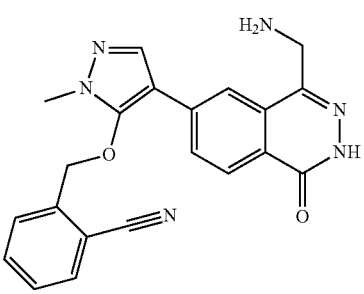 [SMILES: Cn1ncc(-c2ccc3c(=O)[nH]nc(CN)c3c2)c1OCc1ccccc1C#N]
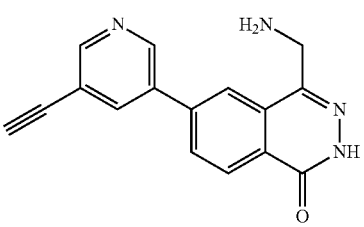 [SMILES: C#Cc1cncc(-c2ccc3c(=O)[nH]nc(CN)c3c2)c1]
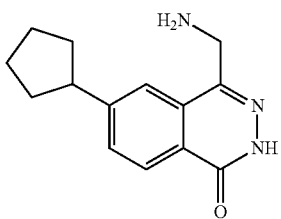 [SMILES: NCc1n[nH]c(=O)c2ccc(C3CCCC3)cc12]
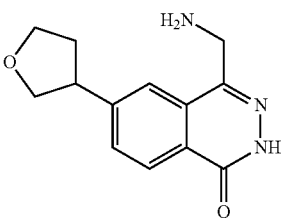 [SMILES: NCc1n[nH]c(=O)c2ccc(C3CCOC3)cc12]

TABLE 3-continued
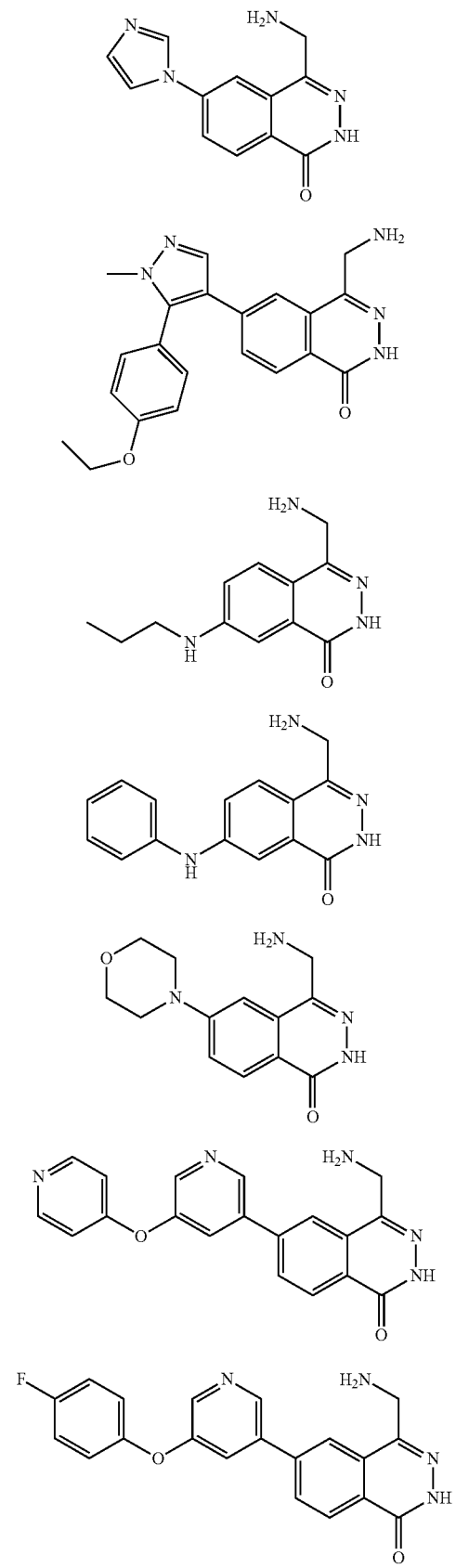
TABLE 3-continued
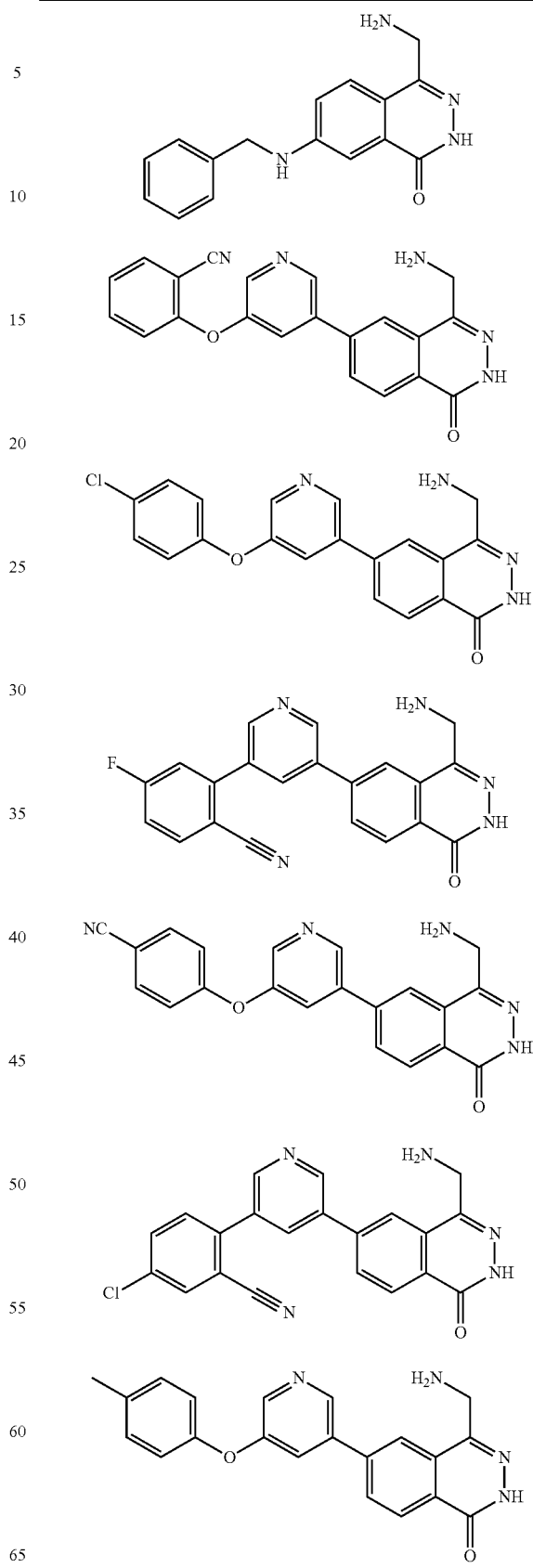

TABLE 3-continued
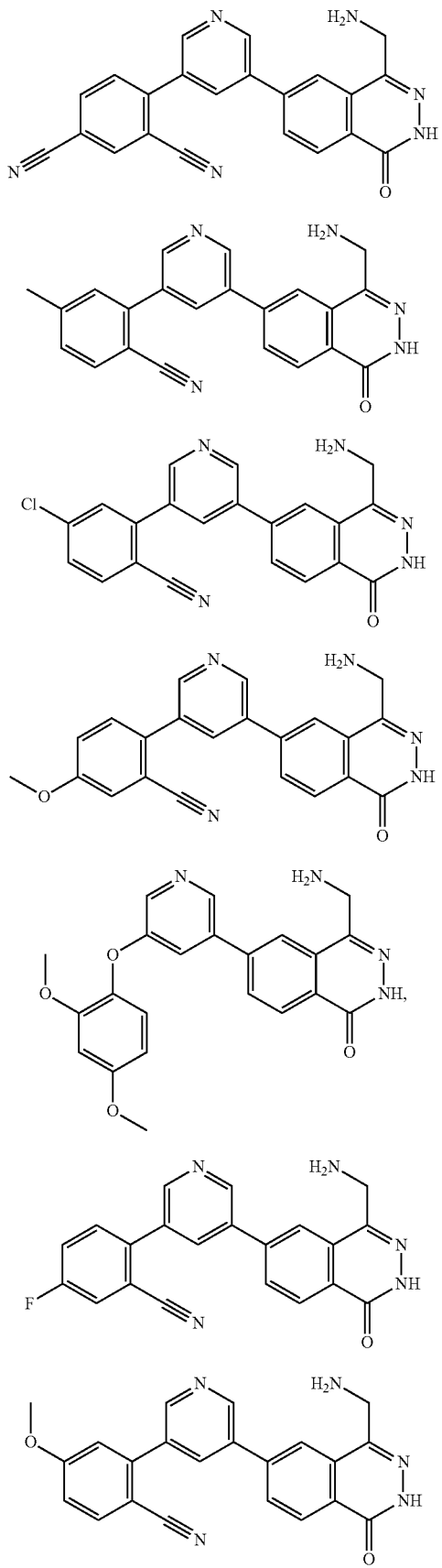
TABLE 3-continued
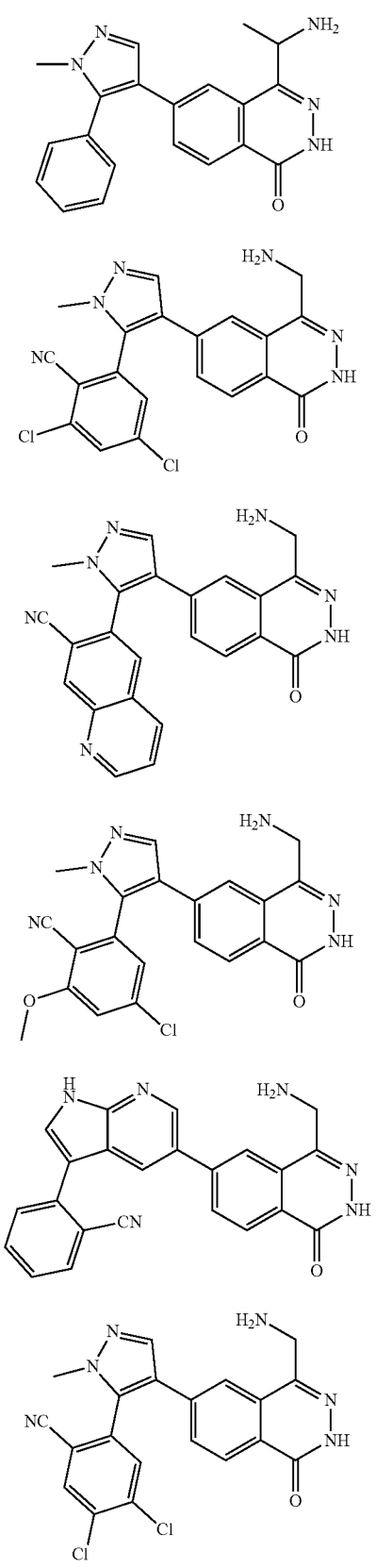

TABLE 3-continued
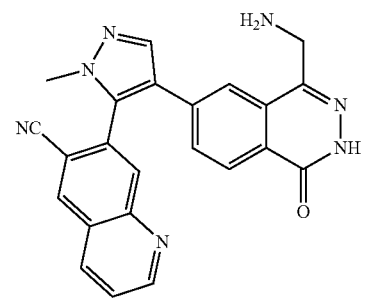 [SMILES: Cn1ncc(-c2ccc3c(=O)[nH]nc(CN)c3c2)c1-c1cc2ncccc2cc1C#N]
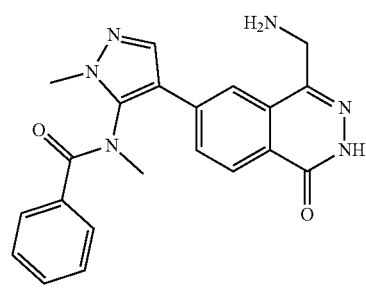 [SMILES: CN(C(=O)c1ccccc1)c1c(-c2ccc3c(=O)[nH]nc(CN)c3c2)cnn1C]
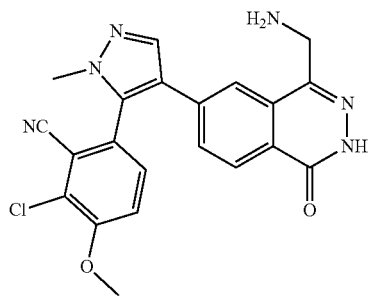 [SMILES: COc1ccc(-c2c(-c3ccc4c(=O)[nH]nc(CN)c4c3)cnn2C)c(C#N)c1Cl]
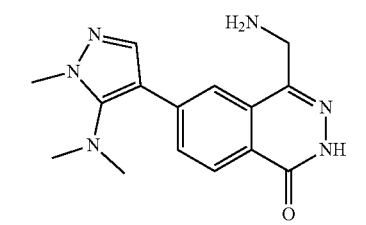 [SMILES: CN(C)c1c(-c2ccc3c(=O)[nH]nc(CN)c3c2)cnn1C]
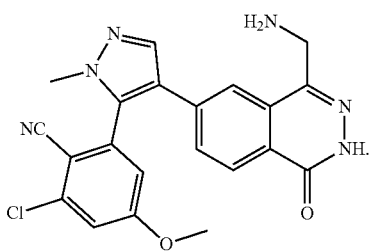 [SMILES: COc1cc(Cl)c(C#N)c(-c2c(-c3ccc4c(=O)[nH]nc(CN)c4c3)cnn2C)c1]
TABLE 3-continued
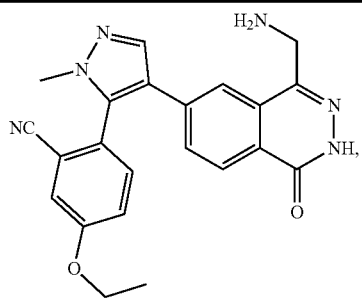
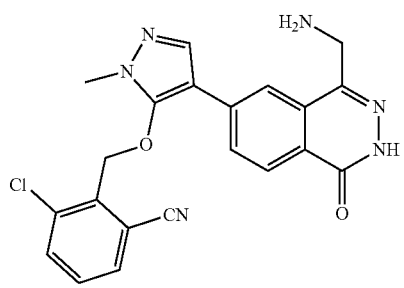 [SMILES: Cn1ncc(-c2ccc3c(=O)[nH]nc(CN)c3c2)c1OCc1c(Cl)cccc1C#N]
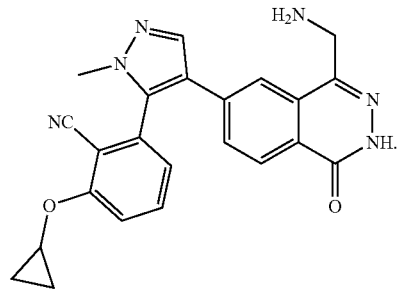 [SMILES: Cn1ncc(-c2ccc3c(=O)[nH]nc(CN)c3c2)c1-c1cccc(OC2CC2)c1C#N]
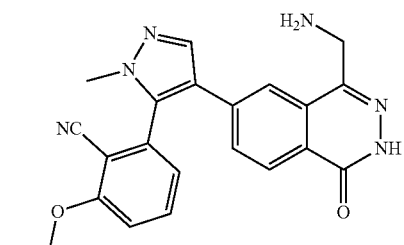
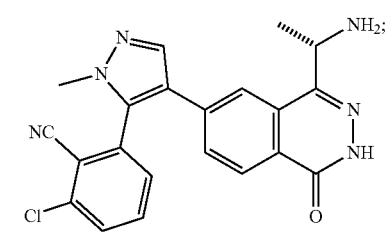 [SMILES: C[C@H](N)c1n[nH]c(=O)c2ccc(-c3cnn(C)c3-c3cccc(Cl)c3C#N)cc12]
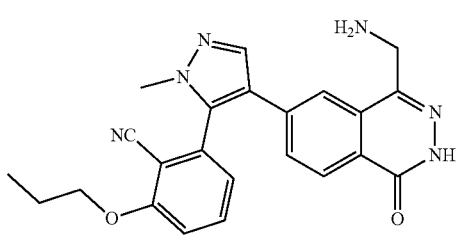 [SMILES: CCCOc1cccc(-c2c(-c3ccc4c(=O)[nH]nc(CN)c4c3)cnn2C)c1C#N]

TABLE 3-continued
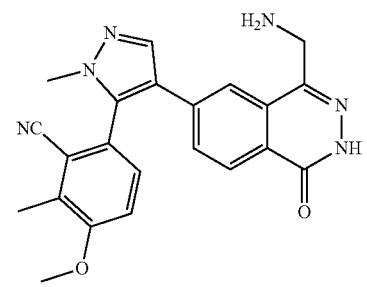 [SMILES: COc1ccc(-c2c(-c3ccc4c(=O)[nH]nc(CN)c4c3)cnn2C)c(C#N)c1C]
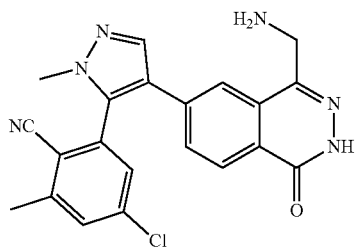 [SMILES: Cc1cc(Cl)cc(-c2c(-c3ccc4c(=O)[nH]nc(CN)c4c3)cnn2C)c1C#N]
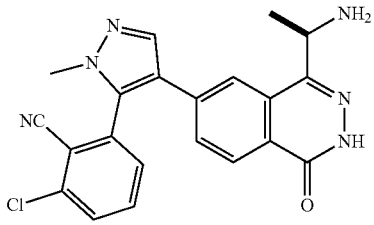 [SMILES: C[C@@H](N)c1n[nH]c(=O)c2ccc(-c3cnn(C)c3-c3cccc(Cl)c3C#N)cc12]
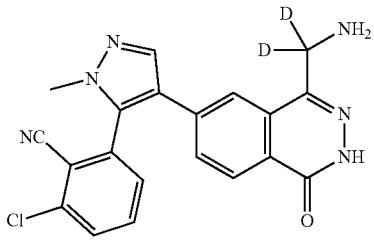 [SMILES: [2H]C([2H])(N)c1n[nH]c(=O)c2ccc(-c3cnn(C)c3-c3cccc(Cl)c3C#N)cc12]
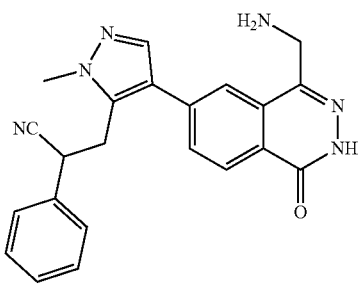 [SMILES: Cn1ncc(-c2ccc3c(=O)[nH]nc(CN)c3c2)c1CC(C#N)c1ccccc1]
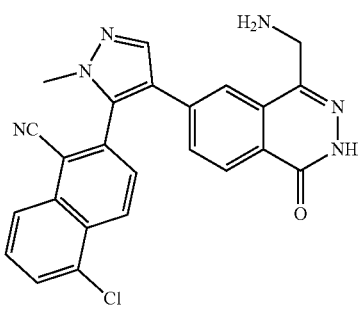 [SMILES: Cn1ncc(-c2ccc3c(=O)[nH]nc(CN)c3c2)c1-c1ccc2c(Cl)cccc2c1C#N]
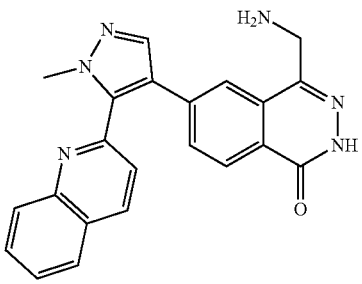 [SMILES: Cn1ncc(-c2ccc3c(=O)[nH]nc(CN)c3c2)c1-c1ccc2ccccc2n1]

TABLE 3-continued
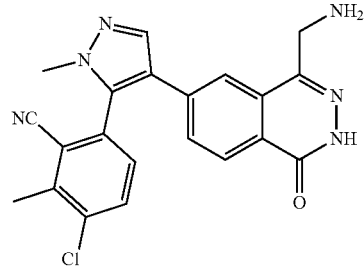 [SMILES: Cc1c(Cl)ccc(-c2c(-c3ccc4c(=O)[nH]nc(CN)c4c3)cnn2C)c1C#N]
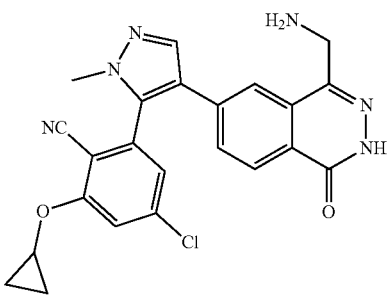 [SMILES: Cn1ncc(-c2ccc3c(=O)[nH]nc(CN)c3c2)c1-c1cc(Cl)cc(OC2CC2)c1C#N]

TABLE 3-continued
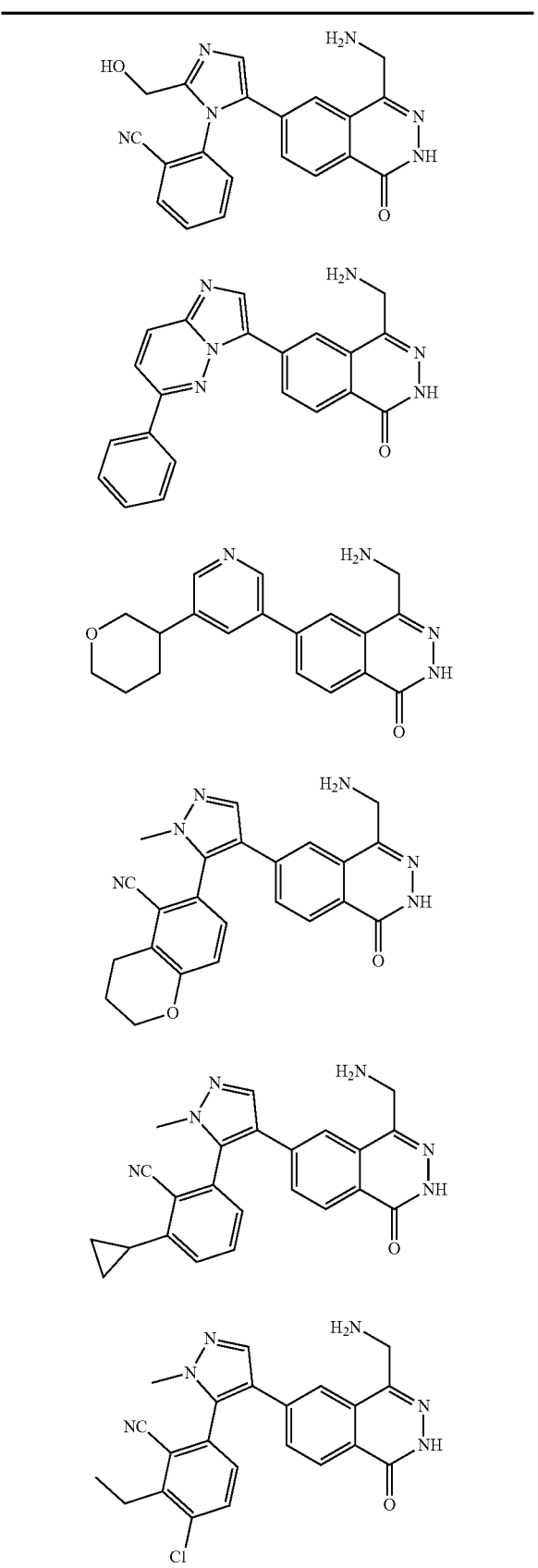
TABLE 3-continued
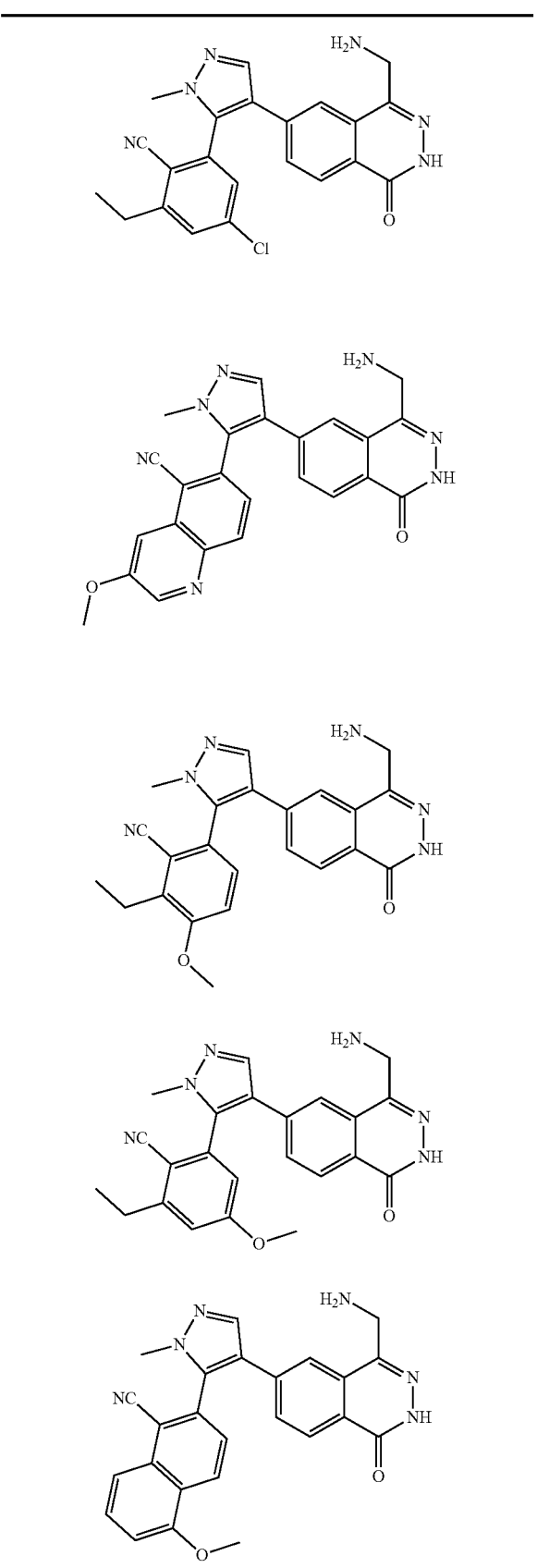

449
TABLE 3-continued
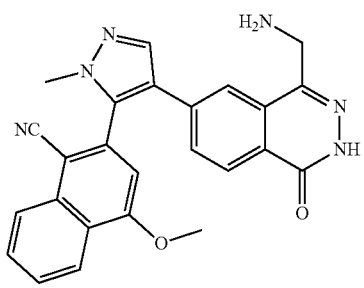 [SMILES: COc1cc(-c2c(-c3ccc4c(=O)[nH]nc(CN)c4c3)cnn2C)c(C#N)c2ccccc12]
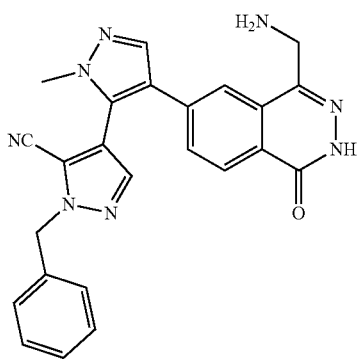
450
TABLE 3-continued
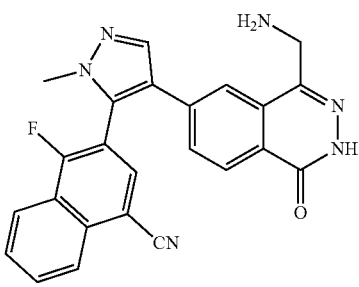 [SMILES: Cn1ncc(-c2ccc3c(=O)[nH]nc(CN)c3c2)c1-c1cc(C#N)c2ccccc2c1F]
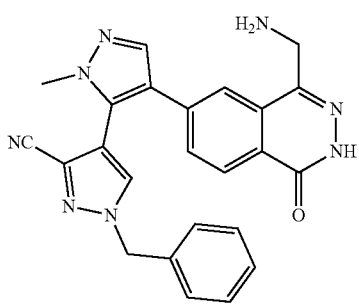 [SMILES: Cn1ncc(-c2ccc3c(=O)[nH]nc(CN)c3c2)c1-c1cn(Cc2ccccc2)nc1C#N]
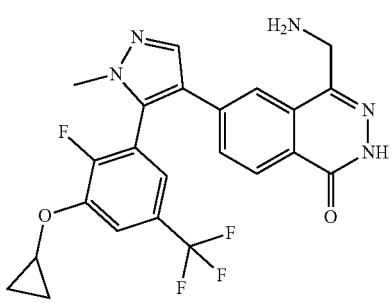 [SMILES: Cn1ncc(-c2ccc3c(=O)[nH]nc(CN)c3c2)c1-c1cc(C(F)(F)F)cc(OC2CC2)c1F]
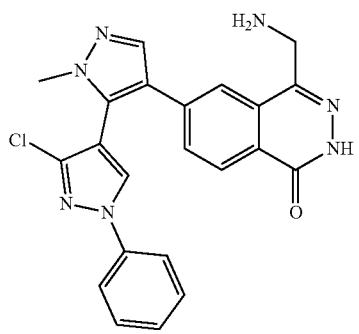 [SMILES: Cn1ncc(-c2ccc3c(=O)[nH]nc(CN)c3c2)c1-c1cn(-c2ccccc2)nc1Cl]

TABLE 3-continued
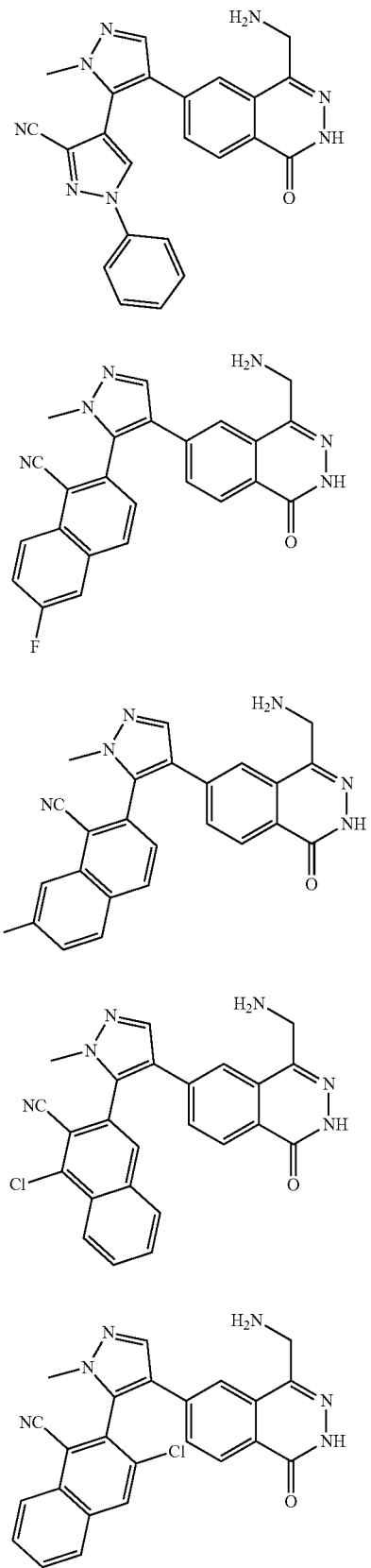
TABLE 3-continued
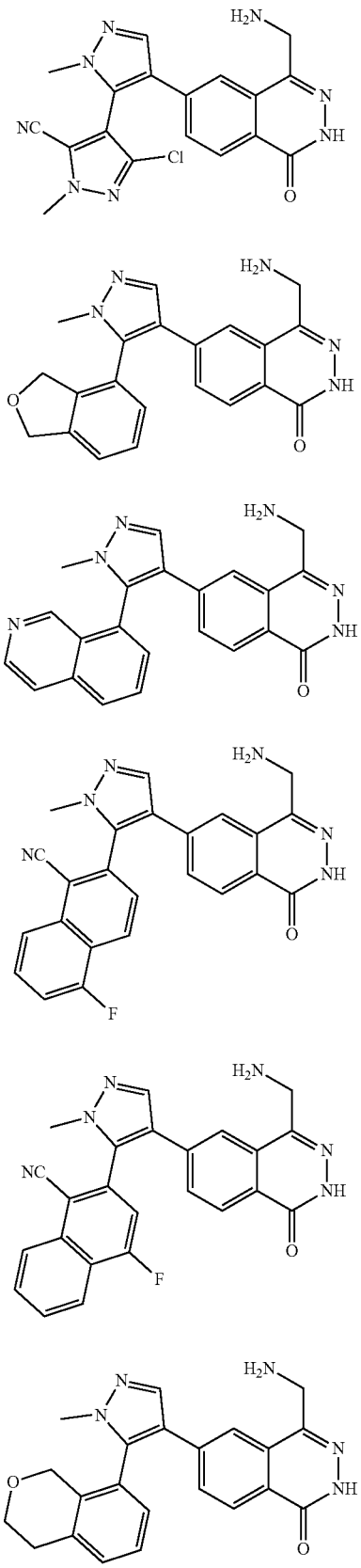

TABLE 3-continued
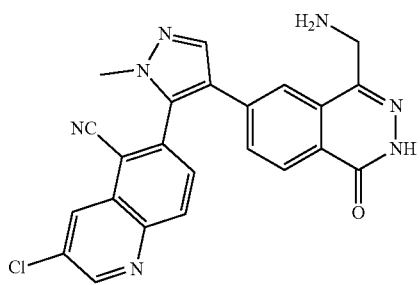 [SMILES: Cn1ncc(-c2ccc3c(=O)[nH]nc(CN)c3c2)c1-c1ccc2ncc(Cl)cc2c1C#N]
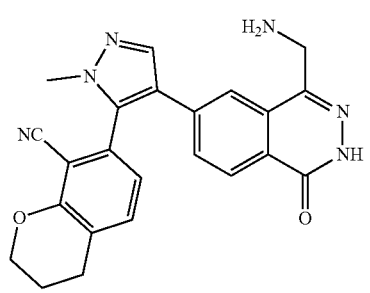 [SMILES: Cn1ncc(-c2ccc3c(=O)[nH]nc(CN)c3c2)c1-c1ccc2c(c1C#N)OCCC2]
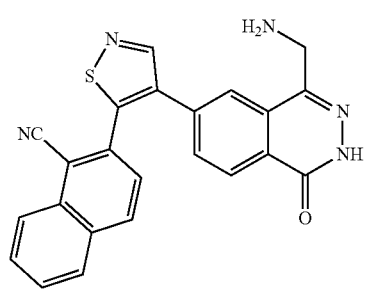 [SMILES: N#Cc1c(-c2sncc2-c2ccc3c(=O)[nH]nc(CN)c3c2)ccc2ccccc12]
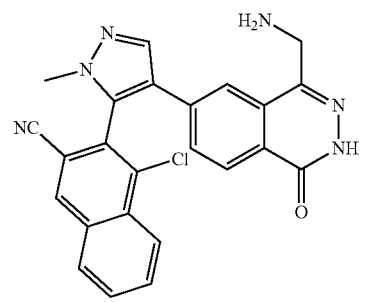 [SMILES: Cn1ncc(-c2ccc3c(=O)[nH]nc(CN)c3c2)c1-c1c(C#N)cc2ccccc2c1Cl]
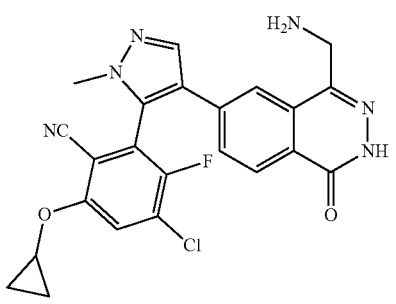 [SMILES: Cn1ncc(-c2ccc3c(=O)[nH]nc(CN)c3c2)c1-c1c(F)c(Cl)cc(OC2CC2)c1C#N]
TABLE 3-continued
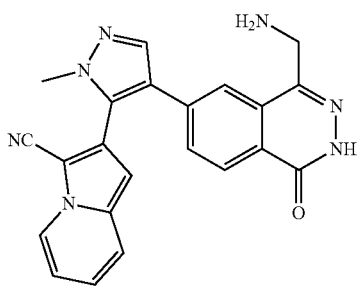 [SMILES: Cn1ncc(-c2ccc3c(=O)[nH]nc(CN)c3c2)c1-c1cc2ccccn2c1C#N]
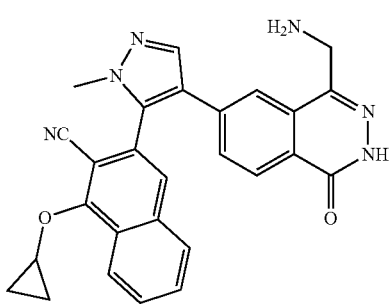 [SMILES: Cn1ncc(-c2ccc3c(=O)[nH]nc(CN)c3c2)c1-c1cc2ccccc2c(OC2CC2)c1C#N]
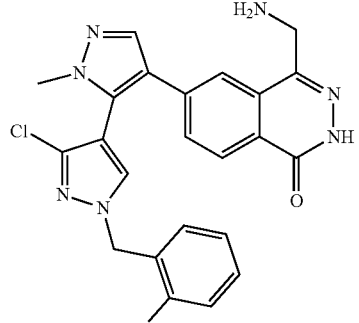
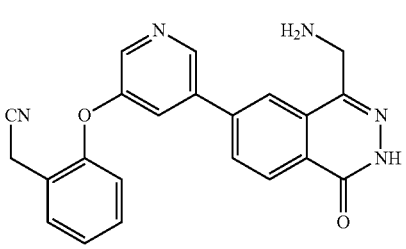 [SMILES: N#CCc1ccccc1Oc1cncc(-c2ccc3c(=O)[nH]nc(CN)c3c2)c1]

TABLE 3-continued
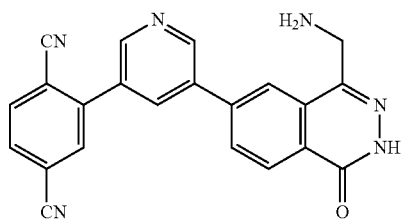 [SMILES: N#Cc1ccc(C#N)c(-c2cncc(-c3ccc4c(=O)[nH]nc(CN)c4c3)c2)c1]
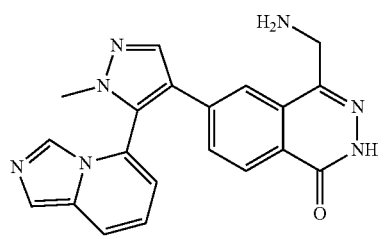 [SMILES: Cn1ncc(-c2ccc3c(=O)[nH]nc(CN)c3c2)c1-c1cccc2cncn12]
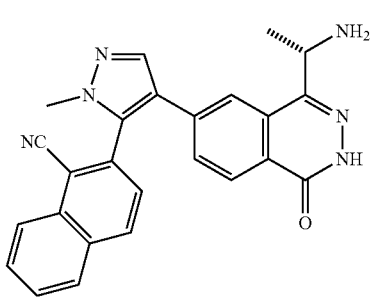 [SMILES: C[C@H](N)c1n[nH]c(=O)c2ccc(-c3cnn(C)c3-c3ccc4ccccc4c3C#N)cc12]
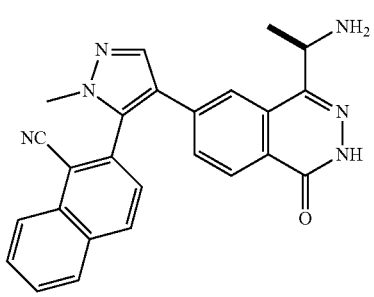 [SMILES: C[C@@H](N)c1n[nH]c(=O)c2ccc(-c3cnn(C)c3-c3ccc4ccccc4c3C#N)cc12]
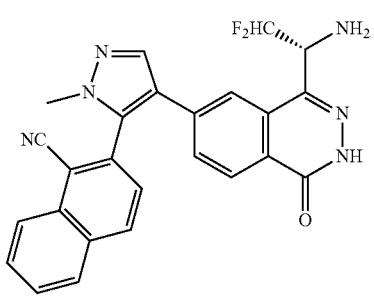 [SMILES: Cn1ncc(-c2ccc3c(=O)[nH]nc([C@@H](N)C(F)F)c3c2)c1-c1ccc2ccccc2c1C#N]
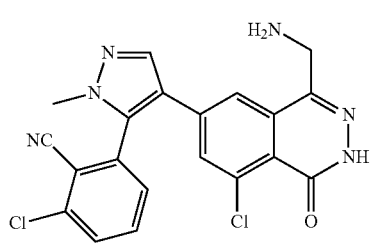
TABLE 3-continued
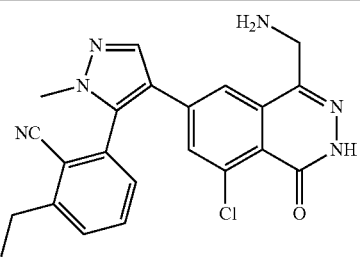
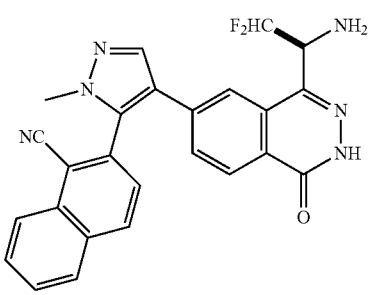 [SMILES: Cn1ncc(-c2ccc3c(=O)[nH]nc([C@H](N)C(F)F)c3c2)c1-c1ccc2ccccc2c1C#N]
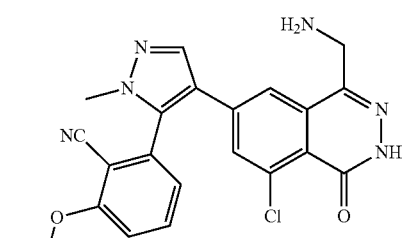
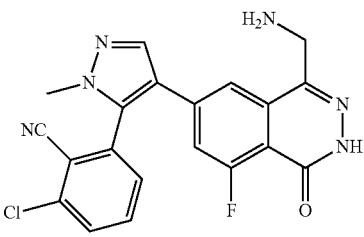 [SMILES: Cn1ncc(-c2cc(F)c3c(=O)[nH]nc(CN)c3c2)c1-c1cccc(Cl)c1C#N]
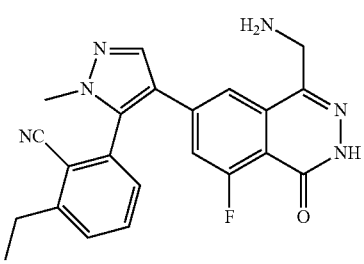 [SMILES: CCc1cccc(-c2c(-c3cc(F)c4c(=O)[nH]nc(CN)c4c3)cnn2C)c1C#N]
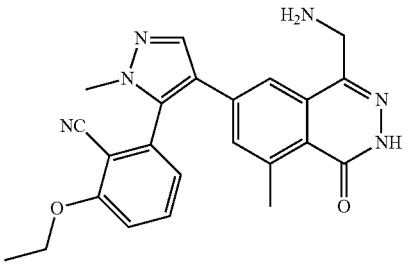 [SMILES: CCOc1cccc(-c2c(-c3cc(C)c4c(=O)[nH]nc(CN)c4c3)cnn2C)c1C#N]

TABLE 3-continued
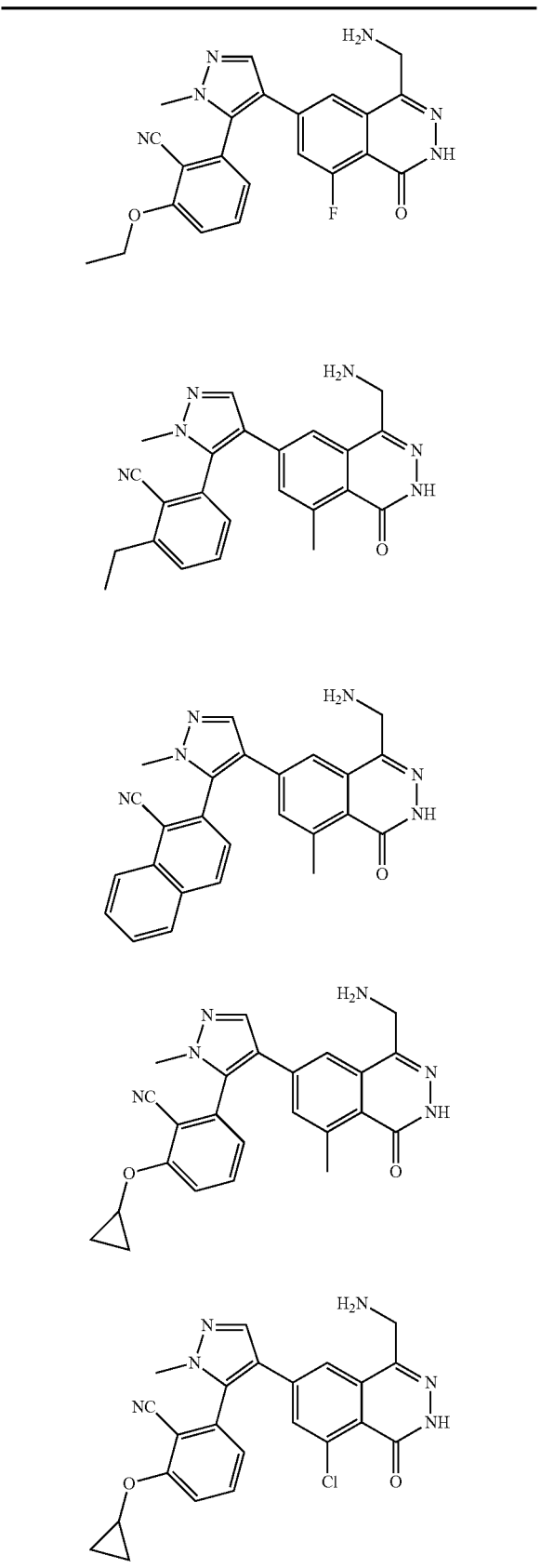
TABLE 3-continued
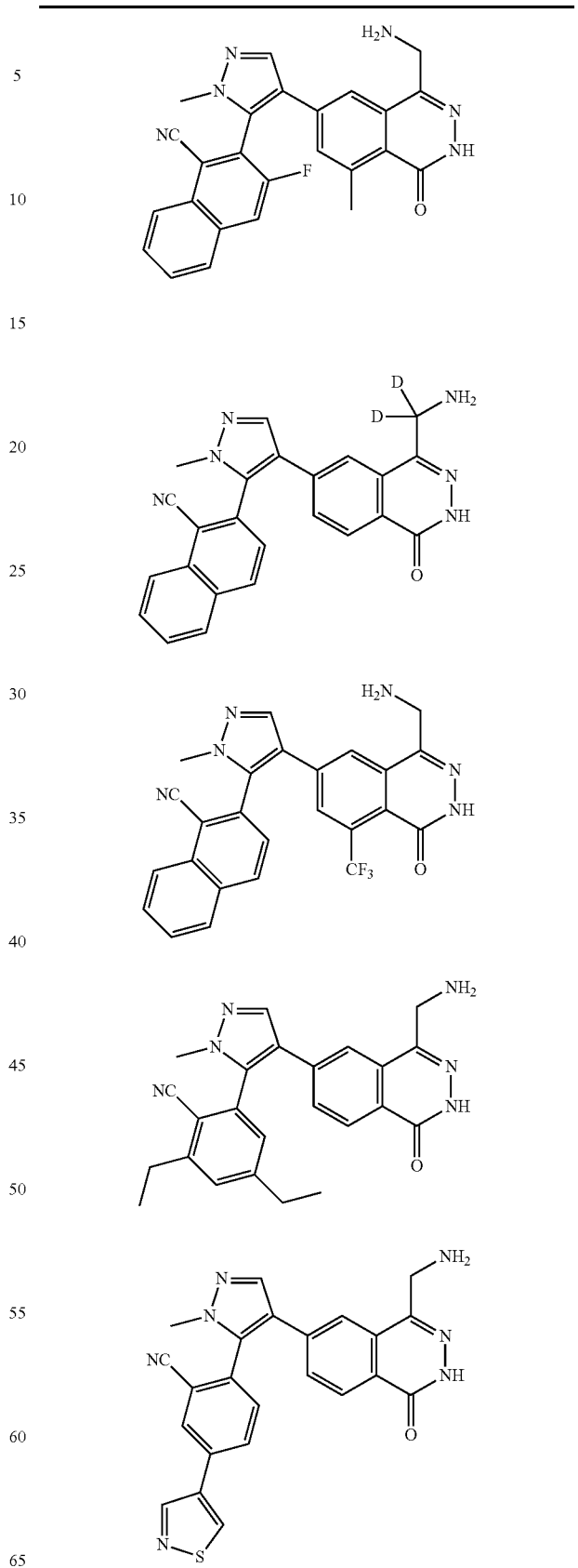

TABLE 3-continued
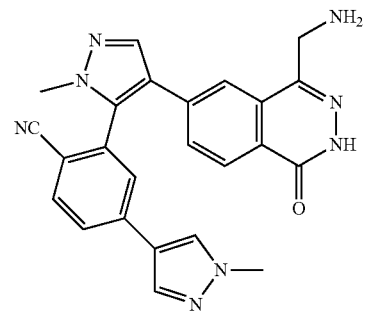 [SMILES: Cn1cc(-c2ccc(C#N)c(-c3c(-c4ccc5c(=O)[nH]nc(CN)c5c4)cnn3C)c2)cn1]
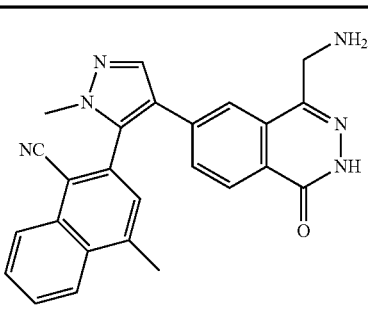
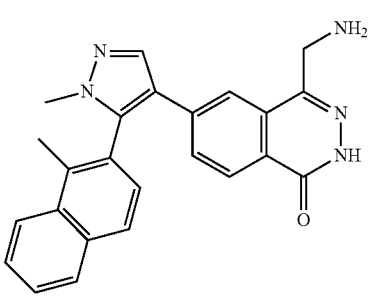 [SMILES: Cc1c(-c2c(-c3ccc4c(=O)[nH]nc(CN)c4c3)cnn2C)ccc2ccccc12]
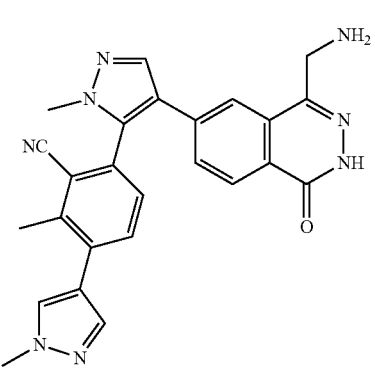 [SMILES: Cc1c(-c2cnn(C)c2)ccc(-c2c(-c3ccc4c(=O)[nH]nc(CN)c4c3)cnn2C)c1C#N]
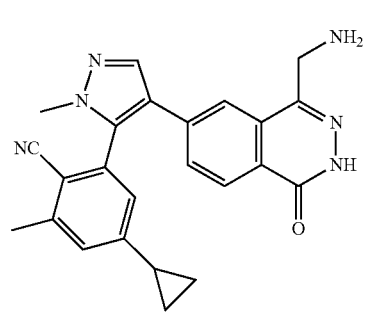 [SMILES: Cc1cc(C2CC2)cc(-c2c(-c3ccc4c(=O)[nH]nc(CN)c4c3)cnn2C)c1C#N]
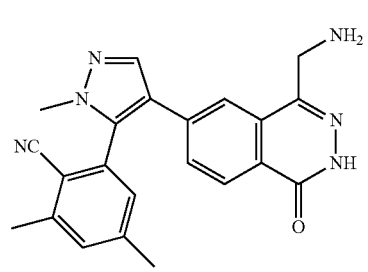 [SMILES: Cc1cc(C)c(C#N)c(-c2c(-c3ccc4c(=O)[nH]nc(CN)c4c3)cnn2C)c1]

461
TABLE 3-continued
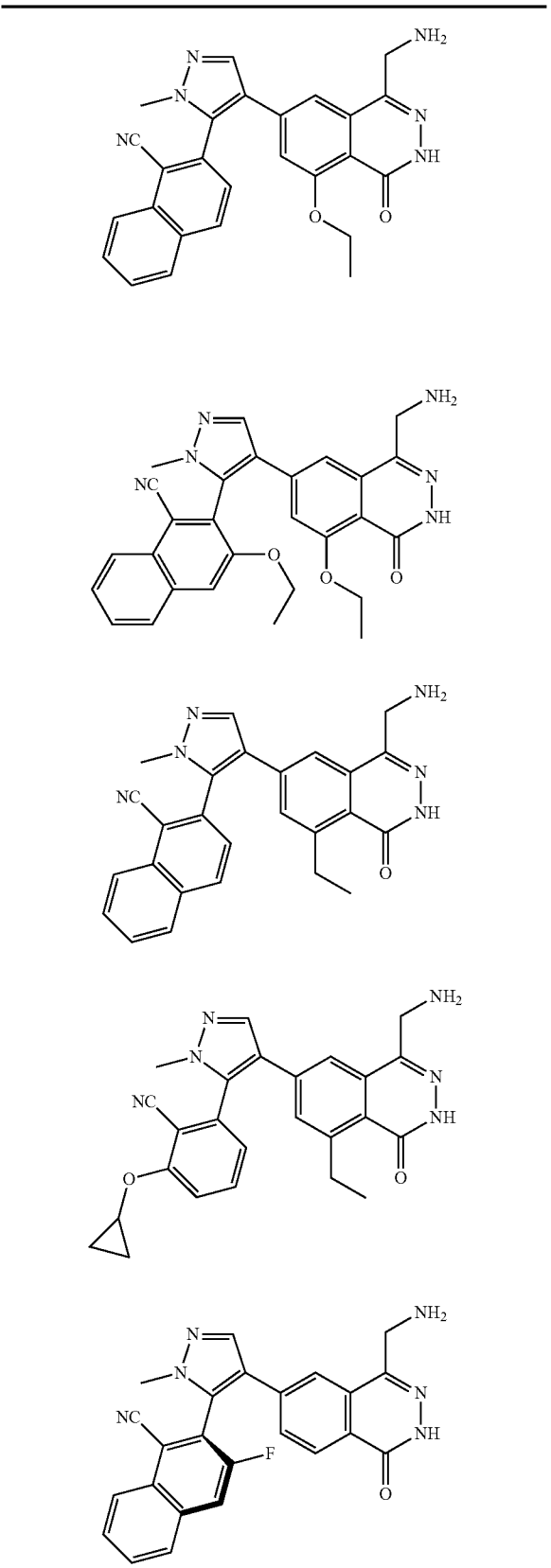
462
TABLE 3-continued
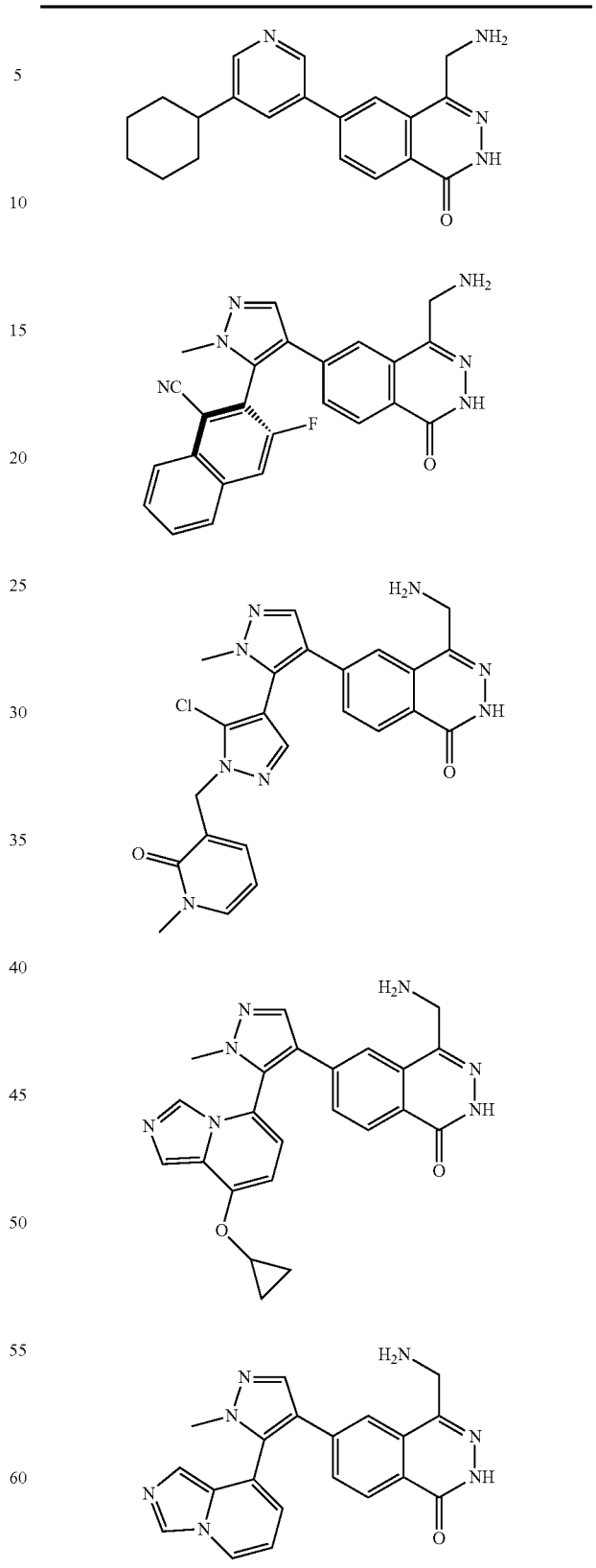

TABLE 3-continued
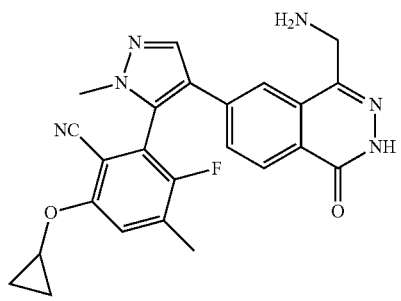 [SMILES: Cc1cc(OC2CC2)c(C#N)c(-c2c(-c3ccc4c(=O)[nH]nc(CN)c4c3)cnn2C)c1F]
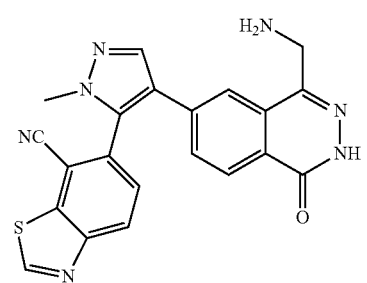 [SMILES: Cn1ncc(-c2ccc3c(=O)[nH]nc(CN)c3c2)c1-c1ccc2ncsc2c1C#N]
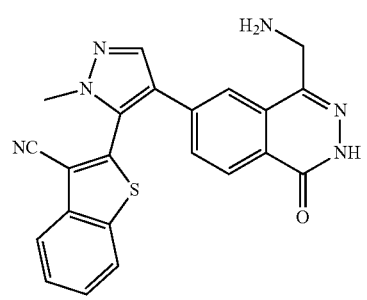 [SMILES: Cn1ncc(-c2ccc3c(=O)[nH]nc(CN)c3c2)c1-c1sc2ccccc2c1C#N]
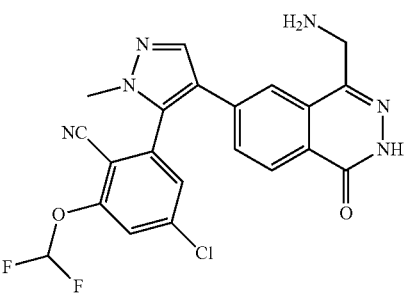 [SMILES: Cn1ncc(-c2ccc3c(=O)[nH]nc(CN)c3c2)c1-c1cc(Cl)cc(OC(F)F)c1C#N]
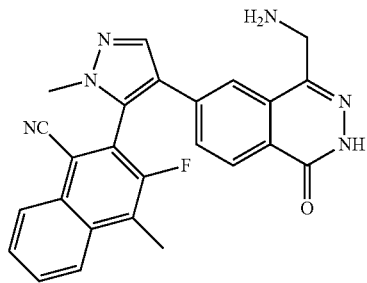 [SMILES: Cc1c(F)c(-c2c(-c3ccc4c(=O)[nH]nc(CN)c4c3)cnn2C)c(C#N)c2ccccc12]
TABLE 3-continued
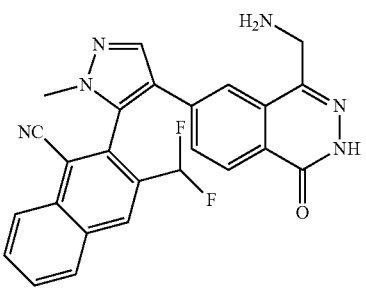 [SMILES: Cn1ncc(-c2ccc3c(=O)[nH]nc(CN)c3c2)c1-c1c(C(F)F)cc2ccccc2c1C#N]
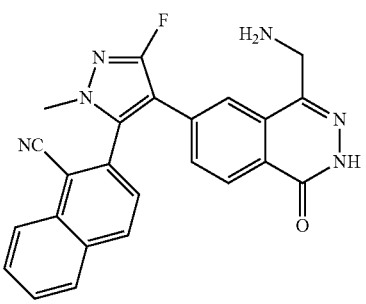 [SMILES: Cn1nc(F)c(-c2ccc3c(=O)[nH]nc(CN)c3c2)c1-c1ccc2ccccc2c1C#N]
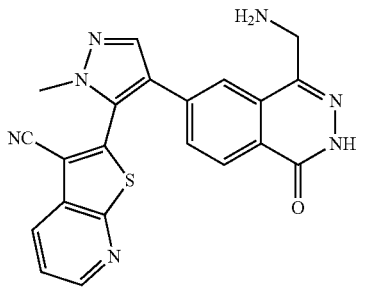
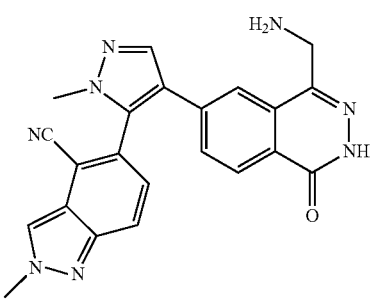 [SMILES: Cn1cc2c(C#N)c(-c3c(-c4ccc5c(=O)[nH]nc(CN)c5c4)cnn3C)ccc2n1]
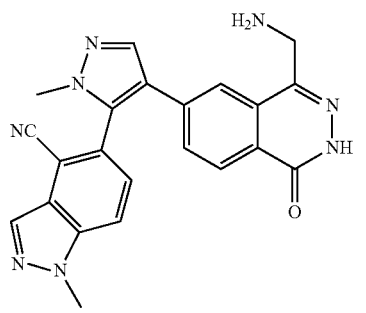 [SMILES: Cn1ncc(-c2ccc3c(=O)[nH]nc(CN)c3c2)c1-c1ccc2c(cnn2C)c1C#N]

TABLE 3-continued
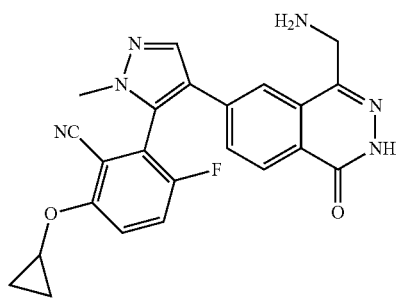 [SMILES: Cn1ncc(-c2ccc3c(=O)[nH]nc(CN)c3c2)c1-c1c(F)ccc(OC2CC2)c1C#N]
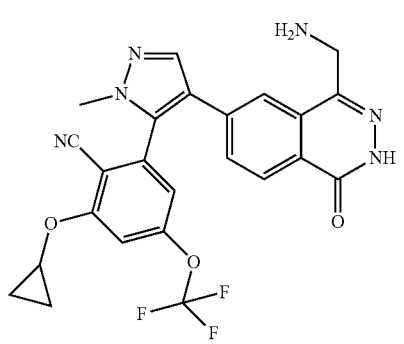 [SMILES: Cn1ncc(-c2ccc3c(=O)[nH]nc(CN)c3c2)c1-c1cc(OC(F)(F)F)cc(OC2CC2)c1C#N]
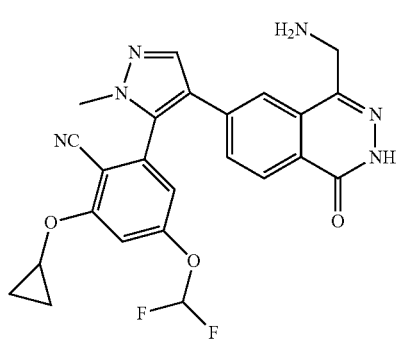 [SMILES: Cn1ncc(-c2ccc3c(=O)[nH]nc(CN)c3c2)c1-c1cc(OC(F)F)cc(OC2CC2)c1C#N]
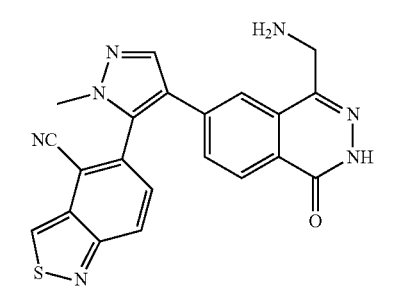 [SMILES: Cn1ncc(-c2ccc3c(=O)[nH]nc(CN)c3c2)c1-c1ccc2nscc2c1C#N]
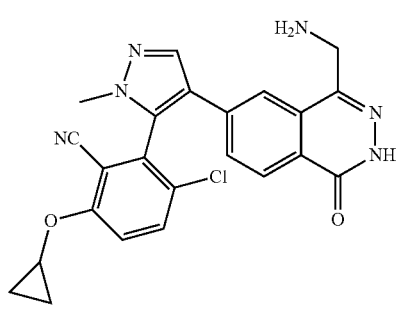 [SMILES: Cn1ncc(-c2ccc3c(=O)[nH]nc(CN)c3c2)c1-c1c(Cl)ccc(OC2CC2)c1C#N]
TABLE 3-continued
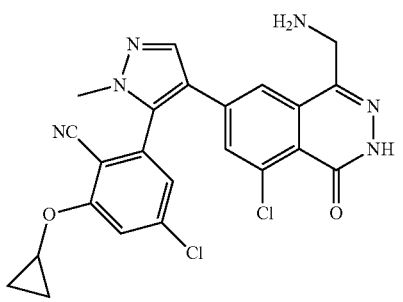 [SMILES: Cn1ncc(-c2cc(Cl)c3c(=O)[nH]nc(CN)c3c2)c1-c1cc(Cl)cc(OC2CC2)c1C#N]
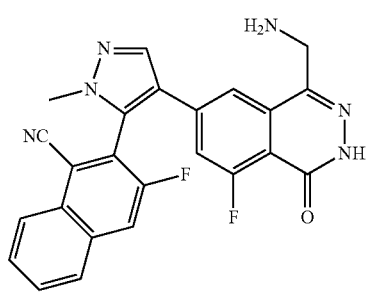 [SMILES: Cn1ncc(-c2cc(F)c3c(=O)[nH]nc(CN)c3c2)c1-c1c(F)cc2ccccc2c1C#N]
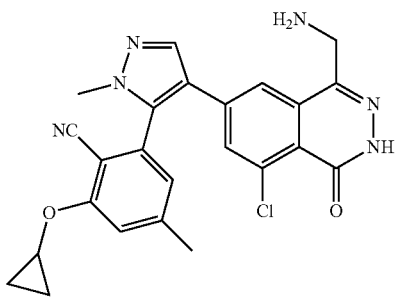 [SMILES: Cc1cc(OC2CC2)c(C#N)c(-c2c(-c3cc(Cl)c4c(=O)[nH]nc(CN)c4c3)cnn2C)c1]
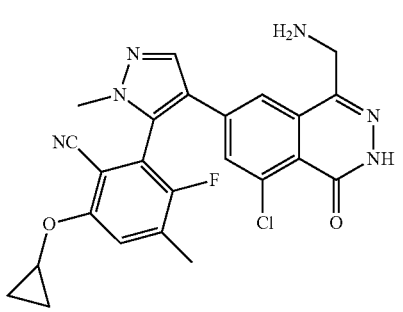 [SMILES: Cc1cc(OC2CC2)c(C#N)c(-c2c(-c3cc(Cl)c4c(=O)[nH]nc(CN)c4c3)cnn2C)c1F]
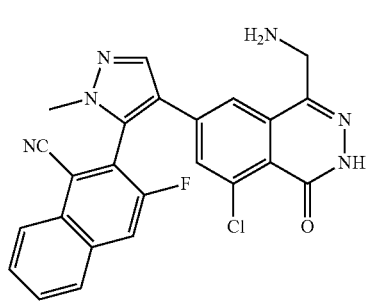 [SMILES: Cn1ncc(-c2cc(Cl)c3c(=O)[nH]nc(CN)c3c2)c1-c1c(F)cc2ccccc2c1C#N]

TABLE 3-continued
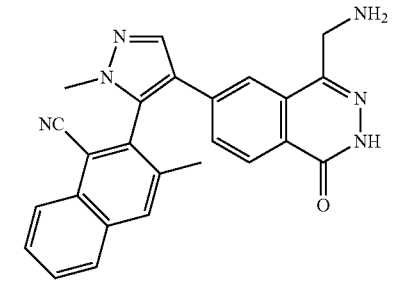 [SMILES: Cc1cc2ccccc2c(C#N)c1-c1c(-c2ccc3c(=O)[nH]nc(CN)c3c2)cnn1C]
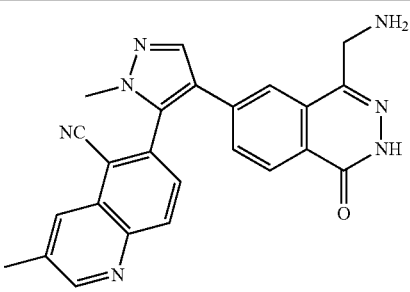
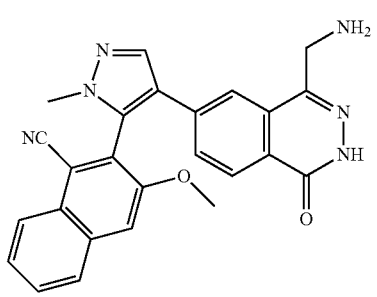 [SMILES: COc1cc2ccccc2c(C#N)c1-c1c(-c2ccc3c(=O)[nH]nc(CN)c3c2)cnn1C]
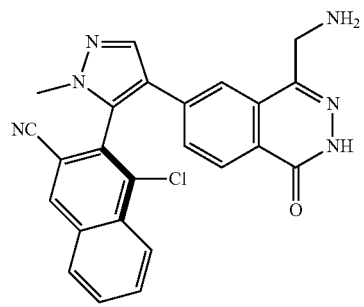
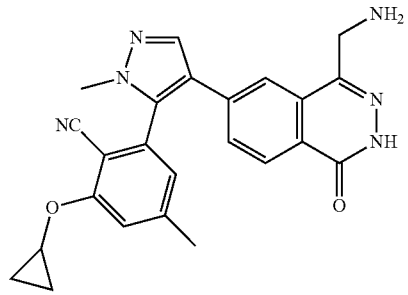 [SMILES: Cc1cc(OC2CC2)c(C#N)c(-c2c(-c3ccc4c(=O)[nH]nc(CN)c4c3)cnn2C)c1]
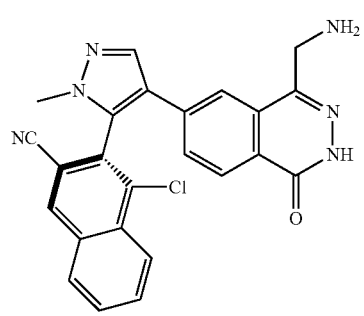
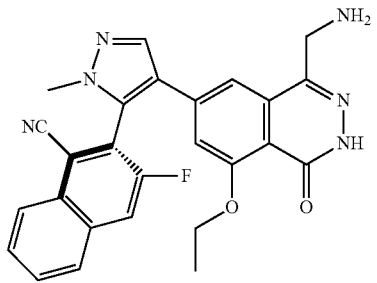
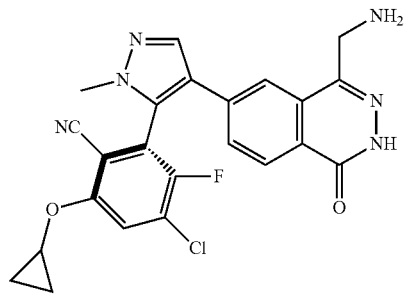
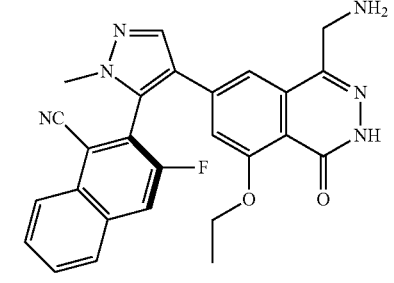
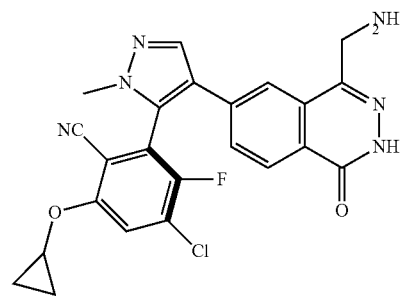
or a pharmaceutically acceptable salt thereof.
In an embodiment, the Type II PRMT5 inhibitor is Compound C:

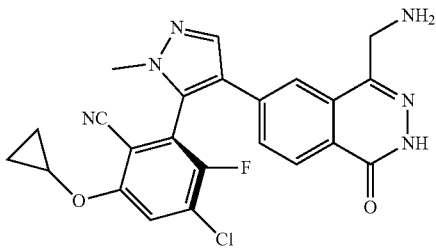

Compound C or a pharmaceutically acceptable salt thereof.

In an embodiment, the Type II PRMT5 inhibitor is Compound D:

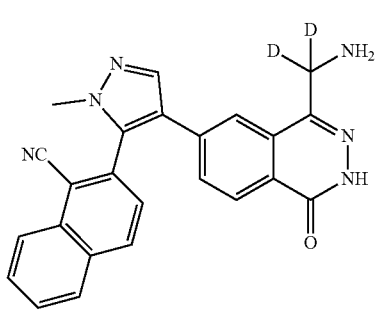

Compound D or a pharmaceutically acceptable salt thereof.

In an embodiment, the Type II PRMT5 inhibitor is Compound E:

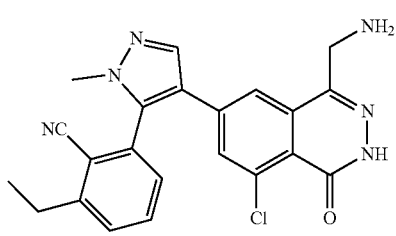

Compound E or a pharmaceutically acceptable salt thereof.

In another embodiment, the Type II PRMT5 inhibitor is a compound of Formula IV:

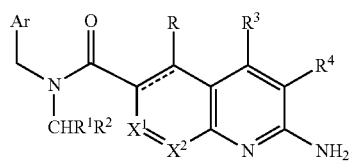

(IV)

or a pharmaceutically acceptable salt thereof;

wherein $X^1$ and $X^2$ are both in each instance independently N or C; wherein if $X^1$ is C it can be optionally substituted with halo or $C_{1-6}$alkyl;

Ar is a six membered aromatic ring having 0-2 N atoms, wherein each Ar could be independently substituted with 0-2 $R^a$ groups;

wherein $R^a$ is in each instance independently selected from cyano, halo, optionally substituted $C_{1-6}$alkyl, $C_{1-6}$haloalkyl, $OR^b$, $NR^cR^d$, —C(O)$NR^cR^d$, =S, —SO$_2$, —SO$_2C_{1-6}$alkyl, —C(O)H, —C(O)$C_{1-6}$ alkyl, C(O)O$C_{1-6}$alkyl, difluoro-pyrrolidinyl, and 4 to 6-membered heterocyclic ring, with 0-2 heteroatoms independently selected from 0 and N, and which heterocyclic ring can be further independently substituted with 0-2 halogen, $C_{1-6}$ alkyl, —C(O)H, —C(O)$C_{1-6}$ alkyl or optionally substituted cycloalcoxyl;

wherein each $R^b$ is in each instance independently selected from H, optionally substituted $C_{1-6}$ alkyl, wherein the substituents can be selected from halo; or oxetanyl; wherein each $R^c$ and $R^d$ is independently selected from H, $C_{1-3}$alkyl, $C_{1-3}$ haloalkyl or —CO;

wherein $R^e$ in each instance is selected from H or $C_{1-6}$alkyl;

wherein $R^f$ and $R^g$ in each instance is independently selected from H and $C_{1-6}$ alkyl; wherein R is H or methyl;

wherein $R^1$ and $R^2$ are in each instance is independently selected from H, optionally substituted $C_{1-6}$alkyl, optionally substituted $C_{1-6}$alkynyl, —C(O$R^e$), optionally substituted single and double cyclyl having 0-3 N, S or O atoms; wherein the substituents are selected from halo, optionally substituted $C_{1-9}$alkyl, —C(O)$NR^fR^g$, OH and an optionally substituted 5-membered ring having 0-3 N atoms;

or $R^1$ and $R^2$ and the carbon atom to which they are attached can form an optionally substituted single or double carbocyclic or heterocyclic ring, which may be saturated, partially saturated or aromatic and further wherein the heterocyclic ring includes 1, 2 or 3 heteroatoms independently selected from N, O, and S;

wherein the substituents are selected from the group of optionally substituted $C_{1-6}$ alkyl, halo, CN, $OR^e$ and —C(O$R^e$), provided that $R^1$ and $R^2$ are not both H at the same time;

and wherein $R^3$ and $R^1$ are in each instance independently selected from H, halogen, alkynyl, cyano and $C_{1-9}$ alkyl, optionally substituted with halo or deuterium.

In another embodiment, the Type II PRMT5 inhibitor is selected from the group consisting of a compound listed below in Table 11 (see WO 2021/163344, which is incorporated by reference in its entirety):

TABLE 11

2-amino-3-methyl-N-(2-methylpropyl)-N-((5-(trifluoromethyl)-2-pyridinyl)methyl)-6-quinolinecarboxamide,
2-amino-3-methyl-N-((2R)-3,3,3-trifluoro-2-methylpropyl)-N-((5-(trifluoromethyl)-2-pyridinyl)methyl)-6-quinolinecarboxamide,
2-amino-3-methyl-N-((2S)-3,3,3-trifluoro-2-methylpropyl)-N-((5-(trifluoromethyl)-2-

TABLE 11-continued pyridinyl)methyl)-6-quinolinecarboxamide,
2-amino-3-methyl-N-((2S)-3,3,3-trifluoro-2-methoxypropyl)-N-((5-(trifluoromethyl)-2-pyridinyl)methyl)-6-quinolinecarboxamide,
2-amino-3-methyl-N-((7R)-4,5,6,7-tetrahydro-1H-indazol-7-yl)-N-((5-(trifluoromethyl)-2-pyridinyl)methyl)-6-quinolinecarboxamide,
2-amino-N-((1R)-1-(6-cyano-2-pyridinyl)ethyl)-3-methyl-N-((5-(trifluoromethyl)-2-pyridinyl)methyl)-6-quinolinecarboxamide,
2-amino-N-((6-methoxy-3-pyridazinyl)methyl)-3-methyl-N-((1R)-1-(1-methyl-1H-1,2,4-triazol-3-yl)ethyl)-6-quinolinecarboxamide,
2-amino-N-((3R,4R)-4-methoxytetrahydro-2H-pyran-3-yl)-3-methyl-N-((5-(trifluoromethyl)-2-pyridinyl)methyl)-6-quinolinecarboxamide,
2-amino-N-((3S,4R)-3-fluorotetrahydro-2H-pyran-4-yl)-3-methyl-N-((5-(trifluoromethyl)-2-pyridinyl)methyl)-6-quinolinecarboxamide,
7-amino-6-bromo-N-((1R)-1-(1,3-thiazol-4-yl)ethyl)-N-((6-(trifluoromethyl)-3-pyridazinyl)methyl)-1,8-naphthyridine-3-carboxamide,
2-amino-N-((3S,4R)-3-hydroxytetrahydro-2H-pyran-4-yl)-3-methyl-N-((5-(trifluoromethyl)-2-pyridinyl)methyl)-6-quinolinecarboxamide,
2-amino-N-((3S,4R)-3-methoxytetrahydro-2H-pyran-4-yl)-3-methyl-N-((5-(trifluoromethyl)-2-pyridinyl)methyl)-6-quinolinecarboxamide,
2-amino-3-methyl-N-((1R)-1-(1,2,4-oxadiazol-3-yl)ethyl)-N-((5-(trifluoromethyl)-2-pyridinyl)methyl)-6-quinolinecarboxamide,
2-amino-N-((1R,2R)-2-cyanocyclopentyl)-3-methyl-N-((5-(trifluoromethyl)-2-pyridinyl)methyl)-6-quinolinecarboxamide,
2-amino-3-methyl-N-(4-pyrimidinylmethyl)-N-((5-(trifluoromethyl)-2-pyridinyl)methyl)-6-quinolinecarboxamide,
2-amino-3-methyl-N-(2-pyrazinylmethyl)-N-((5-(trifluoromethyl)-2-pyridinyl)methyl)-6-quinolinecarboxamide,
2-amino-3-methyl-N-((1-methyl-1H-1,2,4-triazol-3-yl)methyl)-N-((5-(trifluoromethyl)-2-pyridinyl)methyl)-6-quinolinecarboxamide,
2-amino-7-fluoro-3-methyl-N-(2-methylpropyl)-N-((5-(trifluoromethyl)-2-pyridinyl)methyl)-6-quinolinecarboxamide,
2-amino-3-methyl-N-((5-methyl-2-pyrazinyl)methyl)-N-((5-(trifluoromethyl)-2-pyridinyl)methyl)-6-quinolinecarboxamide,
2-amino-7-fluoro-3-methyl-N-(2-pyrazinylmethyl)-N-((5-(trifluoromethyl)-2-pyridinyl)methyl)-6-quinolinecarboxamide,
2-amino-7-fluoro-3-methyl-N-((5-methyl-1,2-oxazol-3-yl)methyl)-N-((5-(trifluoromethyl)-2-pyridinyl)methyl)-6-quinolinecarboxamide,
2-amino-3-methyl-N-((1R)-1-(2-pyrazinyl)ethyl)-N-((5-(trifluoromethyl)-2-pyridinyl)methyl)-6-quinolinecarboxamide,
2-amino-3-methyl-N-(2-pyrimidinylmethyl)-N-((5-(trifluoromethyl)-2-pyridinyl)methyl)-6-quinolinecarboxamide,
2-amino-N-((3-fluoro-5-(trifluoromethyl)-2-pyridinyl)methyl)-3-methyl-N-(2-methylpropyl)-6-quinolinecarboxamide,
2-amino-N-((5-chloro-2-pyrimidinyl)methyl)-3-methyl-N-((5-(trifluoromethyl)-2-pyridinyl)methyl)-6-quinolinecarboxamide,
2-amino-3-bromo-N-(2-pyrimidinylmethyl)-N-((5-(trifluoromethyl)-2-pyridinyl)methyl)-6-quinolinecarboxamide,
2-amino-3-bromo-N-(2-methylpropyl)-N-((5-(trifluoromethyl)-2-pyridinyl)methyl)-6-quinolinecarboxamide,
2-amino-7-fluoro-3-methyl-N-(2-pyrimidinylmethyl)-N-((5-(trifluoromethyl)-2-pyridinyl)methyl)-6-quinolinecarboxamide,
2-amino-N-((5-chloro-2-pyridinyl)methyl)-3-methyl-N-(2-pyrimidinylmethyl)-6-quinolinecarboxamide,
2-amino-N-((5-fluoro-2-pyrimidinyl)methyl)-3-methyl-N-((5-(trifluoromethyl)-2-pyridinyl)methyl)-6-quinolinecarboxamide,
2-amino-N-((3-fluoro-2-pyridinyl)methyl)-3-methyl-N-((5-(trifluoromethyl)-2-pyridinyl)methyl)-6-quinolinecarboxamide,
7-amino-6-bromo-N-((3-fluoro-2-pyridinyl)methyl)-N-((5-(trifluoromethyl)-2-pyridinyl)methyl)-1,8-naphthyridine-3-carboxamide,
7-amino-N-((3-fluoro-2-pyridinyl)methyl)-6-methyl-N-((5-(trifluoromethyl)-2-pyridinyl)methyl)-1,8-naphthyridine-3-carboxamide,
2-amino-N-((5-(difluoromethyl)-2-pyridinyl)methyl)-3-methyl-N-(2-methylpropyl)-6-quinolinecarboxamide,
2-amino-3-methyl-N-((1R)-1-(2-pyrimidinyl)ethyl)-N-((5-(trifluoromethyl)-2-pyridinyl)methyl)-6-quinolinecarboxamide,
2-amino-N-((3-fluoro-2-pyridinyl)methyl)-3-methyl-N-((6-(trifluoromethyl)-3-pyridinyl)methyl)-6-quinolinecarboxamide,
2-amino-N-((4R)-3,4-dihydro-2H-pyrano[3,2-b]pyridin-4-yl)-3-methyl-N-((5-(trifluoromethyl)-2-pyridinyl)methyl)-6-quinolinecarboxamide,
7-amino-6-methyl-N-((1R)-1-(2-pyrazinyl)ethyl)-N-((5-(trifluoromethyl)-2-pyridinyl)methyl)-1,8-naphthyridine-3-carboxamide,
2-amino-N-(cyclopropylmethyl)-3-methyl-N-((5-(trifluoromethyl)-2-pyridinyl)methyl)-6-quinolinecarboxamide,
2-amino-N-((5-bromo-2-pyridinyl)methyl)-3-methyl-N-(2-methylpropyl)-6-quinolinecarboxamide,
2-amino-N-((3,5-difluoro-2-pyridinyl)methyl)-3-methyl-N-((5-(trifluoromethyl)-2-pyridinyl)methyl)-6-quinolinecarboxamide,
2-amino-N-((1R)-1-(3-fluoro-2-pyridinyl)ethyl)-3-methyl-N-((5-(trifluoromethyl)-2-pyridinyl)methyl)-6-quinolinecarboxamide,
2-amino-N-((5-(difluoromethyl)-2-pyridinyl)methyl)-N-((3-fluoro-2-pyridinyl)methyl)-3-

TABLE 11-continued methyl-6-quinolinecarboxamide,
2-amino-N-((1S)-1-(3-fluoro-2-pyridinyl)ethyl)-3-methyl-N-((5-(trifluoromethyl)-2-pyridinyl)methyl)-6-quinolinecarboxamide,
2-amino-N-((3,5-difluoro-2-pyridinyl)methyl)-N-((3-fluoro-2-pyridinyl)methyl)-3-methyl-6-quinolinecarboxamide,
2-amino-N-((5-cyclopropyl-2-pyridinyl)methyl)-3-methyl-N-(2-methylpropyl)-6-quinolinecarboxamide,
2-amino-N-((1R)-1-(5-fluoro-2-pyridinyl)ethyl)-3-methyl-N-((5-(trifluoromethyl)-2-pyrazinyl)methyl)-6-quinolinecarboxamide,
2-amino-3-methyl-N-((1R)-1-(2-pyrimidinyl)ethyl)-N-((5-(trifluoromethyl)-2-pyrazinyl)methyl)-6-quinolinecarboxamide,
7-amino-6-bromo-N-((1R)-1-(3-fluoro-2-pyridinyl)ethyl)-N-((5-(trifluoromethyl)-2-pyridinyl)methyl)-1,8-naphthyridine-3-carboxamide,
7-amino-N-((1R)-1-(3-fluoro-2-pyridinyl)ethyl)-6-methyl-N-((5-(trifluoromethyl)-2-pyridinyl)methyl)-1,8-naphthyridine-3-carboxamide,
2-amino-3-methyl-N-((8R)-5,6,7,8-tetrahydro-8-quinolinyl)-N-((5-(trifluoromethyl)-2-pyridinyl)methyl)-6-quinolinecarboxamide,
2-amino-3-methyl-N-((8R)-5,6,7,8-tetrahydro-8-isoquinolinyl)-N-((5-(trifluoromethyl)-2-pyridinyl)methyl)-6-quinolinecarboxamide,
2-amino-N-((1R)-1-(3-fluoro-2-pyridinyl)ethyl)-N-((3-fluoro-5-(trifluoromethyl)-2-pyridinyl)methyl)-3-methyl-6-quinolinecarboxamide,
2-amino-N-((1R)-1-(5-fluoro-2-pyridinyl)ethyl)-3-methyl-N-((5-(trifluoromethyl)-2-pyridinyl)methyl)-6-quinolinecarboxamide,
2-amino-N-((1S)-1-(5-fluoro-2-pyridinyl)ethyl)-3-methyl-N-((5-(trifluoromethyl)-2-pyridinyl)methyl)-6-quinolinecarboxamide,
2-amino-3-methyl-N-((1R)-1-(5-methyl-1,2-oxazol-3-yl)ethyl)-N-((5-(trifluoromethyl)-2-pyridinyl)methyl)-6-quinolinecarboxamide,
2-amino-N-((3-fluoro-2-pyridinyl)methyl)-3-methyl-N-((1R)-1-(5-(trifluoromethyl)-2-pyridinyl)ethyl)-6-quinolinecarboxamide,
2-amino-N-((1R)-1-cyclopropylethyl)-3-methyl-N-((5-(trifluoromethyl)-2-pyridinyl)methyl)-6-quinolinecarboxamide,
2-amino-3-methyl-N-(2-methylpropyl)-N-((1R)-1-(5-(trifluoromethyl)-2-pyridinyl)ethyl)-6-quinolinecarboxamide,
2-amino-N-((5-cyano-2-pyridinyl)methyl)-N-((3-fluoro-2-pyridinyl)methyl)-3-methyl-6-quinolinecarboxamide,
2-amino-N-((4R)-3,4-dihydro-2H-pyrano[2,3-b]pyridin-4-yl)-3-methyl-N-((5-(trifluoromethyl)-2-pyridinyl)methyl)-6-quinolinecarboxamide,
2-amino-N-((5-bromo-2-pyridinyl)methyl)-N-((1R)-1-(3-fluoro-2-pyridinyl)ethyl)-3-methyl-6-quinolinecarboxamide,
2-amino-N-((1R)-1-(3-fluoro-2-pyridinyl)ethyl)-3-methyl-N-((5-(methylsulfonyl)-2-pyridinyl)methyl)-6-quinolinecarboxamide,
7-amino-6-methyl-N-((1R)-1-(2-pyrimidinyl)ethyl)-N-((5-(trifluoromethyl)-2-pyridinyl)methyl)-1,8-naphthyridine-3-carboxamide,
2-amino-3-methyl-N-((1R)-1-(2-pyrimidinyl)ethyl)-N-((5-(trifluoromethoxy)-2-pyridinyl)methyl)-6-quinolinecarboxamide,
2-amino-3-methyl-N-((1R)-1-(2-pyrimidinyl)ethyl)-N-((6-(trifluoromethyl)-3-pyridazinyl)methyl)-6-quinolinecarboxamide,
2-amino-N-((5-cyano-2-pyridinyl)methyl)-N-((1R)-1-(3-fluoro-2-pyridinyl)ethyl)-3-methyl-6-quinolinecarboxamide,
2-amino-N-((3-fluoro-2-pyridinyl)methyl)-3-methyl-N-(4-(trifluoromethyl)benzyl)-6-quinolinecarboxamide,
2-amino-N-((3-fluoro-2-pyridinyl)methyl)-3-methyl-N-(2-methyl-4-(trifluoromethyl)benzyl)-6-quinolinecarboxamide,
7-amino-6-bromo-N-((1R)-1-(2-pyrimidinyl)ethyl)-N-((5-(trifluoromethyl)-2-pyridinyl)methyl)-1,8-naphthyridine-3-carboxamide,
2-amino-N-((5-(cyclopropylsulfonyl)-2-pyridinyl)methyl)-N-((1R)-1-(3-fluoro-2-pyridinyl)ethyl)-3-methyl-6-quinolinecarboxamide,
2-amino-N-((5-cyano-2-pyridinyl)methyl)-3-methyl-N-((1R)-1-(2-pyrimidinyl)ethyl)-6-quinolinecarboxamide,
2-amino-N-((5-bromo-2-pyridinyl)methyl)-N-((1R)-1-(3-chloro-2-pyridinyl)ethyl)-3-methyl-6-quinolinecarboxamide,
2-amino-N-((1R)-1-(5-chloro-2-pyridinyl)ethyl)-3-methyl-N-((5-(trifluoromethyl)-2-pyridinyl)methyl)-6-quinolinecarboxamide,
2-amino-3-methyl-N-((1R)-1-(2-pyrimidinyl)propyl)-N-((5-(trifluoromethyl)-2-pyridinyl)methyl)-6-quinolinecarboxamide,
2-amino-N-((5-chloro-2-pyridinyl)methyl)-N-((1R)-1-(3-fluoro-2-pyridinyl)ethyl)-3-methyl-6-quinolinecarboxamide,
2-amino-N-((5-chloro-2-pyridinyl)methyl)-3-methyl-N-(2-methylpropyl)-6-quinolinecarboxamide,
2-amino-N-((1R)-1-(4-fluorophenyl)ethyl)-3-methyl-N-((5-(trifluoromethyl)-2-pyridinyl)methyl)-6-quinolinecarboxamide,
7-amino-6-ethynyl-N-((1R)-1-(3-fluoro-2-pyridinyl)ethyl)-N-((5-(trifluoromethyl)-2-pyridinyl)methyl)-1,8-naphthyridine-3-carboxamide,
2-amino-N-((5-bromo-2-pyridinyl)methyl)-3-methyl-N-((1R)-1-(2-pyrimidinyl)ethyl)-6-quinolinecarboxamide,
2-amino-N-((7R)-6,7-dihydro-5H-cyclopenta[b]pyridin-7-yl)-3-methyl-N-((6-(trifluoromethyl)-3-pyridazinyl)methyl)-6-quinolinecarboxamide,
2-amino-7-fluoro-N-((3-fluoro-2-pyridinyl)methyl)-3-methyl-N-((5-(trifluoromethyl)-2-pyridinyl)methyl)-6-quinolinecarboxamide,
7-amino-6-bromo-N-((1R)-1-(2-pyrimidinyl)ethyl)-N-((5-(trifluoromethyl)-2-

TABLE 11-continued pyrazinyl)methyl)-1,8-naphthyridine-3-carboxamide,
2-amino-3-methyl-N-(2-pyridinylmethyl)-N-((5-(trifluoromethyl)-2-pyridinyl)methyl)-6-quinolinecarboxamide,
methyl 6-(((((2-amino-3-methyl-6-quinolinyl)carbonyl)((3-fluoro-2-pyridinyl)methyl)amino)methyl)-3-pyridinecarboxylate,
2-amino-N-((5-(difluoromethoxy)-2-pyridinyl)methyl)-3-methyl-N-((1R)-1-(2-pyrimidinyl)ethyl)-6-quinolinecarboxamide,
2-amino-N-((3-chloro-5-(trifluoromethyl)-2-pyridinyl)methyl)-N-((1R)-1-(3-fluoro-2-pyridinyl)ethyl)-3-methyl-6-quinolinecarboxamide,
2-amino-7-fluoro-3-methyl-N-((1R)-1-(2-pyrimidinyl)ethyl)-N-((5-(trifluoromethyl)-2-pyridinyl)methyl)-6-quinolinecarboxamide,
2-amino-N-(cyclopropylmethyl)-7-fluoro-3-methyl-N-((5-(trifluoromethyl)-2-pyridinyl)methyl)-6-quinolinecarboxamide,
methyl 6-(((((2-amino-3-methyl-6-quinolinyl)carbonyl)((1R)-1-(3-fluoro-2-pyridinyl)ethyl)amino)methyl)-3-pyridinecarboxylate,
2-amino-N-((5-(dimethylcarbamoyl)-2-pyridinyl)methyl)-N-((3-fluoro-2-pyridinyl)methyl)-3-methyl-6-quinolinecarboxamide,
2-amino-3-methyl-N-(1-(2-pyrimidinyl)cyclopropyl)-N-((5-(trifluoromethyl)-2-pyridinyl)methyl)-6-quinolinecarboxamide,
2-amino-3-methyl-N-((1R)-1-(2-pyrimidinyl)ethyl)-N-((5-(trifluoromethyl)-1,3-thiazol-2-yl)methyl)-6-quinolinecarboxamide,
2-amino-3-methyl-N-(3-pyridinylmethyl)-N-((5-(trifluoromethyl)-2-pyridinyl)methyl)-6-quinolinecarboxamide,
2-amino-N-((2-amino-1,3-thiazol-5-yl)methyl)-3-methyl-N-((5-(trifluoromethyl)-2-pyridinyl)methyl)-6-quinolinecarboxamide,
2-amino-N-((5-cyano-2-pyridinyl)methyl)-N-((1R)-1-(3,5-difluoro-2-pyridinyl)ethyl)-3-methyl-6-quinolinecarboxamide,
2-amino-3-methyl-N-((5-((~2~H_3_)methyloxy)-2-pyridinyl)methyl)-N-((1R)-1-(2-pyrimidinyl)ethyl)-6-quinolinecarboxamide,
2-amino-N-(4-carbamoylbenzyl)-3-methyl-N-((5-(trifluoromethyl)-2-pyridinyl)methyl)-6-quinolinecarboxamide,
2-amino-N-((5-(difluoromethyl)-2-pyridinyl)methyl)-N-((1R)-1-(5-fluoro-2-pyrimidinyl)ethyl)-3-methyl-6-quinolinecarboxamide,
2-amino-N-((5-bromo-2-pyridinyl)methyl)-3-methyl-N-((3R)-1-methyl-2-oxo-3-piperidinyl)-6-quinolinecarboxamide,
2-amino-N-((5-(dimethylcarbamoyl)-2-pyridinyl)methyl)-N-((1R)-1-(3-fluoro-2-pyridinyl)ethyl)-3-methyl-6-quinolinecarboxamide,
2-amino-N-((5-cyano-2-pyridinyl)methyl)-3-methyl-N-((1R)-1-(2-pyridinyl)ethyl)-6-quinolinecarboxamide,
2-amino-3-methyl-N-((1R)-1-(2-pyrimidinyl)ethyl)-N-((5-(trifluoromethyl)-2-pyridinyl)methyl)-1,7-naphthyridine-6-carboxamide,
2-amino-N-((3-fluoro-2-pyridinyl)methyl)-3-methyl-N-((5-(trifluoromethyl)-2-pyridinyl)methyl)-1,7-naphthyridine-6-carboxamide,
2-amino-3-methyl-N-(2-methylpropyl)-N-((5-(trifluoromethyl)-2-pyridinyl)methyl)-1,7-naphthyridine-6-carboxamide,
2-amino-N-((5-cyano-2-pyridinyl)methyl)-N-((4R)-3,4-dihydro-2H-pyrano[3,2-b]pyridin-4-yl)-3-methyl-6-quinolinecarboxamide,
2-amino-N-((5-cyano-2-pyridinyl)methyl)-3-methyl-N-((1R)-1-(2-pyrimidinyl)propyl)-6-quinolinecarboxamide,
2-amino-3-methyl-N-(4-pyridinylmethyl)-N-((5-(trifluoromethyl)-2-pyridinyl)methyl)-6-quinolinecarboxamide,
2-amino-3-methyl-N-((3-methyl-2-pyridinyl)methyl)-N-((5-(trifluoromethyl)-2-pyridinyl)methyl)-6-quinolinecarboxamide,
2-amino-3-methyl-N-((4-methyl-1,3-thiazol-2-yl)methyl)-N-((5-(trifluoromethyl)-2-pyridinyl)methyl)-6-quinolinecarboxamide,
2-amino-3-methyl-N-(4-(1-piperidinyl)benzyl)-N-(1H-pyrrolo[2,3-b]pyridin-4-ylmethyl)-6-quinolinecarboxamide,
2-amino-N-(cyclobutylmethyl)-3-methyl-N-((5-(trifluoromethyl)-2-pyridinyl)methyl)-6-quinolinecarboxamide,
2-amino-3-methyl-N-(1,2,3-thiadiazol-4-ylmethyl)-N-((5-(trifluoromethyl)-2-pyridinyl)methyl)-6-quinolinecarboxamide,
2-amino-N-(1H-indol-3-ylmethyl)-3-methyl-N-((5-(trifluoromethyl)-2-pyridinyl)methyl)-6-quinolinecarboxamide,
2-amino-3-methyl-N-((5-methyl-1,3-oxazol-4-yl)methyl)-N-((5-(trifluoromethyl)-2-pyridinyl)methyl)-6-quinolinecarboxamide,
2-amino-4-methyl-N-((1-methyl-1H-pyrazol-3-yl)methyl)-N-((5-(trifluoromethyl)-2-pyridinyl)methyl)-6-quinolinecarboxamide,
2-amino-4-methyl-N-((1-methyl-1H-1,2,4-triazol-3-yl)methyl)-N-((5-(trifluoromethyl)-2-pyridinyl)methyl)-6-quinolinecarboxamide,
2-amino-N-(2-fluorobenzyl)-3-methyl-N-(1H-pyrrolo[3,2-b]pyridin-3-ylmethyl)-6-quinolinecarboxamide,
2-amino-3-methyl-N-((4-methyl-1,3-thiazol-5-yl)methyl)-N-((5-(trifluoromethyl)-2-pyridinyl)methyl)-6-quinolinecarboxamide,
2-amino-N-(3-fluoro-4-(hydroxymethyl)benzyl)-3-methyl-N-((5-(trifluoromethyl)-2-pyridinyl)methyl)-6-quinolinecarboxamide,
2-amino-N-((6-amino-3-pyridinyl)methyl)-3-methyl-N-((5-(trifluoromethyl)-2-pyridinyl)methyl)-6-quinolinecarboxamide,
2-amino-3-methyl-N-(1H-pyrrolo[2,3-b]pyridin-4-ylmethyl)-N-((5-(trifluoromethyl)-2-pyridinyl)methyl)-6-quinolinecarboxamide,
2-amino-N-(2-fluorobenzyl)-3-methyl-N-((3-oxo-3,4-dihydro-2H-1,4-benzoxazin-6-

TABLE 11-continued yl)methyl)-6-quinolinecarboxamide,
2-amino-3-methyl-N-((2-oxo-2,3-dihydro-1H-benzimidazol-5-yl)methyl)-N-((5-(trifluoromethyl)-2-pyridinyl)methyl)-6-quinolinecarboxamide,
2-amino-3-methyl-N-(1,3-oxazol-4-ylmethyl)-N-((5-(trifluoromethyl)-2-pyridinyl)methyl)-6-quinolinecarboxamide,
2-amino-3-methyl-N-((3R)-1-methyl-2-oxo-3-piperidinyl)-N-((5-(trifluoromethyl)-2-pyridinyl)methyl)-6-quinolinecarboxamide,
2-amino-4-methyl-N-((1R)-1-(2-pyrimidinyl)ethyl)-N-((5-(trifluoromethyl)-2-pyridinyl)methyl)-6-quinolinecarboxamide,
2-amino-N-((5-cyano-2-pyridinyl)methyl)-7-fluoro-3-methyl-N-((1R)-1-(2-pyrimidinyl)ethyl)-6-quinolinecarboxamide,
2-amino-N-((5-(difluoromethyl)-2-pyridinyl)methyl)-3-methyl-N-((1R)-1-(2-pyrimidinyl)ethyl)-6-quinolinecarboxamide,
2-amino-3-methyl-N-((3R)-2-oxo-3-piperidinyl)-N-((5-(trifluoromethyl)-2-pyridinyl)methyl)-6-quinolinecarboxamide,
2-amino-N-((5-chloro-2-pyridinyl)methyl)-3-methyl-N-((1R)-1-(2-pyrimidinyl)ethyl)-6-quinolinecarboxamide,
2-amino-3-methyl-N-((1R)-1-(2-pyrimidinyl)propyl)-N-((6-(trifluoromethyl)-3-pyridazinyl)methyl)-6-quinolinecarboxamide,
2-amino-4-chloro-N-((1R)-1-(2-pyrimidinyl)ethyl)-N-((5-(trifluoromethyl)-2-pyridinyl)methyl)-6-quinolinecarboxamide,
2-amino-N-((3R)-1-cyclopropyl-2-oxo-3-piperidinyl)-3-methyl-N-((5-(trifluoromethyl)-2-pyridinyl)methyl)-6-quinolinecarboxamide,
2-amino-3-methyl-N-((2-methyl-6-(trifluoromethyl)-3-pyridinyl)methyl)-N-((1R)-1-(2-pyrimidinyl)ethyl)-6-quinolinecarboxamide,
2-amino-N-((6-bromo-3-pyridazinyl)methyl)-3-methyl-N-((1R)-1-(2-pyrimidinyl)ethyl)-6-quinolinecarboxamide,
2-amino-N-((5-bromo-3-methyl-2-pyridinyl)methyl)-3-methyl-N-((1R)-1-(2-pyrimidinyl)ethyl)-6-quinolinecarboxamide,
2-amino-N-((3-chloro-2-pyridinyl)methyl)-3-methyl-N-((5-(trifluoromethyl)-2-pyridinyl)methyl)-6-quinolinecarboxamide,
2-amino-N-((5-cyano-3-methyl-2-pyridinyl)methyl)-3-methyl-N-((1R)-1-(2-pyrimidinyl)ethyl)-6-quinolinecarboxamide,
2-amino-N-(4-cyanobenzyl)-3-methyl-N-((1R)-1-(2-pyrimidinyl)ethyl)-6-quinolinecarboxamide,
2-amino-N-((5-cyano-2-pyridinyl)methyl)-N-((1R)-1-(2-fluorophenyl)ethyl)-3-methyl-6-quinolinecarboxamide,
2-amino-N-((5-chloro-3-fluoro-2-pyridinyl)methyl)-3-methyl-N-((5-(trifluoromethyl)-2-pyridinyl)methyl)-6-quinolinecarboxamide,
2-amino-N-(2,6-difluorobenzyl)-3-methyl-N-((5-(trifluoromethyl)-2-pyridinyl)methyl)-6-quinolinecarboxamide,
2-amino-3-methyl-N-((1R)-1-(2-pyrimidinyl)propyl)-N-((5-(trifluoromethyl)-2-pyrazinyl)methyl)-6-quinolinecarboxamide,
2-amino-3-chloro-N-((1R)-1-(2-pyrimidinyl)ethyl)-N-((5-(trifluoromethyl)-2-pyridinyl)methyl)-6-quinolinecarboxamide,
2-amino-N-cyclopropyl-7-fluoro-3-methyl-N-((5-(trifluoromethyl)-2-pyridinyl)methyl)-6-quinolinecarboxamide,
7-amino-6-bromo-N-((5-cyano-2-pyridinyl)methyl)-N-((1R)-1-(2-pyrimidinyl)ethyl)-1,8-naphthyridine-3-carboxamide,
7-amino-6-bromo-N-((5-(difluoromethyl)-2-pyridinyl)methyl)-N-((1R)- 1-(2-pyrimidinyl)ethyl)-1,8-naphthyridine-3-carboxamide,
7-amino-6-bromo-N-((1R)-1-(2-pyrimidinyl)ethyl)-N-((6-(trifluoromethyl)-3-pyridazinyl)methyl)-1,8-naphthyridine-3-carboxamide,
2-amino-7-chloro-3-methyl-N-(2-methylpropyl)-N-((5-(trifluoromethyl)-2-pyridinyl)methyl)-6-quinolinecarboxamide,
2-amino-N-((5-methoxy-2-pyrazinyl)methyl)-3-methyl-N-((1R)-1-(2-pyrimidinyl)ethyl)-6-quinolinecarboxamide,
2-amino-N-((3-fluoro-2-pyridinyl)methyl)-3-methyl-N-((5R)-2-(trifluoromethyl)-6,7-dihydro-5H-cyclopenta[b]pyridin-5-yl)-6-quinolinecarboxamide,
2-amino-N-((5-cyano-2-pyrazinyl)methyl)-3-methyl-N-((1R)-1-(2-pyrimidinyl)ethyl)-6-quinolinecarboxamide,
2-amino-N-((R)-cyclopropyl(2-pyrimidinyl)methyl)-3-methyl-N-((5-(trifluoromethyl)-2-pyridinyl)methyl)-6-quinolinecarboxamide,
2-amino-3-chloro-N-((5-cyano-2-pyridinyl)methyl)-N-((1R)-1-(2-pyrimidinyl)ethyl)-6-quinolinecarboxamide,
2-amino-N-((6-methoxy-3-pyridazinyl)methyl)-3-methyl-N-((1R)-1-(2-pyrimidinyl)ethyl)-6-quinolinecarboxamide,
7-amino-N-((5-(difluoromethyl)-2-pyridinyl)methyl)-6-methyl-N-((1R)-1-(2-pyrimidinyl)ethyl)-1,8-naphthyridine-3-carboxamide,
2-methyl-2-propanyl 6-((((2-amino-3-methyl-6-quinolinyl)carbonyl)((1R)-1-(2-pyrimidinyl)ethyl)amino)methyl)-3',6'-dihydro[3,4'-bipyridine]- 1'(2'H)-carboxylate, 2-amino-3-methyl-N-((1R)-1-(2-pyrimidinyl)ethyl)-N-((6-(trifluoromethyl)-3-pyridinyl)methyl)-6-quinolinecarboxamide,
2-amino-3,7-dimethyl-N-(2-methylpropyl)-N-((5-(trifluoromethyl)-2-pyridinyl)methyl)-6-quinolinecarboxamide,
2-amino-N-((1R)-1-(3-fluoro-2-pyridinyl)ethyl)-3-methyl-N-((6-(trifluoromethyl)-3-pyridazinyl)methyl)-6-quinolinecarboxamide,
7-amino-6-bromo-N-((1R)-1-(3-fluoro-2-pyridinyl)ethyl)-N-((6-(trifluoromethyl)-3-pyridazinyl)methyl)-1,8-naphthyridine-3-carboxamide,
N-((1'-acetyl-1',2',3',6'-tetrahydro[3,4'-bipyridin]-6-yl)methyl)-2-amino-3-methyl-N-

TABLE 11-continued ((1R)-1-(2-pyrimidinyl)ethyl)-6-quinolinecarboxamide,
2-amino-N-((5-carbamoyl-2-pyridinyl)methyl)-N-((1R)-1-(2-fluorophenyl)ethyl)-3-methyl-6-quinolinecarboxamide,
7-amino-6-methyl-N-(1H-pyrrolo[2,3-b]pyridin-4-ylmethyl)-N-((5-(trifluoromethyl)-2-pyridinyl)methyl)-1,8-naphthyridine-3-carboxamide,
2-amino-3-methyl-N-((1R)-1-(1-methyl-1H-1,2,4-triazol-3-yl)ethyl)-N-((5-(trifluoromethyl)-2-pyridinyl)methyl)-6-quinolinecarboxamide,
2-amino-N-(1H-indazol-5-ylmethyl)-3-methyl-N-((5-(trifluoromethyl)-2-pyridinyl)methyl)-6-quinolinecarboxamide,
2-amino-3-methyl-N-((8R)-5,6,7,8-tetrahydro[1,2,4]triazolo[1,5-a]pyridin-8-yl)-N-((5-(trifluoromethyl)-2-pyridinyl)methyl)-6-quinolinecarboxamide,
7-amino-6-bromo-N-((1R)-1-(2,4-difluorophenyl)ethyl)-N-((5-(trifluoromethyl)-2-pyridinyl)methyl)-1,8-naphthyridine-3-carboxamide,
2-amino-3-methyl-N-((5-(2-oxa-6-azaspiro[3.3]heptan-6-yl)-2-pyridinyl)methyl)-N-((1R)-1-(2-pyrimidinyl)ethyl)-6-quinolinecarboxamide,
2-amino-3-(~2~H_3_)methyl-N-(2-methylpropyl)-N-((5-(trifluoromethyl)-2-pyridinyl)methyl)-6-quinolinecarboxamide,
2-amino-3-chloro-N-((1R)-1-(2-pyrimidinyl)ethyl)-N-((6-(trifluoromethyl)-3-pyridazinyl)methyl)-6-quinolinecarboxamide,
2-amino-3-methyl-N-((1R)-1-(2-pyrimidinyl)ethyl)-N-(2-quinolinylmethyl)-6-quinolinecarboxamide,
2-amino-3-methyl-N-((1R)-1-(2-pyrimidinyl)ethyl)-N-(3-quinolinyimethyl)-6-quinolinecarboxamide,
2-amino-3-bromo-N-((1R)-1-(2-pyrimidinyl)ethyl)-N-((5-(trifluoromethyl)-2-pyridinyl)methyl)-6-quinolinecarboxamide,
2-amino-N-((5-cyano-2-pyridinyl)methyl)-N-(cyclopropylmethyl)-7-fluoro-3-methyl-6-quinolinecarboxamide,
2-amino-N-((5-(3,6-dihydro-2H-pyran-4-yl)-2-pyridinyl)methyl)-3-methyl-N-((1R)-1-(2-pyrimidinyl)ethyl)-6-quinolinecarboxamide,
2-amino-3-(~2~H_3_)methyl-N-((1R)-1-(2-pyrimidinyl)ethyl)-N-((5-(trifluoromethyl)-2-pyridinyl)methyl)-6-quinolinecarboxamide,
2-amino-N-((1R,2R)-2-hydroxycyclohexyl)-3-methyl-N-((5-(trifluoromethyl)-2-pyridinyl)methyl)-6-quinolinecarboxamide,
2-amino-N-((4-cyano-2-pyridinyl)methyl)-3-methyl-N-((1R)-1-(2-pyrimidinyl)ethyl)-6-quinolinecarboxamide,
2-amino-N-((5-(5,6-dihydro-2H-pyran-3-yl)-2-pyridinyl)methyl)-3-methyl-N-((1R)-1-(2-pyrimidinyl)ethyl)-6-quinolinecarboxamide,
2-amino-N-((6-bromo-3-pyridazinyl)methyl)-3-chloro-N-((1R)-1-(2-pyrimidinyl)ethyl)-6-quinolinecarboxamide,
2-amino-N-((5-fluoro-2-pyridinyl)methyl)-3-methyl-N-((5-(trifluoromethyl)-2-pyridinyl)methyl)-6-quinolinecarboxamide,
2-amino-7-fluoro-3-methyl-N-((1R)-1-(1-methyl-1H-1,2,4-triazol-3-yl)ethyl)-N-((5-(trifluoromethyl)-2-pyridinyl)methyl)-6-quinolinecarboxamide,
2-amino-7-fluoro-3-methyl-N-((1S)-1-(1-methyl-1H-1,2,4-triazol-3-yl)ethyl)-N-((5-(trifluoromethyl)-2-pyridinyl)methyl)-6-quinolinecarboxamide,
2-amino-3-methyl-N-(2,2,2-trifluoroethyl)-N-((5-(trifluoromethyl)-2-pyridinyl)methyl)-6-quinolinecarboxamide,
2-amino-N-((4R)-3,4-dihydro-2H-pyrano[3,2-b]pyridin-4-yl)-3-methyl-N-((6-(trifluoromethyl)-3-pyridazinyl)methyl)-6-quinolinecarboxamide,
2-amino-N-((5-cyano-2-pyridinyl)methyl)-3-methyl-N-((1R)-1-(2-pyrimidinyl)ethyl)-1,7-naphthyridine-6-carboxamide,
2-amino-3-bromo-N-((5-cyano-2-pyridinyl)methyl)-N-((1R)-1-(2-pyrimidinyl)ethyl)-6-quinolinecarboxamide,
2-amino-N-(2-methoxyethyl)-3-methyl-N-((5-(trifluoromethyl)-2-pyridinyl)methyl)-6-quinolinecarboxamide,
2-amino-N-((5-ethoxy-2-pyridinyl)methyl)-3-methyl-N-((1R)-1-(2-pyrimidinyl)ethyl)-6-quinolinecarboxamide,
2-amino-7-chloro-3-methyl-N-((1R)-1-(2-pyrimidinyl)ethyl)-N-((5-(trifluoromethyl)-2-pyridinyl)methyl)-6-quinolinecarboxamide,
2-amino-N-((1R)-2-methoxy-1-(2-pyridinyl)ethyl)-3-methyl-N-((5-(trifluoromethyl)-2-pyridinyl)methyl)-6-quinolinecarboxamide,
2-amino-N-((1S)-2-methoxy-1-(2-pyridinyl)ethyl)-3-methyl-N-((5-(trifluoromethyl)-2-pyridinyl)methyl)-6-quinolinecarboxamide,
2-amino-N-((5-cyano-2-pyridinyl)methyl)-3,4-dimethyl-N-((1R)-1-(2-pyrimidinyl)ethyl)-6-quinolinecarboxamide,
2-amino-N-((5-cyano-2-pyridinyl)methyl)-3,4-dimethyl-N-((1S)-1-(2-pyrimidinyl)ethyl)-6-quinolinecarboxamide,
2-amino-N-((5-chloro-3-pyridinyl)methyl)-3-methyl-N-((5-(trifluoromethyl)-2-pyridinyl)methyl)-6-quinolinecarboxamide,
2-amino-N-(1H-indazol-4-ylmethyl)-3-methyl-N-((5-(trifluoromethyl)-2-pyridinyl)methyl)-6-quinolinecarboxamide,
7-amino-6-bromo-N-((1R)-1-(2-pyrimidinyl)propyl)-N-((5-(trifluoromethyl)-2-pyridinyl)methyl)-1,8-naphthyridine-3-carboxamide,
2-amino-N-((6-bromo-3-pyridazinyl)methyl)-7-fluoro-3-methyl-N-((1R)-1-(2-pyrimidinyl)ethyl)-6-quinolinecarboxamide,
2-amino-3-methyl-N-((2-methyl-1H-pyrrolo[2,3-b]pyridin-4-yl)methyl)-N-((5-(trifluoromethyl)-2-pyridinyl)methyl)-6-quinolinecarboxamide,
2-amino-3-bromo-N-((1R)-1-(2-pyrimidinyl)propyl)-N-((5-(trifluoromethyl)-2-pyridinyl)methyl)-1,7-naphthyridine-6-carboxamide,
7-amino-6-bromo-N-((5-(difluoromethyl)-2-pyridinyl)methyl)-N-((1R)-1-(2-

TABLE 11-continued pyrimidinyl)propyl)-1,8-naphthyridine-3-carboxamide,
2-amino-N-((5-(cyclopropyloxy)-2-pyridinyl)methyl)-3-methyl-N-((1R)-1-(2-pyrimidinyl)ethyl)-6-quinolinecarboxamide,
7-amino-6-bromo-N-((6-bromo-3-pyridazinyl)methyl)-N-((1R)-1-(2-pyrimidinyl)ethyl)-1,8-naphthyridine-3-carboxamide,
2-amino-N-((1R)-1-(3-fluoro-2-pyridinyl)ethyl)-3-(~2~H_3_)methyl-N-((5-(trifluoromethyl)-2-pyridinyl)methyl)-6-quinolinecarboxamide,
2-amino-N-((5-(3,3-difluoro-1-pyrrolidinyl)-2-pyridinyl)methyl)-3-methyl-N-((1R)-1-(2-pyrimidinyl)ethyl)-6-quinolinecarboxamide,
2-amino-N-((2R)-1-methoxy-2-propanyl)-3-methyl-N-((5-(trifluoromethyl)-2-pyridinyl)methyl)-6-quinolinecarboxamide,
7-amino-6-bromo-N-((6-methoxy-3-pyridazinyl)methyl)-N-((1R)-1-(2-pyrimidinyl)ethyl)-1,8-naphthyridine-3-carboxamide,
2-amino-7-fluoro-N-((6-methoxy-3-pyridazinyl)methyl)-3-methyl-N-((1R)-1-(2-pyrimidinyl)ethyl)-6-quinolinecarboxamide,
2-amino-7-fluoro-N-((6-methoxy-3-pyridazinyl)methyl)-3-methyl-N-((1S)-1-(2-pyrimidinyl)ethyl)-6-quinolinecarboxamide,
2-amino-3-bromo-N-((5-(difluoromethyl)-2-pyridinyl)methyl)-N-((1R)-1-(2-pyrimidinyl)ethyl)-6-quinolinecarboxamide,
2-amino-3-bromo-N-((6-methoxy-3-pyridazinyl)methyl)-N-((1R)-1-(2-pyrimidinyl)ethyl)-6-quinolinecarboxamide,
2-amino-N-((5-cyano-2-pyridinyl)methyl)-3-(~2~H_3_)methyl-N-((1R)-1-(2-pyrimidinyl)ethyl)-6-quinolinecarboxamide,
2-amino-N-((5-bromo-6-methyl-2-pyridinyl)methyl)-3-methyl-N-((1R)-1-(2-pyrimidinyl)ethyl)-6-quinolinecarboxamide,
2-amino-3-bromo-N-((1R)-1-(2-pyrimidinyl)ethyl)-N-((5-(trifluoromethyl)-2-pyridinyl)methyl)-1,7-naphthyridine-6-carboxamide,
7-amino-N-((R)-cyclopropyl(2-pyrimidinyl)methyl)-6-methyl-N-((5-(trifluoromethyl)-2-pyridiny)methyl)-1,8-naphthyridine-3-carboxamide,
2-amino-N-((6-(dimethylamino)-3-pyridazinyl)methyl)-3-methyl-N-((1R)-1-(2-pyrimidinyl)ethyl)-6-quinolinecarboxamide,
2-amino-N-((5-cyano-2-pyridinyl)methyl)-3-methyl-N-((1R)-1-(1-methyl-1H-1,2,4-triazol-3-yl)ethyl)-6-quinolinecarboxamide,
2-amino-3-bromo-N-((5-(difluoromethyl)-2-pyridinyl)methyl)-N-((1R)- 1-(2-pyrimidinyl)propyl)-6-quinolinecarboxamide,
2-amino-3-methyl-N-((6-(4-morpholinyl)-3-pyridazinyl)methyl)-N-((1R)-1-(2-pyrimidinyl)ethyl)-6-quinolinecarboxamide,
2-amino-N-((6-ethoxy-3-pyridazinyl)methyl)-3-methyl-N-((1R)-1-(2-pyrimidinyl)ethyl)-6-quinolinecarboxamide,
methyl 6-((((2-amino-3-methyl-6-quinolinyl)carbonyl)((1R)-1-(2-pyrimidinyl)ethyl)amino)methyl)-3',6'-dihydro[3,4'-bipyridine]-1'(2'H)-carboxylate, 2-amino-N-((1R,2S)-3,3-difluoro-2-hydroxycyclohexyl)-3-methyl-N-((5-(trifluoromethyl)-2-pyridinyl)methyl)-6-quinolinecarboxamide,
2-amino-N-((5-(3,3-difluoro-1-azetidinyl)-2-pyridinyl)methyl)-3-methyl-N-((1R)-1-(2-pyrimidinyl)ethyl)-6-quinolinecarboxamide,
7-amino-6-bromo-N-((R)-cyclopropyl(2-pyrimidinyl)methyl)-N-((5-(trifluoromethyl)-2-pyridinyl)methyl)-1,8-naphthyridine-3-carboxamide,
7-amino-6-bromo-N-((2S)-3,3,3-trifluoro-2-methoxypropyl)-N-((5-(trifluoromethyl)-2-pyridinyl)methyl)-1,8-naphthyridine-3-carboxamide,
2-amino-N-((5-(difluoromethyl)-2-pyridinyl)methyl)-3-methyl-N-((1R)-1-(1-methyl-1H-1,2,4-triazol-3-yl)ethyl)-6-quinolinecarboxamide,
2-amino-N-(1,3-dimethoxy-2-propanyl)-3-methyl-N-((5-(trifluoromethyl)-2-pyridinyl)methyl)-6-quinolinecarboxamide,
2-amino-N-((1R)-1-(5-fluoro-2-pyrimidinyl)ethyl)-3-methyl-N-((5-(trifluoromethyl)-2-pyridinyl)methyl)-6-quinolinecarboxamide,
2-amino-3-methyl-N-((1R)-1-(2-pyrimidinyl)ethyl)-N-((5-(tetrahydro-2H-pyran-4-yl)-2-pyridinyl)methyl)-6-quinolinecarboxamide,
2-amino-3-methyl-N-((5R)-5,6,7,8-tetrahydro-5-quinoxalinyl)-N-((5-(trifluoromethyl)-2-pyridinyl)methyl)-6-quinolinecarboxamide,
2-amino-3-methyl-N-((5S)-5,6,7,8-tetrahydro-5-quinoxalinyl)-N-((5-(trifluoromethyl)-2-pyridinyl)methyl)-6-quinolinecarboxamide,
2-amino-3-methyl-N-((1R)-1-(2-pyrimidinyl)ethyl)-N-((6-((2,2,2-trifluoroethyl)amino)-3-pyridazinyl)methyl)-6-quinolinecarboxamide,
2-amino-N-((5-cyano-2-pyridinyl)methyl)-3-methyl-N-((8R)-5,6,7,8-tetrahydro[1,2,4]triazolo[1,5-a]pyridin-8-yl)-6-quinolinecarboxamide,
2-amino-N-((3-fluoro-2-pyridinyl)methyl)-3-methyl-N-((3S)-6-(trifluoromethyl)-2,3-dihydro-1-benzofuran-3-yl)-6-quinolinecarboxamide,
2-amino-3-bromo-N-((5-chloro-2-pyridinyl)methyl)-N-((1R)-1-(2-pyrimidinyl)ethyl)-6-quinolinecarboxamide,
2-amino-3-chloro-N-((6-methoxy-3-pyridazinyl)methyl)-N-((1R)-1-(2-pyrimidinyl)ethyl)-6-quinolinecarboxamide,
7-amino-6-bromo-N-((5-chloro-2-pyridinyl)methyl)-N-((1R)-1-(2-pyrimidinyl)ethyl)-1,8-naphthyridine-3-carboxamide,
2-amino-N-((5-chloro-2-pyridinyl)methyl)-7-fluoro-3-methyl-N-((1R)-1-(2-pyrimidinyl)ethyl)-6-quinolinecarboxamide,
2-amino-N-((1R)-1-(3-chloro-2-pyridinyl)ethyl)-3-methyl-N-((6-(trifluoromethyl)-3-pyridazinyl)methyl)-6-quinolinecarboxamide,
7-amino-6-chloro-N-((1R)-1-(2-pyrimidinyl)ethyl)-N-((5-(trifluoromethyl)-2-pyridinyl)methyl)-1,8-naphthyridine-3-carboxamide,
2-amino-N-((1R,2R)-2-hydroxycyclopentyl)-3-methyl-N-((5-(trifluoromethyl)-2-

TABLE 11-continued pyridinyl)methyl)-6-quinolinecarboxamide,
2-amino-N-((1R,2R)-2-hydroxycyclopentyl)-3-methyl-N-((6-(trifluoromethyl)-3-pyridazinyl)methyl)-6-quinolinecarboxamide,
7-amino-6-chloro-N-((5-(difluoromethyl)-2-pyridinyl)methyl)-N-((1R)-1-(2-pyrimidinyl)ethyl)-1,8-naphthyridine-3-carboxamide,
2-amino-N-((R)-cyclopropyl(2-pyrimidinyl)methyl)-3-methyl-N-((6-(trifluoromethyl)-3-pyridazinyl)methyl)-6-quinolinecarboxamide,
2-amino-N-((5-cyano-2-pyridinyl)methyl)-N-((R)-cyclopropyl(2-pyrimidinyl)methyl)-7-fluoro-3-methyl-6-quinolinecarboxamide,
2-amino-3-chloro-N-((5-cyano-2-pyridinyl)methyl)-N-((1R)-1-(3-fluoro-2-pyridinyl)ethyl)-6-quinolinecarboxamide,
2-amino-3-bromo-N-((5-cyano-2-pyridinyl)methyl)-N-((1R)-1-(3-fluoro-2-pyridinyl)ethyl)-6-quinolinecarboxamide,
2-amino-N-((4R)-6-fluoro-3,4-dihydro-2H-pyrano[3,2-b]pyridin-4-yl)-3-methyl-N-((5-(trifluoromethyl)-2-pyridinyl)methyl)-6-quinolinecarboxamide,
2-amino-N-((5-cyano-2-pyridinyl)methyl)-7-fluoro-N-((1R)-1-(3-fluoro-2-pyridinyl)ethyl)-3-methyl-6-quinolinecarboxamide,
2-amino-N-((6-(3,6-dihydro-2H-pyran-4-yl)-3-pyridazinyl)methyl)-3-methyl-N-((1R)-1-(2-pyrimidinyl)ethyl)-6-quinolinecarboxamide,
2-amino-3-chloro-N-((6-(3,6-dihydro-2H-pyran-4-yl)-3-pyridazinyl)methyl)-N-((1R)-1-(2-pyrimidinyl)ethyl)-6-quinolinecarboxamide,
7-amino-6-bromo-N-((5-cyano-2-pyridinyl)methyl)-N-((1R)-1-(3-fluoro-2-pyridinyl)ethyl)-1,8-naphthyridine-3-carboxamide,
7-amino-N-((1R)-1-(5-fluoro-2-pyrimidinyl)ethyl)-6-methyl-N-((5-(trifluoromethyl)-2-pyridinyl)methyl)-1,8-naphthyridine-3-carboxamide,
2-amino-N-((6-bromo-3-pyridazinyl)methyl)-3-methyl-N-((1R)-1-(1,3-thiazol-2-yl)ethyl)-6-quinolinecarboxamide,
2-amino-3-methyl-N-((1R)-1-(1,3-thiazol-4-yl)ethyl)-N-((6-(trifluoromethyl)-3-pyridazinyl)methyl)-6-quinolinecarboxamide,
2-amino-7-chloro-N-((5-cyano-2-pyridinyl)methyl)-3-methyl-N-((1R)-1-(2-pyrimidinyl)ethyl)-6-quinolinecarboxamide,
2-amino-N-((6-bromo-3-pyridazinyl)methyl)-3-methyl-N-((8R)-5,6,7,8-tetrahydro[1,2,4]triazolo[1,5-a]pyridin-8-yl)-6-quinolinecarboxamide,
2-amino-3-methyl-N-((1R)-1-(2-pyrimidinyl)ethyl)-N-((6-(trifluoromethyl)-2-pyridinyl)methyl)-6-quinolinecarboxamide,
2-amino-N-((6-(difluoromethyl)-3-pyridazinyl)methyl)-3-methyl-N-((1R)-1-(2-pyrimidinyl)ethyl)-6-quinolinecarboxamide,
2-amino-N-((5-(difluoromethyl)-2-pyridinyl)methyl)-N-((1R,2R)-2-hydroxycyclopentyl)-3-methyl-6-quinolinecarboxamide,
2-amino-N-((5-cyano-2-pyridinyl)methyl)-N-((1R,2R)-2-hydroxycyclopentyl)-3-methyl-6-quinolinecarboxamide,
2-amino-N-(6-bromo-3-pyridazinyl)methyl)-N-(1R,2R)-2-hydroxycyclopentyl)-3-methyl-6-quinolinecarboxamide,
2-amino-N-((1R,2R)-2-hydroxycyclopentyl)-N-((6-methoxy-3-pyridazinyl)methyl)-3-methyl-6-quinolinecarboxamide,
2-amino-3-chloro-N-((1R)-1-(2-pyrimidinyl)ethyl)-N-((5-(trifluoromethyl)-2-pyridinyl)methyl)-1,7-naphthyridine-6-carboxamide,
2-amino-N-((5-(difluoromethyl)-2-pyridinyl)methyl)-3-methyl-N-((1R)-1-(5-methyl-1,2,4-oxadiazol-3-yl)ethyl)-6-quinolinecarboxamide,
2-amino-3-bromo-N-((6-bromo-3-pyridazinyl)methyl)-N-((1R)-1-(1,3-thiazol-2-yl)ethyl)-6-quinolinecarboxamide,
2-amino-3-chloro-N-((5-(difluoromethyl)-2-pyridinyl)methyl)-N-((1R)-1-(2-pyrimidinyl)ethyl)-6-quinolinecarboxamide,
2-amino-3-iodo-N-((1R)-1-(2-pyrimidinyl)ethyl)-N-((5-(trifluoromethyl)-2-pyridinyl)methyl)-6-quinolinecarboxamide,
2-amino-N-((5-cyano-2-pyridinyl)methyl)-N-((R)-cyclopropyl(2-pyrimidinyl)methyl)-3-methyl-6-quinolinecarboxamide,
7-amino-6-bromo-N-((6-bromo-3-pyridazinyl)methyl)-N-((1R)-1-(3-fluoro-2-pyridinyl)ethyl)-1,8-naphthyridine-3-carboxamide,
7-amino-6-bromo-N-((5-cyano-2-pyridinyl)methyl)-N-((R)-cyclopropyl(2-pyrimidinyl)methyl)-1,8-naphthyridine-3-carboxamide,
7-amino-6-bromo-N-((5-(difluoromethyl)-2-pyridinyl)methyl)-N-((1R)-1-(1-methyl-1H-1,2,4-triazol-3-yl)ethyl)-1,8-naphthyridine-3-carboxamide,
2-amino-N-((6-bromo-3-pyridazinyl)methyl)-3-methyl-N-((1R)-1-(1-methyl-1H-1,2,4-triazol-3-yl)ethyl)-6-quinolinecarboxamide,
2-amino-N-((4R)-6-fluoro-3,4-dihydro-2H-pyrano[3,2-b]pyridin-4-yl)-3-methyl-N-((6-(trifluoromethyl)-3-pyridazinyl)methyl)-6-quinolinecarboxamide,
N-((5-(1-acetyl-4-piperidinyl)-2-pyridinyl)methyl)-2-amino-3-methyl-N-((1R)-1-(2-pyrimidinyl)ethyl)-6-quinolinecarboxamide,
7-amino-6-bromo-N-((5-(3-oxetanyloxy)-2-pyridinyl)methyl)-N-((1R)-1-(2-pyrimidinyl)ethyl)-1,8-naphthyridine-3-carboxamide,
2-amino-3-methyl-N-((5-(3-oxetanyloxy)-2-pyridinyl)methyl)-N-((1R)-1-(2-pyrimidinyl)ethyl)-6-quinolinecarboxamide,
7-amino-6-bromo-N-((5R)-5,6,7,8-tetrahydro-5-quinoxalinyl)-N-((5-(trifluoromethyl)-2-pyridinyl)methyl)-1,8-naphthyridine-3-carboxamide,
2-amino-N-((5-chloro-6-methyl-2-pyridinyl)methyl)-3-methyl-N-((1R)-1-(2-pyrimidinyl)ethyl)-6-quinolinecarboxamide,
2-amino-N-((2-methoxy-6-(trifluoromethyl)-3-pyridinyl)methyl)-3-methyl-N-((1R)-1-(2-pyrimidinyl)ethyl)-6-quinolinecarboxamide,
7-amino-6-bromo-N-((6-ethoxy-3-pyridazinyl)methyl)-N-((1R)-1-(2-pyrimidinyl)ethyl)-

TABLE 11-continued 1,8-naphthyridine-3-carboxamide,
2-amino-N-((3R,4S)-4-hydroxytetrahydro-3-furanyl)-3-methyl-N-((5-(trifluoromethyl)-2-pyridinyl)methyl)-6-quinolinecarboxamide,
7-amino-6-bromo-N-((5-bromo-6-methyl-2-pyridinyl)methyl)-N-((1R)-1-(2-pyrimidinyl)ethyl)-1,8-naphthyridine-3-carboxamide,
2-amino-N-((3R,4R)-4-hydroxytetrahydro-2H-pyran-3-yl)-3-methyl-N-((5-(trifluoromethyl)-2-pyridinyl)methyl)-6-quinolinecarboxamide,
2-amino-N-((1S)-1-(6-cyano-2-pyridinyl)ethyl)-3-methyl-N-((5-(trifluoromethyl)-2-pyridinyl)methyl)-6-quinolinecarboxamide,
2-amino-N-((6-methoxy-3-pyridazinyl)methyl)-3-methyl-N-((1S)-1-(1-methyl-1H-1,2,4-triazol-3-yl)ethyl)-6-quinolinecarboxamide,
2-amino-N-((3S,4S)-4-methoxytetrahydro-2H-pyran-3-yl)-3-methyl-N-((5-(trifluoromethyl)-2-pyridinyl)methyl)-6-quinolinecarboxamide,
2-amino-N-((2R)-1-methoxy-2-propanyl)-N-((6-methoxy-3-pyridazinyl)methyl)-3-methyl-6-quinolinecarboxamide,
2-amino-3-methyl-N-((1R)-2-methyl-1-(2-pyrimidinyl)propyl)-N-((5-(trifluoromethyl)-2-pyridinyl)methyl)-6-quinolinecarboxamide,
2-amino-3-methyl-N-((1S)-2-methyl-1-(2-pyrimidinyl)propyl)-N-((5-(trifluoromethyl)-2-pyridinyl)methyl)-6-quinolinecarboxamide,
7-amino-6-iodo-N-((1R)-1-(2-pyrimidinyl)ethyl)-N-((5-(trifluoromethyl)-2-pyridinyl)methyl)-1,8-naphthyridine-3-carboxamide,
2-amino-3-methyl-N-((1R)-1-(2-pyrimidinyl)ethyl)-N-((6-(2,2,2-trifluoroethoxy)-3-pyridazinyl)methyl)-6-quinolinecarboxamide,
methyl 4-(6-((((2-amino-3-methyl-6-quinolinyl)carbonyl)((1R)-1-(2-pyrimidinyl)ethyl)amino)methyl)-3-pyridinyl)-1-piperidinecarboxylate,
2-amino-3-methyl-N-((8R)-5,6,7,8-tetrahydroimidazo[1,2-a]pyridin-8-yl)-N-((6-(trifluoromethyl)-3-pyridazinyl)methyl)-6-quinolinecarboxamide,
2-amino-N-((1R,2R)-2-methoxy-2,3-dihydro-1H-inden-1-yl)-3-methyl-N-((5-(trifluoromethyl)-2-pyridinyl)methyl)-6-quinolinecarboxamide,
2-amino-N-((3-chloro-2-pyridinyl)methyl)-7-fluoro-3-methyl-N-((1R)-1-(2-pyrimidinyl)ethyl)-6-quinolinecarboxamide,
2-amino-N-((6-methoxy-3-pyridazinyl)methyl)-3-methyl-N-((2S)-3,3,3-trifluoro-2-methoxypropyl)-6-quinolinecarboxamide,
2-amino-3-bromo-N-((6-bromo-3-pyridazinyl)methyl)-N-((1R)-1-(2-pyrimidinyl)ethyl)-6-quinolinecarboxamide,
2-amino-N-((1R)-1-(2-fluoro-4-pyridinyl)ethyl)-3-methyl-N-((5-(trifluoromethyl)-2-pyridinyl)methyl)-6-quinolinecarboxamide,
2-amino-N-((1S)-1-(2-fluoro-4-pyridinyl)ethyl)-3-methyl-N-((5-(trifluoromethyl)-2-pyridinyl)methyl)-6-quinolinecarboxamide,
2-amino-3-bromo-N-((5-cyano-2-pyridinyl)methyl)-N-((2R)-1-methoxy-2-propanyl)-6-quinolinecarboxamide,
2-amino-N-((1S,2S)-2-methoxy-2,3-dihydro-1H-inden-1-yl)-3-methyl-N-((5-(trifluoromethyl)-2-pyridinyl)methyl)-6-quinolinecarboxamide,
2-amino-N-((R)-cyclopropyl(2-pyrimidinyl)methyl)-N-((6-methoxy-3-pyridazinyl)methyl)-3-methyl-6-quinolinecarboxamide,
2-amino-3-methyl-N-(2-(trifluoromethoxy)ethyl)-N-((5-(trifluoromethyl)-2-pyridinyl)methyl)-6-quinolinecarboxamide,
2-amino-N-((1R)-1-(2-pyrimidinyl)ethyl)-N-((5-(trifluoromethyl)-2-pyridinyl)methyl)-6-quinolinecarboxamide,
2-amino-N-((6-cyano-3-pyridazinyl)methyl)-N-((1R)-1-(3-fluoro-2-pyridinyl)ethyl)-3-methyl-6-quinolinecarboxamide,
2-amino-N-((1R,2R)-4,4-difluoro-2-hydroxycyclopentyl)-3-methyl-N-((5-(trifluoromethyl)-2-pyridinyl)methyl)-6-quinolinecarboxamide,
2-amino-3-bromo-N-((6-ethoxy-3-pyridazinyl)methyl)-N-((1R)-1-(2-pyrimidinyl)ethyl)-6-quinolinecarboxamide,
2-amino-3,5-dimethyl-N-((1R)-1-(2-pyrimidinyl)ethyl)-N-((5-(trifluoromethyl)-2-pyridinyl)methyl)-6-quinolinecarboxamide,
2-amino-N-((2R)-1-methoxy-2-propanyl)-3,5-dimethyl-N-((5-(trifluoromethyl)-2-pyridinyl)methyl)-6-quinolinecarboxamide,
2-amino-N-((3-chloro-2-pyridinyl)methyl)-3-methyl-N-((1R)-1-(2-pyrimidinyl)ethyl)-6-quinolinecarboxamide,
2-amino-N-((3-chloro-2-pyridinyl)methyl)-3-methyl-N-((1S)-1-(2-pyrimidinyl)ethyl)-6-quinolinecarboxamide,
2-amino-N-((5S)-5,8-dihydro-6H-pyrano[3,4-b]pyridin-5-yl)-3-methyl-N-((5-(trifluoromethyl)-2-pyridinyl)methyl)-6-quinolinecarboxamide,
N-((5-acetyl-2-pyridinyl)methyl)-2-amino-3-methyl-N-((1R)-1-(2-pyrimidinyl)ethyl)-6-quinolinecarboxamide,
2-amino-N-((5-(2-hydroxy-2-propanyl)-2-pyridinyl)methyl)-3-methyl-N-((1R)-1-(2-pyrimidinyl)ethyl)-6-quinolinecarboxamide,
2-amino-N-((1R)-1-(3-fluoro-2-pyridinyl)ethyl)-3-methyl-N-((6-(4-morpholinyl)-3-pyridazinyl)methyl)-6-quinolinecarboxamide,
7-amino-6-bromo-N-((1R)-1-(3-fluoro-2-pyridinyl)ethyl)-N-((6-methoxy-3-pyridazinyl)methyl)-1,8-naphthyridine-3-carboxamide,
2-amino-3-bromo-N-((1R)-1-(3-fluoro-2-pyridinyl)ethyl)-N-((6-methoxy-3-pyridazinyl)methyl)-6-quinolinecarboxamide,
2-amino-3-bromo-N-((6-methoxy-3-pyridazinyl)methyl)-N-((1R)-1-(1-methyl-1H-1,2,4-triazol-3-yl)ethyl)-6-quinolinecarboxamide,
2-amino-7-chloro-N-((3-fluoro-2-pyridinyl)methyl)-3-methyl-N-((5-(trifluoromethyl)-2-pyridinyl)methyl)-6-quinolinecarboxamide,
2-amino-N-((3R,4S)-3-fluorotetrahydro-2H-pyran-4-yl)-3-methyl-N-((5-

TABLE 11-continued (trifluoromethyl)-2-pyridinyl)methyl)-6-quinolinecarboxamide,
7-amino-6-bromo-N-((1S)-1-(1,3-thiazol-4-yl)ethyl)-N-((6-(trifluoromethyl)-3-pyridazinyl)methyl)-1,8-naphthyridine-3-carboxamide,
2-amino-N-((6-methoxy-3-pyridinyl)methyl)-3-methyl-N-((1R)-1-(2-pyrimidinyl)ethyl)-6-quinolinecarboxamide,
2-amino-N-((5-cyclopropyl-2-pyridinyl)methyl)-3-methyl-N-((1R)-1-(2-pyrimidinyl)ethyl)-6-quinolinecarboxamide,
7-amino-6-bromo-N-((1R)-1-(3-fluoro-2-pyridinyl)ethyl)-N-((6-(4-morpholinyl)-3-pyridazinyl)methyl)-1,8-naphthyridine-3-carboxamide,
2-amino-N-((3R,4S)-3-hydroxytetrahydro-2H-pyran-4-yl)-3-methyl-N-((5-(trifluoromethyl)-2-pyridinyl)methyl)-6-quinolinecarboxamide,
2-amino-N-((6-bromo-3-pyridazinyl)methyl)-3-iodo-N-((1R)-1-(2-pyrimidinyl)ethyl)-6-quinolinecarboxamide,
2-amino-3-bromo-N-((1R)-1-(3-fluoro-2-pyridinyl)ethyl)-N-((6-(trifluoromethyl)-3-pyridazinyl)methyl)-6-quinolinecarboxamide,
2-amino-N-((3R,4S)-3-methoxytetrahydro-2H-pyran-4-yl)-3-methyl-N-((5-(trifluoromethyl)-2-pyridinyl)methyl)-6-quinolinecarboxamide,
2-amino-N-(3,4-dihydro-2H-pyrano[2,3-c]pyridin-6-ylmethyl)-3-methyl-N-((1R)-1-(2-pyrimidinyl)ethyl)-6-quinolinecarboxamide,
2-amino-N-(3,4-dihydro-2H-pyrano[2,3-c]pyridin-6-ylmethyl)-3-methyl-N-((1S)-1-(2-pyrimidinyl)ethyl)-6-quinolinecarboxamide,
2-amino-3-bromo-N-((5-cyano-2-pyridinyl)methyl)-N-((R)-cyclopropyl(2-pyrimidinyl)methyl)-6-quinolinecarboxamide,
2-amino-N-((6-(difluoromethoxy)-3-pyridazinyl)methyl)-3-methyl-N-((1R)-1-(2-pyrimidinyl)ethyl)-6-quinolinecarboxamide,
2-amino-N-((6-(difluoromethoxy)-3-pyridazinyl)methyl)-3-methyl-N-((1S)-1-(2-pyrimidinyl)ethyl)-6-quinolinecarboxamide,
2-amino-N-((6-bromo-3-pyridazinyl)methyl)-7-fluoro-3-methyl-N-((8R)-5,6,7,8-tetrahydro[1,2,4]triazolo[1,5-a]pyridin-8-yl)-6-quinolinecarboxamide,
2-amino-3-methyl-N-((1S)-1-(1,2,4-oxadiazol-3-yl)ethyl)-N-((5-(trifluoromethyl)-2-pyridinyl)methyl)-6-quinolinecarboxamide,
2-amino-3-methyl-N-((1R)-1-(2-pyrimidinyl)ethyl)-N-((6-(trifluoromethoxy)-3-pyridazinyl)methyl)-6-quinolinecarboxamide,
2-amino-3-methyl-N-((1S)-1-(2-pyrimidinyl)ethyl)-N-((6-(trifluoromethoxy)-3-pyridazinyl)methyl)-6-quinolinecarboxamide,
2-amino-N-(3-isoquinolinyimethyl)-3-methyl-N-((1R)-1-(2-pyrimidinyl)ethyl)-6-quinolinecarboxamide,
2-amino-N-(3-isoquinolinylmethyl)-3-methyl-N-((1S)-1-(2-pyrimidinyl)ethyl)-6-quinolinecarboxamide,
7-amino-6-bromo-N-((1R,2R)-2-methoxycyclohexyl)-N-((5-(trifluoromethyl)-2-pyridinyl)methyl)-1,8-naphthyridine-3-carboxamide,
7-amino-6-bromo-N-((1S,2S)-2-methoxycyclohexyl)-N-((5-(trifluoromethyl)-2-pyridinyl)methyl)-1,8-naphthyridine-3-carboxamide,
2-amino-N-((6-bromo-3-pyridazinyl)methyl)-3-chloro-N-((1R)-1-(3-fluoro-2-pyridinyl)ethyl)-6-quinolinecarboxamide,
2-amino-3-bromo-N-((6-bromo-3-pyridazinyl)methyl)-N-((8R)-5,6,7,8-tetrahydro[1,2,4]triazolo[1,5-a]pyridin-8-yl)-6-quinolinecarboxamide,
7-amino-6-Iodo-N-((1R)-1-(2-pyrimidinyl)propyl)-N-((5-(trifluoromethyl)-2-pyridinyl)methyl)-1,8-naphthyridine-3-carboxamide,
2-amino-3-methyl-N-(4-(3-oxetanyl)benzyl)-N-((1R)-1-(2-pyrimidinyl)ethyl)-6-quinolinecarboxamide,
2-amino-3-methyl-N-(4-(3-oxetanyl)benzyl)-N-((1S)-1-(2-pyrimidinyl)ethyl)-6-quinolinecarboxamide,
2-amino-N-((1R)-1-cyclopropyl-2-methoxyethyl)-3-methyl-N-((5-(trifluoromethyl)-2-pyridinyl)methyl)-6-quinolinecarboxamide,
2-amino-N-((1S)-1-cyclopropyl-2-methoxyethyl)-3-methyl-N-((5-(trifluoromethyl)-2-pyridinyl)methyl)-6-quinolinecarboxamide,
2-amino-N-((3R,4R)-4-fluorotetrahydro-2H-pyran-3-yl)-3-methyl-N-((5-(trifluoromethyl)-2-pyridinyl)methyl)-6-quinolinecarboxamide,
2-amino-N-((1R,2S)-2-cyanocyclopentyl)-3-methyl-N-((5-(trifluoromethyl)-2-pyridinyl)methyl)-6-quinolinecarboxamide,
2-amino-N-((1S,2R)-2-cyanocyclopentyl)-3-methyl-N-((5-(trifluoromethyl)-2-pyridinyl)methyl)-6-quinolinecarboxamide,
2-amino-N-((1S,2S)-2-cyanocyclopentyl)-3-methyl-N-((5-(trifluoromethyl)-2-pyridinyl)methyl)-6-quinolinecarboxamide,
2-amino-N-((1R)-1-(6-fluoro-2-pyridinyl)ethyl)-3-methyl-N-((5-(trifluoromethyl)-2-pyridinyl)methyl)-6-quinolinecarboxamide,
7-amino-6-bromo-N-((1R)-1-(2-pyrimidinyl)ethyl)-N-((6-(2,2,2-trifluoroethoxy)-3-pyridazinyl)methyl)-1,8-naphthyridine-3-carboxamide,
2-amino-7-fluoro-3-methyl-N-((6-(4-morpholinyl)-3-pyridazinyl)methyl)-N-((1R)-1-(2-pyrimidinyl)ethyl)-6-quinolinecarboxamide,
7-amino-N-((5-chloro-2-pyridinyl)methyl)-6-iodo-N-((1R)-1-(2-pyrimidinyl)ethyl)-1,8-naphthyridine-3-carboxamide,
7-amino-6-bromo-N-((1R)-1-(6-fluoro-2-pyridinyl)ethyl)-N-((5-(trifluoromethyl)-2-pyridinyl)methyl)-1,8-naphthyridine-3-carboxamide,
2-amino-3-methyl-N-((5-(4-morpholinyl)-2-pyridinyl)methyl)-N-((1R)-1-(2-pyrimidinyl)ethyl)-6-quinolinecarboxamide,
2-amino-3-bromo-N-((5-cyano-2-pyridinyl)methyl)-N-((1R)-1-(2-pyrimidinyl)propyl)-6-quinolinecarboxamide,
2-amino-N-((6-cyclopropyl-3-pyridazinyl)methyl)-3-methyl-N-((1R)-1-(2-

TABLE 11-continued pyrimidinyl)ethyl)-6-quinolinecarboxamide,
2-amino-N-((1R,2R)-2-(difluoromethoxy)cyclopentyl)-3-methyl-N-((5-(trifluoromethyl)-2-pyridinyl)methyl)-6-quinolinecarboxamide,
2-amino-N-((1S,2S)-2-(difluoromethoxy)cyclopentyl)-3-methyl-N-((5-(trifluoromethyl)-2-pyridinyl)methyl)-6-quinolinecarboxamide,
2-amino-N-((6-chloro-3-pyridazinyl)methyl)-3-methyl-N-((1R)-1-(2-pyrimidinyl)ethyl)-6-quinolinecarboxamide,
2-amino-N-((6-cyano-2-methyl-3-pyridinyl)methyl)-3-methyl-N-((1R)-1-(2-pyrimidinyl)ethyl)-6-quinolinecarboxamide,
2-amino-N-(2-methylpropyl)-3-phenyl-N-((5-(trifluoromethyl)-2-pyridinyl)methyl)-6-quinolinecarboxamide,
7-amino-6-bromo-5-methyl-N-((1R)-1-(2-pyrimidinyl)ethyl)-N-((5-(trifluoromethyl)-2-pyridinyl)methyl)-1,8-naphthyridine-3-carboxamide,
2-amino-N-((5-(difluoromethyl)-2-pyridinyl)methyl)-3-iodo-N-((1R)-1-(1-methyl-1H-1,2,4-triazol-3-yl)ethyl)-6-quinolinecarboxamide,
2-amino-3-bromo-N-((6-cyclopropyl-3-pyridazinyl)methyl)-N-((1R)-1~(2-pyrimidinyl)ethyl)-6-quinolinecarboxamide,
2-amino-N-((4-chloro-5-cyano-2-pyridinyl)methyl)-3-methyl-N-((1R)-1-(2-pyrimidinyl)ethyl)-6-quinolinecarboxamide,
2-amino-N-((1R)-1-(3-fluoro-2-pyridinyl)ethyl)-3-methyl-N-((6-(methylamino)-3-pyridazinyl)methyl)-6-quinolinecarboxamide,
7-amino-6-bromo-N-((5-cyano-2-pyridinyl)methyl)-5-methyl-N-((1R)-1-(2-pyrimidinyl)ethyl)-1,8-naphthyridine-3-carboxamide,
2-amino-3-bromo-N-((1S)-1-cyclopropyl-2-methoxyethyl)-N-((6-(4-morpholinyl)-3-pyridazinyl)methyl)-6-quinolinecarboxamide,
2-amino-3-bromo-N-((4-chloro-5-cyano-2-pyridinyl)methyl)-N-((1R)-1-(2-pyrimidinyl)ethyl)-6-quinolinecarboxamide,
2-amino-N-((5-cyano-6-methyl-2-pyridinyl)methyl)-3-methyl-N-((1R)-1-(2-pyrimidinyl)ethyl)-6-quinolinecarboxamide,
2-amino-3-bromo-N-((1S)-2-cyano-1-cyclopropylethyl)-N-((5-cyano-2-pyridinyl)methyl)-6-quinolinecarboxamide,
2-amino-N-((4-ethyl-1,3-thiazol-2-yl)methyl)-3-methyl-N-((5-(trifluoromethyl)-2-pyridinyl)methyl)-6-quinolinecarboxamide,
2-amino-3-methyl-N-((1R)-1-((3R)-tetrahydro-3-furanyl)ethyl)-N-((5-(trifluoromethyl)-2-pyridinyl)methyl)-6-quinolinecarboxamide,
2-amino-3-methyl-N-((1R)-1-((3S)-tetrahydro-3-furanyl)ethyl)-N-((5-(trifluoromethyl)-2-pyridinyl)methyl)-6-quinolinecarboxamide,
2-amino-3-methyl-N-((1S)-1-((3R)-tetrahydro-3-furanyl)ethyl)-N-((5-(trifluoromethyl)-2-pyridinyl)methyl)-6-quinolinecarboxamide,
2-amino-3-methyl-N-((1S)-1-((3S)-tetrahydro-3-furanyl)ethyl)-N-((5-(trifluoromethyl)-2-pyridinyl)methyl)-6-quinolinecarboxamide,
2-amino-3-bromo-N-(3,4-dihydro-2H-pyrano[2,3-c]pyridin-6-ylmethyl)-N-((1R)-1-(2-pyrimidinyl)ethyl)-6-quinolinecarboxamide,
2-amino-3-bromo-N-((6-chloro-3-pyridazinyl)methyl)-N-((1R)-1-(2-pyrimidinyl)ethyl)-6-quinolinecarboxamide,
2-amino-3-bromo-N-((5-cyano-6-methyl-2-pyridinyl)methyl)-N-((1R)-1-(2-pyrimidinyl)ethyl)-6-quinolinecarboxamide,
2-amino-N-((5-cyano-6-methyl-2-pyridinyl)methyl)-3-iodo-N-((1R)-1-(2-pyrimidinyl)ethyl)-6-quinolinecarboxamide,
2-amino-3-bromo-N-((6-(difluoromethoxy)-3-pyridazinyl)methyl)-N-((1R)-1-(2-pyrimidinyl)ethyl)-6-quinolinecarboxamide,
2-amino-3-bromo-N-((1R,2R)-2-cyanocyclopentyl)-N-((5-cyano-2-pyridinyl)methyl)-6-quinolinecarboxamide,
2-amino-3-bromo-N-((1R,2S)-2-cyanocyclopentyl)-N-((5-cyano-2-pyridinyl)methyl)-6-quinolinecarboxamide,
2-amino-3-bromo-N-((1S,2R)-2-cyanocyclopentyl)-N-((5-cyano-2-pyridinyl)methyl)-6-quinolinecarboxamide,
2-amino-3-bromo-N-((1S,2S)-2-cyanocyclopentyl)-N-((5-cyano-2-pyridinyl)methyl)-6-quinolinecarboxamide,
2-amino-3-bromo-N-((1-cyanocyclopropyl)methyl)-N-((5-(trifluoromethyl)-2-pyridinyl)methyl)-6-quinolinecarboxamide,
2-amino-3-bromo-N-((3S,4R)-3-methoxytetrahydro-2H-pyran-4-yl)-N-((5-(trifluoromethyl)-2-pyridinyl)methyl)-6-quinolinecarboxamide,
2-amino-3-bromo-N-((3R,4R)-3-methyltetrahydro-2H-pyran-4-yl)-N-((5-(trifluoromethyl)-2-pyridinyl)methyl)-6-quinolinecarboxamide,
2-amino-3-bromo-N-((3R,4S)-3-methyltetrahydro-2H-pyran-4-yl)-N-((5-(trifluoromethyl)-2-pyridinyl)methyl)-6-quinolinecarboxamide,
2-amino-3-bromo-N-((3S,4R)-3-methyltetrahydro-2H-pyran-4-yl)-N-((5-(trifluoromethyl)-2-pyridinyl)methyl)-6-quinolinecarboxamide,
2-amino-3-bromo-N-((3S,4S)-3-methyltetrahydro-2H-pyran-4-yl)-N-((5-(trifluoromethyl)-2-pyridinyl)methyl)-6-quinolinecarboxamide,
2-amino-3-bromo-N-((1R,2R)-2-methylcyclopentyl)-N-((5-(trifluoromethyl)-2-pyridinyl)methyl)-6-quinolinecarboxamide,
2-amino-3-bromo-N-((1R,2S)-2-methylcyclopentyl)-N-((5-(trifluoromethyl)-2-pyridinyl)methyl)-6-quinolinecarboxamide,
2-amino-3-bromo-N-((1S,2R)-2-methylcyclopentyl)-N-((5-(trifluoromethyl)-2-pyridinyl) methyl)-6-quinolinecarboxamide,
2-amino-3-bromo-N-((1S,2S)-2-methylcyclopentyl)-N-((5-(trifluoromethyl)-2-pyridinyl)methyl)-6-quinolinecarboxamide,
2-amino-3-bromo-N-((2R,3R)-2-cyclopropyltetrahydro-3-furanyl)-N-((5-

TABLE 11-continued (trifluoromethyl)-2-pyridinyl)methyl)-6-quinolinecarboxamide,
2-amino-3-bromo-N-((2R,3S)-2-cyclopropyltetrahydro-3-furanyl)-N-((5-
(trifluoromethyl)-2-pyridinyl)methyl)-6-quinolinecarboxamide,
2-amino-3-bromo-N-((2S,3R)-2-cyclopropyltetrahydro-3-furanyl)-N-((5-
(trifluoromethyl)-2-pyridinyl)methyl)-6-quinolinecarboxamide,
2-amino-3-bromo-N-((2S,3S)-2-cyclopropyltetrahydro-3-furanyl)-N-((5-
(trifluoromethyl)-2-pyridinyl)methyl)-6-quinolinecarboxamide,
2-amino-3-bromo-N-((1S)-2-cyano-1-cyclopropylethyl)-N-((5-(trifluoromethyl)-2-
pyridinyl)methyl)-6-quinolinecarboxamide,
2-amino-N-((6-chloro-5-cyano-2-pyridinyl)methyl)-3-iodo-N-((1R)-1-(2-
pyrimidinyl)ethyl)-6-quinolinecarboxamide,
2-amino-N-((5-cyano-2-pyridinyl)methyl)-3-iodo-N-((1R)-1-(2-pyrimidinyl)propyl)-6-
quinolinecarboxamide,
2-amino-N-(3,4-dihydro-2H-pyrano[2,3-c]pyridin-6-ylmethyl)-3-iodo-N-((1R)-1-(2-
pyrimidinyl)ethyl)-6-quinolinecarboxamide,
2-amino-N-((1S)-2-cyano-1-cyclopropylethyl)-N-((5-cyano-2-pyridinyl)methyl)-3-iodo-
6-quinolinecarboxamide,
2-amino-N-((6-cyclopropyl-3-pyridazinyl)methyl)-3-iodo-N-((1R)-1-(2-
pyrimidinyl)ethyl)-6-quinolinecarboxamide,
2-amino-7-hydroxy-3-methyl-N-(2-methylpropyl)-N-((5-(trifluoromethyl)-2-
pyridinyl)methyl)-6-quinolinecarboxamide,
7-amino-6-iodo-N-((1R)-1-(2-pyrimidinyl)ethyl)-N-((6-(trifluoromethyl)-3-
pyridazinyl)methyl)-1,8-naphthyridine-3-carboxamide,
7-amino-N-((6-ethoxy-3-pyridazinyl)methyl)-6-iodo-N-((1R)-1-(2-pyrimidinyl)ethyl)-
1,8-naphthyridine-3-carboxamide,
2-amino-3-methyl-N-(((3R,4R)-3-methyltetrahydro-2H-pyran-4-yl)methyl)-N-((5-
(trifluoromethyl)-2-pyridinyl)methyl)-6-quinolinecarboxamide,
2-amino-3-methyl-N-(((3R,4S)-3-methyltetrahydro-2H-pyran-4-yl)methyl)-N-((5-
(trifluoromethyl)-2-pyridinyl)methyl)-6-quinolinecarboxamide,
2-amino-3-methyl-N-(((3S,4S)-3-methyltetrahydro-2H-pyran-4-yl)methyl)-N-((5-
(trifluoromethyl)-2-pyridinyl)methyl)-6-quinolinecarboxamide,
2-amino-3-methyl-N-(((3S,4R)-3-methyltetrahydro-2H-pyran-4-yl)methyl)-N-((5-
(trifluoromethyl)-2-pyridinyl)methyl)-6-quinolinecarboxamide,
2-amino-3-methyl-N-((4R)-4,5,6,7-tetrahydro-1-benzofuran-4-yl)-N-((5-
(trifluoromethyl)-2-pyridinyl)methyl)-6-quinolinecarboxamide,
2-amino-3-methyl-N-((4S)-4,5,6,7-tetrahydro-1-benzofuran-4-yl)-N-((5-
(trifluoromethyl)-2-pyridinyl)methyl)-6-quinolinecarboxamide,
2-amino-N-((4R)-2-chloro-5,6-dihydro-4H-cyclopenta[b]thiophen-4-yl)-3-methyl-N-
((5-(trifluoromethyl)-2-pyridinyl)methyl)-6-quinolinecarboxamide,
2-amino-N-((4S)-2-chloro-5,6-dihydro-4H-cyclopenta[b]thiophen-4-yl)-3-methyl-N-
((5-(trifluoromethyl)-2-pyridinyl)methyl)-6-quinolinecarboxamide,
2-amino-N-((3R)-2,3-dihydro-1-benzofuran-3-yl)-3-methyl-N-((5-(trifluoromethyl)-2-
pyridinyl)methyl)-6-quinolinecarboxamide,
2-amino-N-((3S)-2,3-dihydro-1-benzofuran-3-yl)-3-methyl-N-((5-(trifluoromethyl)-2-
pyridinyl)methyl)-6-quinolinecarboxamide,
2-amino-3-methyl-N-((2R)-3,3,3-trifluoro-2-methoxypropyl)-N-((5-(trifluoromethyl)-2-
pyridinyl)methyl)-6-quinolinecarboxamide,
2-amino-N-((1R,3R)-3-hydroxycyclohexyl)-3-methyl-N-((5-(trifluoromethyl)-2-
pyridinyl)methyl)-6-quinolinecarboxamide,
2-amino-N-((1R,3S)-3-hydroxycyclohexyl)-3-methyl-N-((5-(trifluoromethyl)-2-
pyridinyl)methyl)-6-quinolinecarboxamide,
2-amino-N-((1S,3R)-3-hydroxycyclohexyl)-3-methyl-N-((5-(trifluoromethyl)-2-
pyridinyl)methyl)-6-quinolinecarboxamide,
2-amino-N-((1S,3S)-3-hydroxycyclohexyl)-3-methyl-N-((5-(trifluoromethyl)-2-
pyridinyl)methyl)-6-quinolinecarboxamide,
2-amino-N-((5-fluoro-3-pyridinyl)methyl)-3-methyl-N-((5-(trifluoromethyl)-2-
pyridinyl)methyl)-6-quinolinecarboxamide,
2-amino-3-methyl-N-((5R)-4,5,6,7-tetrahydro-1H-benzimidazol-5-ylmethyl)-N-((5-
(trifluoromethyl)-2-pyridinyl)methyl)-6-quinolinecarboxamide,
2-amino-3-methyl-N-((5S)-4,5,6,7-tetrahydro-1H-benzimidazol-5-ylmethyl)-N-((5-
(trifluoromethyl)-2-pyridinyl)methyl)-6-quinolinecarboxamide,
2-amino-3-methyl-N-(1H-pyrrolo[2,3-b]pyridin-5-ylmethyl)-N-((5-(trifluoromethyl)-2-
pyridinyl)methyl)-6-quinolinecarboxamide,
2-amino-3-methyl-N-((2-oxo-2,5,6,7-tetrahydro-1H-cyclopenta[b]pyridin-3-yl)methyl)-
N-((5-(trifluoromethyl)-2-pyridinyl)methyl)-6-quinolinecarboxamide,
2-amino-N-(3-hydroxybenzyl)-3-methyl-N-((5-(trifluoromethyl)-2-pyridinyl)methyl)-6-
quinolinecarboxamide,
2-amino-N-((1R)-2,3-dihydro-1H-inden-1-yl)-3-methyl-N-((5-(trifluoromethyl)-2-
pyridinyl)methyl)-6-quinolinecarboxamide,
2-amino-3-methyl-N-((1R)-6-methyl-2,3-dihydro-1H-inden-1-yl)-N-((5-
(trifluoromethyl)-2-pyridinyl)methyl)-6-quinolinecarboxamide,
2-amino-3-methyl-N-((1S)-6-methyl-2,3-dihydro-1H-inden-1-yl)-N-((5-
(trifluoromethyl)-2-pyridinyl)methyl)-6-quinolinecarboxamide,
2-amino-N-(4-(4-carbamoyl-1-piperidinyl)benzyl)-N-((2R)-2-cyclopropylpropyl)-3-
methyl-6-quinolinecarboxamide,
2-amino-N-(4-(4-carbamoyl-1-piperidinyl)benzyl)-N-((2S)-2-cyclopropylpropyl)-3-
methyl-6-quinolinecarboxamide,
2-amino-N-((2R)-2-cyclopropylpropyl)-3-methyl-N-((5-(trifluoromethyl)-2-
pyridinyl)methyl)-6-quinolinecarboxamide,
2-amino-N-((2S)-2-cyclopropylpropyl)-3-methyl-N-((5-(trifluoromethyl)-2-

TABLE 11-continued pyridinyl)methyl)-6-quinolinecarboxamide,
(6R)-2-amino-N-(1H-pyrrolo[2,3-b]pyridin-4-yimethyl)-N-((5-(trifluoromethyl)-2-
pyridinyl)methyl)-5,6,7,8-tetrahydro-6-quinolinecarboxamide,
(6S)-2-amino-N-(1H-pyrrolo[2,3-b]pyridin-4-ylmethyl)-N-((5-(trifluoromethyl)-2-
pyridinyl)methyl)-5,6,7,8-tetrahydro-6-quinolinecarboxamide,
2-amino-N-((2R)-2-ethoxypropyl)-3-methyl-N-((5-(trifluoromethyl)-2-pyridinyl)methyl)-
6-quinolinecarboxamide,
2-amino-N-((2S)-2-ethoxypropyl)-3-methyl-N-((5-(trifluoromethyl)-2-pyridinyl)methyl)-
6-quinolinecarboxamide,
2-amino-N-((1,3-dimethyl-1H-indol-2-yl)methyl)-3-methyl-N-((5-(trifluoromethyl)-2-
pyridinyl)methyl)-6-quinolinecarboxamide,
2-amino-N-(2-fluorobenzyl)-N-((5-fluoro-3-pyridinyl)methyl)-3-methyl-6-
quinolinecarboxamide,
2-amino-3-methyl-N-((2R)-3,3,3-trifluoro-2-hydroxypropyl)-N-((5-(trifluoromethyl)-2-
pyridinyl)methyl)-6-quinolinecarboxamide,
2-amino-3-methyl-N-((2S)-3,3,3-trifluoro-2-hydroxypropyl)-N-((5-(trifluoromethyl)-2-
pyridinyl)methyl)-6-quinolinecarboxamide,
2-amino-3-methyl-N-((7S)-4,5,6,7-tetrahydro-1H-indazol-7-yl)-N-((5-(trifluoromethyl)-
2-pyridinyl)methyl)-6-quinolinecarboxamide,
7-amino-N-((1R,2R)-2-cyanocyclopentyl)-6-methyl-N-((5-(trifluoromethyl)-2-
pyridinyl)methyl)-1,8-naphthyridine-3-carboxamide,
7-amino-N-((1R,2S)-2-cyanocyclopentyl)-6-methyl-N-((5-(trifluoromethyl)-2-
pyridinyl)methyl)-1,8-naphthyridine-3-carboxamide,
7-amino-N-((1S,2R)-2-cyanocyclopentyl)-6-methyl-N-((5-(trifluoromethyl)-2-
pyridinyl)methyl)-1,8-naphthyridine-3-carboxamide,
7-amino-N-((1S,2S)-2-cyanocyclopentyl)-6-methyl-N-((5-(trifluoromethyl)-2-
pyridinyl)methyl)-1,8-naphthyridine-3-carboxamide,
2-amino-N-((1R,2R)-2-cyanocyclopentyl)-3-methyl-N-((5-(trifluoromethyl)-2-
pyridinyl)methyl)-1,7-naphthyridine-6-carboxamide,
2-amino-N-((1R,2S)-2-cyanocyclopentyl)-3-methyl-N-((5-(trifluoromethyl)-2-
pyridinyl)methyl)-1,7-naphthyridine-6-carboxamide,
2-amino-N-((1S,2R)-2-cyanocyclopentyl)-3-methyl-N-((5-(trifluoromethyl)-2-
pyridinyl)methyl)-1,7-naphthyridine-6-carboxamide,
2-amino-N-((1S,2S)-2-cyanocyclopentyl)-3-methyl-N-((5-(trifluoromethyl)-2-
pyridinyl)methyl)-1,7-naphthyridine-6-carboxamide,
2-amino-N-((1R,2R)-2-cyanocyclopentyl)-7-fluoro-3-methyl-N-((5-(trifluoromethyl)-2-
pyridinyl)methyl)-6-quinolinecarboxamide,
2-amino-N-((1R,2S)-2-cyanocyclopentyl)-7-fluoro-3-methyl-N-((5-(trifluoromethyl)-2-
pyridinyl)methyl)-6-quinolinecarboxamide,
2-amino-N-((1S,2R)-2-cyanocyclopentyl)-7-fluoro-3-methyl-N-((5-(trifluoromethyl)-2-
pyridinyl)methyl)-6-quinolinecarboxamide,
2-amino-N-((1S,2S)-2-cyanocyclopentyl)-7-fluoro-3-methyl-N-((5-(trifluoromethyl)-2-
pyridinyl)methyl)-6-quinolinecarboxamide,
2-amino-N-((1R,2R)-2-cyanocyclopentyl)-N-((5-cyano-2-pyridinyl)methyl)-7-fluoro-3-
methyl-6-quinolinecarboxamide,
2-amino-N-((1R,2S)-2-cyanocyclopentyl)-N-((5-cyano-2-pyridinyl)methyl)-7-fluoro-3-
methyl-6-quinolinecarboxamide,
2-amino-N-((1S,2R)-2-cyanocyclopentyl)-N-((5-cyano-2-pyridinyl)methyl)-7-fluoro-3-
methyl-6-quinolinecarboxamide,
2-amino-N-((1S,2S)-2-cyanocyclopentyl)-N-((5-cyano-2-pyridinyl)methyl)-7-fluoro-3-
methyl-6-quinolinecarboxamide,
2-amino-N-((1R,2R)-[1,1'-bi(cyclopropyl)]-2-yl)-3-methyl-N-((5-(trifluoromethyl)-2-
pyridinyl)methyl)-6-quinolinecarboxamide,
2-amino-N-((1R,2S)-[1,1'-bi(cyclopropyl)]-2-yl)-3-methyl-N-((5-(trifluoromethyl)-2-
pyridinyl)methyl)-6-quinolinecarboxamide,
2-amino-N-((1S,2R)-[1,1'-bi(cyclopropyl)]-2-yl)-3-methyl-N-((5-(trifluoromethyl)-2-
pyridinyl)methyl)-6-quinolinecarboxamide,
2-amino-N-((1S,2S)-[1,1'-bi(cyclopropyl)]-2-yl)-3-methyl-N-((5-(trifluoromethyl)-2-
pyridinyl)methyl)-6-quinolinecarboxamide,
2-amino-N-((1R)-2,2-dimethylcyclopropyl)-3-methyl-N-((5-(trifluoromethyl)-2-
pyridinyl)methyl)-6-quinolinecarboxamide,
2-amino-N-((1S)-2,2-dimethylcyclopropyl)-3-methyl-N-((5-(trifluoromethyl)-2-
pyridinyl)methyl)-6-quinolinecarboxamide,
2-amino-N-(4-(4-carbamoyl-1-piperidinyl)benzyl)-3-methyl-N-((4-methyl-1,3-thiazol-
5-yl)methyl)-6-quinolinecarboxamide,
2-amino-N-(4-(4-carbamoyl-1-piperidinyl)benzyl)-3-methyl-N-(1H-pyrrolo[2,3-
b]pyridin-4-ylmethyl)-6-quinolinecarboxamide,
2-amino-N-((1-cyanocyclopropyl)methyl)-3-methyl-N-(4-(1-piperidinyl)benzyl)-6-
quinolinecarboxamide,
2-amino-3-methyl-N-(2-(1,2,4-oxadiazol-3-yl)ethyl)-N-(5-(trifluoromethyl)-2-
pyridinyl)methyl)-6-quinolinecarboxamide,
2-amino-N-((1-cyanocyclopropyl)methyl)-3-methyl-N-((5-(trifluoromethyl)-2-
pyridinyl)methyl)-6-quinolinecarboxamide,
2-amino-N-(2-cyclobutylethyl)-3-methyl-N-((5-(trifluoromethyl)-2-pyridinyl)methyl)-6-
quinolinecarboxamide,
2-amino-N-((4-chloro-1-methyl-1H-pyrrol-2-yl)methyl)-3-methyl-N-((5-
(trifluoromethyl)-2-pyridinyl)methyl)-6-quinolinecarboxamide,
2-amino-3-methyl-N-(1H-pyrrol-3-ylmethyl)-N-((5-(trifluoromethyl)-2-
pyridinyl)methyl)-6-quinolinecarboxamide,
2-amino-3-methyl-N-(2-(1,2-oxazol-3-yl)ethyl)-N-((5-(trifluoromethyl)-2-

TABLE 11-continued pyridinyl)methyl)-6-quinolinecarboxamide,
2-amino-N-(2-fluorobenzyl)-3-methyl-N-(cis-3-(4-
(trifluoromethoxy)phenyl)cyclobutyl)-6-quinolinecarboxamide,
2-amino-N-(2-fluorobenzyl)-3-methyl-N-(trans-3-(4-
(trifluoromethoxy)phenyl)cyclobutyl)-6-quinolinecarboxamide,
2-amino-N-((3-fluoro-4-pyridinyl)methyl)-3-methyl-N-((2-oxo-2,3-dihydro-1H-
benzimidazol-5-yl)methyl)-6-quinolinecarboxamide,
2-amino-3-methyl-N-((2-oxo-2,3-dihydro-1H-benzimidazol-5-yl)methyl)-N-(1H-
pyrrolo[2,3-b]pyridin-4-ylmethyl)-6-quinolinecarboxamide,
2-amino-N-((4R)-3,4-dihydro-1H-2-benzopyran-4-yl)-3-methyl-N-((5-(trifluoromethyl)-
2-pyridinyl)methyl)-6-quinolinecarboxamide,
2-amino-N-((4S)-3,4-dihydro-1H-2-benzopyran-4-yl)-3-methyl-N-((5-(trifluoromethyl)-
2-pyridinyl)methyl)-6-quinolinecarboxamide,
2-amino-N-((1R)-3,3-dimethyl-2,3-dihydro-1H-inden-1-yl)-3-methyl-N-((5-
(trifluoromethyl)-2-pyridinyl)methyl)-6-quinolinecarboxamide,
2-amino-N-((1S)-3,3-dimethyl-2,3-dihydro-1H-inden-1-yl)-3-methyl-N-((5-
(trifluoromethyl)-2-pyridinyl)methyl)-6-quinolinecarboxamide,
2-amino-3-methyl-N-((1R,3R)-3-methyl-2,3-dihydro-1H-inden-1-yl)-N-((5-
(trifluoromethyl)-2-pyridinyl)methyl)-6-quinolinecarboxamide,
2-amino-3-methyl-N-((1R,3S)-3-methyl-2,3-dihydro-1H-inden-1-yl)-N-((5-
(trifluoromethyl)-2-pyridinyl)methyl)-6-quinolinecarboxamide,
2-amino-3-methyl-N-((1S,3R)-3-methyl-2,3-dihydro-1H-inden-1-yl)-N-((5-
(trifluoromethyl)-2-pyridinyl)methyl)-6-quinolinecarboxamide,
2-amino-3-methyl-N-((1S,3S)-3-methyl-2,3-dihydro-1H-inden-1-yl)-N-((5-
(trifluoromethyl)-2-pyridinyl)methyl)-6-quinolinecarboxamide,
2-amino-3-methyl-N-((1R,4R)-4-methyl-1,2,3,4-tetrahydro-1-naphthalenyl)-N-((5-
(trifluoromethyl)-2-pyridinyl)methyl)-6-quinolinecarboxamide,
2-amino-3-methyl-N-((1R,4S)-4-methyl-1,2,3,4-tetrahydro-1-naphthalenyl)-N-((5-
(trifluoromethyl)-2-pyridinyl)methyl)-6-quinolinecarboxamide,
2-amino-3-methyl-N-((1S,4R)-4-methyl-1,2,3,4-tetrahydro-1-naphthalenyl)-N-((5-
(trifluoromethyl)-2-pyridinyl)methyl)-6-quinolinecarboxamide,
2-amino-3-methyl-N-((1S,4S)-4-methyl-1,2,3,4-tetrahydro-1-naphthalenyl)-N-((5-
(trifluoromethyl)-2-pyridinyl)methyl)-6-quinolinecarboxamide,
2-amino-N-((4R)-8-methoxy-3,4-dihydro-2H-chromen-4-yl)-3-methyl-N-((5-
(trifluoromethyl)-2-pyridinyl)methyl)-6-quinolinecarboxamide,
2-amino-N-((4S)-8-methoxy-3,4-dihydro-2H-chromen-4-yl)-3-methyl-N-((5-
(trifluoromethyl)-2-pyridinyl)methyl)-6-quinolinecarboxamide,
2-amino-3-methyl-N-((4R)-4,5,6,7-tetrahydro-1H-indol-4-yl)-N-((5-(trifluoromethyl)-2-
pyridinyl)methyl)-6-quinolinecarboxamide,
2-amino-3-methyl-N-((4S)-4,5,6,7-tetrahydro-1H-indol-4-yl)-N-((5-(trifluoromethyl)-2-
pyridinyl)methyl)-6-quinolinecarboxamide,
2-amino-3-methyl-N-((7R)-2-methyl-4,5,6,7-tetrahydro-1,3-benzothiazol-7-yl)-N-((5-
(trifluoromethyl)-2-pyridinyl)methyl)-6-quinolinecarboxamide,
2-amino-3-methyl-N-((7S)-2-methyl-4,5,6,7-tetrahydro-1,3-benzothiazol-7-yl)-N-((5-
(trifluoromethyl)-2-pyridinyl)methyl)-6-quinolinecarboxamide,
2-amino-3-methyl-N-((4R)-2-methyl-4,5,6,7-tetrahydro-2H-indazol-4-yl)-N-((5-
(trifluoromethyl)-2-pyridinyl)methyl)-6-quinolinecarboxamide,
2-amino-3-methyl-N-((4S)-2-methyl-4,5,6,7-tetrahydro-2H-indazol-4-yl)-N-((5-
(trifluoromethyl)-2-pyridinyl)methyl)-6-quinolinecarboxamide,
2-amino-N-((1R,2R)-2-hydroxy-2,3-dihydro-1H-inden-1-yl)-3-methyl-N-((5-
(trifluoromethyl)-2-pyridinyl)methyl)-6-quinolinecarboxamide,
2-amino-N-((3R)-6,7-dimethyl-2,3-dihydro-1-benzofuran-3-yl)-3-methyl-N-((5-
(trifluoromethyl)-2-pyridinyl)methyl)-6-quinolinecarboxamide,
2-amino-N-((3S)-6,7-dimethyl-2,3-dihydro-1-benzofuran-3-yl)-3-methyl-N-((5-
(trifluoromethyl)-2-pyridinyl)methyl)-6-quinolinecarboxamide,
2-amino-N-((2R)-2-methoxy-3-methylbutyl)-3-methyl-N-((5-(trifluoromethyl)-2-
pyridinyl)methyl)-6-quinolinecarboxamide,
2-amino-N-((2S)-2-methoxy-3-methylbutyl)-3-methyl-N-((5-(trifluoromethyl)-2-
pyridinyl)methyl)-6-quinolinecarboxamide,
2-amino-3-methyl-N-((7R)-5,6,7,8-tetrahydroimidazo[1,2-a]pyridin-7-ylmethyl)-N-((5-
(trifluoromethyl)-2-pyridinyl)methyl)-6-quinolinecarboxamide,
2-amino-3-methyl-N-((7S)-5,6,7,8-tetrahydroimidazo[1,2-a]pyridin-7-ylmethyl)-N-((5-
(trifluoromethyl)-2-pyridinyl)methyl)-6-quinolinecarboxamide,
2-amino-3-methyl-N-(1H-pyrrolo[2,3-b]pyridin-6-ylmethyl)-N-((5-(trifluoromethyl)-2-
pyridinyl)methyl)-6-quinolinecarboxamide,
2-amino-N-((2-amino-1H-benzimidazol-5-yl)methyl)-3-methyl-N-((5-(trifluoromethyl)-
2-pyridinyl)methyl)-6-quinolinecarboxamide,
2-amino-N-(1H-indazol-6-ylmethyl)-3-methyl-N-((5-(trifluoromethyl)-2-
pyridinyl)methyl)-6-quinolinecarboxamide,
2-amino-3-methyl-N-((2-oxo-2,3-dihydro-1,3-benzoxazol-6-yl)methyl)-N-((5-
(trifluoromethyl)-2-pyridinyl)methyl)-6-quinolinecarboxamide,
2-amino-N-(imidazo[1,2-a]pyridin-7-ylmethyl)-3-methyl-N-((5-(trifluoromethyl)-2-
pyridinyl)methyl)-6-quinolinecarboxamide,
2-amino-N-(1-benzofuran-6-ylmethyl)-3-methyl-N-((5-(trifluoromethyl)-2-
pyridinyl)methyl)-6-quinolinecarboxamide,
2-amino-N-(1H-indol-5-ylmethyl)-3-methyl-N-((5-(trifluoromethyl)-2-pyridinyl)methyl)-
6-quinolinecarboxamide,
2-amino-3-methyl-N-((1R)-1-(3-oxo-3,4-dihydro-2H-1,4-benzoxazin-6-yl)ethyl)-N-((5-
(trifluoromethyl)-2-pyridinyl)methyl)-6-quinolinecarboxamide,
2-amino-3-methyl-N-((1S)-1-(3-oxo-3,4-dihydro-2H-1,4-benzoxazin-6-yl)ethyl)-N-((5-

TABLE 11-continued (trifluoromethyl)-2-pyridinyl)methyl)-6-quinolinecarboxamide,
2-amino-3-methyl-N-(5-pyrimidinylmethyl)-N-((5-(trifluoromethyl)-2-pyridinyl)methyl)-6-quinolinecarboxamide,
2-amino-3-methyl-N-((2-oxo-1,2-dihydro-3-pyridinyl)methyl)-N-((5-(trifluoromethyl)-2-pyridinyl)methyl)-6-quinolinecarboxamide,
2-amino-N-((1R)-4-hydroxy-2,3-dihydro-1H-inden-1-yl)-3-methyl-N-((5-(trifluoromethyl)-2-pyridinyl)methyl)-6-quinolinecarboxamide,
2-amino-N-((1S)-4-hydroxy-2,3-dihydro-1H-inden-1-yl)-3-methyl-N-((5-(trifluoromethyl)-2-pyridinyl)methyl)-6-quinolinecarboxamide,
2-amino-3-methyl-N-((3aR,4R,7aR)-octahydro-1-benzofuran-4-yl)-N-((5-(trifluoromethyl)-2-pyridinyl)methyl)-6-quinolinecarboxamide,
2-amino-3-methyl-N-((3aR,4R,7aS)-octahydro-1-benzofuran-4-yl)-N-((5-(trifluoromethyl)-2-pyridinyl)methyl)-6-quinolinecarboxamide,
2-amino-3-methyl-N-((3aR,4S,7aR)-octahydro-1-benzofuran-4-yl)-N-((5-(trifluoromethyl)-2-pyridinyl)methyl)-6-quinolinecarboxamide,
2-amino-3-methyl-N-((3aR,4S,7aS)-octahydro-1-benzofuran-4-yl)-N-((5-(trifluoromethyl)-2-pyridinyl)methyl)-6-quinolinecarboxamide,
2-amino-3-methyl-N-(3aS,4R,7aR)-octahydro-1-benzofuran-4-yl)-N-(5-(trifluoromethyl)-2-pyridinyl)methyl)-6-quinolinecarboxamide,
2-amino-3-methyl-N-((3aS,4R,7aS)-octahydro-1-benzofuran-4-yl)-N-((5-(trifluoromethyl)-2-pyridinyl)methyl)-6-quinolinecarboxamide,
2-amino-3-methyl-N-((3aS,4S,7aR)-octahydro-1-benzofuran-4-yl)-N-((5-(trifluoromethyl)-2-pyridinyl)methyl)-6-quinolinecarboxamide,
2-amino-3-methyl-N-((3aS,4S,7aS)-octahydro-1-benzofuran-4-yl)-N-((5-(trifluoromethyl)-2-pyridinyl)methyl)-6-quinolinecarboxamide,
2-amino-3-methyl-N-((2R)-4-methyl-2-pentanyl)-N-((5-(trifluoromethyl)-2-pyridinyl)methyl)-6-quinolinecarboxamide,
2-amino-3-methyl-N-((2S)-4-methyl-2-pentanyl)-N-((5-(trifluoromethyl)-2-pyridinyl)methyl)-6-quinolinecarboxamide,
2-amino-3-methyl-N-((1-oxo-2,3-dihydro-1H-isoindol-5-yl)methyl)-N-((5-(trifluoromethyl)-2-pyridinyl)methyl)-6-quinolinecarboxamide,
2-amino-N-((6-carbamoyl-3-pyridinyl)methyl)-3-methyl-N-((5-(trifluoromethyl)-2-pyridinyl)methyl)-6-quinolinecarboxamide,
2-amino-3-methyl-N-(4-(methylcarbamoyl)benzyl)-N-((5-(trifluoromethyl)-2-pyridinyl)methyl)-6-quinolinecarboxamide,
2-amino-N-((4-chloro-2-pyridinyl)methyl)-3-methyl-N-(2-methylpropyl)-6-quinolinecarboxamide,
2-amino-N-((3-bromo-2-pyridinyl)methyl)-3-methyl-N-(2-methylpropyl)-6-quinolinecarboxamide,
2-amino-N-((2R,3R)-3-hydroxy-2-butanyl)-3-methyl-N-((5-(trifluoromethyl)-2-pyridinyl)methyl)-6-quinolinecarboxamide,
2-amino-N-((2R,3S)-3-hydroxy-2-butanyl)-3-methyl-N-((5-(trifluoromethyl)-2-pyridinyl)methyl)-6-quinolinecarboxamide,
2-amino-N-((2S,3R)-3-hydroxy-2-butanyl)-3-methyl-N-((5-(trifluoromethyl)-2-pyridinyl)methyl)-6-quinolinecarboxamide,
2-amino-N-((2S,3S)-3-hydroxy-2-butanyl)-3-methyl-N-((5-(trifluoromethyl)-2-pyridinyl)methyl)-6-quinolinecarboxamide,
2-amino-3-methyl-N-((2R)-3-methyl-2-butanyl)-N-((5-(trifluoromethyl)-2-pyridinyl)methyl)-6-quinolinecarboxamide,
2-amino-3-methyl-N-((2S)-3-methyl-2-butanyl)-N-((5-(trifluoromethyl)-2-pyridinyl)methyl)-6-quinolinecarboxamide,
2-amino-3-methyl-N-(2-methylpropyl)-N-(4-(1-pyrrolidinyl)benzyl)-6-quinolinecarboxamide,
2-amino-3-methyl-N-(2-methylpropyl)-N-(3-(1H-1,2,4-triazol-1-yl)benzyl)-6-quinolinecarboxamide,
2-amino-3-methyl-N-(4-(2-oxo-1-pyrrolidinyl)benzyl)-N-((5-(trifluoromethyl)-2-pyridinyl)methyl)-6-quinolinecarboxamide,
2-amino-3-methyl-N-(4-(1-pyrrolidinyl)benzyl)-N-((5-(trifluoromethyl)-2-pyridinyl)methyl)-6-quinolinecarboxamide,
2-amino-3-methyl-N-(4-(1H-pyrazol-3-yl)benzyl)-N-((5-(trifluoromethyl)-2-pyridinyl)methyl)-6-quinolinecarboxamide,
2-amino-N-(3-(1H-imidazol-1-yl)benzyl)-3-methyl-N-((5-(trifluoromethyl)-2-pyridinyl)methyl)-6-quinolinecarboxamide,
2-amino-3-methyl-N-(3-(1H-1,2,4-triazol-1-yl)benzyl)-N-((5-(trifluoromethyl)-2-pyridinyl)methyl)-6-quinolinecarboxamide,
2-amino-N-(3-(1H-imidazol-2-yl)benzyl)-3-methyl-N-((5-(trifluoromethyl)-2-pyridinyl)methyl)-6-quinolinecarboxamide,
2-amino-3-methyl-N-(3-(1H-1,2,3-triazol-1-yl)benzyl)-N-((5-(trifluoromethyl)-2-pyridinyl)methyl)-6-quinolinecarboxamide,
2-amino-3-methyl-N-((2-(1H-1,2,4-triazol-1-yl)-3-pyridinyl)methyl)-N-((5-(trifluoromethyl)-2-pyridinyl)methyl)-6-quinolinecarboxamide,
2-amino-N-(2-(1H-imidazol-1-yl)benzyl)-3-methyl-N-((5-(trifluoromethyl)-2-pyridinyl)methyl)-6-quinolinecarboxamide,
2-amino-3-methyl-N-(2-(1H-pyrazol-1-yl)benzyl)-N-((5-(trifluoromethyl)-2-pyridinyl)methyl)-6-quinolinecarboxamide,
2-amino-3-methyl-N-(2-propyn-1-yl)-N-((5-(trifluoromethyl)-2-pyridinyl)methyl)-6-quinolinecarboxamide,
2-amino-N-((2R)-3-butyn-2-yl)-3-methyl-N-((5-(trifluoromethyl)-2-pyridinyl)methyl)-6-quinolinecarboxamide,
2-amino-N-((2S)-3-butyn-2-yl)-3-methyl-N-((5-(trifluoromethyl)-2-pyridinyl)methyl)-6-

TABLE 11-continued quinolinecarboxamide,
2-amino-N-(2-butyn-1-yl)-3-methyl-N-((5-(trifluoromethyl)-2-pyridinyl)methyl)-6-quinolinecarboxamide,
2-amino-N-(4-hydroxy-2-butyn-1-yl)-3-methyl-N-((5-(trifluoromethyl)-2-pyridinyl)methyl)-6-quinolinecarboxamide,
2-amino-N-(3-butyn-1-yl)-3-methyl-N-((5-(trifluoromethyl)-2-pyridinyl)methyl)-6-quinolinecarboxamide,
2-amino-3-methyl-N-(4-((1R)-2,2,2-trifluoro-1-hydroxyethyl)benzyl)-N-((5-(trifluoromethyl)-2-pyridinyl)methyl)-6-quinolinecarboxamide,
2-amino-3-methyl-N-(4-((1S)-2,2,2-trifluoro-1-hydroxyethyl)benzyl)-N-((5-(trifluoromethyl)-2-pyridinyl)methyl)-6-quinolinecarboxamide,
2-amino-N-(4-hydroxybenzyl)-3-methyl-N-((5-(trifluoromethyl)-2-pyridinyl)methyl)-6-quinolinecarboxamide,
2-amino-N-(3-fluoro-4-hydroxybenzyl)-3-methyl-N-((5-(trifluoromethyl)-2-pyridinyl)methyl)-6-quinolinecarboxamide,
2-amino-N-((1R)-1-(3-hydroxyphenyl)ethyl)-3-methyl-N-((5-(trifluoromethyl)-2-pyridinyl)methyl)-6-quinolinecarboxamide,
2-amino-N-((1S)-1-(3-hydroxyphenyl)ethyl)-3-methyl-N-((5-(trifluoromethyl)-2-pyridinyl)methyl)-6-quinolinecarboxamide,
2-amino-3-methyl-N-((1R)-1-(2-oxo-1,2-dihydro-4-pyridinyl)ethyl)-N-((5-(trifluoromethyl)-2-pyridinyl)methyl)-6-quinolinecarboxamide,
2-amino-3-methyl-N-((1S)-1-(2-oxo-1,2-dihydro-4-pyridinyl)ethyl)-N-((5-(trifluoromethyl)-2-pyridinyl)methyl)-6-quinolinecarboxamide,
2-amino-N-((4-bromo-2-pyridinyl)methyl)-3-methyl-N-(2-methylpropyl)-6-quinolinecarboxamide,
2-amino-N-((8R)-4-methoxy-5,6,7,8-tetrahydro-8-quinolinyl)-3-methyl-N-((5-(trifluoromethyl)-2-pyridinyl)methyl)-6-quinolinecarboxamide,
2-amino-N-((8S)-4-methoxy-5,6,7,8-tetrahydro-8-quinolinyl)-3-methyl-N-((5-(trifluoromethyl)-2-pyridinyl)methyl)-6-quinolinecarboxamide,
2-amino-3-methyl-N-((5R)-5,6,7,8-tetrahydro-5-quinolinyl)-N-((5-(trifluoromethyl)-2-pyridinyl)methyl)-6-quinolinecarboxamide,
2-amino-3-methyl-N-((5S)-5,6,7,8-tetrahydro-5-quinolinyl)-N-((5-(trifluoromethyl)-2-pyridinyl)methyl)-6-quinolinecarboxamide,
2-amino-N-((6R)-2-amino-5,6,7,8-tetrahydro-6-quinazolinyl)-3-methyl-N-((5-(trifluoromethyl)-2-pyridinyl)methyl)-6-quinolinecarboxamide,
2-amino-N-((6S)-2-amino-5,6,7,8-tetrahydro-6-quinazolinyl)-3-methyl-N-((5-(trifluoromethyl)-2-pyridinyl)methyl)-6-quinolinecarboxamide,
2-amino-3-methyl-N-((3aR,5R,7aR)-octahydro-1H-inden-5-yl)-N-((5-(trifluoromethyl)-2-pyridinyl)methyl)-6-quinolinecarboxamide,
2-amino-3-methyl-N-((3aR,5R,7aS)-octahydro-1H-inden-5-yl)-N-((5-(trifluoromethyl)-2-pyridinyl)methyl)-6-quinolinecarboxamide,
2-amino-3-methyl-N-((3aR,5S,7aR)-octahydro-1H-inden-5-yl)-N-((5-(trifluoromethyl)-2-pyridinyl)methyl)-6-quinolinecarboxamide,
2-amino-3-methyl-N-((3aR,5S,7aS)-octahydro-1H-inden-5-yl)-N-((5-(trifluoromethyl)-2-pyridinyl)methyl)-6-quinolinecarboxamide,
2-amino-3-methyl-N-((3aS,5R,7aR)-octahydro-1H-inden-5-yl)-N-((5-(trifluoromethyl)-2-pyridinyl)methyl)-6-quinolinecarboxamide,
2-amino-3-methyl-N-((3aS,5R,7aS)-octahydro-1H-inden-5-yl)-N-((5-(trifluoromethyl)-2-pyridinyl)methyl)-6-quinolinecarboxamide,
2-amino-3-methyl-N-((3aS,5S,7aR)-octahydro-1H-inden-5-yl)-N-((5-(trifluoromethyl)-2-pyridinyl)methyl)-6-quinolinecarboxamide,
2-amino-3-methyl-N-((3aS,5S,7aS)-octahydro-1H-inden-5-yl)-N-((5-(trifluoromethyl)-2-pyridinyl)methyl)-6-quinolinecarboxamide,
2-amino-3-methyl-N-((5R)-4,5,6,7-tetrahydro-1H-benzimidazol-5-yl)-N-((5-(trifluoromethyl)-2-pyridinyl)methyl)-6-quinolinecarboxamide,
2-amino-3-methyl-N-((5S)-4,5,6,7-tetrahydro-1H-benzimidazol-5-yl)-N-((5-(trifluoromethyl)-2-pyridinyl)methyl)-6-quinolinecarboxamide,
2-amino-3-methyl-N-((6R)-4,5,6,7-tetrahydro-1H-indazol-6-yl)-N-((5-(trifluoromethyl)-2-pyridinyl)methyl)-6-quinolinecarboxamide,
2-amino-3-methyl-N-((6S)-4,5,6,7-tetrahydro-1H-indazol-6-yl)-N-((5-(trifluoromethyl)-2-pyridinyl)methyl)-6-quinolinecarboxamide,
2-amino-3-methyl-N-((5R)-4,5,6,7-tetrahydro-1H-indazol-5-yl)-N-((5-(trifluoromethyl)-2-pyridinyl)methyl)-6-quinolinecarboxamide,
2-amino-3-methyl-N-((5S)-4,5,6,7-tetrahydro-1H-indazol-5-yl)-N-((5-(trifluoromethyl)-2-pyridinyl)methyl)-6-quinolinecarboxamide,
2-amino-N-((4R)-1-ethyl-4,5,6,7-tetrahydro-1H-indazol-4-yl)-3-methyl-N-((5-(trifluoromethyl)-2-pyridinyl)methyl)-6-quinolinecarboxamide,
2-amino-N-((4S)-1-ethyl-4,5,6,7-tetrahydro-1H-indazol-4-yl)-3-methyl-N-((5-(trifluoromethyl)-2-pyridinyl)methyl)-6-quinolinecarboxamide,
2-amino-N-((1R,2R)-1-hydroxy-2,3-dihydro-1H-inden-2-yl)-3-methyl-N-((5-(trifluoromethyl)-2-pyridinyl)methyl)-6-quinolinecarboxamide,
2-amino-N-((1R,2S)-1-hydroxy-2,3-dihydro-1H-inden-2-yl)-3-methyl-N-((5-(trifluoromethyl)-2-pyridinyl)methyl)-6-quinolinecarboxamide,
2-amino-N-((1S,2R)-1-hydroxy-2,3-dihydro-1H-inden-2-yl)-3-methyl-N-((5-(trifluoromethyl)-2-pyridinyl)methyl)-6-quinolinecarboxamide,
2-amino-N-((1S,2S)-1-hydroxy-2,3-dihydro-1H-inden-2-yl)-3-methyl-N-((5-(trifluoromethyl)-2-pyridinyl)methyl)-6-quinolinecarboxamide,
2-amino-3-methyl-N-((1R)-1-(tetrahydro-2H-pyran-4-yl)ethyl)-N-((5-(trifluoromethyl)-2-pyridinyl)methyl)-6-quinolinecarboxamide,
2-amino-3-methyl-N-((1S)-1-(tetrahydro-2H-pyran-4-yl)ethyl)-N-((5-(trifluoromethyl)-

TABLE 11-continued 2-pyridinyl)methyl)-6-quinolinecarboxamide,
2-amino-N-((trans-4-hydroxycyclohexyl)methyl)-3-methyl-N-((5-(trifluoromethyl)-2-pyridinyl)methyl)-6-quinolinecarboxamide,
2-amino-N-((((1R,3R)-3-hydroxycyclopentyl)methyl)-3-methyl-N-((5-(trifluoromethyl)-2-pyridinyl)methyl)-6-quinolinecarboxamide,
2-amino-N-((((1R,3S)-3-hydroxycyclopentyl)methyl)-3-methyl-N-((5-(trifluoromethyl)-2-pyridinyl)methyl)-6-quinolinecarboxamide,
2-amino-N-((((1S,3R)-3-hydroxycyclopentyl)methyl)-3-methyl-N-((5-(trifluoromethyl)-2-pyridinyl)methyl)-6-quinolinecarboxamide,
2-amino-N-((((1S,3S)-3-hydroxycyclopentyl)methyl)-3-methyl-N-((5-(trifluoromethyl)-2-pyridinyl)methyl)-6-quinolinecarboxamide,
2-amino-N-((((1R,3R)-3-hydroxycyclohexyl)methyl)-3-methyl-N-((5-(trifluoromethyl)-2-pyridinyl)methyl)-6-quinolinecarboxamide,
2-amino-N-((((1R,3S)-3-hydroxycyclohexyl)methyl)-3-methyl-N-((5-(trifluoromethyl)-2-pyridinyl)methyl)-6-quinolinecarboxamide,
2-amino-N-((((1S,3R)-3-hydroxycyclohexyl)methyl)-3-methyl-N-((5-(trifluoromethyl)-2-pyridinyl)methyl)-6-quinolinecarboxamide,
2-amino-N-((((1S,3S)-3-hydroxycyclohexyl)methyl)-3-methyl-N-((5-(trifluoromethyl)-2-pyridinyl)methyl)-6-quinolinecarboxamide,
2-amino-3-methyl-N-((2R,3R)-3-(1H-pyrazol-1-yl)-2-butanyl)-N-((5-(trifluoromethyl)-2-pyridinyl)methyl)-6-quinolinecarboxamide,
2-amino-3-methyl-N-((2R,3S)-3-(1H-pyrazol-1-yl)-2-butanyl)-N-((5-(trifluoromethyl)-2-pyridinyl)methyl)-6-quinolinecarboxamide,
2-amino-3-methyl-N-((2S,3R)-3-(1H-pyrazol-1-yl)-2-butanyl)-N-((5-(trifluoromethyl)-2-pyridinyl)methyl)-6-quinolinecarboxamide,
2-amino-3-methyl-N-((2S,3S)-3-(1H-pyrazol-1-yl)-2-butanyl)-N-((5-(trifluoromethyl)-2-pyridinyl)methyl)-6-quinolinecarboxamide,
2-amino-N-(4-(2-amino-2-oxoethyl)benzyl)-3-methyl-N-((5-(trifluoromethyl)-2-pyridinyl)methyl)-6-quinolinecarboxamide,
2-amino-3-methyl-N-((1R)-1-(tetrahydro-2H-pyran-4-yl)propyl)-N-((5-(trifluoromethyl)-2-pyridinyl)methyl)-6-quinolinecarboxamide,
2-amino-3-methyl-N-((1S)-1-(tetrahydro-2H-pyran-4-yl)propyl)-N-((5-(trifluoromethyl)-2-pyridinyl)methyl)-6-quinolinecarboxamide,
2-amino-N-((1R)-3-amino-3-oxo-1-(tetrahydro-2H-pyran-4-yl)propyl)-3-methyl-N-((5-(trifluoromethyl)-2-pyridinyl)methyl)-6-quinolinecarboxamide,
2-amino-N-((1S)-3-amino-3-oxo-1-(tetrahydro-2H-pyran-4-yl)propyl)-3-methyl-N-((5-(trifluoromethyl)-2-pyridinyl)methyl)-6-quinolinecarboxamide,
2-amino-3-methyl-N-(tetrahydro-2H-pyran-4-ylmethyl)-N-((5-(trifluoromethyl)-2-pyridinyl)methyl)-6-quinolinecarboxamide,
2-amino-3-methyl-N-(1H-pyrrolo[2,3-b]pyridin-4-ylmethyl)-N-((5-(trifluoromethyl)-2-pyridinyl)methyl)-1,7-naphthyridine-6-carboxamide,
2-amino-N-((3,5-difluoro-4-pyridinyl)methyl)-3-methyl-N-(4-(trifluoromethyl)benzyl)-6-quinolinecarboxamide,
2-amino-3-methyl-N-((1-methyl-1H-pyrazol-5-yl)methyl)-N-((5-(trifluoromethyl)-2-pyridinyl)methyl)-6-quinolinecarboxamide,
2-amino-3-methyl-N-((1-methyl-1H-pyrazol-5-yl)methyl)-N-(1H-pyrrolo[2,3-b]pyridin-4-ylmethyl)-6-quinolinecarboxamide,
2-amino-N-(4-hydroxybenzyl)-3-methyl-N-(1H-pyrrolo[2,3-b]pyridin-4-ylmethyl)-6-quinolinecarboxamide,
2-amino-3-methyl-N-(1H-pyrrolo[2,3-b]pyridin-4-ylmethyl)-N-(1H-pyrrol-2-ylmethyl)-6-quinolinecarboxamide,
2-amino-N-(2-hydroxybenzyl)-3-methyl-N-(1H-pyrrolo[2,3-b]pyridin-4-ylmethyl)-6-quinolinecarboxamide,
2-amino-N-((5-amino-2-pyridinyl)methyl)-N-(1H-indol-3-ylmethyl)-3-methyl-6-quinolinecarboxamide,
2-amino-3-methyl-N-(4-pentyn-1-yl)-N-((5-(trifluoromethyl)-2-pyridinyl)methyl)-6-quinolinecarboxamide,
2-amino-N-((2R)-1-cyano-2-propanyl)-3-methyl-N-((5-(trifluoromethyl)-2-pyridinyl)methyl)-6-quinolinecarboxamide,
2-amino-N-((2S)-1-cyano-2-propanyl)-3-methyl-N-((5-(trifluoromethyl)-2-pyridinyl)methyl)-6-quinolinecarboxamide,
2-amino-N-((2R)-2-cyanopropyl)-3-methyl-N-((5-(trifluoromethyl)-2-pyridinyl)methyl)-6-quinolinecarboxamide,
2-amino-N-((2S)-2-cyanopropyl)-3-methyl-N-((5-(trifluoromethyl)-2-pyridinyl)methyl)-6-quinolinecarboxamide,
2-amino-N-(2-cyclopropylethyl)-3-methyl-N-((5-(trifluoromethyl)-2-pyridinyl)methyl)-6-quinolinecarboxamide,
2-amino-N-((2R)-1-cyclopropyl-2-propanyl)-3-methyl-N-((5-(trifluoromethyl)-2-pyridinyl)methyl)-6-quinolinecarboxamide,
2-amino-N-((2S)-1-cyclopropyl-2-propanyl)-3-methyl-N-((5-(trifluoromethyl)-2-pyridinyl)methyl)-6-quinolinecarboxamide,
2-amino-N-(cis-3-cyanocyclobutyl)-3-methyl-N-((5-(trifluoromethyl)-2-pyridinyl)methyl)-6-quinolinecarboxamide,
2-amino-N-(trans-3-cyanocyclobutyl)-3-methyl-N-((5-(trifluoromethyl)-2-pyridinyl)methyl)-6-quinolinecarboxamide and
2-amino-N-(6,6-difluorospiro[3.3]heptan-2-yl)-3-methyl-N-((5-(trifluoromethyl)-2-pyridinyl)methyl)-6-quinolinecarboxamide;

or a pharmaceutically acceptable salt thereof.

In an embodiment, the Type II PRMT5 inhibitor is Compound F:

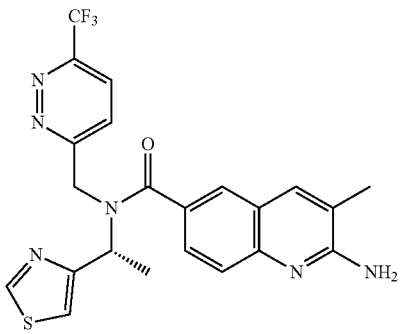

Compound F or a pharmaceutically acceptable salt thereof.

In an embodiment, the Type II PRMT5 inhibitor is Compound G:

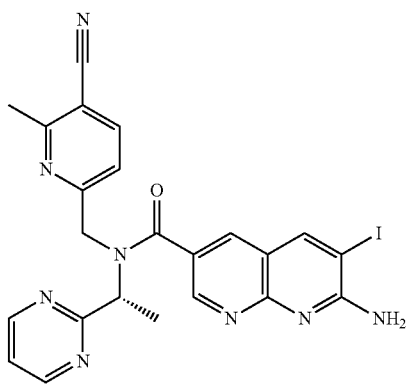

Compound G or a pharmaceutically acceptable salt thereof.

In another embodiment, the Type II PRMT5 inhibitor is a compound of Formula (V):

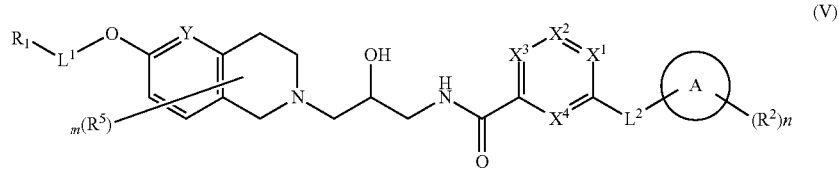

(V)

or a pharmaceutically acceptable salt thereof;
wherein
$X^1$, $X^2$, $X^3$, and $X^4$ are each independently N or $CR^x$;
Y is N, CH or $CR^5$;
$L^1$ is a bond or $C_1$-$C_4$-alkylene substituted with 0-2 instances of $R^6$;
$L^2$ is a bond, —NH— or —O—;
Ring A is a carbocycle, heterocycle, 5-6 member monocyclic heteroaryl or a monocyclic aryl;
$R^1$ is a 3-7 membered carbocycle, a 4-7 membered heterocycle or a 5-6 membered heteroaryl substituted with 0-3 instances of $R^4$;
each $R^2$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, heterocyclylalkyl, cycloalkylalkyl, —$OR^3$, —$N(R^3)_2$, —C(=O)$R^3$, —C(=O)$R^3$, —$CH_2$C(=O)$R^3$, —$NR^3$C(=O)$R^3$, —$NR^3$C(=O)$OR^3$, —C(=O)$N(R^3)_2$, —OC(=O)$N(R^3)_2$, —S(=O)$R^3$, —S(=O)$_2R^3$, —$SR^3$, —S(=O)(=$NR^3$)$R^3$, —$NR^3$S(=O)$_2R^3$ and —S(=O)$_2$ $N(R^3)_2$;

each $R^3$ is independently selected from H, $C_1$-$C_6$ alkyl, $C_1$-$C_6$ heteroalkyl, $C_3$-$C_7$ carbocyclyl, $C_3$-$C_7$ heterocyclyl, cycloalkylalkyl, heterocyclylalkyl, aryl, 5-6 membered heteroaryl, arylalkyl and heteroarylalkyl wherein each alkyl, carbocyclyl, heterocyclyl, cycloalkylalkyl, heterocyclylalkyl, aryl, heteroaryl, arylalkyl and heteroarylalkyl is optionally substituted;

each $R^4$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, heterocyclylalkyl, cycloalkylalkyl, —$OR^3$, —$N(R^3)_2$, —C(=O)$R^3$, —C(=O)$OR^3$, —$NR^3$C(=O)$R^3$, —$NR^3$C(=O)$OR^3$, —C(=O)$N(R^3)_2$, —OC(=O)$N(R^3)_2$, —S(=O)$R^3$, —S(=O)$_2R^3$, —$SR^3$, —S(=O)(=$NR^3$)$R^3$, —$NR^3$S(=O)$_2R^3$ and —S(=O)$_2N(R^3)_2$;

each $R^x$ is independently selected from hydrogen, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, heterocyclylalkyl, cycloalkylalkyl, —$OR^3$, —$N(R^3)_2$, —C(=O)$R^3$, —C(=O)$OR^3$, —$NR^3$C(=O)$R^3$, —$NR^3$C(=O)$OR^3$, —C(=O)$N(R^3)_2$, —OC(=O)$N(R^3)_2$, —S(=O)$R^3$, —S(=O)$_2R^3$, —$SR^3$, —S(=O)(=$NR^3$)$R^3$, —$NR^3$S(=O)$R^3$ and —S(=O)$_2N(R^3)_2$ wherein each alkyl, carbocyclyl, heterocyclyl, heterocyclylalkyl, cycloalkylalkyl is optionally substituted;

each $R^5$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, —$C_3$-$C_9$ heterocyclyl, $C_6$-$C_{10}$ aryl, $C_5$-$C_{10}$ heteroaryl, cycloalkylalkyl, heterocyclylalkyl, arylalkyl, heteroarylalkyl, —$OR^3$, —$N(R^3)_2$, —C(=O)$R^3$, —C(=O)$OR^3$, —$NR^3$C(=O)$R^3$, —$NR^3$C(=O)$OR^3$, —C(=O)$N(R^3)_2$, —OC(=O)$N(R^3)_2$, —S(=O)$R^3$, —S(=O)$_2R^3$, —$SR^3$, —S(=O)(=$NR^3$)$R^3$, —$NR^3$S(=O)$_2R^3$, —S(=O)$_2N(R^3)_2$, or two $R^5$ can be taken together with the atoms to which they are attached to form a $C_3$-$C_9$ carbocycle or a $C_3$-$C_9$ heterocycle;

each $R^6$ is independently selected from halo, —$C_1$-$C_4$ alkyl, —$C_1$-$C_4$ haloalkyl, —$OC_1$-$C_4$ alkyl, —$OC_1$-$C_4$ haloalkyl, or two $R^6$ can be taken together with the atoms to which they are attached to form a $C_3$-$C_7$ carbocycle or a $C_3$-$C_7$ heterocycle;

m is 0, 1, 2 or 3; and
n is 0, 1, 2 or 3.

In another embodiment, the Type II PRMT5 inhibitor is selected from the group consisting of a compound from Table 4 (see U.S. Pat. No. 11,077,101, which is incorporated by TABLE 4
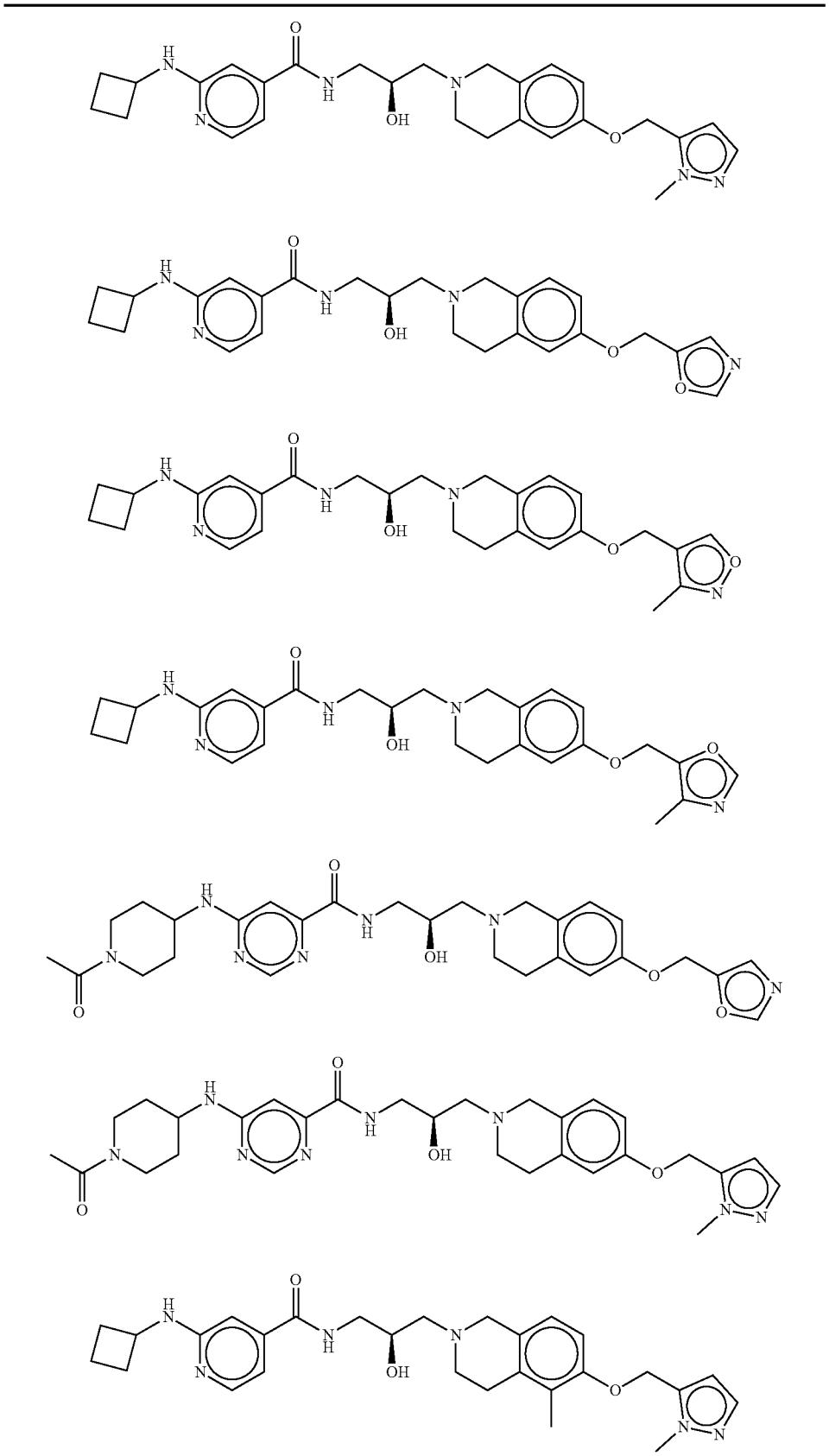

TABLE 4-continued
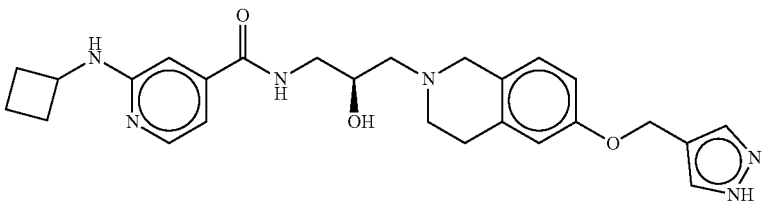
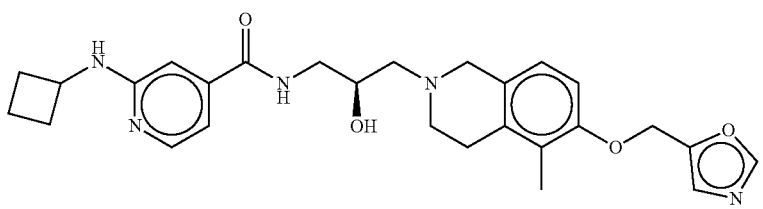
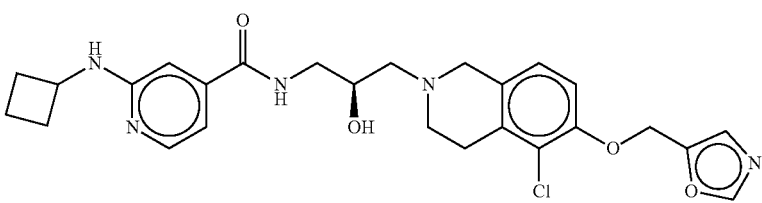
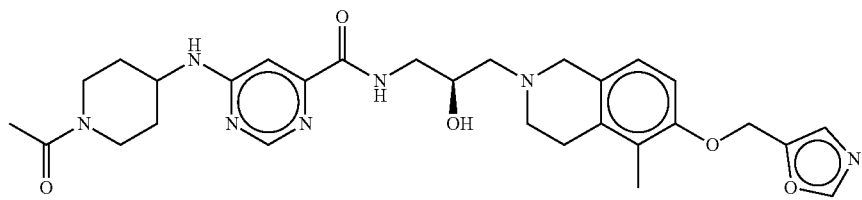
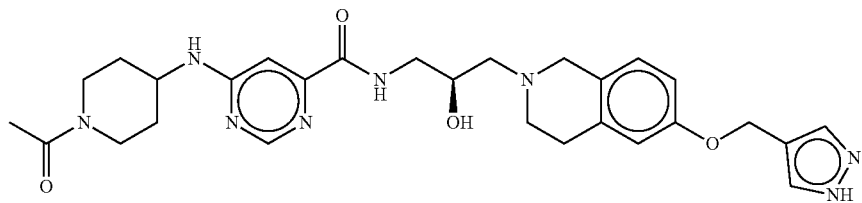
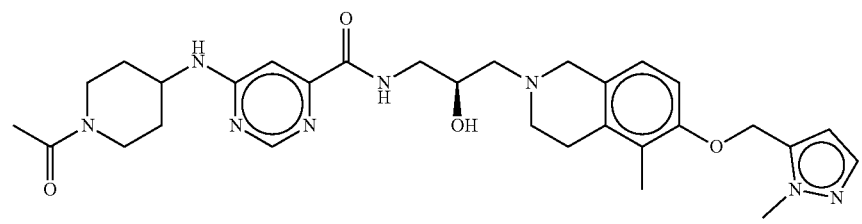
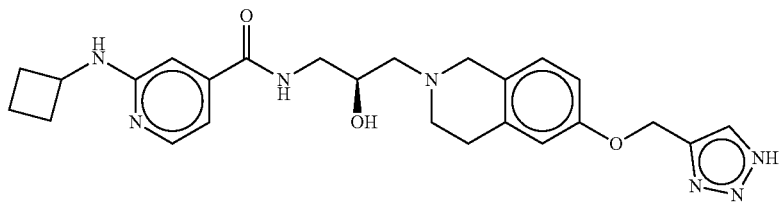

TABLE 4-continued
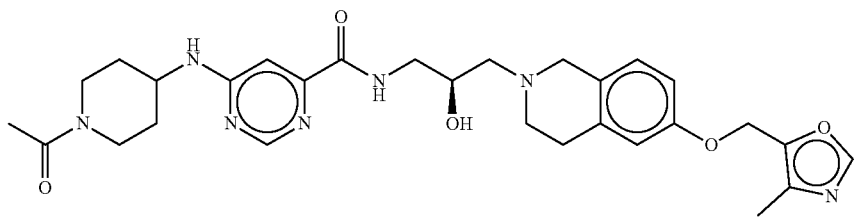
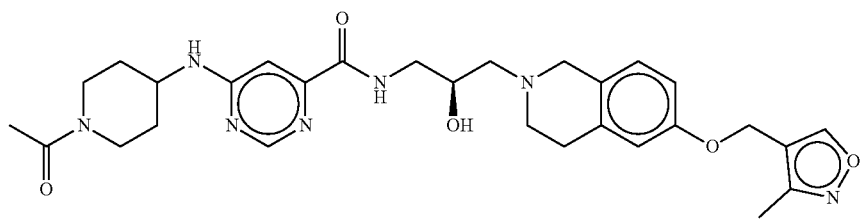
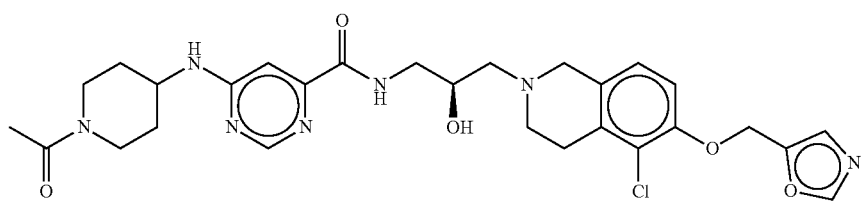
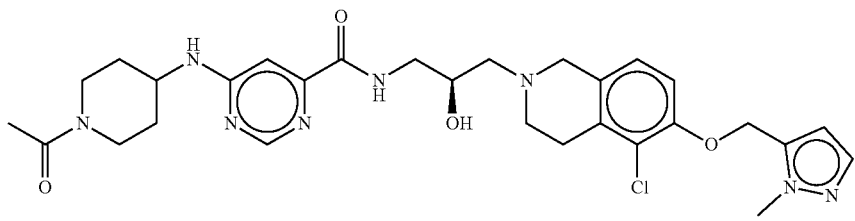
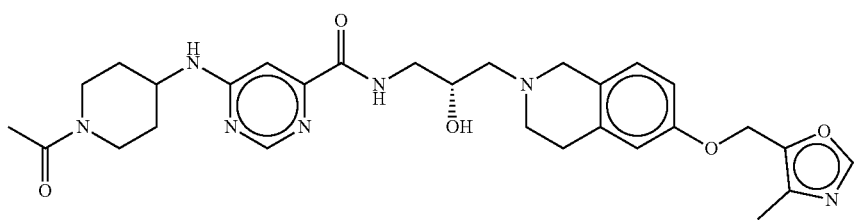
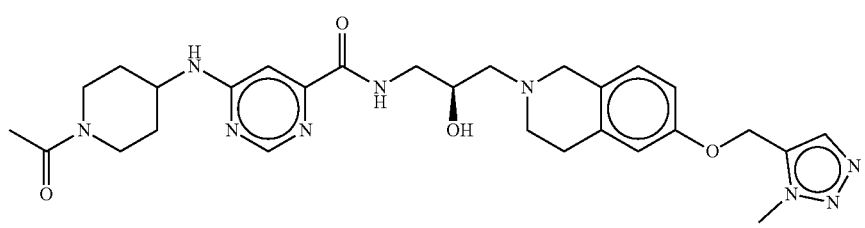
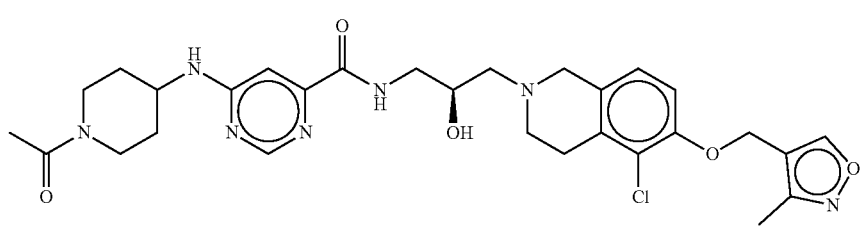

TABLE 4-continued
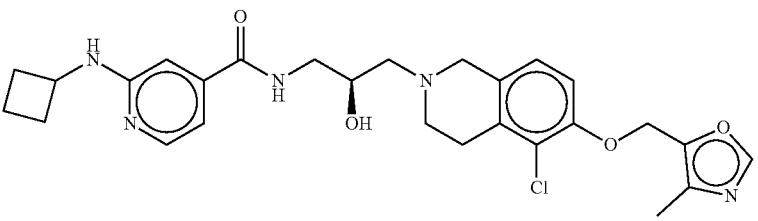
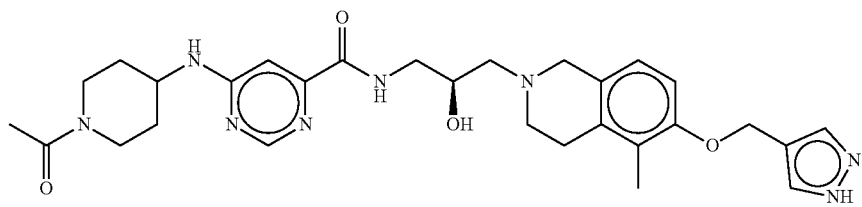
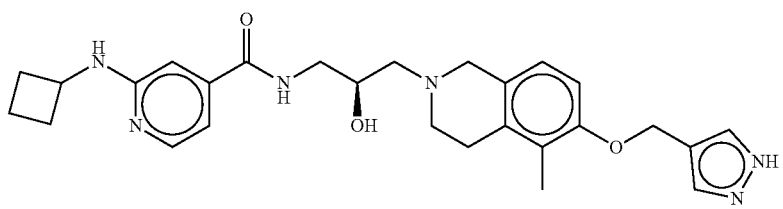
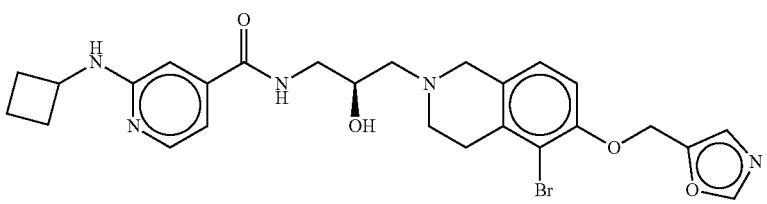
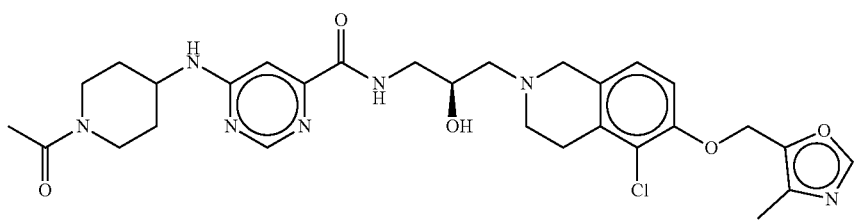
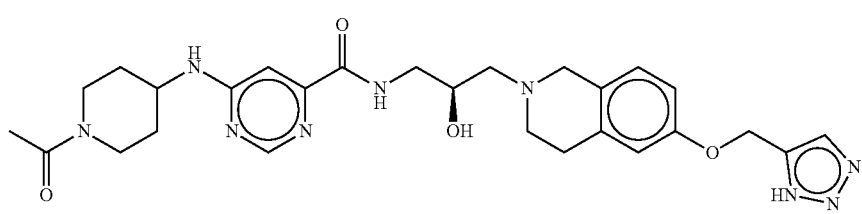
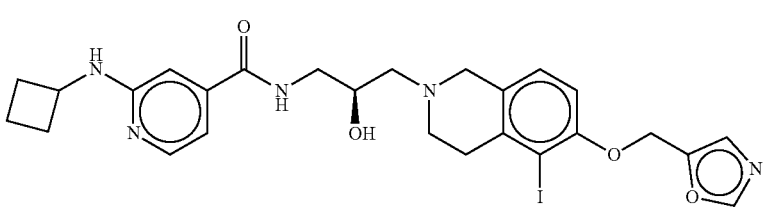

TABLE 4-continued
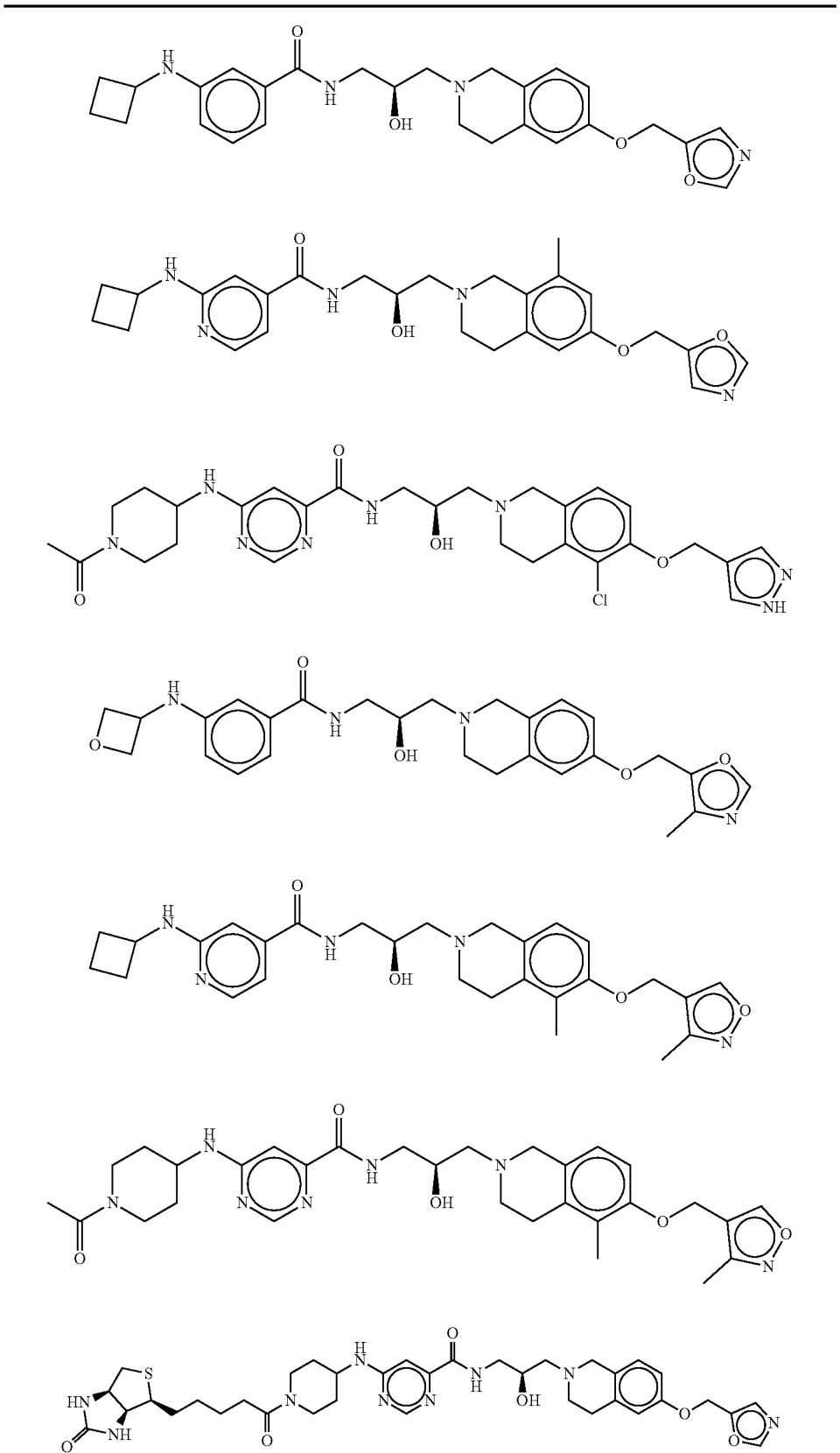

TABLE 4-continued
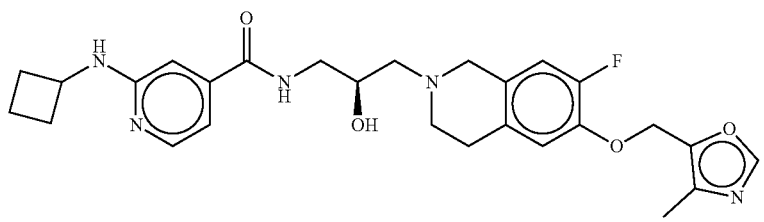
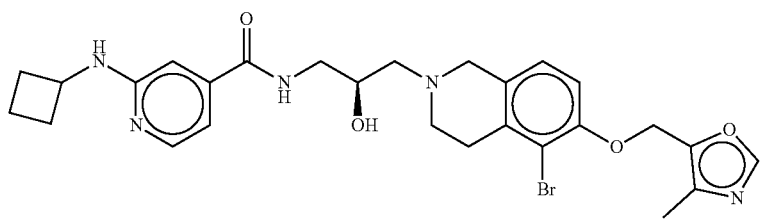
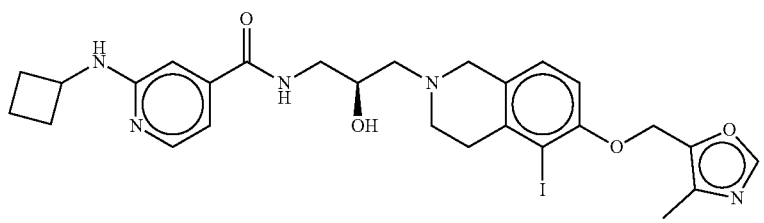
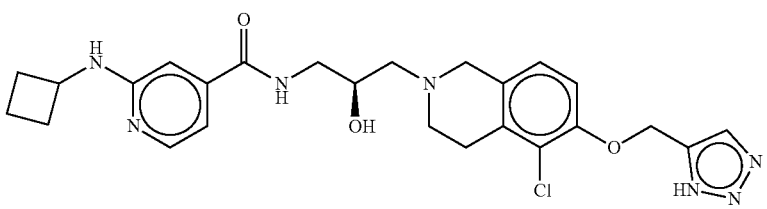
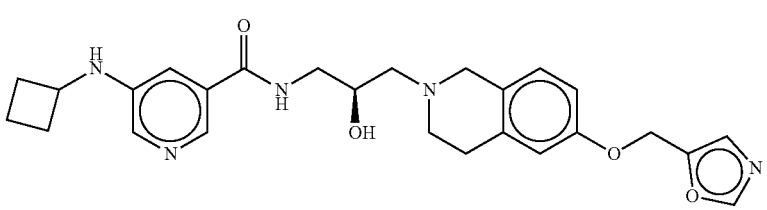
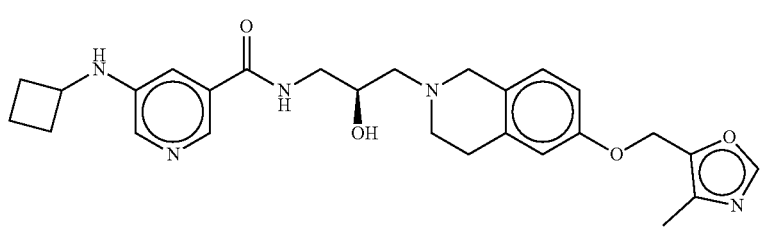
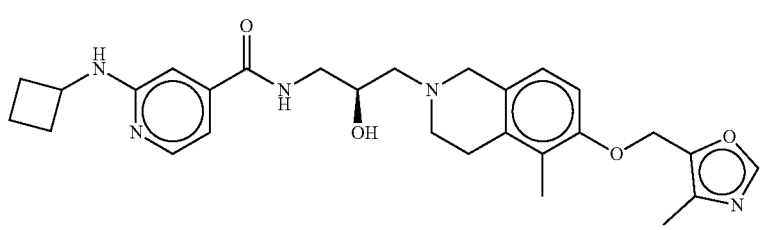

TABLE 4-continued
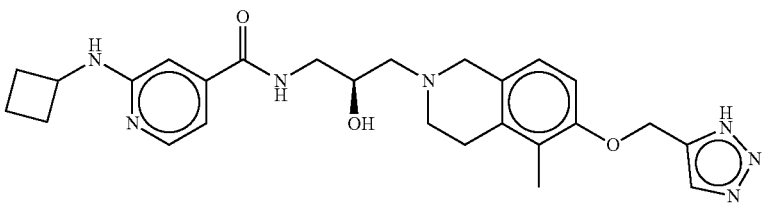
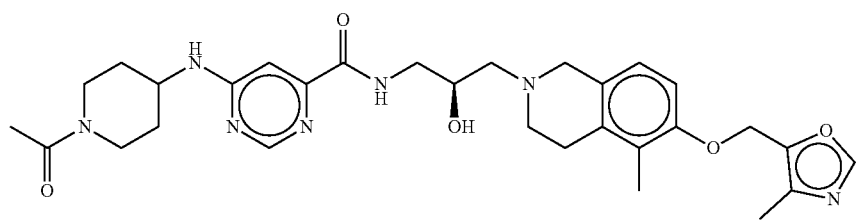
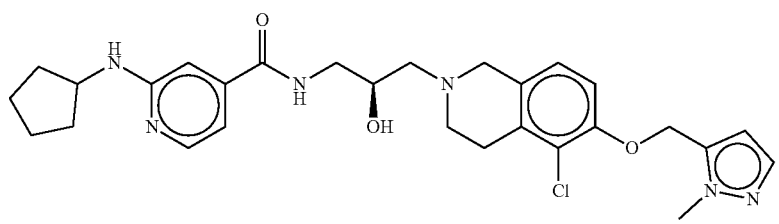
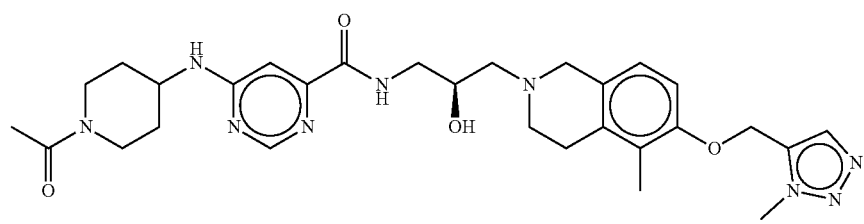
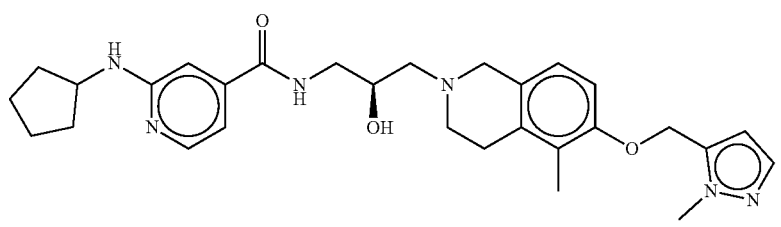
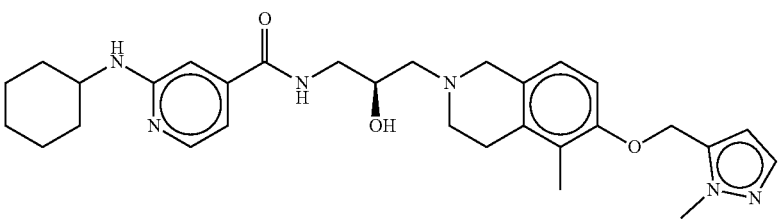
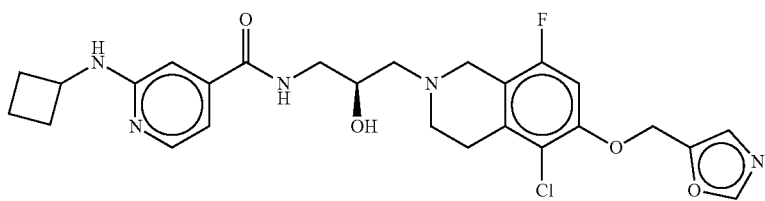

TABLE 4-continued
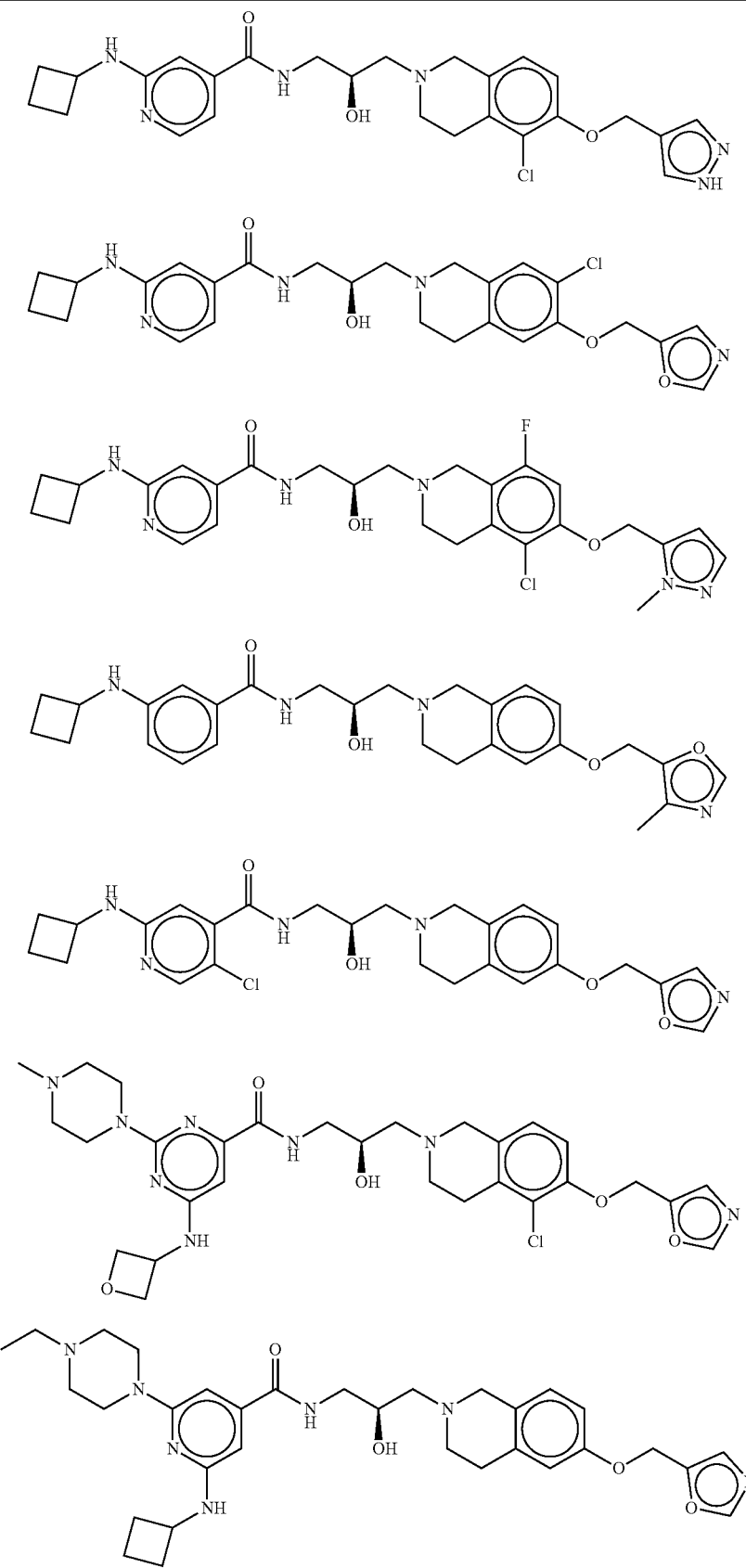

TABLE 4-continued
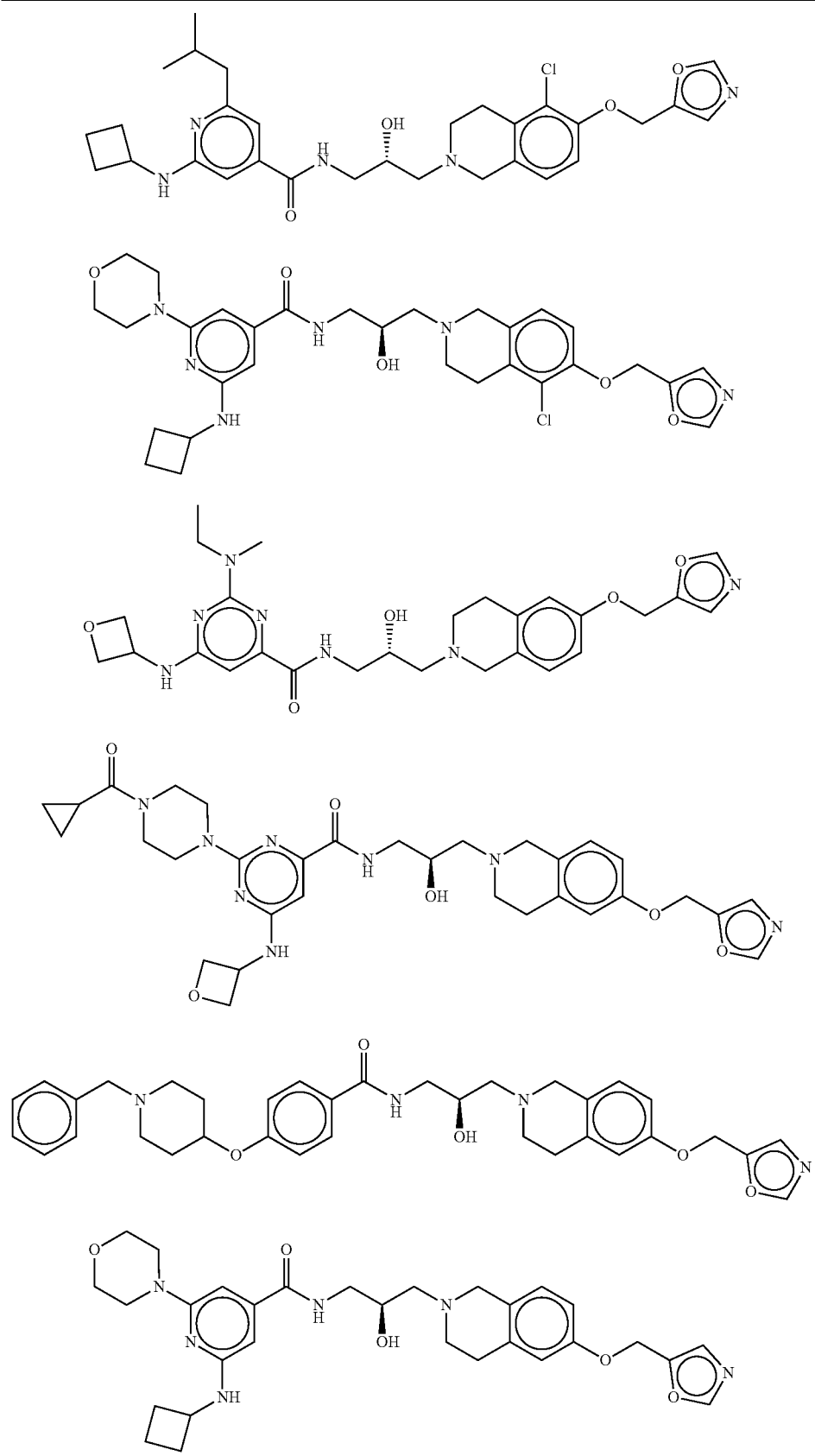

TABLE 4-continued
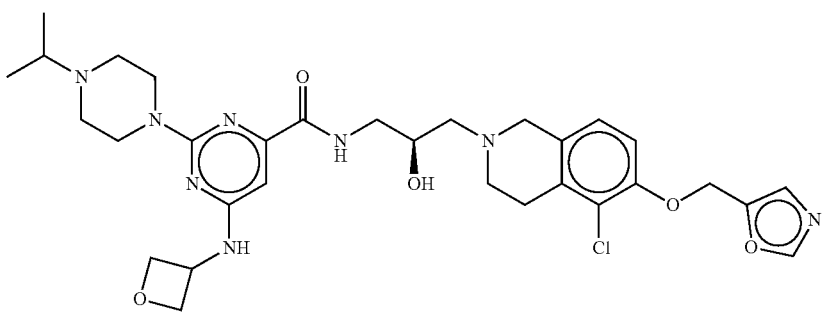
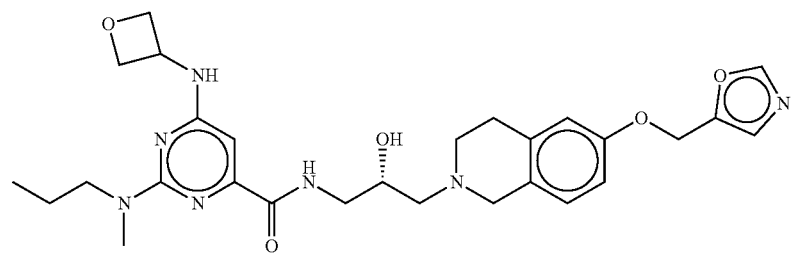
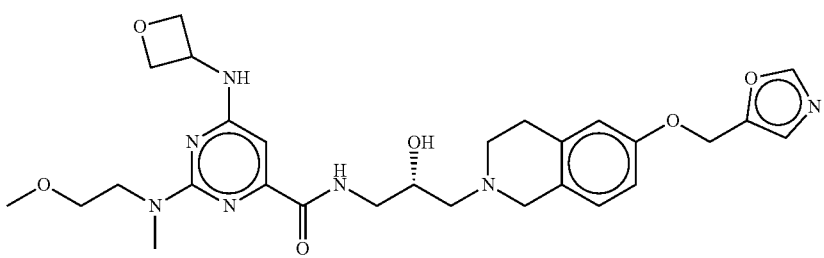
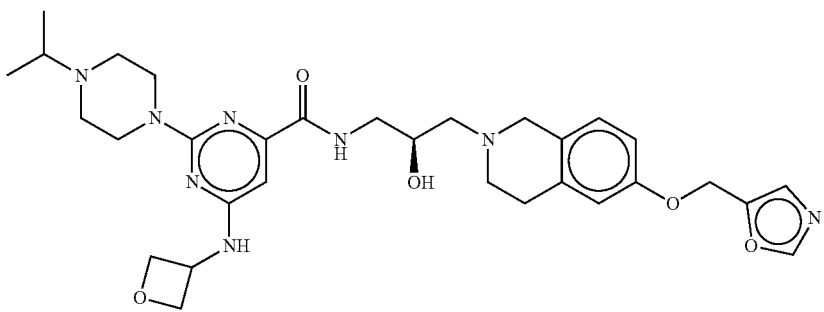
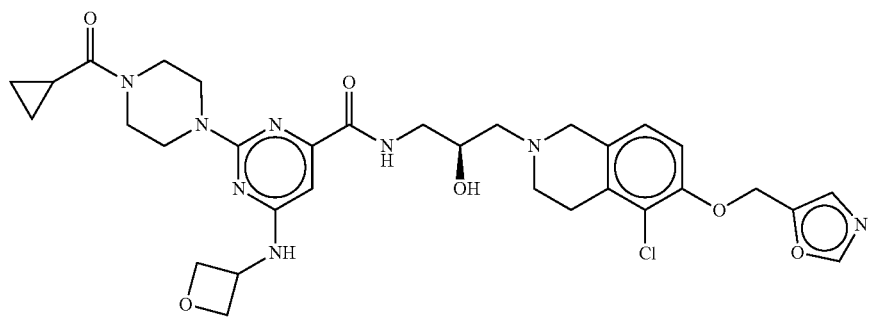

TABLE 4-continued
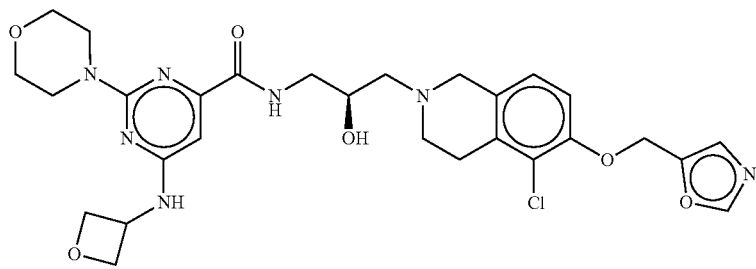
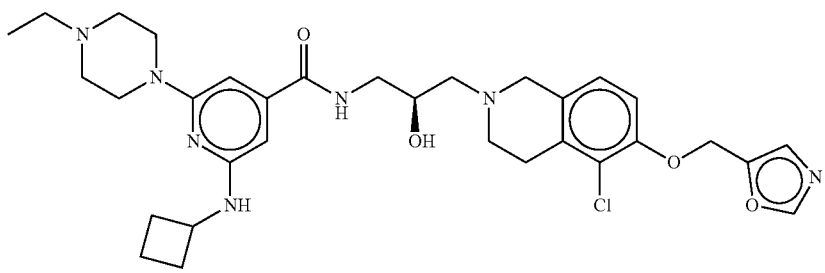
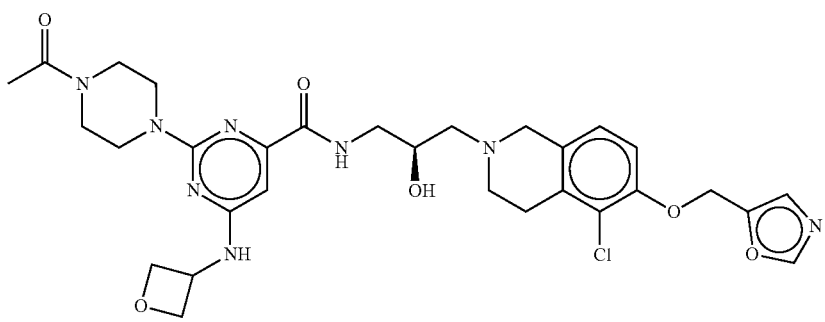
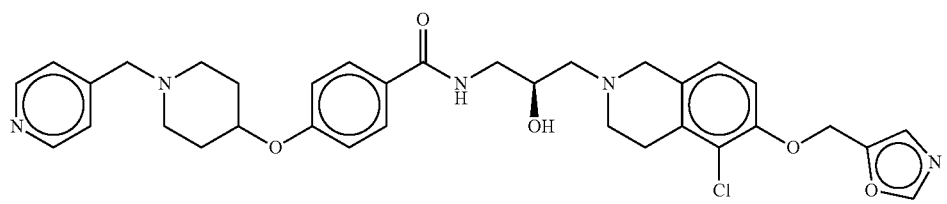
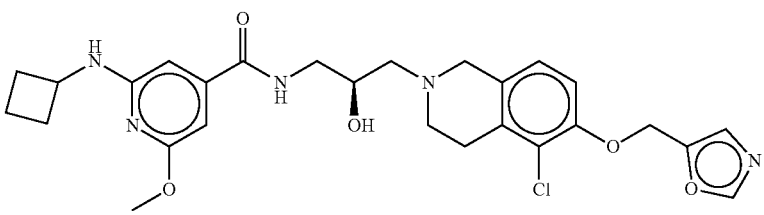
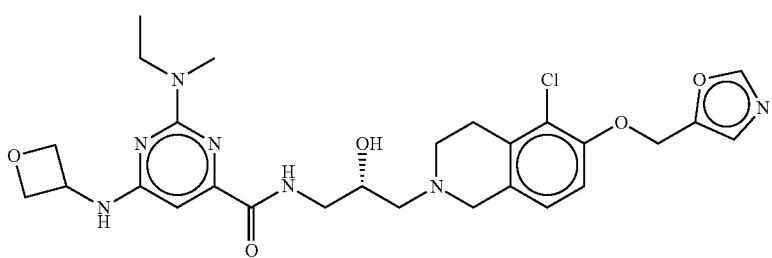

TABLE 4-continued
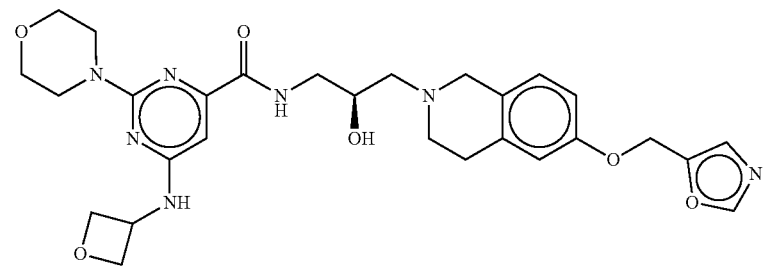
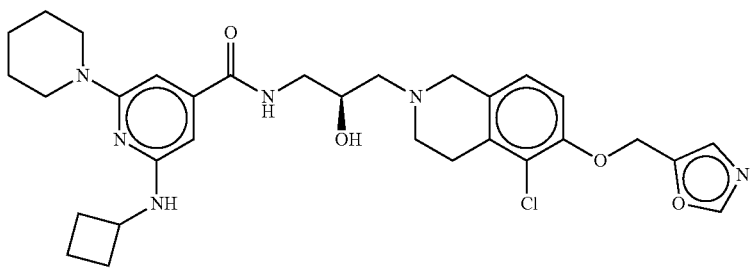
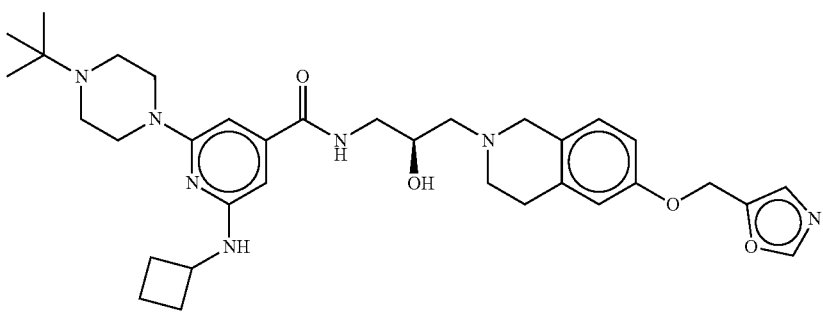
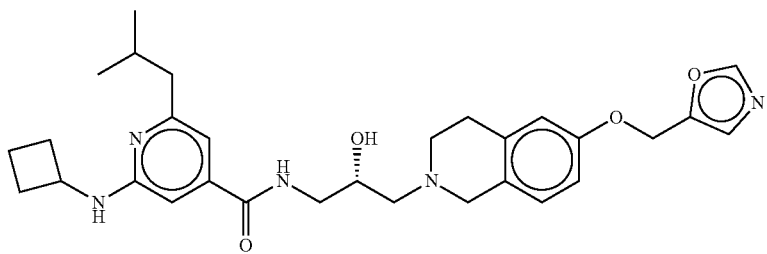
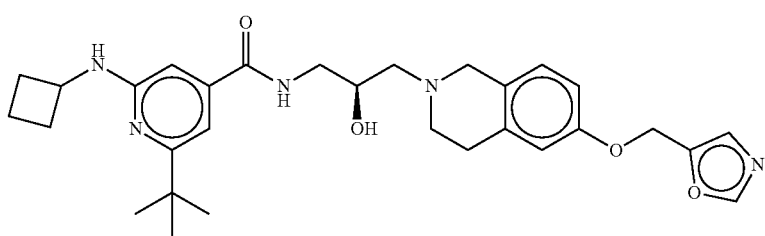
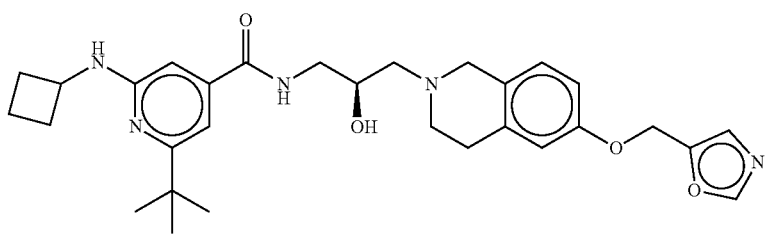

TABLE 4-continued
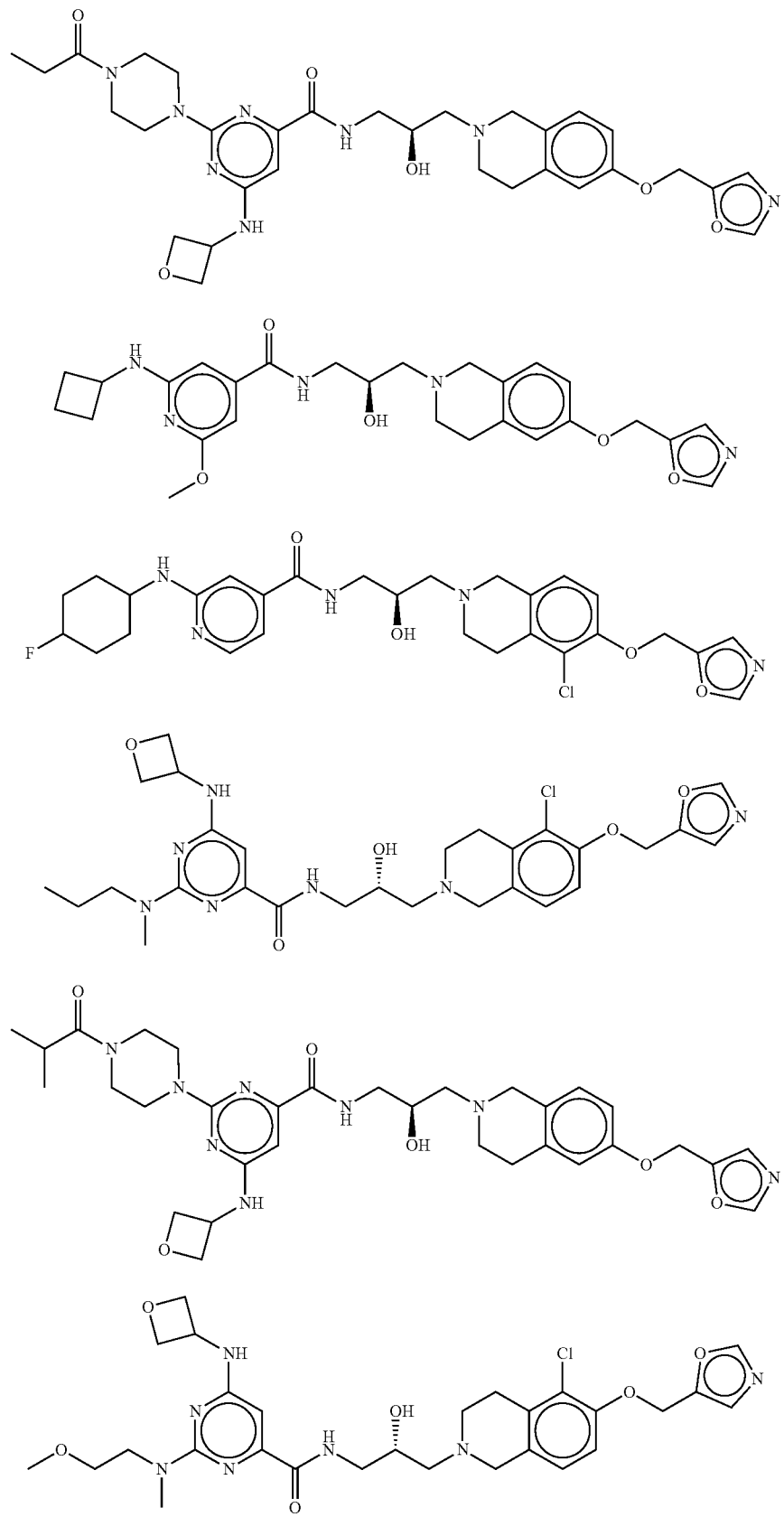

TABLE 4-continued
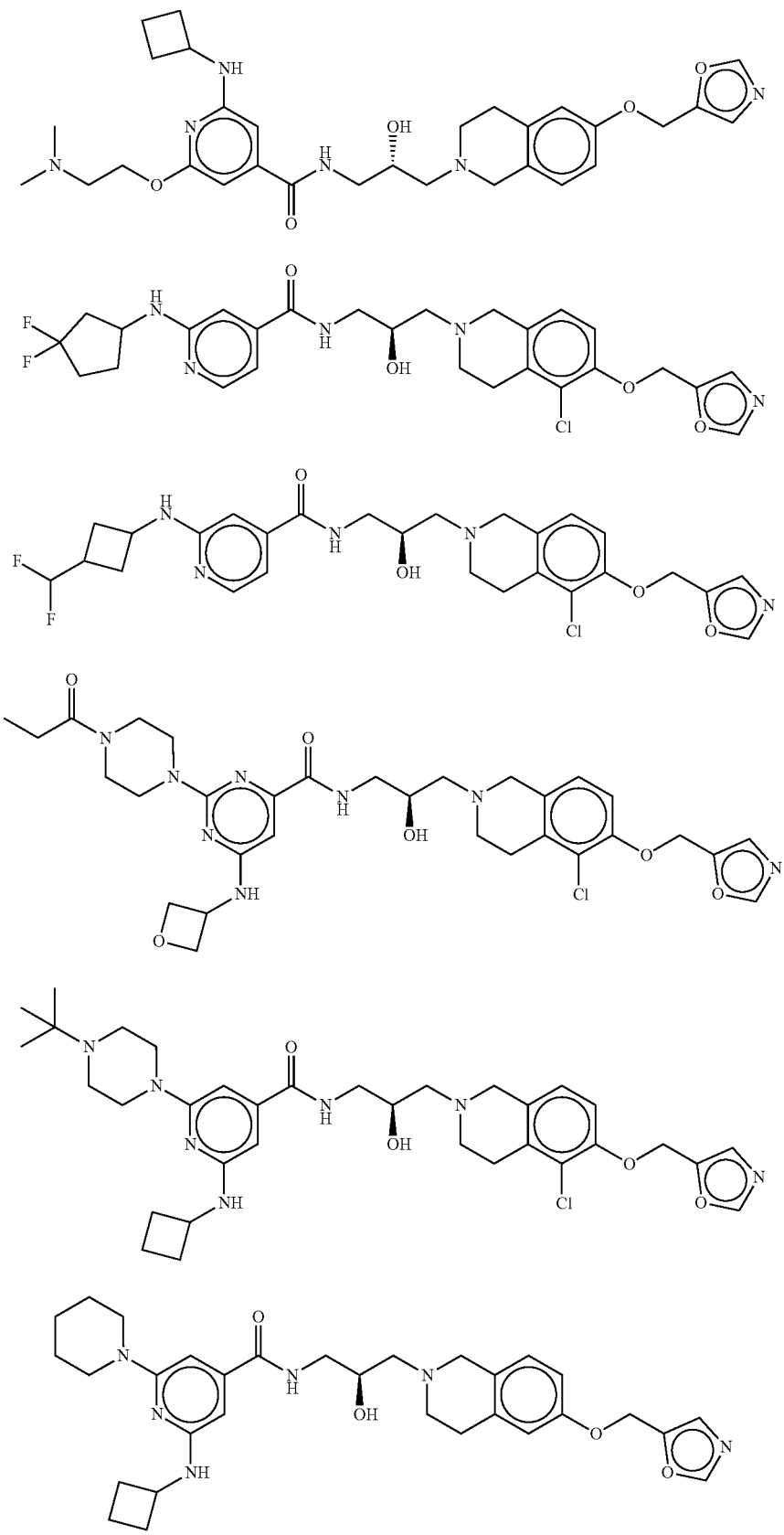

TABLE 4-continued
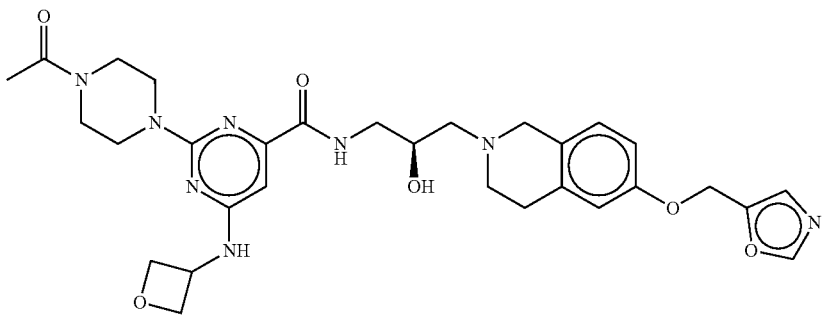
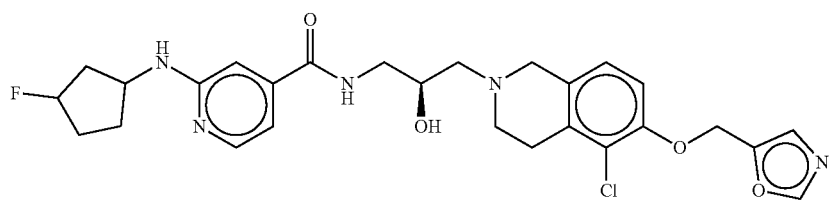
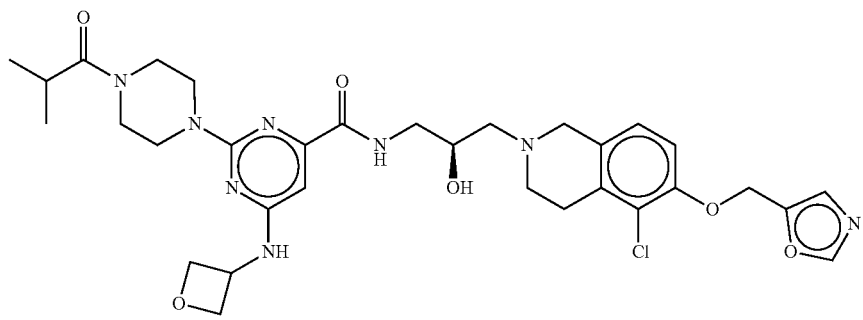
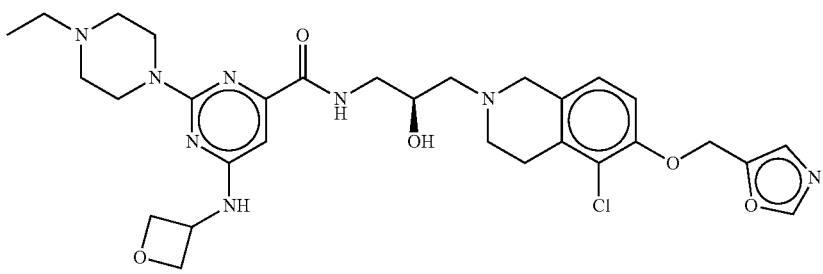
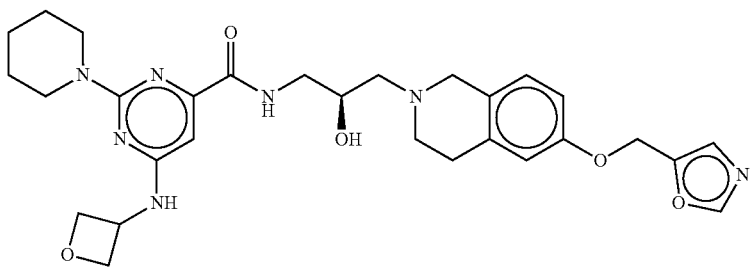
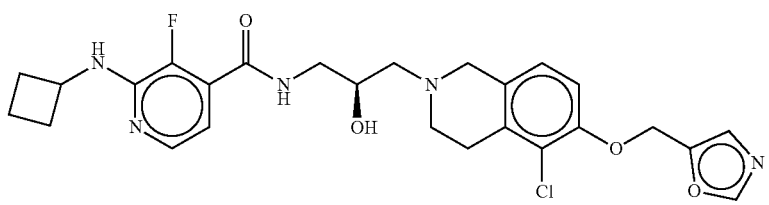

TABLE 4-continued
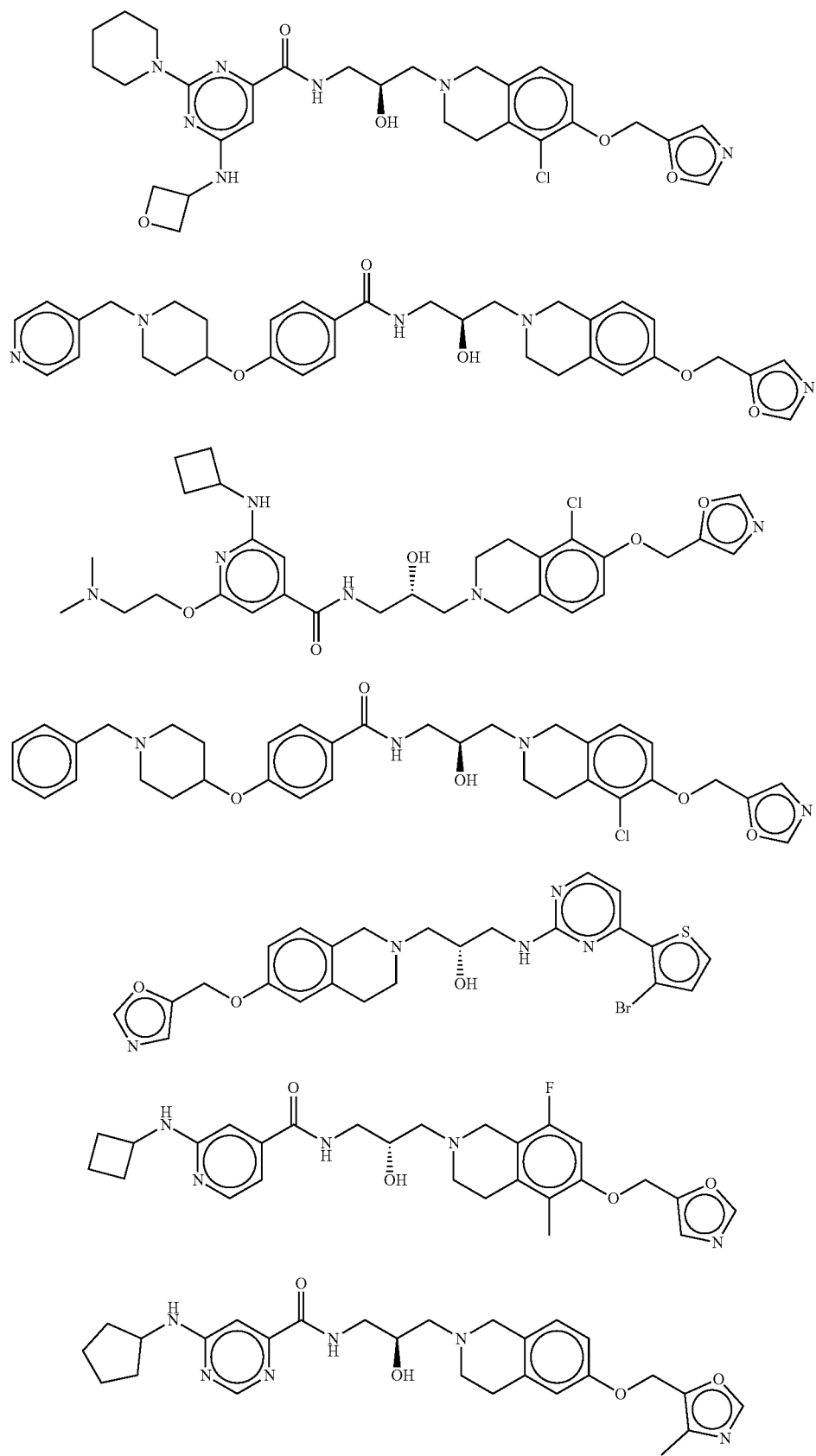

TABLE 4-continued
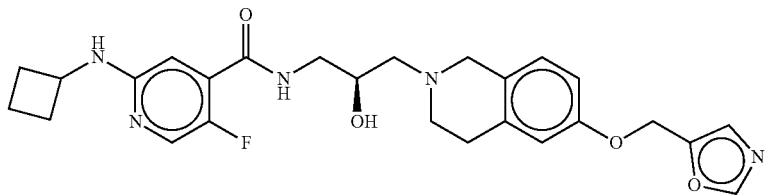
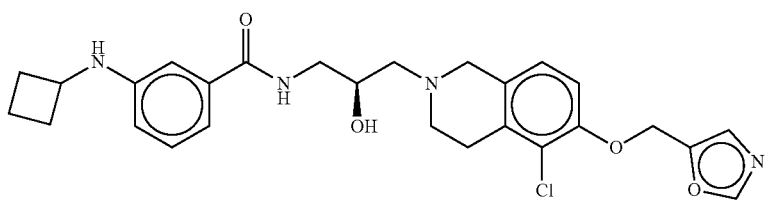
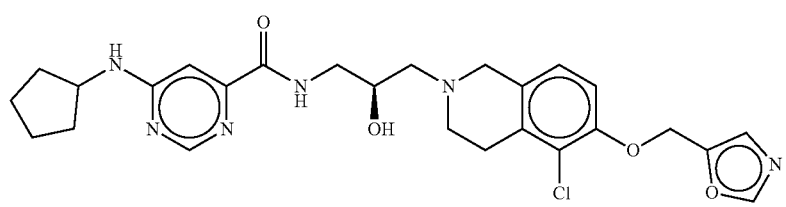
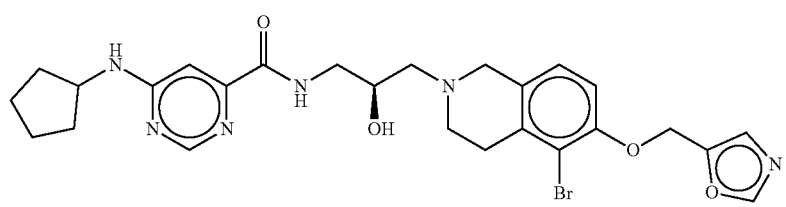
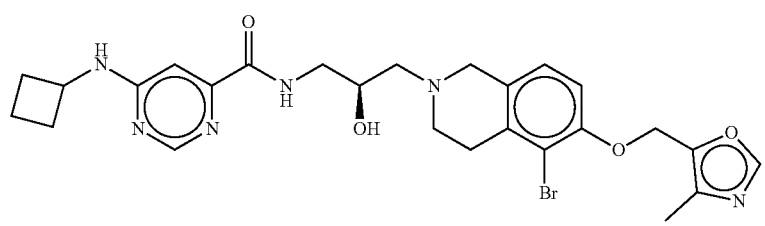
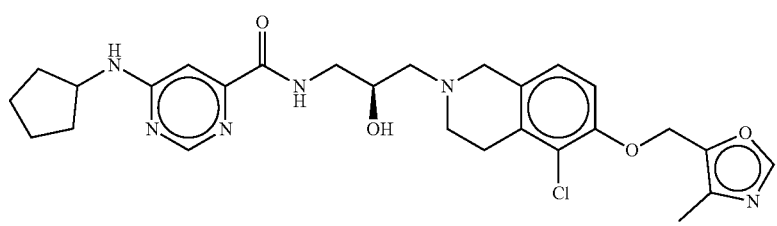
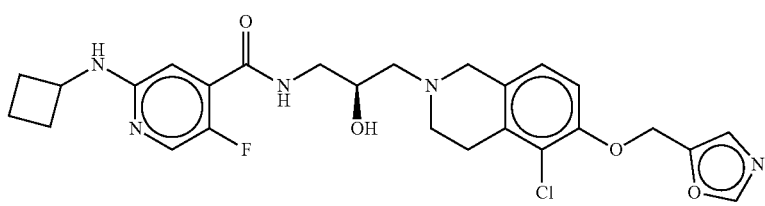

TABLE 4-continued
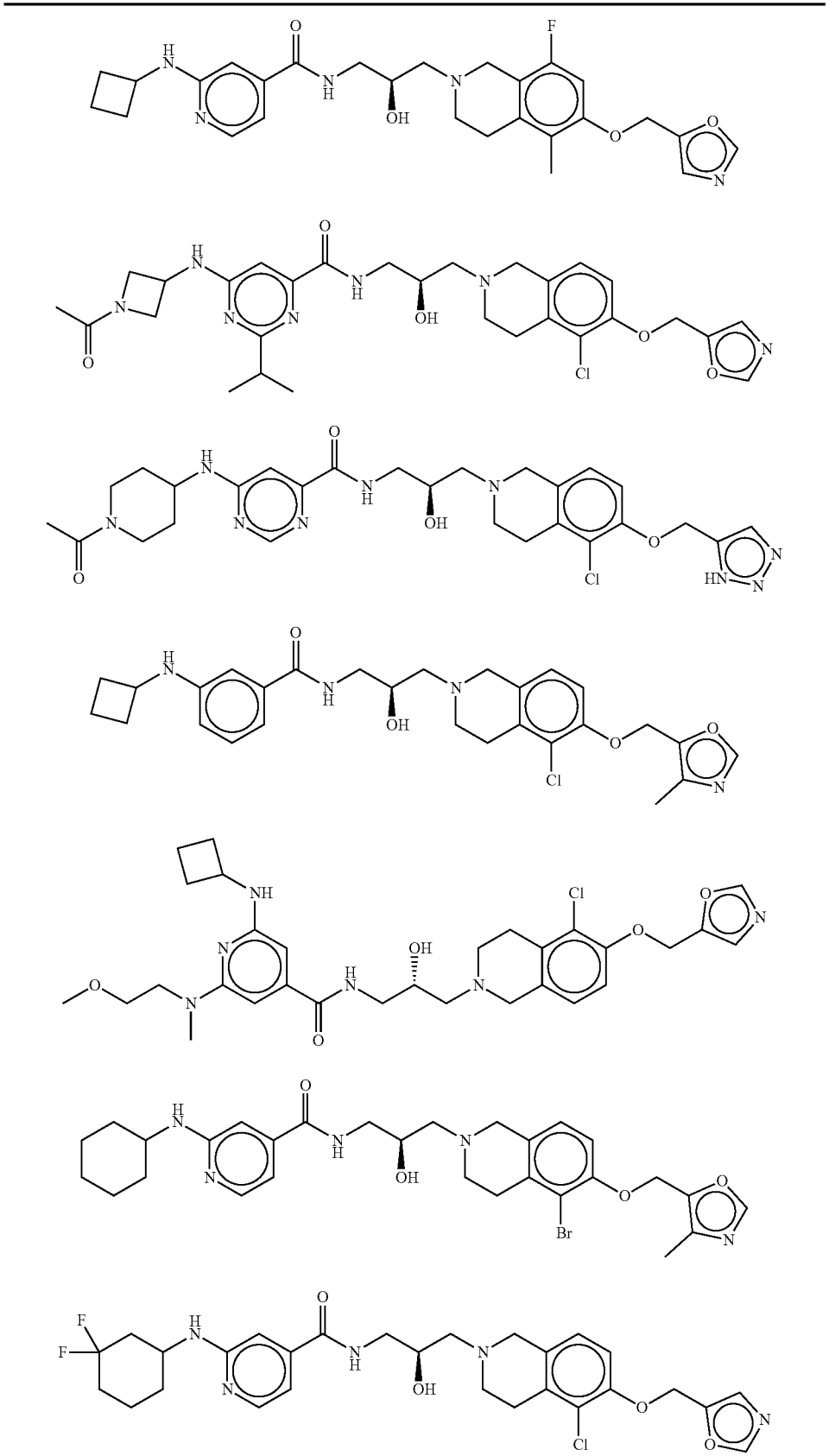

TABLE 4-continued
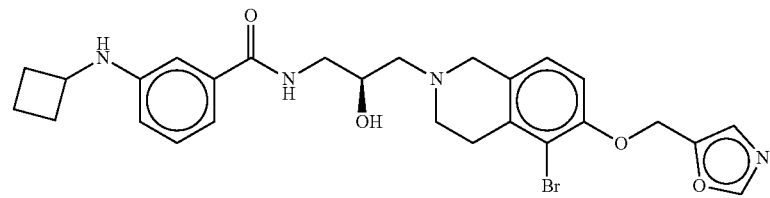
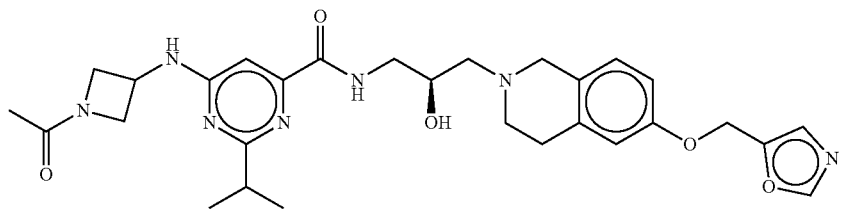
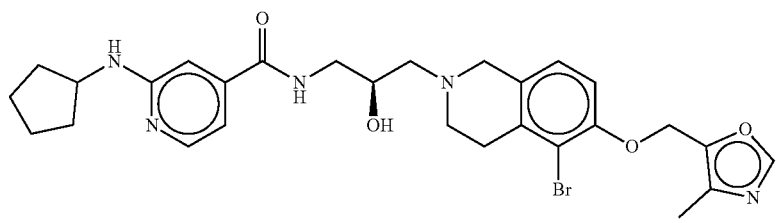
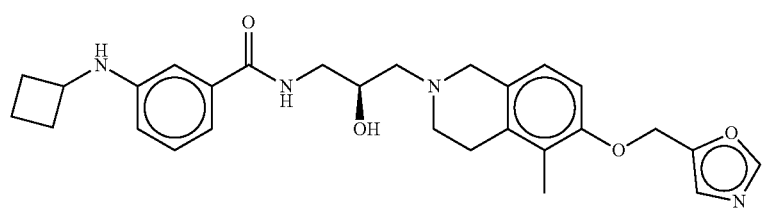
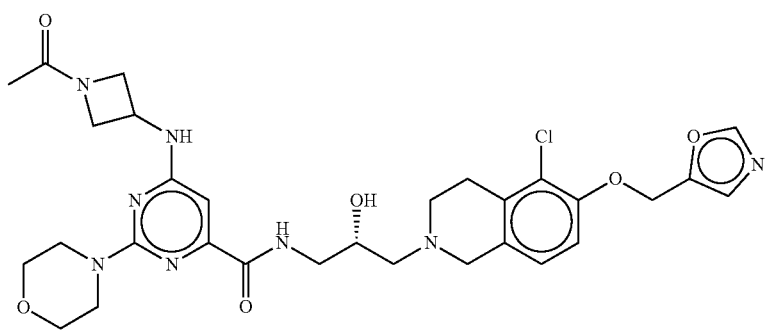
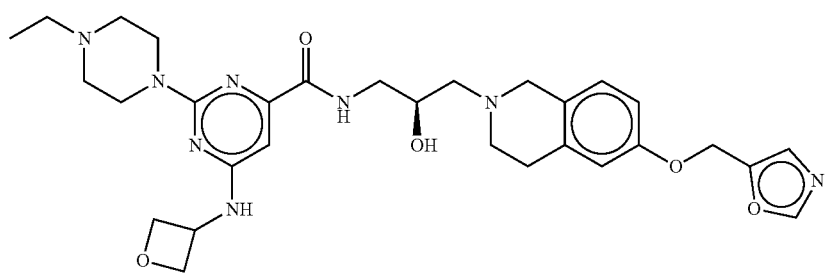

TABLE 4-continued
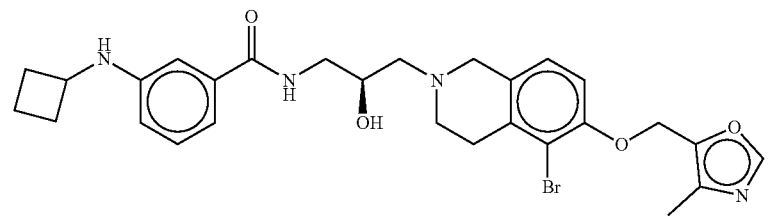
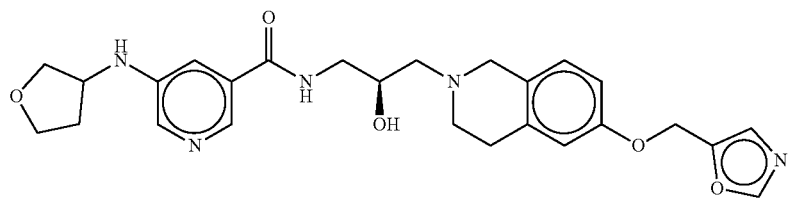
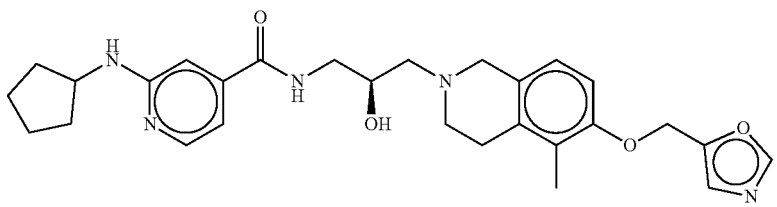
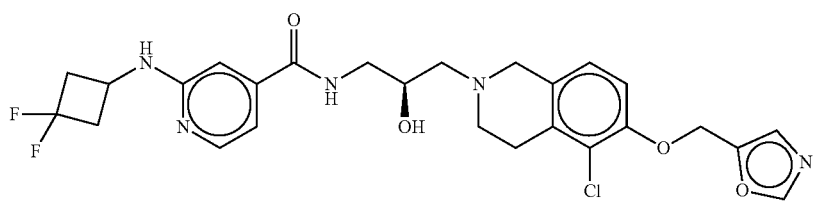
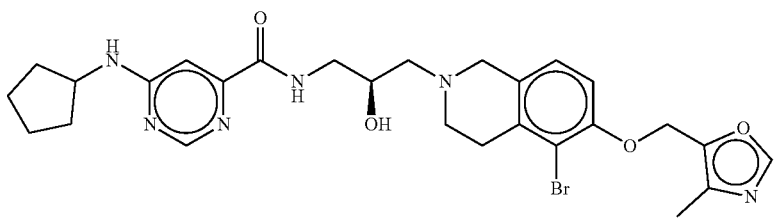
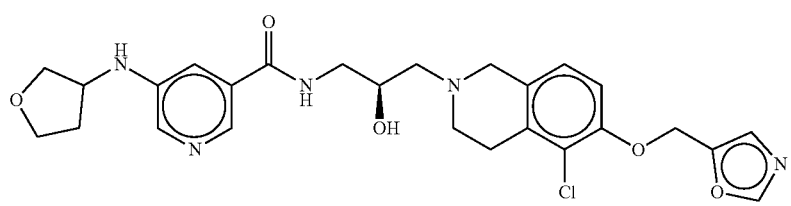
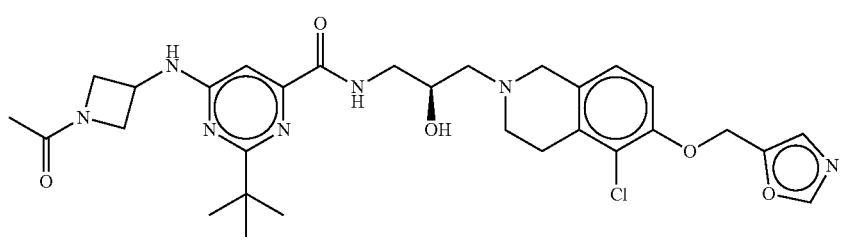

TABLE 4-continued
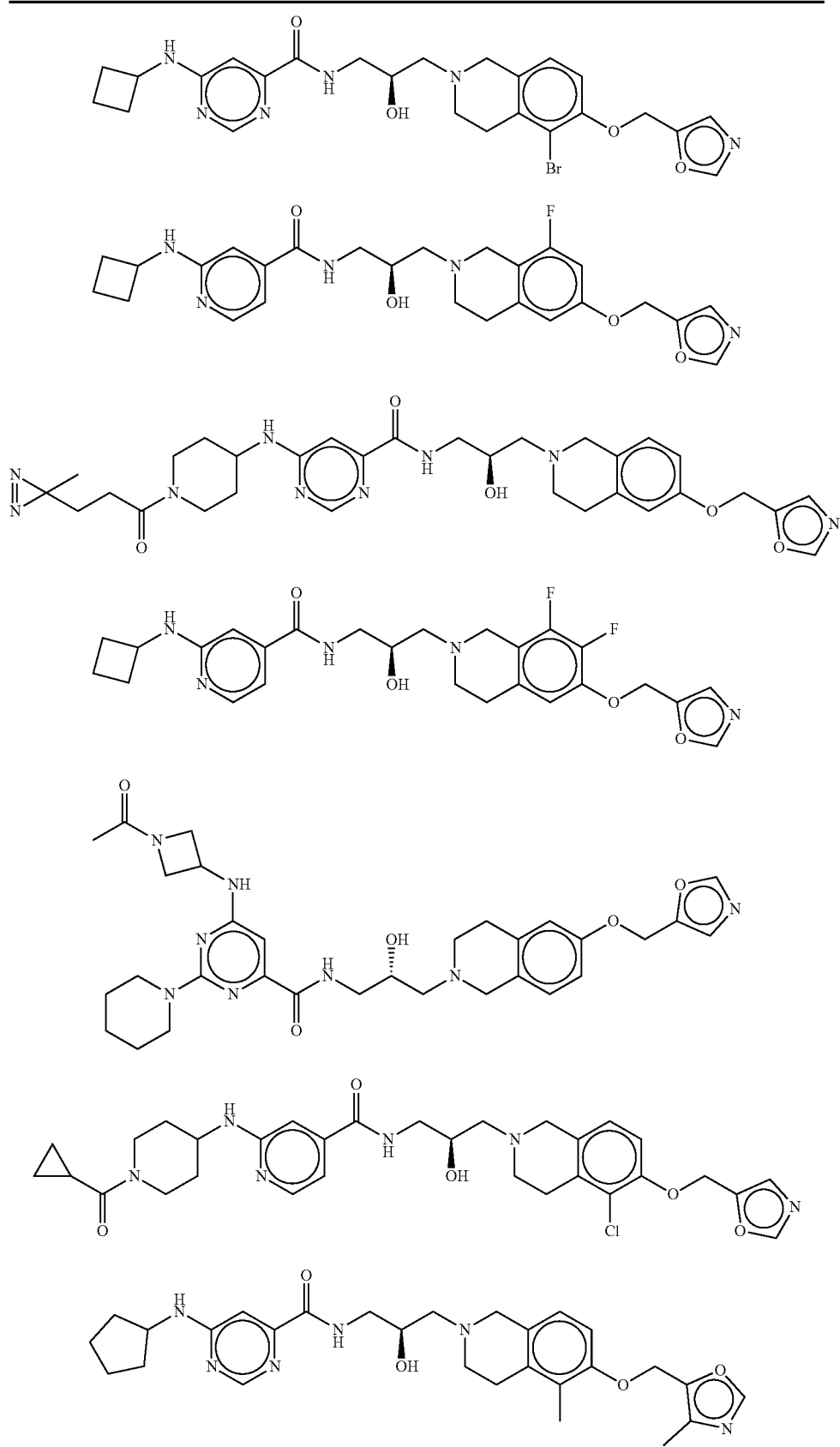

TABLE 4-continued
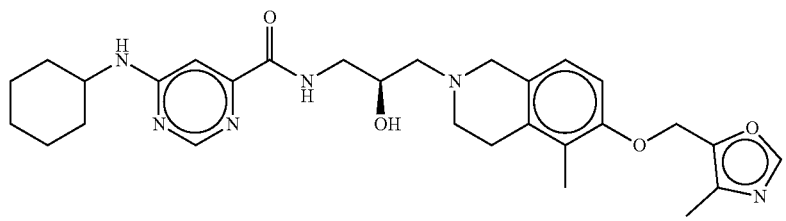
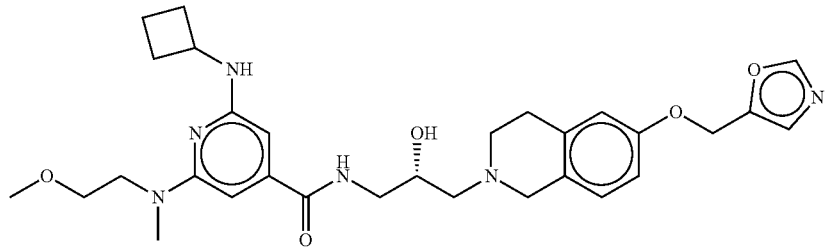
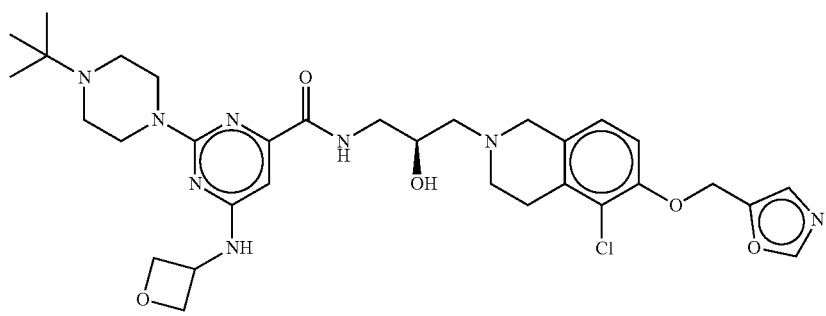
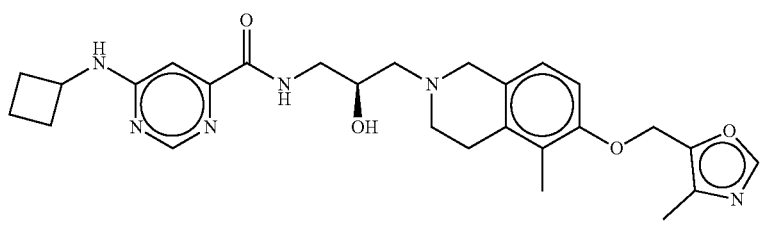
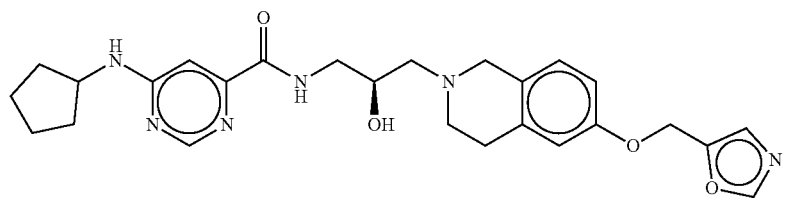
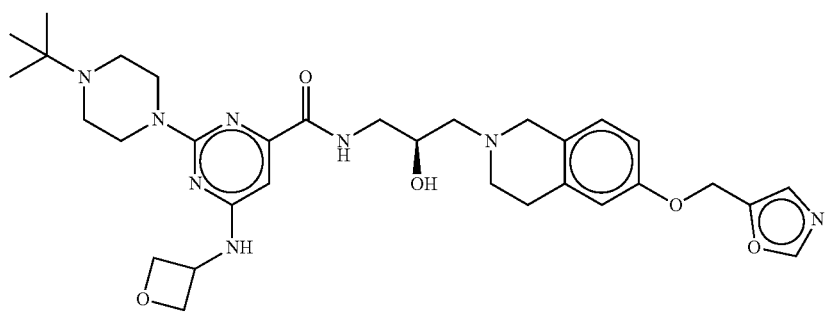

TABLE 4-continued
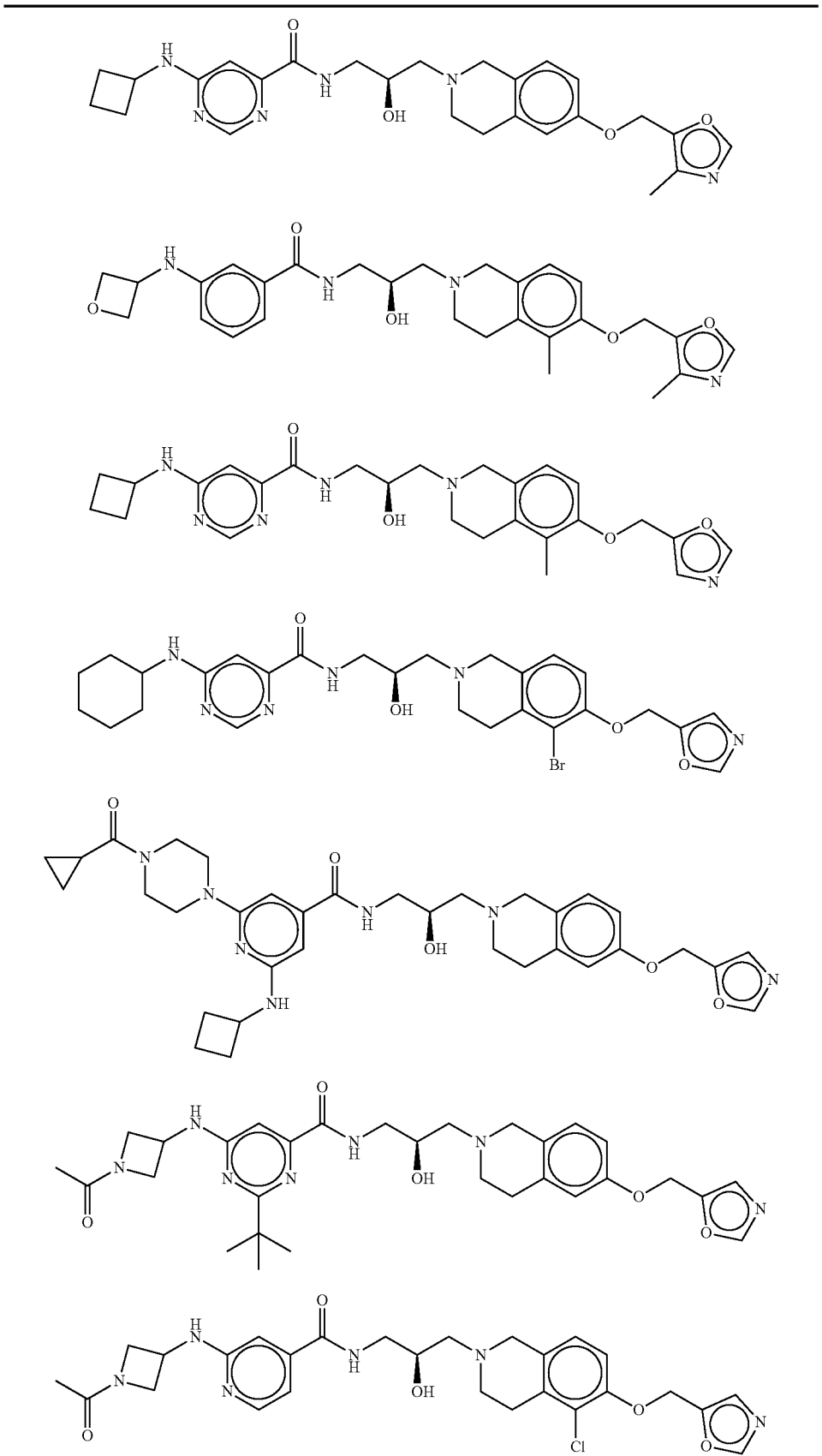

TABLE 4-continued
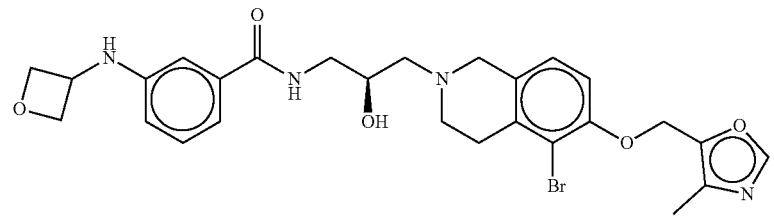
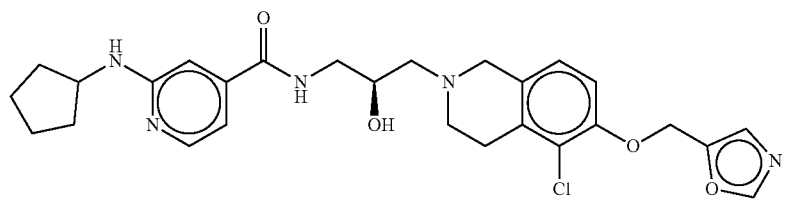
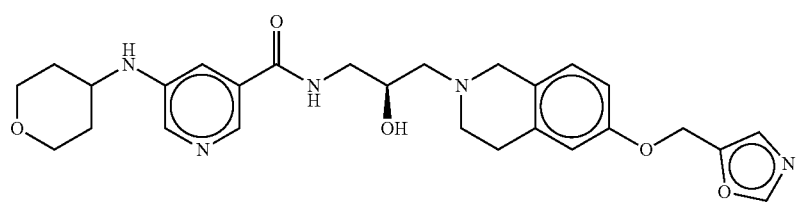
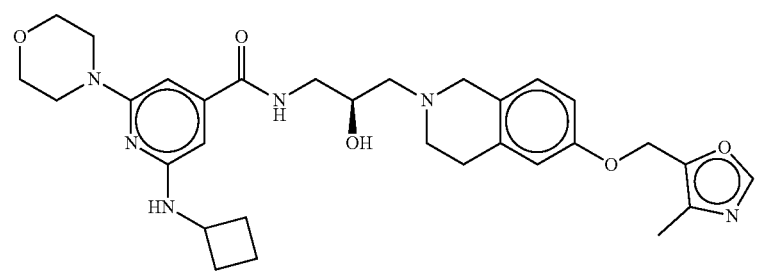
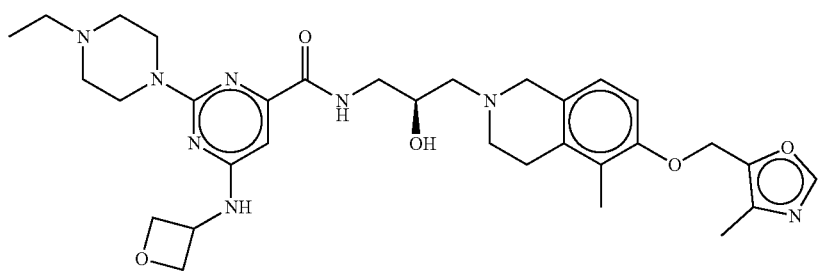
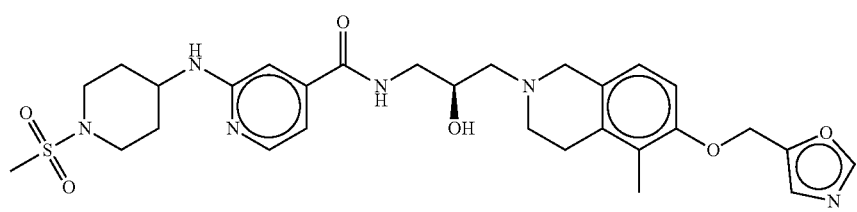

TABLE 4-continued
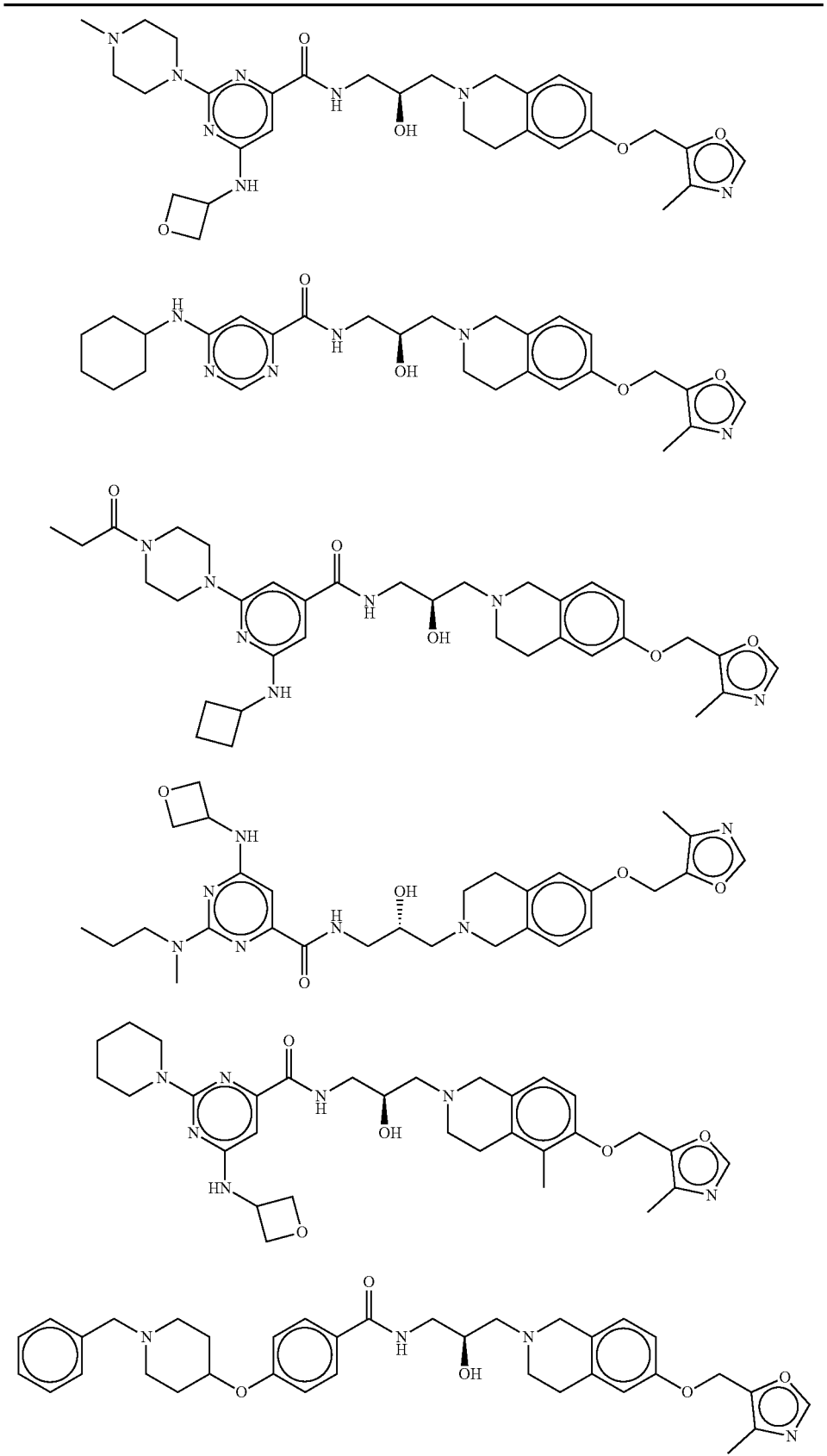

TABLE 4-continued
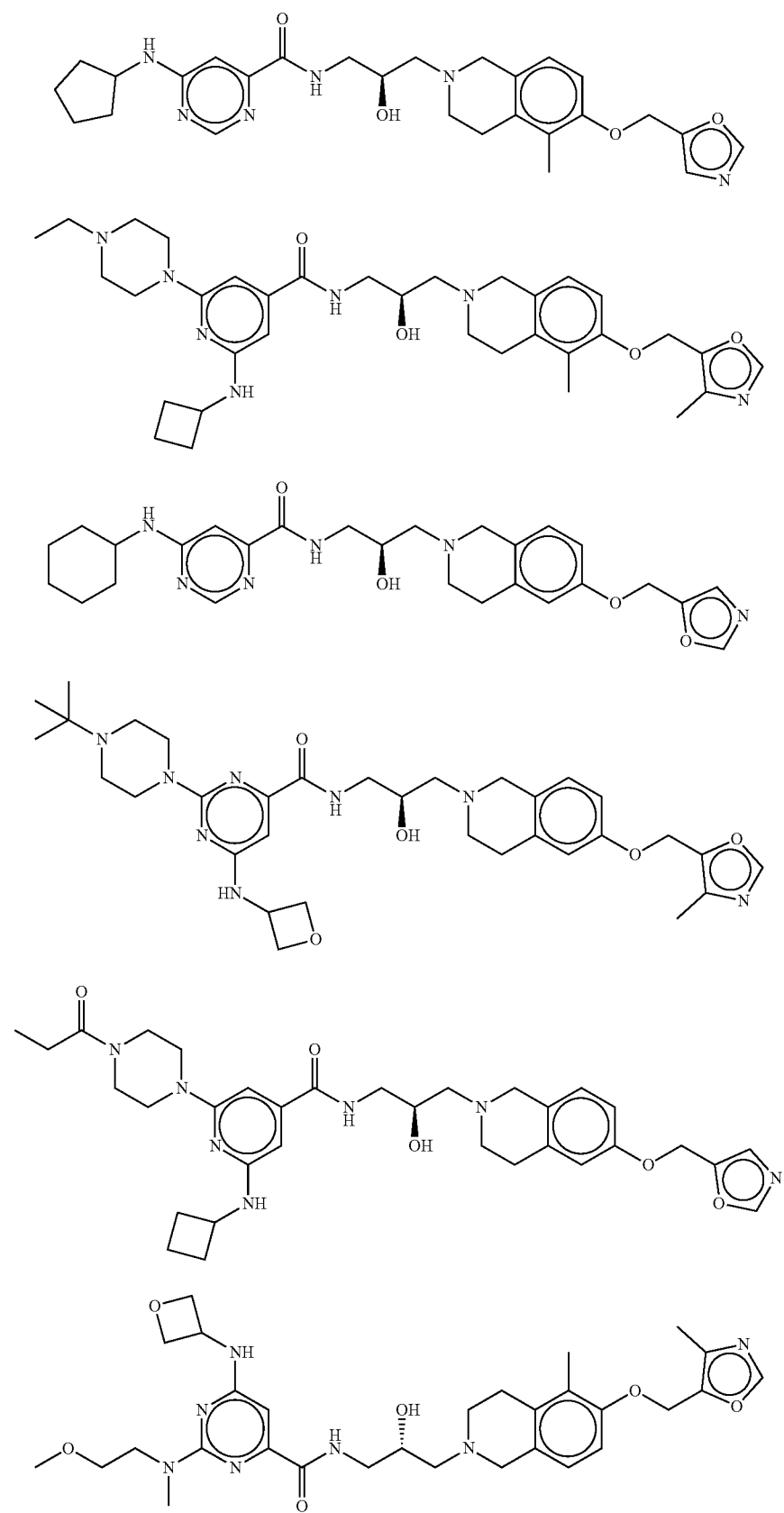

TABLE 4-continued
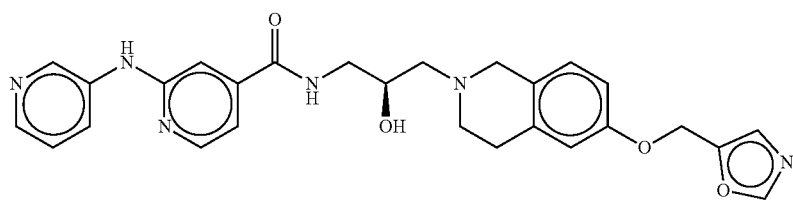
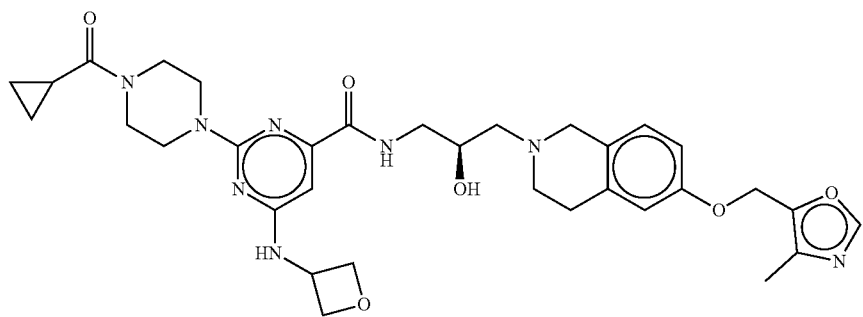
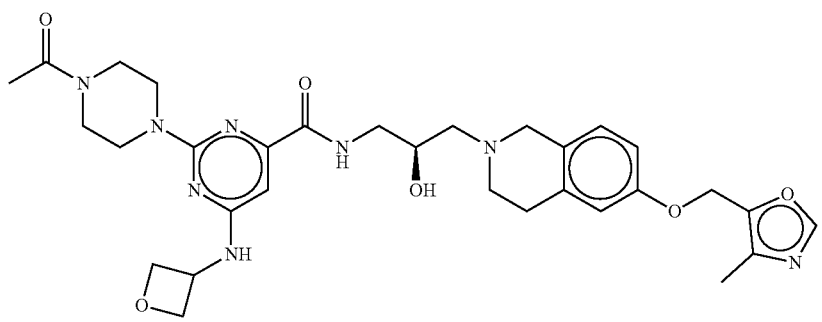
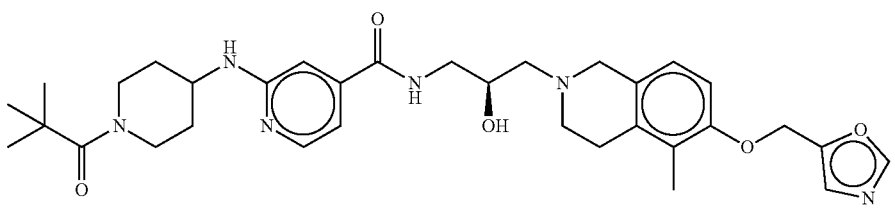
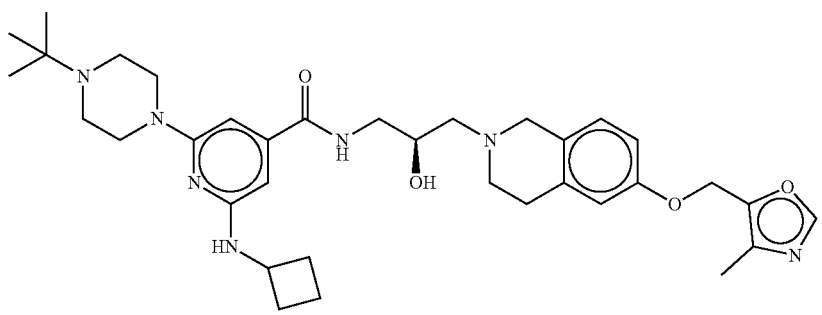
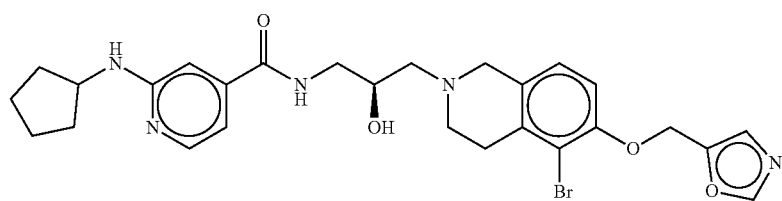

TABLE 4-continued
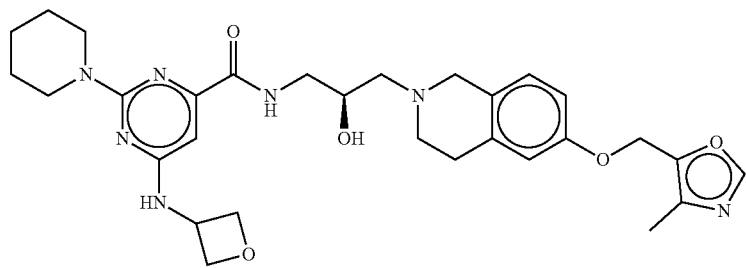
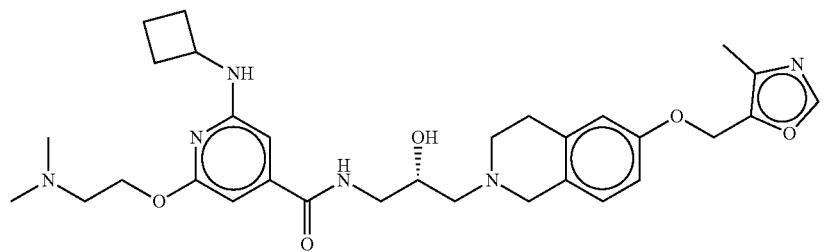
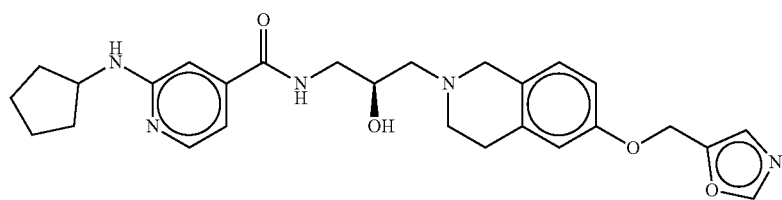
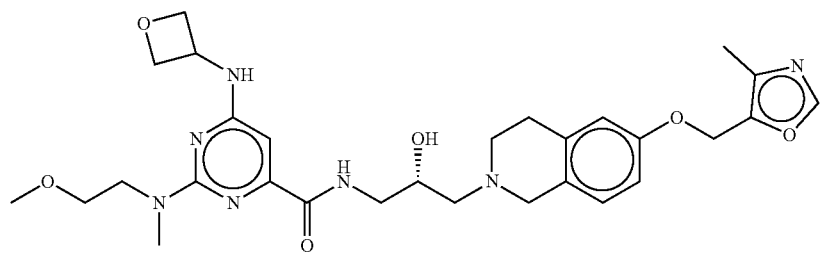
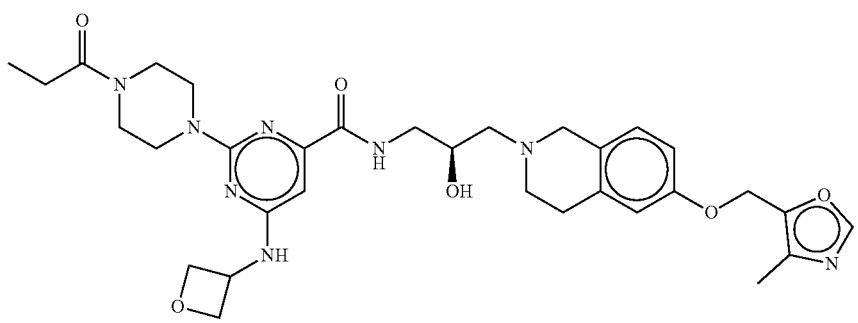
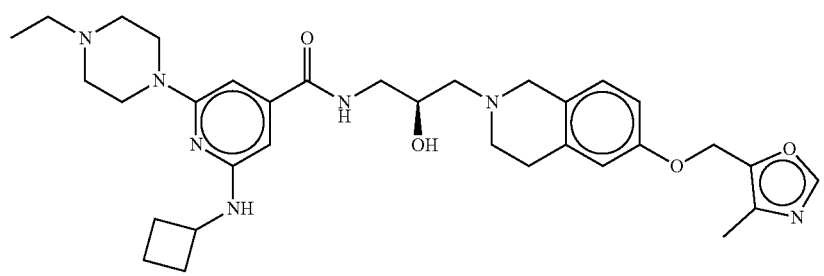

TABLE 4-continued
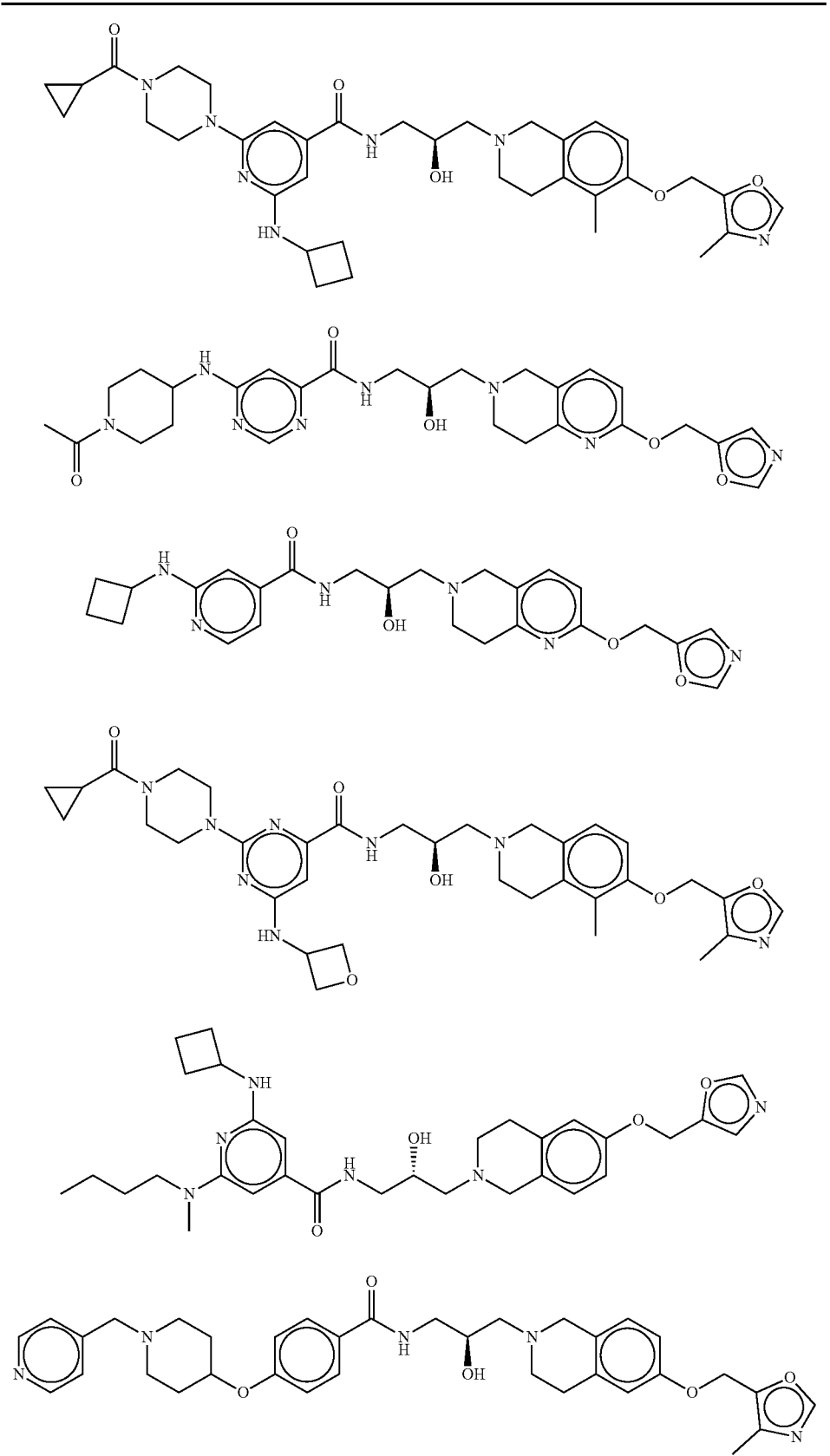

TABLE 4-continued
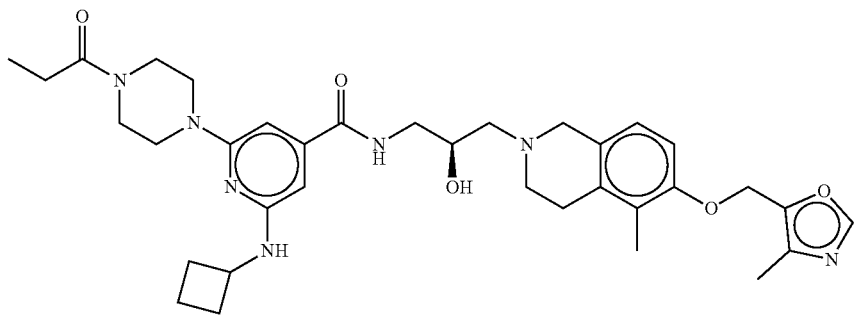
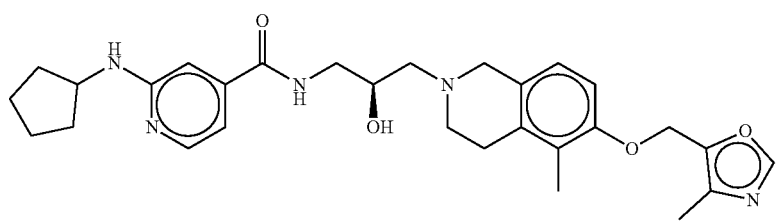
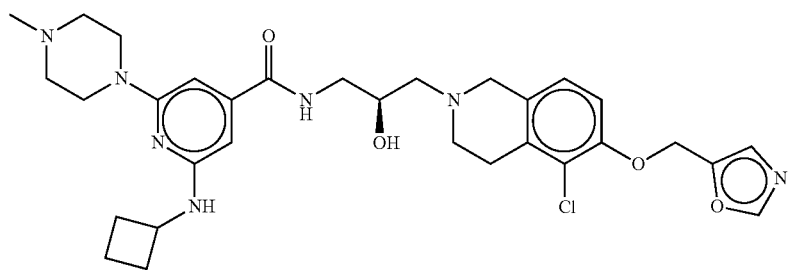
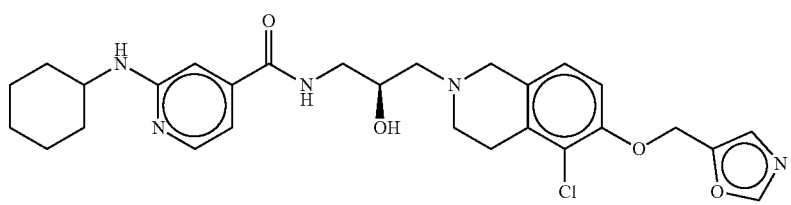
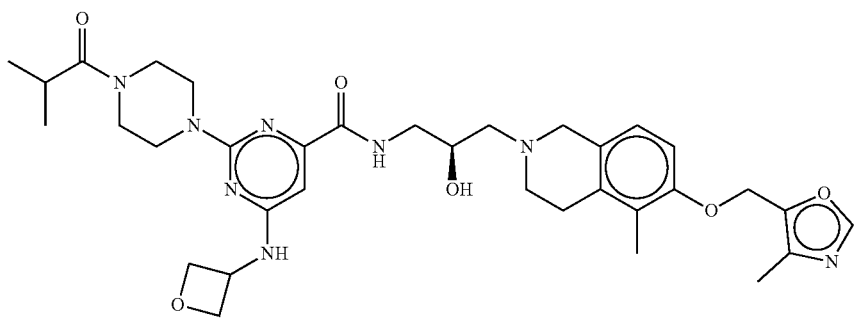
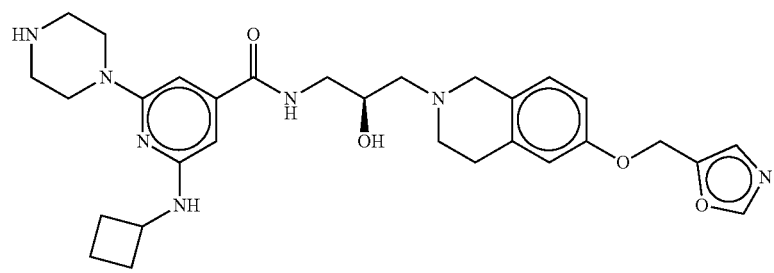

TABLE 4-continued
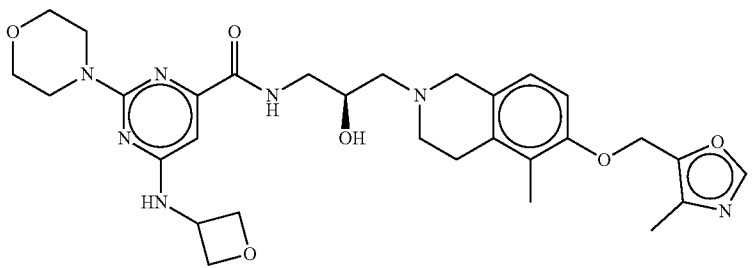
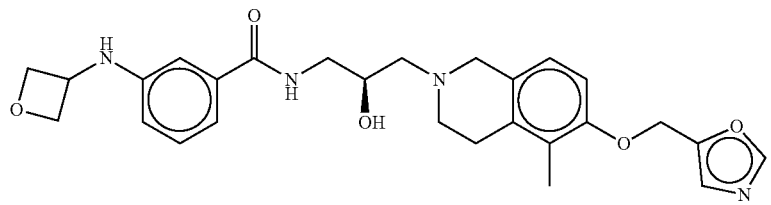
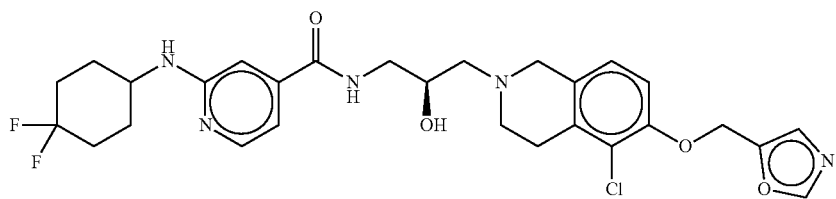
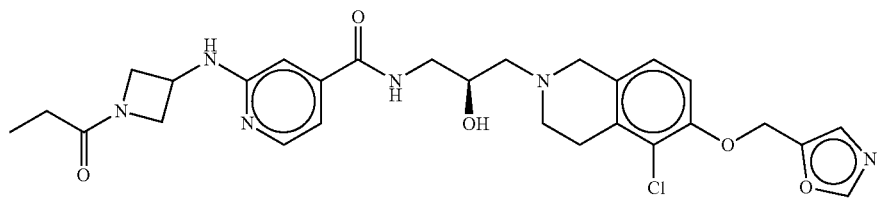
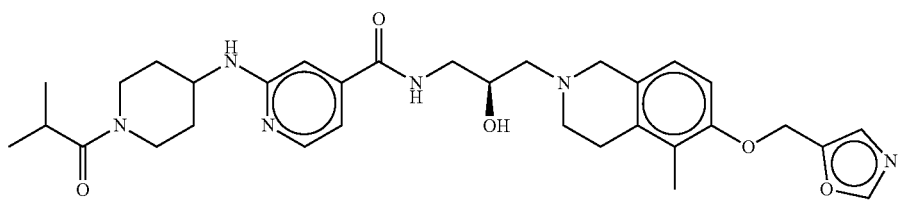
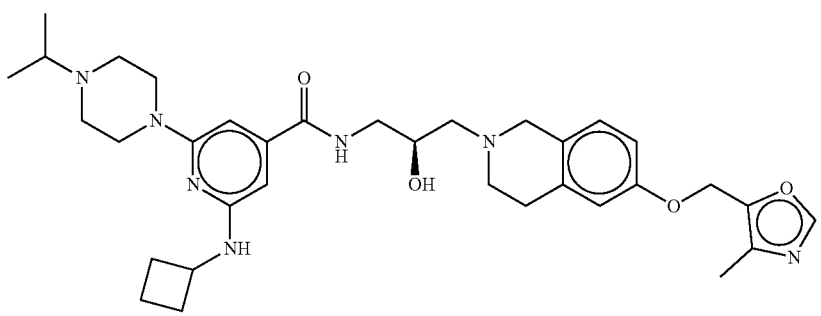
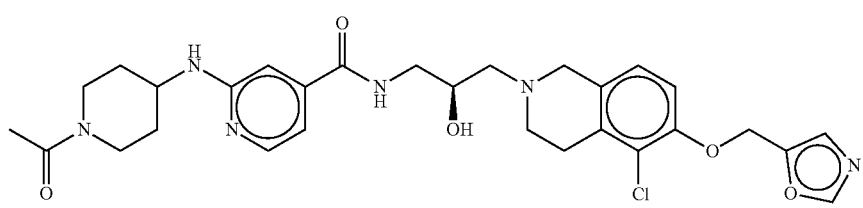

TABLE 4-continued
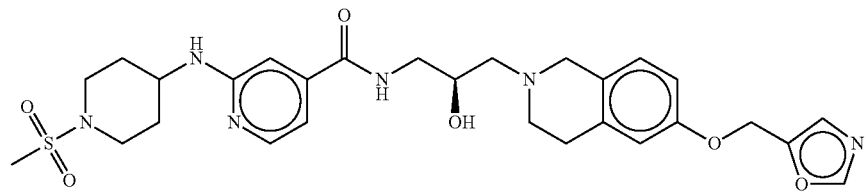
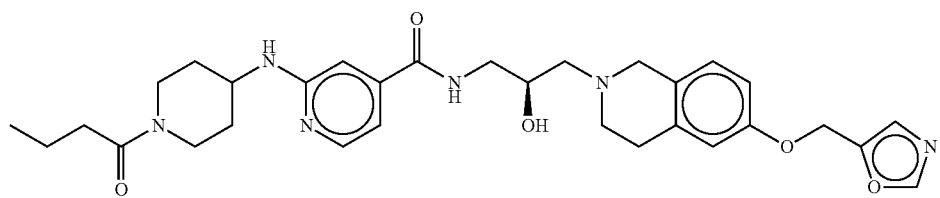
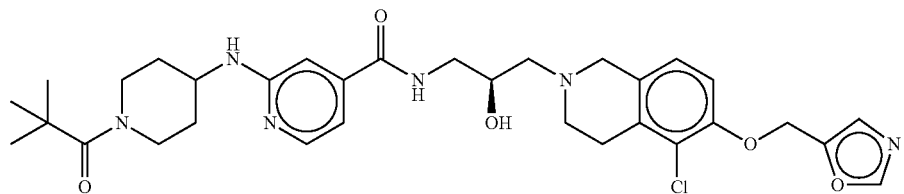
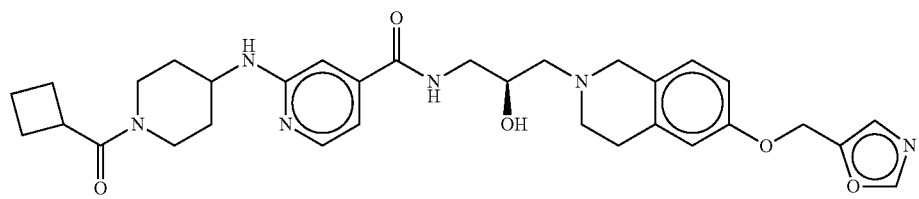
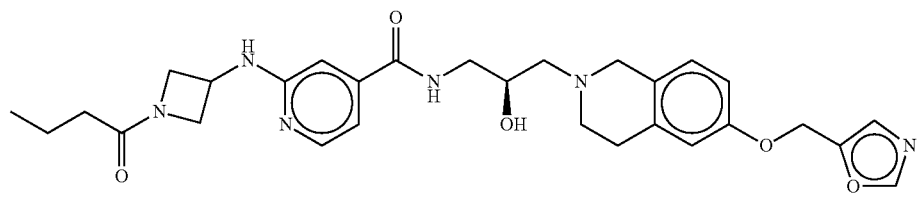
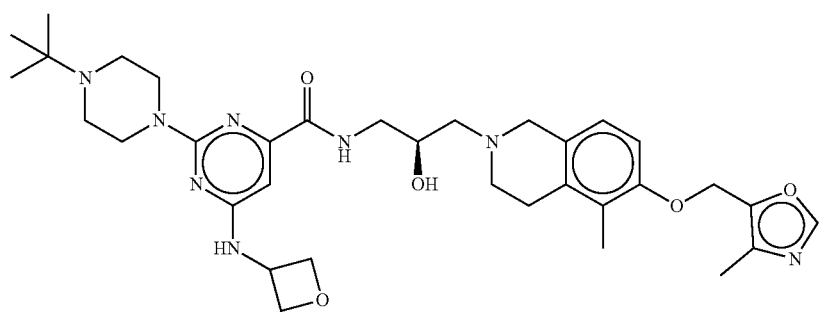
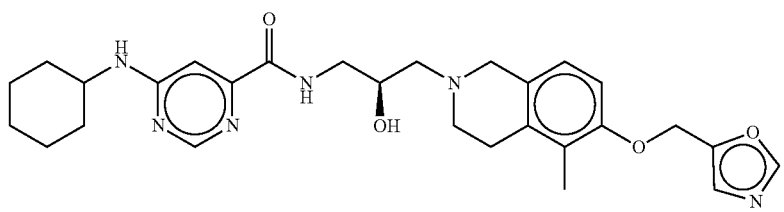

TABLE 4-continued
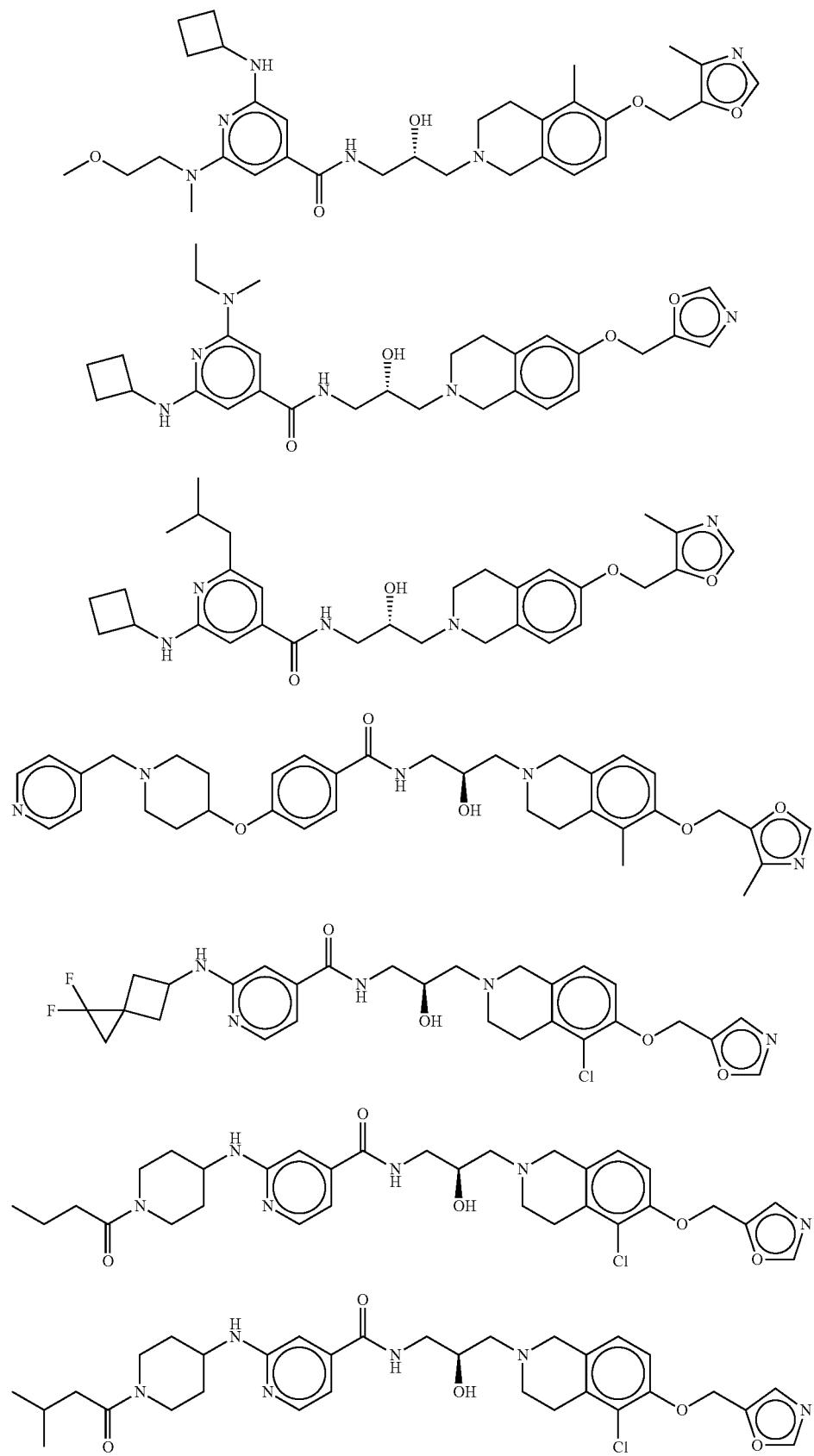

TABLE 4-continued
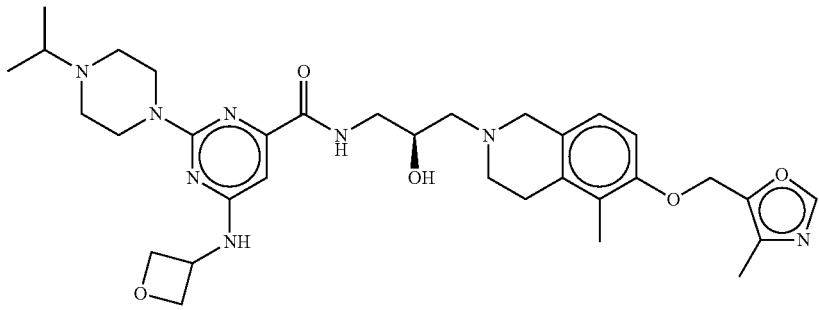
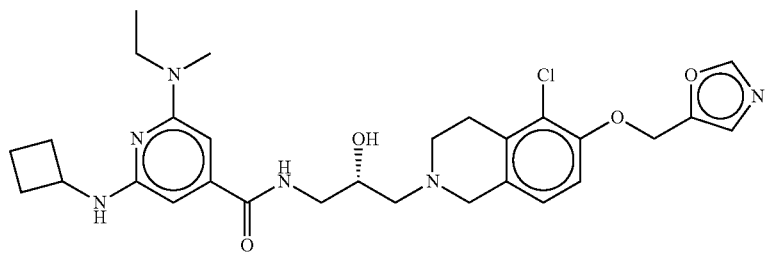
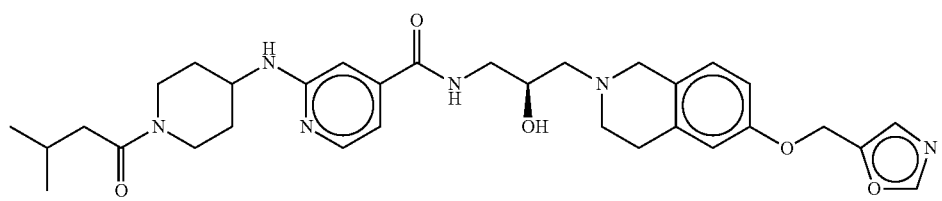
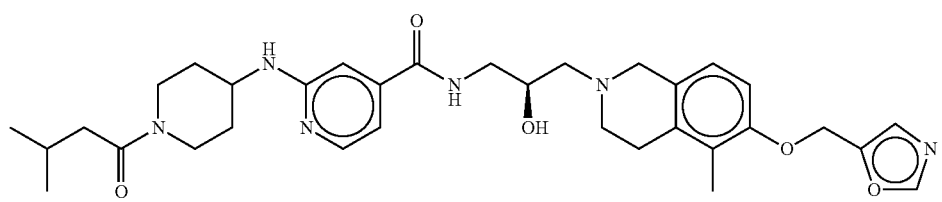
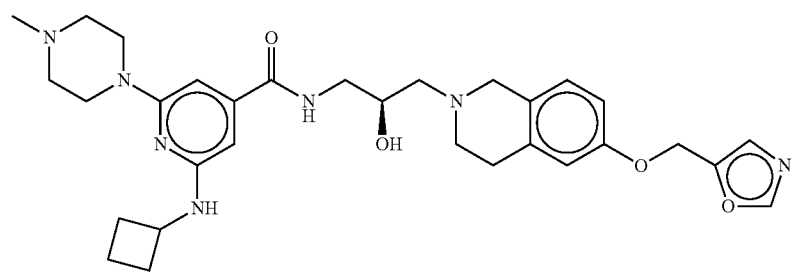
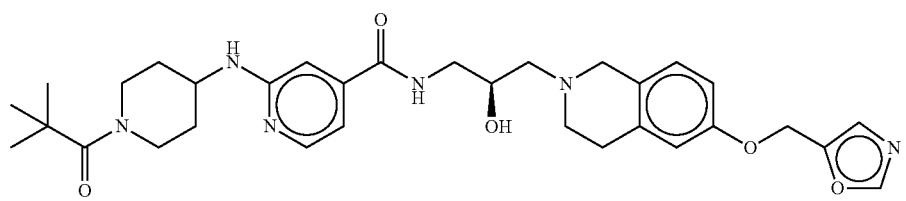

TABLE 4-continued
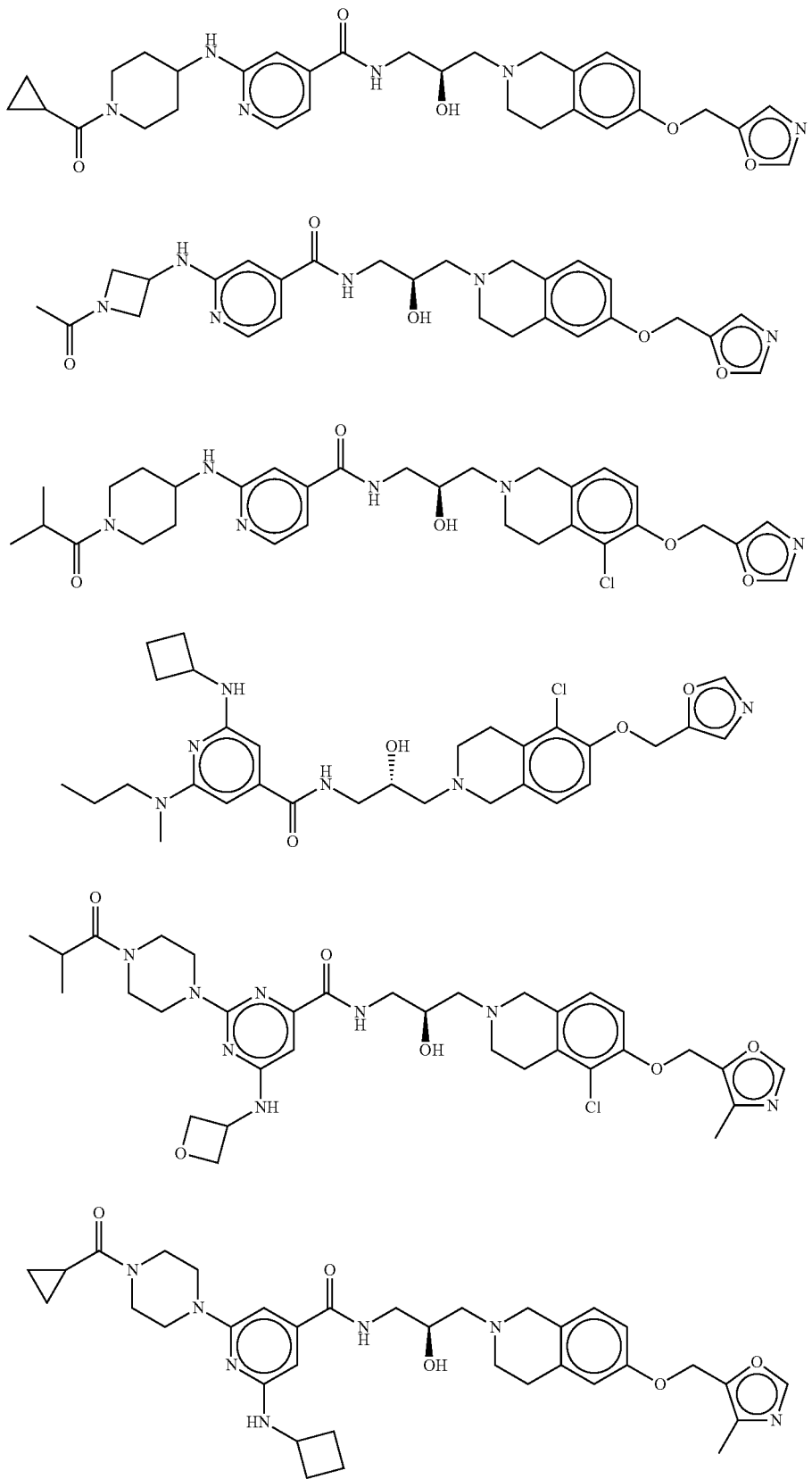

TABLE 4-continued
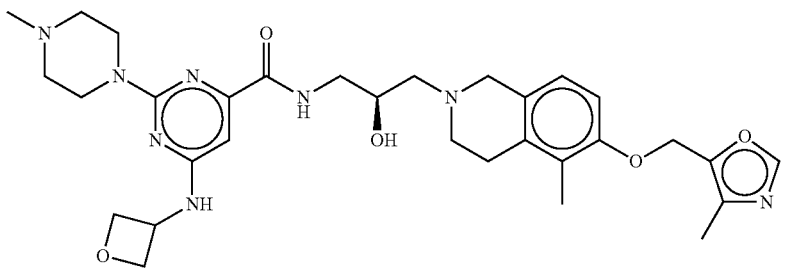
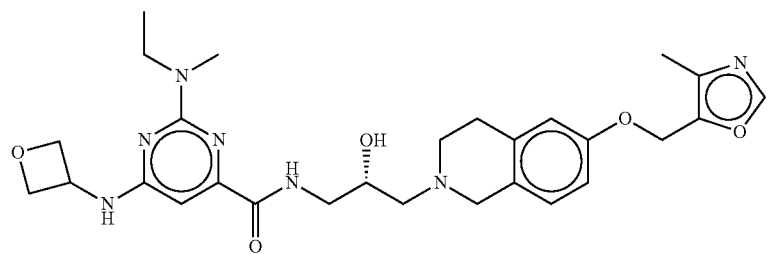
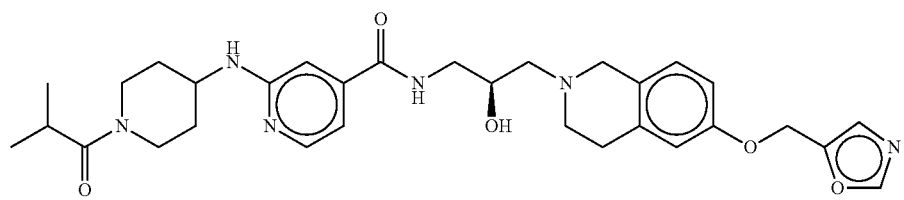
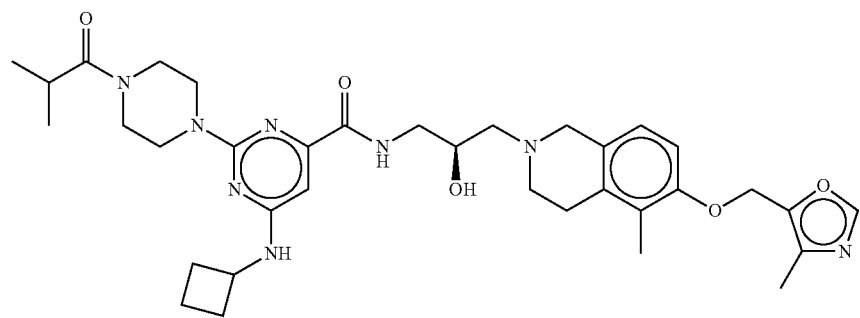
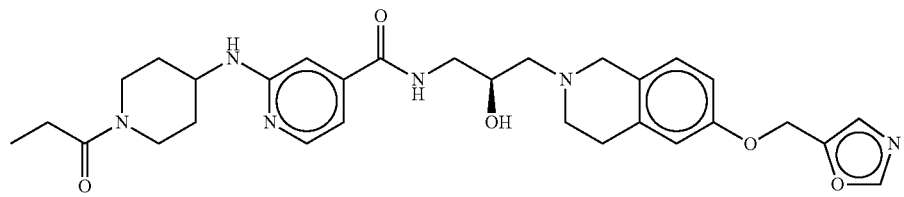
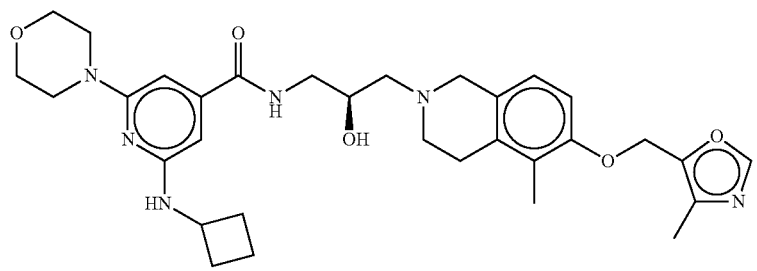

TABLE 4-continued
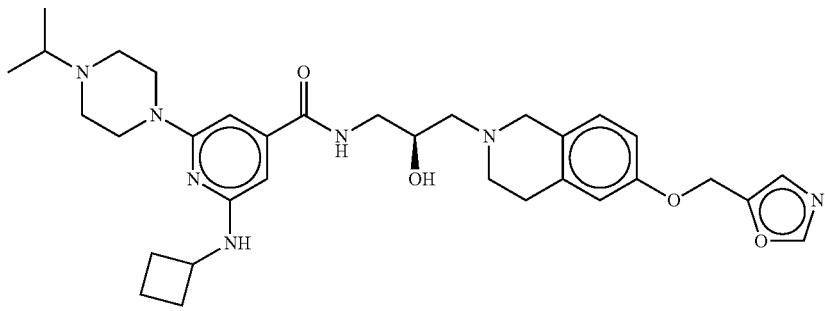
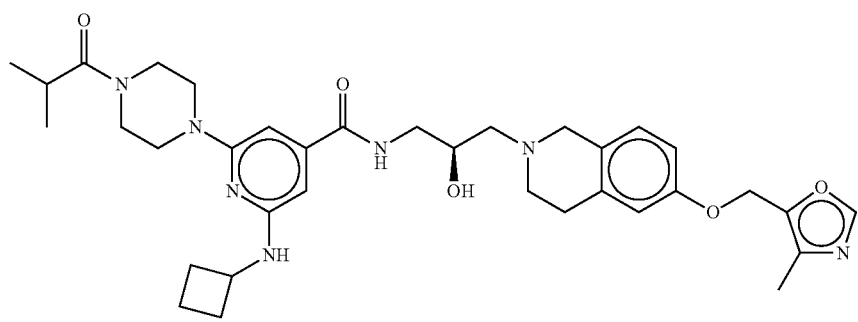
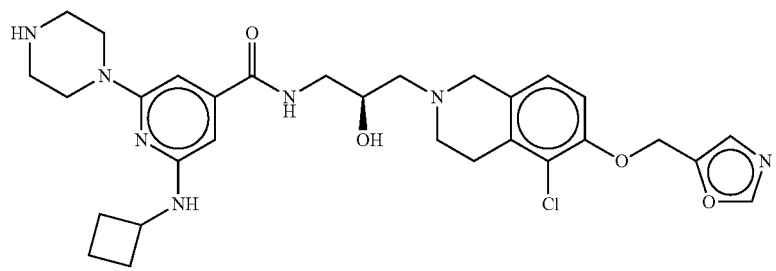
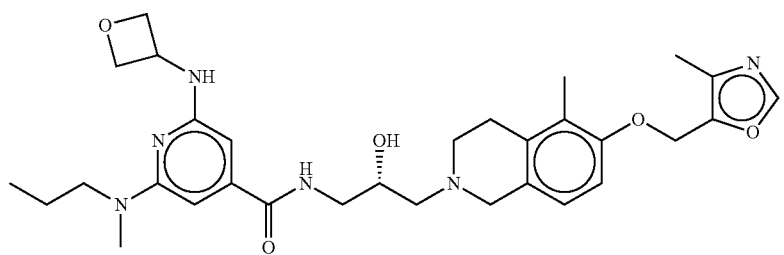
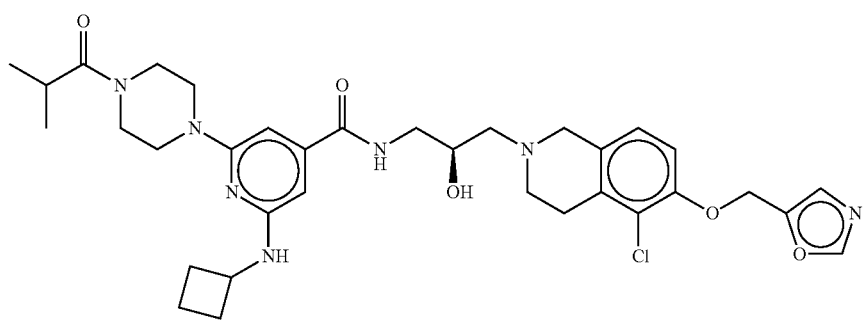

TABLE 4-continued
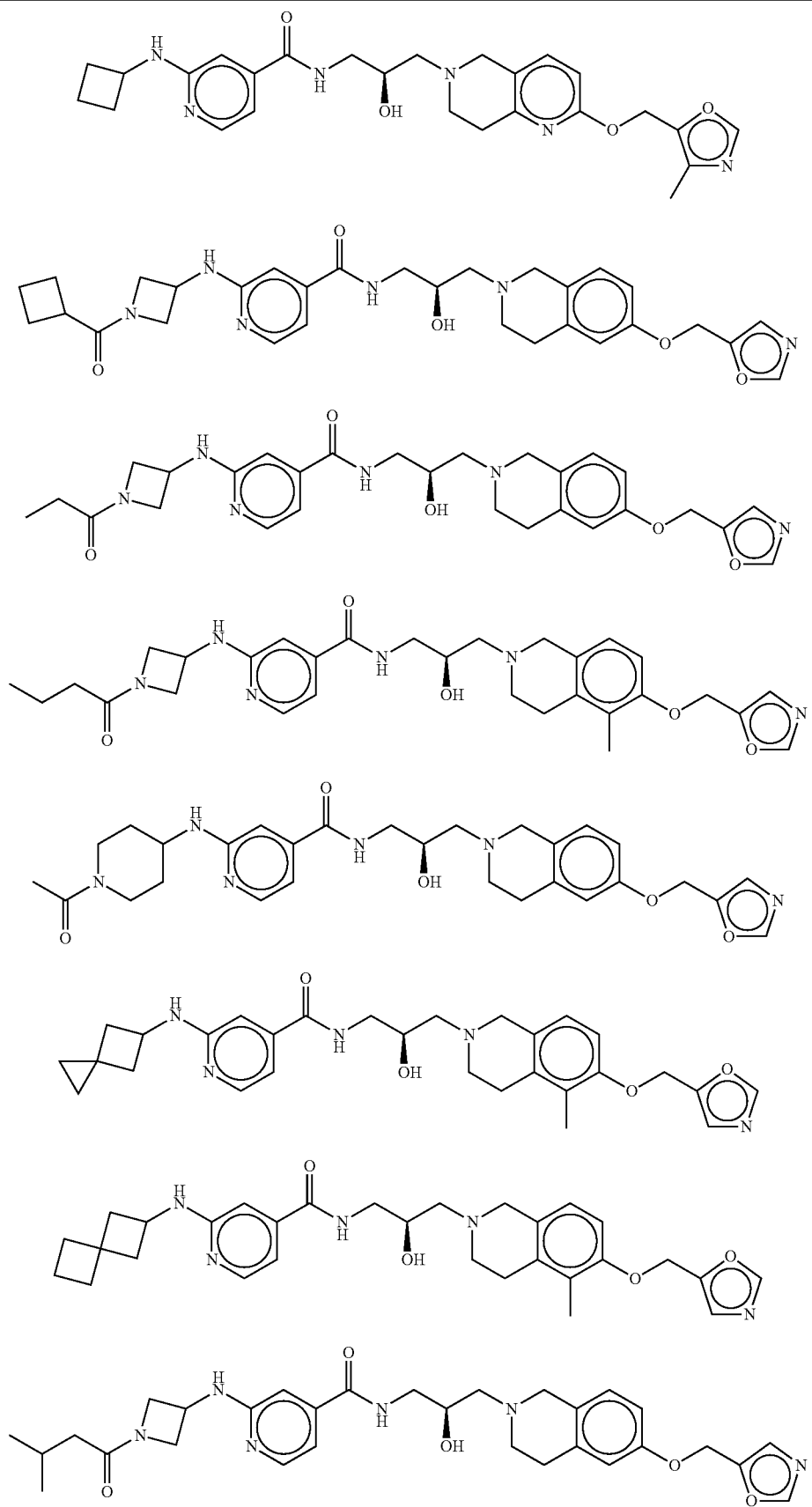

TABLE 4-continued
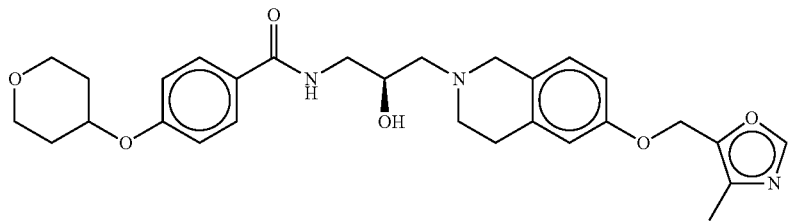
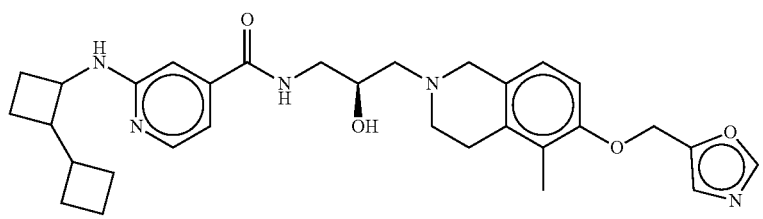
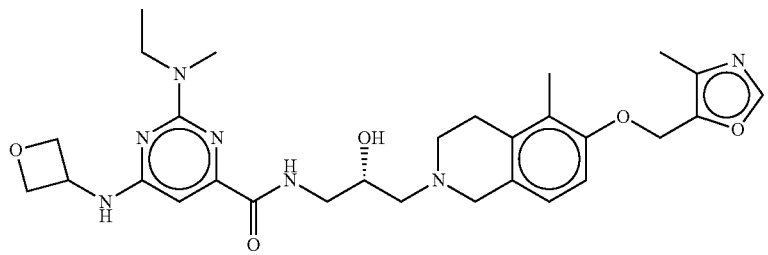
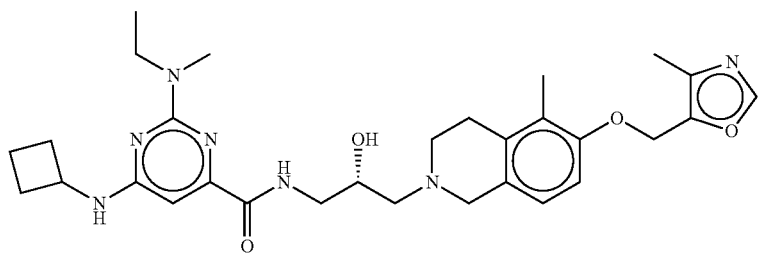
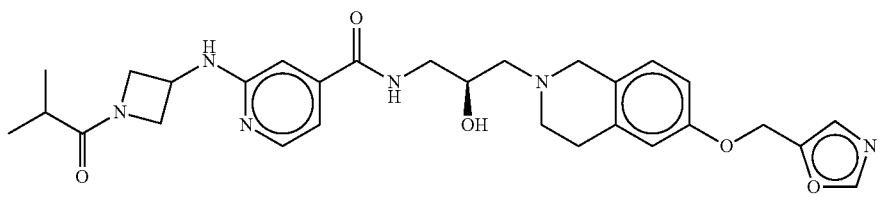
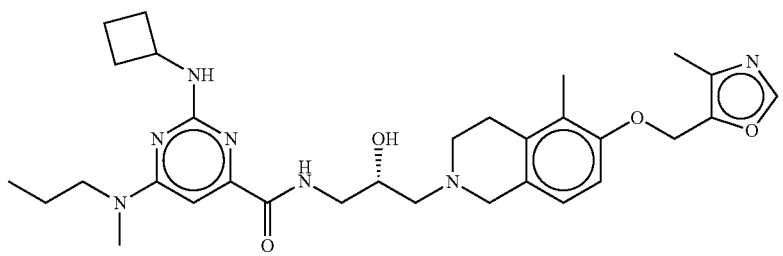

TABLE 4-continued
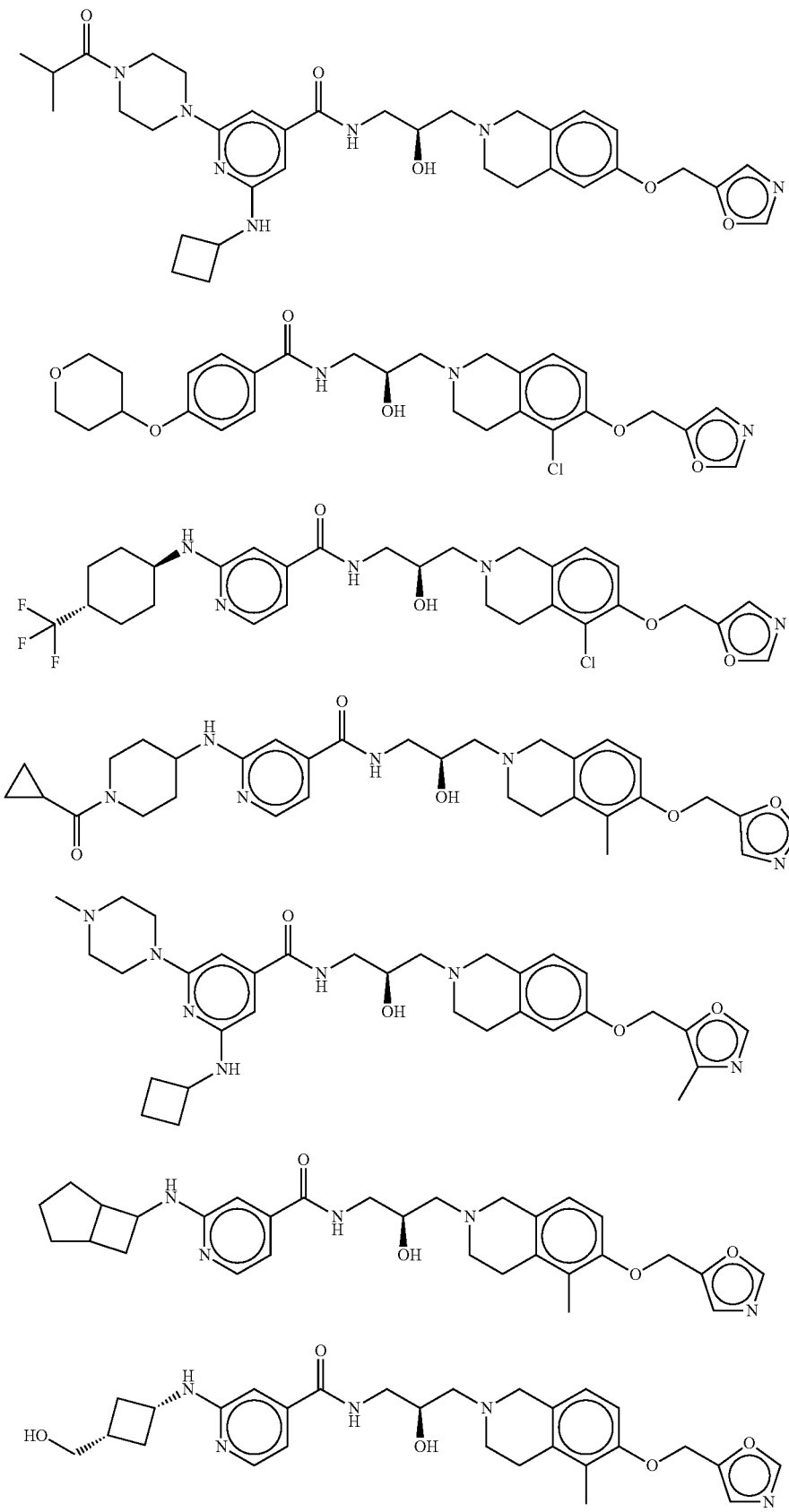

TABLE 4-continued
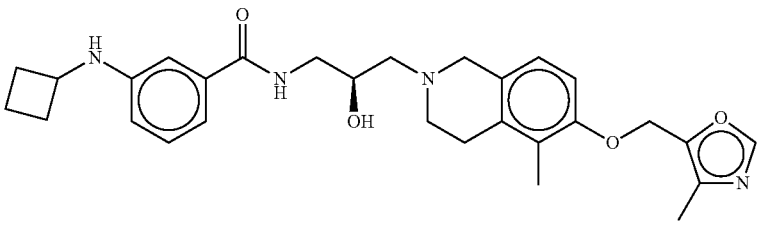
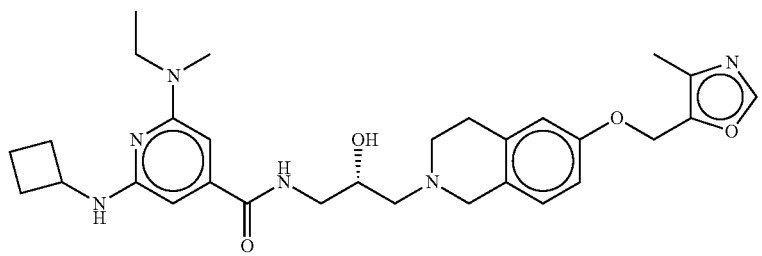
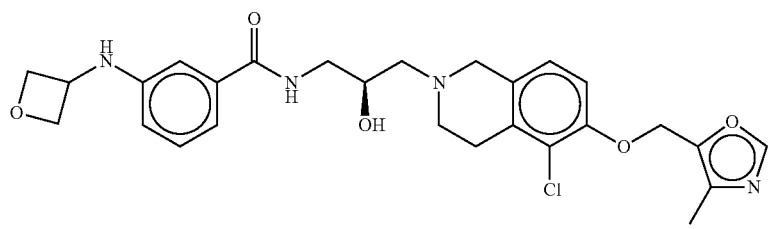
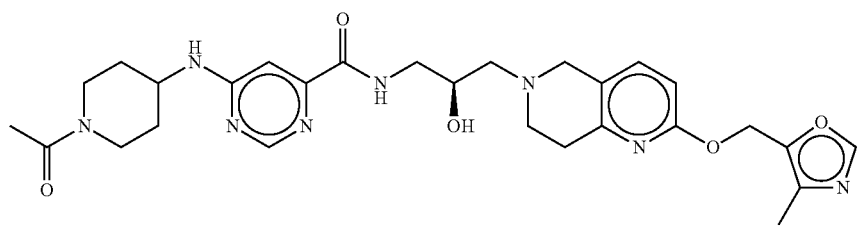
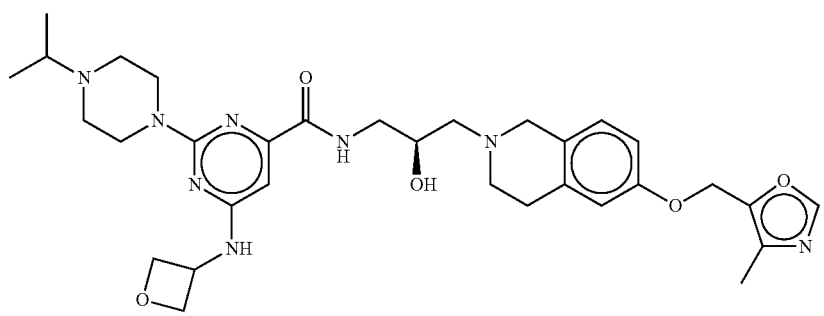
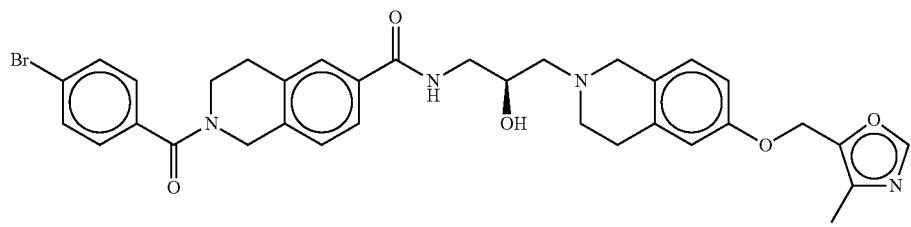

TABLE 4-continued
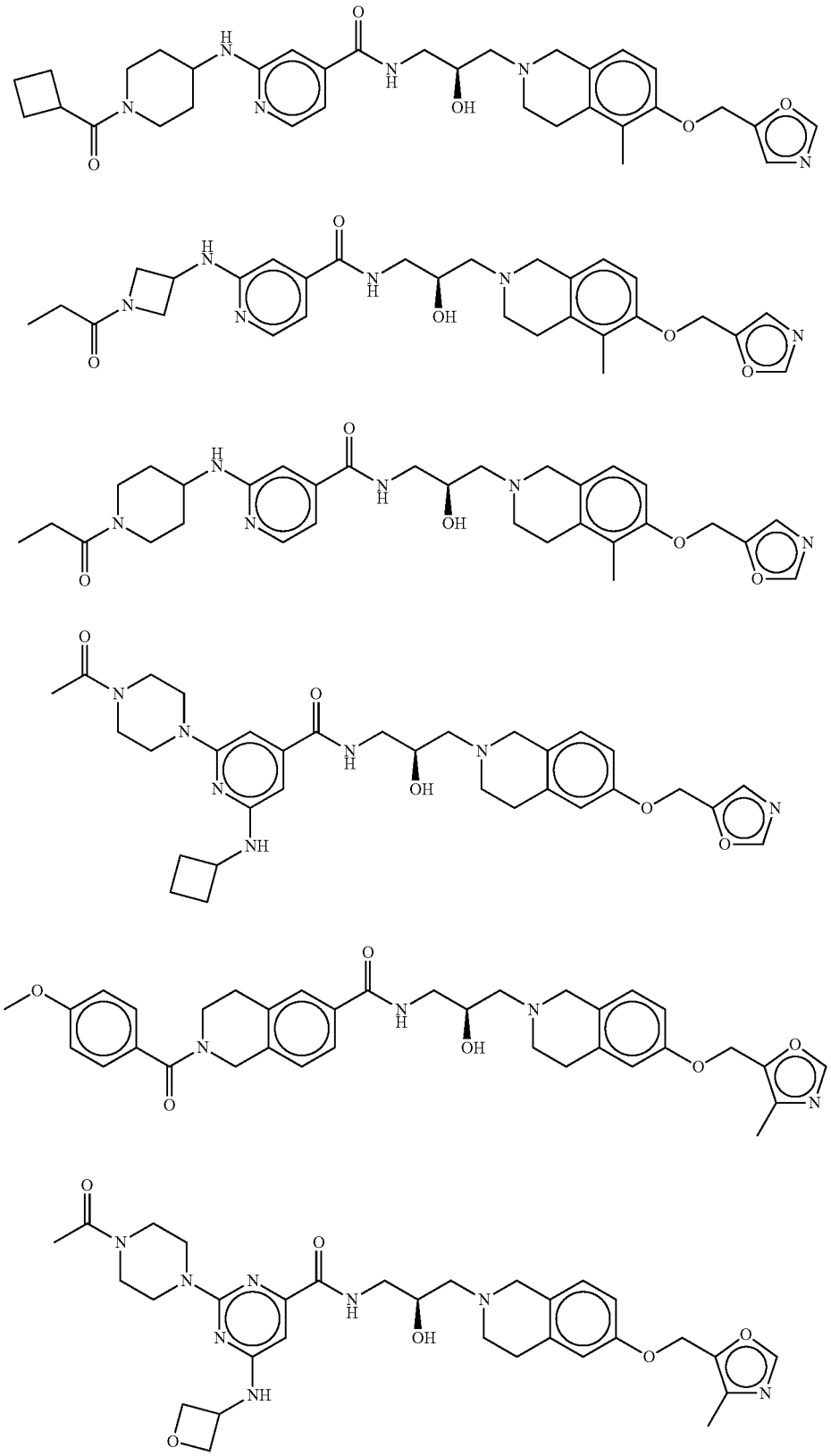

TABLE 4-continued
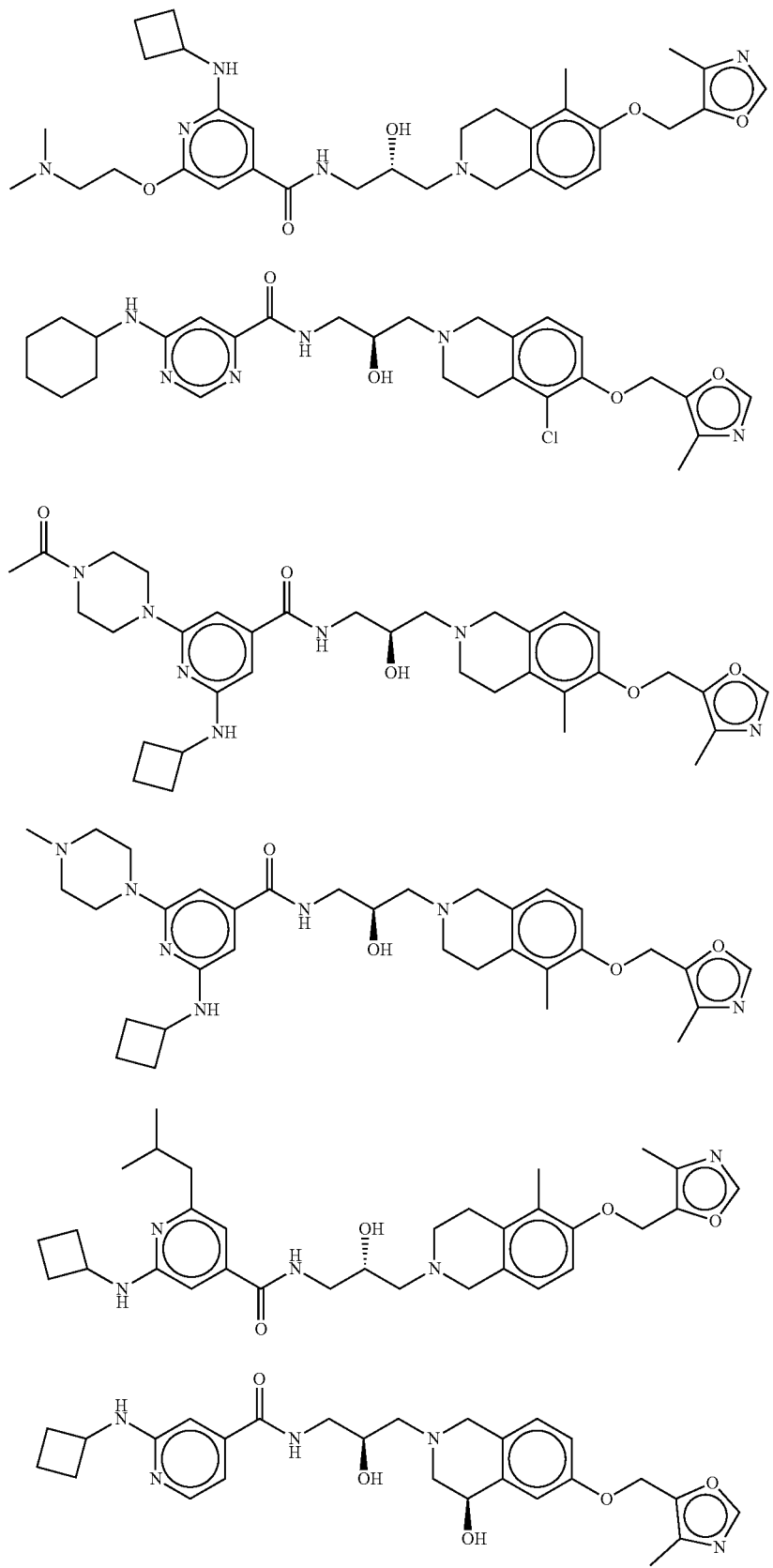

TABLE 4-continued
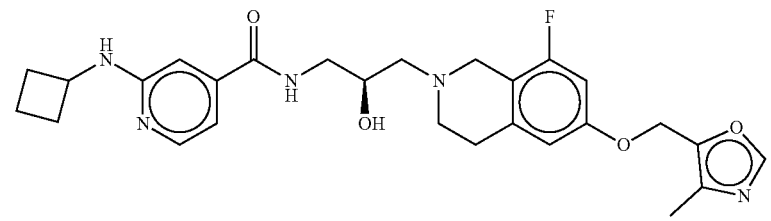
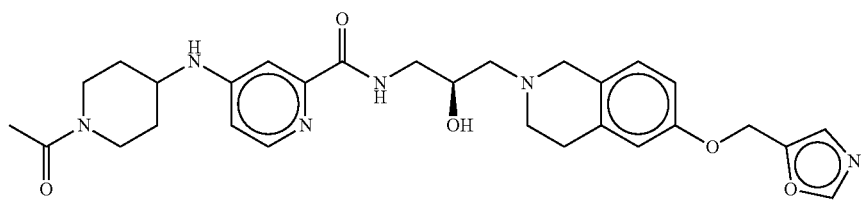
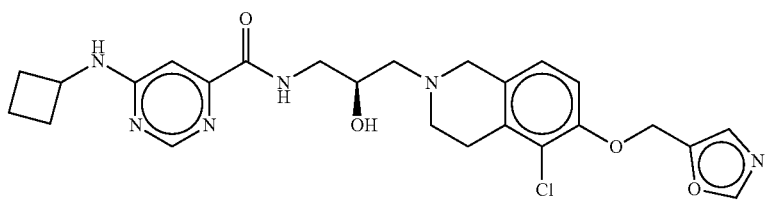
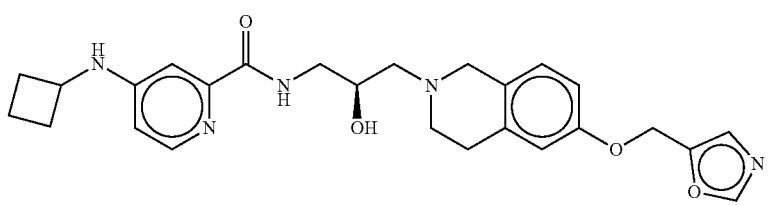
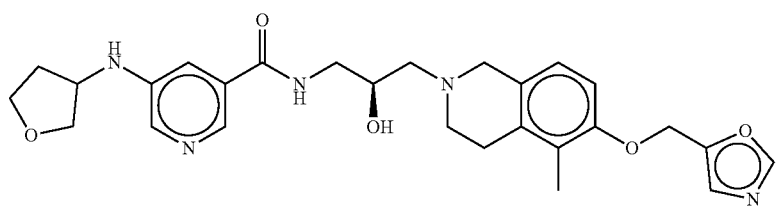
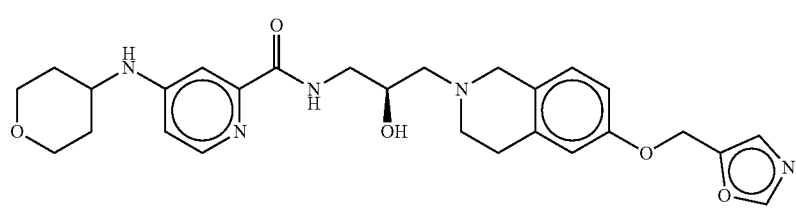
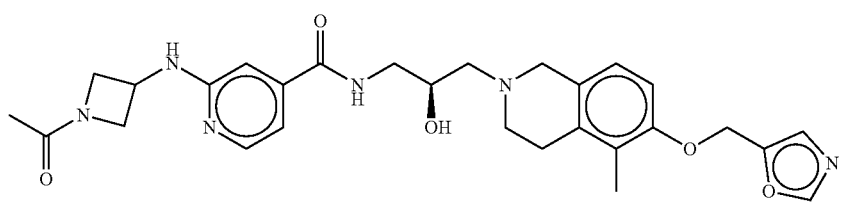

TABLE 4-continued
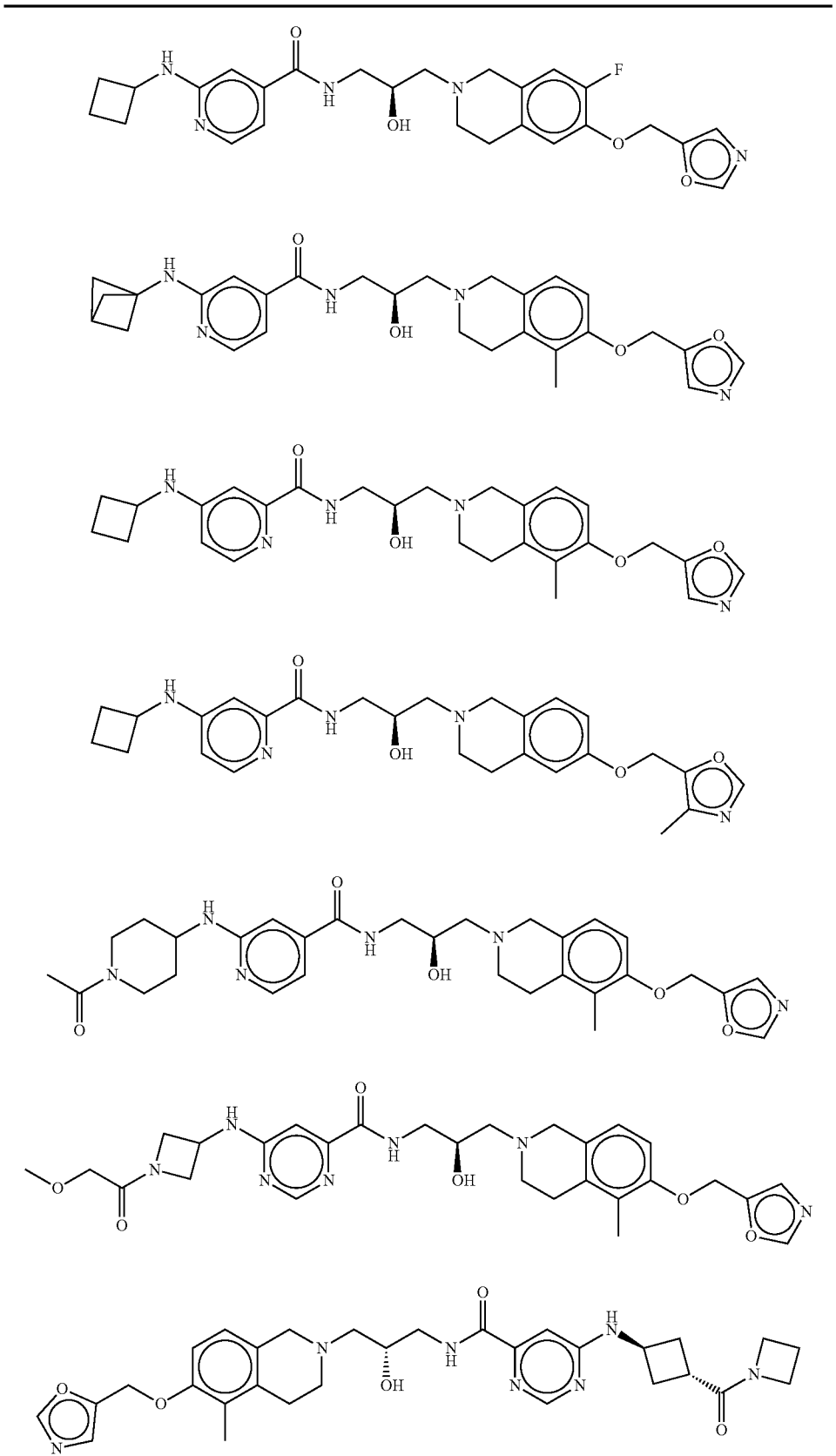

TABLE 4-continued
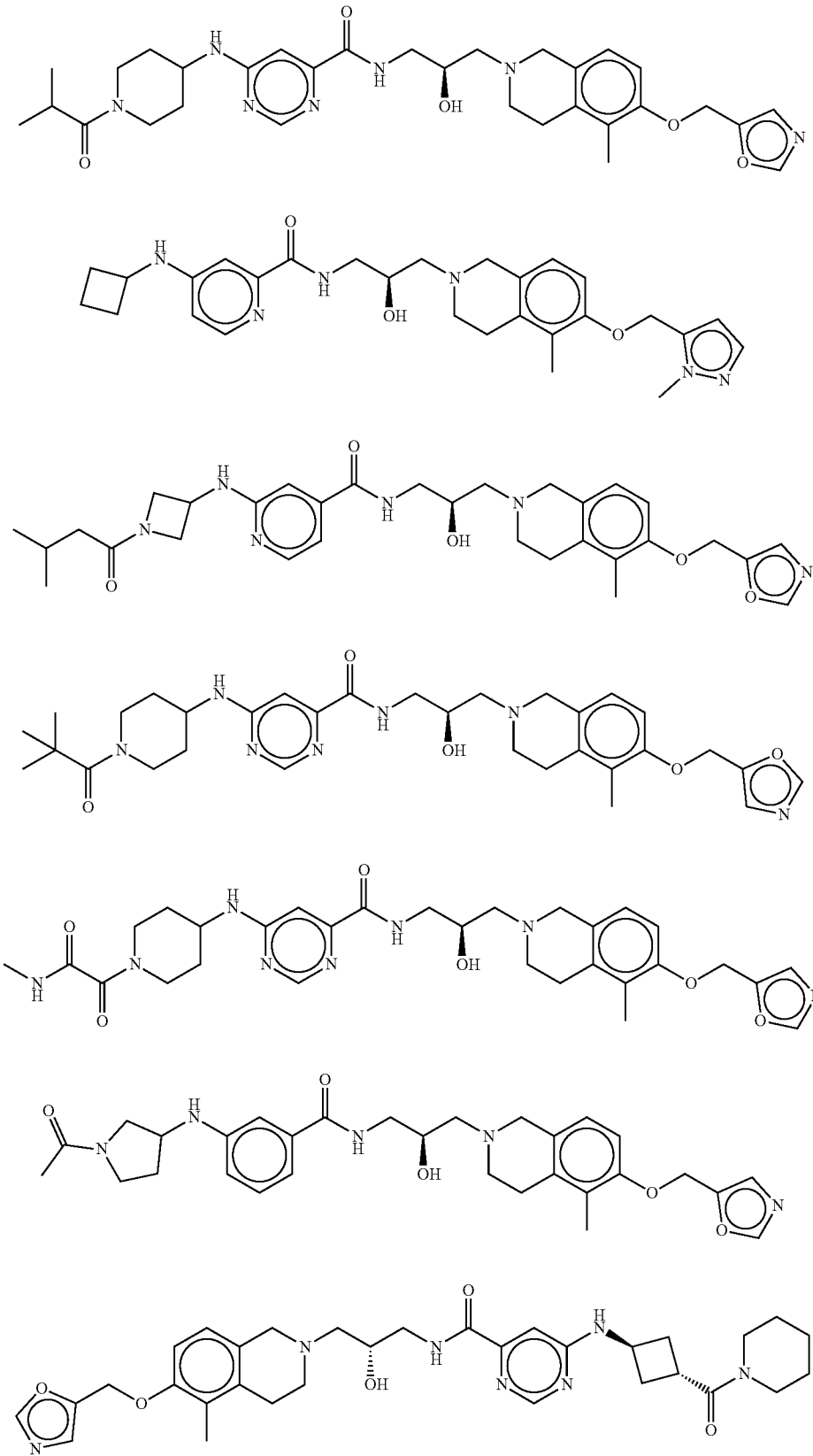

TABLE 4-continued
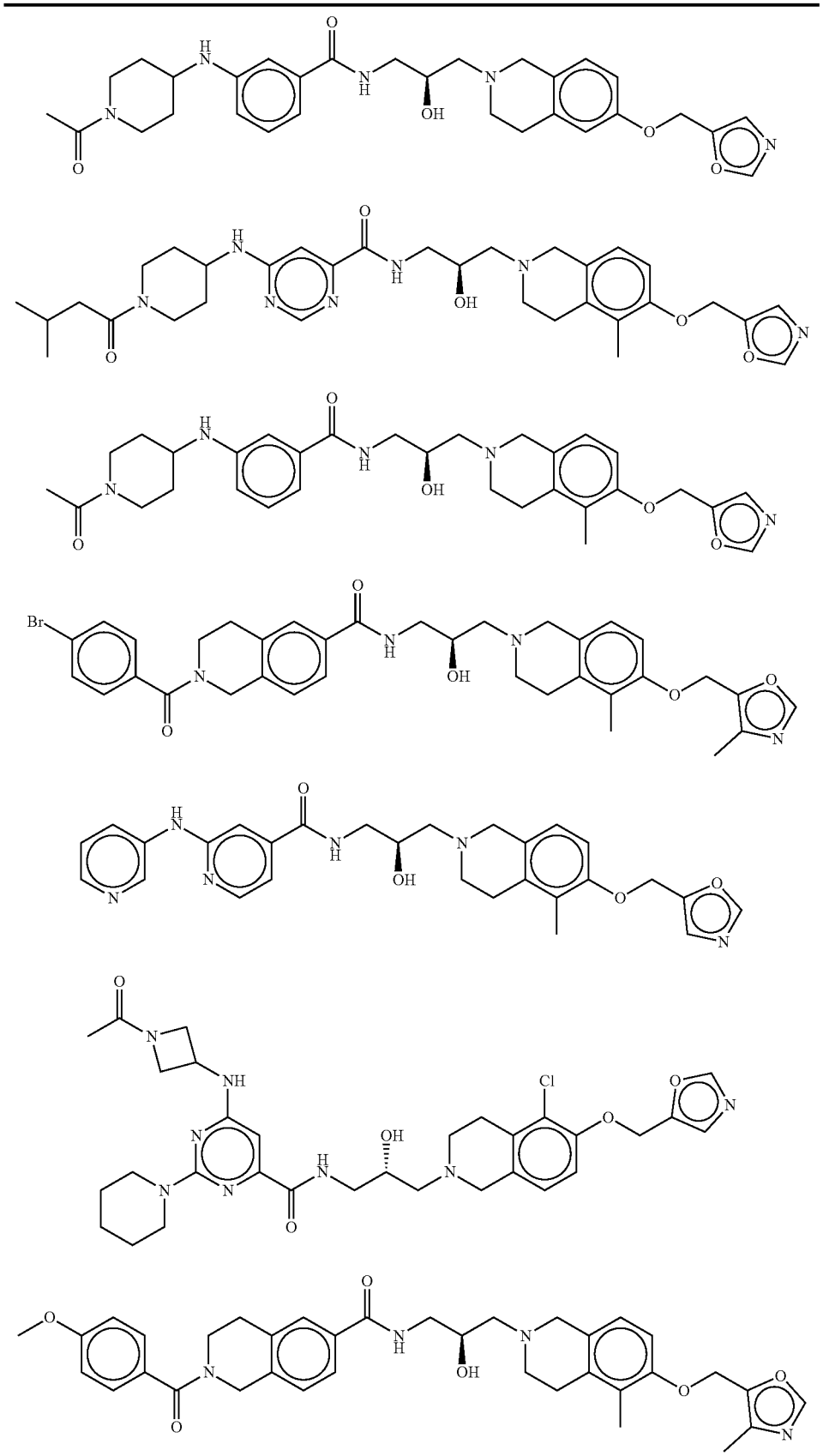

TABLE 4-continued
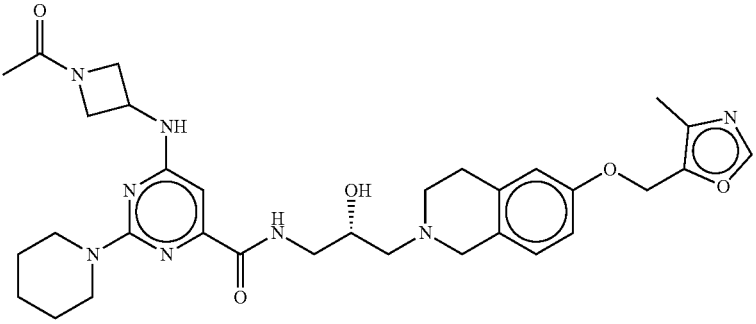
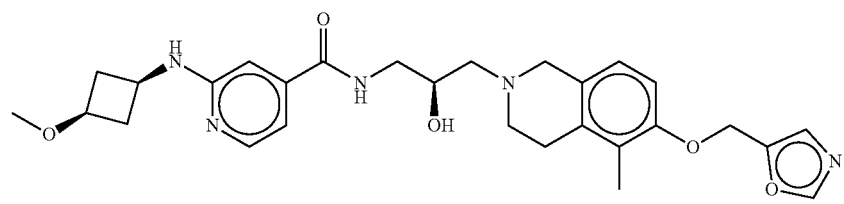
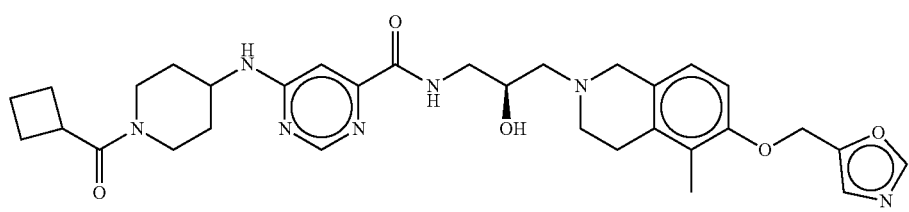
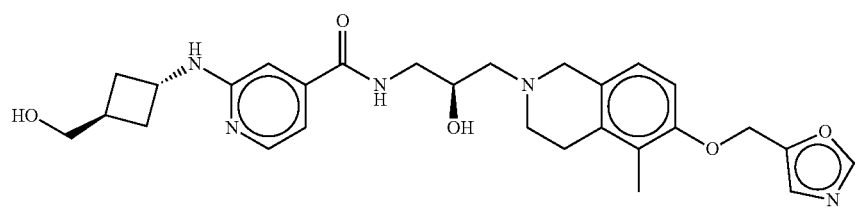
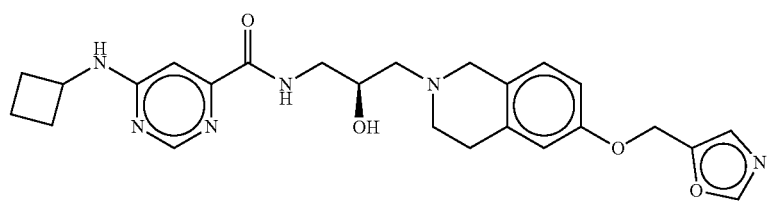
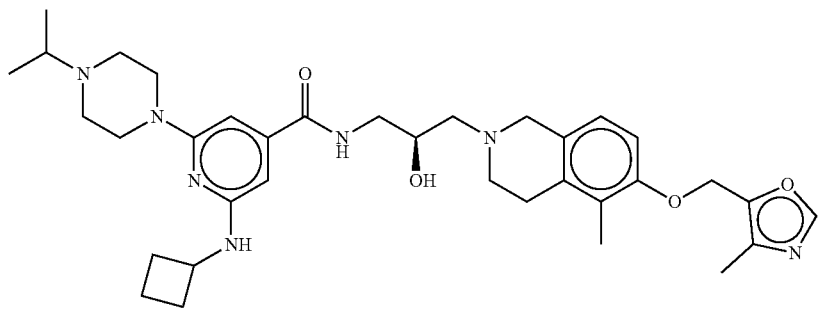

TABLE 4-continued
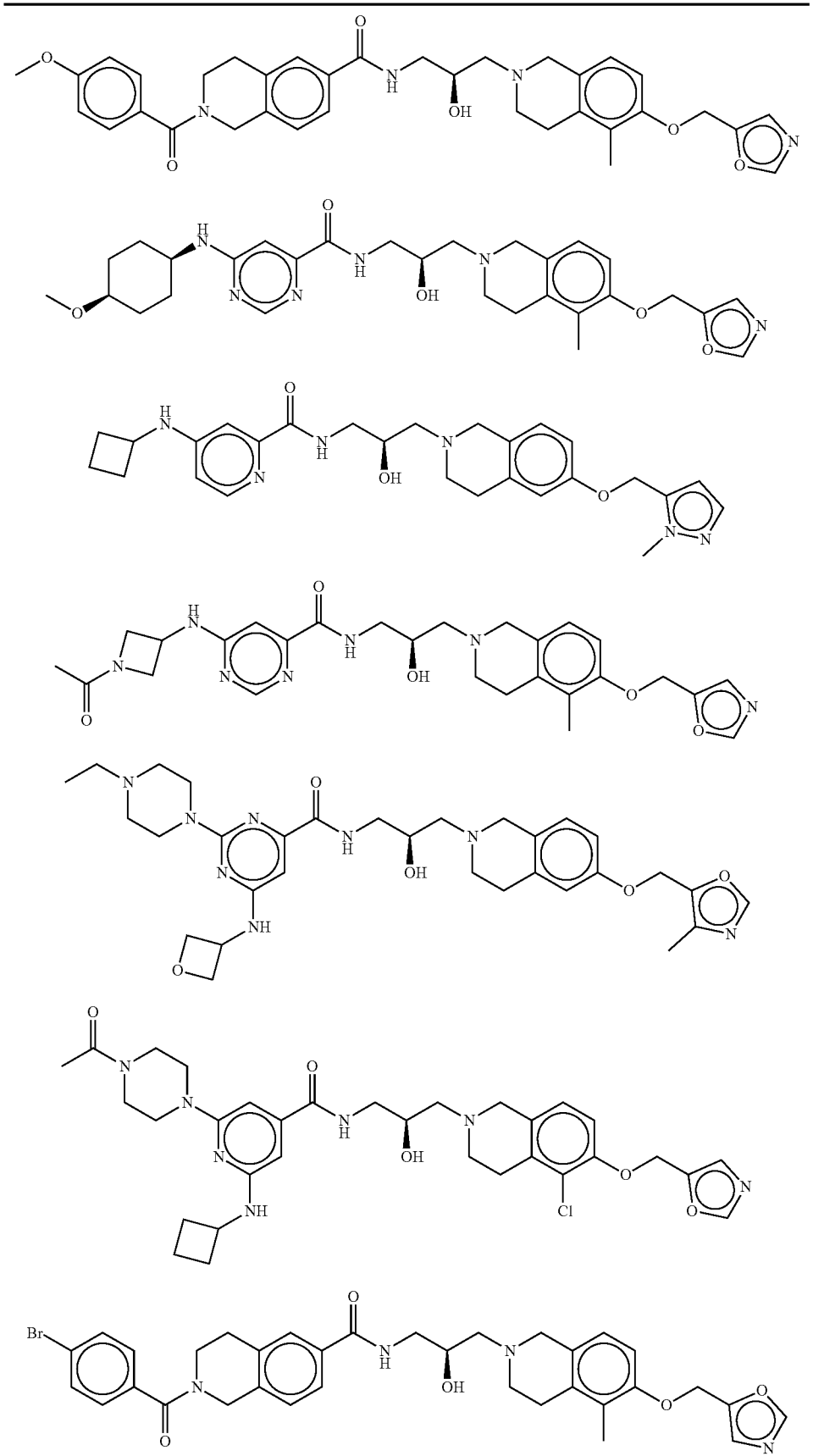

TABLE 4-continued
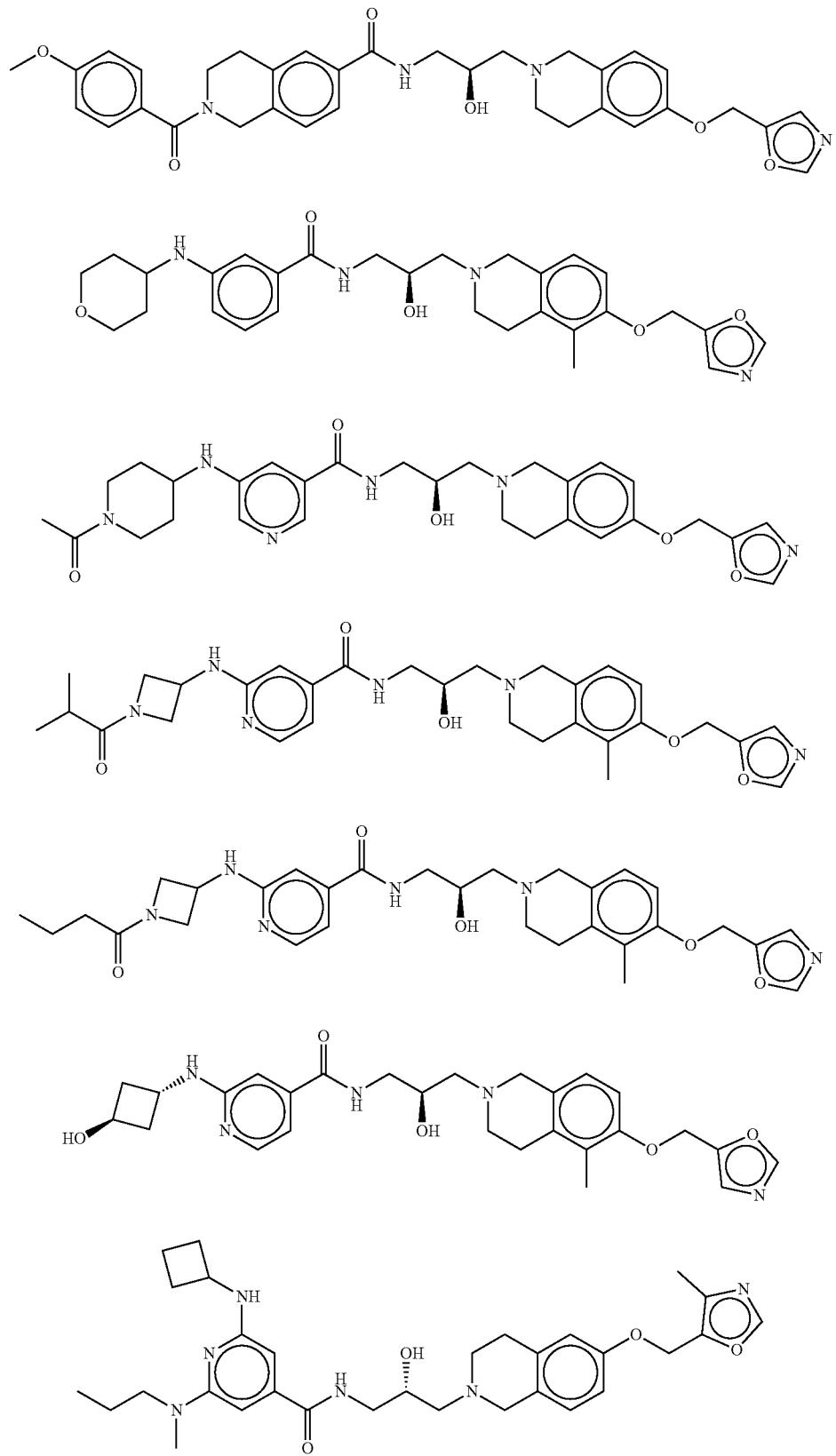

TABLE 4-continued
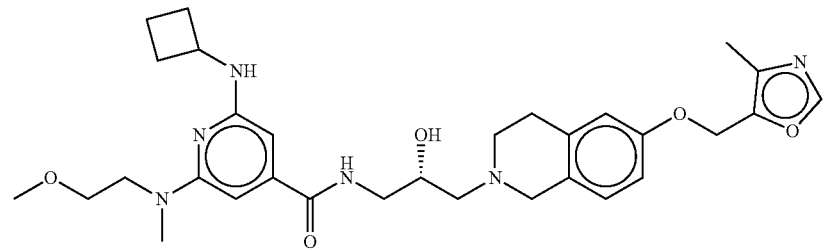
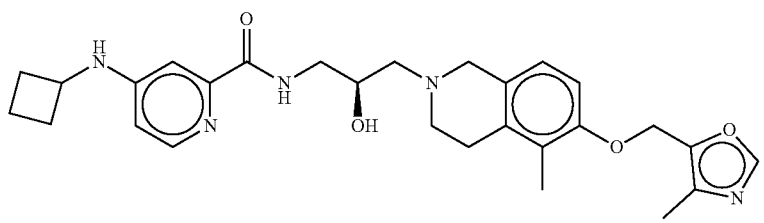
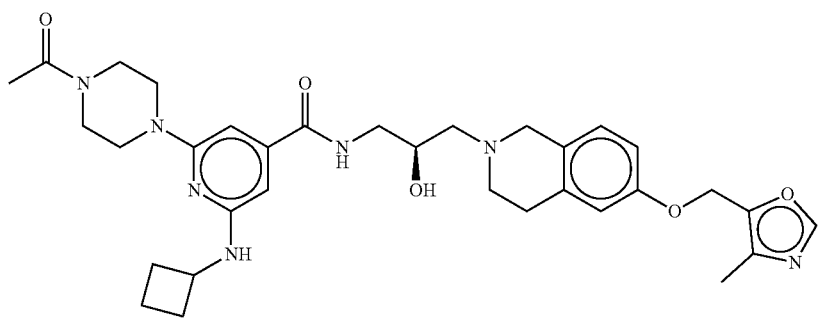
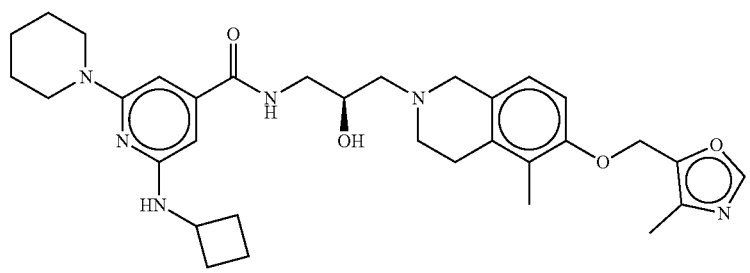
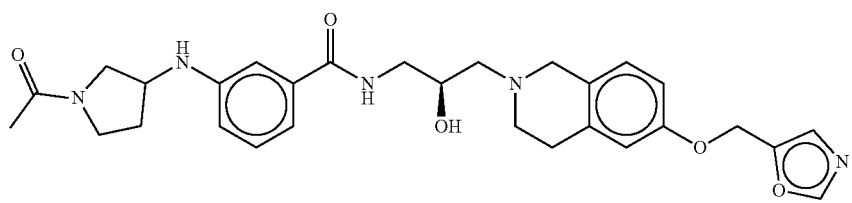
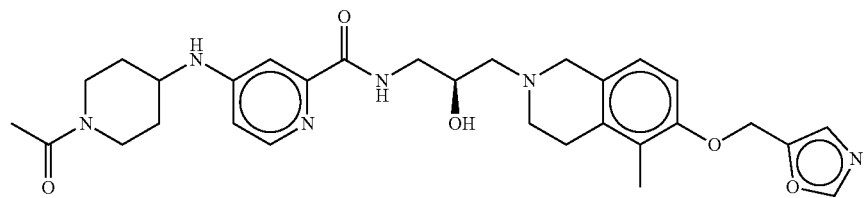

TABLE 4-continued
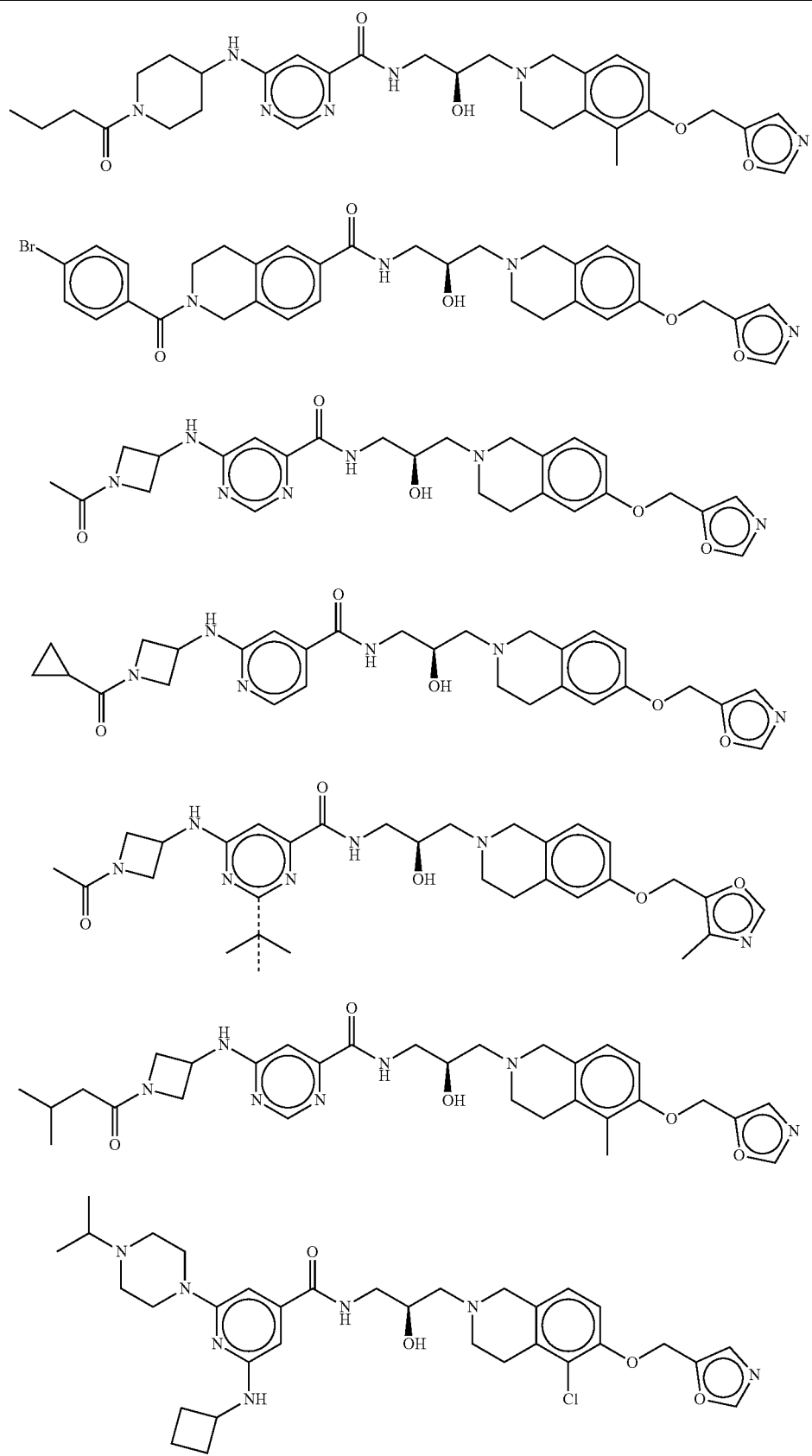

TABLE 4-continued
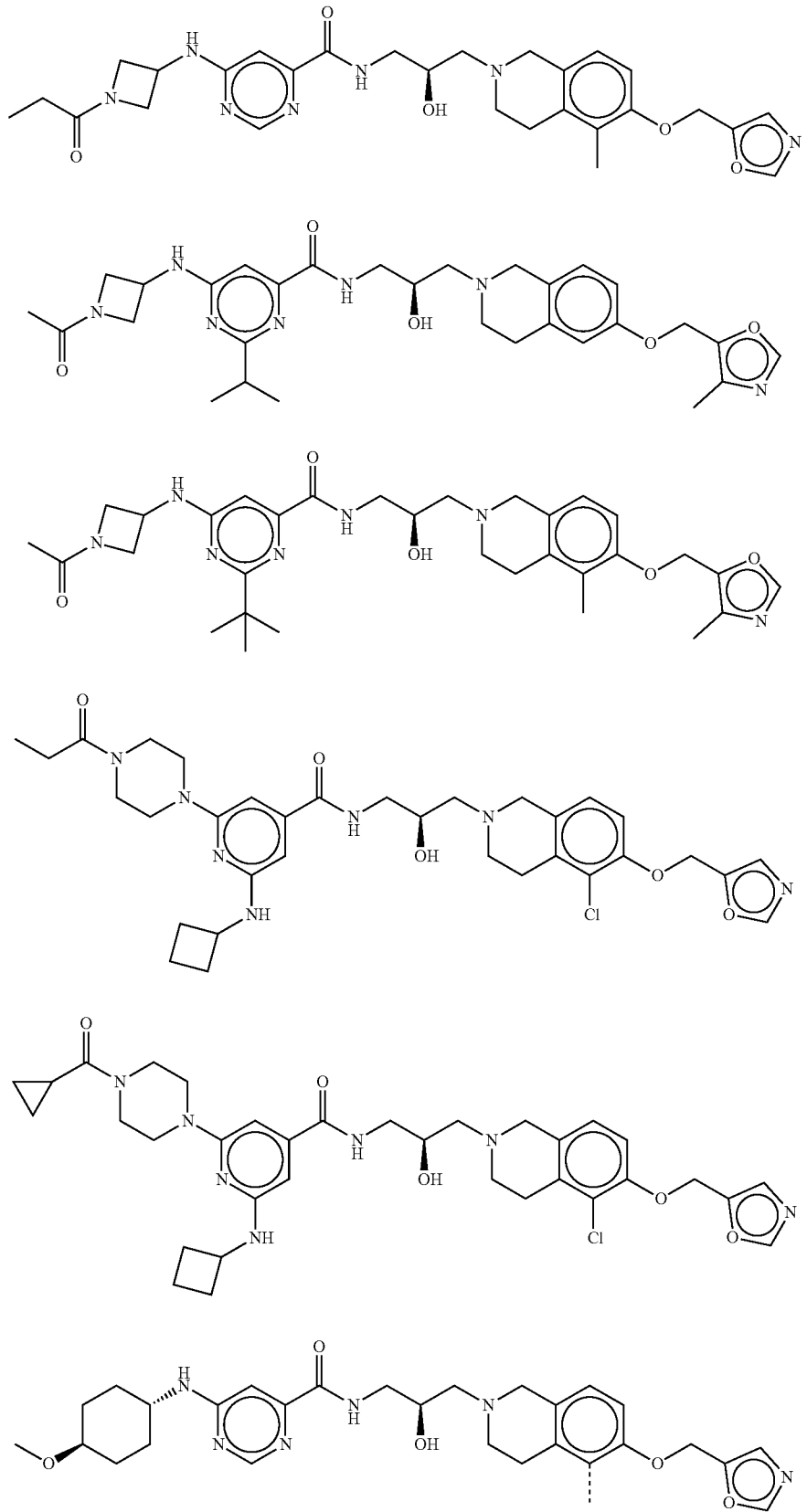

TABLE 4-continued
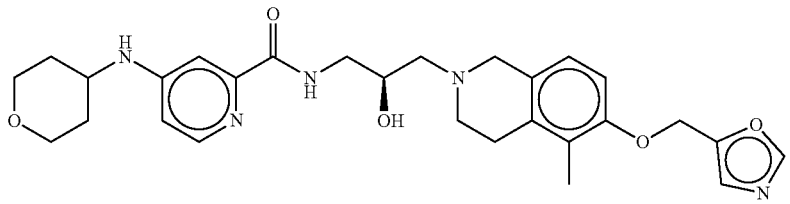
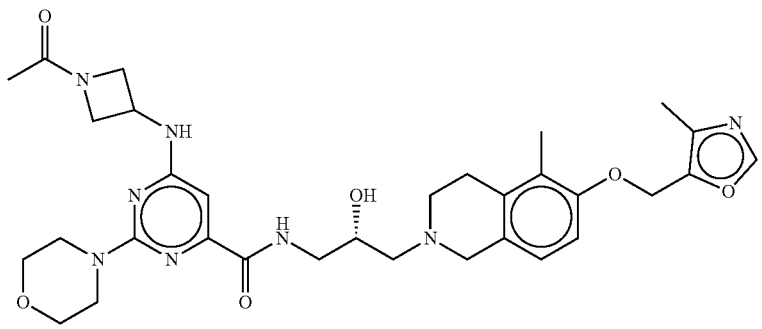
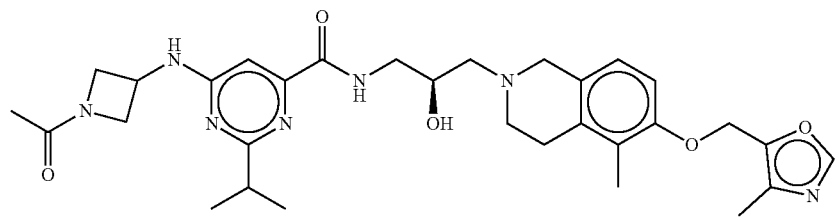
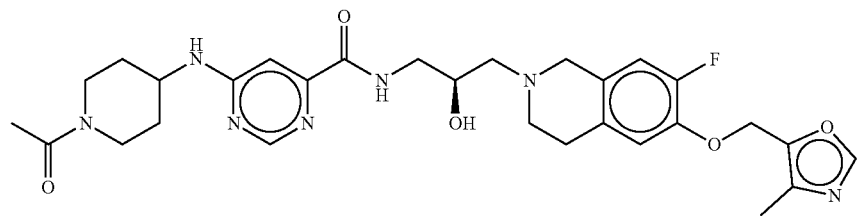
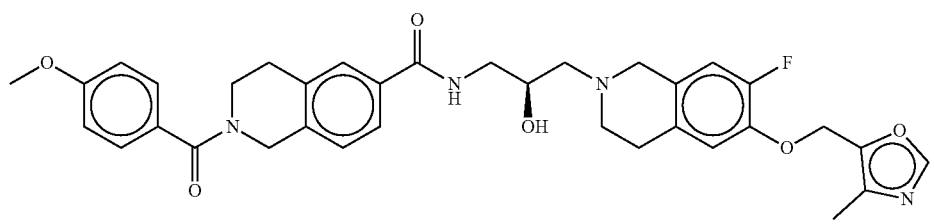
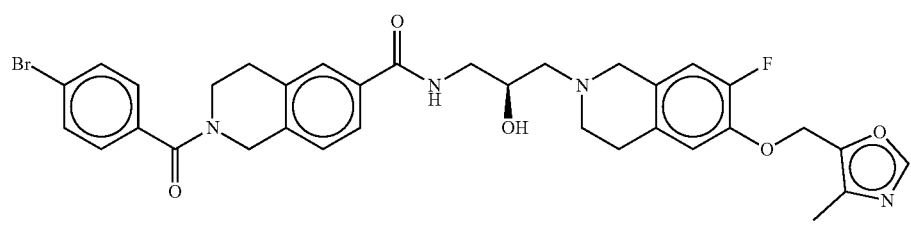

TABLE 4-continued
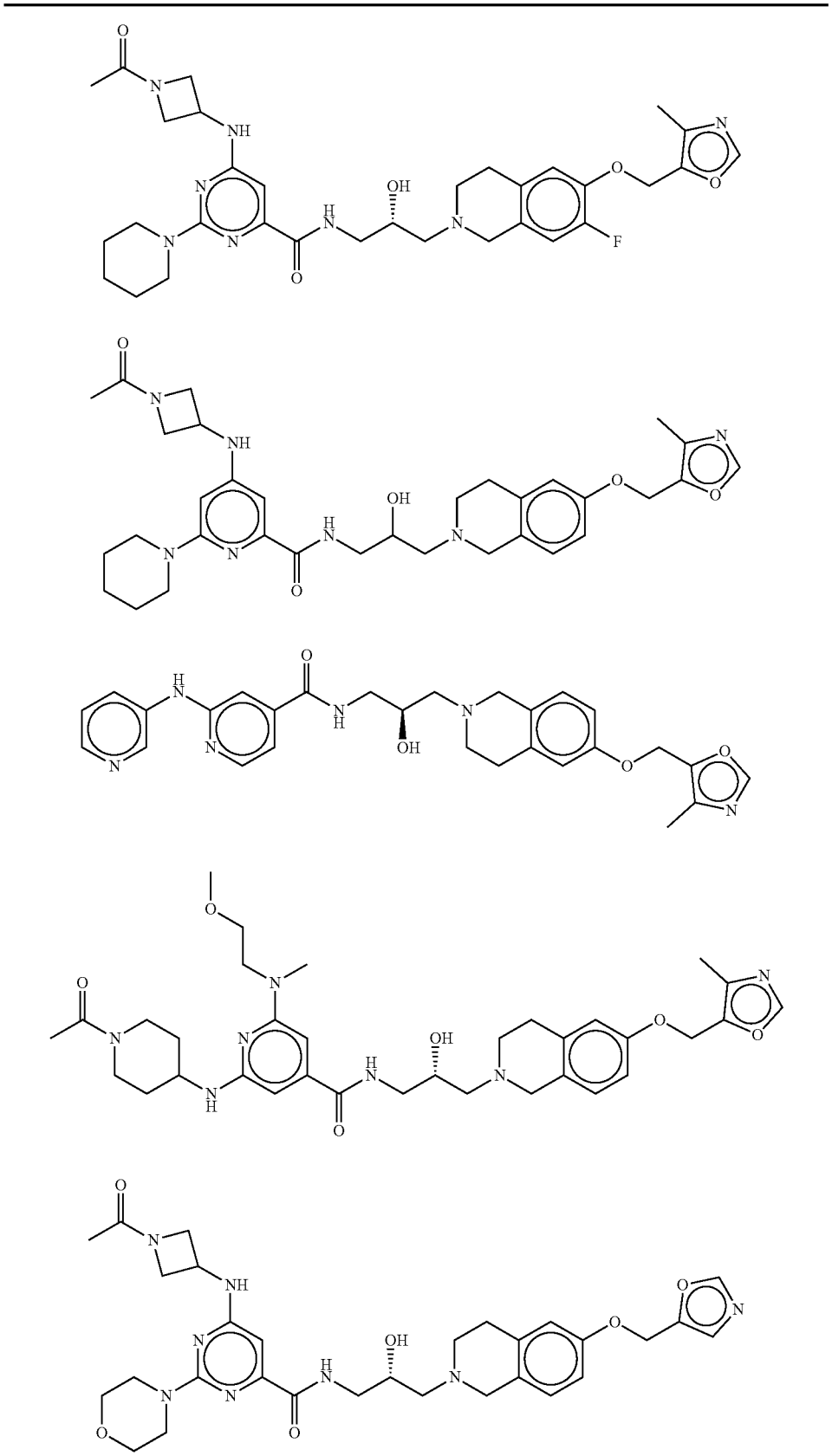

TABLE 4-continued
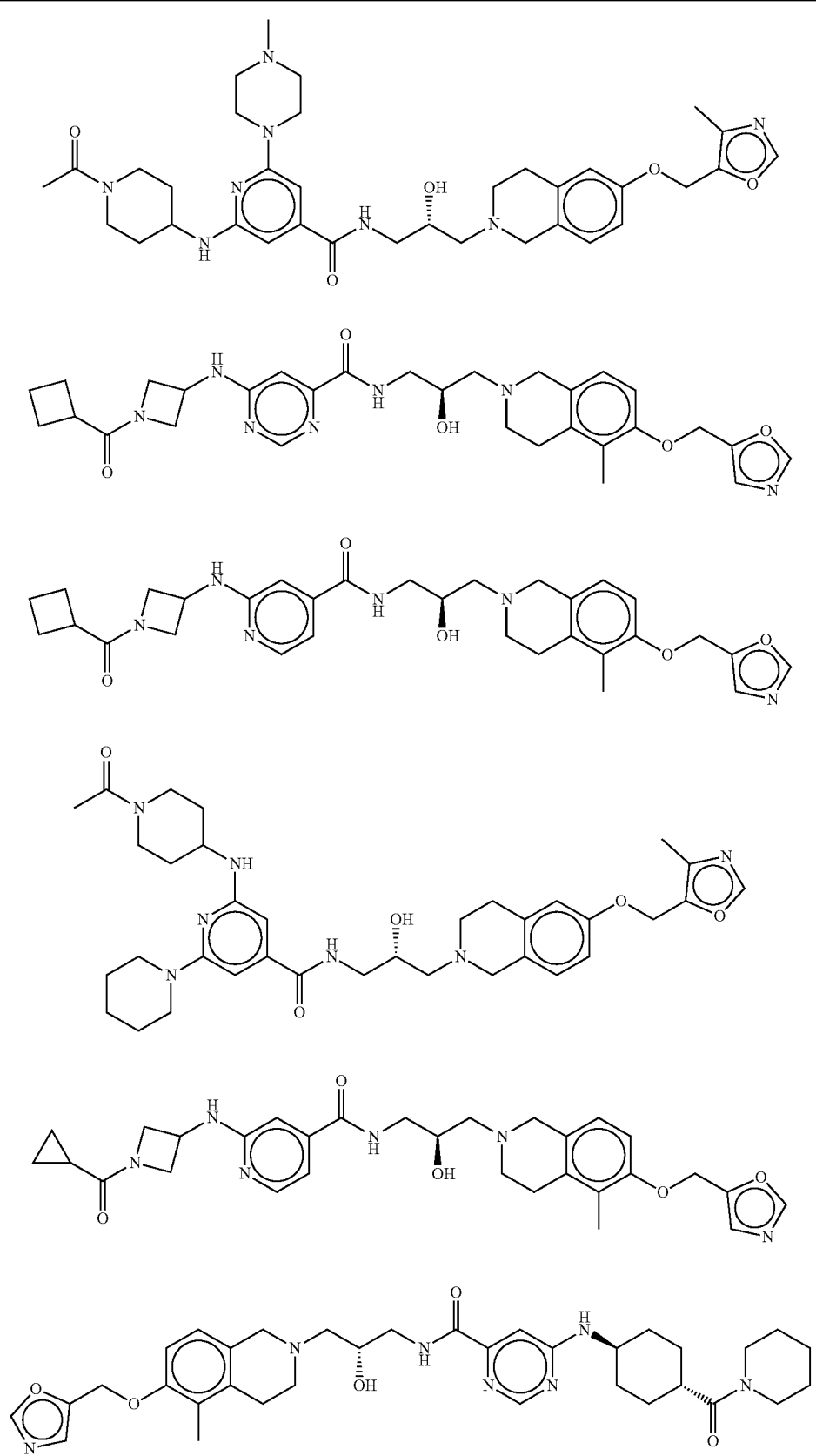

TABLE 4-continued
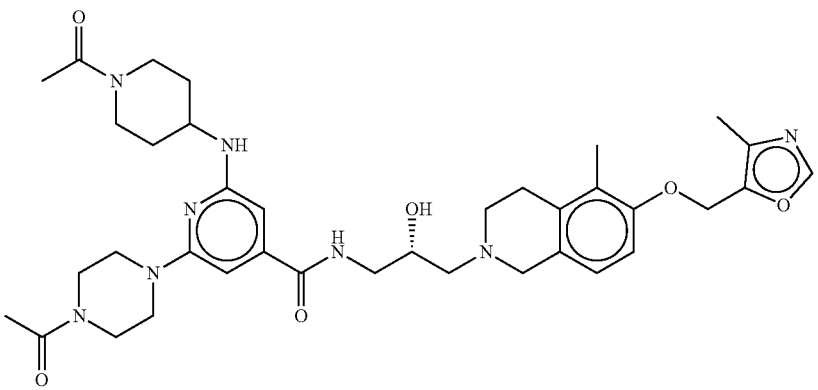
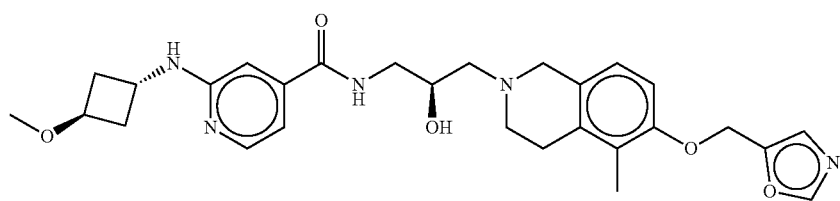
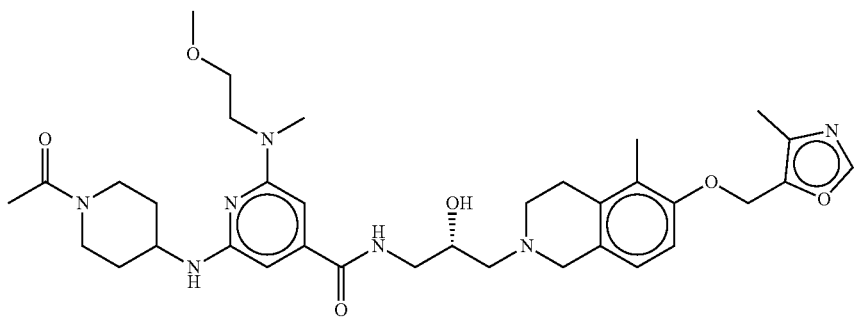
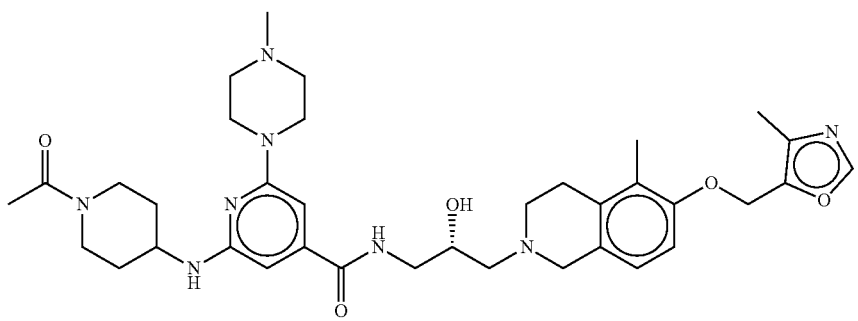
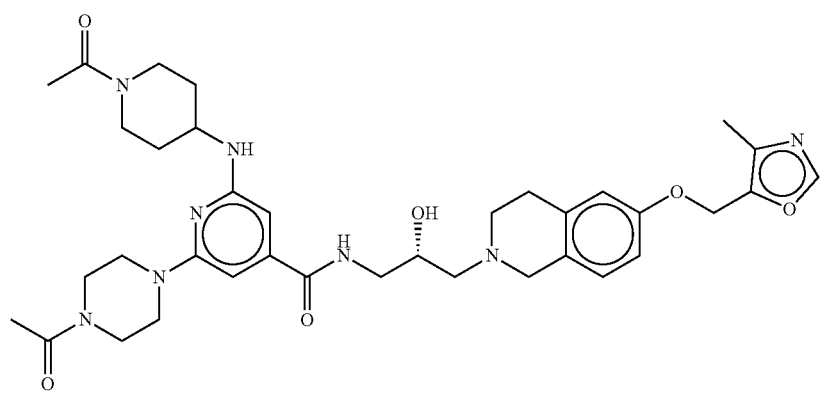

TABLE 4-continued
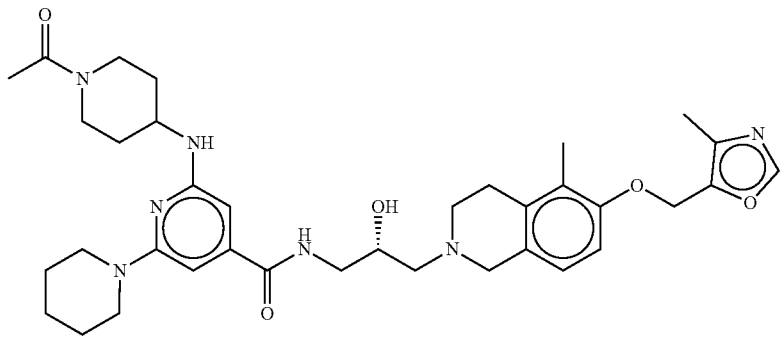
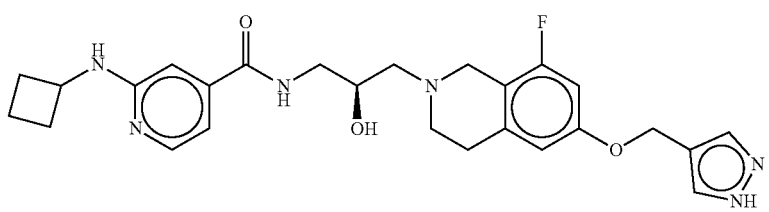
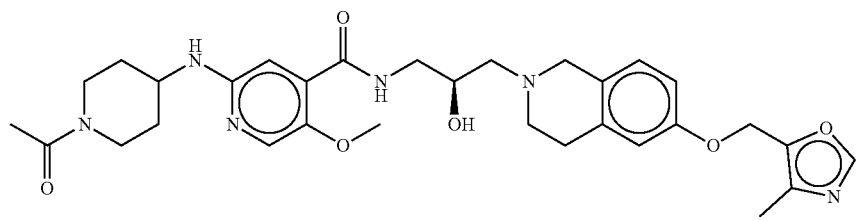
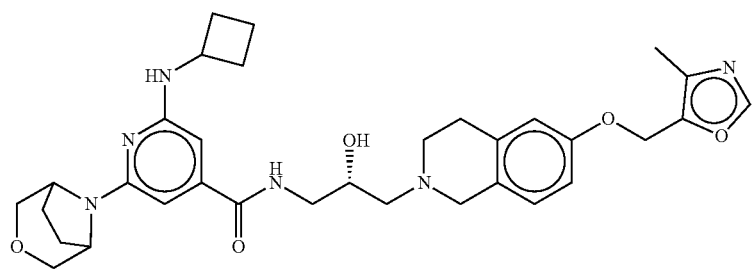
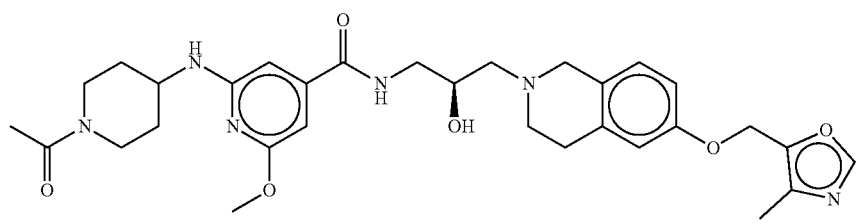
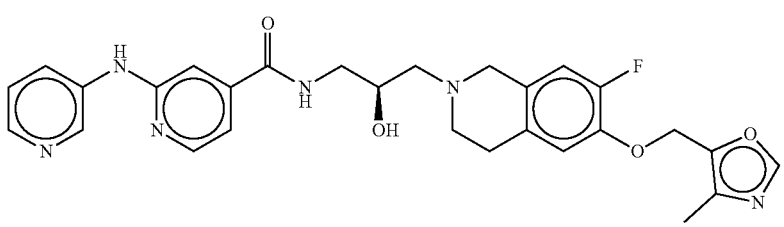

TABLE 4-continued
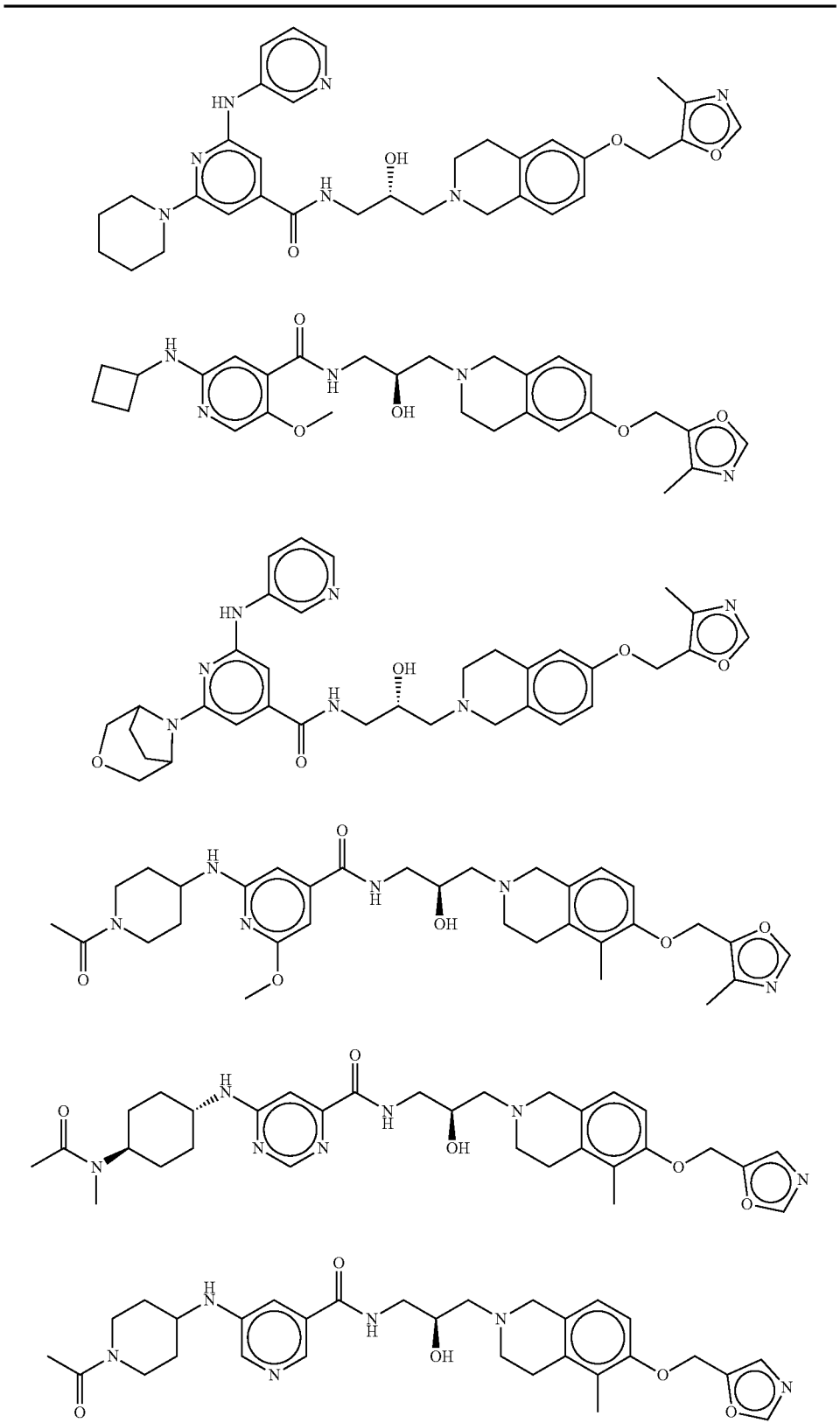

TABLE 4-continued
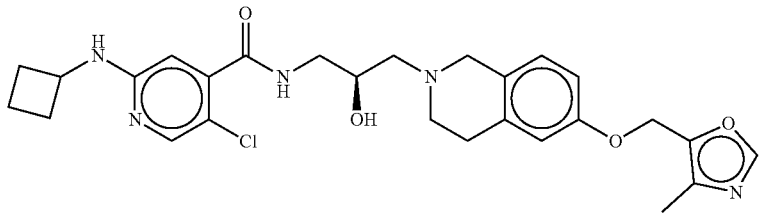
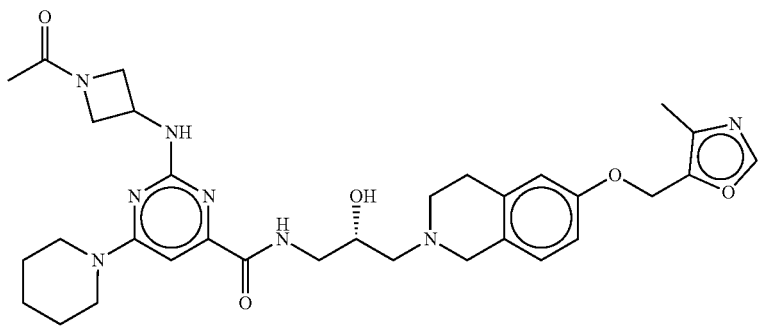
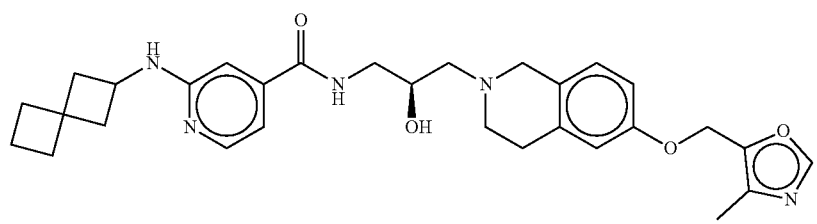
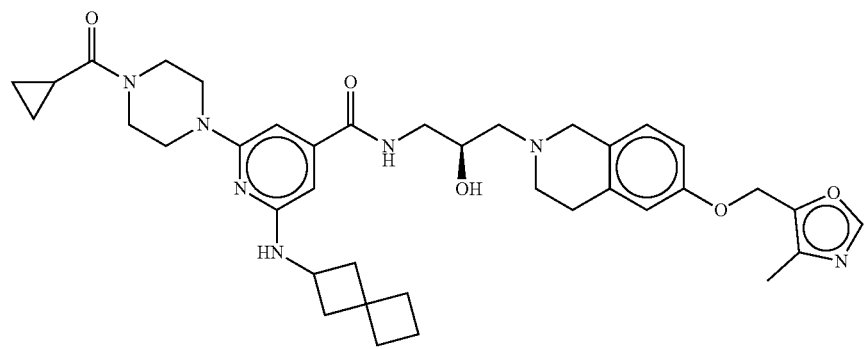
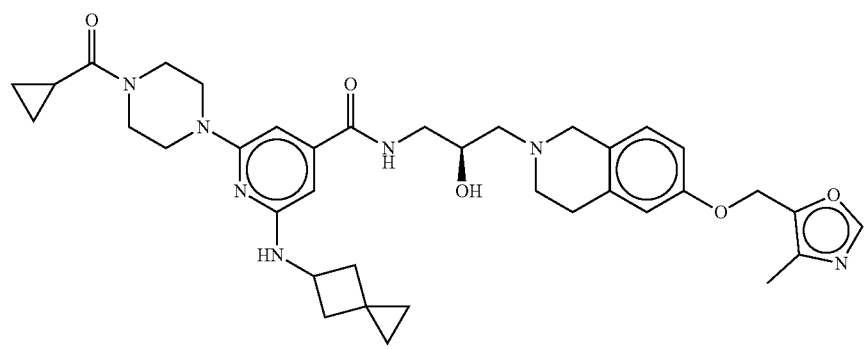

TABLE 4-continued
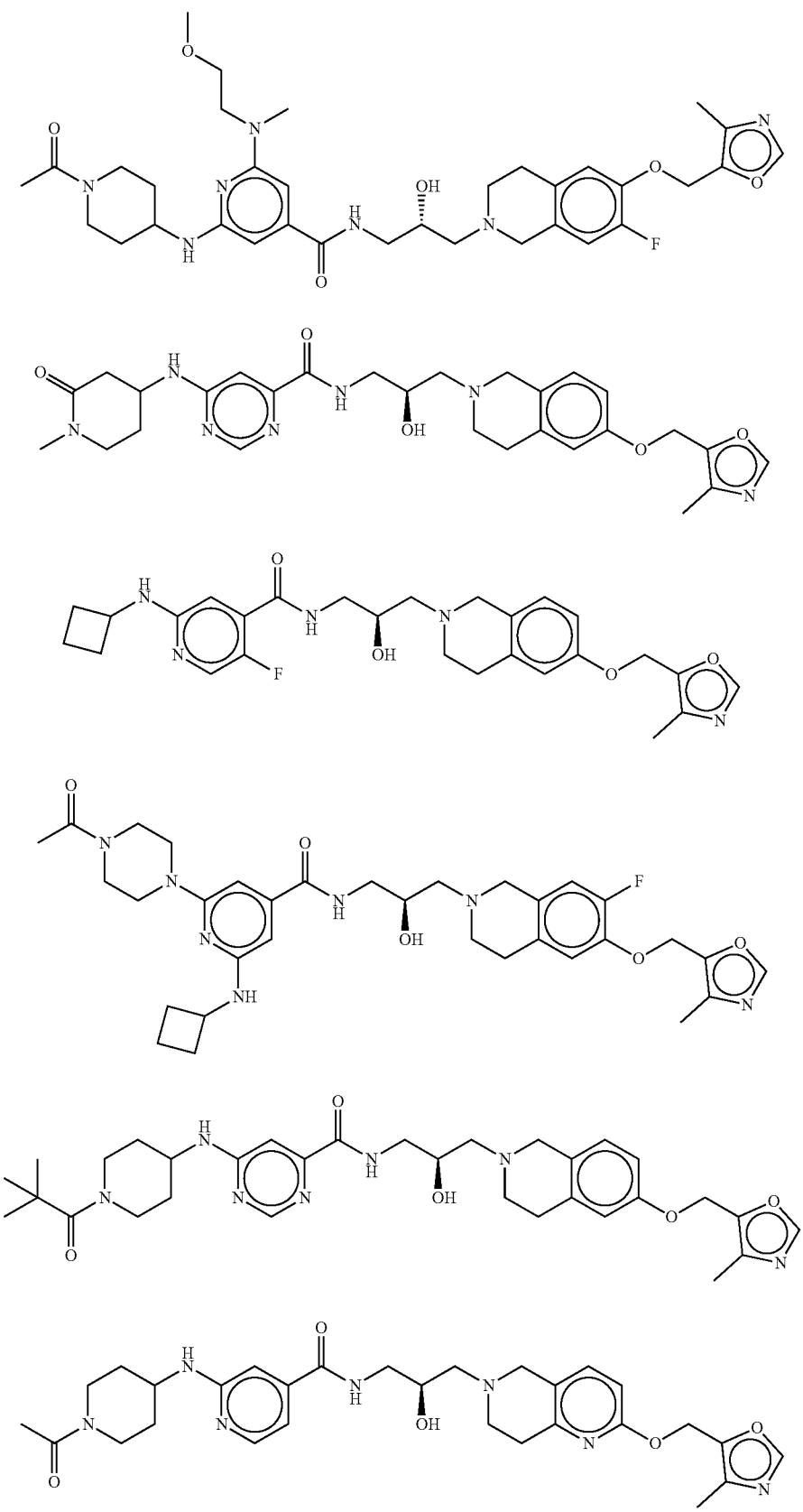

TABLE 4-continued
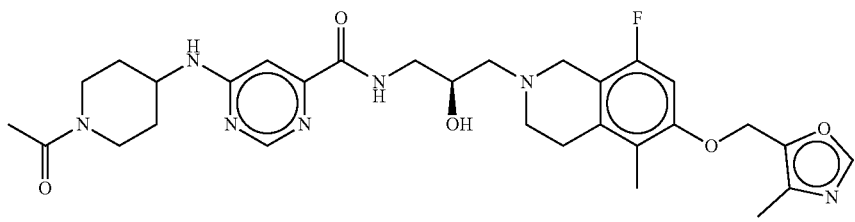
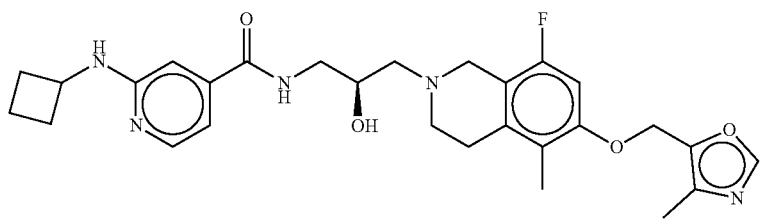
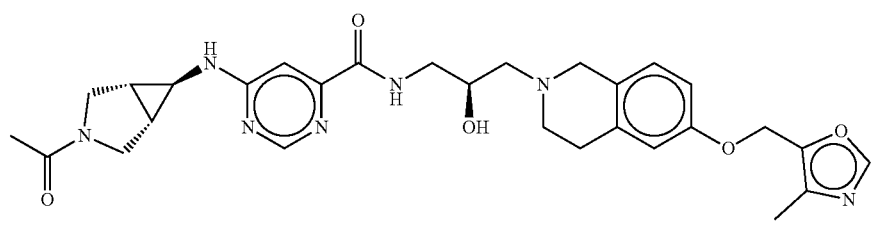
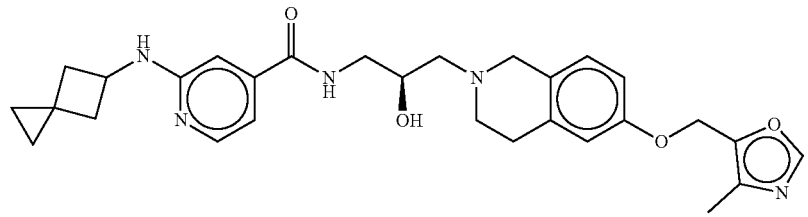
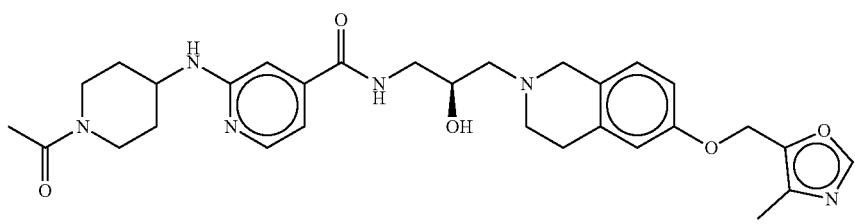
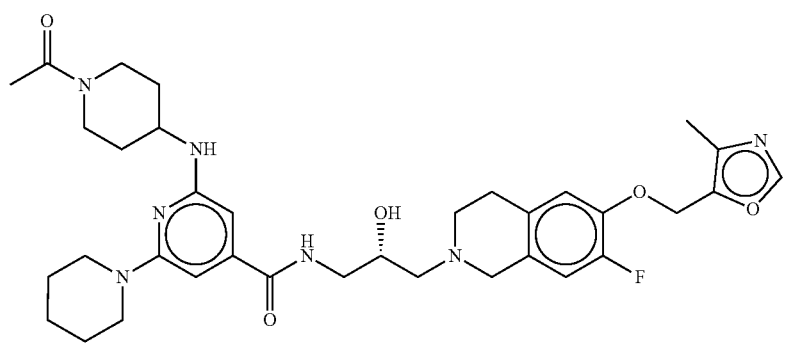

TABLE 4-continued
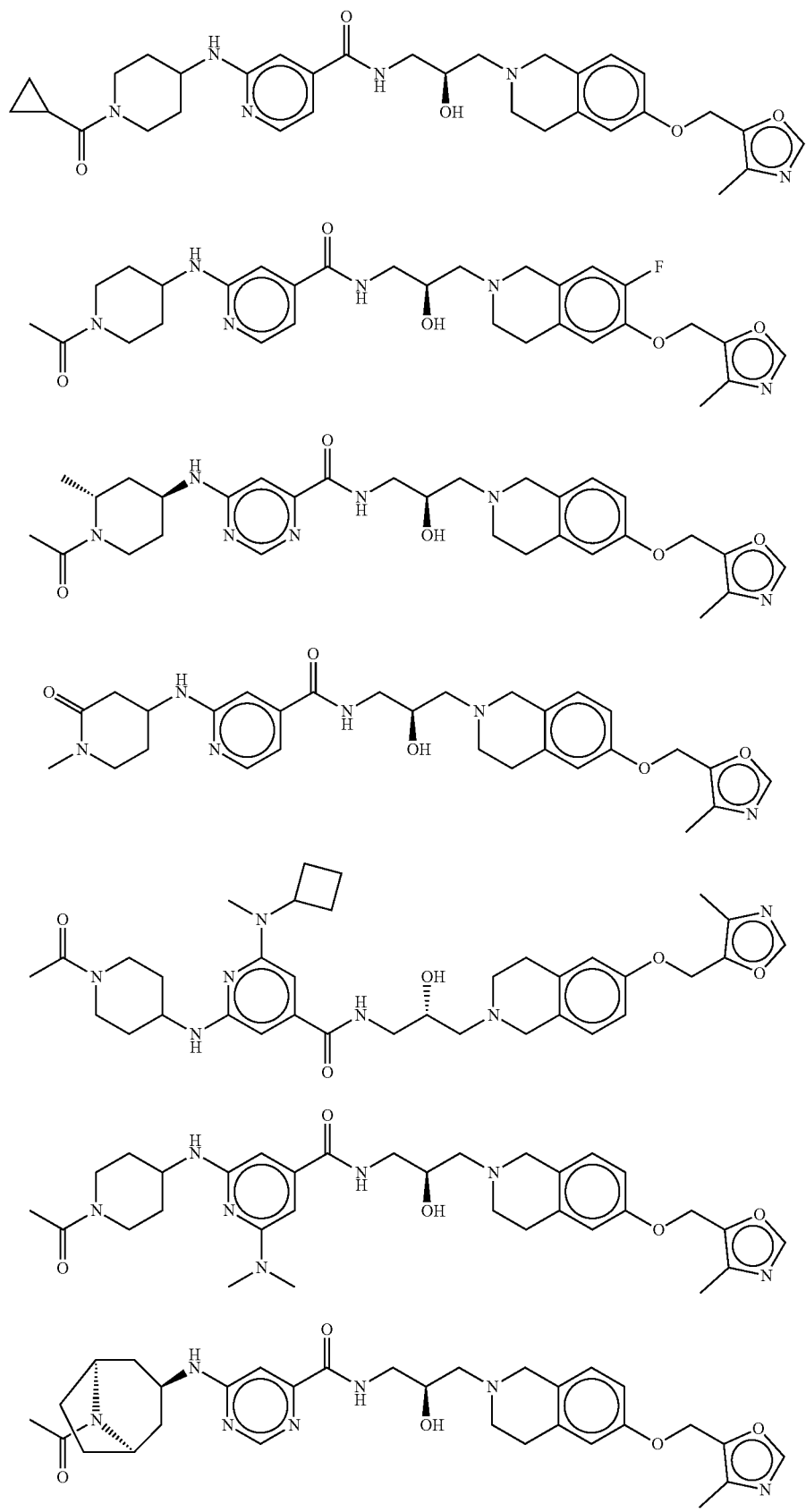

TABLE 4-continued
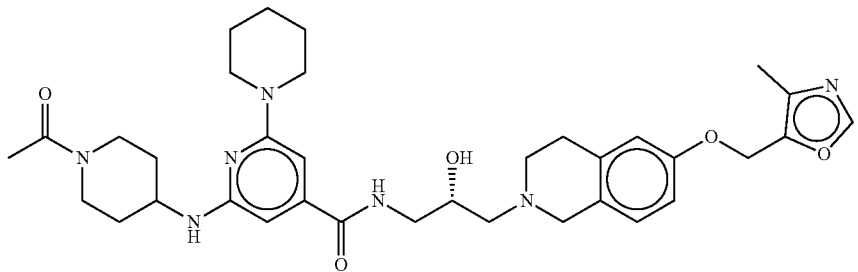
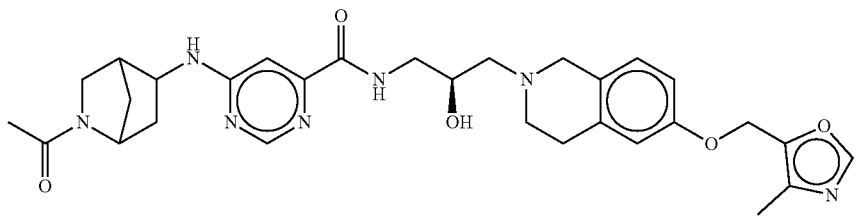
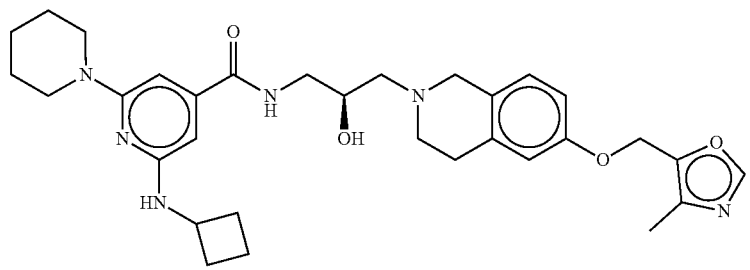
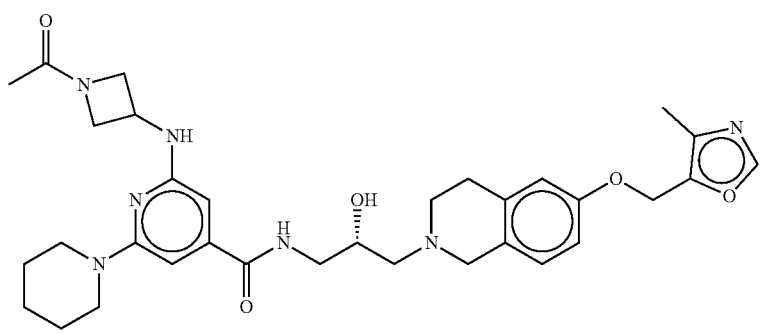
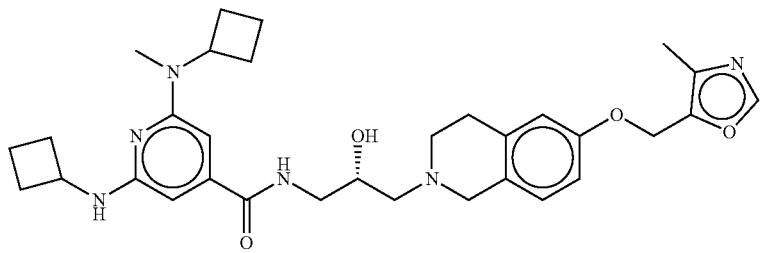
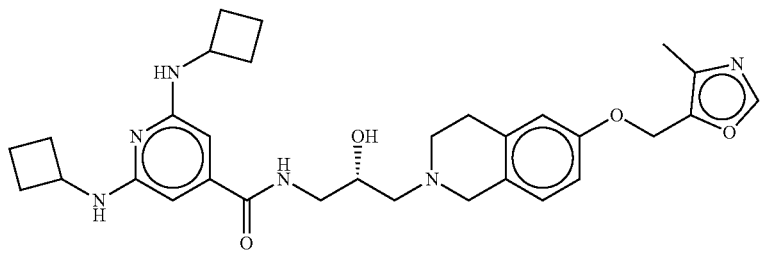

TABLE 4-continued
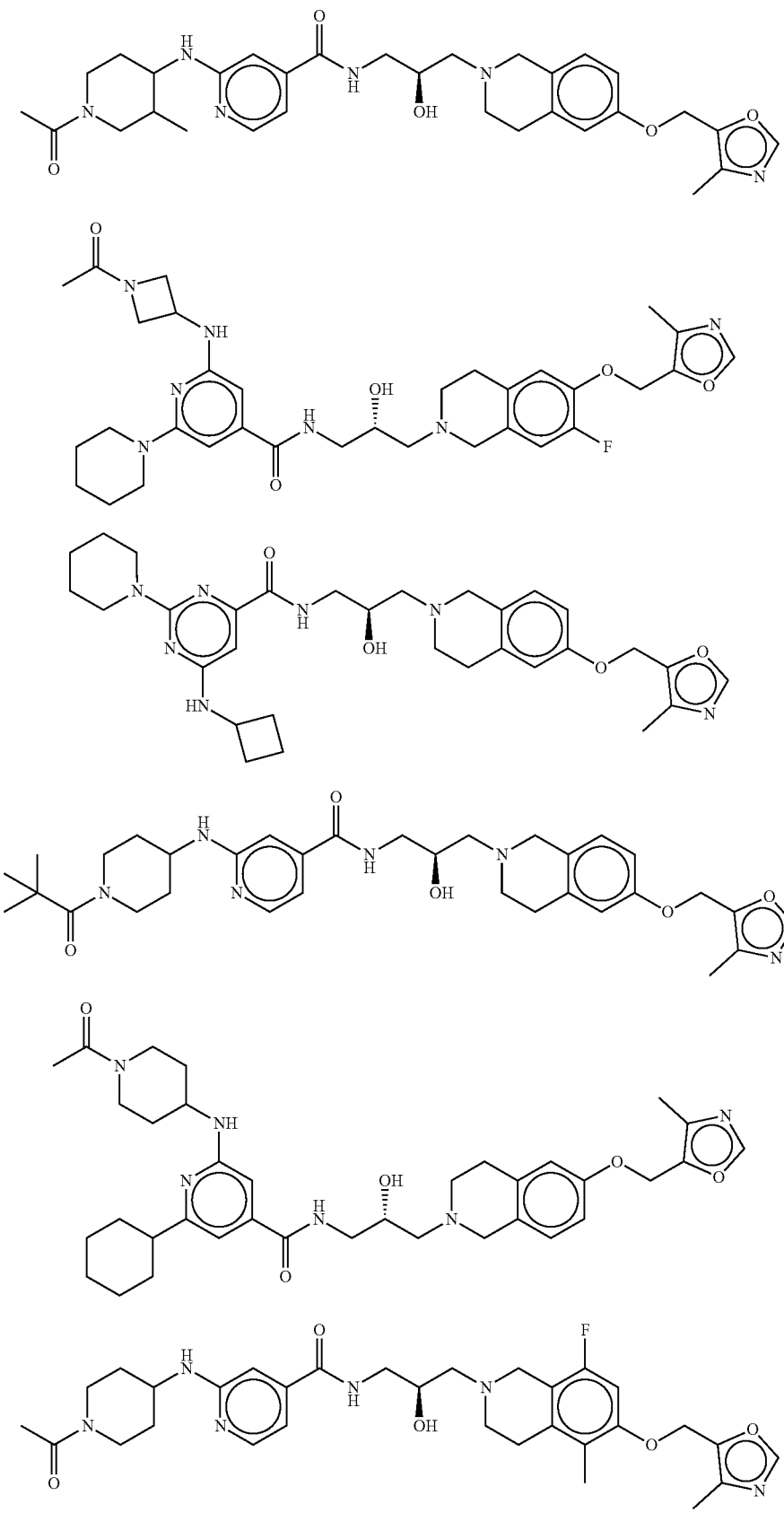

TABLE 4-continued
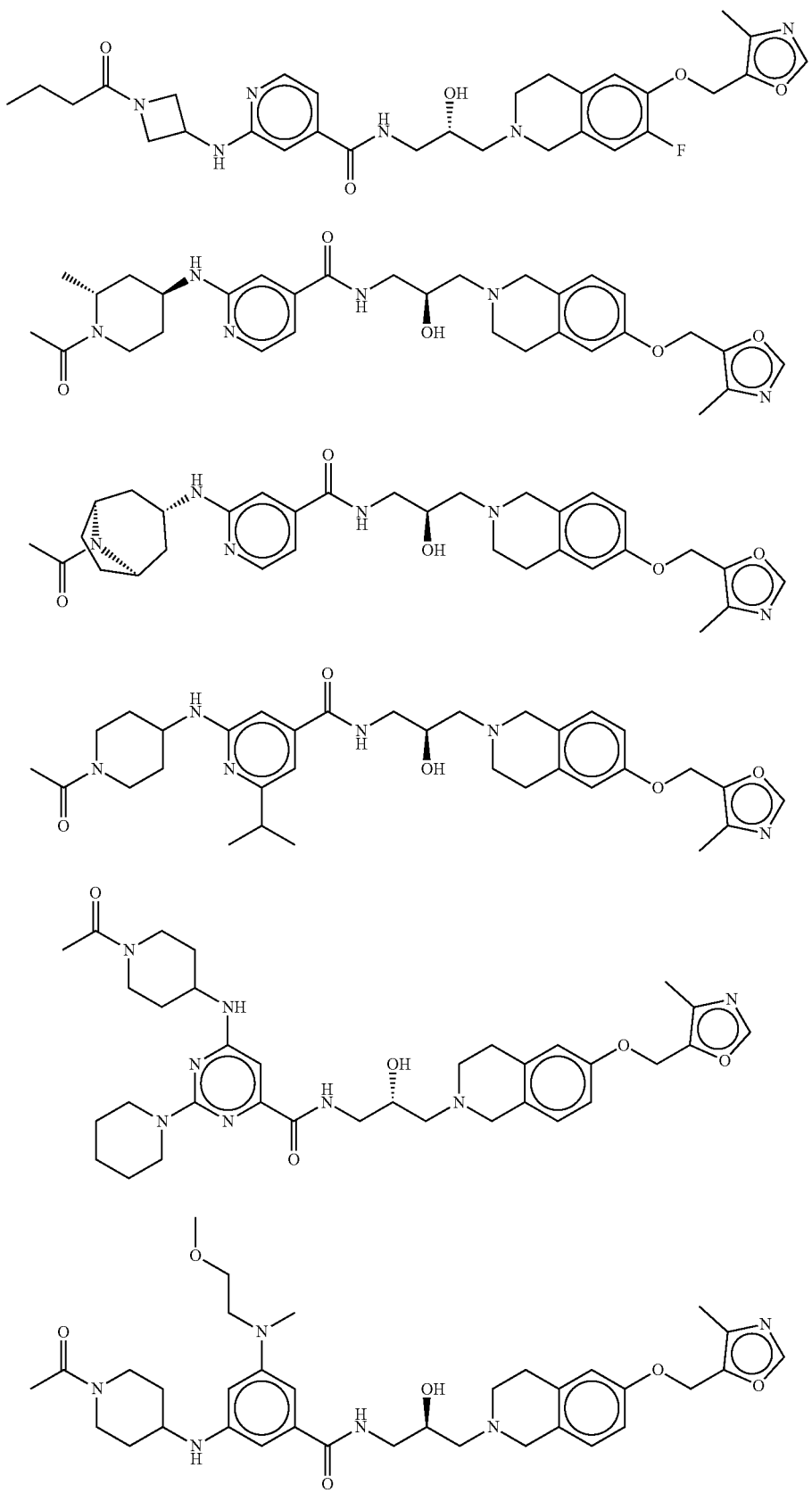

TABLE 4-continued
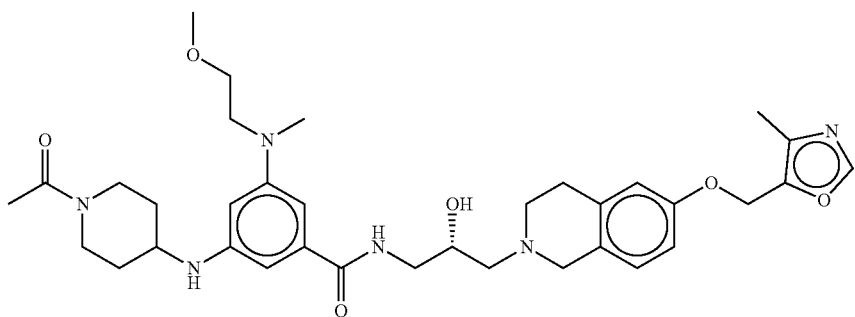
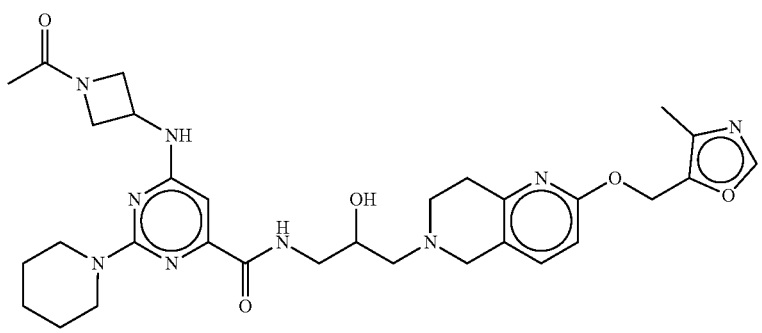
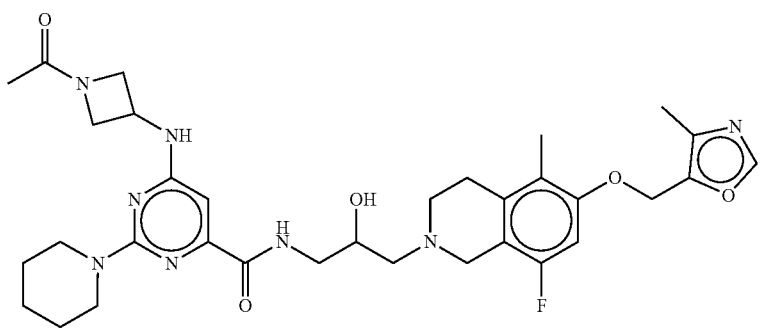
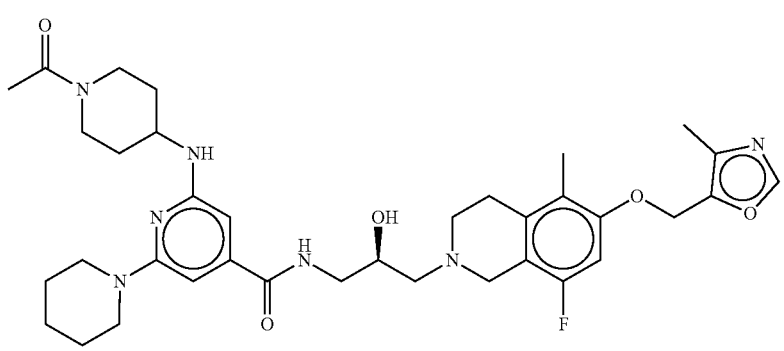

TABLE 4-continued

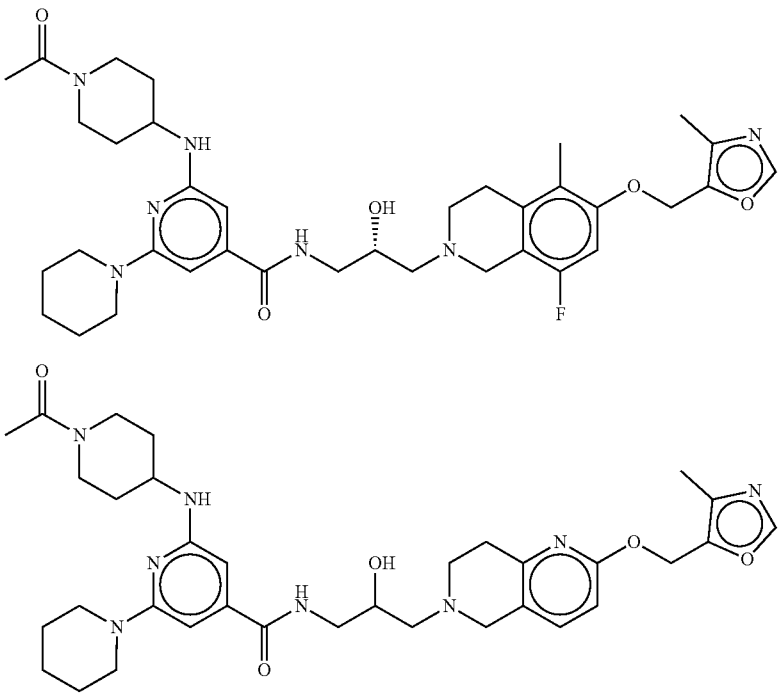

or a pharmaceutically acceptable salt thereof.

In yet another embodiment, the Type II PRMT5 inhibitor is a compound of Formula VI:

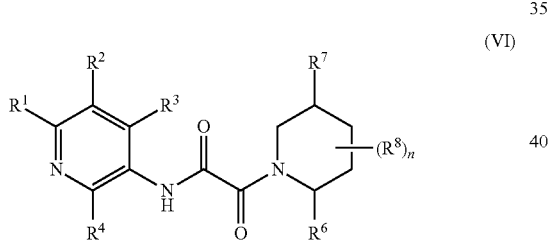

(VI)

or a pharmaceutically acceptable salt thereof;
wherein
each $R^1$ is independently selected from H, -D, halo, —CN, —$C_1$-$C_6$ alkyl, —$C_1$-$C_6$ heteroalkyl, —$C_1$-$C_6$ haloalkyl, —$C_3$-$C_9$ cycloalkyl, 3-10 membered heterocyclyl, heterocyclylalkyl, heteroarylalkyl, arylalkyl, cycloalkylalkyl, —$OR^{a1}$, —$N(R^{a1})_2$, —$C(\!=\!O)R^{a1}$, —$C(\!=\!O)OR^{a1}$, —$NR^{a1}C(\!=\!O)R^{a1}$, —$NR^{a1}C(\!=\!O)OR^{a1}$, —$C(\!=\!O)N(R^{a1})_2$, —$OC(\!=\!O)N(R^{a1})_2$, —$S(\!=\!O)R^{a1}$, —$S(\!=\!O)_2R^{a1}$, —$SR^{a1}$, —$S(\!=\!O)(\!=\!NR^{a1})R^{a1}$, —$NR^{a1}S(\!=\!O)_2R^{a1}$ and —$S(\!=\!O)_2N(R^{a1})_2$;

each $R^2$ is independently selected from halo, —CN, —$C_1$-$C_5$ alkyl, —$C_{1\text{-}6}$ heteroalkyl, —$C_1$-$C_6$ haloalkyl, —$C_1$-$C_6$ haloalkoxy, —$C_3$-$C_9$ cycloalkyl, 3-10 membered heterocyclyl, heterocyclylalkyl, heteroarylalkyl, arylalkyl, cycloalkylalkyl, —$OR^{a2}$, —$N(R^{a2})_2$, —$C(\!=\!O)R^{a2}$, —$C(\!=\!O)OR^{a2}$, —$NR^{a2}C(\!=\!O)R^{a2}$, —$NR^{a2}C(\!=\!O)OR^{a2}$, —$C(\!=\!O)N(R^{a2})_2$, —$C(\!=\!O)N(OR^{a2})(R^{a2})$, —$OC(\!=\!O)N(R^{a2})_2$, —$S(\!=\!O)R^{a2}$, —$S(\!=\!O)_2R^{a2}$, —$SR^{a2}$, —$S(\!=\!O)(\!=\!NR^{a2})R^{a2}$, —$NR^{a2}S(\!=\!O)_2R^{a2}$ and —$S(\!=\!O)_2N(R^{a2})_2$;

each $R^3$ is independently selected from H, -D, halo, —CN, —$C_1$-$C_6$ alkyl, —$C_1$-$C_6$ heteroalkyl, —$C_1$-$C_6$ haloalkyl, —$C_3$-$C_9$ cycloalkyl, 3-10 membered heterocyclyl, heterocyclylalkyl, heteroarylalkyl, arylalkyl, cycloalkylalkyl, —$OR^{a3}$, —$N(R^{a3})_2$, —$C(\!=\!O)R^{a3}$, —$C(\!=\!O)OR^{a3}$, —$NR^{a3}C(\!=\!O)R^{a3}$, —$NR^{a3}C(\!=\!O)OR^{a3}$, —$C(\!=\!O)N(R^{a3})_2$, —$OC(\!=\!O)N(R^{a3})_2$, —$S(\!=\!O)R^{a3}$, —$S(\!=\!O)_2R^{a3}$, —$SR^{a3}$, —$S(\!=\!O)(\!=\!NR^{a3})R^{a3}$, —$NR^{a3}S(\!=\!O)_2R^{a3}$ and —$S(\!=\!O)_2N(R^{a3})_2$;

each $R^4$ is independently selected from H, -D, halo, —CN, —$C_1$-$C_6$ alkyl, —$C_1$-$C_6$ heteroalkyl, —$C_1$-$C_6$ haloalkyl, —$C_3$-$C_9$ cycloalkyl, 3-10 membered heterocyclyl, heterocyclylalkyl, heteroarylalkyl, arylalkyl, cycloalkylalkyl, —$OR^{a4}$, —$N(R^{a4})_2$, —$C(\!=\!O)R^{a4}$, —$C(\!=\!O)OR^{a4}$, —$NR^{a4}C(\!=\!O)R^{a4}$, —$NR^{a4}C(\!=\!O)OR^{a4}$, —$C(\!=\!O)N(R^{a4})_2$, —$OC(\!=\!O)N(R^{a4})_2$, —$S(\!=\!O)R^{a4}$, —$S(\!=\!O)_2R^{a4}$, —$SR^{a4}$, —$S(\!=\!O)(\!=\!NR^{a4})R^{a4}$, —$NR^{a4}S(\!=\!O)_2R^{a4}$ and —$S(\!=\!O)_2N(R^{a4})_2$;

each $R^6$ is independently absent or selected from H, -D, halo, —CN, —$C_1$-$C_8$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, C6-C10 aryl, 5-10 member heteroaryl, heteroarylalkyl, arylalkyl, cycloalkylalkyl, —$OR^{a6}$, —$N(R^{a6})_2$, —$C(\!=\!O)R^{a6}$, —$C(\!=\!O)OR^{a6}$, —$NR^{a6}C(\!=\!O)R^{a6}$, —$NR^{a6}C(\!=\!O)OR^{a6}$, —$C(\!=\!O)N(R^{a6})_2$, —$OC(\!=\!O)N(R^{a6})_2$, —$S(\!=\!O)R^{a6}$, —$S(\!=\!O)_2R^{a6}$, —$SR^{a6}$, —$S(\!=\!O)(\!=\!NR^{a6})R^{a6}$, —$NR^{a6}S(\!=\!O)_2R^{a6}$ and —$S(\!=\!O)_2N(R^{a6})_2$, wherein each alkyl, carbocyclyl, heterocyclyl, cycloalkylalkyl, heterocyclylalkyl, aryl, heteroaryl, arylalkyl and heteroarylalkyl is optionally substituted at any available position;

each $R^7$ is independently absent or selected from H, -D, halo, —CN, —$C_1$-$C_6$ alkyl, —$C_1$-$C_6$ hydroxyalkyl, —C$_1$-C$_6$ haloalkyl, —C$_3$-C$_9$ cycloalkyl, 3-10 membered heterocyclyl, 5-6-membered monocyclic heteroaryl, heterocyclylalkyl, heteroarylalkyl, arylalkyl, cycloalkylalkyl, —OR$^{a7}$, —N(R$^{a7}$)$_2$, —C(=O)R$^{a7}$, —C(=O)OR$^{a7}$, —NR$^{a7}$C(=O)R$^{a7}$, —NR$^{a7}$C(=O)OR$^{a7}$, —C(=O)N(R$^{a7}$)$_2$, —OC(=O)N(R$^{a7}$)$_2$, —S(=O)R$^{a7}$, —S(=O)$_2$R$^{a7}$, —SR$^{a7}$, —S(=O)(=NR$^{a7}$)R$^{a7}$, —NR$^{a7}$S(=O)$_2$R$^{a7}$ and —S(=O)$_2$N(R$^{a7}$)$_2$;

each R$^6$ is independently selected from H, -D, =O, halo, —CN, —C$_1$-C$_6$ alkyl, —C$_1$-C$_6$ heteroalkyl, —C$_1$-C$_6$ haloalkyl, —C$_3$-C$_9$, cycloalkyl, 3-10 membered heterocyclyl, heterocyclylalkyl, heteroarylalkyl, arylalkyl, cycloalkylalkyl, —OR$^{a8}$, —N(R$^{a8}$)$_2$, —C(=O)R$^{a8}$, —C(=O)OR$^{a8}$, —NR$^{a8}$C(=O)R$^{a8}$, —NR$^{a8}$C(=O)OR$^{a8}$, —CH$_2$C(=O)N(R$^{a8}$)$_2$—C(=O)N(R$^{a8}$)$_2$, —OC(=O)N(R$^{a8}$)$_2$, —CH2C(=O)N(R$^{a8}$)$_2$, —S(=O)R$^{a8}$, —S(=O)$_2$R$^{a8}$, —SR$^{a8}$, —S(=O)(=NR$^{a8}$)R$^{a8}$, —NR$^{a8}$S(=O)$_2$R$^{a8}$ and —S(=O)$_2$N(R$^{a8}$)$_2$ wherein two instances of R$^8$ together with the atom or atoms to which they are attached can be taken together to form a 3-10 member cycloalkyl or heterocyclyl ring (e.g., a ring that together with the piperidine ring of Structure I can form a bridged, fused or spiro bicyclic heterocyclic ring);

each R$^{a1}$, R$^{a2}$, R$^{a3}$, R$^{a4}$, R$^{a6}$, R$^{a7}$ and R$^{a8}$ is independently selected from H, C$_1$-C$_6$ alkyl, —C$_1$-C$_6$ heteroalkyl, C$_3$-C$_9$ cycloalkyl, 3-7 membered heterocyclyl, cycloalkylalkyl, heterocyclylalkyl, aryl, 5-6 membered heteroaryl, arylalkyl and heteroarylalkyl wherein each alkyl, cycloalkyl, heterocyclyl, cycloalkylalkyl, heterocyclylalkyl, aryl, heteroaryl, arylalkyl and heteroarylalkyl is optionally substituted at any available position (e.g., substituted with 0, 1, 2 or 3 instances of R$^9$, wherein each R$^9$ is independently selected from =O, halo, —CN, —C$_1$-C$_6$ alkyl, —C$_1$-C$_6$ heteroalkyl, —C$_1$-C$_6$ haloalkyl, —C$_3$-C$_9$ cycloalkyl, 3-10 membered heterocyclyl, C$_6$-C$_{10}$ aryl, 5-10 membered heteroaryl, cycloalkylalkyl, heterocyclylalkyl, arylalkyl, heteroarylalkyl, —OR$^b$, —N(R$^b$)$_2$, —C(=O)R$^b$, —C(=O)OR$^b$, —NR$^b$C(=O)R$^b$, —NR$^b$C(=O)OR$^b$, —C(=O)N(R$^b$)$_2$, —OC(=O)N(R$^b$)$_2$, —S(=O)R$^b$, —S(=O)$_2$R$^b$, —SR$^b$, —S(=O)(=NR$^b$)R$^b$, —NR$^b$S(=O)$_2$R$^b$ and —S(=O)$_2$N(R$^b$)$_2$, wherein each R$^b$ is independently selected from H, —C$_1$-C$_6$ alkyl (e.g., -Me, -Et, —Pr, —$^i$Pr, -$^n$Bu, -$^t$Bu, -sec-Bu, -iso-Bu)), and C$_3$-C$_9$ cycloalkyl (e.g., cyclopropyl, cyclobutyl, cyclopentyl, cyclohexyl); and n is 0, 1, 2 or 3;

provided that:
(i) when R$^1$ is H, R$^2$ is not halo, —OPr, —N(CH$_3$)$_2$ or —CF$_3$;
(ii) when R$^1$ is OR$^{a1}$, R$^2$ is not —OR$^{a2}$;
(iii) when R$^1$ is H and R$^2$ is —CH3, R$^8$ groups cannot be taken together to form a ring and R$^6$ is not absent or H, and is not thiazolyl, furanyl or pyrrolyl;
(iv) when R$^2$ is Me, R$^1$ is not optionally substituted piperidine
(v) the compound is not:
A. 5-(2-(5-methyl-2-(p-tolyl)piperidin-1-yl)-2-oxoacetamido)nicotinamide or any of its enantiomers or diastereomers;
B. 2-(2-(4-(2H-tetrazol-5-yl)phenyl)-5-methylpiperidin-1-yl)-N-(5,6-dimethylpyridin-3-yl)-2-oxoacetamide or any of its enantiomers or diastereomers;
C. 2-cyano-5-(2-(5-methyl-2-phenylpiperidin-1-yl)-2-oxoacetamido)nicotinamide or any of its enantiomers or diastereomers.

In another embodiment, the Type II PRMT5 inhibitor is selected from the group consisting of a compound from Table 5 (see WO 2022/026892, which is incorporated by reference in its entirety).

TABLE 5

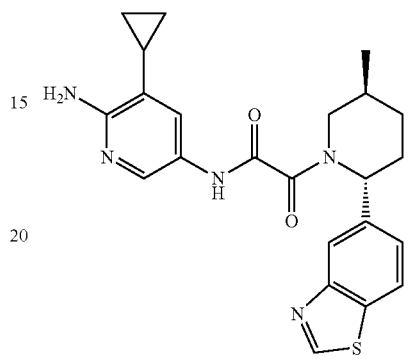

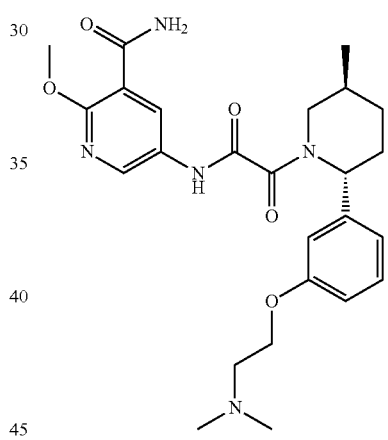

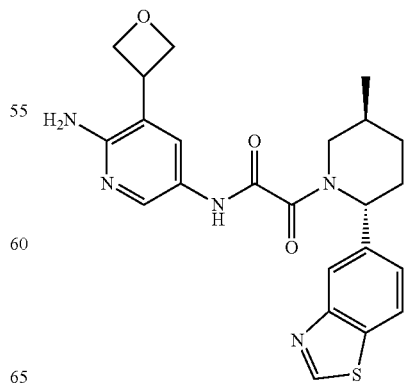

TABLE 5-continued
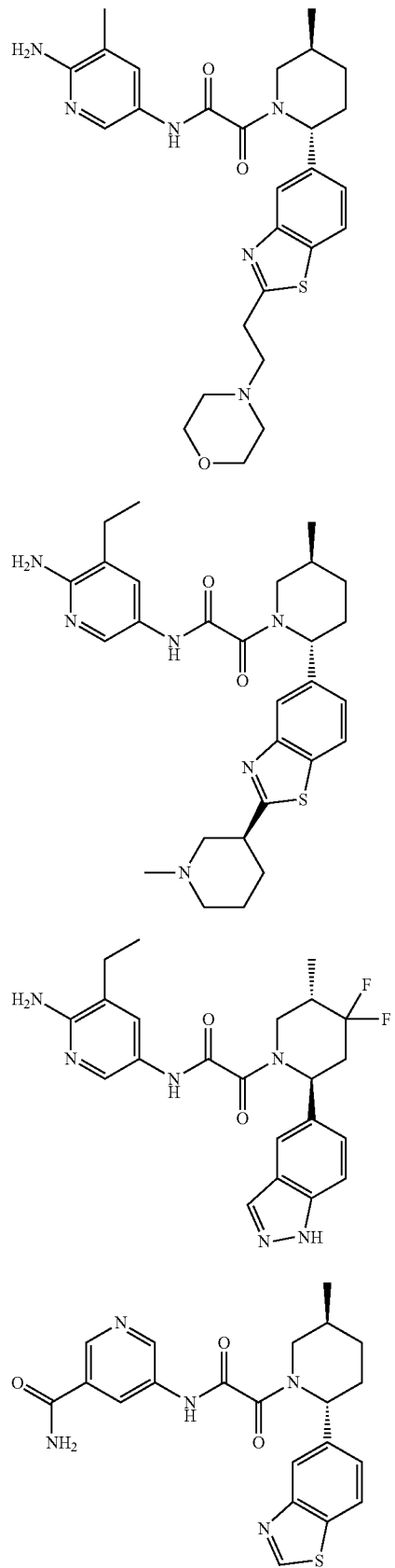
TABLE 5-continued
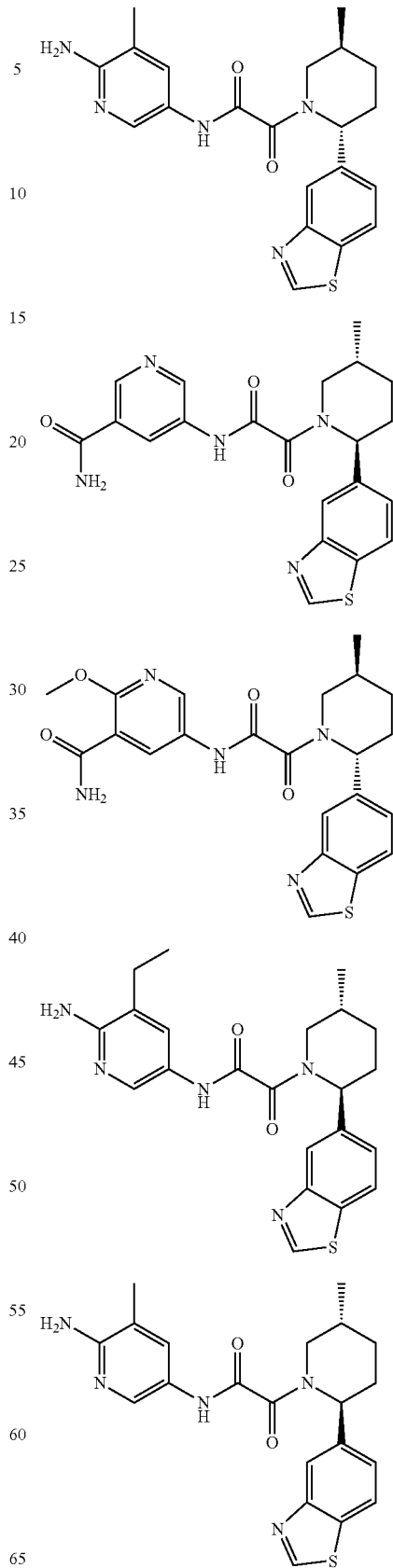

TABLE 5-continued
645
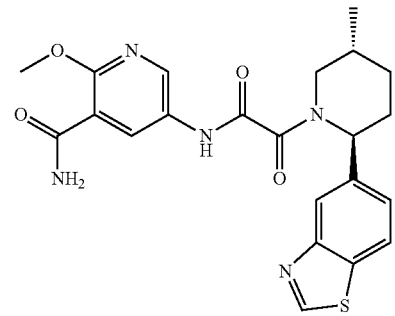 [SMILES: COc1ncc(NC(=O)C(=O)N2C[C@H](C)CC[C@H]2c2ccc3scnc3c2)cc1C(N)=O]
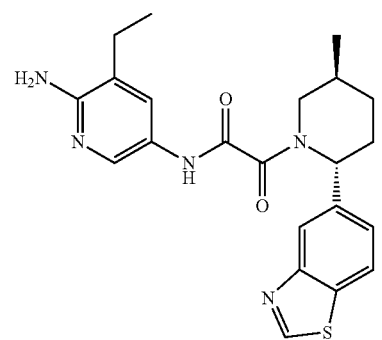 [SMILES: CCc1cc(NC(=O)C(=O)N2C[C@@H](C)CC[C@@H]2c2ccc3scnc3c2)cnc1N]
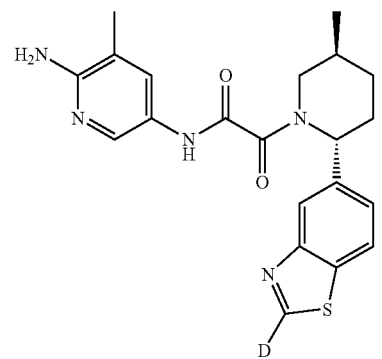 [SMILES: [2H]c1nc2cc([C@H]3CC[C@H](C)CN3C(=O)C(=O)Nc3cnc(N)c(C)c3)ccc2s1]
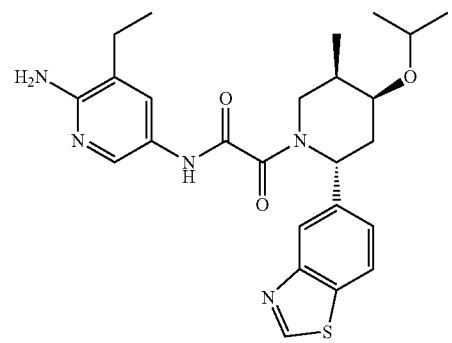 [SMILES: CCc1cc(NC(=O)C(=O)N2C[C@@H](C)[C@@H](OC(C)C)C[C@@H]2c2ccc3scnc3c2)cnc1N]
TABLE 5-continued
646
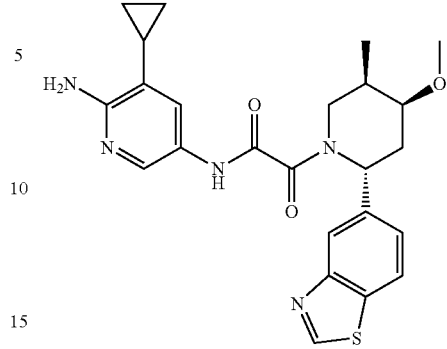
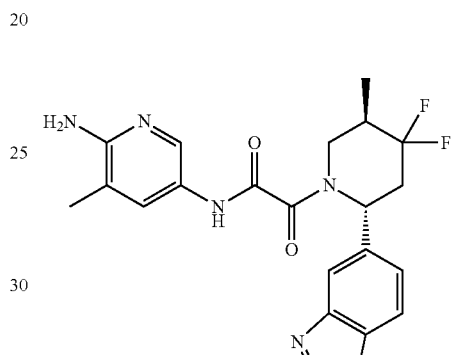
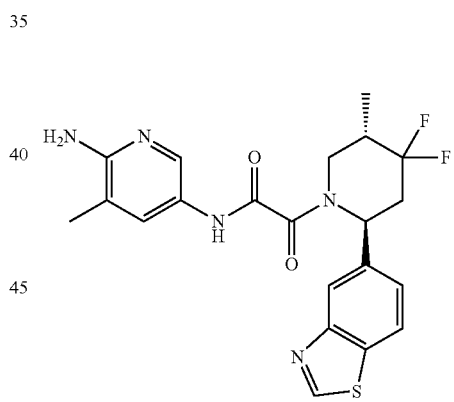
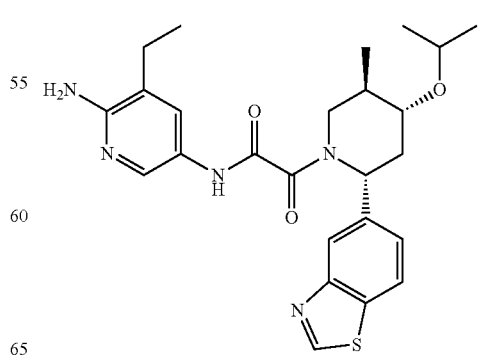

| 647 | 648 |
|---|---|
| TABLE 5-continued | TABLE 5-continued |
| 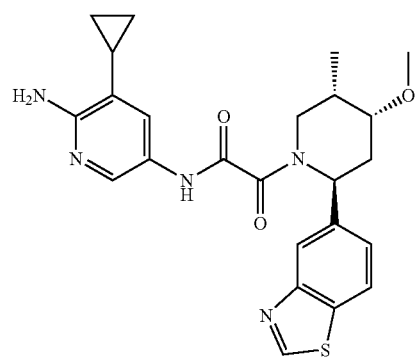 [SMILES: CO[C@@H]1C[C@@H](c2ccc3scnc3c2)N(C(=O)C(=O)Nc2cnc(N)c(C3CC3)c2)C[C@@H]1C] | 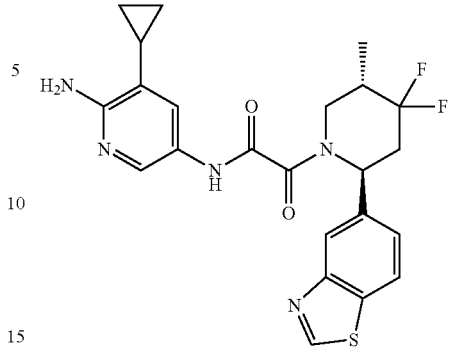 |
| 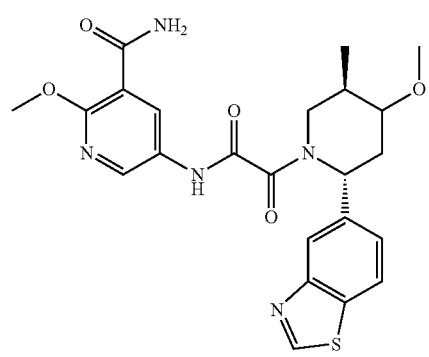 | 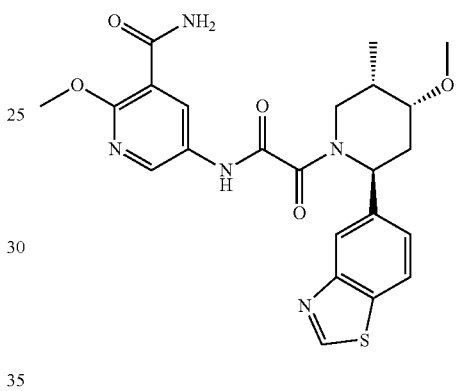 |
| 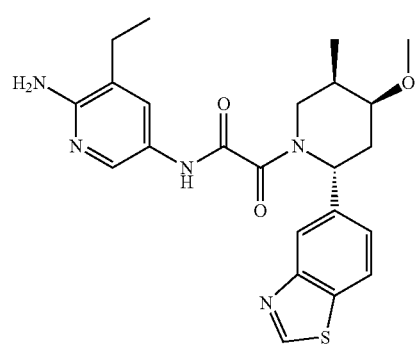 [SMILES: CCc1cc(NC(=O)C(=O)N2C[C@@H](C)[C@@H](OC)C[C@@H]2c2ccc3scnc3c2)cnc1N] | 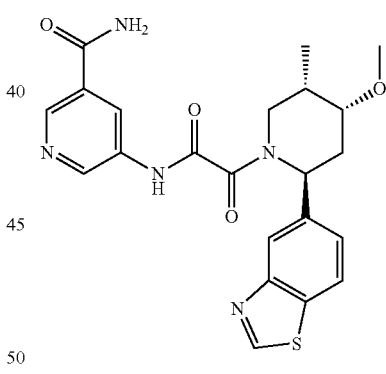 |
| 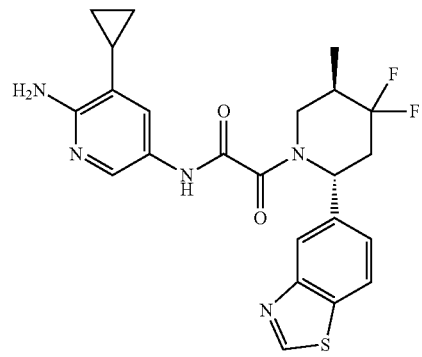 [SMILES: C[C@@H]1CN(C(=O)C(=O)Nc2cnc(N)c(C3CC3)c2)[C@@H](c2ccc3scnc3c2)CC1(F)F] | 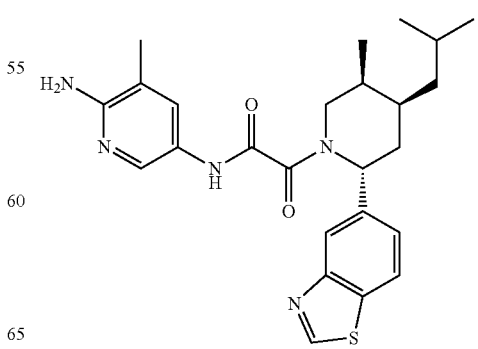 |

TABLE 5-continued
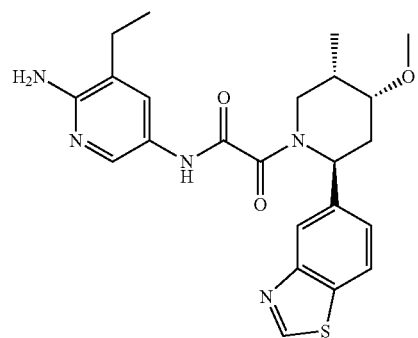 [SMILES: CCc1cc(NC(=O)C(=O)N2C[C@H](C)[C@H](OC)C[C@H]2c2ccc3scnc3c2)cnc1N]
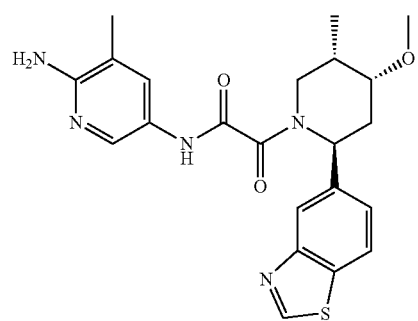 [SMILES: CO[C@@H]1C[C@@H](c2ccc3scnc3c2)N(C(=O)C(=O)Nc2cnc(N)c(C)c2)C[C@@H]1C]
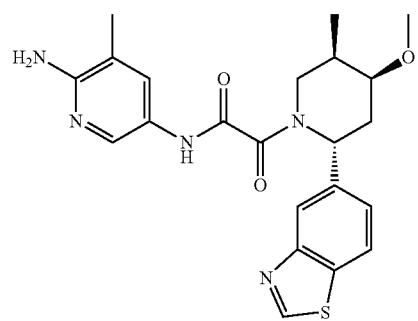 [SMILES: CO[C@H]1C[C@H](c2ccc3scnc3c2)N(C(=O)C(=O)Nc2cnc(N)c(C)c2)C[C@H]1C]
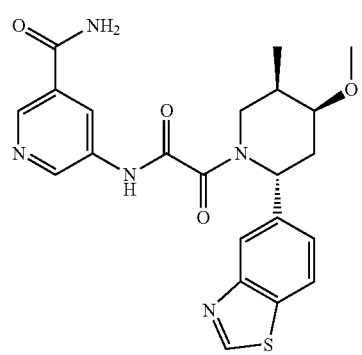 [SMILES: CO[C@H]1C[C@H](c2ccc3scnc3c2)N(C(=O)C(=O)Nc2cncc(C(N)=O)c2)C[C@H]1C]
TABLE 5-continued
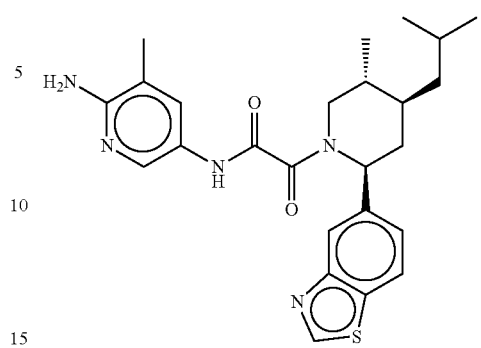
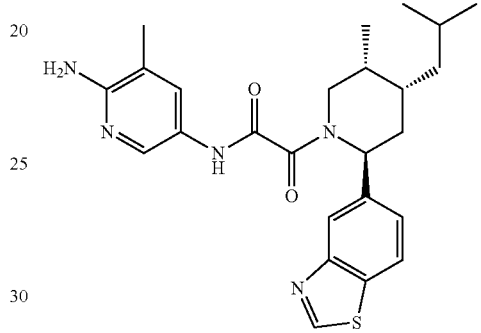
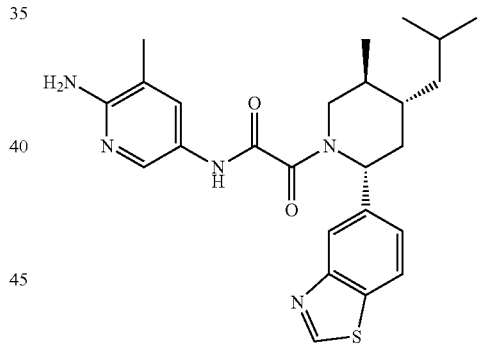
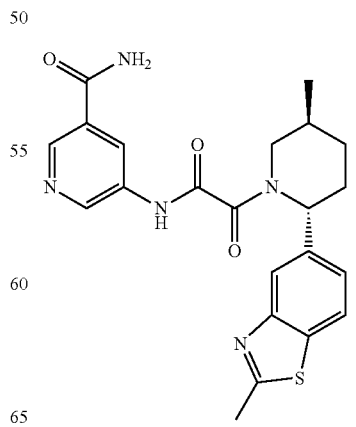

TABLE 5-continued
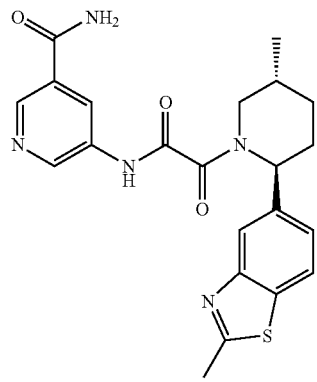 [SMILES: Cc1nc2cc([C@@H]3CC[C@@H](C)CN3C(=O)C(=O)Nc3cncc(C(N)=O)c3)ccc2s1]
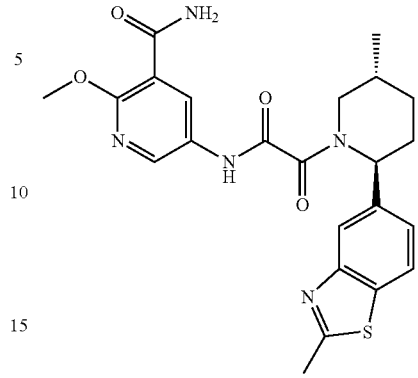
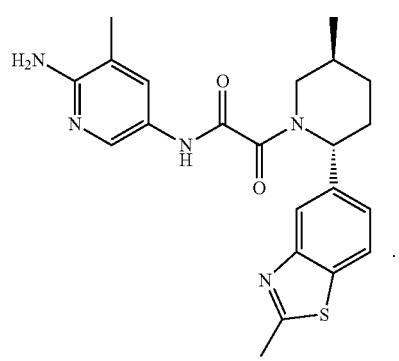 [SMILES: Cc1nc2cc([C@H]3CC[C@H](C)CN3C(=O)C(=O)Nc3cnc(N)c(C)c3)ccc2s1]
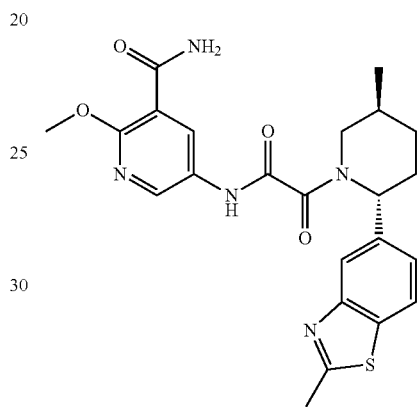
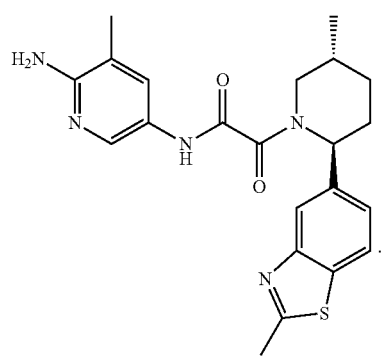 [SMILES: Cc1nc2cc([C@@H]3CC[C@@H](C)CN3C(=O)C(=O)Nc3cnc(N)c(C)c3)ccc2s1]
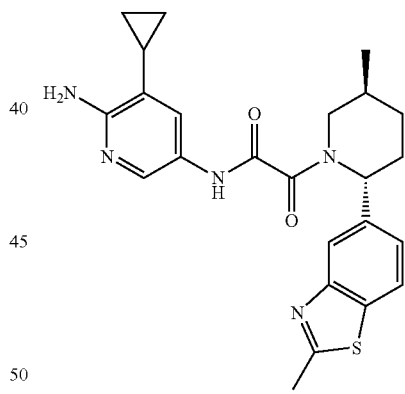
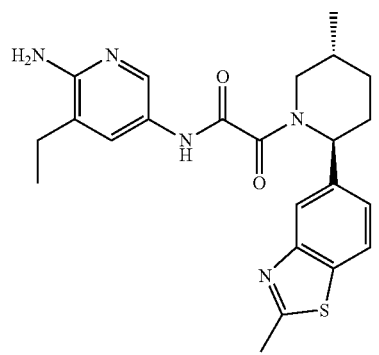 [SMILES: CCc1cc(NC(=O)C(=O)N2C[C@H](C)CC[C@H]2c2ccc3sc(C)nc3c2)cnc1N]
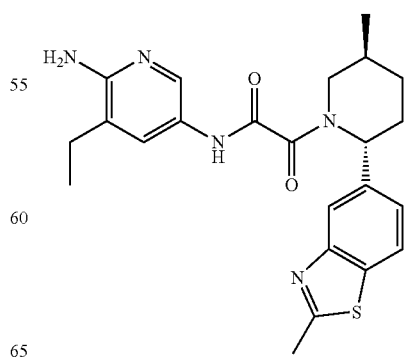

TABLE 5-continued
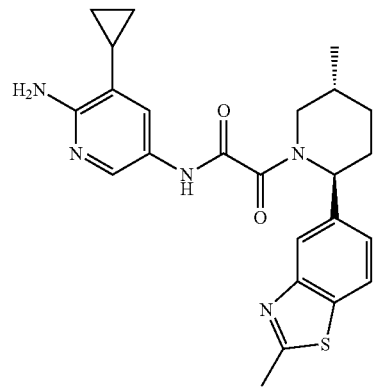 [SMILES: Cc1nc2cc([C@@H]3CC[C@@H](C)CN3C(=O)C(=O)Nc3cnc(N)c(C4CC4)c3)ccc2s1]
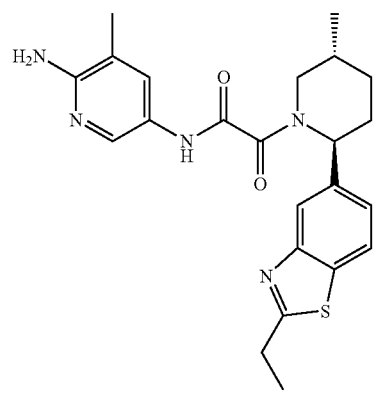 [SMILES: CCc1nc2cc([C@@H]3CC[C@@H](C)CN3C(=O)C(=O)Nc3cnc(N)c(C)c3)ccc2s1]
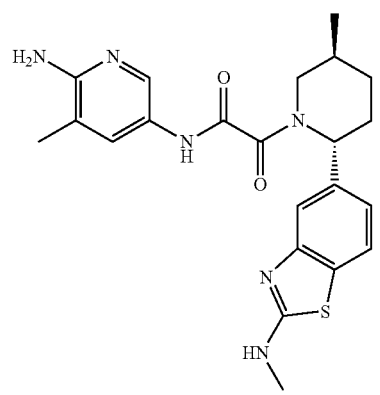 [SMILES: CNc1nc2cc([C@H]3CC[C@H](C)CN3C(=O)C(=O)Nc3cnc(N)c(C)c3)ccc2s1]
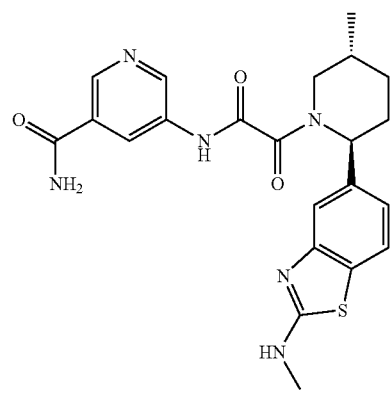 [SMILES: CNc1nc2cc([C@@H]3CC[C@@H](C)CN3C(=O)C(=O)Nc3cncc(C(N)=O)c3)ccc2s1]
TABLE 5-continued
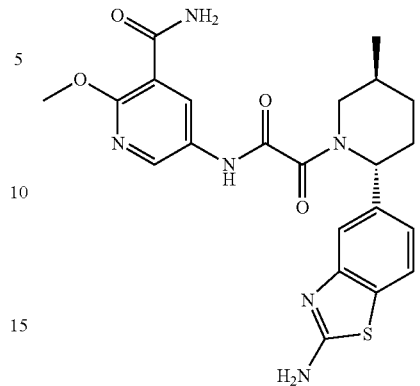
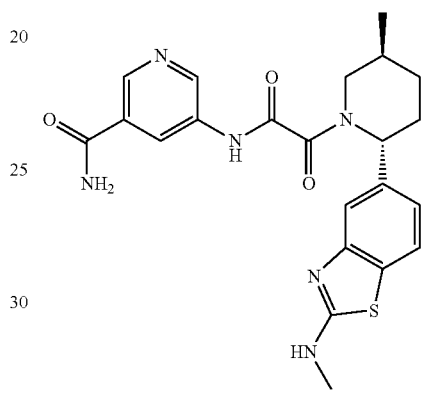
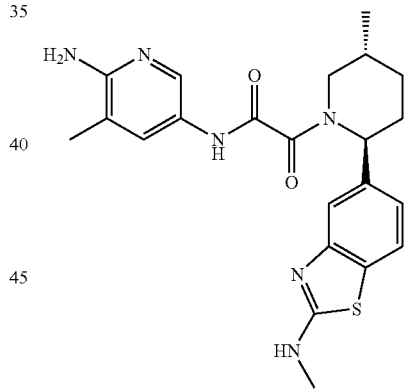
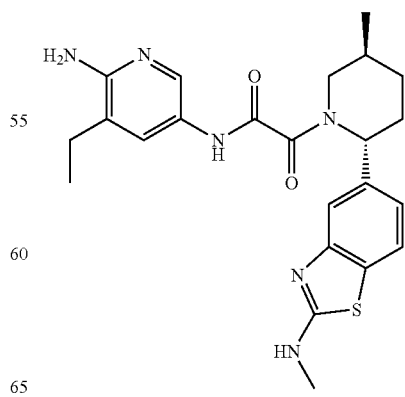

TABLE 5-continued
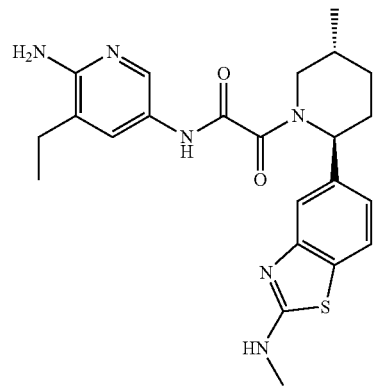 [SMILES: CCc1cc(NC(=O)C(=O)N2C[C@H](C)CC[C@H]2c2ccc3sc(NC)nc3c2)cnc1N]
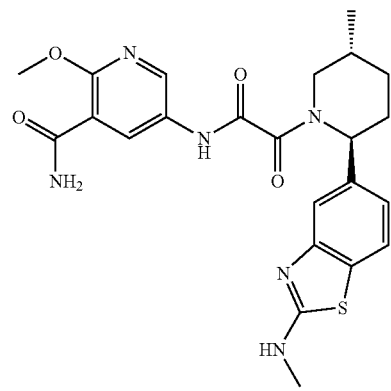 [SMILES: CNc1nc2cc([C@@H]3CC[C@@H](C)CN3C(=O)C(=O)Nc3cnc(OC)c(C(N)=O)c3)ccc2s1]
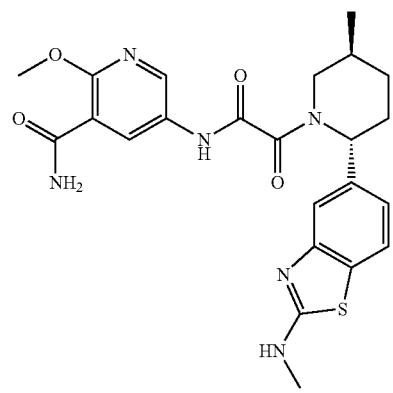 [SMILES: CNc1nc2cc([C@H]3CC[C@H](C)CN3C(=O)C(=O)Nc3cnc(OC)c(C(N)=O)c3)ccc2s1]
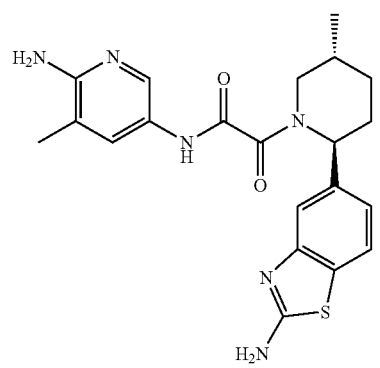 [SMILES: Cc1cc(NC(=O)C(=O)N2C[C@H](C)CC[C@H]2c2ccc3sc(N)nc3c2)cnc1N]
TABLE 5-continued
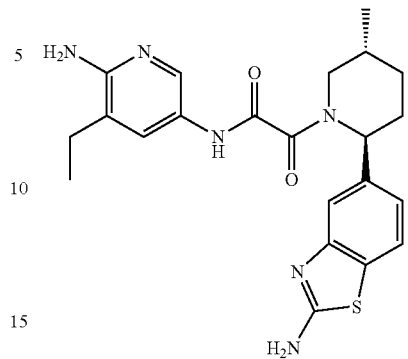
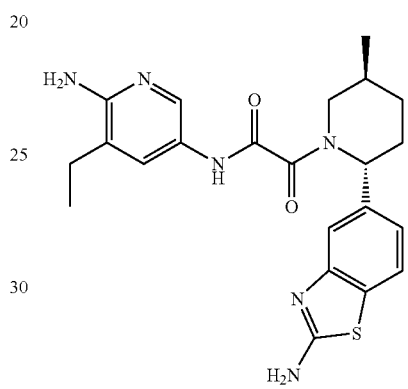
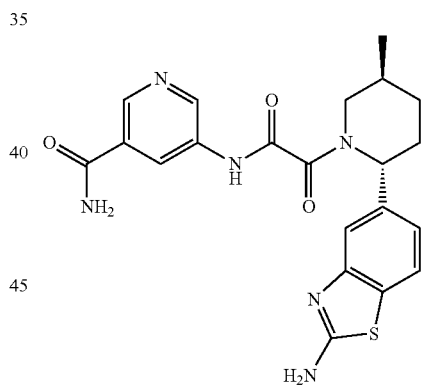
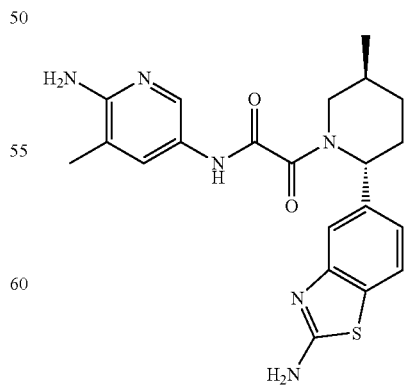

TABLE 5-continued
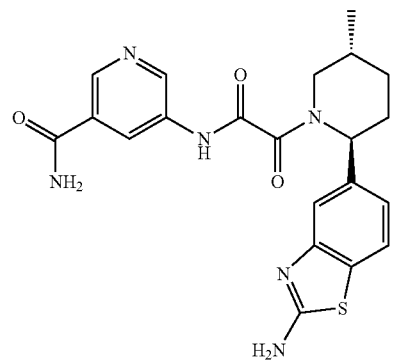 [SMILES: C[C@@H]1CC[C@@H](c2ccc3sc(N)nc3c2)N(C(=O)C(=O)Nc2cncc(C(N)=O)c2)C1]
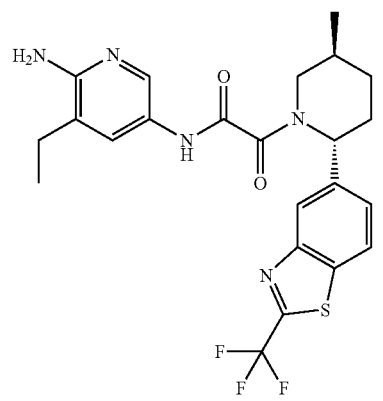 [SMILES: CCc1cc(NC(=O)C(=O)N2C[C@@H](C)CC[C@@H]2c2ccc3sc(C(F)(F)F)nc3c2)cnc1N]
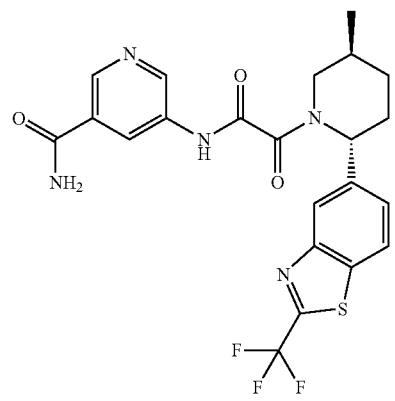 [SMILES: C[C@H]1CC[C@H](c2ccc3sc(C(F)(F)F)nc3c2)N(C(=O)C(=O)Nc2cncc(C(N)=O)c2)C1]
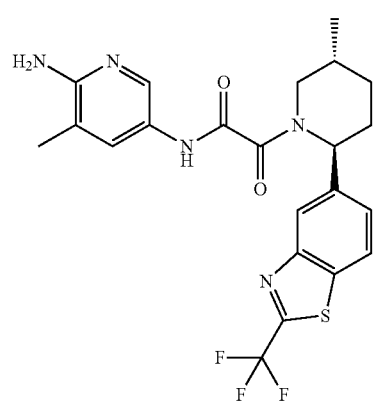 [SMILES: Cc1cc(NC(=O)C(=O)N2C[C@H](C)CC[C@H]2c2ccc3sc(C(F)(F)F)nc3c2)cnc1N]
TABLE 5-continued
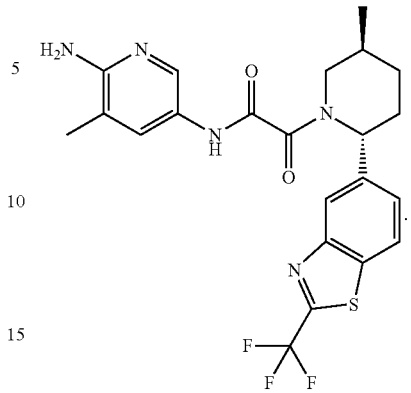
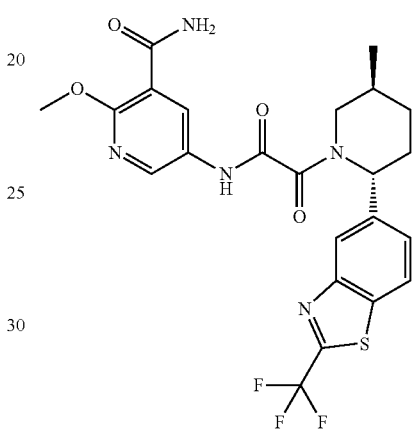
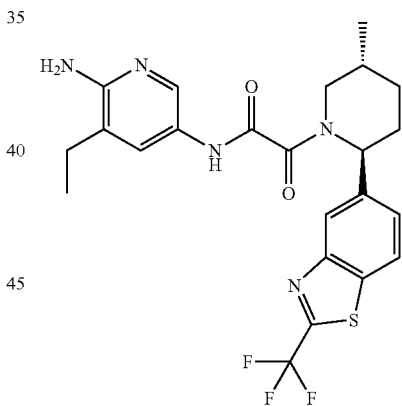
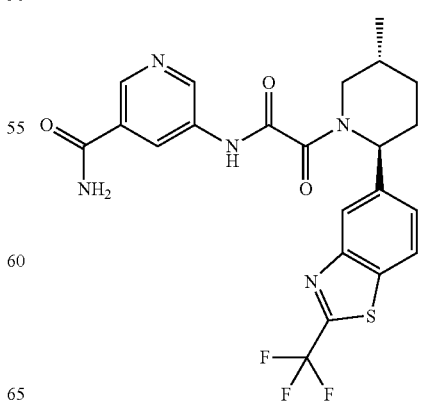

TABLE 5-continued
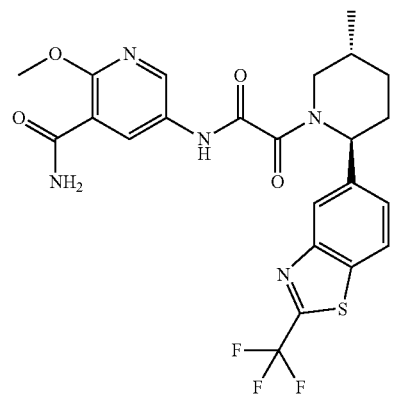 [SMILES: COc1ncc(NC(=O)C(=O)N2C[C@H](C)CC[C@H]2c2ccc3sc(C(F)(F)F)nc3c2)cc1C(N)=O]
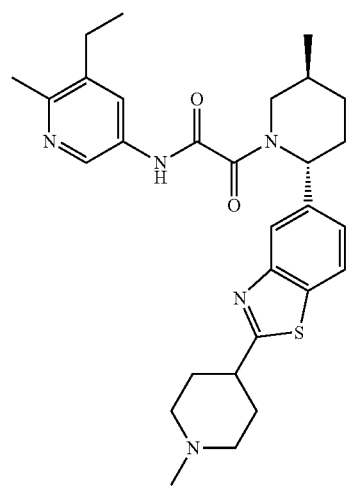 [SMILES: CCc1cc(NC(=O)C(=O)N2C[C@@H](C)CC[C@@H]2c2ccc3sc(C4CCN(C)CC4)nc3c2)cnc1C]
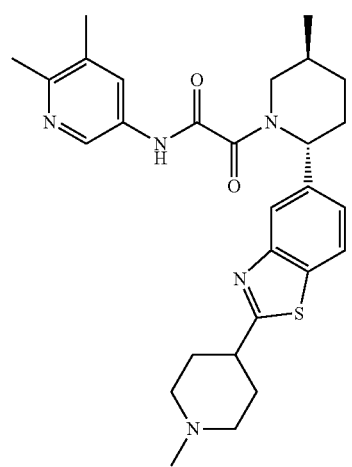 [SMILES: Cc1cc(NC(=O)C(=O)N2C[C@@H](C)CC[C@@H]2c2ccc3sc(C4CCN(C)CC4)nc3c2)cnc1C]
TABLE 5-continued
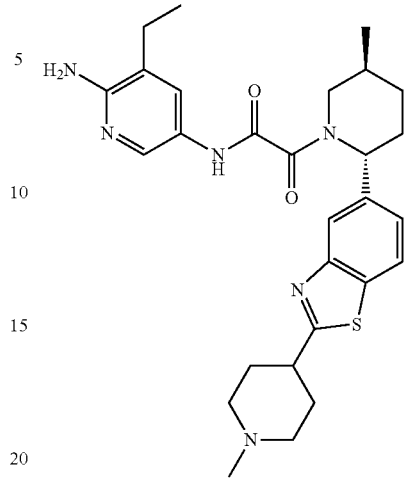
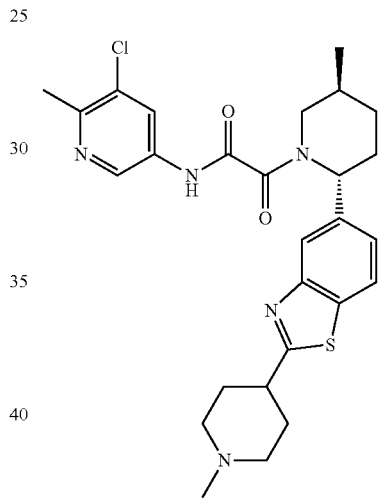
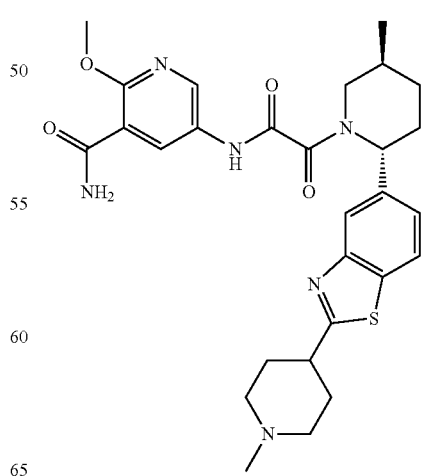

| 661 | 662 |
|---|---|
| TABLE 5-continued | TABLE 5-continued |
| 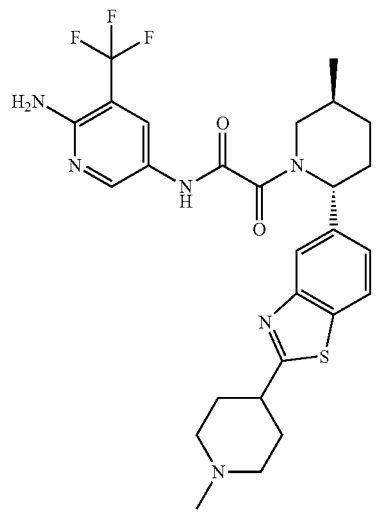 [SMILES: C[C@H]1CC[C@H](c2ccc3sc(C4CCN(C)CC4)nc3c2)N(C(=O)C(=O)Nc2cnc(N)c(C(F)(F)F)c2)C1] | 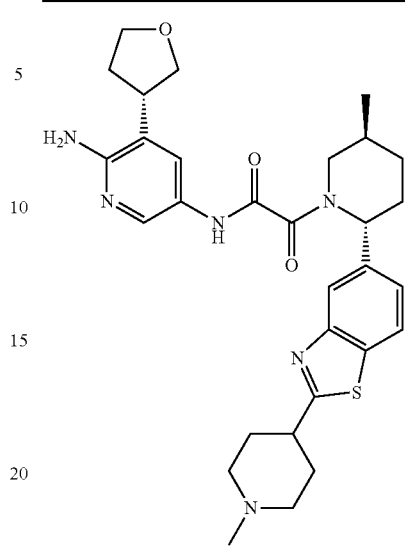 |
| 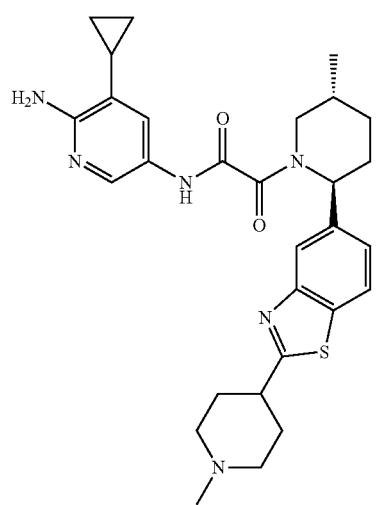 [SMILES: C[C@@H]1CC[C@@H](c2ccc3sc(C4CCN(C)CC4)nc3c2)N(C(=O)C(=O)Nc2cnc(N)c(C3CC3)c2)C1] | 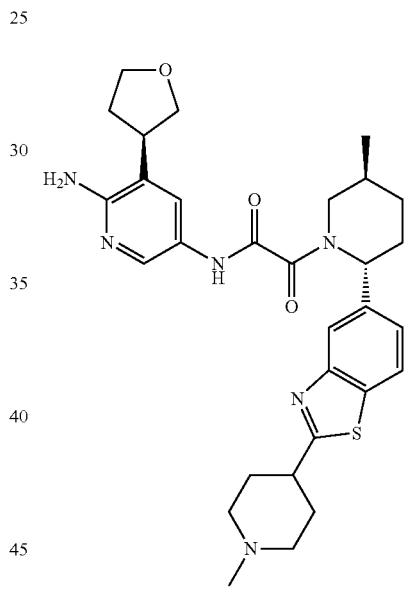 |
| 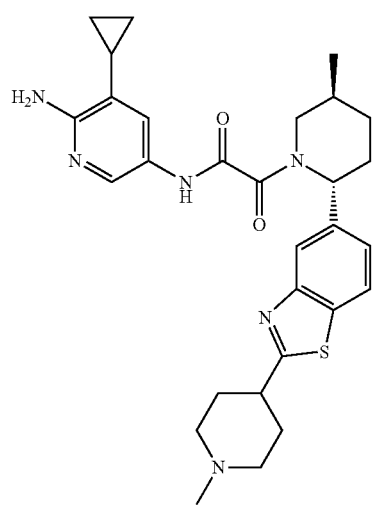 [SMILES: C[C@H]1CC[C@H](c2ccc3sc(C4CCN(C)CC4)nc3c2)N(C(=O)C(=O)Nc2cnc(N)c(C3CC3)c2)C1] | |

TABLE 5-continued
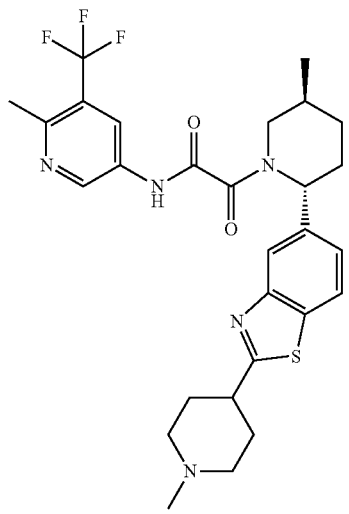 [SMILES: Cc1ncc(NC(=O)C(=O)N2C[C@@H](C)CC[C@@H]2c2ccc3sc(C4CCN(C)CC4)nc3c2)cc1C(F)(F)F]
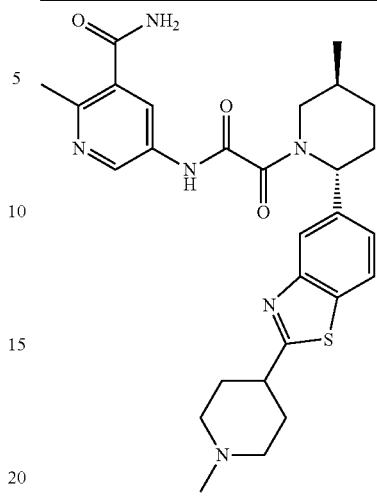
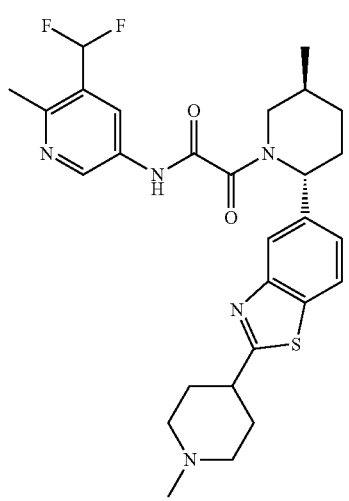 [SMILES: Cc1ncc(NC(=O)C(=O)N2C[C@@H](C)CC[C@@H]2c2ccc3sc(C4CCN(C)CC4)nc3c2)cc1C(F)F]
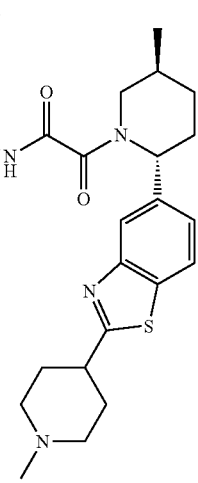
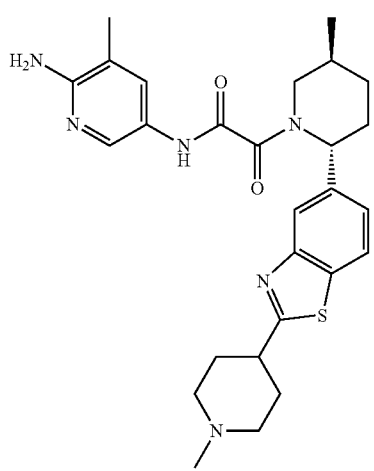
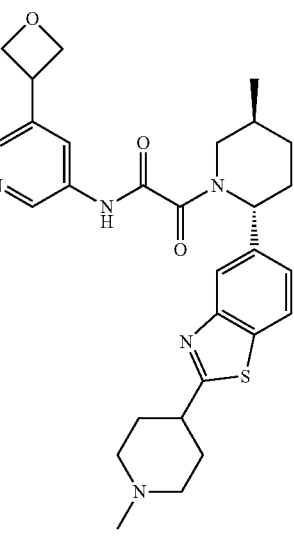

TABLE 5-continued
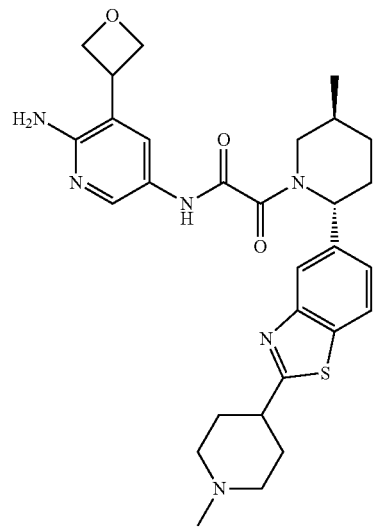 [SMILES: C[C@H]1CC[C@H](c2ccc3sc(C4CCN(C)CC4)nc3c2)N(C(=O)C(=O)Nc2cnc(N)c(C3COC3)c2)C1]
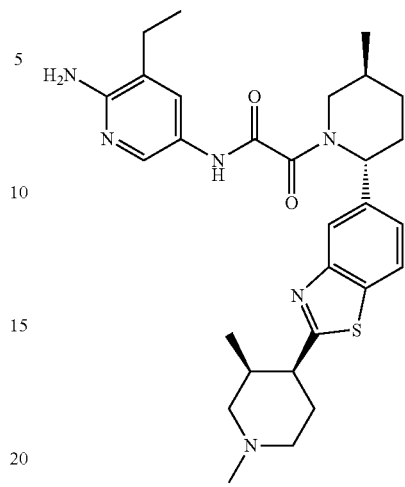
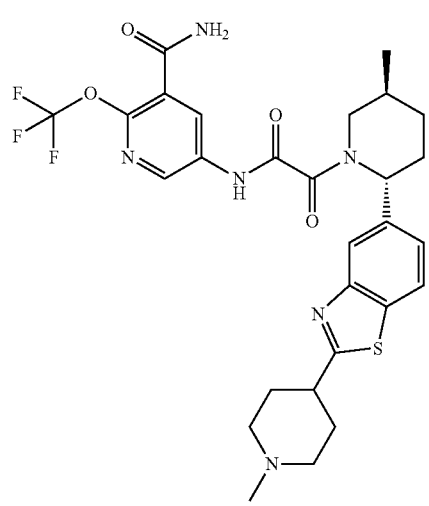 [SMILES: C[C@H]1CC[C@H](c2ccc3sc(C4CCN(C)CC4)nc3c2)N(C(=O)C(=O)Nc2cnc(OC(F)(F)F)c(C(N)=O)c2)C1]
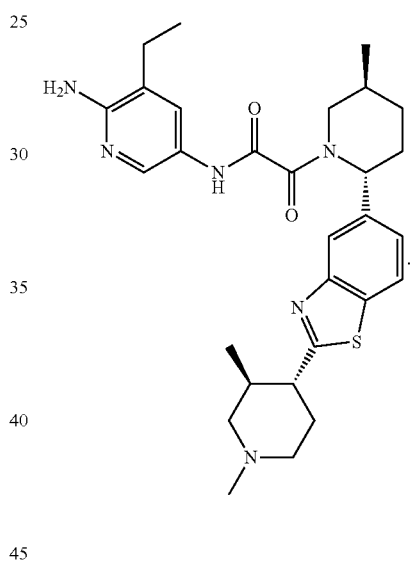
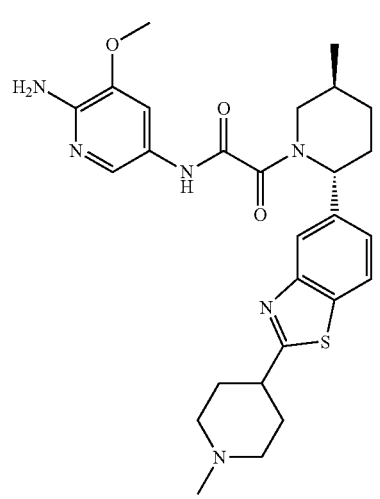 [SMILES: COc1cc(NC(=O)C(=O)N2C[C@@H](C)CC[C@@H]2c2ccc3sc(C4CCN(C)CC4)nc3c2)cnc1N]
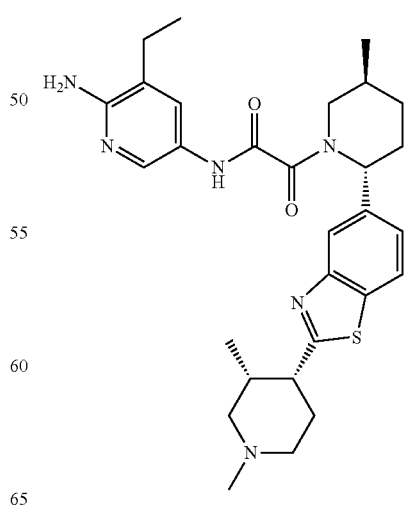

TABLE 5-continued
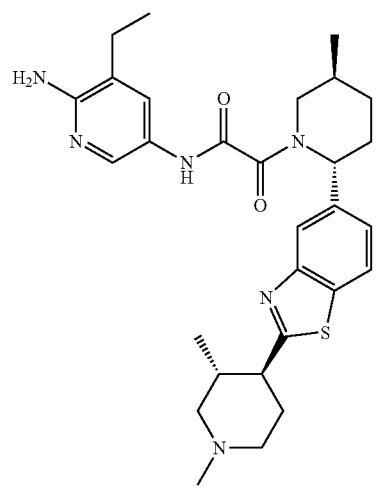 [SMILES: CCc1cc(NC(=O)C(=O)N2C[C@@H](C)CC[C@@H]2c2ccc3sc([C@H]4CCN(C)C[C@@H]4C)nc3c2)cnc1N]
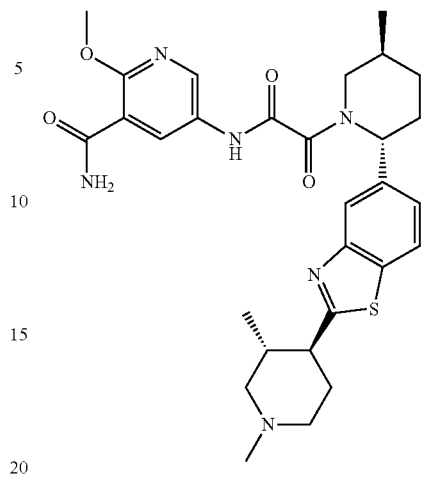
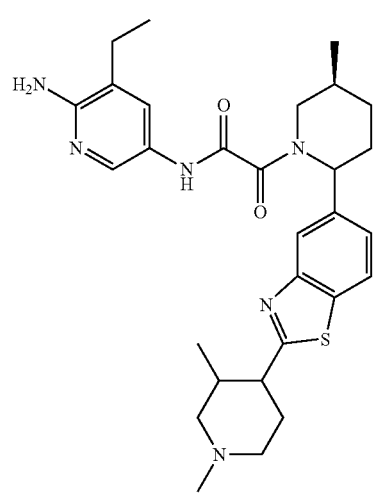 [SMILES: CCc1cc(NC(=O)C(=O)N2C[C@@H](C)CCC2c2ccc3sc(C4CCN(C)CC4C)nc3c2)cnc1N]
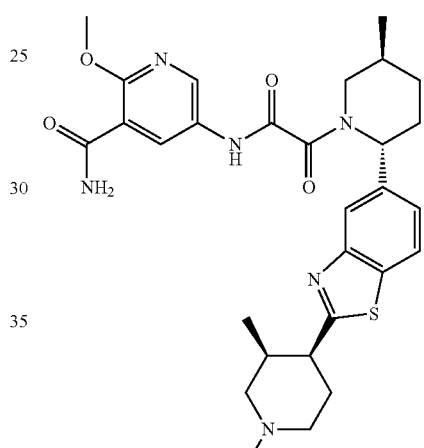
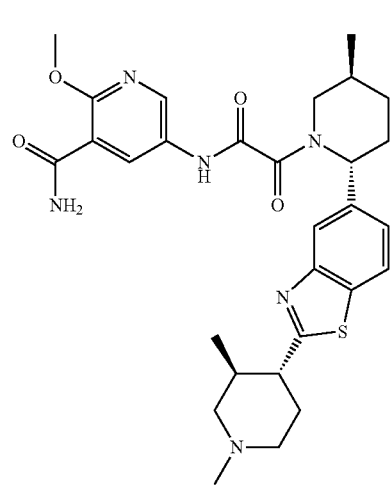 [SMILES: COc1ncc(NC(=O)C(=O)N2C[C@@H](C)CC[C@@H]2c2ccc3sc([C@@H]4CCN(C)C[C@H]4C)nc3c2)cc1C(N)=O]
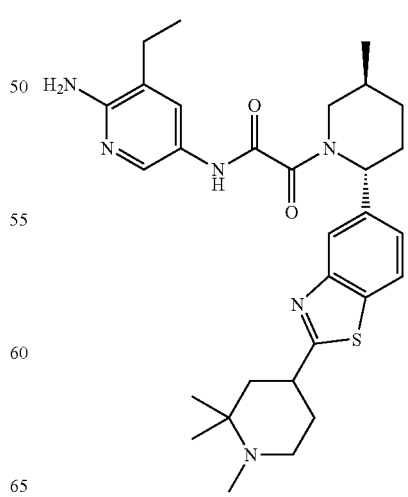

TABLE 5-continued
669
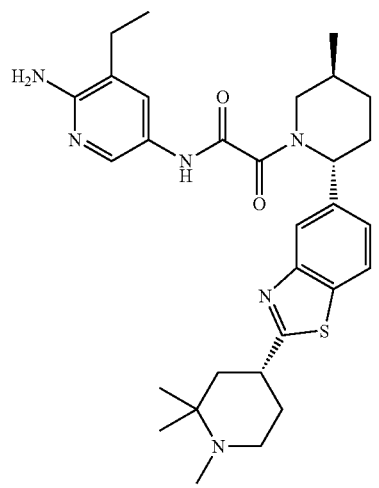 [SMILES: CCc1cc(NC(=O)C(=O)N2C[C@@H](C)CC[C@@H]2c2ccc3sc([C@@H]4CCN(C)C(C)(C)C4)nc3c2)cnc1N]
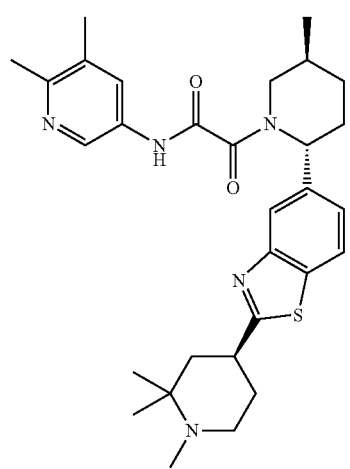 [SMILES: Cc1cc(NC(=O)C(=O)N2C[C@@H](C)CC[C@@H]2c2ccc3sc([C@H]4CCN(C)C(C)(C)C4)nc3c2)cnc1C]
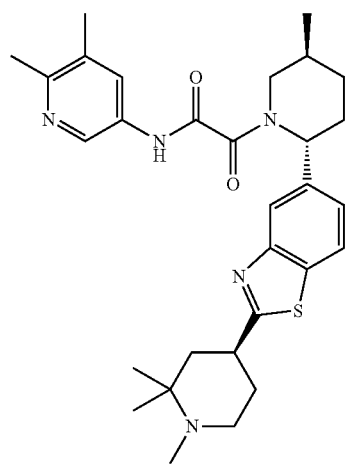 [SMILES: Cc1cc(NC(=O)C(=O)N2C[C@@H](C)CC[C@@H]2c2ccc3sc([C@H]4CCN(C)C(C)(C)C4)nc3c2)cnc1C]
TABLE 5-continued
670
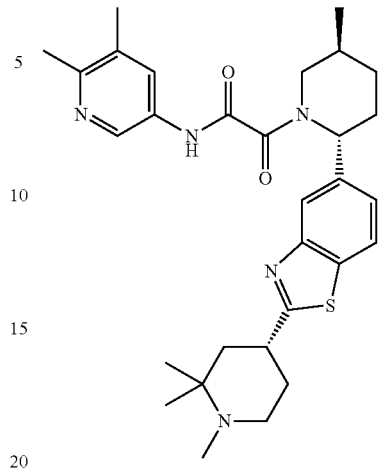
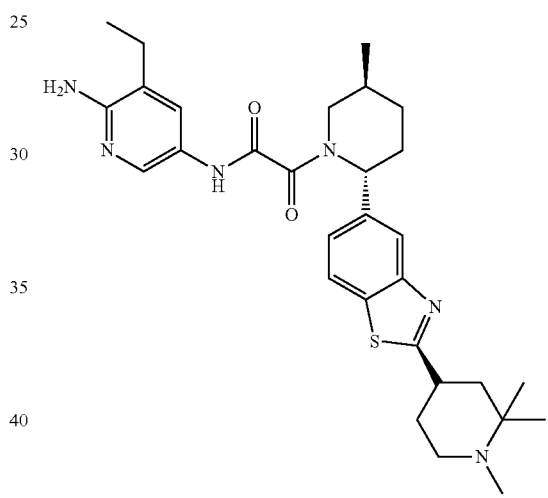
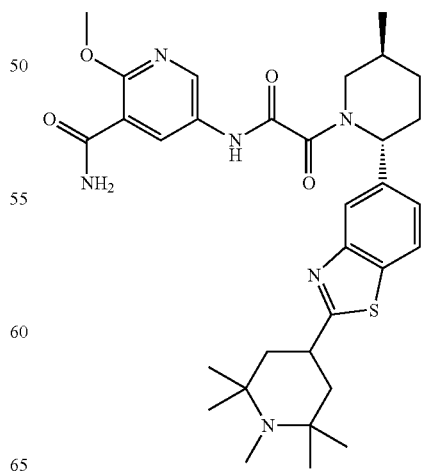

TABLE 5-continued
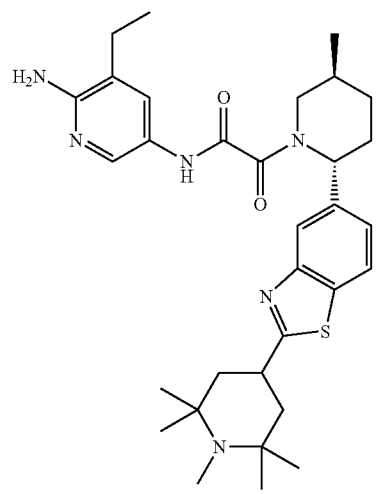 [SMILES: CCc1cc(NC(=O)C(=O)N2C[C@@H](C)CC[C@@H]2c2ccc3sc(C4CC(C)(C)N(C)C(C)(C)C4)nc3c2)cnc1N]
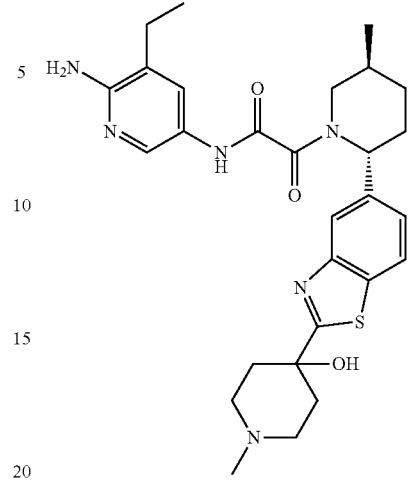
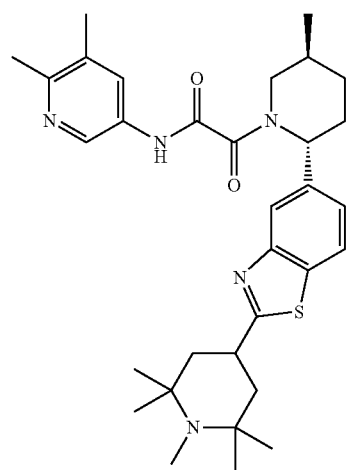 [SMILES: Cc1cc(NC(=O)C(=O)N2C[C@@H](C)CC[C@@H]2c2ccc3sc(C4CC(C)(C)N(C)C(C)(C)C4)nc3c2)cnc1C]
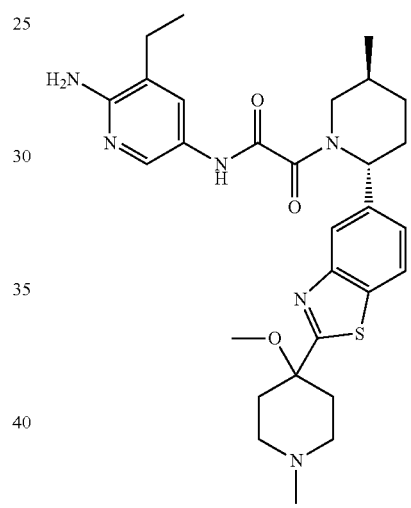
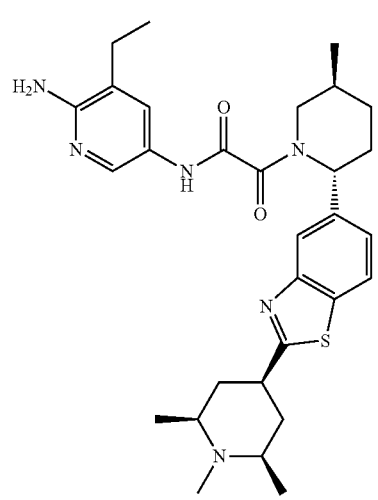 [SMILES: CCc1cc(NC(=O)C(=O)N2C[C@@H](C)CC[C@@H]2c2ccc3sc([C@H]4C[C@@H](C)N(C)[C@@H](C)C4)nc3c2)cnc1N]
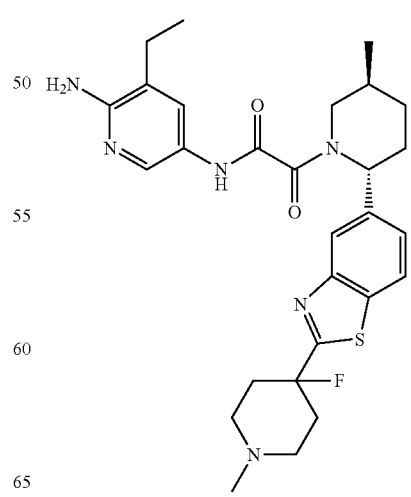

TABLE 5-continued
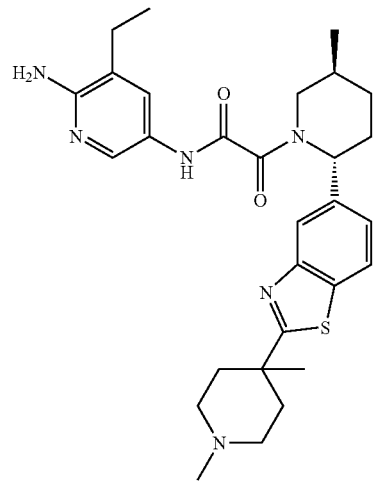 [SMILES: CCc1cc(NC(=O)C(=O)N2C[C@@H](C)CC[C@@H]2c2ccc3sc(C4(C)CCN(C)CC4)nc3c2)cnc1N]
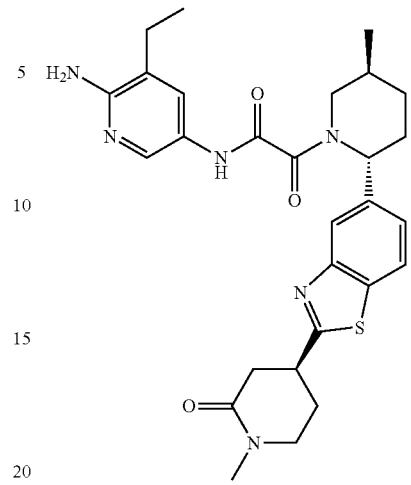
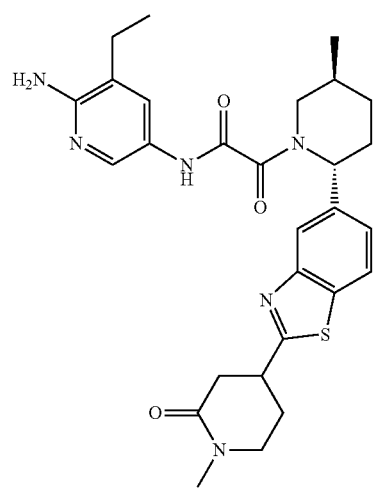 [SMILES: CCc1cc(NC(=O)C(=O)N2C[C@@H](C)CC[C@@H]2c2ccc3sc(C4CCN(C)C(=O)C4)nc3c2)cnc1N]
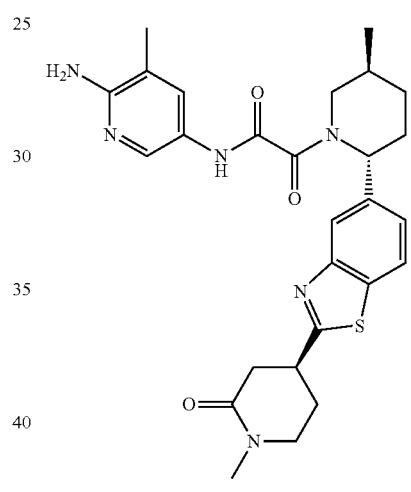
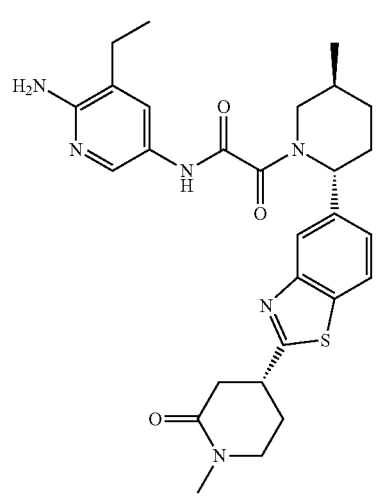 [SMILES: CCc1cc(NC(=O)C(=O)N2C[C@@H](C)CC[C@@H]2c2ccc3sc([C@@H]4CCN(C)C(=O)C4)nc3c2)cnc1N]
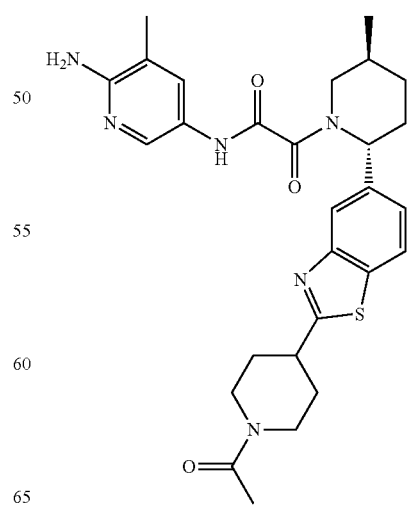

TABLE 5-continued
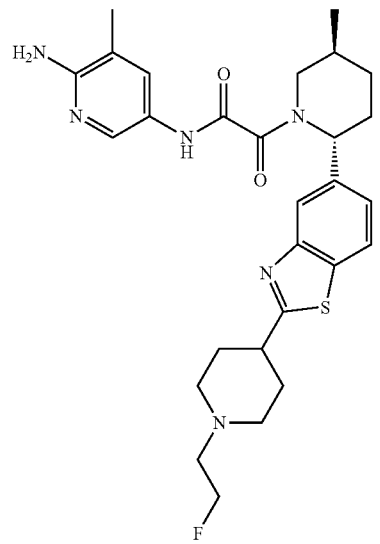 [SMILES: Cc1cc(NC(=O)C(=O)N2C[C@@H](C)CC[C@@H]2c2ccc3sc(C4CCN(CCF)CC4)nc3c2)cnc1N]
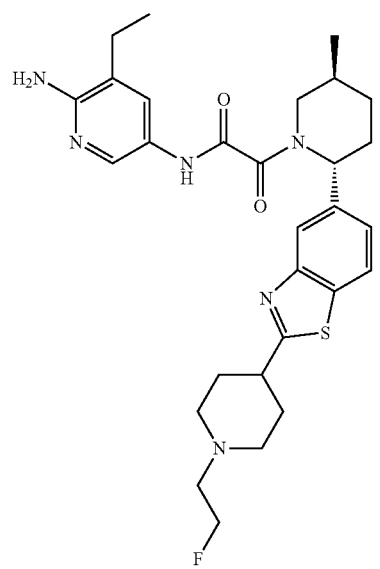 [SMILES: CCc1cc(NC(=O)C(=O)N2C[C@@H](C)CC[C@@H]2c2ccc3sc(C4CCN(CCF)CC4)nc3c2)cnc1N]
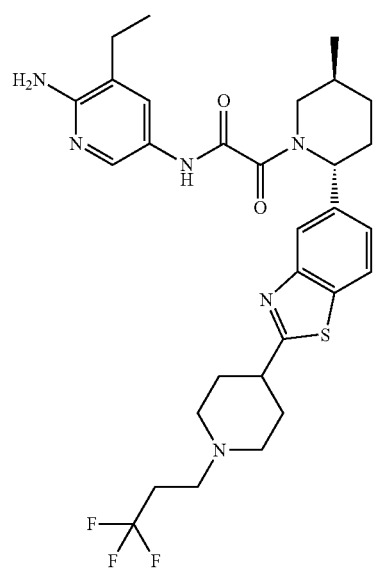 [SMILES: CCc1cc(NC(=O)C(=O)N2C[C@@H](C)CC[C@@H]2c2ccc3sc(C4CCN(CCC(F)(F)F)CC4)nc3c2)cnc1N]
TABLE 5-continued
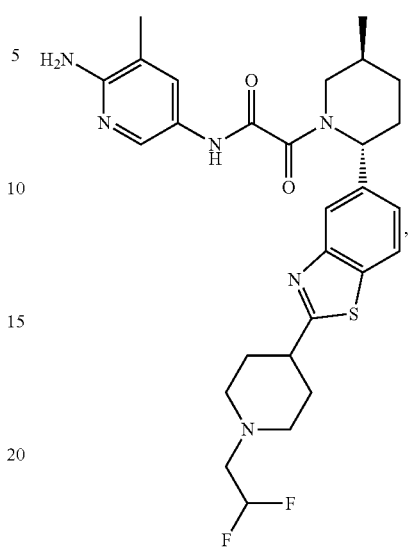
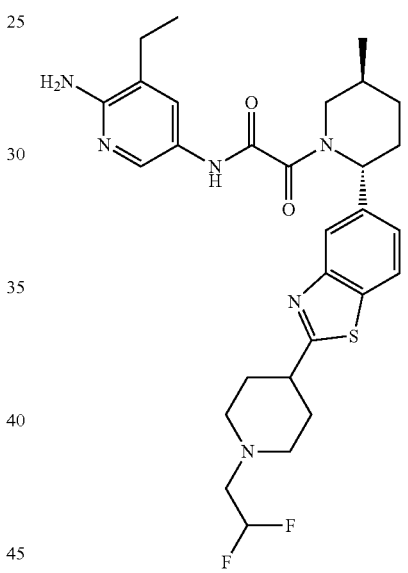
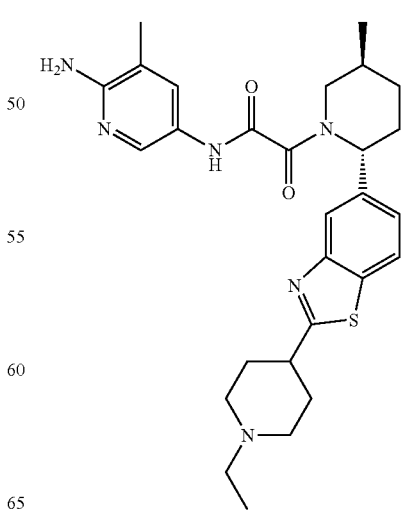

677
TABLE 5-continued
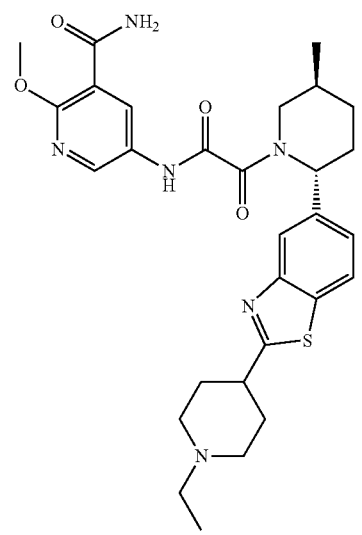 [SMILES: CCN1CCC(c2nc3cc([C@H]4CC[C@H](C)CN4C(=O)C(=O)Nc4cnc(OC)c(C(N)=O)c4)ccc3s2)CC1]
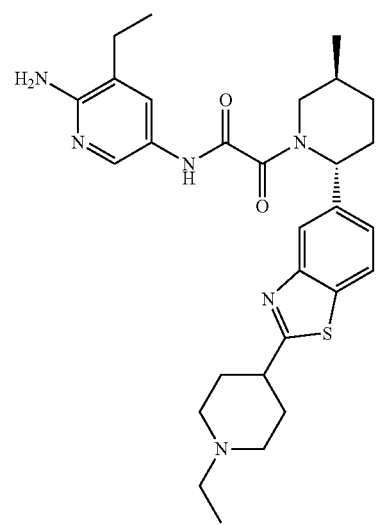 [SMILES: CCc1cc(NC(=O)C(=O)N2C[C@@H](C)CC[C@@H]2c2ccc3sc(C4CCN(CC)CC4)nc3c2)cnc1N]
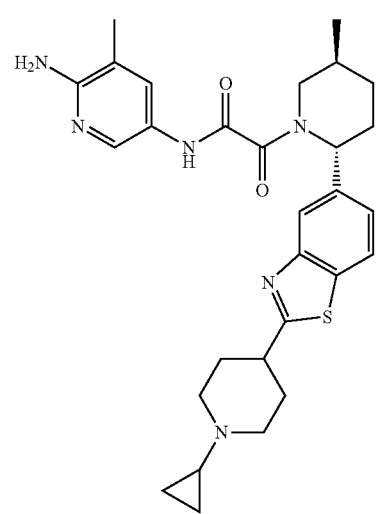 [SMILES: Cc1cc(NC(=O)C(=O)N2C[C@@H](C)CC[C@@H]2c2ccc3sc(C4CCN(C5CC5)CC4)nc3c2)cnc1N]
678
TABLE 5-continued
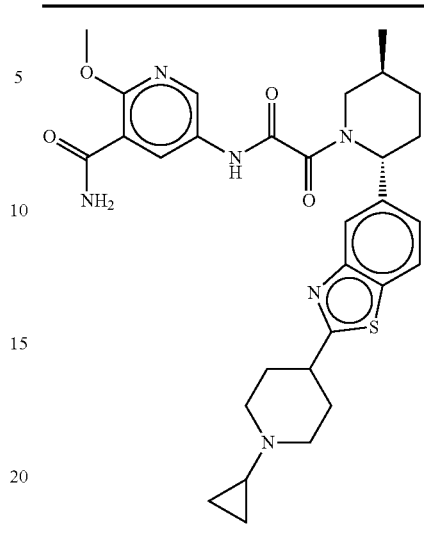
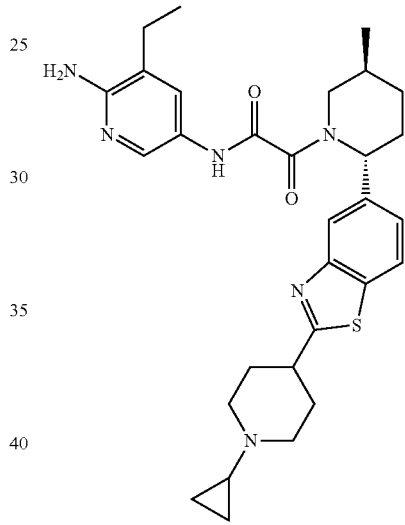
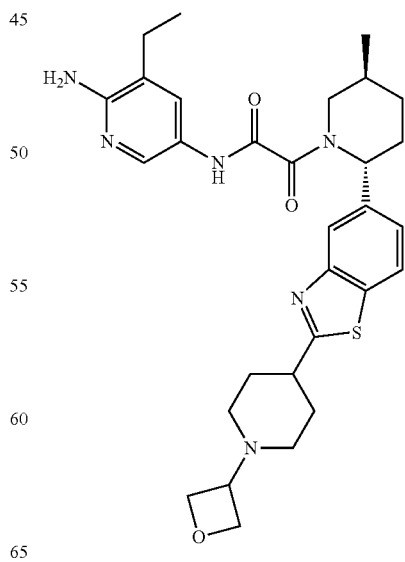

TABLE 5-continued
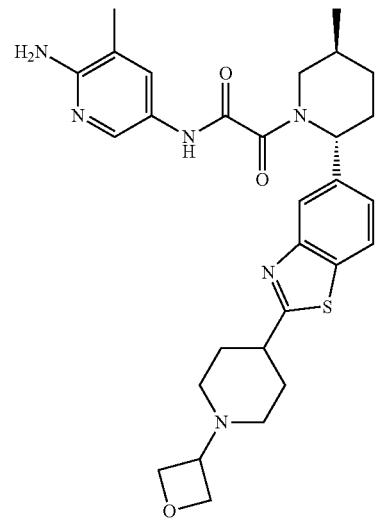 [SMILES: Cc1cc(NC(=O)C(=O)N2C[C@@H](C)CC[C@@H]2c2ccc3sc(C4CCN(C5COC5)CC4)nc3c2)cnc1N]
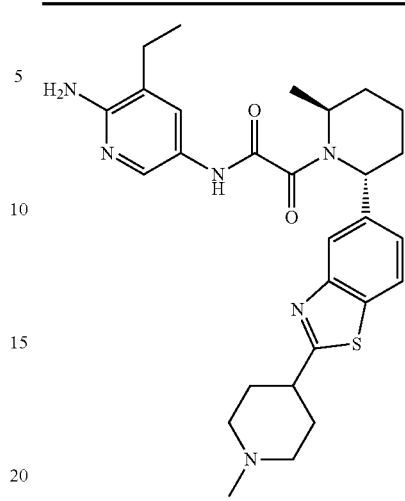
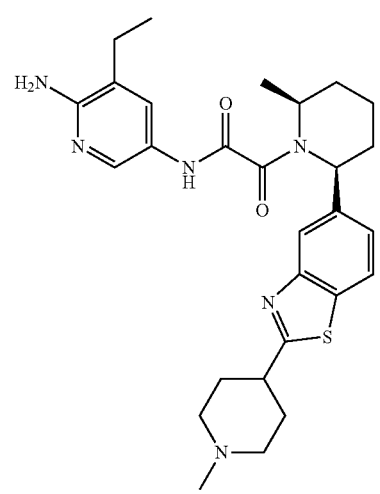 [SMILES: CCc1cc(NC(=O)C(=O)N2[C@@H](C)CCC[C@H]2c2ccc3sc(C4CCN(C)CC4)nc3c2)cnc1N]
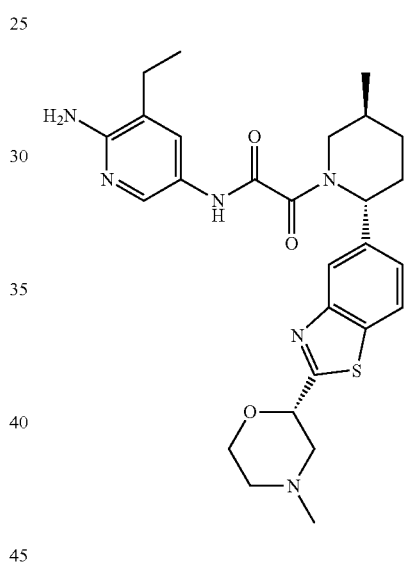
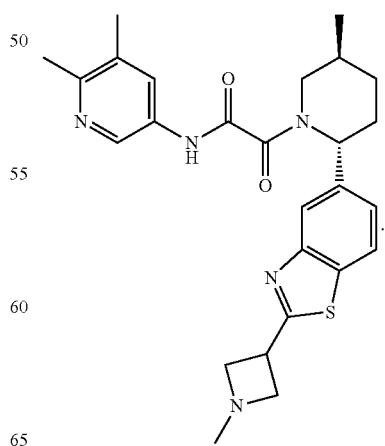

TABLE 5-continued
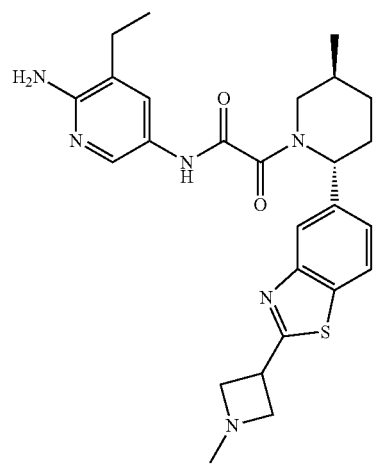 [SMILES: CCc1cc(NC(=O)C(=O)N2C[C@@H](C)CC[C@@H]2c2ccc3sc(C4CN(C)C4)nc3c2)cnc1N]
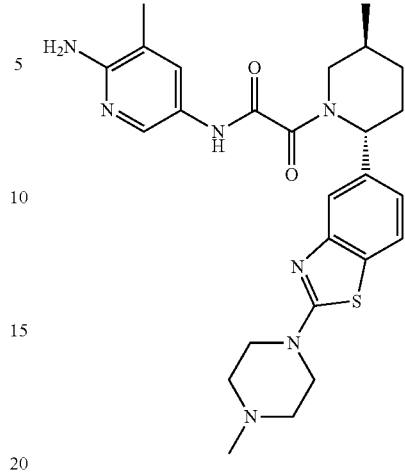
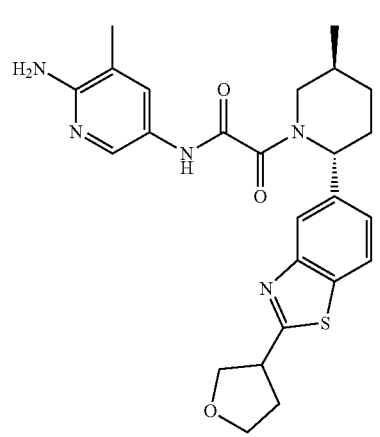 [SMILES: Cc1cc(NC(=O)C(=O)N2C[C@@H](C)CC[C@@H]2c2ccc3sc(C4CCOC4)nc3c2)cnc1N]
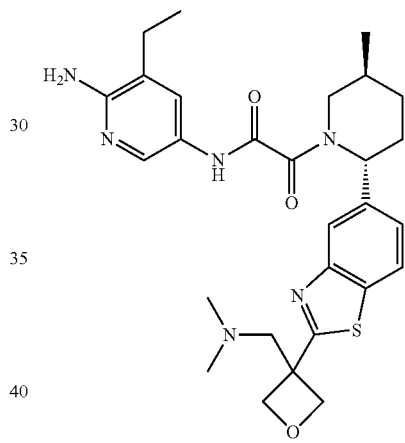
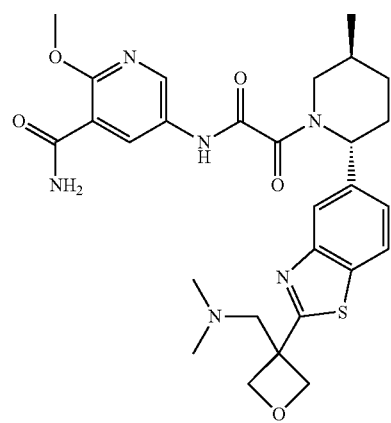 [SMILES: COc1ncc(NC(=O)C(=O)N2C[C@@H](C)CC[C@@H]2c2ccc3sc(C4(CN(C)C)COC4)nc3c2)cc1C(N)=O]
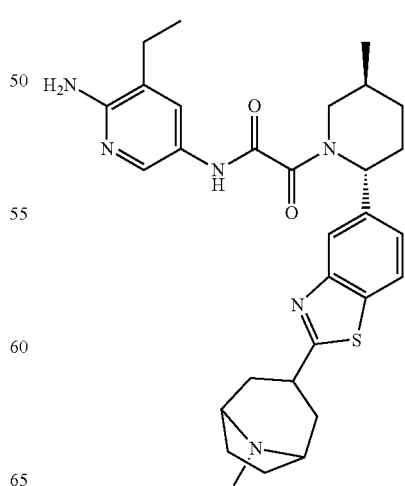

683
TABLE 5-continued
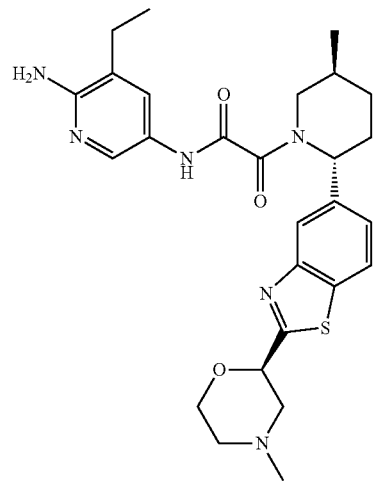 [SMILES: CCc1cc(NC(=O)C(=O)N2C[C@@H](C)CC[C@@H]2c2ccc3sc([C@H]4CN(C)CCO4)nc3c2)cnc1N]
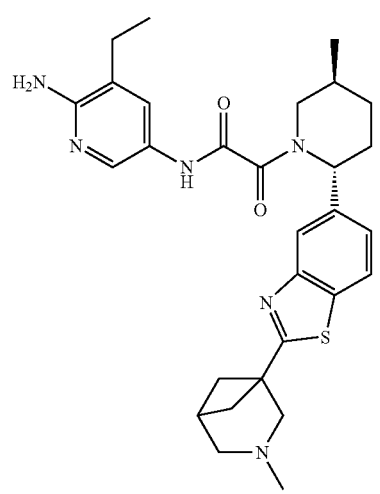 [SMILES: CCc1cc(NC(=O)C(=O)N2C[C@@H](C)CC[C@@H]2c2ccc3sc(C45CC(CN(C)C4)C5)nc3c2)cnc1N]
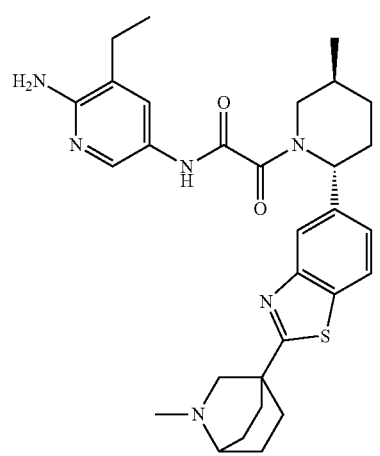 [SMILES: CCc1cc(NC(=O)C(=O)N2C[C@@H](C)CC[C@@H]2c2ccc3sc(C45CCC(CC4)N(C)C5)nc3c2)cnc1N]
684
TABLE 5-continued
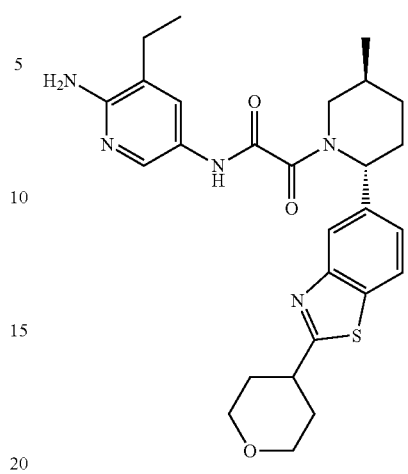
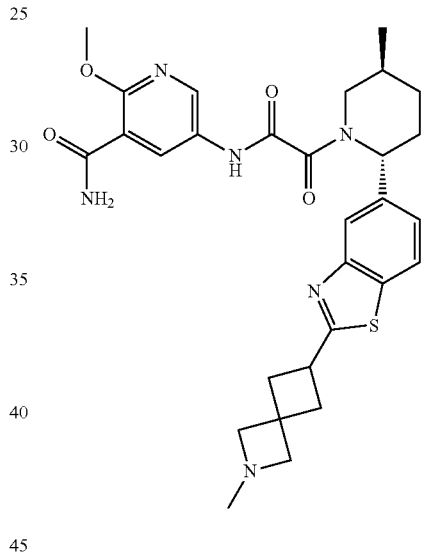
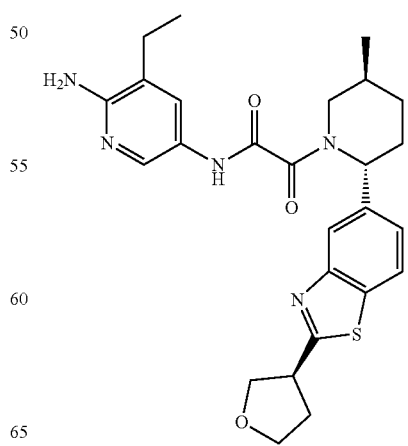

TABLE 5-continued
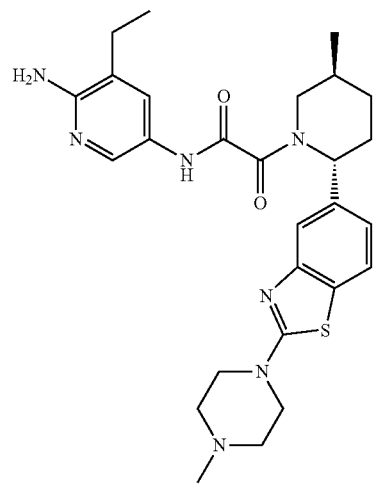 [SMILES: CCc1cc(NC(=O)C(=O)N2C[C@@H](C)CC[C@@H]2c2ccc3sc(N4CCN(C)CC4)nc3c2)cnc1N]
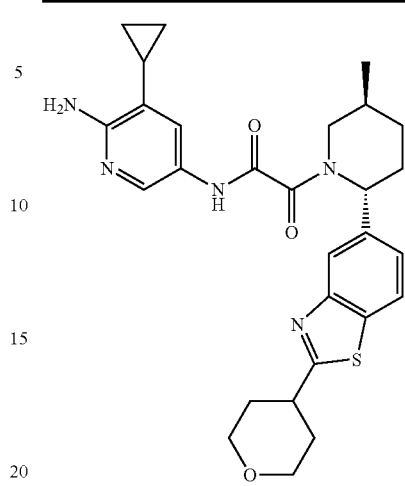
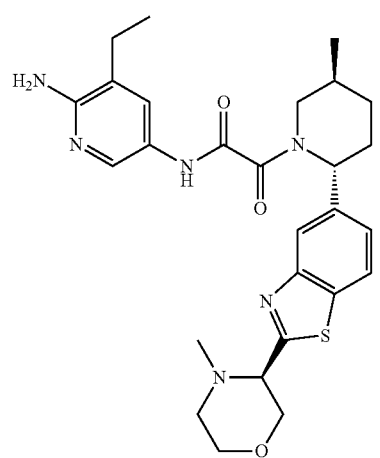 [SMILES: CCc1cc(NC(=O)C(=O)N2C[C@@H](C)CC[C@@H]2c2ccc3sc([C@H]4COCCN4C)nc3c2)cnc1N]
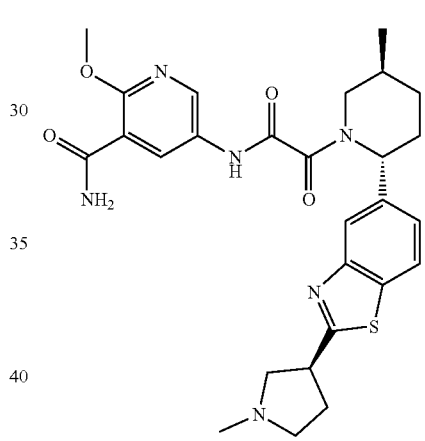
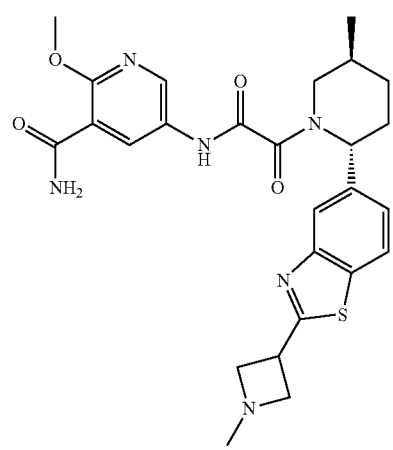 [SMILES: COc1ncc(NC(=O)C(=O)N2C[C@@H](C)CC[C@@H]2c2ccc3sc(C4CN(C)C4)nc3c2)cc1C(N)=O]
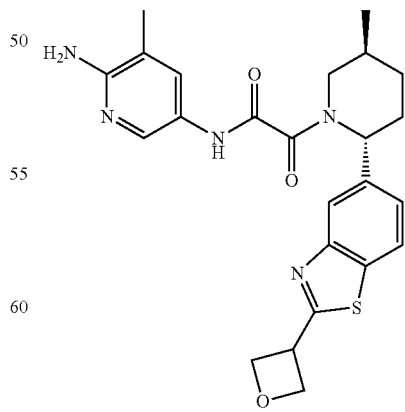

| 687 | 688 |
|---|---|
| TABLE 5-continued | TABLE 5-continued |
| 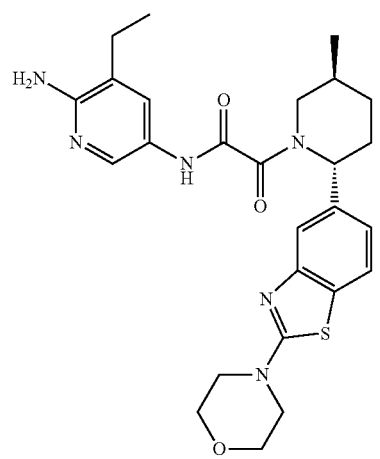 [SMILES: CCc1cc(NC(=O)C(=O)N2C[C@@H](C)CC[C@@H]2c2ccc3sc(N4CCOCC4)nc3c2)cnc1N] | 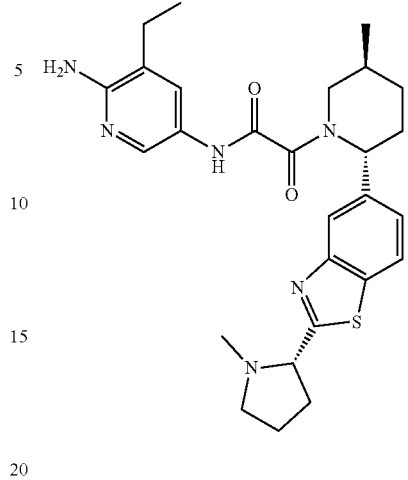 |
| 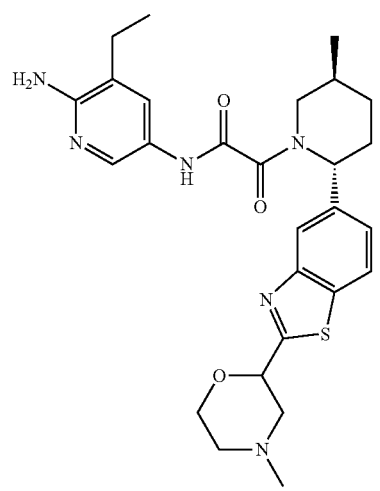 [SMILES: CCc1cc(NC(=O)C(=O)N2C[C@@H](C)CC[C@@H]2c2ccc3sc(C4CN(C)CCO4)nc3c2)cnc1N] | 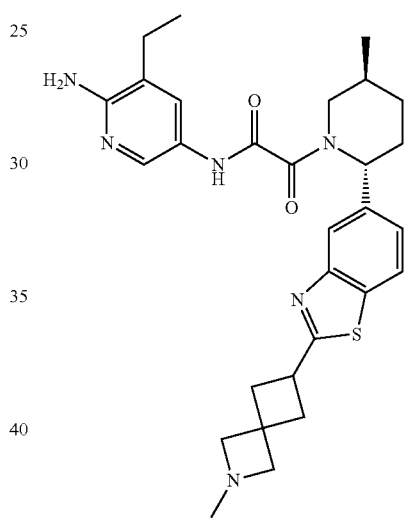 |
| 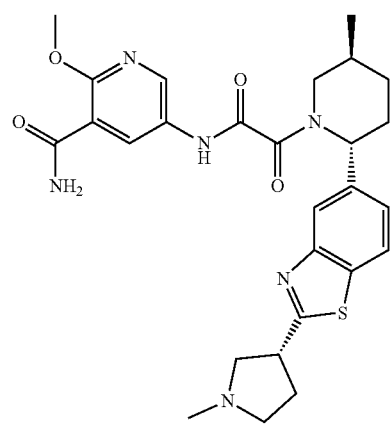 [SMILES: COc1ncc(NC(=O)C(=O)N2C[C@@H](C)CC[C@@H]2c2ccc3sc([C@@H]4CCN(C)C4)nc3c2)cc1C(N)=O] | 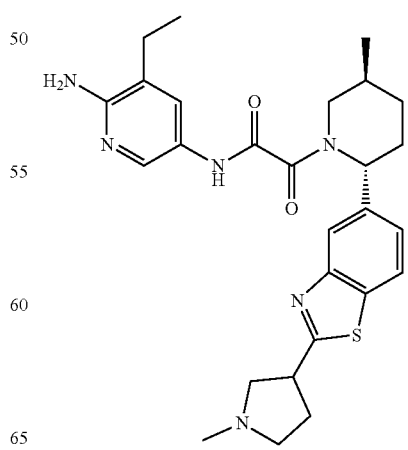 |

| 689 | 690 |
|---|---|
| TABLE 5-continued | TABLE 5-continued |
| 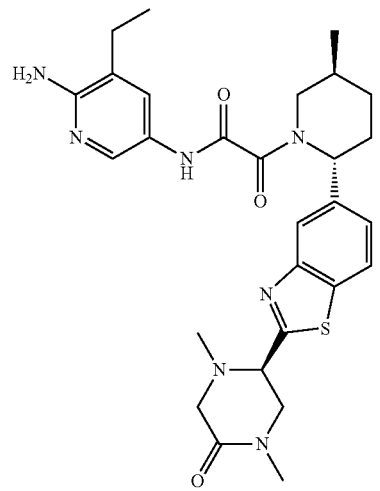 [SMILES: CCc1cc(NC(=O)C(=O)N2C[C@@H](C)CC[C@@H]2c2ccc3sc([C@H]4CN(C)C(=O)CN4C)nc3c2)cnc1N] | 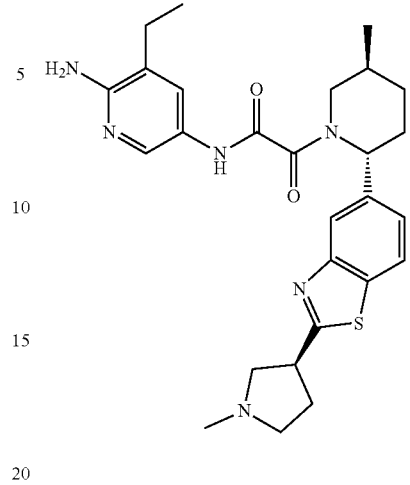 |
| 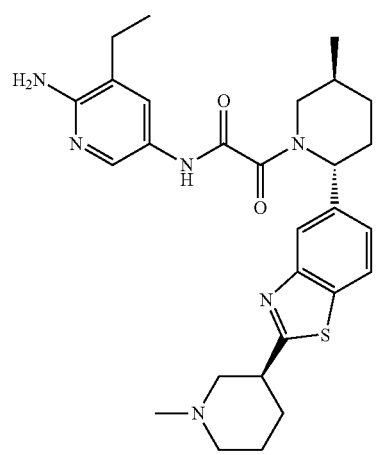 [SMILES: CCc1cc(NC(=O)C(=O)N2C[C@@H](C)CC[C@@H]2c2ccc3sc([C@H]4CCCN(C)C4)nc3c2)cnc1N] | 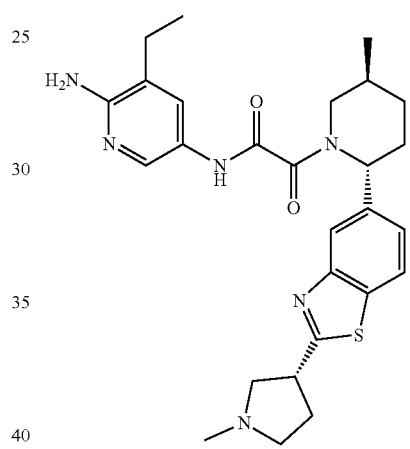 |
| 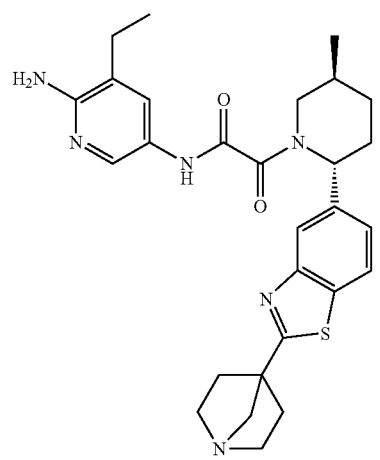 [SMILES: CCc1cc(NC(=O)C(=O)N2C[C@@H](C)CC[C@@H]2c2ccc3sc(C45CCN(CC4)C5)nc3c2)cnc1N] | 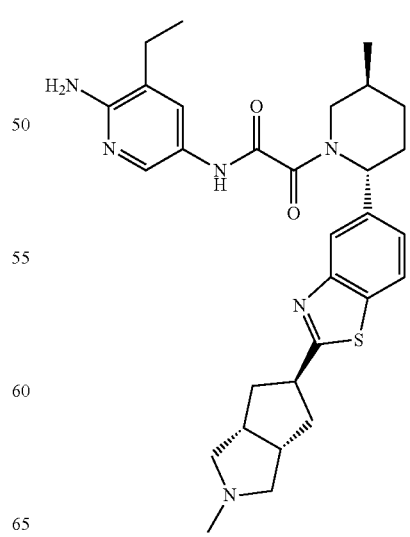 |

691
TABLE 5-continued
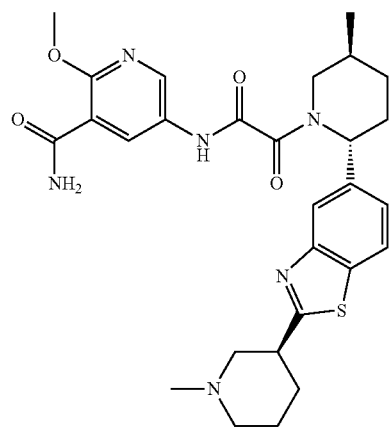 [SMILES: COc1ncc(NC(=O)C(=O)N2C[C@@H](C)CC[C@@H]2c2ccc3sc([C@H]4CCCN(C)C4)nc3c2)cc1C(N)=O]
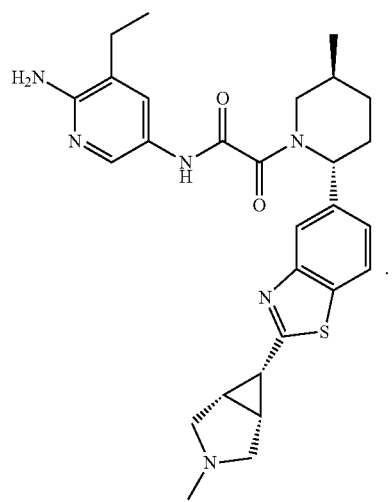 [SMILES: CCc1cc(NC(=O)C(=O)N2C[C@@H](C)CC[C@@H]2c2ccc3sc([C@@H]4[C@@H]5CN(C)C[C@@H]54)nc3c2)cnc1N]
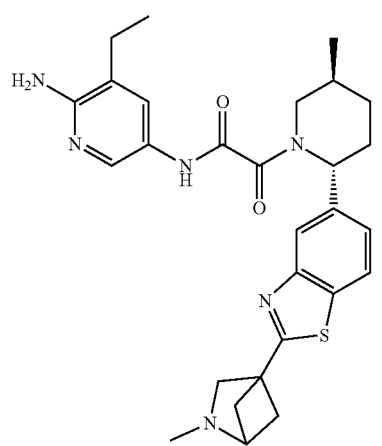 [SMILES: CCc1cc(NC(=O)C(=O)N2C[C@@H](C)CC[C@@H]2c2ccc3sc(C45CC(C4)N(C)C5)nc3c2)cnc1N]
692
TABLE 5-continued
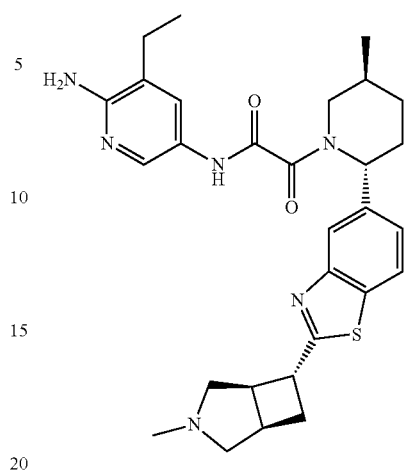
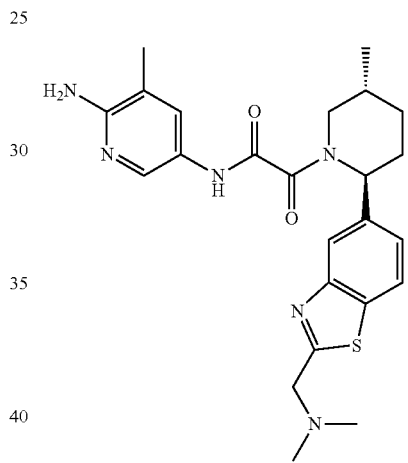
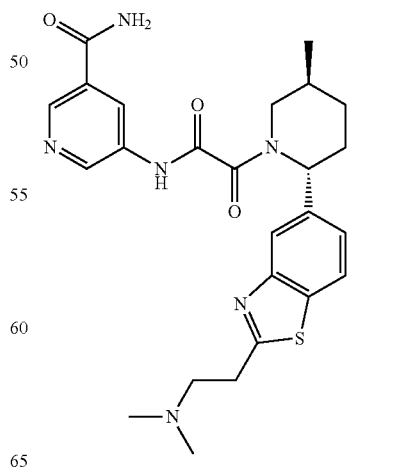

TABLE 5-continued
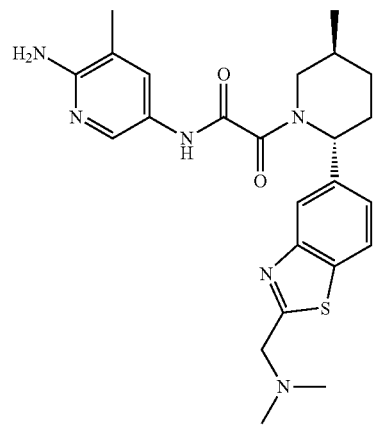 [SMILES: Cc1cc(NC(=O)C(=O)N2C[C@@H](C)CC[C@@H]2c2ccc3sc(CN(C)C)nc3c2)cnc1N]
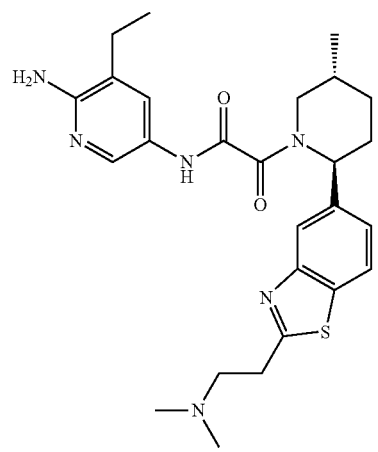 [SMILES: CCc1cc(NC(=O)C(=O)N2C[C@H](C)CC[C@H]2c2ccc3sc(CCN(C)C)nc3c2)cnc1N]
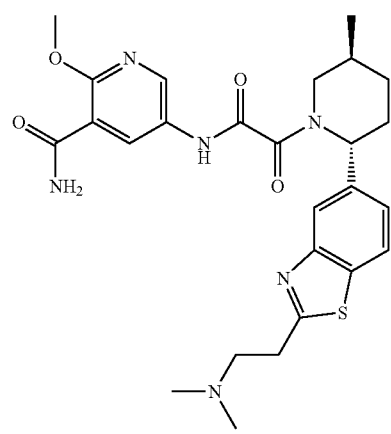 [SMILES: COc1ncc(NC(=O)C(=O)N2C[C@@H](C)CC[C@@H]2c2ccc3sc(CCN(C)C)nc3c2)cc1C(N)=O]
TABLE 5-continued
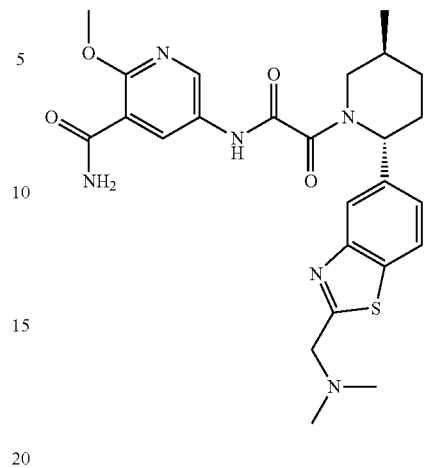
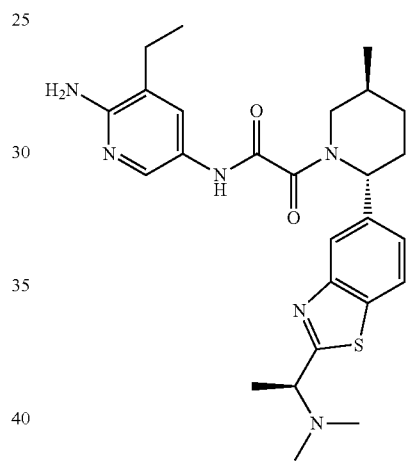
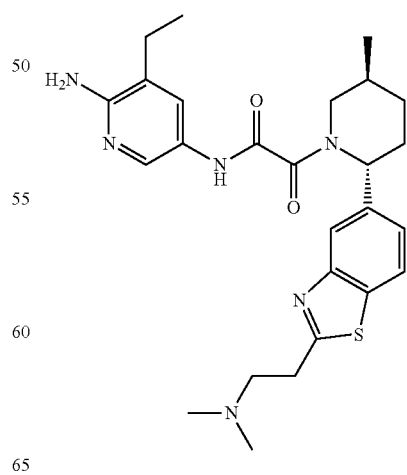

TABLE 5-continued
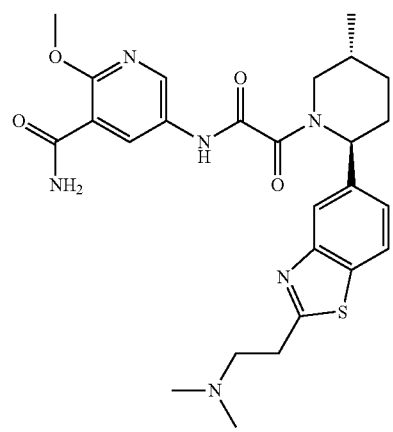 [SMILES: COc1ncc(NC(=O)C(=O)N2C[C@H](C)CC[C@H]2c2ccc3sc(CCN(C)C)nc3c2)cc1C(N)=O]
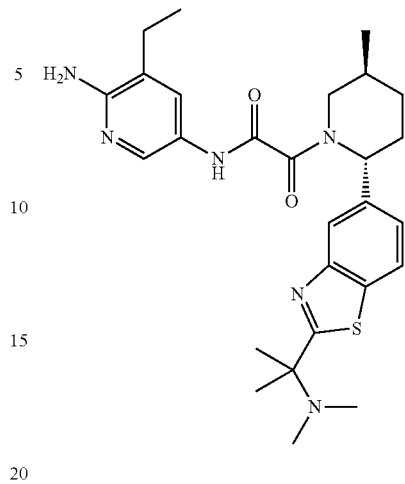
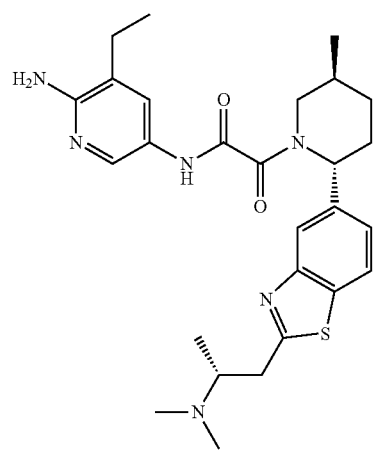 [SMILES: CCc1cc(NC(=O)C(=O)N2C[C@@H](C)CC[C@@H]2c2ccc3sc(C[C@@H](C)N(C)C)nc3c2)cnc1N]
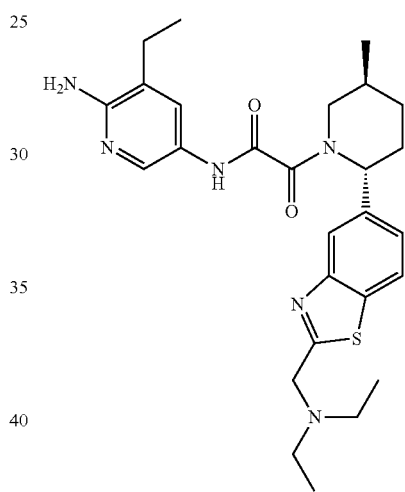
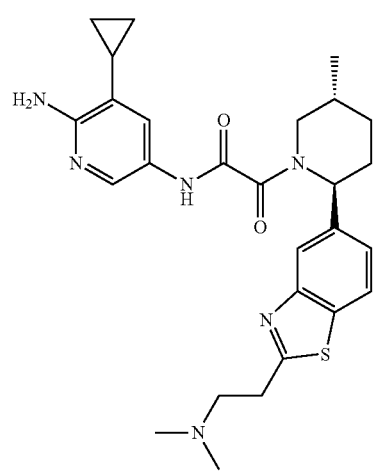 [SMILES: C[C@@H]1CC[C@@H](c2ccc3sc(CCN(C)C)nc3c2)N(C(=O)C(=O)Nc2cnc(N)c(C3CC3)c2)C1]
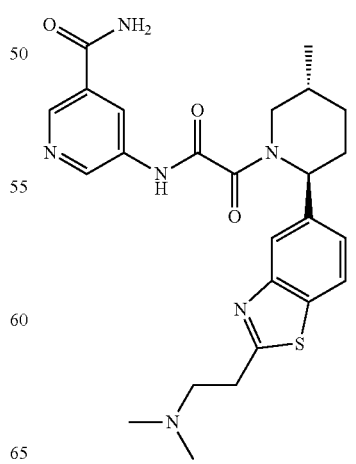

TABLE 5-continued
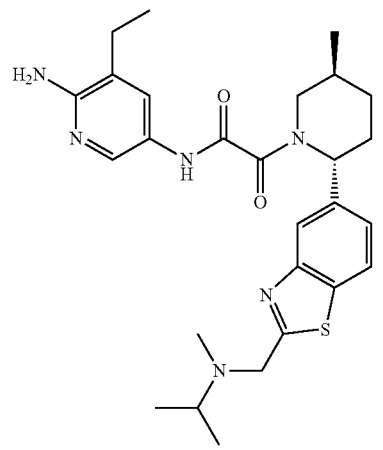 [SMILES: CCc1cc(NC(=O)C(=O)N2C[C@@H](C)CC[C@@H]2c2ccc3sc(CN(C)C(C)C)nc3c2)cnc1N]
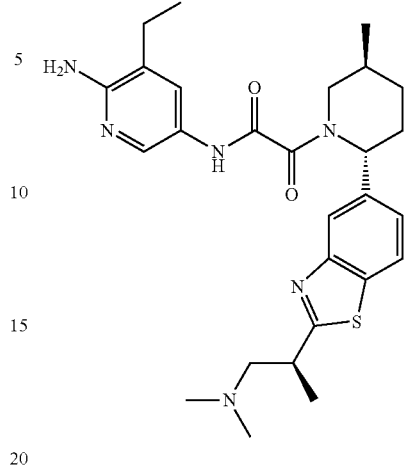
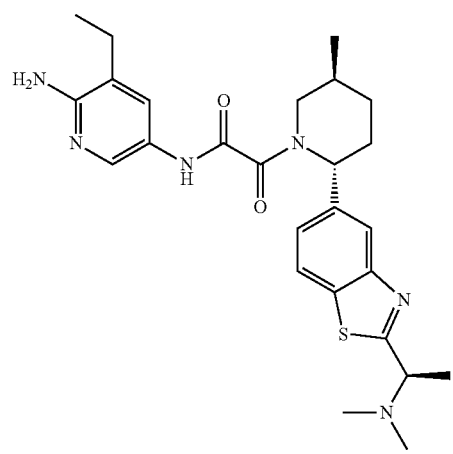 [SMILES: CCc1cc(NC(=O)C(=O)N2C[C@@H](C)CC[C@@H]2c2ccc3sc([C@@H](C)N(C)C)nc3c2)cnc1N]
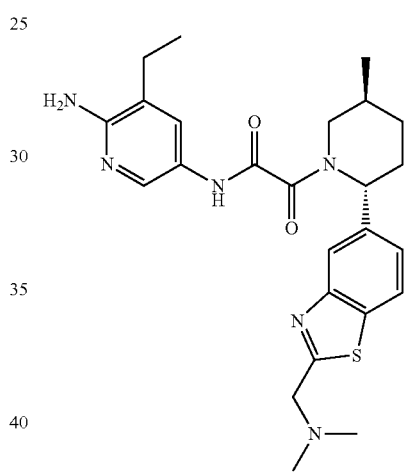
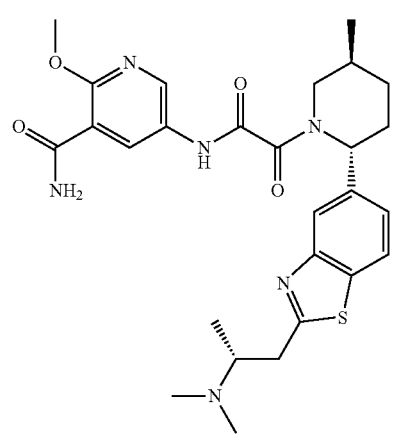 [SMILES: COc1ncc(NC(=O)C(=O)N2C[C@@H](C)CC[C@@H]2c2ccc3sc(C[C@@H](C)N(C)C)nc3c2)cc1C(N)=O]
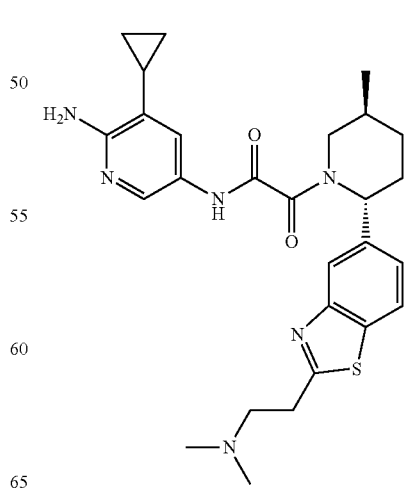

| 699 | 700 |
|---|---|
| TABLE 5-continued | TABLE 5-continued |
| 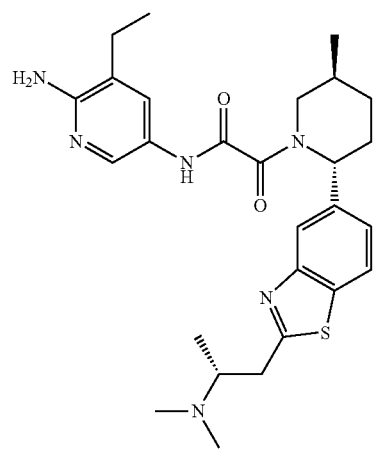 [SMILES: CCc1cc(NC(=O)C(=O)N2C[C@@H](C)CC[C@@H]2c2ccc3sc(C[C@@H](C)N(C)C)nc3c2)cnc1N] | 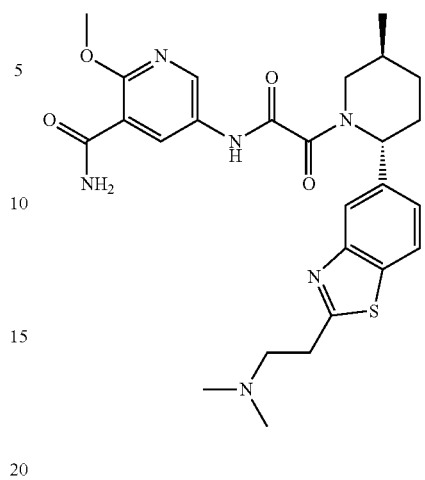 |
| 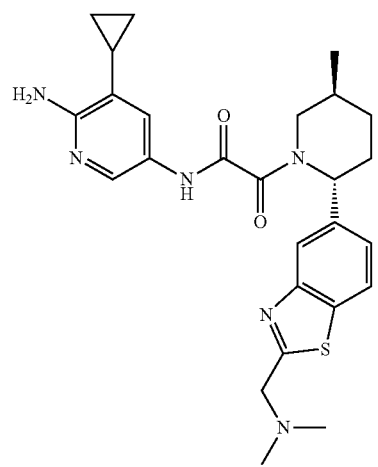 [SMILES: C[C@H]1CC[C@H](c2ccc3sc(CN(C)C)nc3c2)N(C(=O)C(=O)Nc2cnc(N)c(C3CC3)c2)C1] | 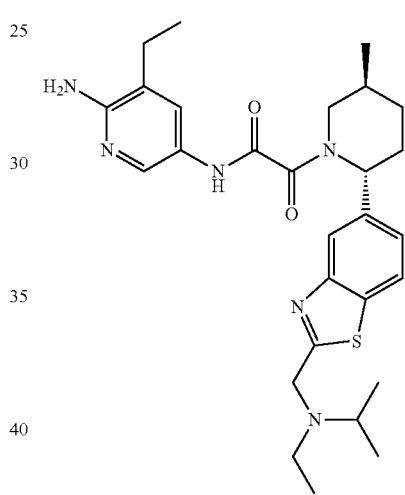 |
| 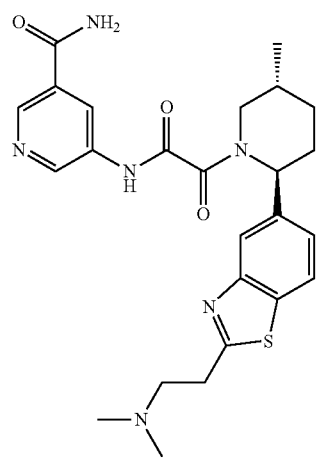 [SMILES: C[C@@H]1CC[C@@H](c2ccc3sc(CCN(C)C)nc3c2)N(C(=O)C(=O)Nc2cncc(C(N)=O)c2)C1] | 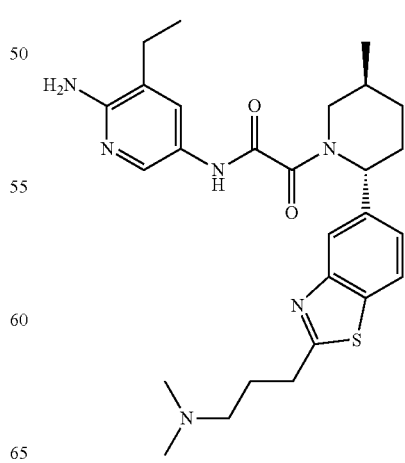 |

TABLE 5-continued
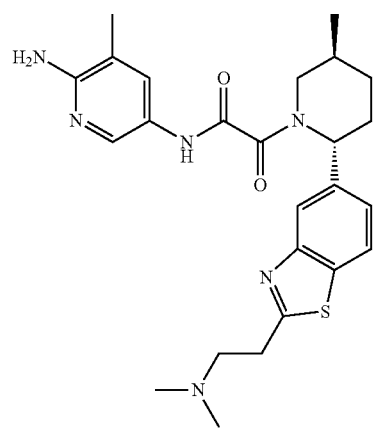 [SMILES: Cc1cc(NC(=O)C(=O)N2C[C@@H](C)CC[C@@H]2c2ccc3sc(CCN(C)C)nc3c2)cnc1N]
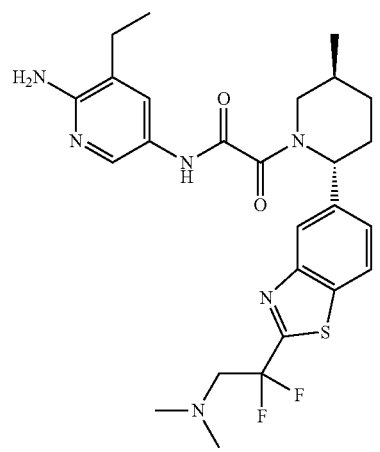 [SMILES: CCc1cc(NC(=O)C(=O)N2C[C@@H](C)CC[C@@H]2c2ccc3sc(C(F)(F)CN(C)C)nc3c2)cnc1N]
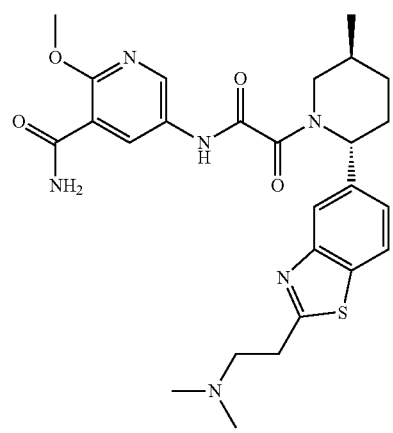 [SMILES: COc1ncc(NC(=O)C(=O)N2C[C@@H](C)CC[C@@H]2c2ccc3sc(CCN(C)C)nc3c2)cc1C(N)=O]
TABLE 5-continued
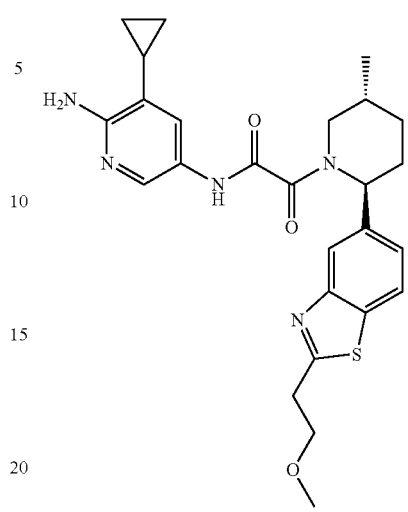
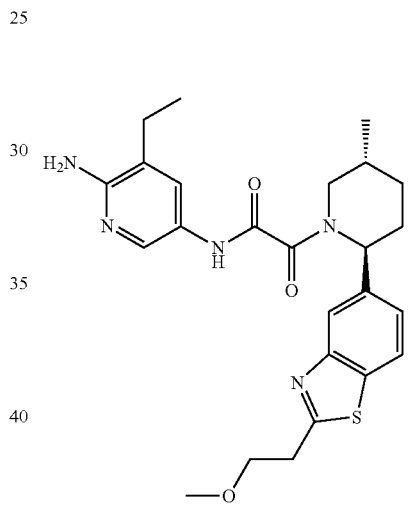
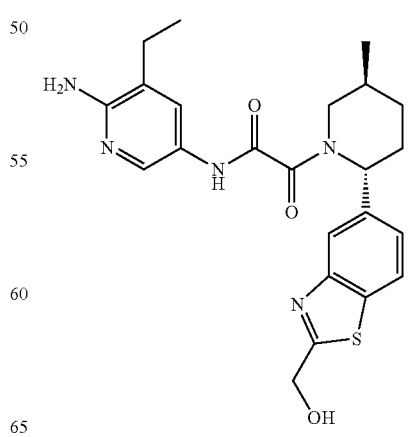

TABLE 5-continued
703
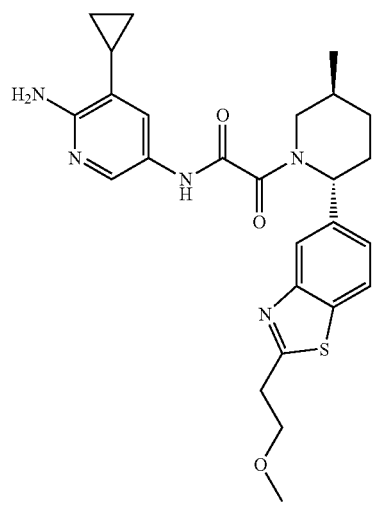 [SMILES: COCCc1nc2cc([C@H]3CC[C@H](C)CN3C(=O)C(=O)Nc3cnc(N)c(C4CC4)c3)ccc2s1]
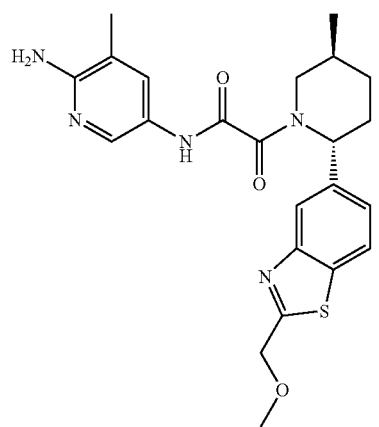 [SMILES: COCc1nc2cc([C@H]3CC[C@H](C)CN3C(=O)C(=O)Nc3cnc(N)c(C)c3)ccc2s1]
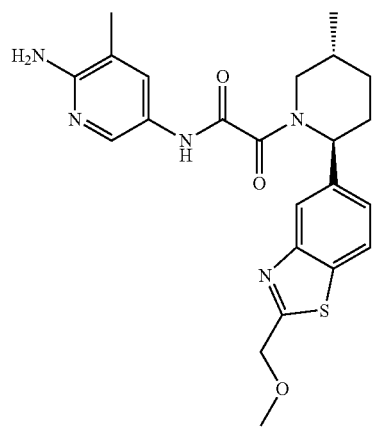 [SMILES: COCc1nc2cc([C@@H]3CC[C@@H](C)CN3C(=O)C(=O)Nc3cnc(N)c(C)c3)ccc2s1]
TABLE 5-continued
704
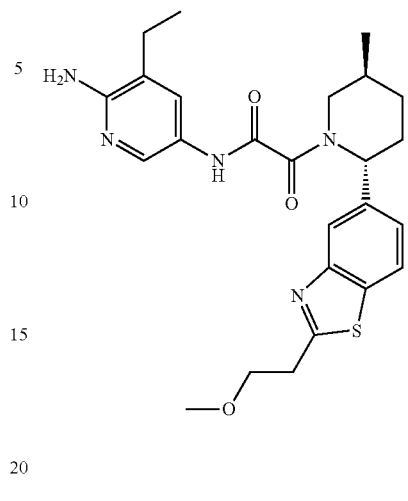
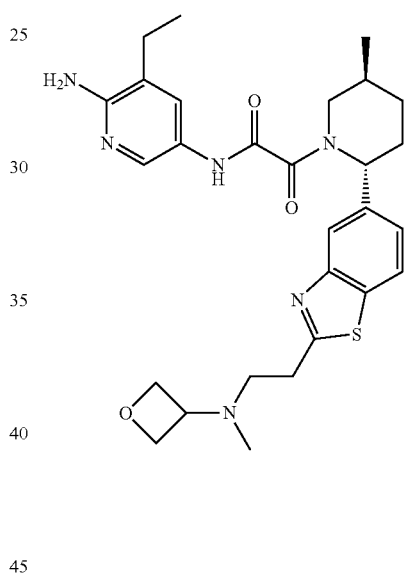
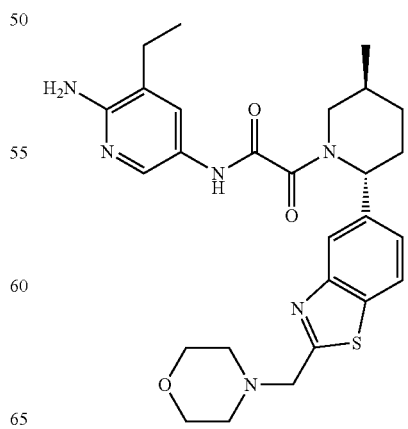

TABLE 5-continued
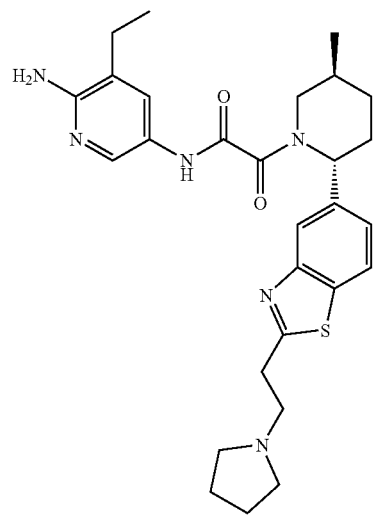 [SMILES: CCc1cc(NC(=O)C(=O)N2C[C@@H](C)CC[C@@H]2c2ccc3sc(CCN4CCCC4)nc3c2)cnc1N]
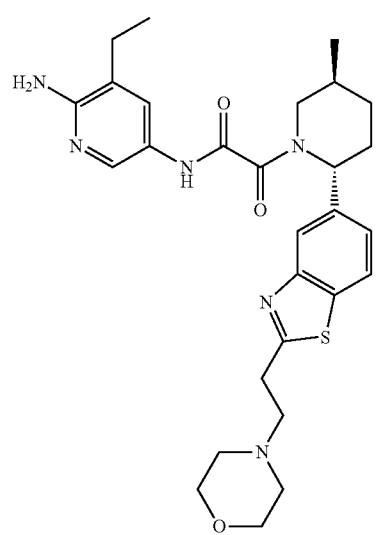 [SMILES: CCc1cc(NC(=O)C(=O)N2C[C@@H](C)CC[C@@H]2c2ccc3sc(CCN4CCOCC4)nc3c2)cnc1N]
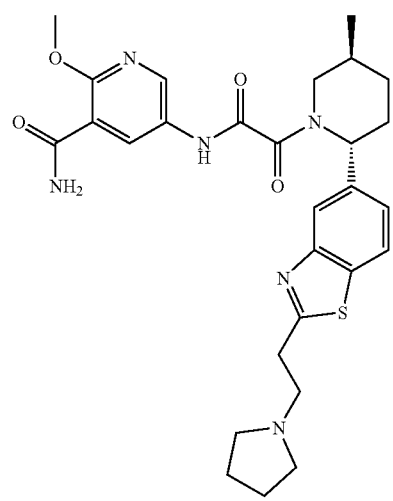 [SMILES: COc1ncc(NC(=O)C(=O)N2C[C@@H](C)CC[C@@H]2c2ccc3sc(CCN4CCCC4)nc3c2)cc1C(N)=O]
TABLE 5-continued
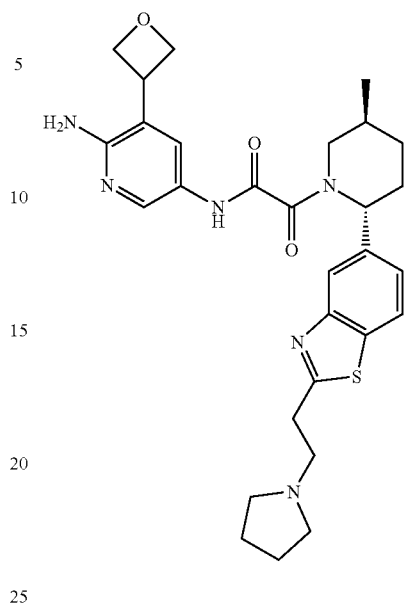
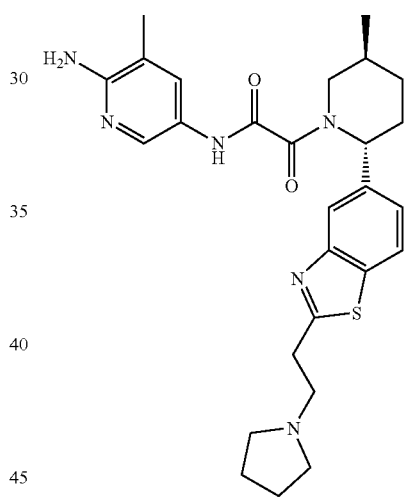
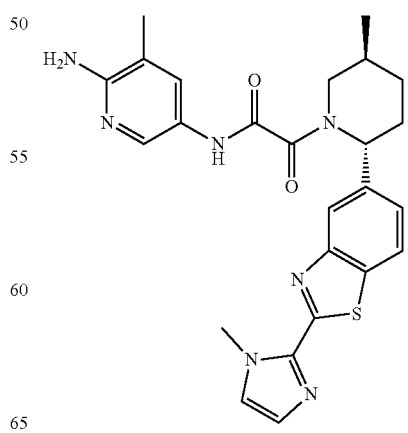

TABLE 5-continued
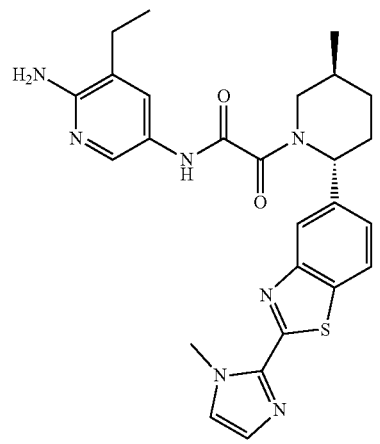 [SMILES: CCc1cc(NC(=O)C(=O)N2C[C@@H](C)CC[C@@H]2c2ccc3sc(-c4nccn4C)nc3c2)cnc1N]
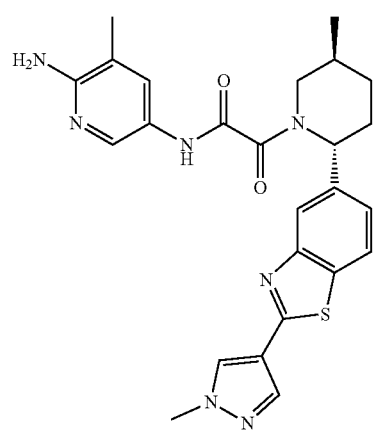 [SMILES: Cc1cc(NC(=O)C(=O)N2C[C@@H](C)CC[C@@H]2c2ccc3sc(-c4cnn(C)c4)nc3c2)cnc1N]
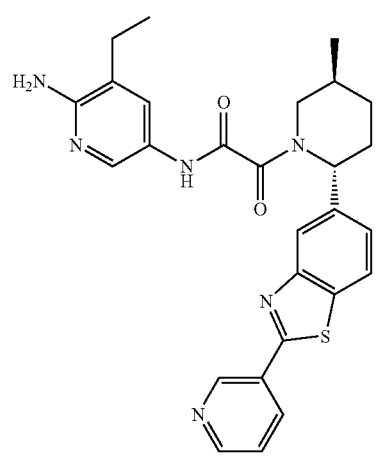 [SMILES: CCc1cc(NC(=O)C(=O)N2C[C@@H](C)CC[C@@H]2c2ccc3sc(-c4cccnc4)nc3c2)cnc1N]
TABLE 5-continued
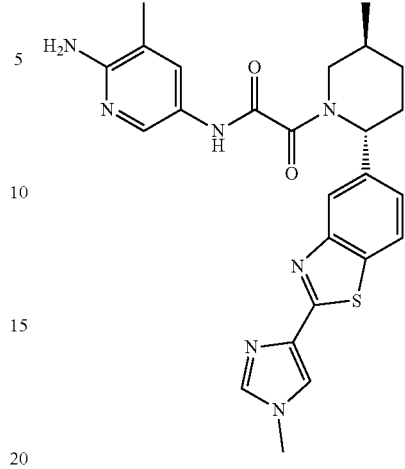
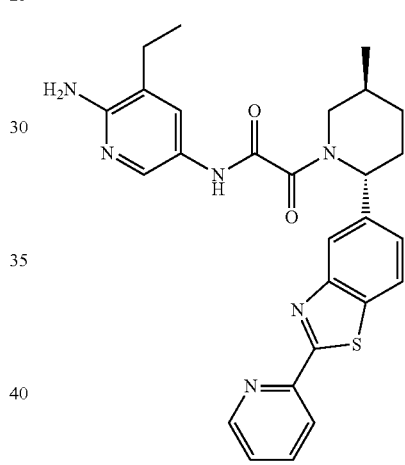

TABLE 5-continued
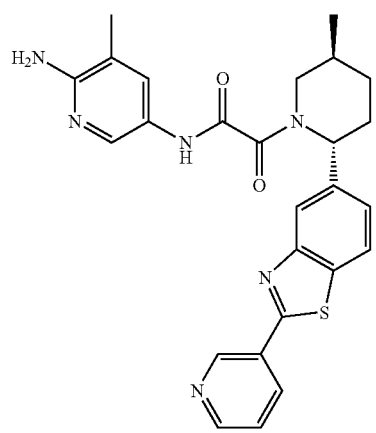 [SMILES: Cc1cc(NC(=O)C(=O)N2C[C@@H](C)CC[C@@H]2c2ccc3sc(-c4cccnc4)nc3c2)cnc1N]
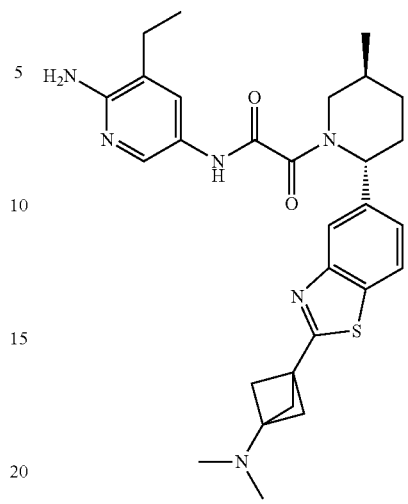
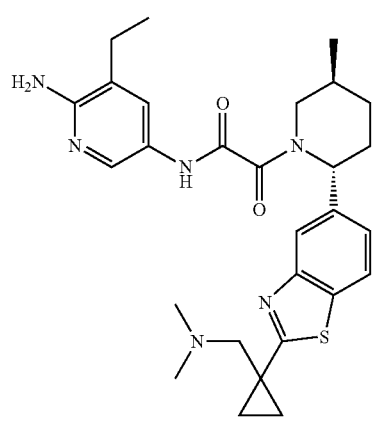 [SMILES: CCc1cc(NC(=O)C(=O)N2C[C@@H](C)CC[C@@H]2c2ccc3sc(C4(CN(C)C)CC4)nc3c2)cnc1N]
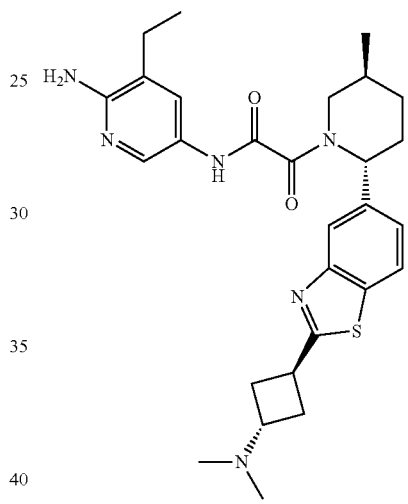
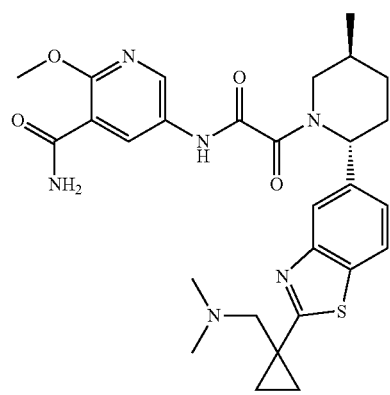 [SMILES: COc1ncc(NC(=O)C(=O)N2C[C@@H](C)CC[C@@H]2c2ccc3sc(C4(CN(C)C)CC4)nc3c2)cc1C(N)=O]
or a pharmaceutically acceptable salt thereof.
In yet another embodiment, the Type II PRMT5 inhibitor is selected from the group consisting of a compound from Table 6.
TABLE 6
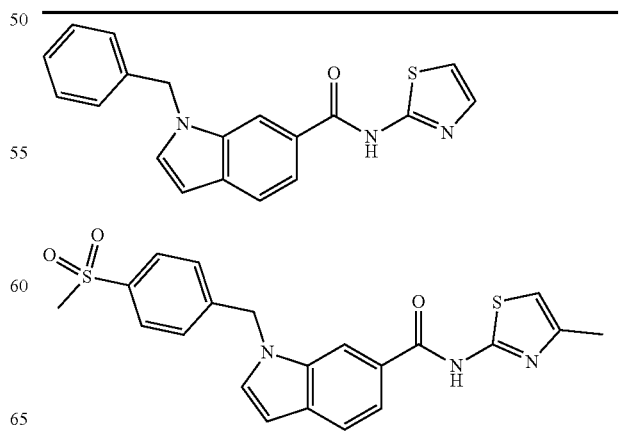

711
TABLE 6-continued
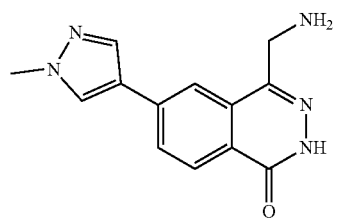 [SMILES: Cn1cc(-c2ccc3c(=O)[nH]nc(CN)c3c2)cn1]
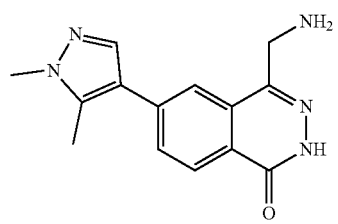 [SMILES: Cc1c(-c2ccc3c(=O)[nH]nc(CN)c3c2)cnn1C]
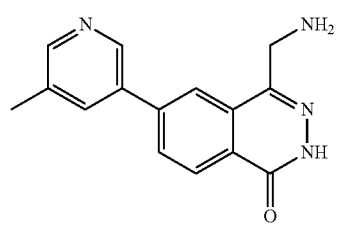 [SMILES: Cc1cncc(-c2ccc3c(=O)[nH]nc(CN)c3c2)c1]
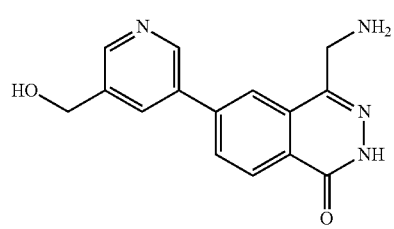 [SMILES: NCc1n[nH]c(=O)c2ccc(-c3cncc(CO)c3)cc12]
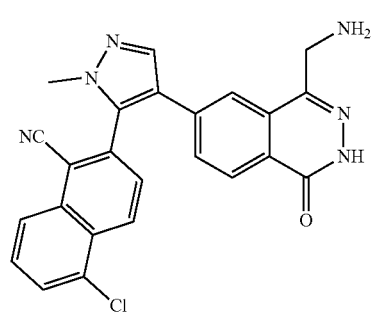 [SMILES: Cn1ncc(-c2ccc3c(=O)[nH]nc(CN)c3c2)c1-c1ccc2c(Cl)cccc2c1C#N]
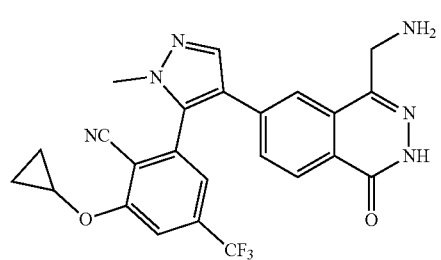 [SMILES: Cn1ncc(-c2ccc3c(=O)[nH]nc(CN)c3c2)c1-c1cc(C(F)(F)F)cc(OC2CC2)c1C#N]
712
TABLE 6-continued
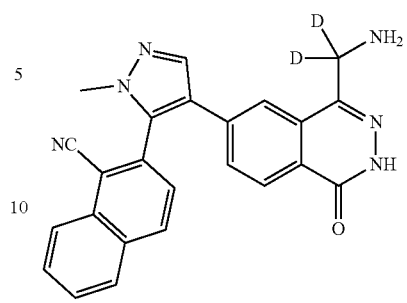
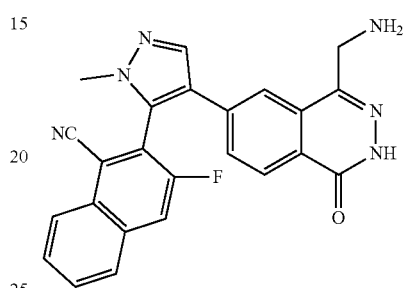
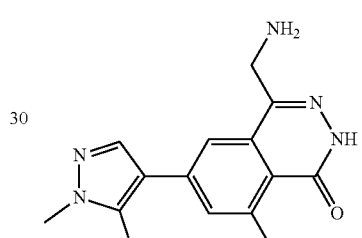
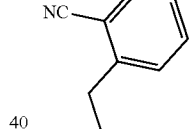
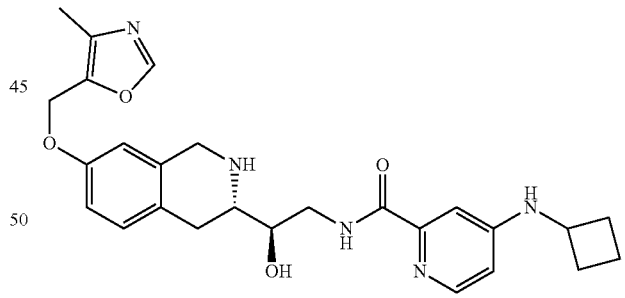
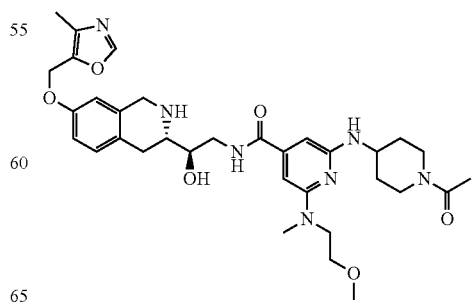

TABLE 6-continued

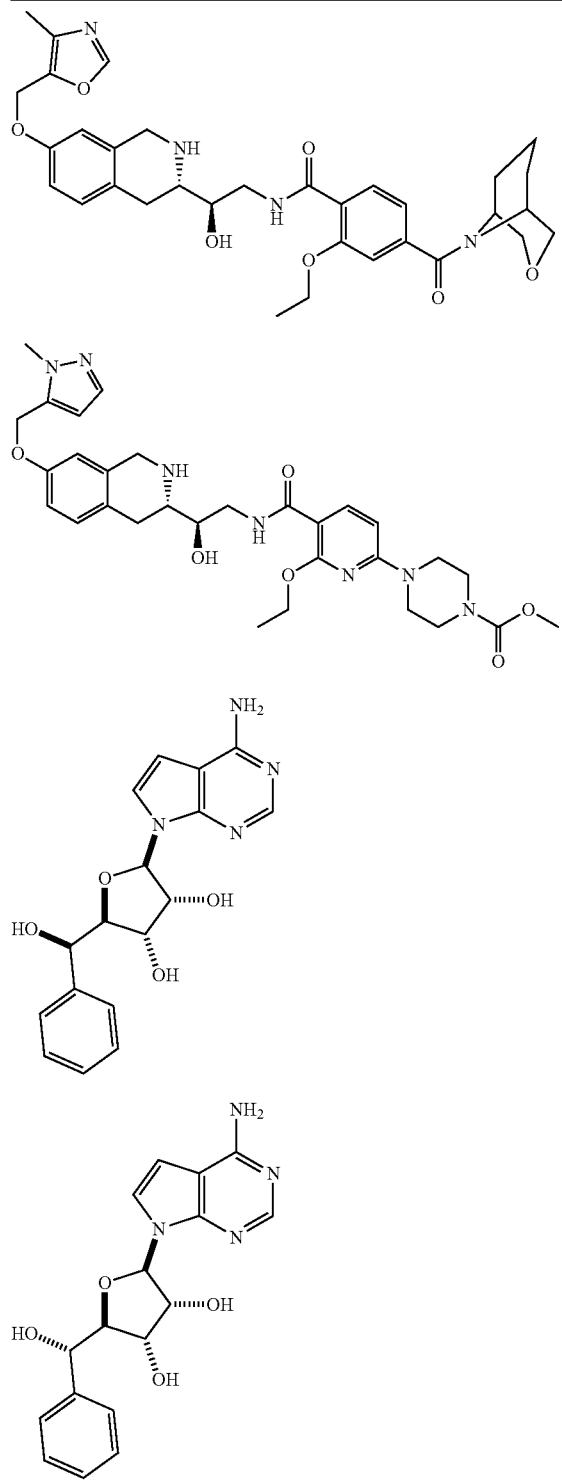

or a pharmaceutically acceptable salt thereof.

In yet another embodiment, the Type II PRMT5 inhibitor is selected from a compound disclosed in PCT/US2020/050457 (WO2021050915), PCT/US2020/057601 (WO2021086879), WO2021/163344, WO2022/026892, U.S. Ser. No. 11/077,101, Malik, R., et al. *AACR Annual Meeting*, 2021, Abstract Number 1140, or Bonday, Z. Q., et al., *ACS Med. Chem. Lett.* 2018, 9, 612-617, the entire contents of which are hereby incorporated by reference in their entireties.

Combination Product

Provided herein is a combination product comprising a MAT2A inhibitor, or a pharmaceutically acceptable salt thereof, and a Type II PRMT inhibitor, or a pharmaceutically acceptable salt thereof. The combination product is useful for the treatment of a variety of cancers, including solid tumors. In another aspect, the combination product is useful for the treatment of any number of MAT2A-associated diseases. In another aspect, the combination product is useful for the treatment of a disease or disorder treatable by inhibiting MAT2A. In another aspect, the combination product is useful for the treating MTAP-deficient tumors. In another aspect, the combination product is useful for the treatment of any number of Type II PRMT-associated diseases. In an embodiment, the Type II PRMT inhibitor is Type II PRMT5 inhibitor.

In an aspect, provided herein is a combination product comprising a MAT2A inhibitor that is a compound of Formula I or a pharmaceutically acceptable salt thereof, and a Type II PRMT5 inhibitor that is a compound selected from Formula II, Formula III, Formula IV, Formula V, and Formula VI, or a pharmaceutically acceptable salt thereof.

In another aspect, provided herein is a combination product comprising a MAT2A inhibitor that is a compound of Formula I or a pharmaceutically acceptable salt thereof, and a Type II PRMT5 inhibitor.

In another aspect, provided herein is a combination product comprising a Type II PRMT5 inhibitor that is a compound selected from Formula II, Formula III, Formula IV, Formula V, and Formula VI, or a pharmaceutically acceptable salt thereof, and a MAT2A inhibitor.

In another aspect, provided herein is a combination product comprising a methionine adenosyltransferase II alpha (MAT2A) inhibitor that is Compound A:

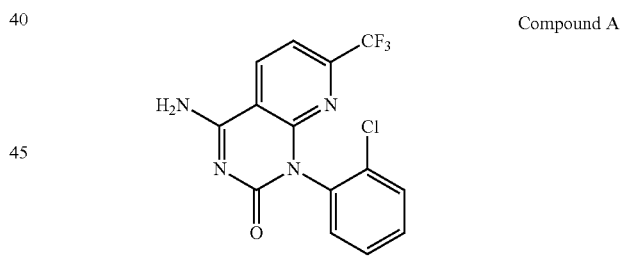

Compound A or a pharmaceutically acceptable salt thereof,
and a PRMT5 inhibitor, or a pharmaceutically acceptable salt thereof.

In another aspect, provided herein is a combination product comprising a MAT2A inhibitor that is Compound A or a pharmaceutically acceptable salt thereof, and a PRMT5 inhibitor that is Compound B, or a pharmaceutically acceptable salt thereof. In an embodiment, the PRMT5 inhibitor is Compound B HCl. In an embodiment, provided herein is a combination product comprising Compound A or a pharmaceutically acceptable salt thereof, and Compound C, or a pharmaceutically acceptable salt thereof. In an embodiment, provided herein is a combination product comprising Compound A or a pharmaceutically acceptable salt thereof, and a compound selected from Compound D, Compound E, Compound F, and Compound G, or a pharmaceutically acceptable salt thereof.

In another aspect, provided herein is a combination product comprising a first pharmaceutical composition comprising a therapeutically effective amount of a MAT2A inhibitor that is a compound of Formula I or a pharmaceutically acceptable salt thereof, and a second pharmaceutical composition comprising a therapeutically effective amount of a Type II PRMT5 inhibitor.

In another aspect, provided herein is a combination product comprising a first pharmaceutical composition comprising a therapeutically effective amount of a Type II PRMT5 inhibitor that is a compound selected from Formula II, Formula III, Formula IV, Formula V, and Formula VI, or a pharmaceutically acceptable salt thereof, and a second pharmaceutical composition comprising a therapeutically effective amount of a MAT2A inhibitor.

In an aspect, provided herein is a combination product comprising a first pharmaceutical composition comprising a therapeutically effective amount of a MAT2A inhibitor that is a compound of Formula I or a pharmaceutically acceptable salt thereof, and a second pharmaceutical composition comprising a therapeutically effective amount of a Type II PRMT5 inhibitor that is a compound selected from Formula II, Formula III, Formula IV, Formula V, and Formula VI, or a pharmaceutically acceptable salt thereof.

In still another aspect, provided herein is a combination product comprising a first pharmaceutical composition comprising a therapeutically effective amount of Compound A or a pharmaceutically acceptable salt thereof and a second pharmaceutical composition comprising a therapeutically effective amount of Compound B or a pharmaceutically acceptable salt thereof. In an embodiment, provided herein is a combination product comprising a first pharmaceutical composition comprising a therapeutically effective amount of Compound A or a pharmaceutically acceptable salt thereof and a second pharmaceutical composition comprising a therapeutically effective amount of Compound C or a pharmaceutically acceptable salt thereof. In an embodiment, provided herein is a combination product comprising a first pharmaceutical composition comprising a therapeutically effective amount of Compound A or a pharmaceutically acceptable salt thereof and a second pharmaceutical composition comprising a therapeutically effective amount of a compound selected from Compound D, Compound E, Compound F, and Compound G, or a pharmaceutically acceptable salt thereof.

The administration of a pharmaceutical combination provided herein may result in a beneficial effect, e.g. a synergistic therapeutic effect, e.g., with regard to alleviating, delaying progression of or inhibiting the symptoms, and may also result in further surprising beneficial effects, e.g., fewer side-effects, an improved quality of life or a decreased morbidity, compared with a monotherapy applying only one of the pharmaceutically active ingredients used in the combination of the invention.

Methods of Treatment

In an aspect, provided herein is a method of treating cancer in a subject in need thereof, the method comprising administering to the subject an effective amount of a methionine adenosyltransferase II alpha (MAT2A) inhibitor and administering to the subject an effective amount of Type II protein arginine methyltransferase (Type II PRMT) inhibitor. In an embodiment, the Type II PRMT inhibitor is a PRMT5 inhibitor.

In an embodiment, provided herein are methods of treating cancer in a subject in need thereof, the methods comprising administering to the subject a combination comprising a MAT2A inhibitor and a Type II PRMT5 inhibitor, together with at least a pharmaceutically acceptable carrier, thereby treating the cancer in the subject.

In an embodiment, provided herein are methods of treating cancer in a subject in need thereof, the methods comprising administering to the subject a therapeutically effective amount of a pharmaceutical composition comprising a MAT2A inhibitor and a therapeutically effective amount of a pharmaceutical composition comprising a Type II PRMT5 inhibitor, thereby treating the cancer in the subject.

In an embodiment, use of a combination of a MAT2A inhibitor and a Type II PRMT5 inhibitor for the manufacture of a medicament is provided. In one embodiment, the MAT2A inhibitor is a compound of Formula I, or a pharmaceutically acceptable salt thereof. In one embodiment, the MAT2A inhibitor is Compound A or a pharmaceutically acceptable salt thereof. In an embodiment, the Type II PRMT5 inhibitor is a compound selected from Formula II, Formula III, Formula IV, Formula V, and Formula VI, or a pharmaceutically acceptable salt thereof. In an embodiment, the Type II PRMT5 inhibitor is selected from Compound B, Compound C, Compound D, Compound E, Compound F, and Compound G or a pharmaceutically acceptable salt thereof. In an embodiment, provided is a combination of a compound of Formula I or a pharmaceutically acceptable salt thereof, and a compound selected from Formula II, Formula III, Formula IV, Formula V, and Formula VI, or a pharmaceutically acceptable salt thereof, for the manufacture of a medicament. In one embodiment, provided is a combination of Compound A or a pharmaceutically acceptable salt thereof, and a compound selected from Compound B, Compound C, Compound D, Compound E, Compound F, and Compound G or a pharmaceutically acceptable salt thereof, for the manufacture of a medicament.

In another embodiment, use of a combination of a MAT2A inhibitor and a Type II PRMT5 inhibitor for the treatment of cancer is provided. In one embodiment, the MAT2A inhibitor is a compound of Formula I or a pharmaceutically acceptable salt thereof. In one embodiment, the MAT2A inhibitor is Compound A or a pharmaceutically acceptable salt thereof. In an embodiment, the Type II PRMT5 inhibitor is a compound selected from Formula II, Formula III, Formula IV, Formula V, and Formula VI, or a pharmaceutically acceptable salt thereof. In an embodiment, the Type II PRMT5 inhibitor is selected from Compound B, Compound C, Compound D, Compound E, Compound F, and Compound G or a pharmaceutically acceptable salt thereof. In one embodiment, provided is use of a combination of a compound of Formula I or a pharmaceutically acceptable salt thereof, and a compound selected from Formula II, Formula III, Formula IV, Formula V, and Formula VI, or a pharmaceutically acceptable salt thereof, for the treatment of cancer. In one embodiment, provided is a use of a combination of Compound A or a pharmaceutically acceptable salt thereof, and a compound selected from Compound B, Compound C, Compound D, Compound E, Compound F, and Compound G or a pharmaceutically acceptable salt thereof, for the treatment of cancer.

In an embodiment, the MAT2A inhibitor is a compound of Formula I:

(I)

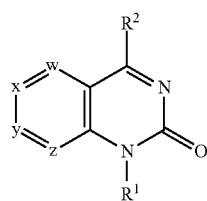

or a pharmaceutically acceptable salt thereof; wherein the variables are defined herein.

In another embodiment, the Type II PRMT5 inhibitor is a compound of Formula II:

(II)

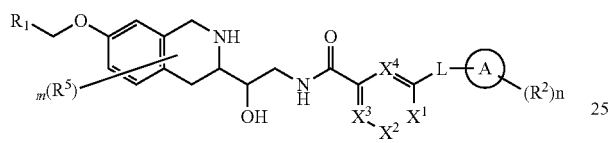

or a pharmaceutically acceptable salt thereof; wherein the variables are defined herein.

In yet another embodiment, the Type II PRMT5 inhibitor is a compound of Formula III:

(III)

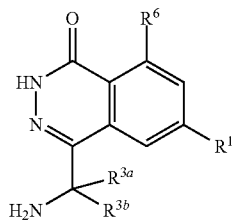

or a pharmaceutically acceptable salt thereof; wherein the variables are defined herein.

In yet another embodiment, the MAT2A inhibitor is Compound A:

Compound A

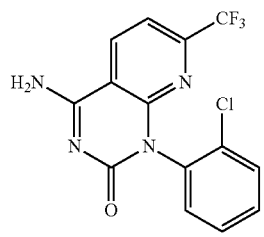

or a pharmaceutically acceptable salt thereof.

In yet another embodiment, the Type II PRMT5 inhibitor is Compound B:

Compound B

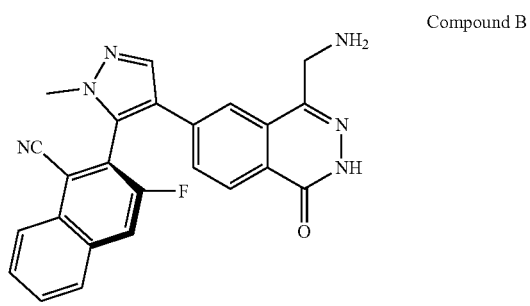

or a pharmaceutically acceptable salt thereof.

In another embodiment, the Type II PRMT5 inhibitor is Compound B HCl.

In still another embodiment, the Type II PRMT5 inhibitor is selected from the group consisting of

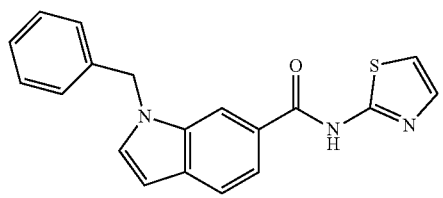

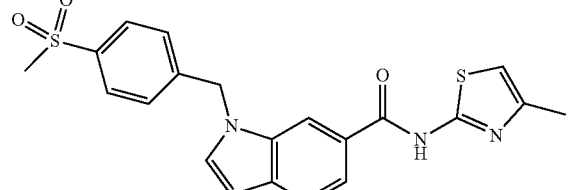

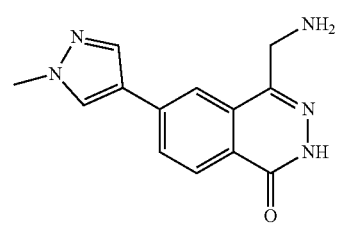

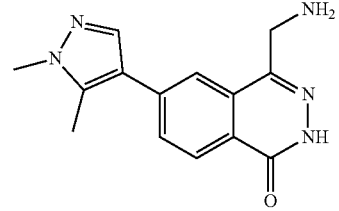

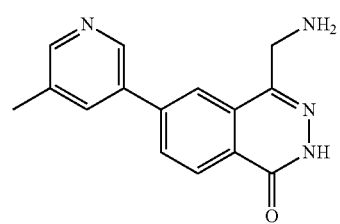

719
-continued
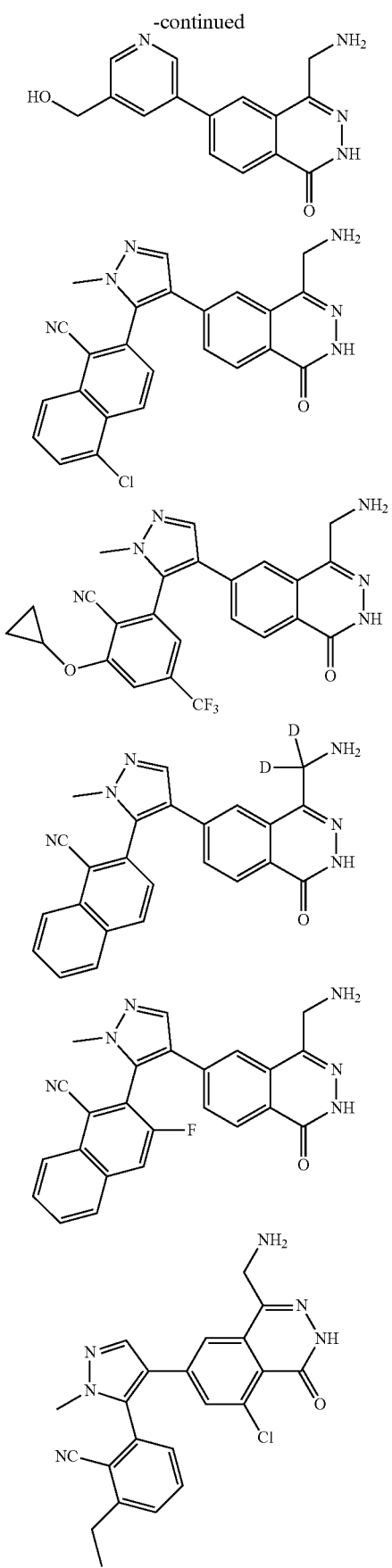
720
-continued
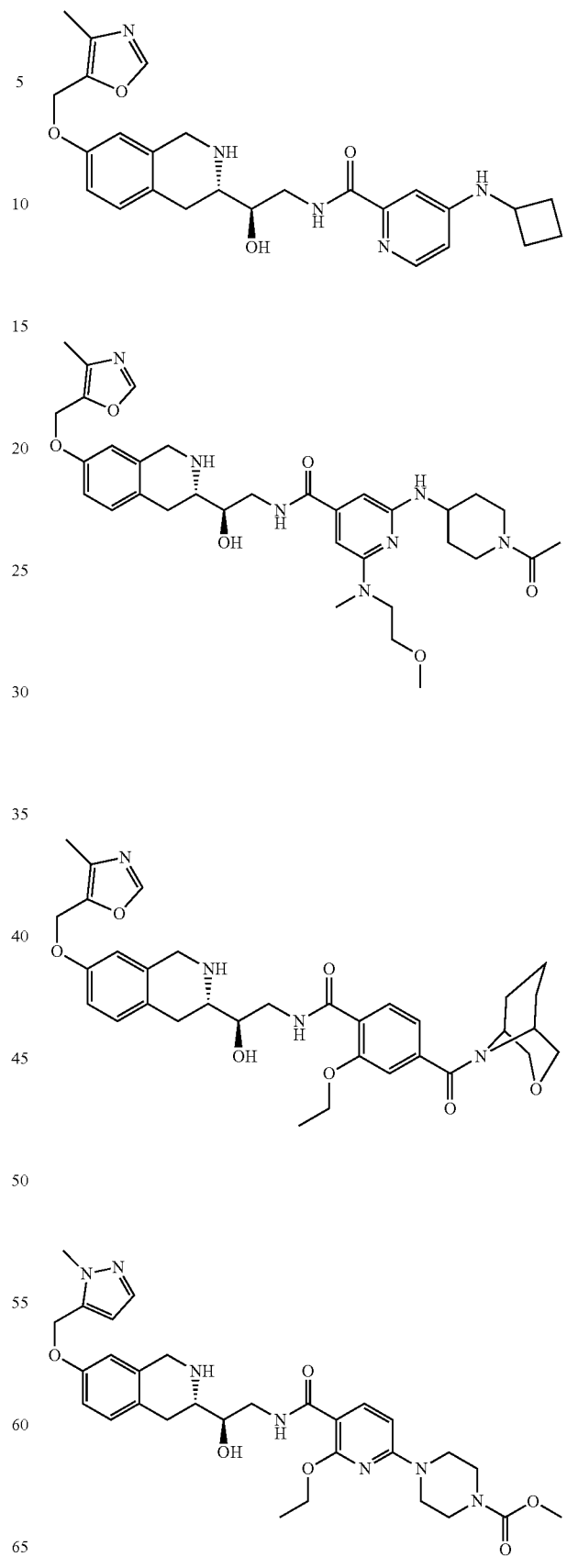

721
-continued

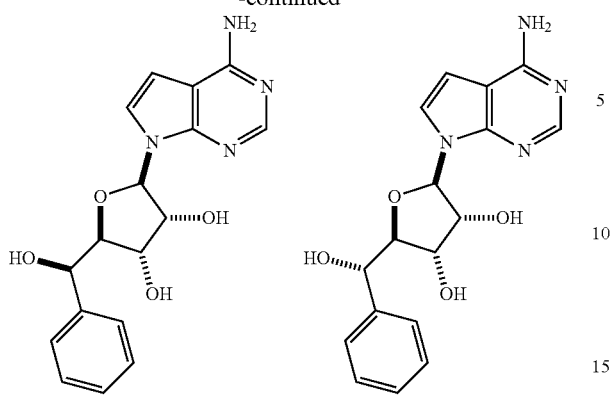

or a pharmaceutically acceptable salt thereof.

In another aspect, provided herein is a method of treating cancer in a subject in need thereof, the method comprising administering to the subject an effective amount of Compound A:

Compound A

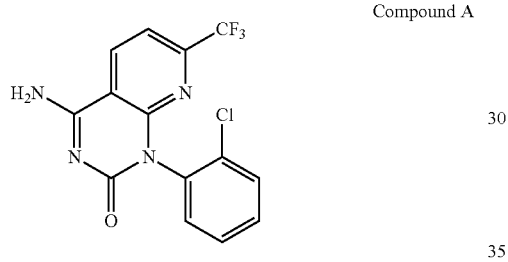

or a pharmaceutically acceptable salt thereof;
and administering to the subject an effective amount of a Type II PRMT5 inhibitor selected from the group consisting of

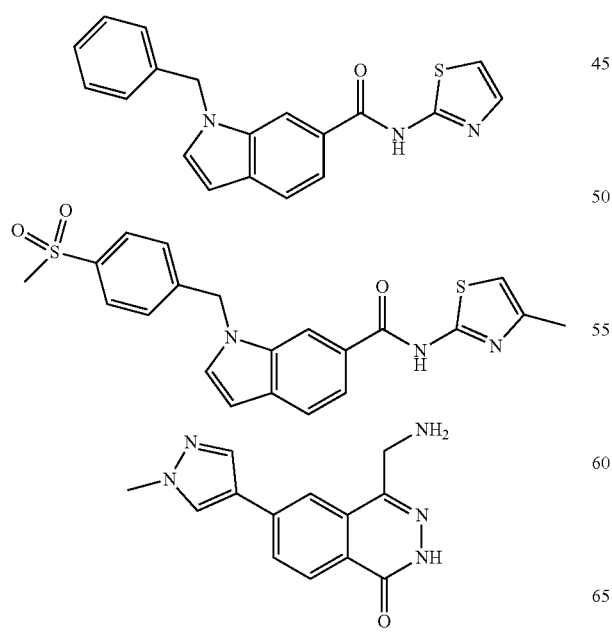

722
-continued

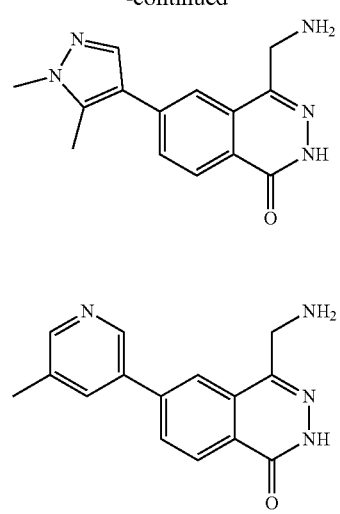

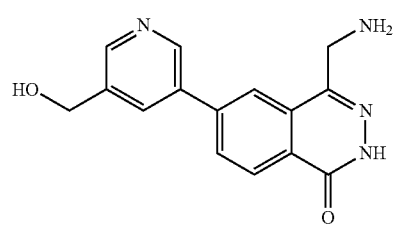

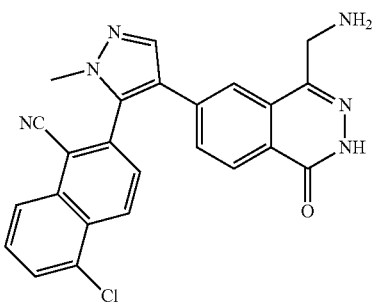

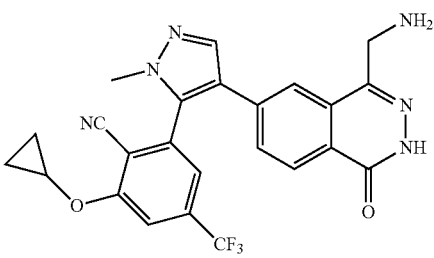

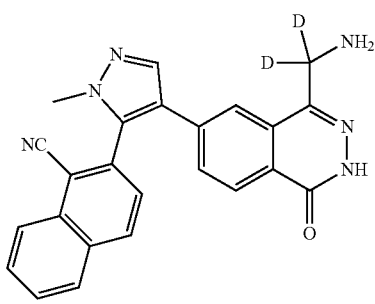

723
-continued

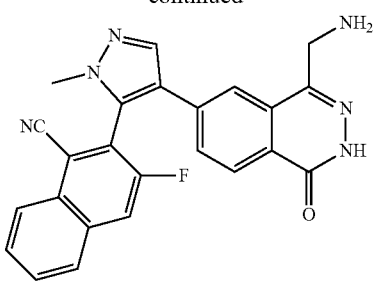

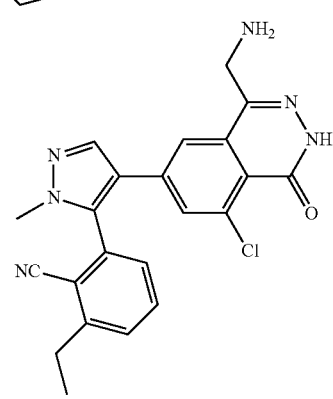

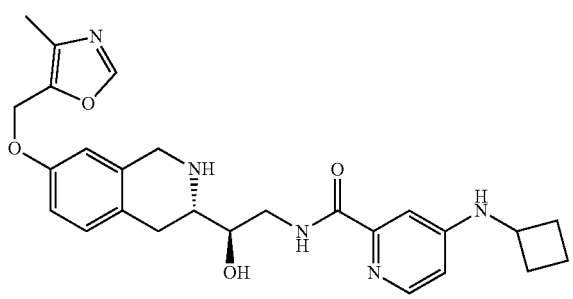 [SMILES: Cc1ncoc1COc1ccc2c(c1)CN[C@H]([C@H](O)CNC(=O)c1cc(NC3CCC3)ccn1)C2]

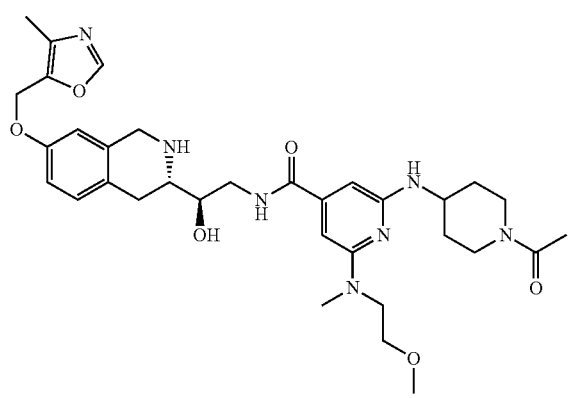 [SMILES: COCCN(C)c1cc(C(=O)NC[C@@H](O)[C@@H]2Cc3ccc(OCc4ocnc4C)cc3CN2)cc(NC2CCN(C(C)=O)CC2)n1]

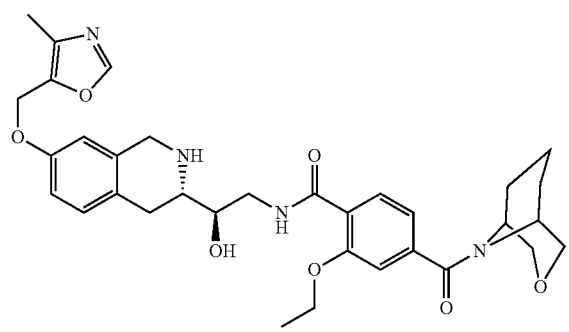 [SMILES: CCOc1cc(C(=O)N2C3CCCC2COC3)ccc1C(=O)NC[C@@H](O)[C@@H]1Cc2ccc(OCc3ocnc3C)cc2CN1]

724
-continued

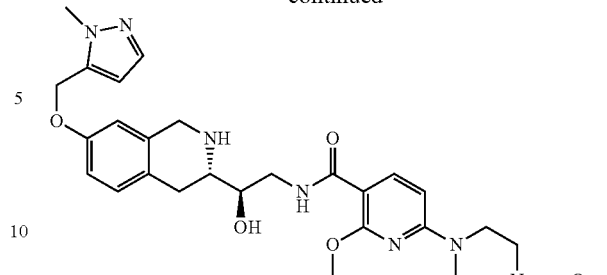

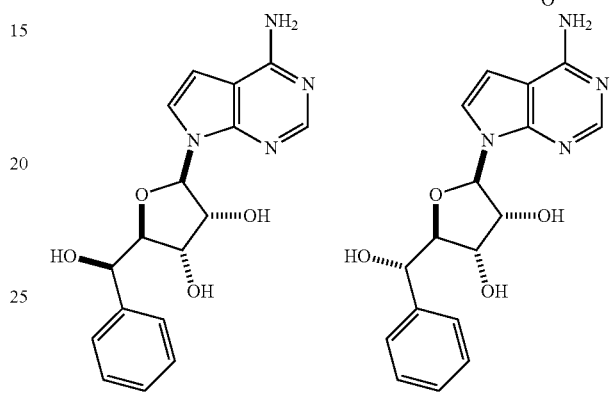

or a pharmaceutically acceptable salt thereof.

In an embodiment provided herein is a method of treating caner in a subject in need thereof, the method comprising administering to the subject an effective amount of Compound A:

Compound A

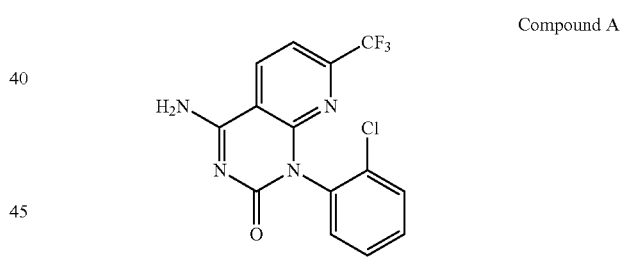

or a pharmaceutically acceptable salt thereof; and administering to the subject an effective amount of Compound B:

Compound B

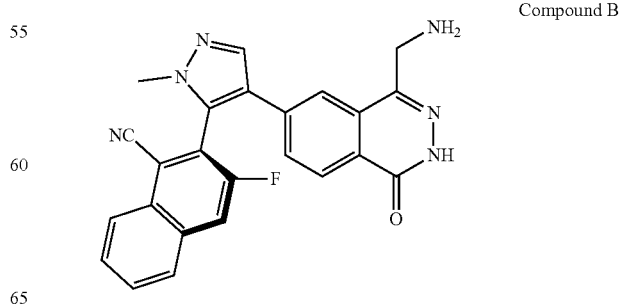

or a pharmaceutically acceptable salt thereof.

In an embodiment, Compound B is in the hydrochloride salt form.

In an embodiment, provided herein is a method of treating cancer in a subject in need thereof, the method comprising administering to the subject an effective amount of Compound A or a pharmaceutically acceptable salt thereof and administering to the subject an effective amount of Compound C or a pharmaceutically acceptable salt thereof.

In an embodiment, provided herein is a method of treating cancer in a subject in need thereof, the method comprising administering to the subject an effective amount of Compound A or a pharmaceutically acceptable salt thereof and administering to the subject an effective amount of Compound D or a pharmaceutically acceptable salt thereof.

In an embodiment, provided herein is a method of treating cancer in a subject in need thereof, the method comprising administering to the subject an effective amount of Compound A or a pharmaceutically acceptable salt thereof and administering to the subject an effective amount of Compound E or a pharmaceutically acceptable salt thereof.

In an embodiment, provided herein is a method of treating cancer in a subject in need thereof, the method comprising administering to the subject an effective amount of Compound A or a pharmaceutically acceptable salt thereof and administering to the subject an effective amount of Compound F or a pharmaceutically acceptable salt thereof.

In an embodiment, provided herein is a method of treating cancer in a subject in need thereof, the method comprising administering to the subject an effective amount of Compound A or a pharmaceutically acceptable salt thereof and administering to the subject an effective amount of Compound G or a pharmaceutically acceptable salt thereof.

In another embodiment, provided herein is a method of treating cancer in a subject in need thereof, the method comprising administering to the subject an effective amount of Compound A, or a pharmaceutically acceptable salt thereof; and administering to the subject an effective amount of a compound selected from Compound D, Compound E, Compound F, and Compound G, or a pharmaceutically acceptable salt thereof.

In another aspect, provided herein is a method of treating cancer in a subject in need thereof, the method comprising administering to the subject an effective amount of Compound A:

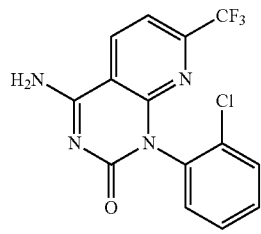

Compound A or a pharmaceutically acceptable salt thereof;
and administering to the subject an effective amount of a Type II PRMT5 inhibitor selected from the group consisting of

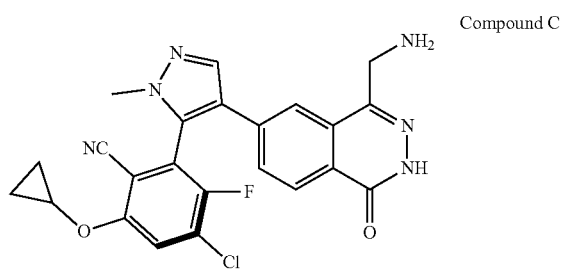

Compound C

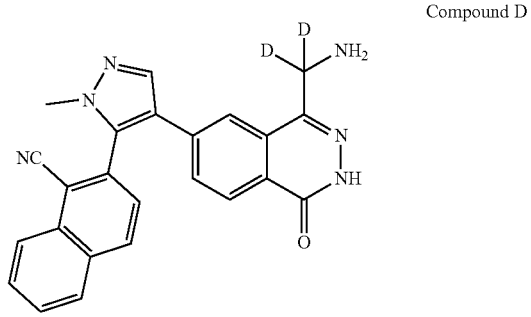

Compound D

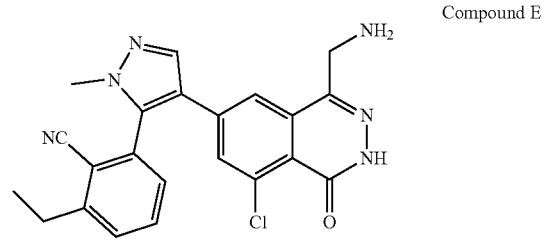

Compound E

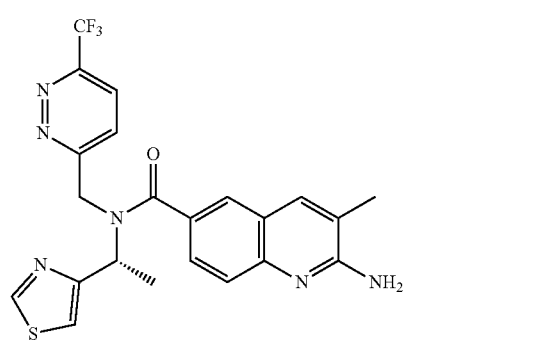

Compound F

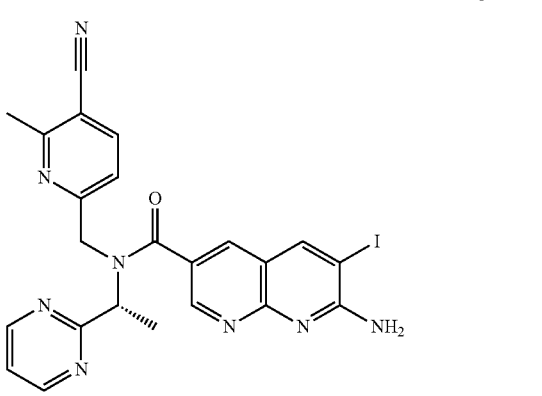

Compound G or a pharmaceutically acceptable salt thereof.

In another embodiment, the Type II PRMT5 inhibitor is a compound of Formula IV:

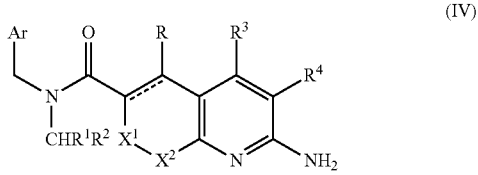

(IV)

or a pharmaceutically acceptable salt thereof.

In an embodiment, the Type II PRMT5 inhibitor is Compound F or a pharmaceutically acceptable salt thereof.

In an embodiment, the Type II PRMT5 inhibitor is Compound G or a pharmaceutically acceptable salt thereof.

In another embodiment, the Type II PRMT5 inhibitor is a compound of Formula (V):

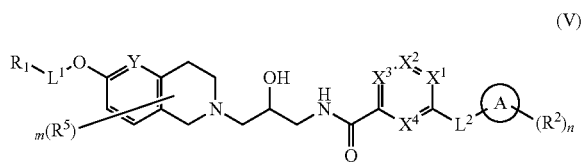

(V)

or a pharmaceutically acceptable salt thereof, wherein the variables are defined herein.

In yet another embodiment, the Type II PRMT5 inhibitor is a compound of Formula (VI):

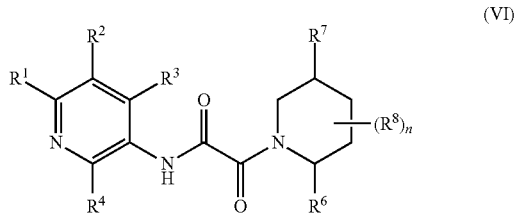

(VI)

or a pharmaceutically acceptable salt thereof, wherein the variables are defined herein.

In an aspect, provided herein is a method of treating cancer in a subject in need thereof comprising administering to the subject a therapeutically effective amount of a MAT2A inhibitor that is a compound of Formula I, or a pharmaceutically acceptable salt thereof; and a therapeutically effective amount of a Type II PRMT5 inhibitor.

In an aspect, provided herein is a method of treating cancer in a subject in need thereof comprising administering to the subject a therapeutically effective amount of a Type II PRMT5 inhibitor that is a compound selected from Formula II, Formula III, Formula IV, Formula V and Formula VI or a pharmaceutically acceptable salt thereof, and a MAT2A inhibitor.

In an aspect, provided herein is a method of treating cancer in a subject in need thereof comprising administering to the subject a therapeutically effective amount of a MAT2A inhibitor that is a compound of Formula I, or a pharmaceutically acceptable salt thereof; and a therapeutically effective amount of a Type II PRMT5 inhibitor that is a compound selected from Formula II, Formula III, Formula IV, Formula V and Formula VI or a pharmaceutically acceptable salt thereof.

In another aspect, provided herein is a method of treating cancer comprising administering to a subject in need thereof a first pharmaceutical composition comprising a therapeutically effective amount of a MAT2A inhibitor that is a compound of Formula I, or a pharmaceutically acceptable salt thereof, and a second pharmaceutical composition comprising a therapeutically effective amount of a Type II PRMT5 inhibitor.

In another aspect, provided herein is a method of treating cancer comprising administering to a subject in need thereof a first pharmaceutical composition comprising a therapeutically effective amount of a Type II PRMT5 inhibitor that is a compound selected from Formula II, Formula III, Formula IV, Formula V, and Formula VI, or a pharmaceutically acceptable salt thereof, and a second pharmaceutical composition comprising a therapeutically effective amount of a MAT2A inhibitor.

In another aspect, provided herein is a method of treating cancer comprising administering to a subject in need thereof a first pharmaceutical composition comprising a therapeutically effective amount of a MAT2A inhibitor that is a compound of Formula I, or a pharmaceutically acceptable salt thereof, and a second pharmaceutical composition comprising a therapeutically effective amount of a Type II PRMT5 inhibitor that is a compound selected from Formula II, Formula III, Formula IV, Formula V, and Formula VI, or a pharmaceutically acceptable salt thereof.

In another aspect, provided herein is a method of treating cancer comprising administering to a subject in need thereof a first pharmaceutical composition comprising a therapeutically effective amount of Compound A or a pharmaceutically acceptable salt thereof; and a second pharmaceutical composition comprising a therapeutically effective amount of a compound selected from Compound B, Compound C, Compound D, Compound E, Compound F, and Compound G, or a pharmaceutically acceptable salt thereof.

In an embodiment, the cancer is characterized by a reduction or absence of MTAP gene expression, the absence of the MTAP gene, reduced function of MTAP protein, reduced level of MTAP protein, MTA accumulation, absence of MTAP protein, or combination thereof. In an embodiment, the cancer is characterized by a reduction or absence of MTAP gene expression, the absence of the MTAP gene, reduced function of MTAP protein, reduced level of MTAP protein, absence of MTAP protein, MTA accumulation, or combination thereof. In another embodiment, the cancer is characterized as MTAP-null. In still another embodiment, the cancer is characterized by a reduction or absence of MTAP gene expression. In still another embodiment, the cancer is characterized by reduced function of MTAP protein. In still another embodiment, the cancer is characterized reduced level or absence of MTAP protein. In still another embodiment, the cancer is characterized by MTA accumulation.

In yet another embodiment, the cancer is selected from the group consisting of leukemia, glioma, melanoma, pancreatic, non-small cell lung cancer, bladder cancer, astrocytoma, osteosarcoma, head and neck cancer, myxoid chondrosarcoma, ovarian cancer, endometrial cancer, breast cancer, soft tissue sarcoma, non-Hodgkin lymphoma, and mesothelioma.

In yet another embodiment, the cancer is selected from the group consisting of leukemia, glioma, melanoma, pancreatic, non-small cell lung cancer, bladder cancer, astrocytoma, osteosarcoma, head and neck cancer, myxoid chondrosarcoma, ovarian cancer, endometrial cancer, breast cancer, anal cancer, stomach cancer, colon cancer, colorectal cancer, soft tissue sarcoma, non-Hodgkin lymphoma, gastric cancer, esophagogastric cancer, esophageal cancer, malignant peripheral nerve sheath tumor, and mesothelioma.

In an embodiment, the cancer is mesothelioma. In an embodiment, the cancer is non-small cell lung cancer. In another embodiment, the cancer is nonsquamous non-small cell lung cancer. In one embodiment, the cancer is cancer of the colon or rectum. In an embodiment, the cancer is adenocarcinoma of the colon or rectum. In an embodiment, the cancer is breast cancer. In an embodiment, the cancer is adenocarcinoma of the breast. In an embodiment, the cancer is gastric cancer. In an embodiment, the cancer is gastric adenocarcinoma. In an embodiment, the cancer is pancreatic cancer. In an embodiment, the cancer is pancreatic adenocarcinoma. In an embodiment, the cancer is bladder cancer.

In an embodiment, the cancer is characterized as being MTAP-deficient.

In still another embodiment, the cancer is a solid tumor. In still another embodiment, the cancer is a MTAP-deleted solid tumor. In still another embodiment, the cancer is a metastatic MTAP-deleted solid tumor.

In still another embodiment, the cancer is metastatic.

In still another embodiment, the cancer is NSCLC, mesothelioma, squamous carcinoma of the head and neck, salivary gland tumors, urothelial cancers, sarcomas, or ovarian cancer. In still another embodiment, the cancer is selected from NSCLC, esophagogastric and pancreatic cancers.

In still another embodiment, the cancer is MTAP-deficient lung or MTAP-deficient pancreatic cancer, including MTAP-deficient NSCLC or MTAP-deficient pancreatic ductal adenocarcinoma (PDAC) or MTAP-deficient esophageal cancer.

In still another embodiment, the cancer is NSCLC, mesothelioma, squamous carcinoma of the head and neck, salivary gland tumors, urothelial cancers, sarcomas, or ovarian cancer. In still another embodiment, the cancer is NSCLC, esophagogastric and pancreatic cancers.

In an aspect, provided herein is a method of treating bladder cancer in a subject in need thereof, the method comprising administering to the subject a therapeutically effective amount of Compound A, or a pharmaceutically acceptable salt thereof; and administering to the subject a therapeutically effective amount of Compound B, or a pharmaceutically acceptable salt thereof.

In another aspect, provided herein is a method of treating gastric cancer in a subject in need thereof, the method comprising administering to the subject a therapeutically effective amount of Compound A or a pharmaceutically acceptable salt thereof; and administering to the subject a therapeutically effective amount of Compound B, or a pharmaceutically acceptable salt thereof.

In yet another aspect, provided herein is a method of treating non-small cell lung cancer in a subject in need thereof, the method comprising administering to the subject a therapeutically effective amount of Compound A or a pharmaceutically acceptable salt thereof; and administering to the subject a therapeutically effective amount of Compound B, or a pharmaceutically acceptable salt thereof.

In an embodiment, the methionine adenosyltransferase II alpha (MAT2A) inhibitor and PRMT type II inhibitor are in separate dosage forms. In an embodiment, the Type II PRMT inhibitor is a PRMT5 inhibitor.

In another embodiment, the methionine adenosyltransferase II alpha (MAT2A) inhibitor and PRMT type II inhibitor are in the same dosage form. In an embodiment, the Type II PRMT inhibitor is a PRMT5 inhibitor.

In another embodiment, the treatment comprises administering the methionine adenosyltransferase II alpha (MAT2A) inhibitor, or a pharmaceutically acceptable salt thereof, and PRMT type II inhibitor, or a pharmaceutically acceptable salt thereof, at substantially the same time. In yet another embodiment, the treatment comprises administering methionine adenosyltransferase II alpha (MAT2A) inhibitor, or a pharmaceutically acceptable salt thereof, and PRMT type II inhibitor, or a pharmaceutically acceptable salt thereof, at different times. In an embodiment, the Type II PRMT inhibitor is a PRMT5 inhibitor.

In still another embodiment, the methionine adenosyltransferase II alpha (MAT2A) inhibitor, or a pharmaceutically acceptable salt thereof, is administered to the subject, followed by administration of the PRMT type II inhibitor, or a pharmaceutically acceptable salt thereof. In an embodiment, the PRMT type II inhibitor, or a pharmaceutically acceptable salt thereof, is administered to the subject, followed by administration of methionine adenosyltransferase II alpha (MAT2A) inhibitor, or a pharmaceutically acceptable salt thereof. In an embodiment, the Type II PRMT inhibitor is a PRMT5 inhibitor.

In yet another embodiment, the method comprises administering to the subject in need thereof a methionine adenosyltransferase II alpha (MAT2A) inhibitor.

In still another embodiment, the method comprises administering to the subject in need thereof Type II protein arginine methyltransferase (Type II PRMT) inhibitor. In an embodiment, the Type II PRMT inhibitor is a PRMT5 inhibitor.

In an embodiment, the methionine adenosyltransferase II alpha (MAT2A) inhibitor, or a pharmaceutically acceptable salt thereof, and the PRMT type II inhibitor, or a pharmaceutically acceptable salt thereof, are administered orally. In an embodiment, the Type II PRMT inhibitor is a PRMT5 inhibitor.

In another embodiment, the cancer to be treated is selected from the group consisting of lung cancer, colon and rectal cancer, breast cancer, prostate cancer, liver cancer, pancreatic cancer, brain cancer, kidney cancer, ovarian cancer, stomach cancer, skin cancer, bone cancer, gastric cancer, glioma, glioblastoma, neuroblastoma, hepatocellular carcinoma, papillary renal carcinoma, head and neck squamous cell carcinoma, leukemia, lymphomas, myelomas, retinoblastoma, cervical cancer, melanoma and/or skin cancer, bladder cancer, uterine cancer, testicular cancer, esophageal cancer, and solid tumors. In some embodiments, the cancer is lung cancer, colon cancer, breast cancer, neuroblastoma, leukemia, and lymphomas. In other embodiments, the cancer is lung cancer, colon cancer, breast cancer, neuroblastoma, leukemia, or lymphoma. In a further embodiment, the cancer is non-small cell lung cancer (NSCLC) or small cell lung cancer.

In an embodiment, the cancer is a hematologic cancer, such as leukemia or lymphoma. In a certain embodiment, lymphoma is Hodgkin's lymphoma or Non-Hodgkin's lymphoma. In certain embodiments, leukemia is myeloid, lymphocytic, myelocytic, lymphoblastic, or megakaryotic leukemia.

In yet another embodiment, the cancer is selected from the group consisting of leukemia, glioma, melanoma, pancreatic, non-small cell lung cancer, bladder cancer, astrocytoma, osteosarcoma, head and neck cancer, myxoid chondrosarcoma, ovarian cancer, endometrial cancer, breast cancer, soft tissue sarcoma, non-Hodgkin lymphoma, and mesothelioma.

In an aspect, provided herein is a methionine adenosyltransferase II alpha (MAT2A) inhibitor, or a pharmaceutically acceptable salt thereof, and PRMT type II inhibitor, or a pharmaceutically acceptable salt thereof, for use in therapy.

In an embodiment, the methionine adenosyltransferase II alpha (MAT2A) inhibitor, or a pharmaceutically acceptable salt thereof, and the PRMT type II inhibitor, or a pharmaceutically acceptable salt thereof, are for use in the treatment of cancer in a subject in need thereof. In an embodiment, the Type II PRMT inhibitor is a PRMT5 inhibitor.

Exemplary lengths of time associated with the course of the treatment methods disclosed herein include: about one week; two weeks; about three weeks; about four weeks; about five weeks; about six weeks; about seven weeks; about eight weeks; about nine weeks; about ten weeks; about eleven weeks; about twelve weeks; about thirteen weeks; about fourteen weeks; about fifteen weeks; about sixteen weeks; about seventeen weeks; about eighteen weeks; about nineteen weeks; about twenty weeks; about twenty-one weeks; about twenty-two weeks; about twenty-three weeks; about twenty four weeks; about seven months; about eight months; about nine months; about ten months; about eleven months; about twelve months; about thirteen months; about fourteen months; about fifteen months; about sixteen months; about seventeen months; about eighteen months; about nineteen months; about twenty months; about twenty one months; about twenty-two months; about twenty-three months; about twenty-four months; about thirty months; about three years; about four years and about five years.

In an embodiment of the methods, the method involves the administration of a therapeutically effective amount of a combination or composition comprising compounds provided herein, or pharmaceutically acceptable salts thereof, to a subject (including, but not limited to a human or animal) in need of treatment (including a subject identified as in need).

In another embodiment of the methods, the treatment includes co-administering the amount of the methionine adenosyltransferase II alpha (MAT2A) inhibitor, or a pharmaceutically acceptable salt thereof, and the amount of the PRMT type II inhibitor, or a pharmaceutically acceptable salt thereof. In an embodiment, the amount of the methionine adenosyltransferase II alpha (MAT2A) inhibitor or a pharmaceutically acceptable salt thereof and the amount of PRMT type II inhibitor or a pharmaceutically acceptable salt thereof are in a single formulation or unit dosage form. In still other embodiments, the amount of methionine adenosyltransferase II alpha (MAT2A) inhibitor or a pharmaceutically acceptable salt thereof and the amount of PRMT type II inhibitor or a pharmaceutically acceptable salt thereof are in a separate formulations or unit dosage forms. In an embodiment, the Type II PRMT inhibitor is a PRMT5 inhibitor.

In the foregoing methods, the treatment can include administering the amount of methionine adenosyltransferase II alpha (MAT2A) inhibitor or a pharmaceutically acceptable salt thereof and the amount of PRMT type II inhibitor or a pharmaceutically acceptable salt thereof at substantially the same time or administering the amount of methionine adenosyltransferase II alpha (MAT2A) inhibitor or a pharmaceutically acceptable salt thereof and the amount of PRMT type II inhibitor or a pharmaceutically acceptable salt thereof at different times. In some embodiments of the foregoing methods, the amount of methionine adenosyltransferase II alpha (MAT2A) inhibitor or a pharmaceutically acceptable salt thereof and/or the amount of PRMT type II inhibitor or a pharmaceutically acceptable salt thereof is administered at dosages that would not be effective when one or both of methionine adenosyltransferase II alpha (MAT2A) inhibitor or a pharmaceutically acceptable salt thereof and PRMT type II inhibitor or a pharmaceutically acceptable salt thereof is administered alone, but which amounts are effective in combination. In an embodiment, the Type II PRMT inhibitor is a PRMT5 inhibitor.

In another embodiment of the methods, the treatment includes co-administering the amount of Compound A, or a pharmaceutically acceptable salt thereof, and the amount of the PRMT type II inhibitor, or a pharmaceutically acceptable salt thereof. In an embodiment, the amount of Compound A or a pharmaceutically acceptable salt thereof and the amount of PRMT type II inhibitor or a pharmaceutically acceptable salt thereof are in a single formulation or unit dosage form. In still other embodiments, the amount of Compound A or a pharmaceutically acceptable salt thereof and the amount of PRMT type II inhibitor or a pharmaceutically acceptable salt thereof are in a separate formulations or unit dosage forms. In an embodiment, the Type II PRMT inhibitor is a PRMT5 inhibitor.

In the foregoing methods, the treatment can include administering the amount of Compound A or a pharmaceutically acceptable salt thereof and the amount of PRMT type II inhibitor or a pharmaceutically acceptable salt thereof at substantially the same time or administering the amount of Compound A or a pharmaceutically acceptable salt thereof and the amount of PRMT type II inhibitor or a pharmaceutically acceptable salt thereof at different times. In some embodiments of the foregoing methods, the amount of Compound A or a pharmaceutically acceptable salt thereof and/or the amount of PRMT type II inhibitor or a pharmaceutically acceptable salt thereof is administered at dosages that would not be effective when one or both of Compound A or a pharmaceutically acceptable salt thereof and PRMT type II inhibitor or a pharmaceutically acceptable salt thereof is administered alone, but which amounts are effective in combination. In an embodiment, the Type II PRMT inhibitor is a PRMT5 inhibitor.

Pharmaceutical Compositions

In an aspect, provided herein is a pharmaceutical composition comprising a methionine adenosyltransferase II alpha (MAT2A) inhibitor, or a pharmaceutically acceptable salt thereof, a Type II protein arginine methyltransferase (Type II PRMT) inhibitor, or a pharmaceutically acceptable salt thereof, and at least one pharmaceutically acceptable carrier. In an embodiment, the Type II PRMT inhibitor is a PRMT5 inhibitor.

In another aspect, provided herein is a combination product comprising a first pharmaceutical composition comprising a therapeutically effective amount of a methionine adenosyltransferase II alpha (MAT2A) inhibitor and a second pharmaceutical composition comprising a therapeutically effective amount of a Type II protein arginine methyltransferase (Type II PRMT) inhibitor. In an embodiment, the Type II PRMT inhibitor is a PRMT5 inhibitor.

In an embodiment, the MAT2A inhibitor is a compound of Formula I:

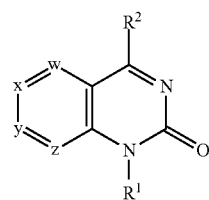

(I)

or a pharmaceutically acceptable salt thereof; wherein the variables are defined herein.

In another embodiment, the Type II PRMT5 inhibitor is a compound of Formula II:

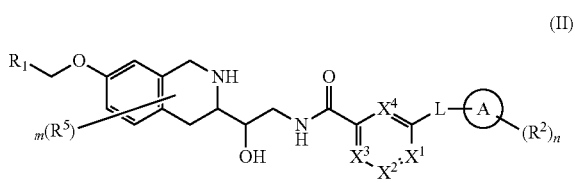

(II)

or a pharmaceutically acceptable salt thereof; wherein the variables are defined herein.

In yet another embodiment, the Type II PRMT5 inhibitor is a compound of Formula III:

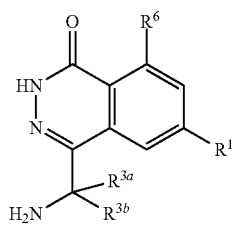

(III)

or a pharmaceutically acceptable salt thereof; wherein the variables are defined herein.

In yet another aspect, provided herein is a combination product comprising a first pharmaceutical composition comprising a therapeutically effective amount of Compound A:

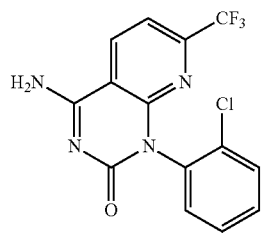

Compound A or a pharmaceutically acceptable salt thereof;
a second pharmaceutical composition comprising a therapeutically effective amount of a Type II PRMT inhibitor, or a pharmaceutically acceptable salt thereof.

In an embodiment, the Type II PRMT inhibitor is a PRMT5 inhibitor.

In another embodiment, the Type II PRMT5 inhibitor is a compound of Formula IV or a pharmaceutically acceptable salt thereof.

In another embodiment, the Type II PRMT5 inhibitor is a compound of Formula V or a pharmaceutically acceptable salt thereof.

In yet another embodiment, the Type II PRMT5 inhibitor is a compound of Formula VI or a pharmaceutically acceptable salt thereof.

In an embodiment, the Type II PRMT5 inhibitor is a Compound selected from Compound B, Compound C, Compound D, Compound E, Compound F, and Compound G, or a pharmaceutically acceptable salt thereof.

In still another aspect, provided herein is a pharmaceutical composition comprising a therapeutically effective amount of Compound A:

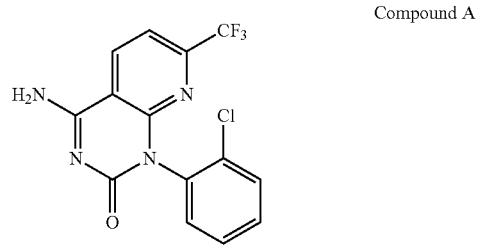 [SMILES: Nc1nc(=O)n(-c2ccccc2Cl)c2nc(C(F)(F)F)ccc12]

Compound A or a pharmaceutically acceptable salt thereof; a Type II PRMT5 inhibitor, or a pharmaceutically acceptable salt thereof; and a pharmaceutically acceptable carrier.

In still another aspect, provided herein is a pharmaceutical composition comprising a therapeutically effective amount of Compound A or a pharmaceutically acceptable salt thereof; a therapeutically effective amount of Compound B or a pharmaceutically acceptable salt thereof; and a pharmaceutically acceptable carrier.

In still another aspect, provided herein is a pharmaceutical composition comprising a therapeutically effective amount of Compound A or a pharmaceutically acceptable salt thereof; a therapeutically effective amount of Compound C or a pharmaceutically acceptable salt thereof; and a pharmaceutically acceptable carrier.

In still another aspect, provided herein is a pharmaceutical composition comprising a therapeutically effective amount of Compound A or a pharmaceutically acceptable salt thereof; a therapeutically effective amount of Compound D or a pharmaceutically acceptable salt thereof; and a pharmaceutically acceptable carrier.

In still another aspect, provided herein is a pharmaceutical composition comprising a therapeutically effective amount of Compound A or a pharmaceutically acceptable salt thereof; a therapeutically effective amount of Compound E or a pharmaceutically acceptable salt thereof; and a pharmaceutically acceptable carrier.

In still another aspect, provided herein is a pharmaceutical composition comprising a therapeutically effective amount of Compound A or a pharmaceutically acceptable salt thereof; a therapeutically effective amount of Compound F or a pharmaceutically acceptable salt thereof; and a pharmaceutically acceptable carrier.

In still another aspect, provided herein is a pharmaceutical composition comprising a therapeutically effective amount of Compound A or a pharmaceutically acceptable salt thereof; a therapeutically effective amount of Compound G or a pharmaceutically acceptable salt thereof; and a pharmaceutically acceptable carrier.

In still another aspect, provided herein is a pharmaceutical composition comprising a therapeutically effective amount of Compound A or a pharmaceutically acceptable salt thereof; a therapeutically effective amount of compound selected from Compound B, Compound C, Compound D, Compound E, Compound F, and Compound G, or a pharmaceutically acceptable salt thereof.

In an embodiment, the pharmaceutical composition is for use in the treatment of cancer in a patient. In an embodiment, the pharmaceutical composition is for use in the treatment of a solid tumor in a patient.

Administration/Dosage/Formulations

In another aspect, provided herein is a pharmaceutical composition or pharmaceutical combination comprising the compounds disclosed herein, together with a pharmaceutically acceptable carrier.

In an embodiment of the combination product, the methionine adenosyltransferase II alpha (MAT2A) inhibitor, or a pharmaceutically acceptable salt thereof, and the PRMT type II inhibitor, or a pharmaceutically acceptable salt thereof, are in the same formulation. In another embodiment of the combination product, the methionine adenosyltransferase II alpha (MAT2A) inhibitor and the PRMT type II inhibitor, are in separate formulations. In a further embodiment of this embodiment, the formulations are for simultaneous or sequential administration. In an embodiment, the Type II PRMT inhibitor is a PRMT5 inhibitor.

Administration of the combination includes administration of the combination in a single formulation or unit dosage form, administration of the individual agents of the combination concurrently but separately, or administration of the individual agents of the combination sequentially by any suitable route. The dosage of the individual agents of the combination may require more frequent administration of one of the agent(s) as compared to the other agent(s) in the combination. Therefore, to permit appropriate dosing, packaged pharmaceutical products may contain one or more dosage forms that contain the combination of agents, and one or more dosage forms that contain one of the combination of agents, but not the other agent(s) of the combination.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could begin administration of the pharmaceutical composition to dose the disclosed compound at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of the disclosed compound calculated to produce the desired therapeutic effect in association with the required pharmaceutical vehicle. The dosage unit forms are dictated by and directly dependent on (a) the unique characteristics of the disclosed compound and the particular therapeutic effect to be achieved, and (b) the limitations inherent in the art of compounding/formulating such a disclosed compound for the treatment of pain, a depressive disorder, or drug addiction in a patient.

In one embodiment, the compounds provided herein are formulated using one or more pharmaceutically acceptable excipients or carriers. In one embodiment, the pharmaceutical compositions provided herein comprise a therapeutically effective amount of a disclosed compound and a pharmaceutically acceptable carrier.

The optimum ratios, individual and combined dosages, and concentrations of the drug compounds that yield efficacy without toxicity are based on the kinetics of the active ingredients' availability to target sites, and are determined using methods known to those of skill in the art.

Routes of administration of any of the compositions discussed herein include oral, nasal, rectal, intravaginal, parenteral, buccal, sublingual or topical. The compounds may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration. In one embodiment, the preferred route of administration is oral.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions are not limited to the particular formulations and compositions that are described herein.

For oral application, particularly suitable are tablets, dragees, liquids, drops, suppositories, or capsules, caplets and gel caps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the disclosed compounds may be formulated for injection or infusion, for example, intravenous, intramuscular or subcutaneous injection or infusion, or for administration in a bolus dose or continuous infusion. Suspensions, solutions or emulsions in an oily or aqueous vehicle, optionally containing other formulatory agents such as suspending, stabilizing or dispersing agents may be used.

Kits

In an aspect, the present disclosure provides a kit for treating cancer comprising a methionine adenosyltransferase II alpha (MAT2A) inhibitor, or a pharmaceutically acceptable salt thereof, and a PRMT type II inhibitor, or a pharmaceutically acceptable salt thereof.

In certain embodiments, the kit comprises a pharmaceutical product comprising a pharmaceutical composition comprising a methionine adenosyltransferase II alpha (MAT2A) inhibitor, or a pharmaceutically acceptable salt thereof, and a pharmaceutically acceptable carrier or diluent; and a pharmaceutical composition comprising a PRMT type II inhibitor, or a pharmaceutically acceptable salt thereof, and a pharmaceutically acceptable carrier or diluent.

In some embodiments, the kit comprises a pharmaceutical composition comprising a methionine adenosyltransferase II alpha (MAT2A) inhibitor, or a pharmaceutically acceptable salt thereof; a PRMT type II inhibitor, or a pharmaceutically acceptable salt thereof; and a pharmaceutically acceptable carrier or diluent. In an embodiment, the Type II PRMT inhibitor is a PRMT5 inhibitor.

In additional embodiments, pharmaceutical kits are provided. The kit includes a sealed container approved for the storage of pharmaceutical compositions, the container containing one of the above-described pharmaceutical compositions. In some embodiments, the sealed container minimizes the contact of air with the ingredients, e.g. an airless bottle. In other embodiments, the sealed container is a sealed tube. An instruction for the use of the composition and the information about the composition are to be included in the kit.

In a particular embodiment, the compounds of the combination can be dosed on the same schedule, whether by administering a single formulation or unit dosage form containing all of the compounds of the combination, or by administering separate formulations or unit dosage forms of the compounds of the combination. However, some of the compounds used in the combination may be administered more frequently than once per day, or with different frequencies that other compounds in the combination. Therefore, in one embodiment, the kit contains a formulation or unit dosage form containing all of the compounds in the combination of compounds, and an additional formulation or unit dosage form that includes one of the compounds in the combination of agents, with no additional active compound, in a container, with instructions for administering the dosage forms on a fixed schedule.

The kits provided herein include comprise prescribing information, for example, to a patient or health care provider, or as a label in a packaged pharmaceutical formulation. Prescribing information may include for example efficacy, dosage and administration, contraindication and adverse reaction information pertaining to the pharmaceutical formulation.

In all of the foregoing the combination of compounds of the invention can be administered alone, as mixtures, or with additional active agents.

A kit provided herein can be designed for conditions necessary to properly maintain the components housed therein (e.g., refrigeration or freezing). A kit can contain a label or packaging insert including identifying information for the components therein and instructions for their use (e.g., dosing parameters, clinical pharmacology of the active ingredient(s), including mechanism(s) of action, pharmacokinetics and pharmacodynamics, adverse effects, contraindications, etc.).

Each component of the kit can be enclosed within an individual container, and all of the various containers can be within a single package. Labels or inserts can include manufacturer information such as lot numbers and expiration dates. The label or packaging insert can be, e.g., integrated into the physical structure housing the components, contained separately within the physical structure, or affixed to a component of the kit (e.g., an ampule, syringe or vial).

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

The following examples further illustrate aspects of the present disclosure. However, they are in no way a limitation of the teachings of the present disclosure as set forth.

EXAMPLES

The compounds and methods disclosed herein are further illustrated by the following examples, which should not be construed as further limiting. The practice of the present disclosure will employ, unless otherwise indicated, conventional techniques of organic synthesis, cell biology, cell culture, and molecular biology, which are within the skill of the art.

Processes for preparing the compounds disclosed herein can be found, at least, in WO 2020/123395, WO 2021/050915, WO 2021/086879, WO2021/163344, WO2022/026892, U.S. Ser. No. 11/077,101, Malik, R., et al. *AACR Annual Meeting,* 2021, Abstract Number 1140, and Bonday, Z. Q., et al., *ACS Med. Chem. Lett.* 2018, 9, 612-617, the contents of which are incorporated in their entirety.

Compound A: the MAT2A inhibitor that is compound 167 in Table 1

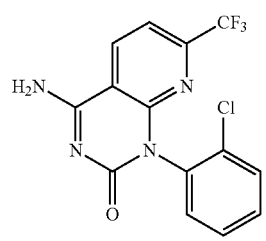

Compound A

Compound B: PRMT5 inhibitor

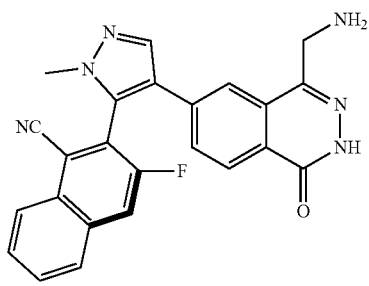

Compound B

Example 1: In Vivo Efficacy of an MAT2A Inhibitor Combined with a PRMT5 Inhibitor Anti-Tumor Efficacy in Mouse Xenografts The effect of Compound A and Compound B as single-agent anti-tumor agents and in combination is assessed in the HCT-116 human colon tumor cell line, MTAP isogenic pair (WT or MTAP-deleted). Cells are expanded in DMEM/F12 GlutaMAX (Fisher Scientific, Catalog Number 10-565-018) and 10% fetal bovine serum. These cells are free of mycoplasma and authenticated as HCT-116 by STR profiling. Two and a half million cells in log growth phase are resuspended in Hanks Balanced Salt Solution containing 50% Matrigel and implanted subcutaneously into the flank of each recipient female CB17/Icr-Prkdc$^{scid}$/IcrIcoCrl mouse. Mice are housed in microisolator cages with corn cob bedding with additional enrichment consisting of sterile nesting material (Innovive) and Bio-huts (Bio-Serv). Water (Innovive) and diet (Teklad Global 19% Protein Extruded Diet 2919, Irradiated) are provided ad libitum. The environment is maintained on a 12-hour light cycle at approximately 68-72° F. and 40-60% relative humidity.

Tumor Volume (TV) is calculated using the following formula TV (mm$^3$)=(width×width×length)/2. No dose holidays are provided for during the study and all mice are euthanized following the final dose on Day fourteen. Tumor growth inhibition (TGI) is calculated by [(TV control$_{final}$−TV treated$_{final}$)/(TV control$_{final}$−TV control$_{initial}$)×100]. TV is analyzed for statistical significance utilizing GraphPad Prism version 9.1.0. Repeated Measures 2-Way ANOVA with Tukey's Multiple Comparisons is utilized, and P-values are presented from the final tumor measurement and are considered statistically significant if less than 0.05.

Mean tumor volume at dosing start is approximately 150 mm$^3$, with seven mice randomized to each treatment group. The study design is identical for both models, with the study consisting of six treatment groups. Mice are dosed orally, once per day, with Vehicle, Compound A at 5 mg/kg, Compound B at 50 mg/kg, or Compound A at 5 mg/kg and Compound B at 50 mg/kg. The Vehicle is 0.5% 400 cps methylcellulose with 0.5% Tween-80 in sterile water.

The combination of a MAT2A inhibitor and a PRMT5 inhibitor resulted in enhancement of TGI over monotherapy.

H838 NSCLC Xenograft Model

In H838 NSCLC xenograft models, a dose-response TGI is assessed with monotherapy and combination.

The NCI-H838 tumor cell line is maintained in vitro as monolayer culture in RPMI-1640 medium supplemented with 10% heat inactivated fetal bovine serum at 37° C. in an atmosphere of 5% CO$_2$ in air. The tumor cells are routinely sub-cultured twice weekly, not to exceed 4-5 passages. The cells growing in an exponential growth phase are harvested and counted for tumor inoculation. Each mouse is inoculated subcutaneously on the right flank with 10 million NCI-H838 tumor cells in 0.1 mL of RPMI-1640 and Matrigel mixture (1:1 ratio) for tumor development. The treatments are started when the mean tumor size reached about 142 mm$^3$ and mice are then assigned to groups such that the mean tumor volume is the same for each treatment group. Each group for efficacy study consists of 10 mice.

Mean tumor volume at dosing start is approximately 150 mm$^3$, with ten mice randomized to each treatment group. Mice are dosed orally, once per day, with Vehicle, Compound A, Compound B, or Compound A and Compound B. The Vehicle is 0.5% 400 cps methylcellulose with 0.5% Tween-80 in sterile water.

The combination of a PRMT5 inhibitor and MAT2A inhibitor resulted in in enhancement of TGI over monotherapy.

LU99 NSCLC Xenograft Model

In LU99 NSCLC xenograft model, a dose-response TGI is assessed with monotherapy and combination. Mean tumor volume at dosing start is approximately 150 mm$^3$, with ten mice randomized to each treatment group. Mice are dosed orally, once per day, with Vehicle, Compound A, Compound B, or Compound A and Compound B. The Vehicle is 0.5% 400 cps methylcellulose with 0.5% Tween-80 in sterile water.

The combination of a PRMT5 inhibitor and MAT2A inhibitor resulted in enhancement of TGI over monotherapy.

Example 2: Pharmacodynamic Biomarkers

MAT2A Inhibition Results in Reduced Plasma and Tumor s-Adenosyl Methionine (SAM) with Efficacious Doses, while PRMT5i Results in No SAM Modulation Tumors treated with Compound A are expected to result in a dose dependent reduction of plasma and tumor SAM. Tumors treated with Compound B are not expected to experience a significant modulation of SAM. The combination of Compound A and Compound B is expected to result in a significant reduction of SAM.

Method for SAM analysis: Tumor samples are homogenized in one volume of 85% acetonitrile in water with 0.1% perchloric acid. Tissue homogenates are diluted with 85% acetonitrile in water with 0.1% perchloric acid as needed.

An aliquot of 30 µL of each plasma, tissue homogenate or diluted tissue homogenate sample is mixed with 100 µL of internal standard solution (D3-SAM in 85% acetonitrile in water with 0.1% perchloric acid). The mixture is vortexed on a shaker for 15 minutes and subsequently centrifuged at 4000 rpm for 15 minutes. An aliquot of 60 µL of the supernatant is mixed with 60 µL of water for the injection to the LC/MS/MS.

SAM powder is solubilized in dimethyl sulfoxide to bring the stock concentration to 1 mg/mL. 10 µL of 1 mg/mL stock solution is spiked into 990 µL of 85% acetonitrile in water with 0.1% perchloric acid. A serial dilution is performed to yield standard concentrations of 2, 5, 20, 100, 200, 1000, 2000, 5000, and QC concentrations of 10, 50 and 500 ng/mL. Calibration standards and quality control samples (30 µL each) are prepared by spiking the testing compounds into 85% acetonitrile in water with 0.1% perchloric acid and the resulting solution is processed with the unknown samples in the same batch. Then 10 µL is subjected to HPLC/MS analysis.

A Shimadzu LC-30AD binary HPLC pump with an autosampler is used for all LC separations. The chromatographic separation of analytes is achieved on a Phenomenex Synergi Polar-RP (150×2.0 mm, 4μ) column, in conjunction with fast gradient conditions and mobile phases A (15 mM Ammonium Acetate in water) and B (Methanol:Acetonitrile 50:50 (v/v) with 0.1% Formic acid). A Sciex QTRAP 5000 (MS/MS) mass spectrometer equipped with a Turbo Ionspray interface from Applied Biosystems (Framingham, MA) is used for detection. The instrument is operated in the positive ion multiple reaction monitoring (MRM) mode employing argon as a collision gas. The following MRM transitions are monitored: m/z 399.1→250 and m/z 402.1→250 for SAM and internal standard (D3-SAM), respectively. Data are acquired and processed by Sciex Analyst 1.7.2 software.

The Monotherapy and Combination Treatment Preferentially Modulate SDMA in MTAP-Deleted Tumors.

MAT2A inhibitor and PRMT5 inhibitor combinations are expected to reduce PRMT5 mediated protein methylation events as measured by symmetric dimethyl arginine (SDMA). SDMA is measured by WB, ELISA or IHC with a commercial antibody from Cell Signaling (Catalog #13222, Danvers, MA) or alternate antibody.

Method for WB analysis: Xenograft tissue pieces are kept on dry ice and 2 mm sections are sliced and transferred to 400 μl of ice-cold TPER lysis buffer (Thermo Fisher #78510). Tissue sections are homogenized using an Omni Tip homogenizer for 45 seconds. Homogenized samples are centrifuged at 13000 rpm at 4 C for 20 minutes. Supernatant is collected and protein is quantified using the bicinchoninic acid assay (Pierce #23225). Fifty micrograms of protein are resolved by SDS-PAGE in a 4-12% gradient Bis-Tris gel (Life Technologies #WG1402BOX) and transferred onto a nitrocellulose membrane using the iBLOT Transfer System (Life Technologies #IB21001; 1B23001). Membranes are blocked in SuperBlock T20 Blocking Buffer (Thermo scientific #37536) or Blotto solution (Thermo scientific #37530) for 1 hour and then incubated with primary antibodies against Symmetric dimethyl Arginine (Cell Signaling #13222), MAT2A (Abcam #186129) and Vinculin (Abcam #219649) overnight. Appropriate secondary antibodies (Cell Signaling #7074S, 7076S) are added to the membrane followed by washes in TBST solution. Membranes are developed using the SuperSignal Pico or West Femto ECL substrate (Fisher Scientific #34580, #34095) and visualized on the BioRad ChemiDoc (BioRad #1708265), or similar method.

In HCT-116 MTAP-deleted tumors, Compound A and Compound B are expected to reduce SDMA. The combination of Compound A and Compound B results in a significant reduction of SDMA.

In H838 NSCLC xenograft, Compound A and Compound B are expected to reduce SDMA. The combination of Compound A and Compound B enhance the reduction of SDMA, when compared to monotherapy of either agent.

In LU99 NSCLC xenograft, Compound A and Compound B are expected to reduce SDMA. The combination of Compound A and Compound B enhance the reduction of SDMA, when compared to monotherapy of either agent.

Example 3: Cell Proliferation Assessment

Four cell lines, HCT116, HCT116 MTAP$^{-/-}$ (CRISPR knockout of MTAP), H838, and KP4, are used to assess the combinatory effect of a MAT2A inhibitor and PRMT5 inhibitor on cell proliferation. All except the H838 cells are stably transduced with Incucyte NucLight Green or Red Lentivirus Reagent. Cells are seeded in a 96-well plate at an optimal density that allows for untreated cells to reach 70-90% confluency after 6 days in culture. 24 hrs later, cells are treated with a MAT2A and PRMT5 inhibitor, each serially diluted 3-fold, in a 6×11 double titration matrix format. Control cells are treated in parallel with each single agent alone in a 10-point, 3-fold serial dilution, titration, or with 0.2% DMSO. All data points are run in technical duplicates. 6 days later, cells are imaged using an IncuCyte Live-Cell Analysis System. Only the H838 cells are labelled with Vybrant DyeCycle Green Stain 90 minutes prior to being imaged. Data are normalized to the average of the DMSO-treated cells. Dose response curves are generated for single agent-treated cells using the 4PL curve fit from the GraphPad software, and synergy/antagonism scores, calculated from the Bliss, HSA, and Loewe models, are generated for combination-treated cells using the Combenefit software.

Example 4: MTA Measurement

Methods

KP4, BxPC3, RT112/84, H647, H460 cells lines evaluated following 30 min and 48 hour of cell culture. After trypsinization and PBS wash, the cells were counted and then pelleted, snap-frozen and stored at −80 C until use. For MTA LC-MS analysis, the cells were homogenized in 30 μL of 85% acetonitrile in water with 0.1% perchloric acid with gentle shake. The homogenate sample is mixed with 100 μL of internal standard solution (D3-MTA in 85% acetonitrile in water with 0.1% perchloric acid). The mixture is vortexed on a shaker for 15 minutes and subsequently centrifuged at 4000 rpm for 15 minutes. An aliquot of 60 μL of the supernatant is mixed with 60 μL of water for the injection to the LC/MS/MS.

MTA powder is solubilized in dimethyl sulfoxide to bring the stock concentration to 1 mg/mL. 10 μL of 1 mg/mL stock solution is spiked into 990 μL of 85% acetonitrile in water with 0.1% perchloric acid. A serial dilution is performed to yield standard concentrations of 1, 2, 5, 20, 100, 200, 1000, 2000, 5000, and QC concentrations of 5, 50 and 500 ng/mL. Calibration standards and quality control samples (30 μL each) are prepared by spiking the testing compounds into 100 μL of internal standard solution (D3-MTA in 85% acetonitrile in water with 0.1% perchloric acid) and the resulting solution is processed with the unknown samples in the same batch. Then 10 μL is subjected to HPLC/MS analysis.

An Agilent 1200 binary HPLC pump with a thermo autosampler is used for all LC separations. The chromatographic separation of analytes is achieved on a Phenomenex Luna Omaga 3 μm Polar C18, 50×2.1 mm HPLC column, in conjunction with fast gradient conditions and mobile phases A (0.1% Formic acid in water) and B (0.1% Formic acid in Acetonitrile (v/v). A Sciex QTRAP 4000 (MS/MS) mass spectrometer equipped with a Turbo Ionspray interface from Applied Biosystems (Framingham, MA) is used for detection. The instrument is operated in the positive ion multiple reaction monitoring (MRM) mode employing nitrogen as a collision gas. The following MRM transitions are monitored: m/z 298.3→250 and m/z 301.3→250 for MTA and internal standard (D3-MTA), respectively. Data are acquired and processed by Sciex Analyst 1.7.2 software. Measured conc. (ng/mL) time with 30 (μL) to give resulted Number (pg) for each cell sample.

Results

There was increase in MTA levels after culturing for 48 hours in all MTAP deleted cell lines (FIG. 1). The pancreatic cancer cell line KP4 showed the maximum increase, followed by RT112/84 (bladder), BxPC3 (Pancreas) and NCI-H647 (Lung). No changes in MTA levels were observed in MTAP WT cell line NCI-H460.

Example 5: Efficacy of Compound a and Compound B in HCT-116 MTAP Isogenic Pair The effect of Compound A and Compound B (HCl salt was used) as single-agent anti-tumor agents and in combination was assessed in the HCT-116 human colon tumor cell line, MTAP isogenic pair (MTAP proficient (WT) or MTAP-deleted). Cells were expanded in DMEM/F12 GlutaMAX (Fisher Scientific, Catalog Number 10-565-018) with 10% fetal bovine serum. These cells were free of mycoplasma and authenticated as HCT-116 by STR profiling. Two and a half million cells in log growth phase were resuspended in Hanks Balanced Salt Solution containing 50% Matrigel and implanted subcutaneously into the flank of each recipient female nu/nu mouse. Mice were housed in microisolator cages with corn cob bedding with additional enrichment consisting of sterile nesting material (Innovive) and Bio-huts (Bio-Serv). Water (Innovive) and diet (Teklad Global 19% Protein Extruded Diet 2919, Irradiated) were provided ad libitum. The environment was maintained on a 12-hour light cycle at approximately 68-72° F. and 40-60% relative humidity.

Tumor Volume (TV) was calculated using the following formula: TV (mm$^3$)=(width×width×length)/2. No dose holidays were provided for during the study and all mice were euthanized following the final dose on Day 21 (MTAP-deleted) or Day 15 (MTAP WT). Tumor growth inhibition (TGI) was calculated by [(TV control$_{final}$−TV treated$_{final}$)/(TV control$_{final}$−TV control$_{initial}$)×100]. A TGI greater than 100% indicates tumor regressions. TV was analyzed for statistical significance utilizing GraphPad Prism version 9.1.0. Repeated Measures 2-Way ANOVA with Tukey's Multiple Comparisons was utilized, and P-values were presented from the final tumor measurement and were considered statistically significant if less than 0.05.

Mean tumor volume at dosing start was approximately 224 mm$^3$, with seven mice randomized to each treatment group. In the HCT-116 MTAP-deleted tumor model, mice were dosed orally, twice per day (BID) with Vehicle, once per day (QD) with Compound A at 1 or 3 mg/kg, or BID with Compound B at 3, 10, or 30 mg/kg, or Compound A combined with Compound B at each dose level. In the HCT-116 WT tumor model, mice were dosed orally, with BID Vehicle, QD with Compound A at 3 mg/kg, or BID with Compound B at 10 or 30 mg/kg, or Compound A combined with Compound B. The Vehicle was 0.5% 400 cps methylcellulose with 0.5% Tween-80 in sterile water.

Figure 2A:
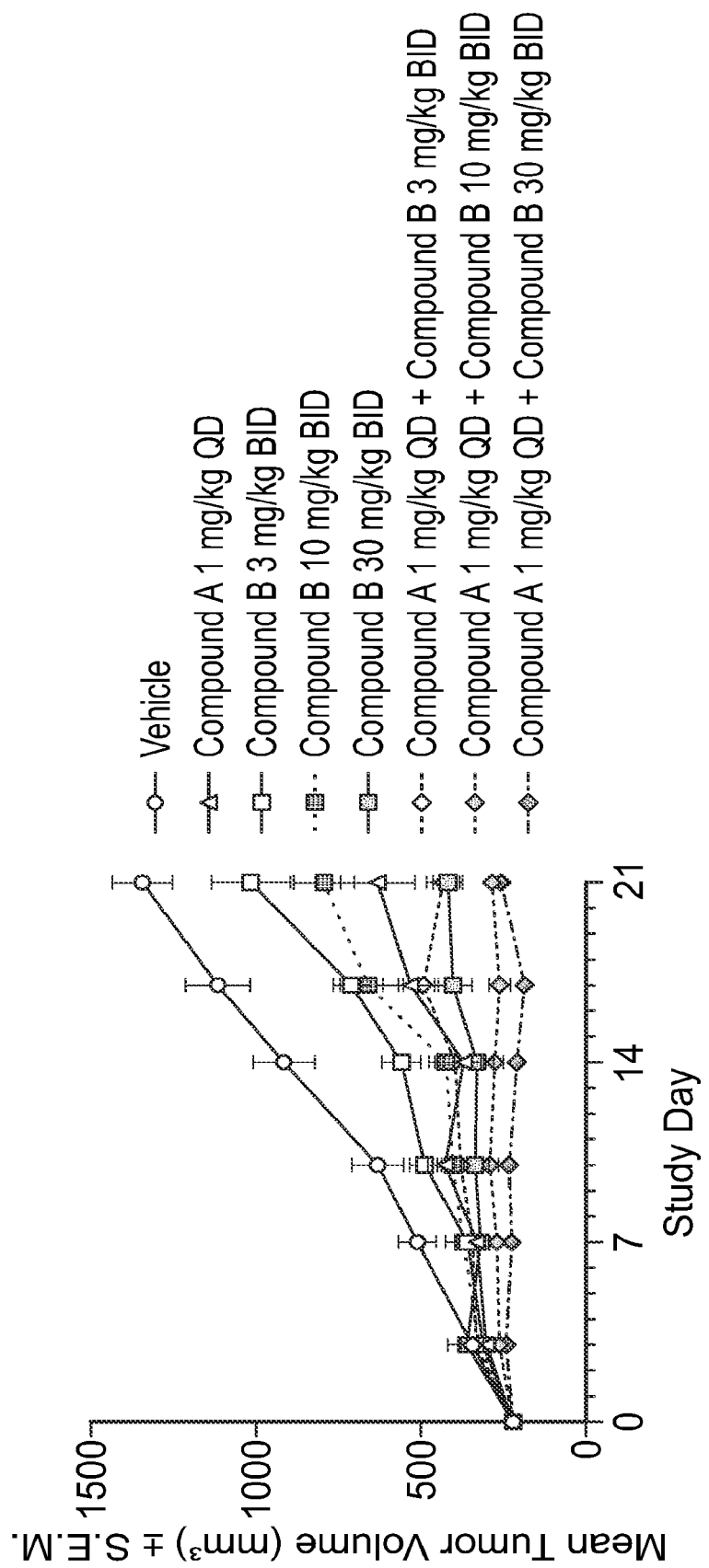
FIG. 2A and FIG. 2B show the efficacy of Compound A and Compound B in HCT-116 MTAP-deleted tumors.
Figure 2B:
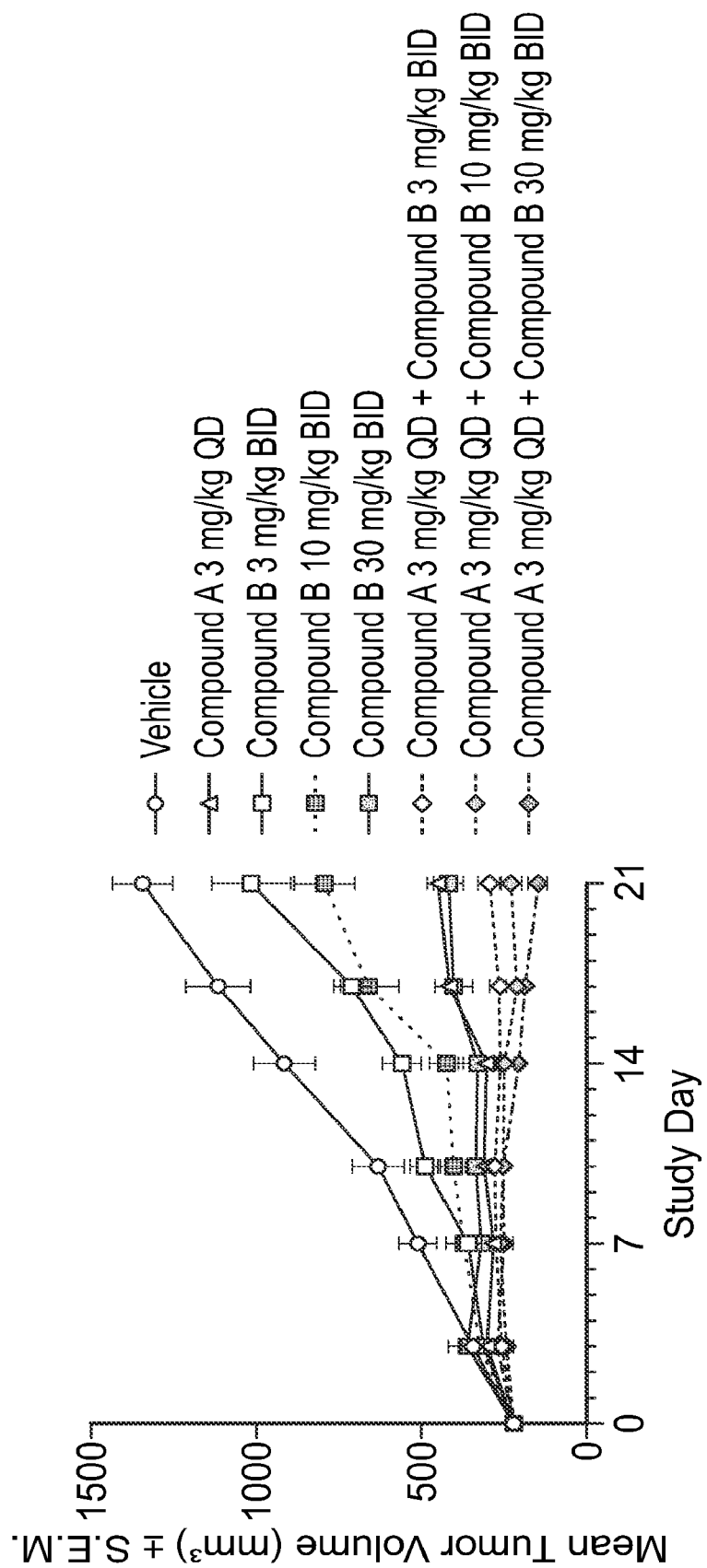

In the HCT-116 MTAP-deleted model, administration of Compound A at 1 or 3 mg/kg QD resulted in 64% and 80% TGI, respectively. Administration of Compound B at 3, 10, or 30 mg/kg BID resulted in 29, 49, and 83% TGI, respectively. The combination of 1 mg/kg QD Compound A and Compound B at 3, 10, or 30 mg/kg BID resulted in 81, 94, and 97% TGI, respectively. The combination of 3 mg/kg QD Compound A and Compound B at 3, 10, or 30 mg/kg BID resulted in 93, 99, and 107% TGI, respectively (Table 7 and FIG. 2). The combination of Compound A and Compound B significantly inhibited tumor growth in a dose dependent manner, and at the highest dose levels administered promoted tumor regression in HCT-116 MTAP-deleted tumors.

TABLE 7

Summary of Efficacy of Compound A and Compound B in HCT-116 MTAP-Deleted Xenografts

| Dose Cmpd A (mg/kg) | Dose Cmpd B (mg/kg) | Initial TV (mean) | Final TV (mean) | TGI (%) | p value, treated vs. Vehicle | p value, Combination vs. 1 mg/kg Cmpd A | p value, Combination vs. 3 mg/kg Cmpd A | p value, Combination vs. 30 mg/kg Cmpd B |
|---|---|---|---|---|---|---|---|---|
| 0 | 0 | 224 | 1343 | NA | NA | NA | NA | NA |
| 1 | 0 | 224 | 632 | 64 | <0.0001 | NA | NA | NA |
| 3 | 0 | 224 | 450 | 80 | <0.0001 | NA | NA | NA |
| 0 | 3 | 224 | 1015 | 29 | <0.0001 | NA | NA | NA |
| 0 | 10 | 224 | 794 | 49 | <0.0001 | NA | NA | NA |
| 0 | 30 | 224 | 420 | 83 | <0.0001 | NA | NA | NA |
| 1 | 3 | 224 | 433 | 81 | <0.0001 | ns | NA | NA |
| 1 | 10 | 224 | 287 | 94 | <0.0001 | ns | NA | NA |
| 1 | 30 | 224 | 258 | 97 | <0.0001 | <0.0001 | NA | NA |
| 3 | 3 | 224 | 297 | 93 | <0.0001 | NA | ns | NA |
| 3 | 10 | 224 | 232 | 99 | <0.0001 | NA | 0.0426 | NA |
| 3 | 30 | 224 | 148 | 107 | <0.0001 | NA | 0.0003 | 0.0023 |

NA = not applicable, ns = not statistically significant

Figure 3:
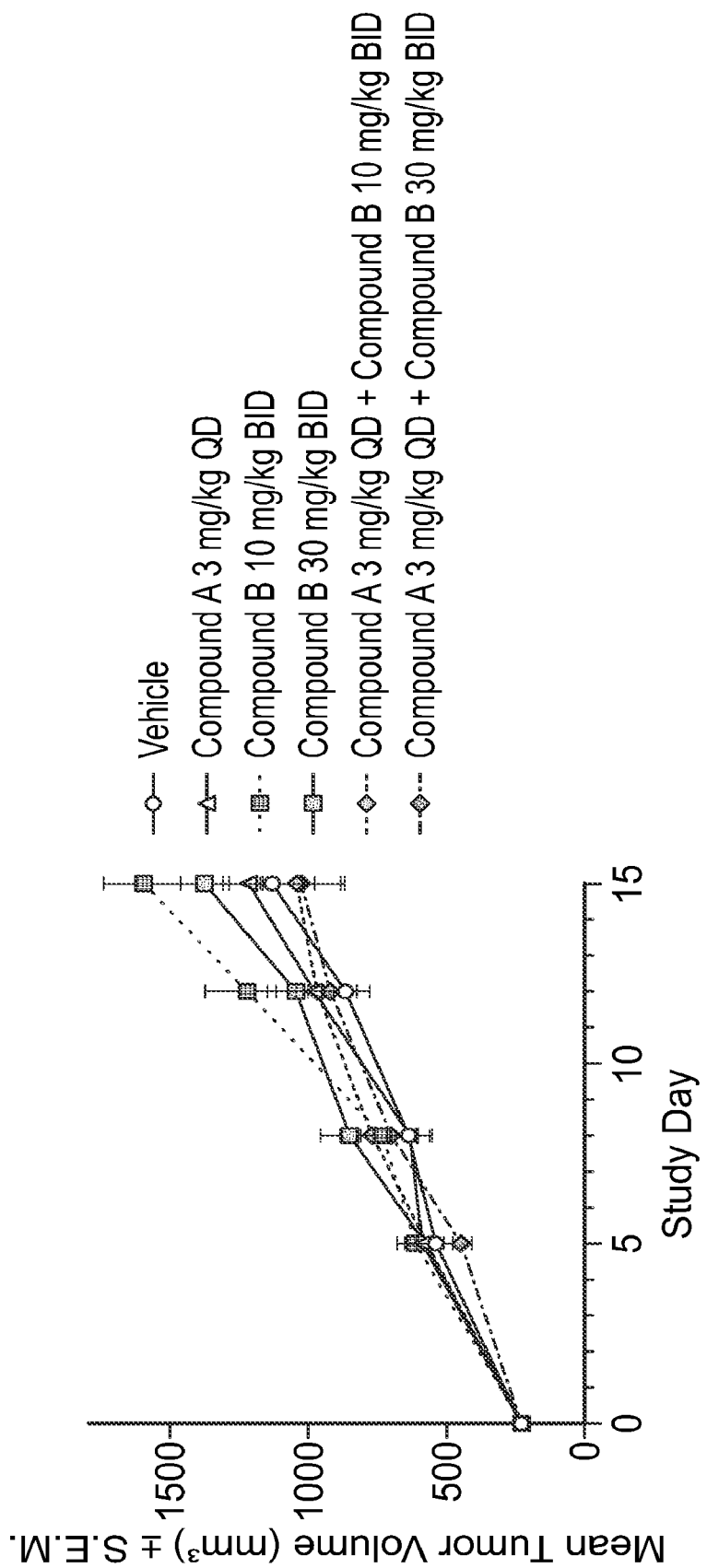
FIG. 3 shows the efficacy of Compound A and Compound B in HCT-116 MTAP WT xenografts.

In HCT-116 MTAP WT, administration of Compound A resulted in −9% TGI, or no tumor growth inhibition, while Compound B at 10 or 30 mg/kg BID alone resulted in −52 and −27% TGI. Compound B at 10 mg/kg BID significantly enhanced tumor growth. The combination of Compound A and Compound B at 10 or 30 mg/kg BID resulted in 11-12% TGI, which was not found to be statistically significant (Table 8 and FIG. 3). The combination of Compound A and Compound B did not prevent tumor growth in HCT-116 WT tumors.

TABLE 8

Summary of Efficacy of Compound A and Compound B in HCT-116 MTAP WT Xenografts

| Dose Cmpd A (mg/kg) | Dose Cmpd B (mg/kg) | Initial TV (mean) | Final TV (mean) | TGI (%) | p value, treated vs. Vehicle | p value, Combination vs. Cmpd A | p value, Combination vs. 30 mg/kg Cmpd B |
|---|---|---|---|---|---|---|---|
| 0 | 0 | 229 | 1128 | NA | NA | NA | NA |
| 3 | 0 | 228 | 1211 | −9 | ns | NA | NA |
| 0 | 10 | 228 | 1596 | −52 | 0.0126 | NA | NA |
| 0 | 30 | 228 | 1372 | −27 | ns | NA | NA |
| 3 | 10 | 228 | 1030 | 11 | ns | ns | ns |
| 3 | 30 | 228 | 1023 | 12 | ns | ns | ns |

NA = not applicable, ns = not statistically significant

Compound A and Compound B were found to result in significant single agent activity in MTAP-deleted models, but no single agent activity in the MTAP WT model. When Compound A was combined with Compound B, the combination resulted in significantly greater anti-tumor activity compared to either agent alone.

Example 6: Efficacy of Compound A and Compound B in NCI-H838 NSCLC Xenograft The effect of Compound A and Compound B (HCl salt was used) as single-agent anti-tumor agents and in combination was assessed in the NCI-H838 human NSCLC tumor cell line, an endogenously MTAP-deleted cell line. Cells were expanded in RPMI with 10% fetal bovine serum. These cells were free of mycoplasma and authenticated by STR profiling. Ten million cells in log growth phase were resuspended in RPMI-1640 containing 50% Matrigel and implanted subcutaneously into the flank of each recipient female BALB/c nude mouse. The mice were be kept in laminar flow rooms at constant temperature and humidity with 3-5 mice in each cage. Animals were housed in polycarbonate cages maintained at a temperature of 23±3° C. and a relative humidity of 40% to 70%. The bedding material was soft wood, which was changed once per week. Water and diet were provided ad libitum.

Tumor Volume (TV) was calculated using the following formula: TV $(mm^3)$=(width×width×length)/2. No dose holidays were provided for during the study. Tumor growth inhibition (TGI) was calculated by [(TV control$_{final}$−TV treated$_{final}$)/(TV control$_{final}$−TV control$_{initial}$)×100]. A TGI greater than 100% indicates tumor regressions. TV was analyzed for statistical significance utilizing GraphPad Prism version 9.1.0. Repeated Measures 2-Way ANOVA with Tukey's Multiple Comparisons was utilized, and P-values were presented from the Study Day 25 tumor measurement and were considered statistically significant if less than 0.05.

Mean tumor volume at dosing start was approximately 140 $mm^3$, with ten mice randomized to each treatment group, with the study consisting of eight treatment groups. Mice were dosed orally, twice per day (BID) with Vehicle, once per day (QD) with Compound A at 3 mg/kg, or BID with Compound B at 1, 10, or 30 mg/kg, or Compound A combined with Compound B at each dose level. The Vehicle was 0.5% 400 cps methylcellulose with 0.5% Tween-80 in sterile water.

Figure 4:
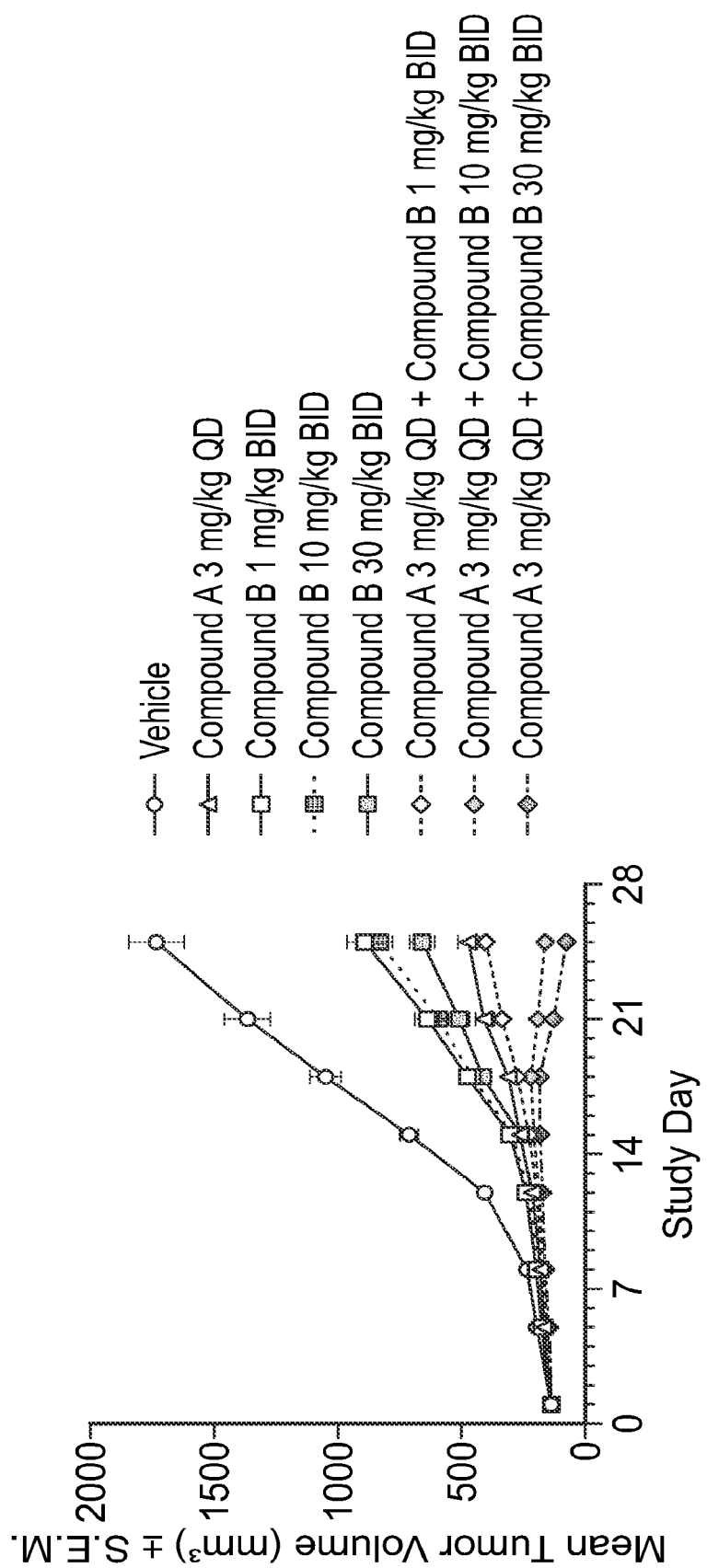
FIG. 4 shows the efficacy of Compound A and Compound B in NCI-H838 MTAP-deleted xenografts.
Figure 4A:
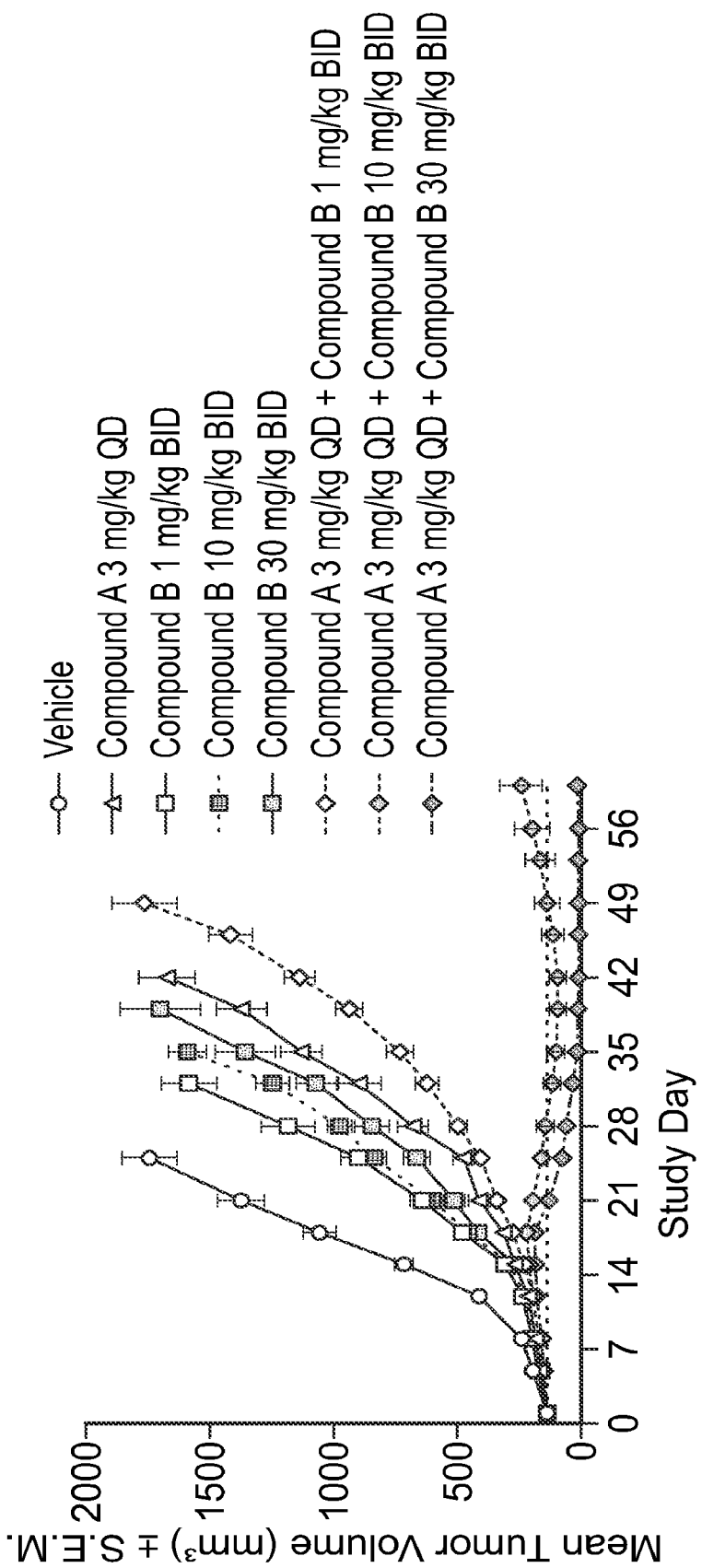
FIG. 4A shows the efficacy of Compound A and Compound B in NCI-H838 MTAP-deleted xenografts (60 Day study).

Administration of Compound A resulted in 79% TGI. Administration of 1, 10, or 30 mg/kg BID Compound B alone resulted in 53, 56, or 67% TGI, respectively. The combination of Compound A and 1, 10, or 30 mg/kg BID Compound B resulted in 83, 99, and 104% TGI, respectively (Table 9 and FIG. 4). The combination of Compound A and Compound B significantly inhibited tumor growth in a dose dependent manner, and at the highest dose levels administered, promoted tumor regression. By Study Day 60, the combination of 3 mg/kg QD Compound A and 30 mg/kg BID Compound B produced 100% tumor regressions (FIG. 4A).

TABLE 9

Efficacy of Compound A and Compound B in NCI-H838 MTAP deleted Xenografts

| Dose Cmpd A (mg/kg) | Dose Cmpd B (mg/kg) | Initial TV (mean) | Final TV (mean) | TGI (%) | p value, treated vs. Vehicle | p value, combination vs. Cmpd A | p value, combination vs. 30 mg/kg Cmpd B |
|---|---|---|---|---|---|---|---|
| 0 | 0 | 140 | 1743 | NA | NA | NA | NA |
| 3 | 0 | 140 | 478 | 79 | <0.0001 | NA | NA |
| 0 | 1 | 140 | 899 | 53 | <0.0001 | NA | NA |
| 0 | 10 | 140 | 839 | 56 | <0.0001 | NA | NA |
| 0 | 30 | 140 | 666 | 67 | <0.0001 | NA | NA |
| 3 | 1 | 139 | 408 | 83 | <0.0001 | ns | NA |
| 3 | 10 | 140 | 163 | 99 | <0.0001 | <0.0001 | NA |
| 3 | 30 | 139 | 81 | 104 | <0.0001 | <0.0001 | <0.0001 |

NA = not applicable, ns = not statistically significant

Example 7: Efficacy of Compound A and Compound B in LU99 NSCLC Xenograft

The effect of Compound A and Compound B (HCl salt was used) as single-agent anti-tumor agents and in combination was assessed in the JCRB LU99 human NSCLC tumor cell line, an endogenously MTAP-deleted cell line. Cells were expanded in RPMI with 10% fetal bovine serum. These cells were free of mycoplasma and authenticated by STR profiling. Ten million cells in log growth phase were resuspended in RPMI-1640 containing 50% Matrigel and implanted subcutaneously into the flank of each recipient female BALB/c nude mouse. The mice were be kept in laminar flow rooms at constant temperature and humidity with 3-5 mice in each cage. Animals were housed in polycarbonate cages maintained at a temperature of 23±3° C. and a relative humidity of 40% to 70%. The bedding material was soft wood, which was changed once per week. Water and diet were provided ad libitum.

Tumor Volume (TV) was calculated using the following formula: TV $(mm^3)$=(width×width×length)/2. No dose holidays were provided for during the study. Tumor growth inhibition (TGI) was calculated by [(TV control$_{final}$−TV treated$_{final}$)/(TV control$_{final}$−TV control$_{initial}$)×100]. A TGI greater than 100% indicates tumor regressions. TV was analyzed for statistical significance utilizing GraphPad Prism version 9.1.0. Repeated Measures 2-Way ANOVA with Tukey's Multiple Comparisons was utilized, and P-values were presented from the final tumor measurement on Study Day 21 and were considered statistically significant if less than 0.05.

Mean tumor volume at dosing start was approximately 141 $mm^3$, with ten mice randomized to each treatment group, with the study consisting of eight treatment groups. Mice were dosed orally, twice per day (BID) with Vehicle, once per day (QD) with Compound A at 3 mg/kg, or BID with Compound B at 1, 10, or 30 mg/kg, or Compound A combined with Compound B at each dose level. The Vehicle was 0.5% 400 cps methylcellulose with 0.5% Tween-80 in sterile water.

Figure 5:
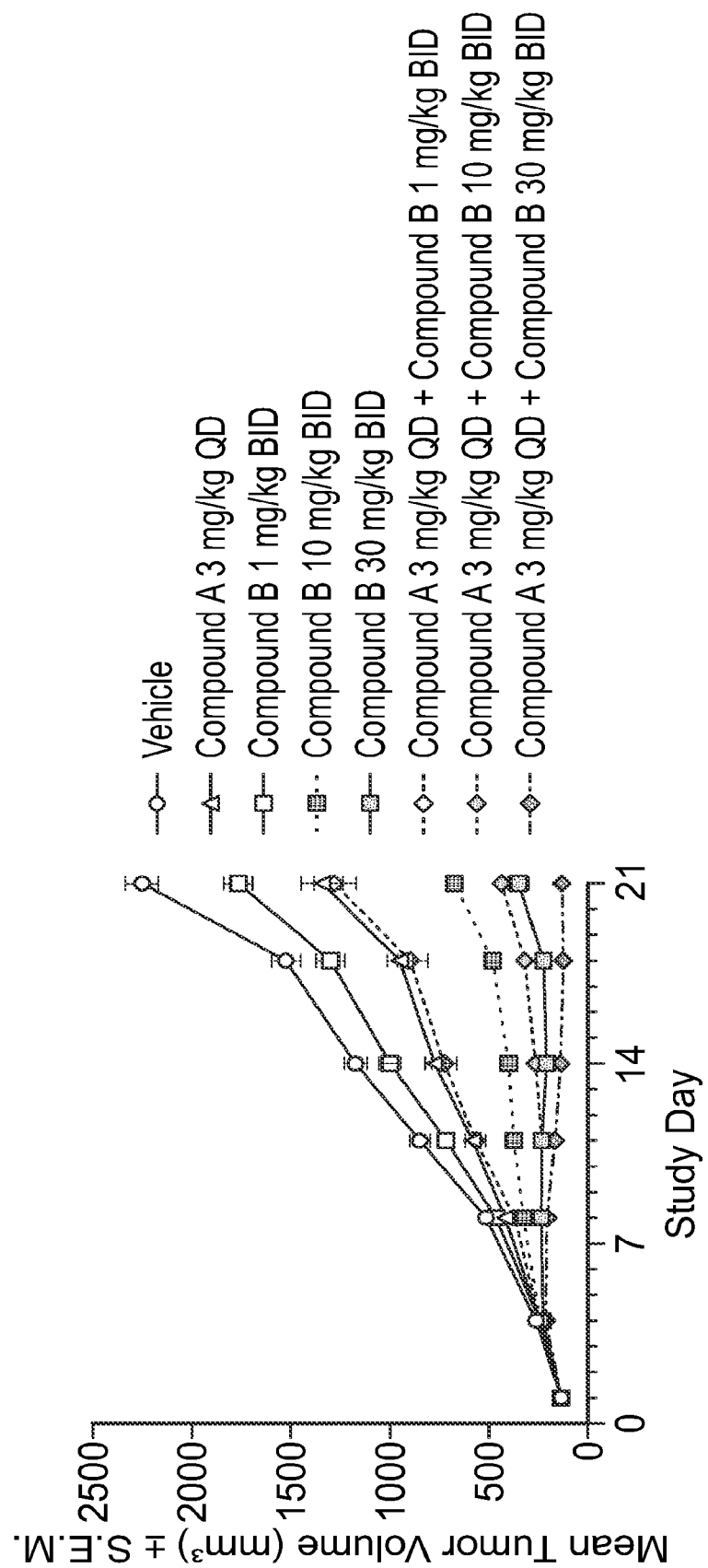
FIG. 5 shows the efficacy of Compound A and Compound B in LU99 MTAP-deleted xenografts.

Administration of Compound A resulted in 43% TGI. Administration of 1, 10, or 30 mg/kg BID Compound B alone resulted in 23, 74, or 90 TGI, respectively. The combination of Compound A and 1, 10, or 30 mg/kg BID Compound B resulted in 46, 86, and 100% TGI, respectively (Table 10 and FIG. 5). The combination of Compound A and Compound B significantly inhibited tumor growth in a dose dependent manner, and at the highest dose levels administered completely inhibited tumor growth.

MAT2A inhibitor Compound A was found to provide statistically significant anti-tumor activity in three MTAP-deleted xenograft models. Compound A when combined with the MTA-cooperative PRMT5 inhibitor Compound B prevented tumor growth in the HCT-116 MTAP-deleted model but not the HCT-116 MTAP WT model. In the endogenously MTAP-deleted NSCLC models NCI-H838 and JCRB LU99, Compound A combination with Compound B provided greater anti-tumor activity than either agent alone. In each MTAP-deleted model, the combination resulted in significantly greater anti-tumor activity compared to either agent alone. In each model, tumor stasis or tumor regressions were achieved with the combination of Compound A and Compound B. Tumor regression was observed with Compound A 3 mg/kg QD and Compound B 30 mg/kg BID in HCT-116 MTAP-deleted and NCI-H838 tumor models.

Example 8: Combinatory Inhibition of MAT2A and Type II PRMT5 Displays Minimal In Vitro Anti-Proliferative Effects in MTAP-Deleted Models

Materials and Methods

The HCT116 isogenic pair, stably transduced with Incucyte Nuclight Red Lentivirus Reagent, and an endogenous MTAP-null cell line, H838, were used to assess the combinatory effect of a MAT2A inhibitor (Compound A) and an MTA-cooperative PRMT5 inhibitors (Compounds B, C, D, E, F, and G) in vitro. Cells were seeded at a density of 110 or 150 cells/well in a 384-well plate, and 24 hrs later, treated with a 6-point, 3-fold titration series of each compound, starting from the highest concentration of 10 µM, in a 6×6 double matrix, using a TECAN liquid dispenser. For the co-treatment of cells with Compounds A and C or Compounds A and G, cells were treated with a 9-point, 2.5-fold titration series of Compound A, and an 11-point, 2-fold titration series of Compound C or G, starting from the highest concentration of 1.25 µM, in an 9×11 double matrix, using a TECAN liquid dispenser. After 5-6 cell population doublings (5 days for HCT116 parental, 6 days for HCT116 MTAP$^{-/-}$, and 7 days for H838 cell line), cells were imaged with an IncuCyte S3 Live-Cell Analysis System for nuclear count determination. Only the H838 cells were incubated with 5 µM of Vybrant DyeCycle Green for 90 minutes prior to being imaged. Each data point were run in technical triplicate.

For only the HCT116 isogenic pair, nuclear counts were obtained at the start of the combination (T0), to normalize

TABLE 10

Efficacy of Compound A and Compound B in LU99 MTAP-deleted Xenografts

| Dose Cmpd A (mg/kg) | Dose Cmpd B (mg/kg) | Initial TV (mean) | Final TV (mean) | TGI (%) | p value, treated vs. Vehicle | p value, Combination vs. Cmpd A | p value, Combination vs. 30 mg/kg Cmpd B |
|---|---|---|---|---|---|---|---|
| 0 | 0 | 141 | 2250 | NA | NA | NA | NA |
| 3 | 0 | 142 | 1341 | 43 | <0.0001 | NA | NA |
| 0 | 1 | 142 | 1765 | 23 | <0.0001 | NA | NA |
| 0 | 10 | 142 | 683 | 74 | <0.0001 | NA | NA |
| 0 | 30 | 141 | 353 | 90 | <0.0001 | NA | NA |
| 3 | 1 | 141 | 1281 | 46 | <0.0001 | ns | NA |
| 3 | 10 | 142 | 444 | 86 | <0.0001 | <0.0001 | NA |
| 3 | 30 | 141 | 137 | 100 | <0.0001 | <0.0001 | 0.0026 |

NA = not applicable, ns = not statistically significant the nuclear counts obtained at the terminal timepoint. The nuclear counts were normalized to the average nuclear counts of the DMSO (vehicle control)-treated cells, as a percent of the control (POC), where POC=(X/average nuclear cell counts of DMSO control)×100. Dose response curves and absolute or relative $IC_{50}$ calculations for single drug activity and drug combination synergy were generated using the Combenefit software, and synergy was evaluated using HSA, Bliss, and Loewe models.

Results

The combination of Compound A and all MTA-cooperative PRMT5 inhibitors resulted in synergistic growth inhibition in all 3 cell lines, HCT116 parental ($MTAP^{WT}$), HCT116 $MTAP^{-/-}$, and H838 ($MTAP^{-/-}$). Notably, although all combinations assessed demonstrated synergy in the HCT116 parental cell line, this synergy required higher concentrations of both agents compared to the synergy observed in either of the MTAP-null cell lines.

Figure 6:
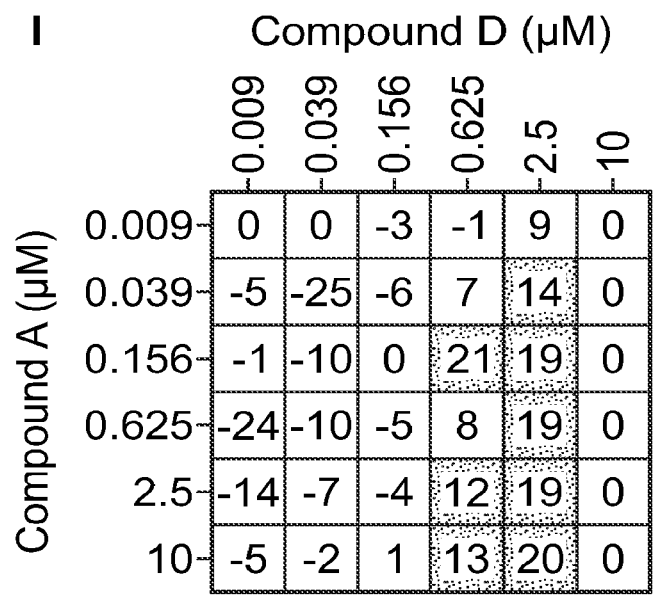
FIGS. 6A-6R show the combination benefit of Compound A and MTA-cooperative PRMT5 inhibitors in the HCT116 parental cell line.
Figure 6:
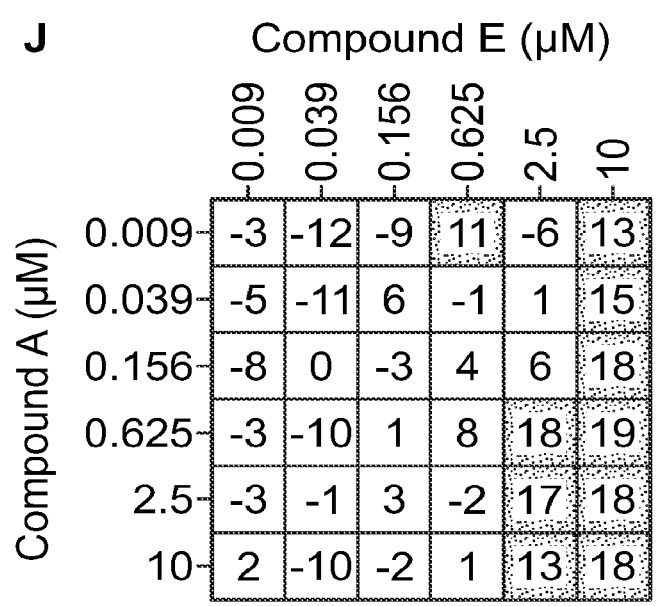
Figure 6:
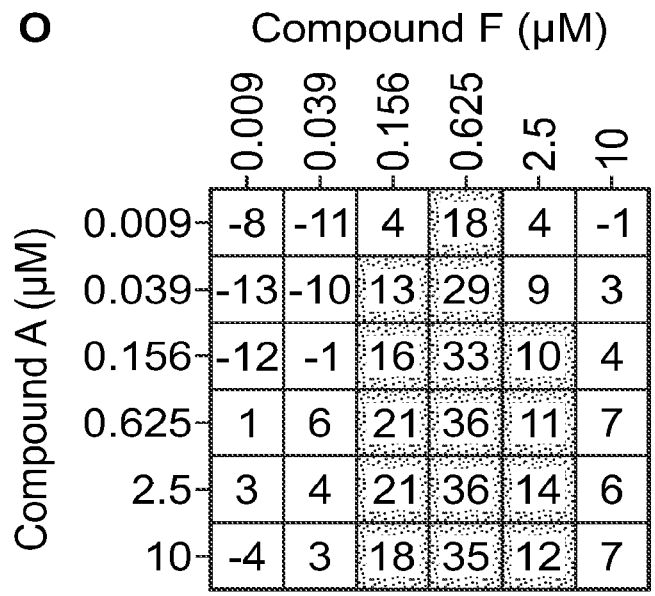
Figure 6:
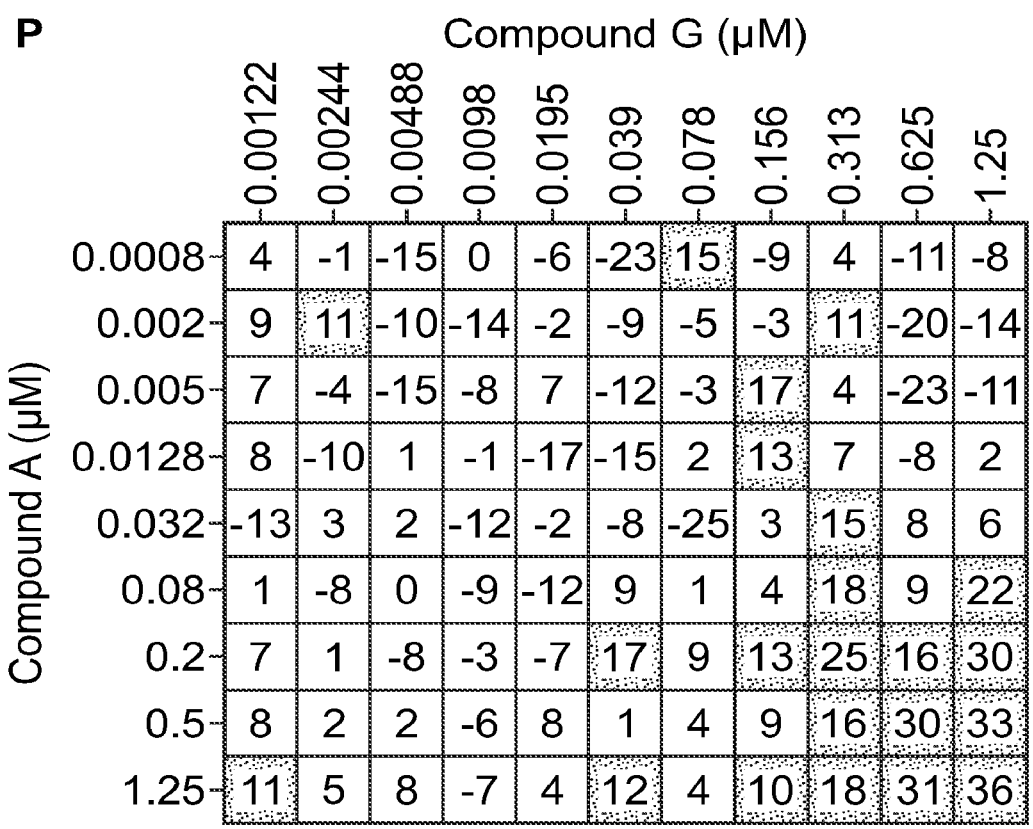
Figure 6:
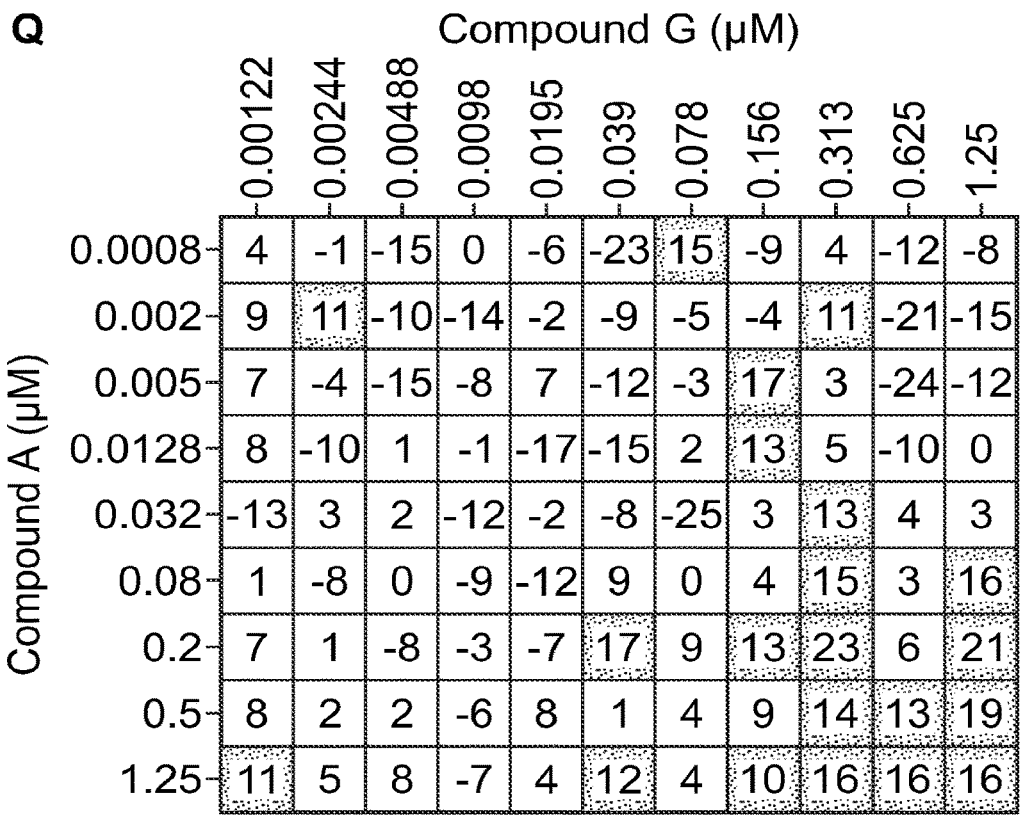
Figure 6:
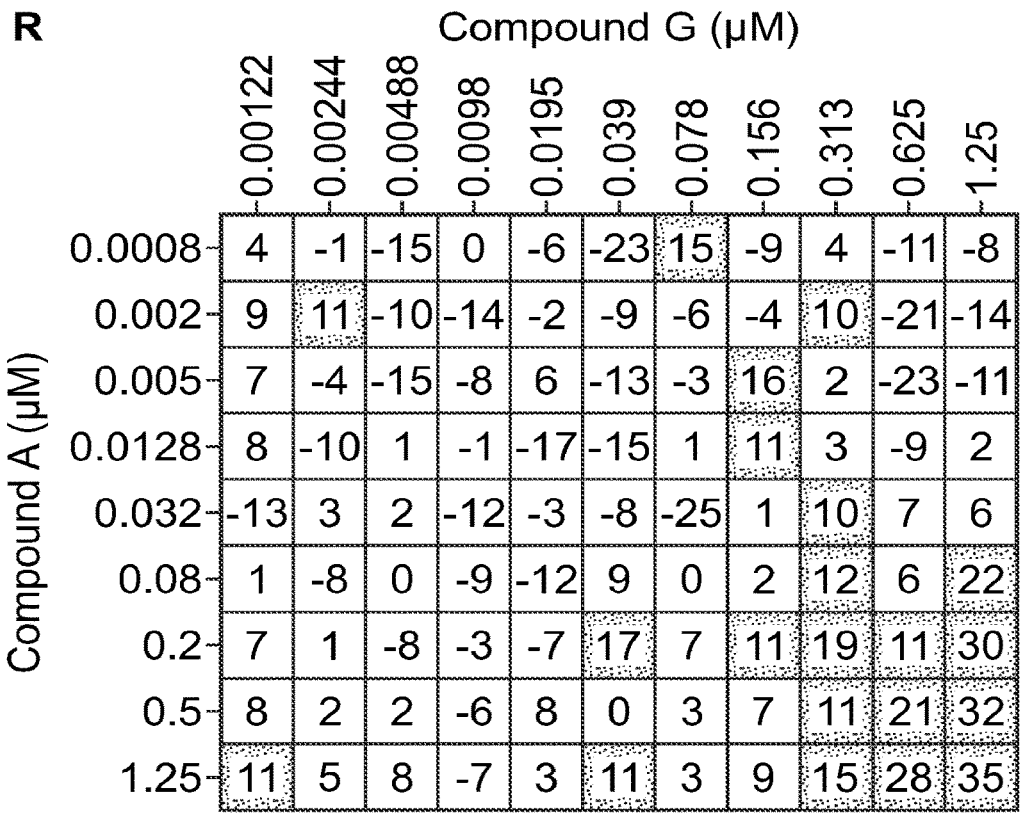

In FIG. 6, the combination benefit between Compound A and MTA-cooperative PRMT5 inhibitors (Compounds B, C, D, E, F, and G) was measured using HSA: FIGS. 6A, 6D, 6G, 6J, 6M, and 6P; Bliss: FIGS. 6B, 6E, 6H, 6K, 6N, and 6Q; or Loewe: FIGS. 6C, 6F, 6I, 6L, 6O, and 6R synergy models from the Combenefit software.

Figure 8:
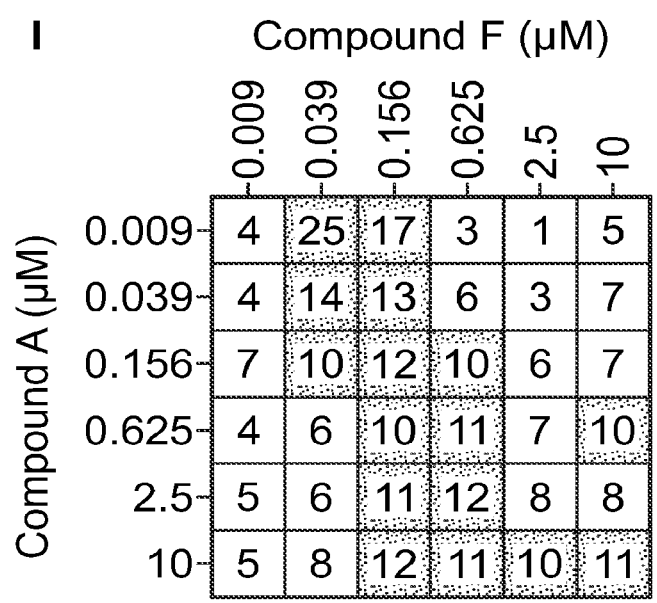
FIGS. 8A-I show the combination benefit of Compound A and MTA-cooperative PRMT5 inhibitors in the H838 cell line.

In FIG. 7, the combination benefit between Compound A and MTA-cooperative PRMT5 inhibitors (Compounds B, C, D, E, F, and G) was measured using HSA: FIGS. 7A, 7D, 7G, 7J, 7M, and 7P; Bliss: FIGS. 7B, 7E, 7H, 7K, 7N, and 7Q; or Loewe: FIGS. 7C, 7F, 7I, 7L, 7O, and 7R synergy models from the Combenefit software In FIG. 8, combination benefit between Compound A and MTA-cooperative PRMT5 inhibitors (Compounds B, C, and F) was measured using HSA: FIGS. 8A, 8D, and 8G; Bliss: FIGS. 8B, 8E, and 8H; or Loewe: FIGS. 8C, 8F, and 8I synergy models from the Combenefit software.

In FIGS. 6-8, synergy scores >10, highlighted in grey, are considered synergistic.

The disclosed subject matter is not to be limited in scope by the specific embodiments and examples described herein. Indeed, various modifications of the disclosure in addition to those described will become apparent to those skilled in the art from the foregoing description and accompanying figures. Such modifications are intended to fall within the scope of the appended claims.

All patent applications, patents, and printed publications cited herein are incorporated herein by reference in the entireties, except for any definitions, subject matter disclaimers or disavowals, and except to the extent that the incorporated material is inconsistent with the express disclosure herein, in which case the language in this disclosure controls.

The invention claimed is:

1. A method of treating cancer in a subject in need thereof, the method comprising administering to the subject an effective amount of a methionine adenosyltransferase II alpha (MAT2A) inhibitor and administering to the subject an effective amount of a protein arginine methyltransferase 5 (PRMT5) inhibitor that is Compound C:

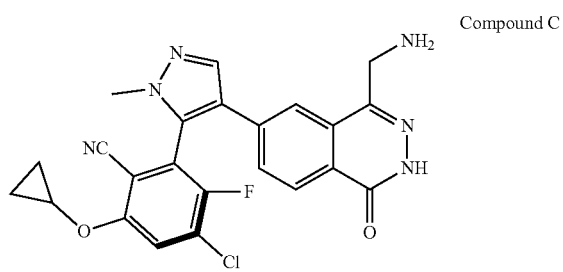

Compound C or a pharmaceutically acceptable salt thereof.

2. The method of claim 1, wherein the PRMT5 inhibitor is Compound C:

Compound C

3. The method of claim 1, wherein the methionine adenosyltransferase II alpha (MAT2A) inhibitor is a compound of Formula I:

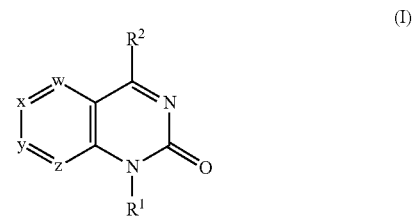

(I)

or a pharmaceutically acceptable salt thereof;
wherein
w is $CR^3$ or N; x is $CR^4$ or N; y is $CR^5$ or N; and z is $CR^6$ or N, provided that no more than two of w, x, y, and z can be N, wherein:
$R^3$ is hydrogen, alkyl, alkenyl, alkynyl, alkoxy, alkylsulfonyl, halo, haloalkyl, haloalkoxy, cycloalkyl, cycloalkylalkyloxy, cyano, amino, alkylamino, dialkylamino, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroaralkyloxy, heteroarylamino, heterocyclyl, heterocyclyloxy, heterocyclylamino, heterocyclylalkyloxy, heterocycly-loxyalkoxy, or heterocyclyloxyalkylamino, wherein heterocyclyl or heteroaryl, by itself or as part of another group, is unsubstituted or substituted with $R^a$, $R^b$, and/or $R^c$ independently selected from alkyl, cycloalkyl, haloalkyl, haloalkoxy, alkoxy, hydroxy, halo, cyano, alkoxycarbonyl, hydroxyalkyl, alkoxyalkyl, and aminoalkyl;
$R^5$ is alkyl, alkenyl, alkynyl, alkoxy, alkylsulfonyl, halo, haloalkyl, haloalkoxy, cycloalkyl, cyano, amino, alkylamino, dialkylamino, alkoxycarbonyl, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroarylamino, heterocyclyl, heterocyclyloxy, heterocyclylamino, heterocyclyloxyalkoxy, or heterocyclyloxyalkylamino, wherein heterocyclyl or heteroaryl, by itself or as part of another group, is unsubstituted or substituted with $R^a$, $R^b$, and/or $R^c$ independently selected from alkyl, cycloalkyl, haloalkyl, haloalkoxy, alkoxy, hydroxy, halo, cyano, hydroxyalkyl, alkoxyalkyl, and aminoalkyl;

$R^4$ and $R^6$ are independently hydrogen, alkyl, alkenyl, alkynyl, alkoxy, alkylthio, alkylsulfonyl, halo, haloalkyl, haloalkoxy, cycloalkyl, cyano, amino, alkylamino, dialkylamino, aminocarbonyl, alkylaminocarbonyl, or dialkylaminocarbonyl;

$R^1$ is $R^7$ wherein $R^7$ is cycloalkyl, bridged cycloalkyl, fused cycloalkyl, spirocycloalkyl, aryl, heteroaryl, heterocyclyl selected from pyrrolidinyl, piperidinyl, piperazinyl, oxetanyl, and morpholinyl, bridged heterocyclyl, fused heterocyclyl, or spiroheterocyclyl, wherein aryl, heteroaryl, or heterocyclyl is unsubstituted or substituted with $R^d$, $R^e$, and/or $R^f$;

$R^2$ is alkyl, haloalkyl, hydroxyalkyl, alkoxyalkyl, aminoalkyl, aminocarbonylalkyl, aminosulfonylalkyl, —O—$R^8$, —$NR^9R^{10}$, or —$X^b$—$R^{11}$ wherein:

$R^8$ is alkyl, haloalkyl, hydroxyalkyl, alkoxyalkyl, aminoalkyl, cycloalkyl, cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heterocyclyl, heterocyclylalkyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^g$, $R^h$, and/or $R^i$;

$R^9$ is hydrogen, alkyl, deuteroalkyl, or cycloalkyl; and $R^{10}$ is hydrogen, alkyl, deuteroalkyl, haloalkyl, hydroxyalkyl, alkoxyalkyl, haloalkoxyalkyl, aminoalkyl, aminosulfonylalkyl, thioureidoalkyl, alkylsulfonyl, alkylsulfonylalkyl, cyanoalkyl, alkylcarbonyl, alkoxycarbonyl, alkylaminocarbonyl, dialkylaminocarbonyl, aminocarbonylalkyl, cycloalkyl, cycloalkylalkyl, substituted cycloalkyl, substituted cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heteroarylcarbonyl, heterocyclyl, heterocyclylalkyl, heterocyclylcarbonyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^j$, $R^k$, and/or $R^l$;

$X^b$ is a bond or alkylene; and $R^{11}$ is cycloalkyl, bridged cycloalkyl, fused cycloalkyl, spirocycloalkyl, monocyclic heteroaryl, oxetanyl, azetidinyl, 2-oxoazetidinyl, pyrrolidinyl, 2-oxopyrrolidinyl, piperidinyl, or morpholinyl, bridged heterocyclyl, fused heterocyclyl, or spiroheterocyclyl, wherein heteroaryl or heterocyclyl is unsubstituted or substituted with $R^m$, $R^n$, and/or $R^o$; and $R^d$, $R^e$, $R^g$, $R^h$, $R^j$, $R^k$, $R^m$, and $R^n$ are independently selected from alkyl, haloalkyl, haloalkoxy, alkoxy, hydroxy, alkylsulfonyl, halo, cyano, carboxy, alkoxycarbonyl, hydroxyalkyl, alkoxyalkyl, aminoalkyl, aminosulfonyl, alkylaminosulfonyl, dialkylaminosulfonyl, sulfonylamino, aminocarbonyl, alkylaminocarbonyl, dialkylaminocarbonyl, heterocyclylcarbonyl, and ureido; and $R^f$, $R^i$, $R^l$, and $R^o$ are independently selected from alkyl, cycloalkyl, haloalkyl, haloalkoxy, alkoxy, hydroxy, halo, amino, alkylamino, cycloalkylsulfonylamino, cyano, cyanoalkyl, alkoxycarbonylalkyl, carboxyalkyl, and —$X^c$—$R^{12}$ where $X^c$ is bond, alkylene, or heteroalkylene; and $R^{12}$ is optionally substituted aryl, or optionally substituted heteroaryl; provided that when $R^1$ is pyrrolidinyl, piperidinyl, piperazinyl, oxetanyl, or morpholinyl then $R^f$ is not hydroxy.

4. The method of claim 1, wherein the methionine adenosyltransferase II alpha (MAT2A) inhibitor is Compound A:

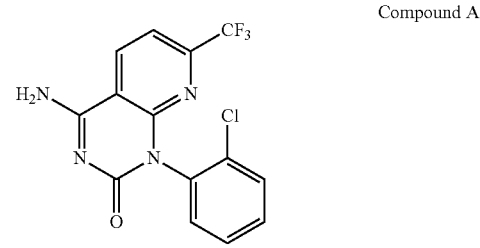 [SMILES: Nc1nc(=O)n(-c2ccccc2Cl)c2nc(C(F)(F)F)ccc12]

Compound A or a pharmaceutically acceptable salt thereof.

5. The method of claim 4, wherein the methionine adenosyltransferase II alpha (MAT2A) inhibitor is Compound A:

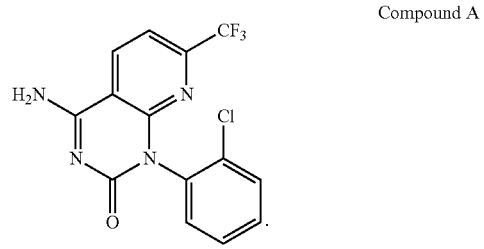

Compound A

6. The method of claim 1, wherein the cancer is characterized by a reduction or absence of MTAP gene expression, an absence of the MTAP gene, a reduced function of MTAP protein, a reduced level of MTAP protein, a MTA accumulation, an absence of MTAP protein, or a combination thereof.

7. The method of claim 1, wherein the cancer is selected from the group consisting of leukemia, glioma, melanoma, pancreatic cancer, non-small cell lung cancer, bladder cancer, astrocytoma, osteosarcoma, head and neck cancer, myxoid chondrosarcoma, ovarian cancer, endometrial cancer, breast cancer, soft tissue sarcoma, non-Hodgkin lymphoma, lung cancer, esophageal cancer, gastric cancer, kidney cancer, hepatocellular carcinoma, myelomas, glioblastoma, uterine cancer, and mesothelioma.

8. The method of claim 7, wherein the cancer is a solid tumor.

9. The method of claim 1, wherein MAT2A inhibitor and PRMT5 inhibitor are administered orally.

10. The method of claim 1, wherein MAT2A inhibitor and PRMT5 inhibitor are administered concurrently.

11. The method of claim 1, wherein MAT2A inhibitor and PRMT5 inhibitor are administered sequentially.

12. The method of claim 4, wherein the cancer is characterized by a reduction or absence of MTAP gene expression, an absence of the MTAP gene, a reduced function of MTAP protein, a reduced level of MTAP protein, a MTA accumulation, an absence of MTAP protein, or a combination thereof.

13. The method of claim 4, wherein the cancer is selected from the group consisting of leukemia, glioma, melanoma, pancreatic cancer, non-small cell lung cancer, bladder cancer, astrocytoma, osteosarcoma, head and neck cancer, myxoid chondrosarcoma, ovarian cancer, endometrial cancer, breast cancer, soft tissue sarcoma, non-Hodgkin lymphoma, lung cancer, esophageal cancer, gastric cancer, kidney cancer, hepatocellular carcinoma, myelomas, glioblastoma, uterine cancer, and mesothelioma.

14. The method of claim 13, wherein the cancer is a solid tumor.

15. The method of claim 4, wherein Compound A, or pharmaceutically acceptable salt thereof, and Compound C, or pharmaceutically acceptable salt thereof, are administered orally.

16. The method of claim 4, wherein Compound A, or pharmaceutically acceptable salt thereof, and Compound C, or pharmaceutically acceptable salt thereof, are administered concurrently.

17. The method of claim 4, wherein Compound A, or pharmaceutically acceptable salt thereof, and Compound C, or pharmaceutically acceptable salt thereof, are administered sequentially.

* * * * *

UNITED STATES PATENT AND TRADEMARK OFFICE
CERTIFICATE OF CORRECTION

PATENT NO. : 12,115,163 B2
APPLICATION NO. : 18/405638
DATED : October 15, 2024
INVENTOR(S) : Michael Patrick Dillon et al.

Page 1 of 1

It is certified that error appears in the above-identified patent and that said Letters Patent is hereby corrected as shown below:

In the Claims

Column 751, Line 66, Claim 3, delete "$R^i$" and insert --$R^j$--.

Signed and Sealed this
Thirty-first Day of December, 2024

Derrick Brent
*Acting Director of the United States Patent and Trademark Office*